(12) United States Patent
Klausen et al.

(10) Patent No.: US 12,207,671 B2
(45) Date of Patent: *Jan. 28, 2025

(54) POLYPEPTIDES HAVING LYSOZYME ACTIVITY, POLYNUCLEOTIDES ENCODING SAME AND USES AND COMPOSITIONS THEREOF

(71) Applicant: Novozymes A/S, Bagsvaerd (DK)

(72) Inventors: Mikkel Klausen, Copenhagen (DK); Kirk Matthew Schnorr, Holte (DK); Soeren Nymand-Grarup, Copenhagen (DK); Peter Bjarke Olsen, Copenhagen (DK); Marianne Thorup Cohn, Copenhagen (DK); Robert Piotr Olinski, Vaerloese (DK); Marc Dominique Morant, Frederiksberg (DK); Ming Li, Beijing (CN); Ye Liu, Beijing (CN); Lars Kobbeeroee Skov, Ballerup (DK); Dominique Aubert Skovlund, Vaerloese (DK); Han Bucong, Beijing (CN)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/469,388

(22) Filed: Sep. 18, 2023

(65) Prior Publication Data

US 2024/0090534 A1     Mar. 21, 2024

Related U.S. Application Data

(62) Division of application No. 16/462,764, filed as application No. PCT/CN2017/117765 on Dec. 21, 2017, now Pat. No. 11,896,033.

(51) Int. Cl.
| | |
|---|---|
| *A23K 20/147* | (2016.01) |
| *A23K 10/30* | (2016.01) |
| *A23K 50/30* | (2016.01) |
| *A23K 50/75* | (2016.01) |
| *C12N 9/36* | (2006.01) |
| *C12N 15/81* | (2006.01) |

(52) U.S. Cl.
CPC ............ *A23K 20/147* (2016.05); *A23K 10/30* (2016.05); *A23K 50/30* (2016.05); *A23K 50/75* (2016.05); *C12N 9/2462* (2013.01); *C12N 15/815* (2013.01); *C12Y 302/01017* (2013.01)

(58) Field of Classification Search
None
See application file for complete search history.

(56) References Cited

U.S. PATENT DOCUMENTS

| | | |
|---|---|---|
| 2012/0288490 A1 | 11/2012 | De Maria |
| 2016/0030528 A1 | 2/2016 | Metcalf et al. |
| 2019/0328005 A1 | 10/2019 | Klausen et al. |
| 2019/0351032 A1 | 11/2019 | Kjaerulff et al. |
| 2020/0305465 A1 | 10/2020 | Aureli et al. |
| 2024/0090534 A1* | 3/2024 | Klausen ............... A23K 20/147 |

FOREIGN PATENT DOCUMENTS

| | | |
|---|---|---|
| CN | 102858968 A | 1/2013 |
| CN | 103957929 A | 7/2014 |
| EP | 2904912 A1 | 8/2015 |
| WO | 2005011587 A2 | 2/2005 |
| WO | 2005080559 A1 | 9/2005 |
| WO | 2009102755 A1 | 8/2009 |
| WO | 2011104339 A1 | 9/2011 |
| WO | 2012027374 A2 | 3/2012 |
| WO | 2012035103 A1 | 3/2012 |
| WO | 2013076253 A1 | 5/2013 |
| WO | 2013076259 A2 | 5/2013 |
| WO | 2013110627 A1 | 8/2013 |
| WO | 2016210238 A1 | 12/2016 |
| WO | 2017001701 A1 | 1/2017 |
| WO | 2022047149 A1 | 3/2022 |

OTHER PUBLICATIONS

Baroncelli et al., 2016, NCBI Reference No. XP 018657583.1.
Berka et al., 2012, NCBI Reference No. XP 003650266.1.
Berka et al., 2012, NCBI Reference No. XP 003662567.1.
Berka et al., 2016, Uniprot accession No. G2QWF5.
Birren et al., 2008, NCBI Reference No. XP 001215317.1.
Chica et al., 2005, Curr Op Biotechnol, 16(4), 378-384.
Corrochano et al., 2016, NCBI Reference No. XP 018287694.1.
Galagan et al., 2015, NCBI Reference No. XP 964535.1.
Jimenez et al., 2016, Genbank No. OIW26653.1.
Kanematsu et al., 2015, Genbank No. GAP89829.1.
Kohler et al., 2015, Genbank No. KIJ42223.1.
Kohler et al., 2015, Genbank No. KIN06446.1.
Kohler et al., 2015, Genbank No. KIN08373.1.
Korczynska et al., 2010, Acta Cryst, F66, 973-977.
Kubicek et al., 2015, NCBI Reference No. XP 013942670.1.
Li et al., 2015, Uniprot accession No. A0A0A2VUR3.
Linde et al., 2015, Genbank No. CDS02619.
Masschalck et al., Journal of Food Protection, 2002, 1916-1923, 65(12).
Meinhardt et al., 2014, NCBI Reference No. XP 007849295.1.
Mondo et al., 2017, EBI Accession No. A0A1Y1Z9R4.
Morin et al., 2014, NCBI Reference No. XP 006463298.1.

(Continued)

*Primary Examiner* — Christian L Fronda
(74) *Attorney, Agent, or Firm* — Adam Rucker

(57) ABSTRACT

The present invention relates animal feed or animal feed additives comprising one or more polypeptides having lysozyme activity. The invention also relates to polypeptides having lysozyme activity, polynucleotides encoding the polypeptides nucleic acid constructs, vectors, and host cells comprising the polynucleotides as well as methods of producing and using the polypeptides.

20 Claims, 6 Drawing Sheets

Specification includes a Sequence Listing.

(56) References Cited

OTHER PUBLICATIONS

Nierman, 2008, NCBI Reference No. XP 001276751.1.
Nowrousian et al., 2011, NCBI Reference No. XP 003352547.1.
Peter et al., 2016, Genbank No. OCK75562.1.
Priebe et al., 2015, Genbank No. CEJ53659.1.
Priebe et al., 2016, Genbank No. CEL10138.1.
Riley et al., 2014, Genbank No. KDQ07276.1.
Schnorr et al., 2013, WO2013076253A1—EBI Accession No. BAP10817.
Shang et al., 2016, Genbank No. OAA73042.1.
Shang et al., 2016, Genbank No. OAA81279.1.
Shang et al., 2016, Uniprot accession No. A0A162JSB9.
Singh et al., 2017, Current Protein and Peptide Science, 18, 1-11.
Sun et al., 2015, Nature communications, 8322(6), 1-12.
Terfehr et al., 2014, Genbank No. KFH43569.1.
Visser et al., 2012, WO2012027374A2—EBI Accession No. AZT73868.
Wang et al, 2016, NCBI Reference No. XP 018175238.1.
Wang et al, 2017, NCBI Reference No. XP 018175238.1.
Wang et al., 2016, NCBI Reference No. XP 018138018.1.
Wang et al., 2016, NCBI Reference No. XP 018142497.1.
Wang et al., 2017, Uniprot accession No. A0A179GAU8.
Zeiner et al., 2016, NCBI Reference No. XP 018032810.1.
Berka et al., 2011, Nature Biotechnology 29, 922-927.
Berka et al., 2016, EBI Accession No. Uniprot G2QCJ9.

\* cited by examiner

```
                            SEQUENCE LISTING

Sequence total quantity: 235
SEQ ID NO: 1            moltype = DNA  length = 858
FEATURE                 Location/Qualifiers
sig_peptide             1..51
mat_peptide             52..855
source                  1..858
                        mol_type = genomic DNA
                        organism = Sporormia fimetaria
CDS                     1..141
CDS                     267..751
CDS                     810..855
SEQUENCE: 1
atgaagtccg cattcgtctt tctagctgca gtagcacagc tagccagcgc tgctgttcct   60
ggctttgaca tctcccacta ccaaagctcg gtgaattacg ccggtgccta ctccagcggt  120
gctcgctttg tcataataaa ggtacgcccc ttctaattcc ttccctcgtc gcggaccegt  180
attgtatacg ttatttctcc aagccgtctc ccttcccgct caatcaatga aagtgacata  240
aaaccgtcag tggctgacat ttccaggcca ctgaggaac aacctacatc gacccaaaat   300
tctctgacca ttacattggc gccacaaatg ccggactgat tcgcggcgcg taccattttg  360
cgcgacccgc cgcctctact ggcgccgctc aggctaatta cttcgtctcc cacggcggag  420
gttggtctgc cgacggcatc actctgcccg gaatgctcga catggagtat gggtcgacat  480
cggcctgcca cgggctctcc cagtccgcaa tggttacctg gatcacgagc tttgtgaacc  540
agtacaacag cctgacaggt cggtatccga tgatttacac cacggcagat tggtggcaaa  600
cttgcacggg aaatagcgcg gctttcaaca ccaaatctcc tctggtactg gcgagatact  660
cgagttctgc gggtacggtc cctggaggct ggccatatta cacgatttgg caatttaatg  720
atgcatatgc ttatggaggg gattcagata cgtaagtgct tttccatgcg caattgatag  780
tatgtattag ggactaacag gacctatagt tttaacggcg acctggccgg cttaaagagg  840
ctcgcgaagg gctcgtag                                                 858

SEQ ID NO: 2            moltype = AA  length = 224
FEATURE                 Location/Qualifiers
source                  1..224
                        mol_type = protein
                        organism = Sporormia fimetaria
SEQUENCE: 2
MKSAFVFLAA VAQLASAAVP GFDISHYQSS VNYAGAYSSG ARFVIIKATE GTTYIDPKFS   60
DHYIGATNAG LIRGAYHFAR PAASTGAAQA NYFVSHGGGW SADGITLPGM LDMEYGSTSA  120
CHGLSQSAMV TWITSFVNQY NSLTGRYPMI YTTADWWQTC TGNSAAFNTK SPLVLARYSS  180
SAGTVPGGWP YYTIWQFNDA YAYGGDSDTF NGDLAGLKRL AKGS                   224

SEQ ID NO: 3            moltype = AA  length = 207
FEATURE                 Location/Qualifiers
source                  1..207
                        mol_type = protein
                        organism = Sporormia fimetaria
SEQUENCE: 3
AVPGFDISHY QSSVNYAGAY SSGARFVIIK ATEGTTYIDP KFSDHYIGAT NAGLIRGAYH   60
FARPAASTGA AQANYFVSHG GGWSADGITL PGMLDMEYGS TSACHGLSQS AMVTWITSFV  120
NQYNSLTGRY PMIYTTADWW QTCTGNSAAF NTKSPLVLAR YSSSAGTVPG GWPYYTIWQF  180
NDAYAYGGDS DTFNGDLAGL KRLAKGS                                      207

SEQ ID NO: 4            moltype = DNA  length = 716
FEATURE                 Location/Qualifiers
sig_peptide             1..51
mat_peptide             52..713
source                  1..716
                        mol_type = genomic DNA
                        organism = Poronia punctata
CDS                     1..141
CDS                     201..713
SEQUENCE: 4
atgaagtctt acatcgcccc cctcctcggc ctcgcccaag gcgcgctcgc cgccgtccga   60
ggcttcgaca tttcgcacta tcagtcgagc gtcaactttg cgccgccaa gagctccggt   120
gctcagtttg tcatcatcaa ggtgagaagg acaagccata aaatgagggg aaagtcgtgt  180
gtaactgacg tgaccaacag gcgactgagg gtacctccta taccgacccc agtttcagct  240
ctcactatac cggcgccacc aatgctggct tgatccgtgg cggttaccac ttcgcccacc  300
tcgattccag ctctggtgct gcgcaggcca agtacttcct cgcccatggt ggtggctggt  360
ctggagacgg catcaccctg cccggtatgc tggatcttga gggcagctgc gtcctctcgg  420
ctagcgctac cgtgtcttgg atcaaggact ttagcaacac ctaccactcg tccacgggcg  480
tgtaccctct aatttacaca aaccccctcg tggtggtctag ctgcaccgt aactccaagg   540
cctttatcga caccaatcct ctcgtacttg cacggtacgc gtcaagcgct ggcaccccctc  600
```

```
ccggtggctg gccttactat accatctggc agtacaacga tgcctacaag tacggaggtg    660
actcggacgt cttcaacgga gaccttgccg gcctcaagag actggctaag ggctaa        716

SEQ ID NO: 5            moltype = AA  length = 218
FEATURE                 Location/Qualifiers
source                  1..218
                        mol_type = protein
                        organism = Poronia punctata
SEQUENCE: 5
MKSYIAPLLG LAQGALAAVQ GFDISHYQSS VNFGAAKSSG AQFVIIKATE GTSYTDPSFS    60
SHYTGATNAG LIRGGYHFAH LDSSSGAAQA KYFLAHGGGW SGDGITLPGM LDLEGSCVLS    120
ASATVSWIKD FSNTYHSSTG VYPLIYTNPS WWSSCTGNSK AFIDTNPLVL ARYASSAGTP    180
PGGWPYYTIW QYNDAYKYGG DSDVFNGDLA GLKRLAKG                            218

SEQ ID NO: 6            moltype = AA  length = 201
FEATURE                 Location/Qualifiers
source                  1..201
                        mol_type = protein
                        organism = Poronia punctata
SEQUENCE: 6
AVQGFDISHY QSSVNFGAAK SSGAQFVIIK ATEGTSYTDP SFSSHYTGAT NAGLIRGGYH    60
FAHLDSSSGA AQAKYFLAHG GGWSGDGITL PGMLDLEGSC VLSASATVSW IKDFSNTYHS    120
STGVYPLIYT NPSWWSSCTG NSKAFIDTNP LVLARYASSA GTPPGGWPYY TIWQYNDAYK    180
YGGDSDVFNG DLAGLKRLAK G                                              201

SEQ ID NO: 7            moltype = DNA  length = 771
FEATURE                 Location/Qualifiers
sig_peptide             1..48
mat_peptide             49..768
source                  1..771
                        mol_type = genomic DNA
                        organism = Poronia punctata
CDS                     1..138
CDS                     256..768
SEQUENCE: 7
atgaagtatc tcgttcccct ttgggcttc gccacggcg cctggccca ggttcaaggc       60
ttcgatatct cgagctacca gcccagcgta gactttgccg gtgcttatgc tgatggcgcc   120
cgattcgtca tcatcaaggt aagaaaaata ctacaatcca gcccataac cataaccaaa    180
accccccgcc ccccattgga ttagatggat gatggactag gtaacctaac ctgctctaac   240
acaaaataat cataggccac cgaaggaact ggctacatcg accccacctt cagcgaccac   300
tacgtaggcg caaccaacgc cggcctgctc cgcggcggtt accactacgc cacctggac    360
tcgacctcgg cgctaccca ggcccagtac ttcctcgcca cggcggtgg ctggtccggc    420
gacggaatca cccctcccgg catgcttgat ctcgaggtg ctgaccgtgc tctcggccgc    480
gacgccgtcg cctggatcaa ggacttcagc gacacctacc acgccagcac gggcgtctac    540
cccctgctgt acaccaaccc ttcgtggtgg gcctcttgca ccggcgactc cagcgccttc    600
atcgacacca cccccctcgt cctcgcccac tacgccgacg ccgccggcac ccccctggt    660
ggctggcccc tctactcctt ctggcagtac aacgatgcct acccctacgg tggcgactcc    720
gaggtctgga acggtgatat ggacggtctt ctccgccttg cttcgggcta a            771

SEQ ID NO: 8            moltype = AA  length = 217
FEATURE                 Location/Qualifiers
source                  1..217
                        mol_type = protein
                        organism = Poronia punctata
SEQUENCE: 8
MKYLVPLLGF AHGALAQVQG FDISSYQPSV DFAGAYADGA RFVIIKATEG TGYIDPTFSD    60
HYVGATNAGL LRGGYHYAHL DSTSGATQAQ YFLANGGGWS GDGITLPGML DLEGDCVLSA    120
ADAVAWIKDF SDTYHASTGV YPLLYTNPSW WASCTGDSSA FIDTNPLVLA HYADAAGTPP    180
GGWPFYSFWQ YNDAYPYGGD SEVWNGDMDG LLRLASG                             217

SEQ ID NO: 9            moltype = AA  length = 201
FEATURE                 Location/Qualifiers
source                  1..201
                        mol_type = protein
                        organism = Poronia punctata
SEQUENCE: 9
QVQGFDISSY QPSVDFAGAY ADGARFVIIK ATEGTGYIDP TFSDHYVGAT NAGLLRGGYH    60
YAHLDSTSGA TQAQYFLANG GGWSGDGITL PGMLDLEGDC VLSAADAVAW IKDFSDTYHA    120
STGVYPLLYT NPSWWASCTG DSSAFIDTNP LVLAHYADAA GTPPGGWPFY SFWQYNDAYP    180
YGGDSEVWNG DMDGLLRLAS G                                              201

SEQ ID NO: 10           moltype = DNA  length = 675
FEATURE                 Location/Qualifiers
sig_peptide             1..63
mat_peptide             64..672
source                  1..675
                        mol_type = genomic DNA
                        organism = Lecanicillium sp.
CDS                     1..672
```

```
SEQUENCE: 10
atgcgaccat ttactgccct ctttgtcgcc ttcgtcagcg ccgccagtgc gctgacccac    60
gccgtcgaca gctcctccga ggtgagcgtc gccatttaca aaaaggccct cggccagggc   120
ttcacccgcg ccatcttccg cggctaccaa gaggcctgct cgcagggcgg ccgcgtcgac   180
ccgaccttg  tgccgagcta caagaatgcc gtcgcggccg gctacaagga ctttgacgcc   240
tacttcttcc cctgcaccgg caagaccaac aagtgcaagc cctacgccgc gcagctcgcg   300
gagctcctcg acaccatcaa gggccagaag ctggcgattc gccgcatctg gctcgacatt   360
gagacggaca gggtgtgcaa cccgtttgac tatggcgcac agggcaacct tgccgaggcc   420
aagaagctcg tggccgcgtt tcgcgacgcc aagcttgact ggggcatcta cacgtctgcg   480
acgcagtggg agaccatctt tggcgccaag accgtcgagc tggtcaagga cgtgccgcta   540
tggtttgcca agtttgacaa tgtcgagacg ctggagctca agacgccgtt tggtggctgg   600
acaaaggcgg atgcgaagca gtatactgac cagtcggcca gcaacaagtt tgacttgaac   660
gtctttctg  cctaa                                                    675

SEQ ID NO: 11             moltype = AA   length = 224
FEATURE                   Location/Qualifiers
source                    1..224
                          mol_type = protein
                          organism = Lecanicillium sp.
SEQUENCE: 11
MRPFTALFVA FVSAASALTH AVDSSSEVSV AIYKKALGQG FTRAIFRGYQ EACSQGGRVD    60
PTFVPSYKNA VAAGYKDFDA YFFPCTGKTN KCKPYAAQLA ELLDTIKGQK LAIRRIWLDI   120
ETDRVCNPFD YGAQGNLAEA KKLVAAFRDA KLDWGIYTSP TQWETIFGAK TVELAKDVPL   180
WFAKFDNVET LELKTPFGGW TKADAKQYTD QSASNKFDLN VFSA                    224

SEQ ID NO: 12             moltype = AA   length = 203
FEATURE                   Location/Qualifiers
source                    1..203
                          mol_type = protein
                          organism = Lecanicillium sp.
SEQUENCE: 12
VDSSSEVSVA IYKKALGQGF TRAIFRGYQE ACSQGGRVDP TFVPSYKNAV AAGYKDFDAY    60
FFPCTGKTNK CKPYAAQLAE LLDTIKGQKL AIRRIWLDIE TDRVCNPFDY GAQGNLAEAK   120
KLVAAFRDAK LDWGIYTSPT QWETIFGAKT VELAKDVPLW FAKFDNVETL ELKTPFGGWT   180
KADAKQYTDQ SASNKFDLNV FSA                                           203

SEQ ID NO: 13             moltype = DNA   length = 796
FEATURE                   Location/Qualifiers
sig_peptide               1..60
mat_peptide               61..793
source                    1..796
                          mol_type = genomic DNA
                          organism = Lecanicillium sp.
CDS                       1..150
CDS                       199..381
CDS                       443..793
SEQUENCE: 13
atgaagtcat tctcatccat tatcgccggc atcgccggcc ttgcctctgt cgcttctgcc    60
acggtgcagg gcttcgatgt ctctggctac cagcccactg tcaactgggg tgcggcctac   120
agcagcggtg ctcgcttcgt catgatcaag gtatgctgca gcggacggtt cgaatcacag   180
atgatcgctg acaggctaggc caccgaggga actggttaca tctcgtccag cttcggctcg   240
cagtaccctg gtgccaccaa tgcgggcttt atccgcggcg gctaccacttt tgcgctgccc   300
gaccggtcct ctgctccgc  acaggccgac tactttctgg cccacggcgg cggctggagc   360
ggcgatggca tcactctacc ggtaagtccc atcaccttcc ttgaatcgaa gcgccatggt   420
agtgctagtc tgacgcatcc agggcatgct ggacattgag tataacccgt acggcgccac   480
ctgctacggc ctctcgcagg gcgccatggt caactggatc agcgactttg tcgagcacta   540
caaggccagg acgacgcagt accccatcat ctacacgacg accgactggt ggaagacgtg   600
cacgggcaac agccctgcct ttggccaaaa gtgcccgctg agcctggccc ggtactcgag   660
cagcgtgggc gagatcccca acggctggcc gttccagact ttctggcaga acagcgacaa   720
gtatgcgtac ggtggcgatt cgcagatttt caacggcgcg tactctcagc tgcagaagat   780
tgctcgcggt ggttag                                                   796

SEQ ID NO: 14             moltype = AA   length = 228
FEATURE                   Location/Qualifiers
source                    1..228
                          mol_type = protein
                          organism = Lecanicillium sp.
SEQUENCE: 14
MKSFSSIIAG IAGLASVASA TVQGFDVSGY QPTVNWGAAY SSGARFVMIK ATEGTGYISS    60
SFGSQYPGAT NAGFIRGGYH FALPDRSSGS AQADYFLAHG GGWSGDGITL PGMLDIEYNP   120
YGATCYGLSQ GAMVNWISDF VEHYKARTTQ YPIIYTTTDW WKTCTGNSPA FGQKCPLSLA   180
RYSSSVGEIP NGWPFQTFWQ NSDKYAYGGD SQIFNGAYSQ LQKIARGG                228

SEQ ID NO: 15             moltype = AA   length = 208
FEATURE                   Location/Qualifiers
source                    1..208
                          mol_type = protein
                          organism = Lecanicillium sp.
SEQUENCE: 15
```

```
TVQGFDVSGY QPTVNWGAAY SSGARFVMIK ATEGTGYISS SFGSQYPGAT NAGFIRGGYH      60
FALPDRSSGS AQADYFLAHG GGWSGDGITL PGMLDIEYNP YGATCYGLSQ GAMVNWISDF     120
VEHYKARTTQ YPIIYTTTDW WKTCTGNSPA FGQKCPLSLA RYSSSVGEIP NGWPFQTFWQ     180
NSDKYAYGGD SQIFNGAYSQ LQKIARGG                                        208

SEQ ID NO: 16            moltype = DNA   length = 734
FEATURE                  Location/Qualifiers
sig_peptide              1..54
mat_peptide              55..731
source                   1..734
                         mol_type = genomic DNA
                         organism = Onygena equina
CDS                      1..144
CDS                      201..731
SEQUENCE: 16
atgttgaaaa caattatcta taccaccctt gccgtcgcta gcctggcgtc agcagccgtt      60
cccggtatcg acgtgtcggg ctaccaaggc aacgtgaact gggcgaacgt cgccaacgct     120
ggaaagaagt ttgcctacgt caaggtatgc gtctccgtaa tgagttatga attgaaacta     180
atcaaatcaa tcgggcatag gccacgtgaa ataccaacta catcaaccct tacttcgccc     240
agcagtacaa tggcgcctac aaccagggca ttattcgagg tgcataccac tacgcccacc     300
ccaacggcgc aagcggagct tctcaggcca actacttcct tgctcacggt ggcggctggt     360
ctgctgatgg gaaaacccct cctggtgccg tcgacctcga gtacggaccc aatgcagca     420
cttgctgggg tatcagtcaa tcggcgatga tcgcttggat ccgtgacttc tccaacacct     480
accgtgccaa gaccggccgg cctccagtca tctacaccag cacctcttgg tggaagacct     540
gcaccggtaa ctatggcggt ttcggaaacg ataatcccct ttggattgct cgttattcaa     600
gcactgtcgg cgaacttcct gctggctggc ctttccacag catctggcag aacaacgata     660
acagcggtgt tggagggac ggtgatatct ggaacggtga cctggctgga ttgcaacgat      720
ttgcaaaggg ctaa                                                       734

SEQ ID NO: 17            moltype = AA   length = 225
FEATURE                  Location/Qualifiers
source                   1..225
                         mol_type = protein
                         organism = Onygena equina
SEQUENCE: 17
MLKTIIYTTL AVASLASAAV PGIDVSGYQG NVNWANVANA GKKFAYVKAT EHTNYINPYF      60
AQQYNGAYNQ GIIRGAYHYA HPNGASGASQ ANYFLAHGGG WSADGKTLPG AVDLEYGPNG     120
STCWGISQSA MIAWIRDFSN TYRAKTGRPP VIYTSTSWWK TCTGNYGGFG NDNPLWIARY     180
SSTVGELPAG WPFHSIWQNN DNSGVGGDGD IWNGDLAGLQ RFAKG                     225

SEQ ID NO: 18            moltype = AA   length = 207
FEATURE                  Location/Qualifiers
source                   1..207
                         mol_type = protein
                         organism = Onygena equina
SEQUENCE: 18
AVPGIDVSGY QGNVNWANVA NAGKKFAYVK ATEHTNYINP YFAQQYNGAY NQGIIRGAYH      60
YAHPNGASGA SQANYFLAHG GGWSADGKTL PGAVDLEYGP NGSTCWGISQ SAMIAWIRDF     120
SNTYRAKTGR PPVIYTSTSW WKTCTGNYGG FGNDNPLWIA RYSSTVGELP AGWPFHSIWQ     180
NNDNSGVGGD GDIWNGDLAG LQRFAKG                                         207

SEQ ID NO: 19            moltype = DNA   length = 742
FEATURE                  Location/Qualifiers
sig_peptide              1..57
                         note = 739
mat_peptide              58..739
                         note = 739
source                   1..742
                         mol_type = genomic DNA
                         organism = Purpureocillium lilacinum
CDS                      1..147
CDS                      206..739
                         note = 739
SEQUENCE: 19
atgaagttcg catccgtcgc cgcctctgtg tccgccctct gcggcgtggc ctctgccgct      60
gtcaagggct tgacatttc ccactaccag cccaacgtcg actttgccaa ggcctatgcc     120
gatgcgcccg cttcgtgat gatcaaggtg cgttcaccca gatgaagagc ttcccccgaa     180
ttccatctaa cgttcacgtc ggcaggccac ggagggcacc acgtacacgg acccagctt     240
cagctcgcac tacacgggcg ccaccaaggc gggcttcatc cgccgcggct accactttgg     300
ccgcccggcg tcctcgtccg gtgccgcgca ggccaagtac tttatcgcgc acggcggcgg     360
ctggtccaag gacggcatca cgctgcctgg catgctcgac atggagtacc agtcgtcgag     420
cagcgcgtgc ggcgggctct cacagagcgc catggtcagc tggatcaacg actttgtcaa     480
cacgtaccac gccgccacgg gcgtctaccc gctcatctac acctcgacca gctggtggac     540
gcagtgcacg ggcaacgcg ccgccttttag cagcaagtgc cctctcgtcg tcgcgcgcta     600
tgctagctcc gtcggcacgc tccctgctgt ctggggcttc tacaccttct ggcagtactc     660
ggacgcggcg cctgggtg gtgatgcgga taccttaac ggcgacatta ctgctctcaa       720
gaagattgcc aacgccggtt aa                                              742

SEQ ID NO: 20            moltype = AA   length = 227
```

```
FEATURE                 Location/Qualifiers
source                  1..227
                        mol_type = protein
                        organism = Purpureocillium lilacinum
SEQUENCE: 20
MKFASVAASV SALCGVASAA VKGFDISHYQ PNVDFAKAYA DGARFVMIKA TEGTTYTDPS    60
FSSHYTGATK AGFIRGGYHF ARPASSSGAA QAKYFIAHGG GWSKDGITLP GMLDMEYQSS   120
SSACGGLSQS AMVSWINDFV NTYHAATGVY PLIYTSTSWW TQCTGNSAAF GSKCPLVVAR   180
YASSVGTLPA GWGFYTFWQY SDAAPWGGDA DTFNGDITAL KKIANAG                227

SEQ ID NO: 21           moltype = AA   length = 208
FEATURE                 Location/Qualifiers
source                  1..208
                        mol_type = protein
                        organism = Purpureocillium lilacinum
SEQUENCE: 21
AVKGFDISHY QPNVDFAKAY ADGARFVMIK ATEGTTYTDP SFSSHYTGAT KAGFIRGGYH    60
FARPASSSGA AQAKYFIAHG GGWSKDGITL PGMLDMEYQS SSACGGLSQ SAMVSWINDF   120
VNTYHAATGV YPLIYTSTSW WTQCTGNSAA FGSKCPLVVA RYASSVGTLP AGWGFYTFWQ   180
YSDAAPWGGD ADTFNGDITA LKKIANAG                                      208

SEQ ID NO: 22           moltype = DNA   length = 895
FEATURE                 Location/Qualifiers
sig_peptide             1..54
mat_peptide             55..876
source                  1..895
                        mol_type = genomic DNA
                        organism = Trichobolus zukalii
CDS                     1..144
CDS                     293..750
CDS                     820..892
SEQUENCE: 22
atgaagctca ccacttttat cacgggcctt gtatcggcca gcaccgctct tgctgccgtt    60
ccaggattcg atatcccca ctaccaaccg tccgttaact agccggcgc ctacaactcc   120
ggcgctcgtt tcgtcatcat caaagtcctc ttcccttact ctccttctc cccttctccc   180
cttctcccct tctcccttc tcccttctc ccttctccc cttctccct tctcccttc   240
tccccttctc cccttctcct ctcaacatcc catcctaact cccttctcct aggcgaccga   300
aggtacaacc tacactgacc ccgtattctc cactcactat accggagcta ccaaagctgg   360
cttaatccgg ggaggctacc acttcgctcg tcccgcctcg tcgtccggct ccgcccaagc   420
cgatttcttc ttcaaaaacg gaggcgggtg gtctgctgac ggtatcacac ttcctggtat   480
gctcgatatg gaatatggca gcacttcatc atgccatgga cttctcaaa ctgctatggt   540
gaattggatc agcgatttcg tgaaccggta taaaacgttg agtgggaggt atccgatgat   600
ttatactggt tactattggt gggtggagtg tacagggaac tctaacaagt ttgcaacgac   660
ttgtcctttg gtgcttgcaa ggtattcgag ttcgtggga gagattccgg gaggctgggg   720
gtatcaaacg atttggcagt ttaatgataa gtaagtggtt ttccgaaggt gagatgaagt   780
gaggacggga ggatgtaggc taattagaca ccgctgcagg tacgcttatg gcggtgactc   840
ggatagtttc aatggctcgc tcgatcgcct taaggcgctt gccaagggga cttaa         895

SEQ ID NO: 23           moltype = AA   length = 225
FEATURE                 Location/Qualifiers
source                  1..225
                        mol_type = protein
                        organism = Trichobolus zukalii
SEQUENCE: 23
MKLTTFITGL VSASTALAAV PGFDISHYQP SVNYAGAYNS GARFVIIKAT EGTTYTDPVF    60
STHYTGATKA GLIRGGYHFA RPASSSGSAQ ADFFFKNGGG WSADGITLPG MLDMEYGSTS   120
SCHGLSQTAM VNWISDFVNR YKTLSGRYPM IYTGYYWWVE CTGNSNKFAT TCPLVLARYS   180
SSVGEIPGGW GYQTIWQFND KYAYGGDSDS FNGSLDRLKA LAKGT                   225

SEQ ID NO: 24           moltype = AA   length = 207
FEATURE                 Location/Qualifiers
source                  1..207
                        mol_type = protein
                        organism = Trichobolus zukalii
SEQUENCE: 24
AVPGFDISHY QPSVNYAGAY NSGARFVIIK ATEGTTYTDP VFSTHYTGAT KAGLIRGGYH    60
FARPASSSGA AQADFFFKNG GGWSADGITL PGMLDMEYGS TSSCHGLSQT AMVNWISDFV   120
NRYKTLSGRY PMIYTGYYWW VECTGNSNKF ATTCPLVLAR YSSSVGEIPG GWGYQTIWQF   180
NDKYAYGGDS DSFNGSLDRL KALAKGT                                       207

SEQ ID NO: 25           moltype = DNA   length = 672
FEATURE                 Location/Qualifiers
sig_peptide             1..48
mat_peptide             49..669
source                  1..672
                        mol_type = genomic DNA
                        organism = Penicillium citrinum
CDS                     1..669
SEQUENCE: 25
```

-continued

```
atgcgcccct ccgtcatatt gctcgctttt gccagcgcag ccagcgctct catccacgct     60
gtcgacagct cctccgaagt atccgtcgac atttacaaaa aggccttgag cgagggcttc    120
tcgcgcgcaa tcttccgcgg ttaccaggag gcctgctccc agggcggccg cgtcgaccca    180
accttttgc ccagctacaa gaatgcgcaa acagccggct acaaagactt tgacgcctat     240
ttcttcccct gcacgggctc cggaaacaaa tgcaagccat acgacgtgca gattggcgag    300
ctcgtcgacg ctattaaaaa gaacaacatg gccattcgcc gcatctgggt cgactttgaa    360
aaggacaaga cctgcaaccc gtttaactgg gaccctaaac gcaacattga tgaggccaag    420
aggattatag tgcagtgcg caagacaaag ttcgattttg gcgtgtacac ctcagcaaca     480
cagtggactt ccatctttgg ctccaaggac gtagtcctgg ctaatgatgt gccgctttgg    540
tttgccaagt ttgataatgt cgagaacctt gacctggcgc agccttttgg aggctggaca    600
aaggcggacg gaaagcaata caccgacaag tcagctagta agaagtttga tttgaacgtg    660
ttttctgctt aa                                                         672

SEQ ID NO: 26          moltype = AA  length = 223
FEATURE                Location/Qualifiers
source                 1..223
                       mol_type = protein
                       organism = Penicillium citrinum
SEQUENCE: 26
MRPSVILLAF ASAASALIHA VDSSSEVSVD IYKKALSEGF SRAIFRGYQE ACSQGGRVDP     60
TFLPSYKNAQ TAGYKDFDAY FFPCTGSGNK CKPYDVQIGE LVDAIKKNNM AIRRIWVDFE    120
KDKTCNPFNW DPKRNIDEAK RIIGAVRKTK FDFGVYTSAT QWTSIFGSKD VVLANDVPLW    180
FAKFDNVENL DLAQPFGGWT KADGKQYTDK SASKKFDLNV FSA                      223

SEQ ID NO: 27          moltype = AA  length = 207
FEATURE                Location/Qualifiers
source                 1..207
                       mol_type = protein
                       organism = Penicillium citrinum
SEQUENCE: 27
LIHAVDSSSE VSVDIYKKAL SEGFSRAIFR GYQEACSQGG RVDPTFLPSY KNAQTAGYKD     60
FDAYFFPCTG SGNKCKPYDV QIGELVDAIK KNNMAIRRIW VDFEKDKTCN PFNWDPKRNI    120
DEAKRIIGAV RKTKFDFGVY TSATQWTSIF GSKDVVLAND VPLWFAKFDN VENLDLAQPF    180
GGWTKADGKQ YTDKSASKKF DLNVFSA                                        207

SEQ ID NO: 28          moltype = DNA  length = 690
FEATURE                Location/Qualifiers
sig_peptide            1..66
mat_peptide            67..687
source                 1..690
                       mol_type = genomic DNA
                       organism = Cladorrhinum bulbillosum
CDS                    1..687
SEQUENCE: 28
atgaagctcc tccccctttc caccacctta ttgcccgtgg cctcctcgc caccgaggcc     60
tcggcggcag tccaaggctt cgacatctcg cactaccaat cctcagtcaa cttccaggcg    120
gcctacaact cgggcgcccg cttcgtcatc atcaaggcga cagaggcac gacctacatc    180
gacccccaagt tttcgtctca ctacacggga gccaccaacg ccgggctaat ccggggcggg    240
taccactttg cccatccgga ctcgtcgacc ggcgccgcgc aggcagattt tttcctcgcc    300
cacggcggcg gctggtccgg cgacggcatc accctgcccg ggatgctcga cctcgaatcc    360
gtctccggaa aggcgacctg cttcgggctc tcggcctcgt ccatggtggc ctggatcaag    420
tcgttctctg accggtacca caccccggacc ggacgtaccc cgatgctgta caccaacccg    480
tcttggtgga ccacctgcac cggaaacagc aacgcgttcg tcaacacgaa cccgctcgtt    540
ctggctcggt acgccagcgc gcccgggacc atccccggtg gatggccgta tcagaccatc    600
tggcagaatt cggactcgta tacctacgga ggggattcgg atattttaa cggcgcgctg    660
agtgggttgc aaaagttggc cagcggttaa                                     690

SEQ ID NO: 29          moltype = AA  length = 229
FEATURE                Location/Qualifiers
source                 1..229
                       mol_type = protein
                       organism = Cladorrhinum bulbillosum
SEQUENCE: 29
MKLLPLSTTL LPVALLATEA SAAVQGFDIS HYQSSVNFQA AYNSGARFVI IKATEGTTYI     60
DPKFSSHYTG ATNAGLIRGG YHFAHPDSST GAAQADFFLA HGGGWSGDGI TLPGMLDLES    120
VSGKATCFGL SASSMVAWIK SFSDRYHTRT GRYPMLYTNP SWWTTCTGNS NAFVNTNPLV    180
LARYASAPGT IPGGWPYQTI WQNSDSYTYG GDSDIFNGAL SGLQKLASG                229

SEQ ID NO: 30          moltype = AA  length = 207
FEATURE                Location/Qualifiers
source                 1..207
                       mol_type = protein
                       organism = Cladorrhinum bulbillosum
SEQUENCE: 30
AVQGFDISHY QSSVNFQAAY NSGARFVIIK ATEGTTYIDP KFSSHYTGAT NAGLIRGGYH     60
FAHPDSSTGA AQADFFLAHG GGWSGDGITL PGMLDLESVS GKATCFGLSA SSMVAWIKSF    120
SDRYHTRTGR YPMLYTNPSW WTTCTGNSNA FVNTNPLVLA RYASAPGTIP GGWPYQTIWQ    180
NSDSYTYGGD SDIFNGALSG LQKLASG                                        207
```

```
SEQ ID NO: 31              moltype = DNA  length = 687
FEATURE                    Location/Qualifiers
sig_peptide                1..60
mat_peptide                61..684
source                     1..687
                           mol_type = genomic DNA
                           organism = Umbelopsis westeae
CDS                        1..684
SEQUENCE: 31
atgaagctca cctttgcctc tctaactctc ctatcttccg ctcttgttgg agtgtcagct   60
aaattgaaag gattggatgt tagcggttac caaccaaatg tagcttggtc aaccgtcaag  120
gccaatggtg catcctttgc ttatatcaaa gctactgaag cactaattta taaaaaccca  180
tcgtttgctc aacagtacaa cggagcatat aatgctggct tgattcgcgg ctcgtaccat  240
tttgctcagc cttcctcctc taccggtgct gctcaagcca actacttcct tgcgcacgga  300
ggtggctggt ctcctgatgg caagactctt cccggtgctt tggatatgga atataaccct  360
catggctcta catgctatgg cttatccaag gatgctatgg taaagtggat taaggatttc  420
agtaatacct accactctgc cactggccgt atcccgtca tttacactac cactagttgg  480
tggacgactt gcaccggtaa cagtgctgca tttggcgtta ccaaccctct ttggatcgct  540
agatactcct ctacgctggg aacttgccc aatggttggg cattctactc tttctggcaa  600
aatgccgaca gtggcatctt ccctggtgat caagatattt ggaacggtga tgctgctgct  660
ttgtctagga tggccaaagg agcctaa                                      687

SEQ ID NO: 32              moltype = AA  length = 228
FEATURE                    Location/Qualifiers
source                     1..228
                           mol_type = protein
                           organism = Umbelopsis westeae
SEQUENCE: 32
MKLTFASLTL LSSALVGVSA KLKGLDVSGY QPNVAWSTVK ANGASFAYIK ATEGTNYKNP   60
SFAQQYNGAY NAGLIRGSYH FAQPSSSTGA AQANYFLAHG GGWSPDGKTL PGALDMEYNP  120
HGSTCYGLSK DAMVKWIKDF SNTYHSATGR YPVIYTTTSW WTTCTGNSAA FGATNPLWIA  180
RYSSTAGNLP NGWAFYSFWQ NADSGIFPGD QDIWNGDAAA LSRMAKGA              228

SEQ ID NO: 33              moltype = AA  length = 208
FEATURE                    Location/Qualifiers
source                     1..208
                           mol_type = protein
                           organism = Umbelopsis westeae
SEQUENCE: 33
KLKGLDVSGY QPNVAWSTVK ANGASFAYIK ATEGTNYKNP SFAQQYNGAY NAGLIRGSYH   60
FAQPSSSTGA AQANYFLAHG GGWSPDGKTL PGALDMEYNP HGSTCYGLSK DAMVKWIKDF  120
SNTYHSATGR YPVIYTTTSW WTTCTGNSAA FGATNPLWIA RYSSTAGNLP NGWAFYSFWQ  180
NADSGIFPGD QDIWNGDAAA LSRMAKGA                                    208

SEQ ID NO: 34              moltype = DNA  length = 684
FEATURE                    Location/Qualifiers
sig_peptide                1..57
mat_peptide                58..681
source                     1..684
                           mol_type = genomic DNA
                           organism = Zygomycetes sp.
CDS                        1..681
SEQUENCE: 34
atgaaagcaa tcgtaacagc attagcatta tccttgttat gggcgggtgc ccatgcaact   60
ttgcccggct tagacgtcag cagctaccaa ggtaacgtca attggggaac agtggcgagt  120
caaggagcaa aatttgctta cgtcaaggct accgaggtg cgacctacac gaatccctat  180
tttgcgtccc aatacgacgg atcctacaac gcgggcctaa ttcgcggtgc ctatcacttt  240
gcccatcccg attcttcctc tggagctacc aagcaaaact atttccttgc tcatggtggc  300
ggctggtccg ctgacggaaa accttacct ggtgcgctag atattgagta caatcctaac  360
ggcgctgaat gctacggctt gtctcaattg gccatgatta gctggattca agacttcagc  420
aacacctatc actcccacac gggcagatat ccggtcattt acgactac ggactggtgg  480
accacctgca cgggtaacag cgcagccttt ggaaccaaca ccctctctg gattgctcgg  540
tattcgtctt cggtgggcac cctgcctgca ggttgggct acgagagctt ctggcagaag  600
gcatcttcgg gtacgttccc tggagaccaa gatatctgga tggcgatgc tgctggactc  660
tccagattcg ccaccggcaa atga                                         684

SEQ ID NO: 35              moltype = AA  length = 227
FEATURE                    Location/Qualifiers
source                     1..227
                           mol_type = protein
                           organism = Zygomycetes sp.
SEQUENCE: 35
MKAIVTALAL SLLWAGAHAT LPGLDVSSYQ GNVNWGTVAS QGAKFAYVKA TEGTTYTNPY   60
FASQYDGSYN AGLIRGAYHF AHPDSSSGAT QANYFLAHGG GWSADGKTLP GALDIEYNPN  120
GAECYGLSQL AMISWIQDFS NTYHSHTGRY PVIYTTTDWW TTCTGNSAAF GTNNPLWIAR  180
YSSSVGTLPA GWGYESFWQK ASSGTFPGDQ DIWNGDAAGL SRFATGK               227

SEQ ID NO: 36              moltype = AA  length = 208
FEATURE                    Location/Qualifiers
```

```
                              source           1..208
                                               mol_type = protein
                                               organism = Zygomycetes sp.
SEQUENCE: 36
TLPGLDVSSY QGNVNWGTVA SQGAKFAYVK ATEGTTYTNP YFASQYDGSY NAGLIRGAYH     60
FAHPDSSSGA TQANYFLAHG GGWSADGKTL PGALDIEYNP NGAECYGLSQ LAMISWIQDF    120
SNTYHSHTGR YPVIYTTTDW WTTCTGNSAA FGTNNPLWIA RYSSSVGTLP AGWGYESFWQ    180
KASSGTFPGD QDIWNGDAAG LSRFATGK                                      208

SEQ ID NO: 37                  moltype = DNA   length = 747
FEATURE                        Location/Qualifiers
sig_peptide                    1..51
mat_peptide                    52..744
source                         1..747
                               mol_type = genomic DNA
                               organism = Chaetomium cupreum
CDS                            1..141
CDS                            217..744
SEQUENCE: 37
atgaaatccg ccatcctcgc ctgtgtcggt tttgctgccg cggtgcaagc cacggtccag     60
ggctttgaca tctccggcta tcagccaaat gtcaactttg ccgccgccta tgccgcaggc    120
gcccgcttcg tcatcatcaa ggtgagcagc ccaagtcctc acagtcaccc actacctgag    180
gtacggtagt caaggcaatc agctaacctc tgccaggcca ccgagggcac cagctacatc    240
agccctcct tctcctcgca gtacacgggc gccaccaacg ccggcttcat ccgcggcggc    300
taccacttcg cccacccggg cgcgtcgtcc ggcaccaccc aggccgacta cttcatcgcg    360
cacggcggcg gctggactcc tgacggcatc acgctgccgg gcatgctgga cctcgagtcc    420
gagtcgagtg gcacgtgctg gggcctgtcg gcgagcgcca tggtggcctg gatcaaggac    480
ttcagcgacc actaccactc gcggatgggc gtctacccgc tgctgtacac gaacccgtcg    540
tggtgggagg agtgcacggg caactccaac gccttcgtcg acaccaaccc gctcgtgctg    600
gcgcactaca gcagcagcgt cggaacgatc cccggcgggt ggccgtatga cgatcctgg     660
cagaactcgg actcgtatgc gtacggcggt gactcggatg tgtttaatgg ggatctggct    720
gggctgcaga gacttgcgag gggttaa                                        747

SEQ ID NO: 38                  moltype = AA    length = 223
FEATURE                        Location/Qualifiers
source                         1..223
                               mol_type = protein
                               organism = Chaetomium cupreum
SEQUENCE: 38
MKSAILACVG FAAAVQATVQ GFDISGYQPN VNFAAAYAAG ARFVIIKATE GTSYISPSFS     60
SQYTGATNAG FIRGGYHFAH PGASSGTTQA DYFIAHGGGW TPDGITLPGM LDLESESSGT    120
CWGLSASAMV AWIKDFSDHY HSRMGVYPLL YTNPSWWEEC TGNSNAFVDT NPLVLAHYSS    180
SVGTIPGGWP YETIWQNSDS YAYGGDSDVF NGDLAGLQRL ARG                      223

SEQ ID NO: 39                  moltype = AA    length = 206
FEATURE                        Location/Qualifiers
source                         1..206
                               mol_type = protein
                               organism = Chaetomium cupreum
SEQUENCE: 39
TVQGFDISGY QPNVNFAAAY AAGARFVIIK ATEGTSYISP SFSSQYTGAT NAGFIRGGYH     60
FAHPGASSGT TQADYFIAHG GGWTPDGITL PGMLDLESES SGTCWGLSAS AMVAWIKDFS    120
DHYHSRMGVY PLLYTNPSWW EECTGNSNAF VDTNPLVLAH YSSSVGTIPG GWPYETIWQN    180
SDSYAYGGDS DVFNGDLAGL QRLARG                                         206

SEQ ID NO: 40                  moltype = DNA   length = 675
FEATURE                        Location/Qualifiers
sig_peptide                    1..51
mat_peptide                    52..672
source                         1..675
                               mol_type = genomic DNA
                               organism = Cordyceps cardinalis
CDS                            1..672
SEQUENCE: 40
atgcgcgcct ttattccagt ctttctcgcc ctagccggcg cagccaacgc cctcattcac     60
gccgtcgaca gctcctccga ggtgtccgtc gacgtctaca aaaaggccct cgccgagggc    120
ttcacacgcg ccatcttccg cggctaccag gaggcctgct cgcagggcgg ccgcgtcgac    180
cctaccttcc tgcccagcta caagaacgcc cagaaggcgg gctacaagga ctttgacgcc    240
tacttcttcc cgtgcaaccg gctccgcaac aagtgcaagc cctacgcgaa gcagattgac    300
gagctcgtcg acgccatcga gggcaatcag ctggccatcc gccgcatctg gatcgacatc    360
gagacggaca aggtctgcaa cgcgtttaac tggggcgccg agggcaacat ccagagggcc    420
aagaagctca tcgccgccgt gcgaggcaca aagcgcgact ttggcatcta cgtcggcg     480
acgcaatggg agaacatctt tggctccagg actgtggaac tggccaagga cgtgccgctg    540
tggtttgcca agttgacaa tgttgagacg ctggagctga gacgcctttg gcggctgg      600
acaaaggccg acgcgaagca gtatactgac aagtcggcta gcaagaaatt tgatctcaac    660
gttttctctg cctaa                                                     675

SEQ ID NO: 41                  moltype = AA    length = 224
FEATURE                        Location/Qualifiers
```

```
                        source              1..224
                                            mol_type = protein
                                            organism = Cordyceps cardinalis
SEQUENCE: 41
MRAFIPVFLA  LAGAANALIH  AVDSSSEVSV  DVYKKALAEG  FTRAIFRGYQ  EACSQGGRVD   60
PTFLPSYKNA  QKAGYKDFDA  YFFPCTGSGN  KCKPYAKQIG  ELVDAIEGNQ  LAIRRIWIDI  120
ETDKVCNAFN  WGAEGNIQEA  KKLIAAVRGT  KRDFGIYTSA  TQWENIFGSR  TVELAKDVPL  180
WFAKFDNVET  LELKTPFGGW  TKADAKQYTD  KSASKKFDLN  VFSA                    224

SEQ ID NO: 42           moltype = AA    length = 207
FEATURE                 Location/Qualifiers
source                  1..207
                        mol_type = protein
                        organism = Cordyceps cardinalis
SEQUENCE: 42
LIHAVDSSSE  VSVDVYKKAL  AEGFTRAIFR  GYQEACSQGG  RVDPTFLPSY  KNAQKAGYKD   60
FDAYFFPCTG  SGNKCKPYAK  QIGELVDAIE  GNQLAIRRIW  IDIETDKVCN  AFNWGAEGNI  120
QEAKKLIAAV  RGTKRDFGIY  TSATQWENIF  GSRTVELAKD  VPLWFAKFDN  VETLELKTPF  180
GGWTKADAKQ  YTDKSASKKF  DLNVFSA                                         207

SEQ ID NO: 43           moltype = DNA    length = 761
FEATURE                 Location/Qualifiers
sig_peptide             1..51
mat_peptide             52..758
source                  1..761
                        mol_type = genomic DNA
                        organism = Penicillium sp.
CDS                     1..165
CDS                     225..758
SEQUENCE: 43
atgaagacta cgggtgtctc tcttctgctt gcagcaggta ctgcctacgc atcgacaatc    60
cagcctcggg caagcggcgt ccagggattc gatatctcaa gctaccaagg caccgtcaac   120
tttgccggcg cctacggagc cggtgcacga ttcgtcatga tcaaggtgag cctcggcata   180
aacttgtgac cggcgagttg tttggactaa ctgaaacgcg ctaggcgacc gaaggcacca   240
cctacataga ttccaccttc tccagccact atgacggtac tcagccgcgc ggcttgatcc   300
gcggggctta ccacttcgcc cacccggact ccagctctgg cgctaccag gccgagtact   360
tcctggctca cggaggtggc tggaccaacg atggcatcac cttgccccgg catgctggaca  420
tcgaatacaa ccccctcggg tctacctgct acggtctgag tgcttccgcc atggtctcct   480
ggatcaagga cttcggagag acctacaaca gcaagactgg tcggtacccct atgatctaca   540
gcacggccga ttggtggagc acctgcacag gagacagcac atccttcagt agtgactacc   600
ctctggtgct tgctcagtat gctagctcca ttagcaccgt ccccgaggc tggccttacc    660
agagcttctg gcagaacgcg gactcataca gctatgcgg tgattctgat ctgtggaatg    720
gtagcgagga ctctctgaag acctttgcca agggttctta a                       761

SEQ ID NO: 44           moltype = AA    length = 233
FEATURE                 Location/Qualifiers
source                  1..233
                        mol_type = protein
                        organism = Penicillium sp.
SEQUENCE: 44
MKTTGVSLLL  AAGTAYASTI  QPRASGVQGF  DISSYQGTVN  FAGAYGAGAR  FVMIKATEGT   60
TYIDSTFSSH  YDGATSAGLI  RGAYHFAHPD  SSSGATQAEY  FLAHGGGWTN  DGITLPGMLD  120
IEYNPSGSTC  YGLSASAMVS  WIKDFGETYN  SKTGRYPMIY  STADWWSTCT  GDSTSFSSDY  180
PLVLAQYASS  ISTVPGGWPY  QSFWQNADSY  SYGGDSDLWN  GSEDSLKTFA  KGS         233

SEQ ID NO: 45           moltype = AA    length = 216
FEATURE                 Location/Qualifiers
source                  1..216
                        mol_type = protein
                        organism = Penicillium sp.
SEQUENCE: 45
STIQPRASGV  QGFDISSYQG  TVNFAGAYGA  GARFVMIKAT  EGTTYIDSTF  SSHYDGATSA   60
GLIRGAYHFA  HPDSSSGATQ  AEYFLAHGGG  WTNDGITLPG  MLDIEYNPSG  STCYGLSASA  120
MVSWIKDFGE  TYNSKTGRYP  MIYSTADWWS  TCTGDSTSFS  SDYPLVLAQY  ASSISTVPGG  180
WPYQSFWQNA  DSYSYGGDSD  LWNGSEDSLK  TFAKGS                              216

SEQ ID NO: 46           moltype = DNA    length = 781
FEATURE                 Location/Qualifiers
sig_peptide             1..54
mat_peptide             55..778
source                  1..781
                        mol_type = genomic DNA
                        organism = Aspergillus sp.
CDS                     1..174
CDS                     245..778
SEQUENCE: 46
atgaagttca ctaccattgc cactaccgcg gccatctctg ccttgccac agccttgcct    60
accaaactgc tgctcgata tagcactgtg caaggatttg atgtgtccaa ttaccaaccg   120
aacgtggact tctctgccgc aaagagtgct ggtgccgaat ttgtcattat caggtacat    180
```

-continued

```
ccagctttat cccttttcta cccagtaaca tggtacagat aagttaacaa gtcattcata   240
acaggccacc gaaggaaccg attacaaaga cacctatttc aactcccact acaccggcgc   300
caccaacgct ggcctcatcc gcggtggcta tcatttcgcg cgccctgata atcttccgg    360
taccgcgcaa gccgagtatt tcctcgcgca cggtggcggc tggagcaaag atggcagaac   420
cctccctggc atgctagaca tcgagtataa cccgtacggc gccacctgct acggtctcag   480
tcactccgcg atggtctcat gggtcaacga attcctcaac gaatatcaca gcaagacggg   540
tgtttatccg ttgctctata ccacggcaga ttggtggaat cagtgcacag ggaatgctca   600
tggatttggt aacaagagcc ctcttgttct ggcttcatat agcagtgagt cacctcggac   660
tgtgcctgga gattggcaga cgtggactat ctggcagaac gcggataagt ataagtatgg   720
gggtgattcc gatattttca atggcgatct cacgcagttg aagaagattg tcgagggta   780
g                                                                  781

SEQ ID NO: 47          moltype = AA  length = 236
FEATURE                Location/Qualifiers
source                 1..236
                       mol_type = protein
                       organism = Aspergillus sp.
SEQUENCE: 47
MKFTTIATTA AISGLATALP TKLAARYSTV QGFDVSNYQP NVDFSAAKSA GAEFVIIKAT    60
EGTDYKDTYF NSHYTGATNA GLIRGGYHFA RPDKSSGTAQ AEYFLAHGGG WSKDGRTLPG   120
MLDIEYNPYG ATCYGLSHSA MVSWVNEFLN EYHSKTGVYP LLYTTADWWN QCTGNAHGFG   180
NKSPLVLASY SSESPRTVPG DWQTWTIWQN ADKYKYGGDS DIFNGDLTQL KKIVEG       236

SEQ ID NO: 48          moltype = AA  length = 218
FEATURE                Location/Qualifiers
source                 1..218
                       mol_type = protein
                       organism = Aspergillus sp.
SEQUENCE: 48
LPTKLAARYS TVQGFDVSNY QPNVDFSAAK SAGAEFVIIK ATEGTDYKDT YFNSHYTGAT    60
NAGLIRGGYH FARPDKSSGT AQAEYFLAHG GGWSKDGRTL PGMLDIEYNP YGATCYGLSH   120
SAMVSWVNEF LNEYHSKTGV YPLLYTTADW WNQCTGNAHG FGNKSPLVLA SYSSESPRTV   180
PGDWQTWTIW QNADKYKYGG DSDIFNGDLT QLKKIVEG                           218

SEQ ID NO: 49          moltype = DNA  length = 747
FEATURE                Location/Qualifiers
sig_peptide            1..57
mat_peptide            58..744
source                 1..747
                       mol_type = genomic DNA
                       organism = Paecilomyces sp.
CDS                    1..135
CDS                    211..744
SEQUENCE: 49
atgaagtctg ttgctgtctt tgccggtctg gctccatgg tcagcattgc cacagccacc    60
gttgcaggct tcgatatttc caactaccaa ccttcggtca actttgcaaa agcatacgcg   120
gacggtgcac gcttcgtcat tatcaaggca agcaggccag accagcgcct gccagctcaa   180
acaagaccag attgctaact ctcttctcag gccaccgaag caccaccta catcgacccc    240
agtttcagct cccattacac cggggccact aacgccggtc tcatccgcgg aggctaccat   300
tttgccatc cgggatccag caccggcgcc gctcaggcca cctacttcct tgcccacggc    360
ggcggctggt ccaaggacgg catcacgctc cctggcatga tcgacctgga gtacaacccg   420
agtggcgcga cctgctatgg cctctcgacc agcgccatga tcagctggat ctccgacttt   480
gtcgagacgt accacagcaa gacgggcgtc taccccgctca tttatacctc gacaagctgg   540
tggaaccagt gtaccggcag cagcaccgcc tttgccagca gtgtcctct tgtggttgct   600
cgctacgcca gcagcgttgg cactcttcct gccggttggg gctaccagac catctggcag   660
aatagcgata gctcgccctg gggcggtgac aatgatattt caacggcag tctggaccag   720
ctcaagcgca ttgcgaatgc ttcttag                                       747

SEQ ID NO: 50          moltype = AA  length = 223
FEATURE                Location/Qualifiers
source                 1..223
                       mol_type = protein
                       organism = Paecilomyces sp.
SEQUENCE: 50
MKSVAVFAGL ASMVSIATAT VAGFDISNYQ PSVNFAKAYA DGARFATEGT TYIDPSFSSH    60
YTGATNAGLI RGGYHFAHPG SSTGAAQATY FLAHGGGWSK DGITLPGMID LEYNPSGATC   120
YGLSTSAMVS WISDFVETYH SKTGVYPLIY TSTSWWNQCT GSSTAFASKC PLVVARYASS   180
VGTLPAGWGY QTIWQNSDSS PWGGDNDIFN GSLDQLKRIA NAS                     223

SEQ ID NO: 51          moltype = AA  length = 204
FEATURE                Location/Qualifiers
source                 1..204
                       mol_type = protein
                       organism = Paecilomyces sp.
SEQUENCE: 51
TVAGFDISNY QPSVNFAKAY ADGARFATEG TTYIDPSFSS HYTGATNAGL IRGGYHFAHP    60
GSSTGAAQAT YFLAHGGGWS KDGITLPGMI DLEYNPSGAT CYGLSTSAMV SWISDFVETY   120
HSKTGVYPLI YTSTSWWNQC TGSSTAFASK CPLVVARYAS SVGTLPAGWG YQTIWQNSDS   180
SPWGGDNDIF NGSLDQLKRI ANAS                                          204
```

```
SEQ ID NO: 52               moltype = DNA  length = 669
FEATURE                     Location/Qualifiers
sig_peptide                 1..57
mat_peptide                 58..666
source                      1..669
                            mol_type = genomic DNA
                            organism = Paecilomyces sp.
CDS                         1..666
SEQUENCE: 52
atgaagctca cgagtgtgtt gaccctggtt ggctgtgccg tcacaggcac atctgccgcc   60
gtgcaaggac acgacgtcag ccattggcag ggtaacatca ctggggcgc ggtcaaggca   120
gccggcgtca agtttacata cattaaagca acagagtcaa ccaactacat cgaccccagc  180
ttcaacgcaa attatgtcgg cgccaccaat accggactga tacgcggcgc ataccacttt  240
gcccggccag gggattcatc aggtgccgcg caggcaaatt attttgtcag ccatggtggt  300
gggtggtccg cagacgggag aactttgcct ggcgctcttg atcttgaggc gggctgtagc  360
ggattgtcgc aatcagcaat gacggcctgg atccgggact tcagcaacac ctatcacgcg  420
cggactggtc ggttccccgt catttacaca actaccagtc ggtgaagac ttgcaccggc   480
aatgcgtccg gatttcagaa cgaccatccg ctttggattg cgcgatgggg cccttcacct  540
ggggagttgc cggcaggata tggctttcac accttttggc agtatgcgga caagggacct  600
cttccaggcg accaggacaa ctttaatggc gatgaggccg tcttgcaag gcttgctaga   660
ggttcgtaa                                                          669

SEQ ID NO: 53               moltype = AA  length = 222
FEATURE                     Location/Qualifiers
source                      1..222
                            mol_type = protein
                            organism = Paecilomyces sp.
SEQUENCE: 53
MKLTSVLTLV GCAVTGTSAA VQGHDVSHWQ GNINWGAVKA AGVKFTYIKA TESTNYIDPS  60
FNANYVGATN TGLIRGAYHF ARPGDSSGAA QANYFVSHGG GWSADGRTLP GALDLEAGCS  120
GLSQSAMTAW IRDFSNTYHA RTGRFPVIYT TTSWWKTCTG NASGFQNDHP LWIARWGPSP  180
GELPAGYGFH TFWQYADKGP LPGDQDNFNG DEAGLARLAR GS                     222

SEQ ID NO: 54               moltype = AA  length = 203
FEATURE                     Location/Qualifiers
source                      1..203
                            mol_type = protein
                            organism = Paecilomyces sp.
SEQUENCE: 54
AVQGHDVSHW QGNINWGAVK AAGVKFTYIK ATESTNYIDP SFNANYVGAT NTGLIRGAYH  60
FARPGDSSGA AQANYFVSHG GWSADGRTL PGALDLEAGC SGLSQSAMTA WIRDFSNTYH   120
ARTGRFPVIY TTTSWWKTCT GNASGFQNDH PLWIARWGPS PGELPAGYGF HTFWQYADKG  180
PLPGDQDNFN GDEAGLARLA RGS                                          203

SEQ ID NO: 55               moltype = DNA  length = 944
FEATURE                     Location/Qualifiers
sig_peptide                 1..60
mat_peptide                 61..941
source                      1..944
                            mol_type = genomic DNA
                            organism = Rhizomucor pusillus
CDS                         1..184
CDS                         241..242
CDS                         244..484
CDS                         555..688
CDS                         757..825
CDS                         885..941
SEQUENCE: 55
atgaagtttg cactcctagt atctgctatc gcaggccttg cagcaaccgc cgtccaagcc  60
tacgaaactg gcgttgatgt ctctgccttg acttccacct ccgctgagg ctgtgcaaag   120
aaactcggtt acgatcacgc tattgtccgc tgctacattg aggcatacgg aggcaaccct  180
gcaagtatca tgcatcagag aagacgacta ctacgttcta gcgtgctaac aatgtactag  240
ggtggtaaaa ttgacagcaa ctgcttccag aactacaaga acgccaaagc aggtggattc  300
accagcgttg acatttacat gttccctgc actggccgct ccacatgcaa gtcgcccgct   360
gctcaggtca aggaggtcgt tgactacgtt ggctccaaca agatgactgt ggacgtctc   420
tggctcgacg tcgaaatcga tccttctgct aacaactggc catccgccag tagcgctcgc  480
agcagtaaga aagaggacaa gaaaccaatt caggatgctc acaatgttgc taacatttt   540
tattacttgt taagccttga agtccttcaa gtctgctctt gactcgactg gctggaaata  600
cggtatctat tcttctgctt cccaatggtc gcagattacc ggatcctcct cctgggagct  660
tgattcctcg ttgccacttt ggtacgctgt aagtagctct cacgttattc cgtatattgt  720
gggagaacgt ggctgatctg aatttattac cacaagcact acgacgcttc tctcagcttc  780
agcgactttt cgccatttgg tggctggact aagcctacca tcaaggtaaa tattcaggtc  840
atccggtgct tgacgcatat gtactcaatt aaatcgccat ttagcaatat gctggctctg  900
taagcttctg ctccgctggc tgggacaaga actactatgc taa                    944

SEQ ID NO: 56               moltype = AA  length = 229
FEATURE                     Location/Qualifiers
source                      1..229
```

```
                        mol_type = protein
                        organism = Rhizomucor pusillus
SEQUENCE: 56
MKFALLVSAI  AGLAATAVQA  YETGVDVSAL  TSTSAWSCAK  KLGYDHAIVR  CYIEAYGGNP   60
ARGKIDSNCF  QNYKNAKAGG  FTSVDIYMFP  CTGRSTCKSP  AAQVKEVVDY  VGSNKMTVGR  120
LWLDVEIDPS  ANNWPSASSA  RSTLKSFKSA  LDSTGWKYGI  YSSASQWSQI  TGSSSWELDS  180
SLPLWYAHYD  ASLSFSDFSP  FGGWTKPTIK  QYAGSVSFCS  AGWDKNYYG              229

SEQ ID NO: 57           moltype = AA  length = 209
FEATURE                 Location/Qualifiers
source                  1..209
                        mol_type = protein
                        organism = Rhizomucor pusillus
SEQUENCE: 57
YETGVDVSAL  TSTSAWSCAK  KLGYDHAIVR  CYIEAYGGNP  ARGKIDSNCF  QNYKNAKAGG   60
FTSVDIYMFP  CTGRSTCKSP  AAQVKEVVDY  VGSNKMTVGR  LWLDVEIDPS  ANNWPSASSA  120
RSTLKSFKSA  LDSTGWKYGI  YSSASQWSQI  TGSSSWELDS  SLPLWYAHYD  ASLSFSDFSP  180
FGGWTKPTIK  QYAGSVSFCS  AGWDKNYYG                                      209

SEQ ID NO: 58           moltype = DNA  length = 887
FEATURE                 Location/Qualifiers
sig_peptide             1..51
mat_peptide             52..884
source                  1..887
                        mol_type = genomic DNA
                        organism = Pycnidiophora cf.
CDS                     1..144
CDS                     205..265
CDS                     358..781
CDS                     839..884
SEQUENCE: 58
atgaagtccg tactcgccct gctcgccgct ggcgcccaac ttgccagtgc ggccgtctcc   60
ggcatggata tctcccacta ccaagggaca aactacaact tgccggcgc atactcctct  120
ggtgctcgct ttgtcatcat caaggtacat gcccattcta gcttaaggat ttgaccccaa  180
tgttcggcct ttaacgcatc ctaggccacc gaaggaacca catatacgaa tcctcagttc  240
tccgctaact acattggtgc cacgagtaag tagatttccc catgaggtag ctggtcgtta  300
gtcttctcct ctcctaccac actgtccatg ctggggagac ccattaacac tgagtagatg  360
ctggttttat ccgcggcgcg taccatttcg cccgccctgc cgcctctact ggggccgtcc  420
aagcctccta cttcgtctcc catgcggtg ggtggtcatc ggatggcatc acactcccg  480
gcatgcttga catggaatat ggctctacct ccacttgcca cggcctttct gtctccgcca  540
tgaacacgtg gatcgcctcc ttcgtgaacc agtacaagag tttgacgggc gcataccca  600
tgatttacac cacagccgat tggtggaaga cttgcacagg agacagcacg gcttggaaca  660
ccaagtgccc tttggttatt gccaggtact ctagttctgt gcaggtagtt cctggaggtt  720
ggccgtatca taccatttgg caatattccg attcctatgc gtacggtggg gattcggata  780
cgtaagttcg acatgctcaa gcgaatggaa cggatggagt ggctaacggg atggacagat  840
tcaatggcga cttggctggc ttaaagaggc ttgcgaaggg cagctaa                 887

SEQ ID NO: 59           moltype = AA  length = 225
FEATURE                 Location/Qualifiers
source                  1..225
                        mol_type = protein
                        organism = Pycnidiophora cf.
SEQUENCE: 59
MKSVLALLAA  GAQLASAAVS  GMDISHYQGT  NYNFAGAYSS  GARFVIIKAT  EGTTYTDPQF   60
SANYIGATNA  GFIRGAYHFA  RPAASTGAVQ  ASYFVSHGGG  WSSDGITLPG  MLDMEYGSTS  120
TCHGLSVSAM  NTWIASFVNQ  YKSLTGAYPM  IYTTADWWKT  CTGDSTAWNT  KCPLVLARYS  180
SSVGTIPGGW  PYHTIWQYSD  SYAYGGDSDT  FNGDLAGLKR  LAKGS                   225

SEQ ID NO: 60           moltype = AA  length = 208
FEATURE                 Location/Qualifiers
source                  1..208
                        mol_type = protein
                        organism = Pycnidiophora cf.
SEQUENCE: 60
AVSGMDISHY  QGTNYNFAGA  YSSGARFVII  KATEGTTYTD  PQFSANYIGA  TNAGFIRGAY   60
HFARPAASTG  AVQASYFVSH  GGGWSSDGIT  LPGMLDMEYG  STSTCHGLSV  SAMNTWIASF  120
VNQYKSLTGA  YPMIYTTADW  WKTCTGDSTA  WNTKCPLVLA  RYSSSVGTIP  GGWPYHTIWQ  180
YSDSYAYGGD  SDTFNGDLAG  LKRLAKGS                                       208

SEQ ID NO: 61           moltype = DNA  length = 974
FEATURE                 Location/Qualifiers
sig_peptide             1..66
mat_peptide             67..971
source                  1..974
                        mol_type = genomic DNA
                        organism = Thermomucor indicae
CDS                     1..186
CDS                     250..493
CDS                     579..712
```

```
CDS                      777..851
CDS                      915..971
SEQUENCE: 61
atgaagtttt caatctttgc tattgctgct gctgctgctg ccgccgtggc caccttggtt    60
caaggctacc aaaccggtct ggatgtatct gccttgacct cgacatcgtc ctttagctgt   120
gcgaaaaacc ttggatatga ccatgtgatt gctcgatgct acatggaagc ctacggcaac   180
aacccggtaa aaccaacatc gaactcaaag gaagatggaa atgaaataac aaaaaagggt   240
tatacgcagg gtggcaaagt ggatcccaac tgttatagca attacaagaa cgccaaggca   300
gctggattca cgtcggtgga tatctacatg ttcccatga ccggccgatc cacctgcaag    360
tcgccagcga ctcaagtcca agaaatcgtg gattacgtcg gggcccacaa gatgattgtc   420
ggaactttgt ggttggatgt cgaggtcgat tcggctgcta ataactggcc gtccacgtcc   480
gaagcccggt ccagtaagtt cccccgtcca gagctgtcta tctatctatc tatcaattgt   540
atgaaccgtt cgtcataact cacggtgcgc atcgttagca ctccgagctt tcaagacggc   600
gttggataag tccggatgga aatggggcgt ttattccagc aagtcgcaat ggacgcgtat   660
caccggatca gcttcatggg ttttagaccc gtcggtgcct ttgtggtatt cggtaagttg   720
ttacataaca gctgcgattt ccgtgccatg atctttctta tctgtttcat acgtagcact   780
acgacgatac ccttagtttc agtgactatc catcgcacgc tttcggtggc tggtccaaac   840
caacaatcaa ggtacgttag catttttttc aaaataaaat agttctctgc cgtattaatc   900
ctctccatgc tcagcaatat acgggagatg cttccttttg ctctgccagt gggacaaga    960
actactatgg ttag                                                     974

SEQ ID NO: 62            moltype = AA  length = 232
FEATURE                  Location/Qualifiers
source                   1..232
                         mol_type = protein
                         organism = Thermomucor indicae
SEQUENCE: 62
MKFSIFAIAA AAAAAVATLV QGYQTGLDVS ALTSTSSFSC AKNLGYDHVI ARCYMEAYGN    60
NPGGKVDPNC YSNYKNAKAA GFTSVDIYMF PCTGRSTCKS PATQVQEIVD YVGAHKMIVG   120
TLWLDVEVDS AANNWPSTSE ARSTLRAFKT ALDKSGWKWG VYSSKSQWTR ITGSASWVLD   180
PSVPLWYSHY DDTLSFSDYP SHAFGGWSKP TIKQYTGDAS FCSASWDKNY YG           232

SEQ ID NO: 63            moltype = AA  length = 210
FEATURE                  Location/Qualifiers
source                   1..210
                         mol_type = protein
                         organism = Thermomucor indicae
SEQUENCE: 63
YQTGLDVSAL TSTSSFSCAK NLGYDHVIAR CYMEAYGNNP GGKVDPNCYS NYKNAKAAGF    60
TSVDIYMFPC TGRSTCKSPA TQVQEIVDYV GAHKMIVGTL WLDVEVDSAA NNWPSTSEAR   120
STLRAFKTAL DKSGWKWGVY SSKSQWTRIT GSASWVLDPS VPLWYSHYDD TLSFSDYPSH   180
AFGGWSKPTI KQYTGDASFC SASWDKNYYG                                    210

SEQ ID NO: 64            moltype = DNA  length = 675
FEATURE                  Location/Qualifiers
sig_peptide              1..51
mat_peptide              52..672
source                   1..675
                         mol_type = genomic DNA
                         organism = Isaria farinosa
CDS                      1..672
SEQUENCE: 64
atgcgcgcct ctacagccct ctttatcgcc tttgccggcg tggccactgc cctgacccac    60
gccgtcgaca gctcctccga ggtgagcgtc gacatttaca aaaaggcgct cggccagggc   120
ttcacgcgcg ccatcttccg cggctaccag gaggcgtgct cgctcggcgg ccgcgtcgac   180
ccgaccttg tgcccagcta caaaaacgcc gtcgcggccg gctacaagga ctttgacgcg    240
tacttcttcc cctgcaccgg cacgaccaac aagtgcaagc cgtacgcgac gcagctcgcc   300
gagctgctcg acaccatcag cagccagaag ctggcgatcc gccgcatctg gctcgacatt   360
gagacggacc aggtctgcag cccgttcgac tatggcgcg agggcaacat tgccgaggcc    420
aagaagctcg tcgccgcgtt tcgcgccgca aagcacgact ggggcatcta cacgtcgccg   480
acgcagtggg agactatctt tggctccaag acattcgtgc tggccaatga tgtgccgctc   540
tggtttgcca agtttgacaa tgtcgagacg ctggacctga gacgccgtt tggcggctgg    600
acaaaggccg acgcaaaaca gtacacggac cagtcggcta gcaagaagtt tgacttgaac   660
gtcttctctg cataa                                                    675

SEQ ID NO: 65            moltype = AA  length = 224
FEATURE                  Location/Qualifiers
source                   1..224
                         mol_type = protein
                         organism = Isaria farinosa
SEQUENCE: 65
MRASTALFIA FAGVATALTH AVDSSSEVSV DIYKKALGQG FTRAIFRGYQ EACSLGGRVD    60
PTFVPSYKNA VAAGYKDFDA YFFPCTGTTN KCKPYATQLA ELLDTISSQK LAIRRIWLDI   120
ETDQVCSPFD YGAQGNIAEA KKLVAAFRAA KHDWGIYTSP TQWETIFGSK TFVLANDVPL   180
WFAKFDNVET LDLKTPFGGW TKADAKQYTD QSASKKFDLN VFSA                    224

SEQ ID NO: 66            moltype = AA  length = 207
FEATURE                  Location/Qualifiers
source                   1..207
```

```
                        mol_type = protein
                        organism = Isaria farinosa
SEQUENCE: 66
LTHAVDSSSE VSVDIYKKAL GQGFTRAIFR GYQEACSLGG RVDPTFVPSY KNAVAAGYKD    60
FDAYFPPCTG TTNKCKPYAT QLAELLDTIS SQKLAIRRIW LDIETDQVCS PFDYGAQGNI   120
AEAKKLVAAF RAAKHDWGIY TSPTQWETIF GSKTFVLAND VPLWFAKFDN VETLDLKTPF   180
GGWTKADAKQ YTDQSASKKF DLNVFSA                                       207

SEQ ID NO: 67           moltype = DNA   length = 829
FEATURE                 Location/Qualifiers
sig_peptide             1..57
mat_peptide             58..826
source                  1..829
                        mol_type = genomic DNA
                        organism = Lecanicillium sp.
CDS                     1..147
CDS                     210..393
CDS                     480..826
SEQUENCE: 67
atgaagtctt ttggcctgtt cgcctcactc gcctctctgg ctggcatcgc cagcgcctcg    60
gtccagggtt ttgacatttc ccactaccag agctctgtca actttggcgc ggcctacgct   120
gacggcgctc gcttcgtcat tatcaaggtg cgatttgtc gcctgcgttc ttctcaaccc   180
tggctaccta ctcacaacct tatcattagg caaccgaggg aacgacgtac cgcgaccca   240
agttcagcga gcactacggc ggcgccacca aggccggctt catccgcggc ggctatcact   300
ttgcccagct gcctcatcc tctggcgccg cgcaggccaa cttttttcctc gctcacggcg   360
gcggctggag cggcgacggc atcaccctgc ccggtaacgc tcgcgcttat acacgcatgc   420
tttttcacacc ccagctcgac aaagaaccct catttctgat taaacttttt gtggcttagg   480
tatgctggat ctcgagtatg gcccgaacgg gaacacctgc tacggcctcg gcccggcgtc   540
catgcggagc tggatcagcg actttgtcga gacgtaccac gccaagacgg gccgctaccc   600
cctcatctac acgtcgacga gctggtggaa gacgtgcggc aacacgctgc ccctcttcgc   660
cgacaagtgc gcctggtcg tcgcgcgcta taacagccag gtcggcgagc tccctgccgg   720
ctggggcttc tacactttct ggcagttcaa cgatcactac aagcatggcg gcgactcgga   780
cgtgttcaac ggcgcctact ctcagcttca gaagattgcc actggttag                829

SEQ ID NO: 68           moltype = AA   length = 226
FEATURE                 Location/Qualifiers
source                  1..226
                        mol_type = protein
                        organism = Lecanicillium sp.
SEQUENCE: 68
MKSFGLFASL ASLAGIASAS VQGFDISHYQ SSVNFGAAYA DGARFVIIKA TEGTTYRDPK    60
FSEHYGGATK AGFIRGGYHF AQPASSSGAA QANFFLAHGG GWSGDGITLP GMLDLEYGPN   120
GNTCYGLGPA SMRSWISDFV ETYHAKTGRY PLIYTSTSWW KTCTGNTSLF ADKCPLVVAR   180
YNSQVGELPA GWGFYTFWQF NDHYKHGGDS DVFNGAYSQL QKIATG                  226

SEQ ID NO: 69           moltype = AA   length = 207
FEATURE                 Location/Qualifiers
source                  1..207
                        mol_type = protein
                        organism = Lecanicillium sp.
SEQUENCE: 69
SVQGFDISHY QSSVNFGAAY ADGARFVIIK ATEGTTYRDP KFSEHYGGAT KAGFIRGGYH    60
FAQPASSSGA AQANFFLAHG GGWSGDGITL PGMLDLEYGP NGNTCYGLGP ASMRSWISDF   120
VETYHAKTGR YPLIYTSTSW WKTCTGNTSL FADKCPLVVA RYNSQVGELP AGWGFYTFWQ   180
FNDHYKHGGD SDVFNGAYSQ LQKIATG                                       207

SEQ ID NO: 70           moltype = DNA   length = 742
FEATURE                 Location/Qualifiers
sig_peptide             1..51
mat_peptide             52..739
source                  1..742
                        mol_type = genomic DNA
                        organism = Zopfiella sp.
CDS                     1..141
CDS                     206..739
SEQUENCE: 70
atgaaatcca tcctcctctc agctgcttcc ctcatcgggg ccgcccaagc cgcggtccag    60
ggattcgacg tctcccattg gcagtccagc gtcaactttg ccgcgccta caactcgggg   120
gctcggtttg tgatcatcaa ggtctttttt tttccttcat tcattcacca ataactacct   180
actgacccgt gagatgtcat gacaggccac cgagagcaac aactacatcg acccaagtt   240
caacacgtac tatccggccg ccaccagcac cggtctgatc cggggcgggt accacttcgc   300
ccacccgggg gagaccacgg cgccgtgca ggcggactac ttcatcgcgc acggcggggg   360
ttggtccagc gacggcatca ctctccccggg aatgctcgac ctggagaacg caagcggcta   420
cccggctgc tggggcctgt cgcagagcgc catgctcgtc tggatcaagg cctttcagcga  480
ccggtacaag gcccgcaccg gcgtctaccc catgctctac accaaccgtt cctggtggac   540
cagctgcacc ggcaactcca acgccttcgt caacaccaac cccctcgtcc tgcccgcta   600
cgccagctcc cccggcacca tccccggcgg ctgcccctac cagaccatct ggcagaactc   660
ggactcgtat acctacggcg cgcgactcgga catctttaat ggggatctgg ctggtctcaa   720
gaggttggcc aagggttctt aa                                            742
```

```
SEQ ID NO: 71              moltype = AA   length = 225
FEATURE                    Location/Qualifiers
source                     1..225
                           mol_type = protein
                           organism = Zopfiella sp.
SEQUENCE: 71
MKSILLSAAS LIGAAQAAVQ GFDVSHWQSS VNFAAAYNSG ARFVIIKATE SNNYIDPKFN    60
TYYPAATSAG LIRGGYHFAH PGETTGAVQA DYFIAHGGGW SSDGITLPGM LDLENASGYP   120
ACWGLSQSAM VSWIKAFSDR YKARTGVYPM LYTNPSWWTS CTGNSNAFVN TNPLVLARYA   180
SSPGTIPGGW PYQTIWQNSD SYTYGGDSDI FNGDLAGLKR LAKGS                   225

SEQ ID NO: 72              moltype = AA   length = 208
FEATURE                    Location/Qualifiers
source                     1..208
                           mol_type = protein
                           organism = Zopfiella sp.
SEQUENCE: 72
AVQGFDVSHW QSSVNFAAAY NSGARFVIIK ATESNNYIDP KFNTYYPAAT SAGLIRGGYH    60
FAHPGETTGA VQADYFIAHG GGWSSDGITL PGMLDLENAS GYPACWGLSQ SAMVSWIKAF   120
SDRYKARTGV YPMLYTNPSW WTSCTGNSNA FVNTNPLVLA RYASSPGTIP GGWPYQTIWQ   180
NSDSYTYGGD SDIFNGDLAG LKRLAKGS                                      208

SEQ ID NO: 73              moltype = DNA   length = 767
FEATURE                    Location/Qualifiers
sig_peptide                1..54
mat_peptide                55..764
source                     1..767
                           mol_type = genomic DNA
                           organism = Malbranchea flava
CDS                        1..174
CDS                        234..764
SEQUENCE: 73
atgaagctgt ctctcctcct tattgttgct gcatcactgg ccgtggccag tgcaggcccc    60
aaggagttcg agtcacgcgc gtcgggcgtc cagggctttg acatctctgg ttggcagtcc   120
aacgtcaatt ttgcaggtgc atacaattct ggcgcacgct tcgtcatgat caaggtacat   180
ttgagtgaat tcgtttctcc tggtataata ccctgactaa tgtaaagatc aggctagcg    240
agggtaccac cttcaaggac cgtcaattca gcaatcatta cattggcgcc accaaggctg   300
gctttatccg tggcggctac cactttgcgt tgccagacgt cagcagcgcc actgcccaag   360
tgaaccattt cctggccagc ggtggtggct ggagcagaga cggcatcacg ctgccgggca   420
tgctggacat cgagagcaac ccgtatggcg cccagtgcta cggccttgac gctggtcgta   480
tggttgcctg gatccgggag tttgttacgc gtacaagcg cgcaactgga cggtatcctc    540
tgatctacac gtctcccagc tggtggcaga cttgcacggg caatagcaat gcctttatag   600
acaagtgccc gcttgtgttg gcacggtggg cgagtagccc tggcactccg cctggtgggt   660
ggccgttcca cagttttgg cagtacgccg attcctatca attcggtggt gacgcccagg    720
tattcaatgg cgatgaggct gggttgaaga gaatggcccc aggttaa                 767

SEQ ID NO: 74              moltype = AA   length = 235
FEATURE                    Location/Qualifiers
source                     1..235
                           mol_type = protein
                           organism = Malbranchea flava
SEQUENCE: 74
MKLSLLLIVA ASLAVASAGP KEFESRASGV QGFDISGWQS NVNFAGAYNS GARFVMIKAS    60
EGTTFKDRQF SNHYIGATKA GFIRGGYHFA LPDVSSATAQ VNHFLASGGG WSRDGITLPG   120
MLDIESNPYG AQCYGLDAGR MVAWIREFVD AYKRATGRYP LIYTSPSWWQ TCTGNSNAFI   180
DKCPLVLARW ASSPGTPPGG WPFHSFWQYA DSYQFGGDAQ VFNGDEAGLK RMALG        235

SEQ ID NO: 75              moltype = AA   length = 217
FEATURE                    Location/Qualifiers
source                     1..217
                           mol_type = protein
                           organism = Malbranchea flava
SEQUENCE: 75
GPKEFESRAS GVQGFDISGW QSNVNFAGAY NSGARFVMIK ASEGTTFKDR QFSNHYIGAT    60
KAGFIRGGYH FALPDVSSAT AQVNHFLASG GGWSRDGITL PGMLDIESNP YGAQCYGLDA   120
GRMVAWIREF VDAYKRATGR YPLIYTSPSW WQTCTGNSNA FIDKCPLVLA RWASSPGTPP   180
GGWPFHSFWQ YADSYQFGGD AQVFNGDEAG LKRMALG                            217

SEQ ID NO: 76              moltype = DNA   length = 935
FEATURE                    Location/Qualifiers
sig_peptide                1..60
mat_peptide                61..932
source                     1..935
                           mol_type = genomic DNA
                           organism = Hypholoma polytrichi
CDS                        1..396
CDS                        454..552
CDS                        620..703
```

```
CDS                           770..798
CDS                           857..932
SEQUENCE: 76
atggctaagc tcttgaaaca actcgtgctc cttcctttcc tcgcgctcgc ggcgcacgcg    60
ctcgtctacg gcgtggactc ctccagcctg gtccccgtcg cgacgtacca gaaggcgctc   120
ggcgagggct tcacgaaggc ggttatccgc gggtacgagg aggcgtgcgg cgtggggggc   180
gaggtcgacc ccaacttcgt cccgtcgtac aagaacgcgc gcgcggcggg gtacacggac   240
attgacatgt actggttccc gtgcaacggc tcgacgcaca gctgcaagtc gtatgcggcg   300
cagctcgccg cgatcgcggc cgcgttctct gcgaatgcga tgaagatcgg cacgatctgg   360
atcgacatcg agaaggacgc ggcgatctgc aacaacgtgg tggtccgtcc gtgttgtgcg   420
gcgcacggcg tgagtgacc gttttggcaca cagtgggact atggcacggc ggggaacctc   480
gcgcaggcga agcgctgat cgcggctgcg aaggcgtcgg gattcaattt tggcatctac   540
agtagccctg gggtatgtgt ggtgctgcat tagcctgcca atggatcttc actgaaaatt   600
tggattctcg tatacacagg agtggagcac aatttcgtc tcgacgagtg tcgtcgtcga   660
caactcggca ccgctctggt ttgctactta caacaacgtc caagtacgtc ctcacattaa   720
ttgactgcta tctgctgctt ttcgttgctt acctctcact tcgtggcaga cccttacttt   780
gggaacaccg ttcggcgggt aagtcatgcg cccaacgtca attctgattc tgtgattctc   840
aaattgtgcg ccttagctgg agtacggctg tgggccacca atatactgac gtctcggcgt   900
cggggttatt cgatctcaac gttttgtgcc actaa                             935

SEQ ID NO: 77             moltype = AA  length = 228
FEATURE                   Location/Qualifiers
source                    1..228
                          mol_type = protein
                          organism = Hypholoma polytrichi
SEQUENCE: 77
MAKLLKQLVL LPFLALAAHA LVYGVDSSSL VPVATYQKAL GEGFTKAVIR GYEEACGVGG    60
EVDPNFVPSY KNARAAGYTD IDMYWFPCNG STHSCKSYAA QLAAIAAAFS ANAMKIGTIW   120
IDIEKDAAIC NNWDYGTAGN LAQAKALIAA AKASGFNFGI YSSPGEWSTI FGSTSVVVDN   180
SAPLWFATYN NVQTLTLGTP FGGWSTAVGH QYTDVSASGL FDLNVFAH               228

SEQ ID NO: 78             moltype = DNA  length = 687
FEATURE                   Location/Qualifiers
sig_peptide               1..60
mat_peptide               61..684
source                    1..687
                          mol_type = other DNA
                          organism = Synthetic construct
CDS                       1..684
SEQUENCE: 78
atggcaaagc tcctcaagca gttggtgttg ctcccgttcc tcgcgttggc agcacacgca    60
ttggtctacg gagtcgattc gtcctcgttg gtccctgtgg cgacgtatca gaaggcattg   120
ggagaaggct tcacaaaggc cgtcattagg ggctacgaag aggcctgtgg agtcggagga   180
gaggtcgatc ccaacttcgt cccctcctac aaaaacgcac gagcggcagg atacacagac   240
atcgatatgt actggttccc ctgtaacggc tccactcatt cgtgtaaatc gtatgccgca   300
cagttggcag ccattgccgc agccttctcg gcgaacgcca tgaagatcgg tactatttgg   360
atcgacatcg aaaaagatgc agccatctgt aacaactgga attacggcac tgcaggtaac   420
ttggcccagg cgaaggcatt gattgccgca gcgaaggcat ccggtttcaa cttcggcatc   480
tactcgtcgc ctggagagtg gtcgaccatc ttcggctcga cctcggtcgt cgtcgacaac   540
tccgcaccgc tctggttcgc gacctataac aacgtccaga ccctcacgct cggcactcct   600
ttcggaggct ggtcgacagc cgtcggtcat cagtataccg atgtgtccgc ctccggactc   660
ttcgacctca acgtcttcgc ccactaa                                      687

SEQ ID NO: 79             moltype = AA  length = 228
FEATURE                   Location/Qualifiers
REGION                    1..228
                          note = Synthetic construct
source                    1..228
                          mol_type = protein
                          organism = Synthetic construct
SEQUENCE: 79
MAKLLKQLVL LPFLALAAHA LVYGVDSSSL VPVATYQKAL GEGFTKAVIR GYEEACGVGG    60
EVDPNFVPSY KNARAAGYTD IDMYWFPCNG STHSCKSYAA QLAAIAAAFS ANAMKIGTIW   120
IDIEKDAAIC NNWDYGTAGN LAQAKALIAA AKASGFNFGI YSSPGEWSTI FGSTSVVVDN   180
SAPLWFATYN NVQTLTLGTP FGGWSTAVGH QYTDVSASGL FDLNVFAH               228

SEQ ID NO: 80             moltype = AA  length = 208
FEATURE                   Location/Qualifiers
source                    1..208
                          mol_type = protein
                          organism = Hypholoma polytrichi
SEQUENCE: 80
LVYGVDSSSL VPVATYQKAL GEGFTKAVIR GYEEACGVGG EVDPNFVPSY KNARAAGYTD    60
IDMYWFPCNG STHSCKSYAA QLAAIAAAFS ANAMKIGTIW IDIEKDAAIC NNWDYGTAGN   120
LAQAKALIAA AKASGFNFGI YSSPGEWSTI FGSTSVVVDN SAPLWFATYN NVQTLTLGTP   180
FGGWSTAVGH QYTDVSASGL FDLNVFAH                                     208

SEQ ID NO: 81             moltype = DNA  length = 701
FEATURE                   Location/Qualifiers
```

```
sig_peptide              1..45
mat_peptide              46..698
source                   1..701
                         mol_type = genomic DNA
                         organism = Aspergillus deflectus
CDS                      1..135
CDS                      186..698
SEQUENCE: 81
atgaagcttc tttccgccct tgcgctccct ggtctggcct acgccgcagt ccaaggcttc    60
gacatttcgc actaccagtc gagtgtcgac tatgccggcg cctactcctc gggtgcccgc   120
ttcgtcatga tcaaggtacc ctcctagcct ctaccagcag aaacaaggga ctaagagaga   180
gaaaggccac cgaaggaacg acgtatacgg acccggcttt tagtactcac tatacggggt   240
ctacaaacgc tggcctgatc cgtggcggtt atcactttgc tcgccccggt tctagttctg   300
gtgccgccca agcagaatat tccttgccca atggcggtgg gtgagctggt gatggaatca   360
cccttcctgg tatgttggac cttgaggctg atgctctgg tctgtcggcc tcagccatgg    420
tctcctggat ccaggacttt ggcgagacct acaaggcaag cacgggacgg tatccaatga   480
tctatacca acaagctgg tggagttcct gtacaggcaa caatggtggc tttggcgatt     540
atcctctggt ccttgcgaga tgggcttcat cgccaggcga gcttccgaac ggctggtcgg   600
tgcactcttt ctggcaaaat gccgatactt atgagtatgg gggtgattcc gagatttgga   660
acggaagtca agaaaatctt gtcaagtttg cctctcagtg a                       701

SEQ ID NO: 82            moltype = AA  length = 216
FEATURE                  Location/Qualifiers
source                   1..216
                         mol_type = protein
                         organism = Aspergillus deflectus
SEQUENCE: 82
MKLLSALALP GLAYAAVQGF DISHYQSSVD YAGAYSSGAR FVMIKATEGT TYTDPAFSTH    60
YTGATNAGLI RGGYHFARPG SSSGAAQAEY FLAHGGGWTG DGITLPGMLD LEAGCSGLSA   120
SAMVSWIQDF GETYKASTGR YPMIYTTTSW WSSCTGNNGG FGDYPLVLAR WASSPGELPN   180
GWSVHSFWQN ADTYEYGGDS EIWNGSQENL VKFASQ                             216

SEQ ID NO: 83            moltype = AA  length = 201
FEATURE                  Location/Qualifiers
source                   1..201
                         mol_type = protein
                         organism = Aspergillus deflectus
SEQUENCE: 83
AVQGFDISHY QSSVDYAGAY SSGARFVMIK ATEGTTYTDP AFSTHYTGAT NAGLIRGGYH    60
FARPGSSSGA AQAEYFLAHG GGWTGDGITL PGMLDLEAGC SGLSASAMVS WIQDFGETYK   120
ASTGRYPMIY TTTSWWSSCT GNNGGFGDYP LVLARWASSP GELPNGWSVH SFWQNADTYE   180
YGGDSEIWNG SQENLVKFAS Q                                             201

SEQ ID NO: 84            moltype = DNA  length = 820
FEATURE                  Location/Qualifiers
sig_peptide              1..48
mat_peptide              49..817
source                   1..820
                         mol_type = genomic DNA
                         organism = Ascobolus stictoideus
CDS                      1..138
CDS                      230..675
CDS                      748..817
SEQUENCE: 84
atgaagtggc ttggtctcat caccctcctc gtcggaacag cctcggctgc agtccctggc    60
ttcgacatct cccactacca aagcaccgtc aatttcgccg atgccactac ctcaggagct   120
cgattcgtca tcatcaaggt aatattcctc ctcttacccc ttcctcctat cgacctcaag   180
ccattatcaa ttccatcatg atcgatcagt gctaaccttc tctctccagg ccaccgaagg   240
cacaacctac aaagacccaa aattctcctc ccactacacg gcgcaacca acgccggtct    300
aattcgcggc ggctaccatt tcgcccgtcc cgcctccagc accggcgccg tgcaagccca   360
atactttgtc agtaacggtg gtggttggtc cggcgatggc cttactctcc ccggcatgct   420
tgatcttgag ggagattgtg ccggattatc acaagccggt atggtatcat ggattacatc   480
attcgtcaac aagtacaagg ctttgactac aagtatccaa atgatttata ctaccaattc   540
ttggtggaat acttgtacgg ggaatagtca gcttttagt gcgaattgtc ccttggttat    600
tgcgaggtat aattcggttg ttggaactat tcctggaggc tggccttatt atactatttg   660
gcagtttaat gatgcgtaag ttactcccca tgagcctgtt tttggatgag ggggagtag    720
agtttggcta actaggtggc tttataggta ctccatggt ggtgattctg ataccttcaa    780
tggggcttac tcgcagcttg ttaagctcgc tactggttaa                         820

SEQ ID NO: 85            moltype = AA  length = 218
FEATURE                  Location/Qualifiers
source                   1..218
                         mol_type = protein
                         organism = Ascobolus stictoideus
SEQUENCE: 85
MKWLGLITLL VGTASAAVPG FDISHYQSTV NFADAYSSGA RFVIIKATEG TTYKDPKFSS    60
HYTGATNAGL IRGGYHFARP ASSTGAVQAQ YFVSNGGGWS GDGLTLPGML DLEGDCAGLS   120
QAGMVSWITS FVNKYKALTT RYPMIYTTNS WWNTCTGNSQ AFSANCPLVI ARYNSVVGTI   180
PGGWPYYTIW QFNDAYSYGG DSDTFNGAYS QLVKLATG                           218
```

```
SEQ ID NO: 86              moltype = AA  length = 202
FEATURE                    Location/Qualifiers
source                     1..202
                           mol_type = protein
                           organism = Ascobolus stictoideus
SEQUENCE: 86
AVPGFDISHY QSTVNFADAY SSGARFVIIK ATEGTTYKDP KFSSHYTGAT NAGLIRGGYH    60
FARPASSTGA VQAQYFVSNG GGWSGDGLTL PGMLDLEGDC AGLSQAGMVS WITSFVNKYK   120
ALTTRYPMIY TTNSWWNTCT GNSQAFSANC PLVIARYNSV VGTIPGGWPY YTIWQFNDAY   180
SYGGDSDTFN GAYSQLVKLA TG                                            202

SEQ ID NO: 87              moltype = DNA  length = 734
FEATURE                    Location/Qualifiers
sig_peptide                1..51
mat_peptide                52..731
source                     1..734
                           mol_type = genomic DNA
                           organism = Coniochaeta sp.
CDS                        1..141
CDS                        201..731
SEQUENCE: 87
atgaagtcca cattcatcac cgctctaggc ctagcaggcg tcgcgcaggc gactgtccag    60
ggcttcgaca tctcgcacta ccagcccacg gtcaactatg ccggtgctta taacgcaggt   120
gcacgcttcg tcatcatcaa ggtcagtcac ctcggttgaa ccttctgctt cacacatgtc   180
aaagattaac atcaagccag gccaccgagg aacaacttca caccgaccct tccttcagca   240
cccactacaa cggcgcaacc aaggccggtc tcatccgcgg cggctaccac ttcgcccacc   300
ccggcgtcac caccggcgcc gcggaggcca acttcttcct cgcccacggc ggcggctggt   360
cgggcgacgg catcaccctc cccggcatgc tcgacctcga gtccgagggc tccaacccgc   420
agtgctgggg cctgtccacc tccggcatgg tcgcgtggat caagtccttc agcgaccggt   480
accacaccgt caccgcccgg tatcccatgc tctacaccaa cccgtcctgg tggagcacct   540
gcaccggcaa cagcaacgct ttcgtcaaca ccaacccgct cgtcctggcg cggtatgctt   600
ccgcgcccgg caccatcccc ggcggctggc cgtatcagac catctggcag aacagcgact   660
cgtactctta tggcggtgat tcggacatct tcaacgggaa cttggctagc ttgcagaagt   720
tggctactgg ttag                                                     734

SEQ ID NO: 88              moltype = AA  length = 224
FEATURE                    Location/Qualifiers
source                     1..224
                           mol_type = protein
                           organism = Coniochaeta sp.
SEQUENCE: 88
MKSTFITALG LAGVAQATVQ GFDISHYQPT VNYAGAYNAG ARFVIIKATE GTTYTDPSFS    60
THYNGATKAG LIRGGYHFAH PGVTTGAAEA NFFLAHGGGW SGDGITLPGM LDLESEGSNP   120
QCWGLSTSGM VAWIKSFSDR YHTVTGRYPM LYTNPSWWST CTGNSNAFVN TNPLVLARYA   180
SAPGTIPGGW PYQTIWQNSD SYSYGGDSDI FNGNLASLQK LATG                    224

SEQ ID NO: 89              moltype = AA  length = 207
FEATURE                    Location/Qualifiers
source                     1..207
                           mol_type = protein
                           organism = Coniochaeta sp.
SEQUENCE: 89
TVQGFDISHY QPTVNYAGAY NAGARFVIIK ATEGTTYTDP SFSTHYNGAT KAGLIRGGYH    60
FAHPGVTTGA AEANFFLAHG GGWSGDGITL PGMLDLESEG SNPQCWGLST SGMVAWIKSF   120
SDRYHTVTGR YPMLYTNPSW WSTCTGNSNA FVNTNPLVLA RYASAPGTIP GGWPYQTIWQ   180
NSDSYSYGGD SDIFNGNLAS LQKLATG                                       207

SEQ ID NO: 90              moltype = DNA  length = 815
FEATURE                    Location/Qualifiers
sig_peptide                1..60
mat_peptide                61..812
source                     1..815
                           mol_type = genomic DNA
                           organism = Daldinia fissa
CDS                        1..150
CDS                        226..712
CDS                        784..812
SEQUENCE: 90
atgaagacct cattacaagt tgtctaggc ctcgctggcc tcgctagcct tgccctcgct    60
gctgtcccag gcttcgacat ttcccattat cagtcgagcg tagactttgg ggcagcatat   120
agttctggag cccgtttcgt tatcatcaaa gtgagtccta cctaggtacc tacctatatc   180
taccaaccaa atacgtcccc ctcgaaactt accatatgag accaggctac agagggcacc   240
acctaccagg acccccaaatt cagcagccac tacgccggtc taccaacgc ggcctcatc   300
cgcggcggct accacttcgc gcgccccgcg tcgtcctccg cgccgcccca agcaacgttc   360
ttcctcgcgc acggtggcgg gtggtcgggc gatgggatca cgctgccggg aatgctggac   420
ttagaaggtg attgtgcggg cttgtcgacc agcgccatgg tctcgtggat cagggacttt   480
agcgatacgt atcacggcaa gacggggcgg tatcccctgc tgtacacgaa tccgtcgtgg   540
tggtcgagtt gtacgggcgg gtcgagcgcg ttcgtgaata cgaatccgct cgtgcttgcg   600
```

```
cggtatgcta gtagcccggg ggcgttgccg gggggctggc cgtattatac catttggcag  660
tttaatgatg cgtataagta tgggggcgac tcgatacgt ttaatggcga tcgtgagtaa   720
cctagtttta cttgtctttc tctgttcctt tttttgtccc cttttgctaa cgtagtgttg  780
cagtcacgca gttgaagaaa ttggcttcgg ggtaa                              815

SEQ ID NO: 91              moltype = AA   length = 222
FEATURE                    Location/Qualifiers
source                     1..222
                           mol_type = protein
                           organism = Daldinia fissa
SEQUENCE: 91
MKTFITSCLG LAGLASLALA AVPGFDISHY QSSVDFGAAY SSGARFVIIK ATEGTTYQDP   60
KFSSHYAGAT NAGLIRGGYH FARPASSSGA AQATFFLAHG GGWSGDGITL PGMLDLEGDC  120
AGLSTSAMVS WIRDFSDTYH GKTGRYPLLY TNPSWWSSCT GGSSAFVNTN PLVLARYASS  180
PGALPGGWPY YTIWQFNDAY KYGGDSDTFN GDLTQLKKLA SG                     222

SEQ ID NO: 92              moltype = AA   length = 202
FEATURE                    Location/Qualifiers
source                     1..202
                           mol_type = protein
                           organism = Daldinia fissa
SEQUENCE: 92
AVPGFDISHY QSSVDFGAAY SSGARFVIIK ATEGTTYQDP KFSSHYAGAT NAGLIRGGYH   60
FARPASSSGA AQATFFLAHG GGWSGDGITL PGMLDLEGDC AGLSTSAMVS WIRDFSDTYH  120
GKTGRYPLLY TNPSWWSSCT GGSSAFVNTN PLVLARYASS PGALPGGWPY YTIWQFNDAY  180
KYGGDSDTFN GDLTQLKKLA SG                                            202

SEQ ID NO: 93              moltype = DNA   length = 732
FEATURE                    Location/Qualifiers
sig_peptide                1..51
mat_peptide                52..725
source                     1..732
                           mol_type = genomic DNA
                           organism = Delitschia sp.
CDS                        1..141
CDS                        217..729
SEQUENCE: 93
atgaaggcta ctctcgcttc cctcctcggt cttgccaacg gcgccctcgc ggctgtccag   60
ggcttcgaca tctcccacta ccagtcgagc gtcaacttcg ccggtgcgta tagcgccggt  120
gcccgtttcg tcatcatcaa ggtgagaccc gtcgacgcac atcagcccac gagaaagaaa  180
aaaccagtca ggagaactaa cccggcgcgt gcacaggcga cagagggcac gtcctacatc  240
gaccccaagt tcagctccca ctacatcggt gccacgaatg ccggcctgat ccgcggtggc  300
taccacttcg cccacctggg ctcgagctcc ggtgcggccc aggctaacta cttcctgcc   360
cacggcggtg gctggtccgg cgacggcatc accctccccg gcatgctcga cctcgagggc  420
gactgcgtgc tctcggccag cggcgccgtg gcctggatca aggacttcag cgacacctac  480
cactccaaga ccggtgtgta ccccctgctc tacaccaacc cctcgtggtg gtcgtcctgc  540
acgggcaact ccaacgcctt cgtcaacacc aaccccctgg tgctcgcccg ctacagctcc  600
agcgccggca cccctcccgg tggctggccc tactacacca tctggcagta caacgacgcc  660
tacgcgtacg gtggtgactc ggacgtgttc aacggcgaca tggctggcct cctccgcctt  720
gccaagggat aa                                                       732

SEQ ID NO: 94              moltype = AA   length = 218
FEATURE                    Location/Qualifiers
source                     1..218
                           mol_type = protein
                           organism = Delitschia sp.
SEQUENCE: 94
MKATLASLLG LANGALAAVQ GFDISHYQSS VNFAGAYSAG ARFVIIKATE GTSYIDPKFS   60
SHYIGATNAG LIRGGYHFAH LGSSSGAAQA NYFLAHGSGD GITLPGM LDLEGDCVLS     120
ASGAVAWIKD FSDTYHSKTG VYPLLYTNPS WWSSCTGNSN AFVNTNPLVL ARYSSSAGTP  180
PGGWPYYTIW QYNDAYAYGG DSDVFNGDMA GLLRLAKG                           218

SEQ ID NO: 95              moltype = AA   length = 201
FEATURE                    Location/Qualifiers
source                     1..201
                           mol_type = protein
                           organism = Rosellinia sp.
SEQUENCE: 95
AVQGFDISHY QSSVNFAGAY SAGARFVIIK ATEGTSYIDP KFSSHYIGAT NAGLIRGGYH   60
FAHLGSSSGA AQANYFLAHG GGWSGDGITL PGMLDLEGDC VLSASGAVAW IKDFSDTYHS  120
KTGVYPLLYT NPSWWSSCTG NSNAFVNTNP LVLARYSSSA GTPPGGWPYY TIWQYNDAYA  180
YGGDSDVFNG DMAGLLRLAK G                                            201

SEQ ID NO: 96              moltype = DNA   length = 784
FEATURE                    Location/Qualifiers
sig_peptide                1..48
mat_peptide                49..781
source                     1..784
                           mol_type = genomic DNA
```

```
                              organism = Ascobolus sp.
CDS                           1..138
CDS                           195..640
CDS                           712..781
SEQUENCE: 96
atgaagtggc tcggtctcgt caccctcctt gtcggcgcgg cgcaagctgc agtccctggt    60
ttcgacatct cccactggca gagcagtgtc aactttgcct ctgcctactc ctctggtgcc   120
cgtttcgtca tcatcaaggt agtccaacac ctccatccac cctagagtcc gagtattaac   180
caccttctct ccaggctacc gaaggcacga cctacaagga cccaaagttc tcctcccact   240
acactggcgc caccaaggcc ggtttcatcc gcggaggcta ccactttgcc cgccctgcgt   300
ccagcactgg cgccgcgcaa gcccaattct tcgccagtaa cggcggcggg tggtccggcg   360
atggcatcac gctccccggc atgttggatc ttgagggaga ctgtgctggt ctttctcagt   420
ccggcatggt gtcatggatt agctctttcg tcaacaagta caggtcgctc acaggcagat   480
acccaatgat ctacaccacc aactcgtggt gggttacctg cactggtaac agcaaagctt   540
tcagctcaaa ctgcccgttg gtcattgcta gatacaactc ggtggttgga actattccgg   600
gaggttggcc ttattatacc atttggcagt acaacgatgc gtaagttttc ctccgtgctg   660
ggtgtgtggg agacattggg aacattgact aactctggtt ttcctttta gctataagta   720
tggtggtgat tcggatactt tcaacggtgc ttactctcag ctcgtcaagc tcgccactgg   780
ttaa                                                                784

SEQ ID NO: 97                 moltype = AA  length = 218
FEATURE                       Location/Qualifiers
source                        1..218
                              mol_type = protein
                              organism = Ascobolus sp.
SEQUENCE: 97
MKWLGLVTLL VGAAQAAVPG FDISHWQSSV NFASAYSSGA RFVIIKATEG TTYKDPKFSS    60
HYTGATKAGF IRGGYHFARP ASSTGAAQAQ FFASNGGGWS GDGITLPGML DLEGDCAGLS   120
QSGMVSWISS FVNKYRSLTG RYPMIYTTNS WWVTCTGNSK AFSSNCPLVI ARYNSVVGTI   180
PGGWPYYTIW QYNDAYKYGG DSDTFNGAYS QLVKLATG                           218

SEQ ID NO: 98                 moltype = AA  length = 202
FEATURE                       Location/Qualifiers
source                        1..202
                              mol_type = protein
                              organism = Ascobolus sp.
SEQUENCE: 98
AVPGFDISHW QSSVNFASAY SSGARFVIIK ATEGTTYKDP KFSSHYTGAT KAGFIRGGYH    60
FARPASSTGA AQAQFFASNG GGWSGDGITL PGMLDLEGDC AGLSQSGMVS WISSFVNKYR   120
SLTGRYPMIY TTNSWWVTCT GNSKAFSSNC PLVIARYNSV VGTIPGGWPY YTIWQYNDAY   180
KYGGDSDTFN GAYSQLVKLA TG                                            202

SEQ ID NO: 99                 moltype = DNA  length = 956
FEATURE                       Location/Qualifiers
sig_peptide                   1..54
mat_peptide                   55..953
source                        1..956
                              mol_type = genomic DNA
                              organism = Curreya sp.
CDS                           1..214
CDS                           275..331
CDS                           385..450
CDS                           506..648
CDS                           700..821
CDS                           884..953
SEQUENCE: 99
atgaatctct ctggtcttct cgcaatcgcg tcctaccttg ctctttcggc agcaaccgtg    60
cctgggttcg acatttccca ctaccaaggc actgtgaact tcgctggtgc ttactcctca   120
ggggcgcgct ttgtgatcat caaagcaact gagggcacca cttatacgga cccaaacttc   180
tccaacaact atgttggtgc gacgaatgct aaatgtatgc aagccctcg gcataactcc   240
gatacctgcc tgctaacggt gcatgcacat ccagttattc gcggtgctta tcatttcgct   300
cgaccagatg gcggatcggg ctccacccaa ggttcgctat tctttggtca aacttacatt   360
ggagtcaccc taatgaagc tcagcacaat tctttcattc tcatggtggt gggtggtctg   420
gcgatggcat caccctgcct gggatgttgg gtaagtctgc tcaagctcat gggattttcc   480
cttgactaac gtcctgggta cgaagacatc gaatatggcc ctacatcgac atgctatggc   540
ctctccacgt ctgctatggt cacatggatt actgattttg tcaacgagta ccatgctttg   600
acaggtcgct accctctcat ctacaccacc aatgactggt ggaacactgt gagtatactg   660
taccgtcacc gtctccggag ctctttctca cagtaatagt gcaccggaaa cacaaacaag   720
tttagcacta cttgcccgct tgtcctcgca cggtacagca gctccgtggg gaccatccc   780
ggaggttggc cgttccagac aatctggcaa ttcaatgaca agtaagtgct tcaccttagt   840
tgtaacgaag aaattggact tcgctgatgc agttgtattg cagttacgct tatggtggcg   900
actctgatac atttaacgga gatctggcgg gattgaagaa gcttgcgacc ggataa       956

SEQ ID NO: 100                moltype = AA  length = 224
FEATURE                       Location/Qualifiers
source                        1..224
                              mol_type = protein
                              organism = Curreya sp.
SEQUENCE: 100
```

```
MNLSGLLAIA SYLALSAATV PGFDISHYQG TVNFAGAYSS GARFVIIKAT EGTTYTDPNF    60
SNNYVGATNA KFIRGAYHFA RPDGGSGSTQ AQFFHSHGGG WSGDGITLPG MLDIEYGPTS   120
TCYGLSTSAM VTWITDFVNE YHALTGRYPL IYTTNDWWNT CTGNTNKFST TCPLVLARYS   180
SSVGTIPGGW PFQTIWQFND NYAYGGDSDT FNGDLAGLKK LATG                   224

SEQ ID NO: 101           moltype = AA   length = 206
FEATURE                  Location/Qualifiers
source                   1..206
                         mol_type = protein
                         organism = Curreya sp.
SEQUENCE: 101
TVPGFDISHY QGTVNFAGAY SSGARFVIIK ATEGTTYTDP NFSNNYVGAT NAKFIRGAYH    60
FARPDGGSGS TQAQFFHSHG GGWSGDGITL PGMLDIEYGP TSTCYGLSTS AMVTWITDFV   120
NEYHALTGRY PLIYTTNDWW NTCTGNTNKF STTCPLVLAR YSSSVGTIPG GWPFQTIWQF   180
NDNYAYGGDS DTFNGDLAGL KKLATG                                       206

SEQ ID NO: 102           moltype = DNA   length = 814
FEATURE                  Location/Qualifiers
sig_peptide              1..48
mat_peptide              49..811
source                   1..814
                         mol_type = genomic DNA
                         organism = Coniothyrium sp
CDS                      1..231
CDS                      389..811
SEQUENCE: 102
atgaagtgtc tttcattcct tccattgttg gctgcaacag ctcatggcgc ggtccaaggc    60
ttcgacatct cccattatca agcatccgtc aatttcgctg cagcctactc gggcggccta   120
cgcttcgtat acatcaaagc tacagaaggc acgacatacc aggatccagc cttctcctcg   180
cattacagtg gcgccacgtc tgcagggttc atccgcggcg gctaccactt cgtaagctct   240
ccccatacac aattgccaat cgatgaagca tgagatgttc gagtccctgg agctcataaa   300
cagaatgcaa aatttacccc cgatcttttc cgcaacgttt tcatcctcat gcgaaagaca   360
accactaacc tgtaccgcac actcacaggc acgccccgcc tcctccaccg gcgcagccca   420
agcctcctac ttcgtcgcgc acggcggcgg gtggtcgaac gacggcataa cgctcccagg   480
gatgctcgac ctggaaggcg actgcgcggg cctctctacc gcctccatgg tatcctggat   540
cagcagcttc tccaaccagt accacagcct gacgggccgc tggcccgtca tctacacgac   600
gaacagctgg tggacgacgt gcacggggaa cagcgcggcg ttcaacgcga acagcccgct   660
gatgctggcg cggtggggaa gcacggcggg cacgatcccg gggggctggc cttattatac   720
gatttggcag tacaaggata gcaatacgta tgggggtgat agcgatgtgt tcaacggtga   780
tgcgacgcag ttgaagaaat tggcgacagg ttaa                              814

SEQ ID NO: 103           moltype = AA   length = 218
FEATURE                  Location/Qualifiers
source                   1..218
                         mol_type = protein
                         organism = Coniothyrium sp
SEQUENCE: 103
MKCLSFLPLL AATAHGAVQG FDISHYQASV NFAAAYSGGL RFVYIKATEG TTYQDPAFSS    60
HYSGATSAGF IRGGYHFARP ASSTGAAQAS YFVAHGGGWS NDGITLPGML DLEGDCAGLS   120
TASMVSWISS FSNQYHSLTG RWPVIYTTNS WWTTCTGNSA AFNANSPLML ARWGSTAGTI   180
PGGWPYYTIW QYKDSNTYGG DSDVFNGDAT QLKKLATG                          218

SEQ ID NO: 104           moltype = AA   length = 202
FEATURE                  Location/Qualifiers
source                   1..202
                         mol_type = protein
                         organism = Coniothyrium sp
SEQUENCE: 104
AVQGFDISHY QASVNFAAAY SGGLRFVYIK ATEGTTYQDP AFSSHYSGAT SAGFIRGGYH    60
FARPASSTGA AQASYFVAHG GGWSNDGITL PGMLDLEGDC AGLSTASMVS WISSFSNQYH   120
SLTGRWPVIY TTNSWWTTCT GNSAAFNANS PLMLARWGST AGTIPGGWPY YTIWQYKDSN   180
TYGGDSDVFN GDATQLKKLA TG                                           202

SEQ ID NO: 105           moltype = DNA   length = 802
FEATURE                  Location/Qualifiers
sig_peptide              1..51
mat_peptide              52..799
source                   1..802
                         mol_type = genomic DNA
                         organism = Hypoxylon sp.
CDS                      1..141
CDS                      210..696
CDS                      771..799
SEQUENCE: 105
atgaaagctt tcattactac ctgtctaagc ttgagcagcc ttgccctcgc tgctgtccct    60
ggctttgata tttctcacta ccagtcgaac gtagacttcg gggcagcata tagttccggg   120
gcacgattcg ttatcatcaa agtgagctta acctacctat atctataact caaatatatc   180
ccccgcgaaa ctcaccagat gaaaacagg ctacagaagg caccacttac caagaccca    240
gcttcagcac ccactacacc ggcgccacca aagccggcct catccgcggc agctaccact   300
```

```
tcgcgcgccc cggatcgtcc tccggcgctg cccaagcgac gtacttcctc gcgcacggcg    360
gcggtggtc  gggcgacggg atcacgctgc cggggatgct ggacctagaa ggcgattgcg    420
cgggcctgtc gaccaacgcc atggtcgcgt ggatcaggga ctttagcgat acgtaccacg    480
gcaggacggg acggtatccg ctgctgtaca cgaacccgtc gtggtggtcg ggttgcgcgg    540
gcgggtcggc cgcgttcgtc ggtacgaatc cgcttgtgct tgcgcggtat gctgggagcc    600
cgggggcgtt gccgggaggg tggccgtatt atacgatttg gcagtttgac gatgcgtata    660
agtatggggg cgattcggat acgtttaatg gcgatcgtga gtacctatcg ttgcttaatt    720
tttcttttct attattttct tgtcctttgg ctaacgtggt ggtgttgcag tcacgcagtt    780
aaagaaattg gcttctggct ag                                             802

SEQ ID NO: 106            moltype = AA  length = 219
FEATURE                   Location/Qualifiers
source                    1..219
                          mol_type = protein
                          organism = Hypoxylon sp.
SEQUENCE: 106
MKAFITTCLS LSSLALAAVP GFDISHYQSN VDFGAAYSSG ARFVIIKATE GTTYQDPSFS     60
THYTGATKAG LIRGSYHFAR PGSSSGAAQA TYFLAHGGGW SGDGITLPGM LDLEGDCAGL   120
STNAMVAWIR DFSDTYHGRT GRYPLLYTNP SWWSGCAGGS AAFVGTNPLV LARYAGSPGA   180
LPGGWPYYTI WQFDDAYKYG GDSDTFNGDL TQLKKLASG                          219

SEQ ID NO: 107            moltype = AA  length = 202
FEATURE                   Location/Qualifiers
source                    1..202
                          mol_type = protein
                          organism = Hypoxylon sp.
SEQUENCE: 107
AVPGFDISHY QSNVDFGAAY SSGARFVIIK ATEGTTYQDP SFSTHYTGAT KAGLIRGSYH     60
FARPGSSSGA AQATYFLAHG GGWSGDGITL PGMLDLEGDC AGLSTNAMVA WIRDFSDTYH   120
GRTGRYPLLY TNPSWWSGCA GGSAAFVGTN PLVLARYAGS PGALPGGWPY YTIWQFDDAY   180
KYGGDSDTFN GDLTQLKKLA SG                                            202

SEQ ID NO: 108            moltype = DNA  length = 837
FEATURE                   Location/Qualifiers
sig_peptide               1..51
mat_peptide               52..834
source                    1..837
                          mol_type = genomic DNA
                          organism = Xylariaceae sp.
CDS                       1..141
CDS                       199..685
CDS                       806..834
SEQUENCE: 108
atgaagctct tcattgccac gtgtttgggc ctgggtagca tcgccctcgc agctgtccca     60
ggattcgata tctcccacta tcaatcgagc gtggatttg cggcagctta cagtgctgga    120
gctcgcttcg ttattatcaa ggtagcacta accccaaaa ttgaagccat gaaaggaga     180
actaacaagt aatactaggc tacagagggt accacctaca ttgacccgag tttcagcagt   240
cactacaccg gtgccaccaa cgccgggctc atccgcggcg gctaccactt cgcacatccc   300
ggttcctctt cgggtgccac gcaggccaac tatttcctag cacatggcgg aggctggtca   360
ggagacggaa ttactctccc aggcatgttg gacttagagg gtgactgcgc aggcctctca   420
acaagcgcca tggtctcctg gatcaaagac ttcagcatg catatcacag caaaacgggt   480
cgctacccac tcctctacac aaacccgtcg tggtggtcca gttgcactgg tagctcaagt   540
gcttttgtca atacgaaccc tcttgtcctt gcacggtata gcagcagtgc tggaacacct   600
cctggtggct ggccgtacta cacgatttgg cagttcaatg atgcgtacaa gtatggtggc   660
gactcggata ctttcaatgg agaatgtaag tcaacctaac tcatttcctg cttcttttgtc   720
ttgatctgcg agtggcagat ccctaatggc agtgcaaact ttctcagtgc tgagcaataa   780
ctctggctaa tacacggtgt tgtagatgct tcattgcaaa agctggctac tggttaa       837

SEQ ID NO: 109            moltype = AA  length = 219
FEATURE                   Location/Qualifiers
source                    1..219
                          mol_type = protein
                          organism = Xylariaceae sp.
SEQUENCE: 109
MKLFIATCLG LGSIALAAVP GFDISHYQSS VDFAAAYSAG ARFVIIKATE GTTYIDPSFS     60
SHYTGATNAG LIRGGYHFAH PGSSSGATQA NYFLAHGGGW SGDGITLPGM LDLEGDCAGL   120
STSAMVSWIK DFSNAYHSKT GRYPLLYTNP SWWSSCTGSS SAFVNTNPLV LARYSSSAGT   180
PPGGWPYYTI WQFNDAYKYG GDSDTFNGEY ASLQKLATG                          219

SEQ ID NO: 110            moltype = AA  length = 202
FEATURE                   Location/Qualifiers
source                    1..202
                          mol_type = protein
                          organism = Xylariaceae sp.
SEQUENCE: 110
AVPGFDISHY QSSVDFAAAY SAGARFVIIK ATEGTTYIDP SFSSHYTGAT NAGLIRGGYH     60
FAHPGSSSGA TQANYFLAHG GGWSGDGITL PGMLDLEGDC AGLSTSAMVS WIKDFSNAYH   120
SKTGRYPLLY TNPSWWSSCT GSSSAFVNTN PLVLARYSSS AGTPPGGWPY YTIWQFNDAY   180
KYGGDSDTFN GEYASLQKLA TG                                            202
```

```
SEQ ID NO: 111           moltype = DNA  length = 835
FEATURE                  Location/Qualifiers
sig_peptide              1..51
mat_peptide              52..832
source                   1..835
                         mol_type = genomic DNA
                         organism = Hypoxylon sp.
CDS                      1..141
CDS                      201..687
CDS                      804..832
SEQUENCE: 111
atgaagttct tcgttgccac tttcttaggt ctaagcagcg ttgccctcgc agcagtgcca    60
ggattcgata tttctcacta ccaatcgagt gtggattttg cagcagccta caattccggg   120
gcgcgctttg ttattatcaa ggtaaccctg aatcctaaag agaaaagtcg ttcgaaatag   180
atttaacccg ttccgaatag gctactgagg caccacgta catcgaccca agtttcagta    240
gtcactatac cggtgctacc aaggctggat tcatccgcgg tggctatcat tttgcacatc   300
ccggttcttc gtcgggagcg cgcaagcca actatttcct agcacatggc ggtggctggt    360
cgggcgacgg aatcactttc ccaggcatgt tggatttaga gggtgactgc gcgggcctct   420
cgacaagtgc tatggtctct tggatcaagg acttcagcga tacatatcac agtaagacgg   480
gacgctaccc tctcctctac acaaaccctt cgtggtggtc gagctgcacc ggtgattcga   540
gtgcctttgt caatacgaac cccctcgtcc tcgcacgata tagcagcagc gctggaacgc   600
cgcccggcgg ctggccgtat tacacgatct ggcagtttaa cgacgcatac aaatatggtg   660
gtgactcgga tactttcaat ggaaactgta agtgaacttg cgatcgtttt ggccaccatc   720
gaaacctata aatgcgaggt cgtcgatggc agtgcaaact ctaccactc ttagcaacaa    780
tttcagctaa tatgatattt tagatgcttc gctgcaaaag ttagctactg gttag         835

SEQ ID NO: 112           moltype = AA  length = 219
FEATURE                  Location/Qualifiers
source                   1..219
                         mol_type = protein
                         organism = Hypoxylon sp.
SEQUENCE: 112
MKFFVATFLG LSSVALAAVP GFDISHYQSS VDFAAAYNSG ARFVIIKATE GTTYIDPSFS    60
SHYTGATKAG FIRGGYHFAH PGSSSGAAQA NYFLAHGGGW SGDGITFPGM LDLEGDCAGL   120
STSAMVSWIK DFSDTYHSKT GRYPLLYTNP SWWSSCTGDS SAFVNTNPLV LARYSSSAGT   180
PPGGWPYYTI WQFNDAYKYG GDSDTFNGNY ASLQKLATG                          219

SEQ ID NO: 113           moltype = AA  length = 202
FEATURE                  Location/Qualifiers
source                   1..202
                         mol_type = protein
                         organism = Hypoxylon sp.
SEQUENCE: 113
AVPGFDISHY QSSVDFAAAY NSGARFVIIK ATEGTTYIDP SFSSHYTGAT KAGFIRGGYH    60
FAHPGSSSGA AQANYFLAHG GGWSGDGITF PGMLDLEGDC AGLSTSAMVS WIKDFSDTYH   120
SKTGRYPLLY TNPSWWSSCT GDSSAFVNTN PLVLARYSSS AGTPPGGWPY YTIWQFNDAY   180
KYGGDSDTFN GNYASLQKLA TG                                            202

SEQ ID NO: 114           moltype = DNA  length = 748
FEATURE                  Location/Qualifiers
sig_peptide              1..54
mat_peptide              55..743
source                   1..748
                         mol_type = genomic DNA
                         organism = Yunnania penicillata
CDS                      1..144
CDS                      218..745
SEQUENCE: 114
atgaagtcca ttaccgccgc cgctcttctg ggcctcgccg ccactgtcca ggccgatgtc    60
gacggctttg acatctccca ctaccaggag actgtcgact atgccggtgc ctacggcgct   120
ggtgcccgct tcgtcatcat caaggtgagc acaccacatc accaaacagt ggatgtgtct   180
tatcgagaca agtgacagtg actaaccccg tccacaggcg actgagggca cgaactacat   240
cgactcctct ttcaacacgc actacgctgg tgccaccgac gcgggcctca tccgcggcgg   300
ctaccacttc gcgcacccgg gcgagacgac gggcgcggag caggccgact acttcatcgc   360
gcacggcgg aactggtcca acgacggcat cacgctgccg gcatgctgg acctcgaggg     420
cgagggcagc accacgtgct gggacctgag cgccgccgac atggtcgcct ggatcaaggc   480
cttcagcgac cggtaccagg aggtcacgag ccggtacccc ctgctctaca ccaacccgtc   540
gtggtggtcc gagtgcacgg gcaactcgga cgccttcgtg gacaccaacc cgctggtgct   600
tgcgcggtac gcgagctcgc ctggcgagat cccggcggc tggccggcgc agaccatctg    660
gcagaactcg gacagctact cgttcggtgg agactcggac atcttcaacg gcgacgaggc   720
cggcctgaag aagcttgcga gcggttaa                                      748

SEQ ID NO: 115           moltype = AA  length = 224
FEATURE                  Location/Qualifiers
source                   1..224
                         mol_type = protein
                         organism = Yunnania penicillata
SEQUENCE: 115
```

```
MKSITAAALL GLAATVQADV DGFDISHYQE TVDYAGAYGA GARFVIIKAT EGTNYIDSSF     60
NTHYAGATDA GLIRGGYHFA HPGETTGAEQ ADYFIAHGGN WSNDGITLPG MLDLEGEGST    120
TCWDLSAADM VAWIKAFSDR YQEVTSRYPL LYTNPSWWSE CTGNSDAFVD TNPLVLARYA    180
SSPGEIPGGW PAQTIWQNSD SYSFGGDSDI FNGDEAGLKK LASG                    224

SEQ ID NO: 116           moltype = AA   length = 206
FEATURE                  Location/Qualifiers
source                   1..206
                         mol_type = protein
                         organism = Yunnania penicillata
SEQUENCE: 116
DVDGFDISHY QETVDYAGAY GAGARFVIIK ATEGTNYIDS SFNTHYAGAT DAGLIRGGYH     60
FAHPGETTGA EQADYFIAHG GNWSNDGITL PGMLDLEGEG STTCWDLSAA DMVAWIKAFS    120
DRYQEVTSRY PLLYTNPSWW SECTGNSDAF VDTNPLVLAR YASSPGEIPG GWPAQTIWQN    180
SDSYSFGGDS DIFNGDEAGL KKLASG                                        206

SEQ ID NO: 117           moltype = DNA   length = 782
FEATURE                  Location/Qualifiers
sig_peptide              1..60
mat_peptide              61..779
source                   1..782
                         mol_type = genomic DNA
                         organism = Engyodontium album
CDS                      1..150
CDS                      200..383
CDS                      433..779
SEQUENCE: 117
atgaagtctt ttggtgttat tgctaccggt ttggccaccc ttgtgggtgt tgcctctgcc     60
agagtccaag gtttcgacat ctcccactat cagcccagcg tcgacttcaa tgcggcctat    120
gctgacggag ctcgctttgt gatcatcaag gtataacaaa ccataacttg gcttatgaac    180
accatctaat gtattgcagg caaccgaggg taccacctac aaagatccca agttcgcca    240
gcactacatc ggtgctacca acgcggatt catccgcggt ggctaccact ttgctcagcc    300
tgcttcctct tctggtgcag cgcaggcaga ctatttcctc aagaacggag gtggttggtc    360
tagcgatgga attactctcc caggtgagca aagtcacaa cgttcgaggg cagttcacta    420
atatcgtggc aggtatgctt gatatggagt acaaccccaa tggcagtgct tgctacggct    480
tttcccaggc ttccatgcgc aactggatca cgactttgt caacacctac cactcccgca    540
cgggtgtcta ccctctcctt tacaccacca ccagctggtg gaaaacctgc acgggtaaca    600
ctgccatgtt tgccgacaag tgccctctcg tcatcgctcg ctacaacagc gtagtcggag    660
agctccccgc tggttggtct ttctggacaa tttggcagta caacgaccac tacaagcatg    720
gtggtgactc agacgctttt aacggagact actctcagct tcagagaatc gccagaggct    780
aa                                                                  782

SEQ ID NO: 118           moltype = AA   length = 227
FEATURE                  Location/Qualifiers
source                   1..227
                         mol_type = protein
                         organism = Engyodontium album
SEQUENCE: 118
MKSFGVIATG LATLVGVASA RVQGFDISHY QPSVDFNAAY ADGARFVIIK ATEGTTYKDP     60
KFSQHYIGAT NAGFIRGGYH FAQPASSSGA AQADYFLKNG GWSSDGITL PGMLDMEYNP    120
NGSACYGLSQ ASMRNWINDF VNTYHSRTGV YPLLYTTTSW WKTCTGNTAM FADKCPLVIA    180
RYNSVVGELP AGWSFWTIWQ YNDHYKHGGD SDAFNGDYSQ LQRIARG                  227

SEQ ID NO: 119           moltype = AA   length = 207
FEATURE                  Location/Qualifiers
source                   1..207
                         mol_type = protein
                         organism = Engyodontium album
SEQUENCE: 119
RVQGFDISHY QPSVDFNAAY ADGARFVIIK ATEGTTYKDP KFSQHYIGAT NAGFIRGGYH     60
FAQPASSSGA AQADYFLKNG GWSSDGITL PGMLDMEYNP NGSACYGLSQ ASMRNWINDF    120
VNTYHSRTGV YPLLYTTTSW WKTCTGNTAM FADKCPLVIA RYNSVVGELP AGWSFWTIWQ    180
YNDHYKHGGD SDAFNGDYSQ LQRIARG                                       207

SEQ ID NO: 120           moltype = DNA   length = 741
FEATURE                  Location/Qualifiers
sig_peptide              1..57
mat_peptide              58..738
source                   1..741
                         mol_type = genomic DNA
                         organism = Metapochonia bulbillosa
CDS                      1..147
CDS                      205..738
SEQUENCE: 120
atgaagtctg ttactttcat cgccagtctc gctccattg tgagcgtagc caccgccacc      60
gttgctgggt tgacattc aaactaccaa cccaccgttg actttaaaaa ggcctacgca     120
gacggtgctc gcttcgtcat tatcaaagta agacaaatag cacagtgtac aaaagtgaaa    180
acaatactct aacaaaaacca ccaggccacc gaaggcacaa catacaccga tcccagcttc    240
agctcccact acactggcgc cacgcaggcc ggctccatcc ggggaggcta ccacttcgca    300
```

```
caccccggat caggcaccgg cgccgcccag gcgaattact tcctcgccca cggcggcggc    360
tggtccaagg atggcatcac gctcccgggc atgattgatc tcgagtacaa ccccagcggt    420
gctacgtgct acggtctctc ggccagcggc atggtcagct ggatctctga ctttgtcgag    480
acgtaccata gcaagactgg ggtttatcct cttatttaca cgtcgacgag ctggtggaac    540
cagtgtacgg gtagcagtac tgcctttggt aataagtgcc cgcttgtgct tgcgcggtat    600
gctagctctg ttggggcgtt gcctgctggt tggggatttc agactatttg gcagaatagc    660
gataagtcgc cttggggtgg tgacaatgat attttcaacg gtagccttga tcagcttaag    720
cgtattgcta acgcttcgta a                                              741

SEQ ID NO: 121           moltype = AA  length = 227
FEATURE                  Location/Qualifiers
source                   1..227
                         mol_type = protein
                         organism = Metapochonia bulbillosa
SEQUENCE: 121
MKSVTFIASL ASIVSVATAT VAGFDISNYQ PTVDFKKAYA DGARFVIIKA TEGTTYTDPS    60
FSSHYTGATQ AGLIRGGYHF AHPGSGTGAA QANYFLAHGG GWSKDGITLP GMIDLEYNPS    120
GATCYGLSAS GMVSWISDFV ETYHSKTGVY PLIYTSTSWW NQCTGSSTAF GNKCPLVVAR    180
YASSVGALPA GWGFQTIWQN SDKSPWGGDN DIFNGSLDQL KRIANAS                  227

SEQ ID NO: 122           moltype = AA  length = 208
FEATURE                  Location/Qualifiers
source                   1..208
                         mol_type = protein
                         organism = Metapochonia bulbillosa
SEQUENCE: 122
TVAGFDISNY QPTVDFKKAY ADGARFVIIK ATEGTTYTDP SFSSHYTGAT QAGLIRGGYH    60
FAHPGSGTGA AQANYFLAHG GGWSKDGITL PGMIDLEYNP SGATCYGLSA SGMVSWISDF    120
VETYHSKTGV YPLIYTSTSW WNQCTGSSTA FGNKCPLVVA RYASSVGALP AGWGFQTIWQ    180
NSDKSPWGGD NDIFNGSLDQ LKRIANAS                                       208

SEQ ID NO: 123           moltype = DNA  length = 756
FEATURE                  Location/Qualifiers
sig_peptide              1..54
mat_peptide              55..753
source                   1..756
                         mol_type = genomic DNA
                         organism = Hamigera paravellanea
CDS                      1..168
CDS                      223..753
SEQUENCE: 123
atgaaggctt cttccatcct ctccctgctg gcctccctgg ccctcaccag cgcagctcct    60
ctcgaggcgc gcgccggcag cgtgcaaggc ttcgacatct gcactacca agcgaaggtc    120
gacttcgccg ccgcatacccg cagcggtgct cgcttcgtca tcatcaaggt acttactcct    180
cgtgctcgtc ctcacagaca cagacactga ccacagaaca aggccaccga aggaaccacg    240
tacaccgacc cggccttctc ctcgcactac acctccgcca ccaacgccgg cttcatccgg    300
ggcggctacc acttcgcaca cccggactcc agctcgggcg cagcgcaagc cacctacttc    360
cttgcccacg gcggcggctg gtccggcgac ggcatcacgc tgcccggaat gctggacctc    420
gagtacaacc cctcggggc gacgtgctac gggctcagcg atgcggccat ggtcgcctgg    480
atccaggact tcgtggacac gtaccacgcc cgcacggggc gctacccgat gatctacacc    540
acggccgact ggtggaacac ctgcacgggc aacagcagca agttcagcca gacgtgccgg    600
ttggtgctgg cccggtacgc cagcagcgtc ggcaccgttc ccggcggctg ggggtatcag    660
accatctggc agaattcgga tagctatgcg tatggcgggg attcggatat ttttaacggg    720
gatgagacgc agttgaagaa gttggcgagt ggatga                              756

SEQ ID NO: 124           moltype = AA  length = 233
FEATURE                  Location/Qualifiers
source                   1..233
                         mol_type = protein
                         organism = Hamigera paravellanea
SEQUENCE: 124
MKASSILSLL ASLALTSAAP LEARAGSVQG FDISHYQAKV DFAAAYRSGA RFVIIKATEG    60
TTYTDPAFSS HYTSATNAGF IRGGYHFAHP DSSSGAAQAT YFLAHGGGWS GDGITLPGML    120
DLEYNPSGAT CYGLSDAAMV AWIQDFVDTY HARTGRYPMI YTTADWWNTC TGNSSKFSQT    180
CPLVLARYAS SVGTVPGGWG YQTIWQNSDS YAYGGDSDIF NGDETQLKKL ASG           233

SEQ ID NO: 125           moltype = AA  length = 215
FEATURE                  Location/Qualifiers
source                   1..215
                         mol_type = protein
                         organism = Hamigera paravellanea
SEQUENCE: 125
APLEARAGSV QGFDISHYQA KVDFAAAYRS GARFVIIKAT EGTTYTDPAF SSHYTSATNA    60
GFIRGGYHFA HPDSSSGAAQ ATYFLAHGGG WSGDGITLPG MLDLEYNPSG ATCYGLSDAA    120
MVAWIQDFVD TYHARTGRYP MIYTTADWWN TCTGNSSKFS QTCPLVLARY ASSVGTVPGG    180
WGYQTIWQNS DSYAYGGDSD IFNGDETQLK KLASG                               215

SEQ ID NO: 126           moltype = DNA  length = 774
FEATURE                  Location/Qualifiers
```

```
sig_peptide             1..60
mat_peptide             61..771
source                  1..774
                        mol_type = genomic DNA
                        organism = Metarhizium iadini
CDS                     1..180
CDS                     241..771
SEQUENCE: 126
atgaagactt caggcgccat ttcccttggc ctcgccgctc tcgtcagctc agcagccgcc    60
tcccccgtgg agctcgagca gcgcgccgcc agcgtcaagg gcttcgacat ctcgggatac   120
cagcccaacg ttgacttcaa caaggcctat gccgacggcg ctcgcttcgt catcatcaag   180
gtaagttcgc acctggacac atgtctgacc ttggcagcac agccgtctaa ccacgtcaag   240
gccaccgagg gaaccaccta catcgacaag accttctcca agcactacac gggcgcaacc   300
aaggccaagc tcatccgcgg cgcgtaccac ttcccgcacc cggggcagaa caaggcctcg   360
gccgaggctg acttcttcgt ccagcacggc ggcaactggt ccaaggacgc catcaccctg   420
cccggcatgg tcgatctaga gtccgaaaag ggccacccc cgtgctgggg gttgtcgcat   480
tccgcaatgg tcgcttggat cagcgagttt gtcgccgctt accacaagaa aacgaccgga   540
tatcccatgc tgtacaccaa cccgtcgtgg tggtccgctt gcaccggcaa cagcaaggcc   600
ttcaaggata cctgccctct ggtcctggcc agatacgcca gctcgccccgg cgccattcct   660
ggtggctggc ctgctcagac catctggcaa aacagcgata gagcccgtg gggtggtgac   720
tctgacatgt tcaacggcga cttggcccag ttgaagaagc ttgctaccgg ttag         774

SEQ ID NO: 127          moltype = AA   length = 237
FEATURE                 Location/Qualifiers
source                  1..237
                        mol_type = protein
                        organism = Metarhizium iadini
SEQUENCE: 127
MKTSGAISLG LAALVSSAAA SPVELEQRAA SVKGFDISGY QPNVDFNKAY ADGARFVIIK    60
ATEGTTYIDK TFSKHYTGAT KAKLIRGAYH FAHPGQNKAS AEADFFVQHG GNWSKDAITL   120
PGMVDLESEK GHPPCWGLSH SAMVAWISEF VAAYHKKTTR YPMLYTNPSW WSACTGNSKA   180
FKDTCPLVLA RYASSPGAIP GGWPAQTIWQ NSDKSPWGGD SDMFNGDLAQ LKKLATG     237

SEQ ID NO: 128          moltype = AA   length = 217
FEATURE                 Location/Qualifiers
source                  1..217
                        mol_type = protein
                        organism = Metarhizium iadini
SEQUENCE: 128
SPVELEQRAA SVKGFDISGY QPNVDFNKAY ADGARFVIIK ATEGTTYIDK TFSKHYTGAT    60
KAKLIRGAYH FAHPGQNKAS AEADFFVQHG GNWSKDAITL PGMVDLESEK GHPPCWGLSH   120
SAMVAWISEF VAAYHKKTTR YPMLYTNPSW WSACTGNSKA FKDTCPLVLA RYASSPGAIP   180
GGWPAQTIWQ NSDKSPWGGD SDMFNGDLAQ LKKLATG                            217

SEQ ID NO: 129          moltype = DNA   length = 747
FEATURE                 Location/Qualifiers
sig_peptide             1..48
mat_peptide             49..746
source                  1..747
                        mol_type = genomic DNA
                        organism = Thermoascus aurantiacus
CDS                     1..159
CDS                     214..744
SEQUENCE: 129
atgaagatcg ctcctctcct cctcgccggc ctcgccgcgg ccgccccccga gctcgacaag    60
cgcgcccgcg gcgtccaggg ctttgatatc tcgcactacc agcccaacgt cgacttcaag   120
ggcgcgtaca acagcggcgc ccgcttcgtc atcatcaagg tatgcctctc tctctctctc   180
tatcttcttc gcacctctac tgatgcaggc caggccaccg agggcacgac gtacaaggac   240
ccggccttct ccaagcacta catcggcgcc accgaggccg gcctcatccg cggcggatac   300
cacttcgccc accggacaa gagcagcggc gccgcgcagg ccaacttctt cctcgcccac   360
ggcggcggct ggtccggcga cggcatcacg ctgcccggca tggtcgacct cgagtacaac   420
ccctcgggcg acgcctgcta cggcctgtcc gactcgcaga tggtcctg gatccgggac   480
tttgtcaaca cctaccacgc gcacacggga cgctacccca tgatctacac cacggccgac   540
tggtggaaga ggtgcaccgg cgacagccac gccttctcga caacctgccc gctcgtcctg   600
gcgcggtaca acagctcacc gggcacggtg cccggcggct ggccctacca caccatctgg   660
cagaactcgg acaagtaccg cttcggcggc gactcggaca tcttcaacgg cgacctggcg   720
gggctgaaga ggctggccaa gggctga                                        747

SEQ ID NO: 130          moltype = AA   length = 230
FEATURE                 Location/Qualifiers
source                  1..230
                        mol_type = protein
                        organism = Thermoascus aurantiacus
SEQUENCE: 130
MKIAPLLLAG LAAAAPELDK RARGVQGFDI SHYQPNVDFK GAYNSGARFV IIKATEGTTY    60
KDPAFSKHYI GATEAGLIRG GYHFAHPDKS SGAAQANFFL AHGGGWSGDG ITLPGMVDLE   120
YNPSGDACYG LSDSQMVSWI RDFVNTYHAH TGRYPMIYTT ADWWKRCTGD SHAFSTTCPL   180
VLARYNSSPG TVPGGWPYHT IWQNSDKYRF GGDSDIFNGD LAGLKRLAKG              230
```

```
SEQ ID NO: 131           moltype = AA  length = 214
FEATURE                  Location/Qualifiers
source                   1..214
                         mol_type = protein
                         organism = Thermoascus aurantiacus
SEQUENCE: 131
ELDKRARGVQ GFDISHYQPN VDFKGAYNSG ARFVIIKATE GTTYKDPAFS KHYIGATEAG    60
LIRGGYHFAH PDKSSGAAQA NFFLAHGGGW SGDGITLPGM VDLEYNPSGD ACYGLSDSQM   120
VSWIRDFVNT YHAHTGRYPM IYTTADWWKR CTGDSHAFST TCPLVLARYN SSPGTVPGGW   180
PYHTIWQNSD KYRFGGDSDI FNGDLAGLKR LAKG                              214

SEQ ID NO: 132           moltype = DNA  length = 753
FEATURE                  Location/Qualifiers
sig_peptide              1..54
mat_peptide              55..750
source                   1..753
                         mol_type = genomic DNA
                         organism = Clonostachys rossmaniae
CDS                      1..144
CDS                      217..750
SEQUENCE: 132
atgaagagtt ctctgtacct tgcttttgtt gcacttgcga cggtggccgt agcagcagtg    60
ccaggatttg atatatccgg gtggcagaaa tccactgact tgctaagtc atacgcaaac   120
ggagatcgtt ttgtgtacat caaggtaaaa cccaagtcat attttcact ggaacattcc   180
ccgtttagtt caactgagca ggctaacacc ttgtaggcta cagagggtac aacctttaag   240
aatcctcttt tctcgaagca gtataccggt gctacaaatg cccgtctcat tcgtggtgca   300
tatcactttg cccagccggc atcttcatcc ggggcctcac aggctcgttt ctttgttgca   360
aatggcggag gttggtccaa cgatggcatc accttgcctg gtgcggtgga tatggagtac   420
aaccccagtg gcgccacatg ctacgggctg tccaaaaccg ccatggtgaa ctggatcgag   480
gactttgtgt caacataccc ggctttgacc gggcgctggc ctgtcgttta taccacgctt   540
gactggtgga cccaatgcac tggcaacagc gccaagtttg gggatcggtg cccgctgtgt   600
gtggcacgat atgcaagtgc tgtcggccaa atcccgcag gttggagctt tcacactata   660
tggcaatata acgcgaaata ccctgaaggt ggagactctg atatattcaa tggcgacgag   720
actcgcctta aagctttagc ttccggggcc tga                               753

SEQ ID NO: 133           moltype = AA  length = 226
FEATURE                  Location/Qualifiers
source                   1..226
                         mol_type = protein
                         organism = Clonostachys rossmaniae
SEQUENCE: 133
MKSSLYLAFV ALATVAVAAV PGFDISGWQK STDFAKSYAN GDRFVYIKAT EGTTFKNPLF    60
SKQYTGATNA RLIRGAYHFA QPASSSGASQ ARFFVANGGG WSNDGITLPG AVDMEYNPSG   120
ATCYGLSKTA MVNWIEDFVS TYQALTGRWP VVYTTLDWWT QCTGNSAKFG DRCPLWVARY   180
ASAVGQIPAG WSFHTIWQYN AKYPEGGDSD IFNGDETRLK ALASGA                 226

SEQ ID NO: 134           moltype = AA  length = 208
FEATURE                  Location/Qualifiers
source                   1..208
                         mol_type = protein
                         organism = Clonostachys rossmaniae
SEQUENCE: 134
AVPGFDISGW QKSTDFAKSY ANGDRFVYIK ATEGTTFKNP LFSKQYTGAT NARLIRGAYH    60
FAQPASSSGA SQARFFVANG GGWSNDGITL PGAVDMEYNP SGATCYGLSK TAMVNWIEDF   120
VSTYQALTGR WPVVYTTLDW WTQCTGNSAK FGDRCPLWVA RYASAVGQIP AGWSFHTIWQ   180
YNAKYPEGGD SDIFNGDETR LKALASGA                                     208

SEQ ID NO: 135           moltype = DNA  length = 669
FEATURE                  Location/Qualifiers
sig_peptide              1..57
mat_peptide              58..666
source                   1..669
                         mol_type = genomic DNA
                         organism = Simplicillium obclavatum
CDS                      1..666
SEQUENCE: 135
atgaagcttg ccaccgtgct aaacgttctt gcacttgctg tttctagcgt tatcggcgca    60
ccgaaaggga ttgacgtcag ccattggcag ggatccatca actggggtgc agtgaaggcg   120
aacggtatcg aatgggcata catcaaagcc acagaatcca cgaactacaa agacccaaac   180
ttcaatgcaa actacgttgg tgctaccaat gcggggctca tccgcggcgc ataccatttt   240
gctagacccg gcgattcttc aggtgcggcc aggcaaatt attttgctag caacggcggc   300
ggttggtcag cagacggcat aactctgcct ggtgccgttg atctcgaagc aggatgttct   360
ggactgtccc agtccgcaat gactgcttgg ataaaggact tcagcaacac ctatcacgcg   420
cgcaccgggc ggtacccagc tatttacacc accacgctt ggtggaaaca atgcactggc   480
aatgcatctc gtttccaaaa caataacccg ctatggattc tcgctgggc ttcttccgta   540
ggagagttgc ctgcgggtta cagctatcac acatttggc aatatgcgga ccacggaccg   600
aacccaggcg accaggacgt tttcaatggt gattctgctg gcctcaagag gatggccaag   660
ggtagttag                                                          669
```

```
SEQ ID NO: 136          moltype = AA  length = 222
FEATURE                 Location/Qualifiers
source                  1..222
                        mol_type = protein
                        organism = Simplicillium obclavatum
SEQUENCE: 136
MKLATVLNVL ALAVSSVIGA PKGIDVSHWQ GSINWGAVKA NGIEWAYIKA TESTNYKDPN    60
FNANYVGATN AGLIRGAYHF ARPGDSSGAA QANYFASNGG GWSADGITLP GAVDLEAGCS   120
GLSQSAMTAW IKDFSNTYHA RTGRYPAIYT TTSWWKQCTG NASGFQNNNP LWIARWASSV   180
GELPAGYSYH TFWQYADHGP NPGDQDVFNG DSAGLKRMAK GS                     222

SEQ ID NO: 137          moltype = AA  length = 203
FEATURE                 Location/Qualifiers
source                  1..203
                        mol_type = protein
                        organism = Simplicillium obclavatum
SEQUENCE: 137
APKGIDVSHW QGSINWGAVK ANGIEWAYIK ATESTNYKDP NFNANYVGAT NAGLIRGAYH    60
FARPGDSSGA AQANYFASNG GGWSADGITL PGAVDLEAGC SGLSQSAMTA WIKDFSNTYH   120
ARTGRYPAIY TTTSWWKQCT GNASGFQNNN PLWIARWASS VGELPAGYSY HTFWQYADHG   180
PNPGDQDVFN GDSAGLKRMA KGS                                          203

SEQ ID NO: 138          moltype = DNA  length = 771
FEATURE                 Location/Qualifiers
sig_peptide             1..51
mat_peptide             52..768
source                  1..771
                        mol_type = genomic DNA
                        organism = Aspergillus inflatus
CDS                     1..165
CDS                     235..768
SEQUENCE: 138
atgaagttct ctgccattgc tctcctggct tctgcctctg ccgtggccgc ggcccctctt    60
gaggtcgtg ccaacactgt ccaggggttc gacatctcca gcttccagcc caatgttgac   120
tttgccgctg cctacaaggc cggtgccgt tttgtcatga tgaaggtcgg tcccattgaa   180
ttcatcgacg cagatataga tcaaccgaaa tcactggtac tgactgcgcg ctaggccacc   240
caaaacacca actacgttga caagaccttt aacgcacact acgagggtgc caccaaggct   300
ggcctcatcc gtggtggtta ccatttcgcc attcccaacg gccctccgg cgctgcccag   360
gccgactact tcctcgccca tggtggcggg tggtccgacg atggcaagac cctgcccggc   420
atgatcgatc ttgagtacaa ccccctatggc caaacctgct acgacctctc cgccgcgaag   480
atggtcgact ggatcaagga cttctccaac acctaccacg ccaagaccaa gcgctacccc   540
atgatctaca ctaccgccaa ctggtggaag gagtgcactg gcgacagcaa agagttcagc   600
cagaccaaac ccttggttct ggctcgctac tccagctccg cgggcactgt ccctggtggc   660
tggcccgcct actcttttct gcagaacgcc gacaagtaca agttcggagg agactctgac   720
atctggaacg gcagtgagga caacctcaag aagtttgcca aggtgcttta a            771

SEQ ID NO: 139          moltype = AA  length = 233
FEATURE                 Location/Qualifiers
source                  1..233
                        mol_type = protein
                        organism = Aspergillus inflatus
SEQUENCE: 139
MKFSAIALLA SASAVAAAPL EARANTVQGF DISSFQPNVD FAAAYKAGAR FVMMKATQNT    60
NYVDKTFNAH YEGATKAGLI RGGYHFAIPN GPSGAAQAEY FLAHGGGWSD DGKTLPGMID   120
LEYNPYGQTC YDLSAAKMVD WIKDFSNTYH AKTKRYPMIY TTANWWKECT GDSKEFSQTN   180
PLVLARYSSS AGTVPGGWPA YSFWQNADKY KFGGDSDIWN GSEDNLKKFA KGA          233

SEQ ID NO: 140          moltype = AA  length = 216
FEATURE                 Location/Qualifiers
source                  1..216
                        mol_type = protein
                        organism = Aspergillus inflatus
SEQUENCE: 140
APLEARANTV QGFDISSFQP NVDFAAAYKA GARFVMMKAT QNTNYVDKTF NAHYEGATKA    60
GLIRGGYHFA IPNGPSGAAQ AEYFLAHGGG WSDDGKTLPG MIDLEYNPYG QTCYDLSAAK   120
MVDWIKDFSN TYHAKTKRYP MIYTTANWWK ECTGDSKEFS QTNPLVLARY SSSAGTVPGG   180
WPAYSFWQNA DKYKFGGDSD IWNGSEDNLK KFAKGA                            216

SEQ ID NO: 141          moltype = DNA  length = 738
FEATURE                 Location/Qualifiers
sig_peptide             1..63
mat_peptide             64..735
source                  1..738
                        mol_type = genomic DNA
                        organism = Paracremonium inflatum
CDS                     1..153
CDS                     205..735
SEQUENCE: 141
atgaaaactt tcggctattt gggccttggc atggtgtccc ttgcgatcac ctcggtgtct    60
```

```
gcaaaggtgt tgggttttga tattagtcat taccaggcca ctgttgactt caacgctgct    120
aaagacgcgg gagcccgatt tgtgatcatc aaggtagact acctaccaa ccagatggcg    180
acgttcccga gttaataaga ccaggccaca gagggaacaa cctacaaaga cccagcgttc    240
agcaaacatt atacggggc cacaaaggca ggcctgatcc gaggcggcta tcacttcgct    300
cagccagctt cctcgtctgg cgctgctcag gcgactttct tcctcgcaca cggcggcggt    360
tggtcgtctg atggcataac attgccggc atgctggatt tagagtacaa ccccagtggc    420
tcgacttgct acgggctgtc acaaagcagc atggttcagt ggatttccga cttcatcgac    480
acataccact ccaaaacagg gcgatatccg ttgatatata catctaccag ctggtggaaa    540
acttgcacgg gaaactcaag caagtttgca gcgaactgcc cgtcgtcgt tgctcgctac    600
tcgagttctg tcggagagct ccctgctggc tggacgattt acacgatctg gcaaaattcg    660
gatagctata aatacggggg tgattcggat atcttcaatg gagacgagtc gcaactccag    720
aaacttgcca agggttaa                                                  738

SEQ ID NO: 142         moltype = AA  length = 228
FEATURE                Location/Qualifiers
source                 1..228
                       mol_type = protein
                       organism = Paracremonium inflatum
SEQUENCE: 142
MKTFGYLGLG MVSLAITSVS AKVLGFDISH YQATVDFNAA KDAGARFVII KATEGTTYKD    60
PAFSKHYTGA TKAGLIRGGY HFAQPASSSG AAQATFFLAH GGGWSSDGIT LPGMLDLEYN   120
PSGSTCYGLS QSSMVQWISD FIDTYHSKTG RYPLIYTSTS WWKTCTGNSS KFAANCPLVV   180
ARYSSSVGEL PAGWTYYTIW QNSDSYKYGG DSDIFNGDES QLQKLAKG                228

SEQ ID NO: 143         moltype = AA  length = 207
FEATURE                Location/Qualifiers
source                 1..207
                       mol_type = protein
                       organism = Paracremonium inflatum
SEQUENCE: 143
KVLGFDISHY QATVDFNAAK DAGARFVIIK ATEGTTYKDP AFSKHYTGAT KAGLIRGGYH    60
FAQPASSSGA AQATFFLAHG GGWSSDGITL PGMLDLEYNP SGSTCYGLSQ SSMVQWISDF   120
IDTYHSKTGR YPLIYTSTSW WKTCTGNSSK FAANCPLVVA RYSSSVGELP AGWTYYTIWQ   180
NSDSYKYGGD SDIFNGDESQ LQKLAKG                                       207

SEQ ID NO: 144         moltype = DNA  length = 872
FEATURE                Location/Qualifiers
sig_peptide            1..51
mat_peptide            52..869
source                 1..872
                       mol_type = genomic DNA
                       organism = Westerdykella sp.
CDS                    1..144
CDS                    199..259
CDS                    342..765
CDS                    824..869
SEQUENCE: 144
atgaagtctg tactcgccct cctcgccgct ggcgcccagt ttgccagcgc tgccgtctcc    60
ggcatggaca tctctcatta ccaaggcacg aactacaact tcgccggcgc atactcgtct   120
ggtgctcgtt tcgtcatcat caaggtacat attcgtcaac gcataggacc caaagtccag   180
ccattgaacc catcttaggc aaccgaaggg accacctaca cggatcccca attttctgct   240
aactatattg cggccaccag tacgtaatac ctctatgtgc cgtcgacttt ctgtgcccca   300
atcacgctgc atgttcacgg acatcaacta cacctagca gatgcgggct tcatcagggg   360
gggctaccat ttcgcccgcc ctgcggactc taccggcgcc gcccaagcca aatacttcgt   420
ctcccacggc ggtggctggt cttccgatgg tatcactctc cccggaatgc tcgacctcga   480
gtacggctca tcgtccgcat gccacgggct ttccgtatcg gccatgaaca catggatcgc   540
ctcgttcatc aaccagtata ggagcttgac gggcgcgtat cccatgatct acactacggc   600
ggattggtgg aagacgtgca ccggagatag ccaggcttgg aacaccaagt gccctctggt   660
attggcccgg tactccagct ctgttggac gatcccaggc ggctggcctt atcagactat   720
ctggcagttc aacgattcgt ataagtatgg cggggattcg gacacgctgag ttctcccaaa   780
ttgcggagtc gccaattgat gaatgtgctg acggaacgga tagattcaat ggtgacttgg   840
ctggcttgaa gaggctcgcc aaaggcagct ga                                  872

SEQ ID NO: 145         moltype = AA  length = 225
FEATURE                Location/Qualifiers
source                 1..225
                       mol_type = protein
                       organism = Westerdykella sp.
SEQUENCE: 145
MKSVLALLAA GAQFASAAVS GMDISHYQGT NYNFAGAYSS GARFVIIKAT EGTTYTDPQF    60
SANYIAATNA GFIRGGYHFA RPADSTGAAQ AKYFVSHGGG WSSDGITLPG MLDLEYGSSS   120
ACHGLSVSAM NTWIASFINQ YRSLTGAYPM IYTTADWWKT CTGDSQAWNT KCPLVLARYS   180
SSVGTIPGGW PYQTIWQFND SYKYGGDSDT FNGDLAGLKR LAKGS                   225

SEQ ID NO: 146         moltype = AA  length = 208
FEATURE                Location/Qualifiers
source                 1..208
                       mol_type = protein
                       organism = Westerdykella sp.
```

```
SEQUENCE: 146
AVSGMDISHY QGTNYNFAGA YSSGARFVII KATEGTTYTD PQFSANYIAA TNAGFIRGGY    60
HFARPADSTG AAQAKYFVSH GGGWSSDGIT LPGMLDLEYG SSSACHGLSV SAMNTWIASF    120
INQYRSLTGA YPMIYTTADW WKTCTGDSQA WNTKCPLVLA RYSSSVGTIP GGWPYQTIWQ    180
FNDSYKYGGD SDTFNGDLAG LKRLAKGS                                       208

SEQ ID NO: 147          moltype = DNA   length = 909
FEATURE                 Location/Qualifiers
sig_peptide             1..60
mat_peptide             61..906
source                  1..909
                        mol_type = genomic DNA
                        organism = Stropharia semiglobata
CDS                     1..393
CDS                     447..545
CDS                     608..691
CDS                     744..772
CDS                     831..906
SEQUENCE: 147
atgttctctt tcgtcaaagc gctcatcctc ctcccggccc ttgtgacttc cgcgtatgcc    60
ctcgtatatg gcgtagactc gtctaccttg gtttctactg caacctacaa gaaagccaag    120
agcgaggget tcactaaggc tatcatccgc gggtatcagg aagcatgtgg cagtggtgga    180
cgcgtcgacc ccaacttcgt cgcgacctac aagaatgcac gggccgcggg tatcaccgat    240
atcgacatgt actggttccc atgcaacggg tccggtaact catgcaagtc gtacgctaag    300
cagctctccg agatcgcgaa tgtcttcagt gcgaatagca tgaaaattgg acaaatttgg    360
attgattttg agaaggattc tggttgcaac aacgtgagtt tcatggacat tatgtccttc    420
ataataaaat gacggatttt atcaagtgga actacggcac cacgggtaat ctcaaccatg    480
caaaggcact catctccgcg attaaagcga ctgggtttaa attcggtatc tacagctcac    540
ctggcgtaag gcttttttacc tttcgtatcc gcttcatcaa gttaacttag tccgcgactc    600
gttttaggaa tggggtaccc tgtttgggtc caccgggtga gtactcgata gctcggcccc    660
cctttggttc gctacgtgga acaatgtaaa ggtatgtgac cccgcctact acagaaataa    720
catctctcaa agtttaacca tagactctta ccttgggaac gcatttcggg ggtaagtgc     780
aatatatata catcgaaata tgggatattg aatactgacg ttgcttgaag gtggactaaa    840
gccgttggcc accagtatac agatgtgtcc gcctctggcc aattcgacct caatgtcttt    900
gcaaattaa                                                            909

SEQ ID NO: 148          moltype = AA   length = 227
FEATURE                 Location/Qualifiers
source                  1..227
                        mol_type = protein
                        organism = Stropharia semiglobata
SEQUENCE: 148
MFSFVKALIL LPALVTSAYA LVYGVDSSTL VSTATYKKAK SEGFTKAIIR GYQEACGSGG    60
RVDPNFVATY KNARAAGITD IDMYWFPCNG SGNSCKSYAK QLSEIANVFS ANSMKIGTIW    120
IDFEKDSGCN NWNYGTTGNL NHAKALISAI KATGFKFGIY SSPGEWGTLF GSTGVVLDSS    180
APLWFATWNN VKTLTLGTHF GGWTKAVGHQ YTDVSASGQF DLNVFAN                  227

SEQ ID NO: 149          moltype = AA   length = 207
FEATURE                 Location/Qualifiers
source                  1..207
                        mol_type = protein
                        organism = Stropharia semiglobata
SEQUENCE: 149
LVYGVDSSTL VSTATYKKAK SEGFTKAIIR GYQEACGSGG RVDPNFVATY KNARAAGITD    60
IDMYWFPCNG SGNSCKSYAK QLSEIANVFS ANSMKIGTIW IDFEKDSGCN NWNYGTTGNL    120
NHAKALISAI KATGFKFGIY SSPGEWGTLF GSTGVVLDSS APLWFATWNN VKTLTLGTHF    180
GGWTKAVGHQ YTDVSASGQF DLNVFAN                                        207

SEQ ID NO: 150          moltype = DNA   length = 909
FEATURE                 Location/Qualifiers
sig_peptide             1..60
mat_peptide             61..906
source                  1..909
                        mol_type = genomic DNA
                        organism = Stropharia semiglobata
CDS                     1..393
CDS                     447..545
CDS                     608..691
CDS                     743..771
CDS                     831..906
SEQUENCE: 150
atgttcccctt tcgtcaaaac gctcatacta ctcccgaccc ttgtgacctc cgcatacgcc    60
cttgtatatg gcgtagactc gtccactcta gtctctactg caacgtacag taaagccaag    120
agcgaggget tcactaaggc tatcatccgc gggtatcagg aagcatgtgg cagtggtgga    180
cgcgtcgacc ccaacttcgt cgcgacctac aagaatgcac gggccgcggg catcaccgat    240
atcgacatgt actggttccc atgcaacggg tccggtaact cttgcaagtc gtacgctaca    300
cagctctccg agatcgcgaa tgcgttcagt gcgaatagca tgaaaattgg acaaatttgg    360
attgattttg agaaggattc tacctgcaac aacgtgagtt tcatggacat tatgtccttc    420
ataataaatt gacggatttt atcaagtgga actacggcac cacgggtaat ctcaaccatg    480
```

```
caaaggcact catctccgcg attaaagcga ctgggtttaa attcggtatc tacagctcac   540
ctggcgtaag gcttttracc tttcgtatcc gcttcatcaa gttaacttag tccgcgactc   600
gttttaggaa tggggtaccc tgtttgggtc caccggggta gtactcgata gctcggcccc   660
cctttggttc gctacgtgga acaatgtaaa ggtatgtgac cccgcctact acagaaataa   720
catctctcaa agtttaacat agactcttac cttgggaacg catttcgggg ggtaagtgca   780
atatatatac atcgaaagat ggaataatta aatactgaaa tcgcttaaag gtggactaca   840
gccgcgggtc accagtacac agacgtgtct tcctctggcc aattcgacct caatgtgttt   900
gcaaattaa                                                           909

SEQ ID NO: 151         moltype = AA   length = 227
FEATURE                Location/Qualifiers
source                 1..227
                       mol_type = protein
                       organism = Stropharia semiglobata
SEQUENCE: 151
MFPFVKTLIL LPTLVTSAYA LVYGVDSSTL VSTATYSKAK SEGFTKAIIR GYQEACGSGG    60
RVDPNFVATY KNARAAGITD IDMYWFPCNG SGNSCKSYAT QLSEIANAFS ANSMKIGTIW   120
IDFEKDSTCN NWNYGTTGNL NHAKALISAI KATGFKFGIY SSPGEWGTLF GSTGVVLDSS   180
APLWFATWNN VKTLTLGTHF GGWTTAAGHQ YTDVSSSGQF DLNVFAN                 227

SEQ ID NO: 152         moltype = AA   length = 207
FEATURE                Location/Qualifiers
source                 1..207
                       mol_type = protein
                       organism = Stropharia semiglobata
SEQUENCE: 152
LVYGVDSSTL VSTATYSKAK SEGFTKAIIR GYQEACGSGG RVDPNFVATY KNARAAGITD    60
IDMYWFPCNG SGNSCKSYAT QLSEIANAFS ANSMKIGTIW IDFEKDSTCN NWNYGTTGNL   120
NHAKALISAI KATGFKFGIY SSPGEWGTLF GSTGVVLDSS APLWFATWNN VKTLTLGTHF   180
GGWTTAAGHQ YTDVSSSGQF DLNVFAN                                       207

SEQ ID NO: 153         moltype = DNA   length = 917
FEATURE                Location/Qualifiers
sig_peptide            1..57
mat_peptide            58..914
source                 1..917
                       mol_type = genomic DNA
                       organism = Stropharia semiglobata
CDS                    1..393
CDS                    464..562
CDS                    617..700
CDS                    757..785
CDS                    842..914
SEQUENCE: 153
atggtcaaaa tcttgagcct tctagccctc cttccctgc tcacgcagtc ctatgcgctc     60
acgtacgccg tggactcgtc cacgctcgtc tcggtcgcga cgtacaccaa ggcaaagagc   120
cagggcttca ccaaggccat tatccgcggc taccaggagg cgtgcggctc cggggggca   180
gtcgatccca acttcgtcca aacttacaag aacgcgcgcg cagcaggcta caccgacatc   240
gacatgtact ggttcccatg caacgggtcc acgcacaact gcaagtgta cgcgacgcag   300
attgccgcta tagccgcgac gttcagcgcg aactcgatga agatcggcag gatctggatc   360
gacatcgaga aggacgctgc cgtctgcaat aacgtacgtg ctgtggtgta ctgactgggg   420
agtgagcgca ctgatgacac gcgaatgacg cctcggtttg cagtggaatt atggcacggc   480
cggtaatcta tcccaggcga aagcactgat ctcggccatt aaggcttcgg gtttcgtgta   540
cggcatctac agcagtcctg gggtatgttt ctttttttat cgtttttttt agggtactca   600
ccgttaaatt ttgtaggaat ggggcaatat cttcggttcc acaagcgtcg ttgttgacaa   660
ctctgcccca ctctggtttg ctacatgaa caacgttcag gtacctaaat tcacaatcat   720
ttttgcttct ccactgtttc tgatgataat tctcagactc tgactatggg aaccaagttt   780
ggagggtgtg tatccctgta cttttttatta tgtttcact caataacgac gcgttcttca   840
ggtggacttc ggcaatgggc catcaataca cggacgtctc tgcctctgga caattcgacc   900
tgagcgtatt cgcatag                                                  917

SEQ ID NO: 154         moltype = AA   length = 226
FEATURE                Location/Qualifiers
source                 1..226
                       mol_type = protein
                       organism = Stropharia semiglobata
SEQUENCE: 154
MVKILSLLAL LPLLTQSYAL TYAVDSSTLV SVATYTKAKS QGFTKAIIRG YQEACGSGGA    60
VDPNFVQTYK NARAAGYTDI DMYWFPCNGS THNCKSYATQ IAAIAATFSA NSMKIGRIWI   120
DIEKDAAVCN NWNYGTAGNL SQAKALISAI KASGFVYGIY SSPGEWGNIF GSTSVVVDNS   180
APLWFATWNN VQTLTMGTKF GGWTSAMGHQ YTDVSASGQF DLSVFA                  226

SEQ ID NO: 155         moltype = AA   length = 207
FEATURE                Location/Qualifiers
source                 1..207
                       mol_type = protein
                       organism = Stropharia semiglobata
SEQUENCE: 155
LTYAVDSSTL VSVATYTKAK SQGFTKAIIR GYQEACGSGG AVDPNFVQTY KNARAAGYTD    60
```

```
IDMYWFPCNG STHNCKSYAT QIAAIAATFS ANSMKIGRIW IDIEKDAAVC NNWNYGTAGN    120
LSQAKALISA IKASGFVYGI YSSPGEWGNI FGSTSVVVDN SAPLWFATWN NVQTLTMGTK    180
FGGWTSAMGH QYTDVSASGQ FDLSVFA                                       207

SEQ ID NO: 156              moltype = DNA   length = 765
FEATURE                     Location/Qualifiers
sig_peptide                 1..54
mat_peptide                 55..762
source                      1..765
                            mol_type = genomic DNA
                            organism = Gelasinospora cratophora
CDS                         1..144
CDS                         229..762
SEQUENCE: 156
atgaagtcct tcgtcctcac ggccttcgcc ggcctcatcg gcgctgctca ggctaccgtc    60
cagggcttcg atatctccca ctaccagagc agcgtcaact tgccggcgc ttactcttcc   120
ggtgcccgct tcgtcatcat caaggtgcgt cttttcttgt ctcagagcaa gccccatatc   180
ttcacaggac ctccatccat ccatactaac ccacgaccc gctcacaggc caccgaagga   240
accacctaca tcgactcctc gttctcctcc cactacaccg cgccaccctc cgccggcctg   300
atccgcggcg gctaccactt cgcgcacccg gactcctcca ccggcgccgc tcaggccgac   360
tacttcctcg cgcacggcgg cggctggtcc gccgacggca tcaccttgcc cggcatgatc   420
gacctggagt ccgtctcggg caaagccact tgcttcggcc tgtcgacttc ggccatggtc   480
tcgtggatca agtccttctc ggatcgctac tacgccaaga cgggccgcta ccccatgatc   540
tacaccaact actcgtggtg gaaccagtgc acgggtaact ctgccagctt tgccgcgacc   600
aacccgctgt tgctggcgag gtggtcgagc acggtgggca ccctgccggg ggttggagt   660
gttcagacta tttggcagaa tgcggatacg tatacttatg gtggtgactc ggatgttttt   720
aacggtagcc ttgatcgcct taaggctctt gctaagggat cttaa                   765

SEQ ID NO: 157              moltype = AA   length = 226
FEATURE                     Location/Qualifiers
source                      1..226
                            mol_type = protein
                            organism = Gelasinospora cratophora
SEQUENCE: 157
MKSFVLTAFA GLIGAAQATV QGFDISHYQS SVNFAGAYSS GARFVIIKAT EGTTYIDSSF    60
SSHYTGATSA GLIRGGYHFA HPDSSTGAAQ ADYFLAHGGG WSADGITLPG MIDLESVSGK   120
ATCFGLSTSA MVSWIKSFSD RYYAKTGRYP MIYTNYSWWN QCTGNSASFA ATNPLVLARW   180
SSTVGTLPGG WSVQTIWQNA DTYTYGGDSD VFNGSLDRLK ALAKGS                  226

SEQ ID NO: 158              moltype = AA   length = 208
FEATURE                     Location/Qualifiers
source                      1..208
                            mol_type = protein
                            organism = Gelasinospora cratophora
SEQUENCE: 158
TVQGFDISHY QSSVNFAGAY SSGARFVIIK ATEGTTYIDS SFSSHYTGAT SAGLIRGGYH    60
FAHPDSSTGA AQADYFLAHG GGWSADGITL PGMIDLESVS GKATCFGLST SAMVSWIKSF   120
SDRYYAKTGR YPMIYTNYSW WNQCTGNSAS FAATNPLVLA RWSSTVGTLP GGWSVQTIWQ   180
NADTYTYGGD SDVFNGSLDR LKALAKGS                                      208

SEQ ID NO: 159              moltype = AA   length = 208
FEATURE                     Location/Qualifiers
source                      1..208
                            mol_type = protein
                            organism = Acremonium alcalophilum
SEQUENCE: 159
RIPGFDISGW QPTTDFARAY ANGDRFVYIK ATEGTTFKSS AFSRQYTGAT QNGFIRGAYH    60
FAQPAASSGA AQARYFASNG GGWSKDGITL PGALDIEYNP NGATCYGLSQ SAMVNWIEDF   120
VTTYHGITSR WPVIYTTTDW WTQCTGNSNR FANRCPLWIA RYASSVGTLP NGWGFYTFWQ   180
YNDKYPQGGD SNWFNGDASR LRALANGD                                      208

SEQ ID NO: 160              moltype = AA   length = 4
FEATURE                     Location/Qualifiers
REGION                      1..4
                            note = Conserved motif YKNA
source                      1..4
                            mol_type = protein
                            organism = synthetic construct
SEQUENCE: 160
YKNA                                                                  4

SEQ ID NO: 161              moltype = AA   length = 5
FEATURE                     Location/Qualifiers
REGION                      1..5
                            note = Conserved motif FGGW[S/T].
SITE                        5
                            note = MISC_FEATURE - The amino acid in position 1 of the
                             conserved motif is either serine (Ser, S) or threonine (T,
                             Thr).
```

```
source                     1..5
                           mol_type = protein
                           organism = synthetic construct
SEQUENCE: 161
FGGWX                                                                    5

SEQ ID NO: 162             moltype = DNA   length = 52
FEATURE                    Location/Qualifiers
misc_feature               1..52
                           note = Primer
source                     1..52
                           mol_type = other DNA
                           organism = synthetic construct
SEQUENCE: 162
acacaactgg ggatccacca tgttgaaaac aattatctat accacccttg cc              52

SEQ ID NO: 163             moltype = DNA   length = 41
FEATURE                    Location/Qualifiers
misc_feature               1..41
                           note = Primer
source                     1..41
                           mol_type = other DNA
                           organism = synthetic construct
SEQUENCE: 163
agatctcgag aagcttagcc ctttgcaaat cgttgcaatc c                          41

SEQ ID NO: 164             moltype = DNA   length = 40
FEATURE                    Location/Qualifiers
misc_feature               1..40
                           note = Primer
source                     1..40
                           mol_type = other DNA
                           organism = synthetic construct
SEQUENCE: 164
acacaactgg ggatccacca tgaagttcgc atccgtcgcc                            40

SEQ ID NO: 165             moltype = DNA   length = 38
FEATURE                    Location/Qualifiers
misc_feature               1..38
                           note = Primer
source                     1..38
                           mol_type = other DNA
                           organism = synthetic construct
SEQUENCE: 165
agatctcgag aagcttaacc ggcgttggca atcttctt                              38

SEQ ID NO: 166             moltype = DNA   length = 41
FEATURE                    Location/Qualifiers
misc_feature               1..41
                           note = Primer
source                     1..41
                           mol_type = other DNA
                           organism = synthetic construct
SEQUENCE: 166
acacaactgg ggatccacca tgcgcccctc cgtcatattg c                          41

SEQ ID NO: 167             moltype = DNA   length = 50
FEATURE                    Location/Qualifiers
misc_feature               1..50
                           note = Primer
source                     1..50
                           mol_type = other DNA
                           organism = synthetic construct
SEQUENCE: 167
agatctcgag aagcttaagc agaaaacacg ttcaaatcaa acttcttact                 50

SEQ ID NO: 168             moltype = DNA   length = 46
FEATURE                    Location/Qualifiers
misc_feature               1..46
                           note = Primer
source                     1..46
                           mol_type = other DNA
                           organism = synthetic construct
SEQUENCE: 168
acacaactgg ggatccacca tgaagctcac ctttgcctct ctaact                     46

SEQ ID NO: 169             moltype = DNA   length = 40
FEATURE                    Location/Qualifiers
misc_feature               1..40
```

```
                        note = Primer
source                  1..40
                        mol_type = other DNA
                        organism = synthetic construct
SEQUENCE: 169
agatctcgag aagcttaggc tcctttggcc atcctagaca                          40

SEQ ID NO: 170          moltype = DNA   length = 42
FEATURE                 Location/Qualifiers
misc_feature            1..42
                        note = Primer
source                  1..42
                        mol_type = other DNA
                        organism = synthetic construct
SEQUENCE: 170
acacaactgg ggatccacca tgcgcgcctt tattccagtc tt                       42

SEQ ID NO: 171          moltype = DNA   length = 48
FEATURE                 Location/Qualifiers
misc_feature            1..48
                        note = Primer
source                  1..48
                        mol_type = other DNA
                        organism = synthetic construct
SEQUENCE: 171
agatctcgag aagcttaggc agagaaaacg ttgagatcaa atttcttg                 48

SEQ ID NO: 172          moltype = DNA   length = 48
FEATURE                 Location/Qualifiers
misc_feature            1..48
                        note = Primer
source                  1..48
                        mol_type = other DNA
                        organism = synthetic construct
SEQUENCE: 172
acacaactgg ggatccacca tgaagctgtc tctcctcctt attgttgc                 48

SEQ ID NO: 173          moltype = DNA   length = 41
FEATURE                 Location/Qualifiers
misc_feature            1..41
                        note = Primer
source                  1..41
                        mol_type = other DNA
                        organism = synthetic construct
SEQUENCE: 173
agatctcgag aagcttaacc tagggccatt ctcttcaacc c                        41

SEQ ID NO: 174          moltype = DNA   length = 48
FEATURE                 Location/Qualifiers
misc_feature            1..48
                        note = Primer
source                  1..48
                        mol_type = other DNA
                        organism = synthetic construct
SEQUENCE: 174
acacaactgg ggatccacca tgaagtcttt tggtgttatt gctaccgg                 48

SEQ ID NO: 175          moltype = DNA   length = 39
FEATURE                 Location/Qualifiers
misc_feature            1..39
                        note = Primer
source                  1..39
                        mol_type = other DNA
                        organism = synthetic construct
SEQUENCE: 175
agatctcgag aagcttagcc tctggcgatt ctctgaagc                           39

SEQ ID NO: 176          moltype = DNA   length = 48
FEATURE                 Location/Qualifiers
misc_feature            1..48
                        note = Primer
source                  1..48
                        mol_type = other DNA
                        organism = synthetic construct
SEQUENCE: 176
ctatatacac aactggggat ccaccatgaa gtccttcgtc ctcacggc                 48

SEQ ID NO: 177          moltype = DNA   length = 55
FEATURE                 Location/Qualifiers
```

```
misc_feature            1..55
                        note = Primer
source                  1..55
                        mol_type = other DNA
                        organism = synthetic construct
SEQUENCE: 177
tagagtcgac ccagccgcgc cggccattaa gatcccttag caagagcctt aaggc            55

SEQ ID NO: 178          moltype = DNA  length = 54
FEATURE                 Location/Qualifiers
misc_feature            1..54
                        note = Primer
source                  1..54
                        mol_type = other DNA
                        organism = synthetic construct
SEQUENCE: 178
ctatatacac aactgggat ccaccatgaa gtctgttact ttcatcgcca gtct            54

SEQ ID NO: 179          moltype = DNA  length = 54
FEATURE                 Location/Qualifiers
misc_feature            1..54
                        note = Primer
source                  1..54
                        mol_type = other DNA
                        organism = synthetic construct
SEQUENCE: 179
tagagtcgac ccagccgcgc cggccattac gaagcgttag caatacgctt aagc            54

SEQ ID NO: 180          moltype = DNA  length = 50
FEATURE                 Location/Qualifiers
misc_feature            1..50
                        note = Primer
source                  1..50
                        mol_type = other DNA
                        organism = synthetic construct
SEQUENCE: 180
ctatatacac aactgggat ccaccatgaa ggcttcttcc atcctctccc            50

SEQ ID NO: 181          moltype = DNA  length = 51
FEATURE                 Location/Qualifiers
misc_feature            1..51
                        note = Primer
source                  1..51
                        mol_type = other DNA
                        organism = synthetic construct
SEQUENCE: 181
tagagtcgac ccagccgcgc cggccatcat ccactcgcca acttcttcaa c            51

SEQ ID NO: 182          moltype = DNA  length = 50
FEATURE                 Location/Qualifiers
misc_feature            1..50
                        note = Primer
source                  1..50
                        mol_type = other DNA
                        organism = synthetic construct
SEQUENCE: 182
ctatatacac aactgggat ccaccatgtt ctctttcgtc aaagcgctca            50

SEQ ID NO: 183          moltype = DNA  length = 58
FEATURE                 Location/Qualifiers
misc_feature            1..58
                        note = Primer
source                  1..58
                        mol_type = other DNA
                        organism = synthetic construct
SEQUENCE: 183
tagagtcgac ccagccgcgc cggccattaa tttgcaaaga cattgaggtc gaattggc            58

SEQ ID NO: 184          moltype = DNA  length = 50
FEATURE                 Location/Qualifiers
misc_feature            1..50
                        note = Primer
source                  1..50
                        mol_type = other DNA
                        organism = synthetic construct
SEQUENCE: 184
ctatatacac aactgggat ccaccatgtt cccttcgtc aaaacgctca            50

SEQ ID NO: 185          moltype = DNA  length = 57
```

```
FEATURE                 Location/Qualifiers
misc_feature            1..57
                        note = Primer
source                  1..57
                        mol_type = other DNA
                        organism = synthetic construct
SEQUENCE: 185
tagagtcgac ccagccgcgc cggccattaa tttgcaaaca cattgaggtc gaattgg      57

SEQ ID NO: 186          moltype = DNA  length = 52
FEATURE                 Location/Qualifiers
misc_feature            1..52
                        note = Primer
source                  1..52
                        mol_type = other DNA
                        organism = synthetic construct
SEQUENCE: 186
ctatatacac aactggggat ccaccatggt caaaatcttg agccttctag cc           52

SEQ ID NO: 187          moltype = DNA  length = 53
FEATURE                 Location/Qualifiers
misc_feature            1..53
                        note = Primer
source                  1..53
                        mol_type = other DNA
                        organism = synthetic construct
SEQUENCE: 187
tagagtcgac ccagccgcgc cggccactat gcgaatacgc tcaggtcgaa ttg          53

SEQ ID NO: 188          moltype = DNA  length = 37
FEATURE                 Location/Qualifiers
misc_feature            1..37
                        note = Primer
source                  1..37
                        mol_type = other DNA
                        organism = synthetic construct
SEQUENCE: 188
acacaactgg ggatccacca tgaagactac gggtgtc                            37

SEQ ID NO: 189          moltype = DNA  length = 35
FEATURE                 Location/Qualifiers
misc_feature            1..35
                        note = Primer
source                  1..35
                        mol_type = other DNA
                        organism = synthetic construct
SEQUENCE: 189
ccctctagat ctcgagttaa gaaccttgg caaag                               35

SEQ ID NO: 190          moltype = DNA  length = 39
FEATURE                 Location/Qualifiers
misc_feature            1..39
                        note = Primer
source                  1..39
                        mol_type = other DNA
                        organism = synthetic construct
SEQUENCE: 190
acacaactgg ggatccacca tgaagttcac taccattgc                          39

SEQ ID NO: 191          moltype = DNA  length = 34
FEATURE                 Location/Qualifiers
misc_feature            1..34
                        note = Primer
source                  1..34
                        mol_type = other DNA
                        organism = synthetic construct
SEQUENCE: 191
ccctctagat ctcgagctac ccctcgacaa tctt                               34

SEQ ID NO: 192          moltype = DNA  length = 38
FEATURE                 Location/Qualifiers
misc_feature            1..38
                        note = Primer
source                  1..38
                        mol_type = other DNA
                        organism = synthetic construct
SEQUENCE: 192
acacaactgg ggatccacca tgaagtctgt tgctgtct                           38
```

```
SEQ ID NO: 193              moltype = DNA   length = 36
FEATURE                     Location/Qualifiers
misc_feature                1..36
                            note = Primer
source                      1..36
                            mol_type = other DNA
                            organism = synthetic construct
SEQUENCE: 193
ccctctagat ctcgagctaa gaagcattcg caatgc                                     36

SEQ ID NO: 194              moltype = DNA   length = 37
FEATURE                     Location/Qualifiers
misc_feature                1..37
                            note = Primer
source                      1..37
                            mol_type = other DNA
                            organism = synthetic construct
SEQUENCE: 194
acacaactgg ggatccacca tgaagctcac gagtgtg                                    37

SEQ ID NO: 195              moltype = DNA   length = 35
FEATURE                     Location/Qualifiers
misc_feature                1..35
                            note = Primer
source                      1..35
                            mol_type = other DNA
                            organism = synthetic construct
SEQUENCE: 195
ccctctagat ctcgagttac gaacctctag caagc                                      35

SEQ ID NO: 196              moltype = DNA   length = 40
FEATURE                     Location/Qualifiers
misc_feature                1..40
                            note = Primer
source                      1..40
                            mol_type = other DNA
                            organism = synthetic construct
SEQUENCE: 196
acacaactgg ggatccacca tgaagtctta catcgccccc                                 40

SEQ ID NO: 197              moltype = DNA   length = 39
FEATURE                     Location/Qualifiers
misc_feature                1..39
                            note = Primer
source                      1..39
                            mol_type = other DNA
                            organism = synthetic construct
SEQUENCE: 197
gtgcggccgc aagcttaatc agaggcttcc tcccatagg                                  39

SEQ ID NO: 198              moltype = DNA   length = 43
FEATURE                     Location/Qualifiers
misc_feature                1..43
                            note = Primer
source                      1..43
                            mol_type = other DNA
                            organism = synthetic construct
SEQUENCE: 198
acacaactgg ggatccacca tgaagtatct cgttcccctt ttg                             43

SEQ ID NO: 199              moltype = DNA   length = 38
FEATURE                     Location/Qualifiers
misc_feature                1..38
                            note = Primer
source                      1..38
                            mol_type = other DNA
                            organism = synthetic construct
SEQUENCE: 199
agatctcgag aagcttatta gcccttagcc agtctctt                                   38

SEQ ID NO: 200              moltype = DNA   length = 43
FEATURE                     Location/Qualifiers
misc_feature                1..43
                            note = Primer
source                      1..43
                            mol_type = other DNA
                            organism = synthetic construct
SEQUENCE: 200
acacaactgg ggatccacca tgaagctcac cacttttatc acg                             43
```

```
SEQ ID NO: 201           moltype = DNA   length = 38
FEATURE                  Location/Qualifiers
misc_feature             1..38
                         note = Primer
source                   1..38
                         mol_type = other DNA
                         organism = synthetic construct
SEQUENCE: 201
ctagatctcg agaagctttt aagtcccctt ggcaagcg                                 38

SEQ ID NO: 202           moltype = DNA   length = 44
FEATURE                  Location/Qualifiers
misc_feature             1..44
                         note = Primer
source                   1..44
                         mol_type = other DNA
                         organism = synthetic construct
SEQUENCE: 202
acacaactgg ggatccacca tgaagtttgc actcctagta tctg                          44

SEQ ID NO: 203           moltype = DNA   length = 42
FEATURE                  Location/Qualifiers
misc_feature             1..42
                         note = Primer
source                   1..42
                         mol_type = other DNA
                         organism = synthetic construct
SEQUENCE: 203
ctagatctcg agaagctttt agccatagta gttcttgtcc ca                            42

SEQ ID NO: 204           moltype = DNA   length = 37
FEATURE                  Location/Qualifiers
misc_feature             1..37
                         note = Primer
source                   1..37
                         mol_type = other DNA
                         organism = synthetic construct
SEQUENCE: 204
acacaactgg ggatccacca tggcaaagct cctcaag                                  37

SEQ ID NO: 205           moltype = DNA   length = 35
FEATURE                  Location/Qualifiers
misc_feature             1..35
                         note = Primer
source                   1..35
                         mol_type = other DNA
                         organism = synthetic construct
SEQUENCE: 205
agatctcgag aagcttatta gtgggcgaag acgtt                                    35

SEQ ID NO: 206           moltype = DNA   length = 39
FEATURE                  Location/Qualifiers
misc_feature             1..39
                         note = Primer
source                   1..39
                         mol_type = other DNA
                         organism = synthetic construct
SEQUENCE: 206
acacaactgg ggatccacca tgaagcttct ttccgccct                                39

SEQ ID NO: 207           moltype = DNA   length = 38
FEATURE                  Location/Qualifiers
misc_feature             1..38
                         note = Primer
source                   1..38
                         mol_type = other DNA
                         organism = synthetic construct
SEQUENCE: 207
agatctcgag aagcttatca ctgagaggca aacttgac                                 38

SEQ ID NO: 208           moltype = DNA   length = 39
FEATURE                  Location/Qualifiers
misc_feature             1..39
                         note = Primer
source                   1..39
                         mol_type = other DNA
                         organism = synthetic construct
SEQUENCE: 208
```

```
acacaactgg ggatccacca tggcttccag actgaccct                              39

SEQ ID NO: 209          moltype = DNA   length = 38
FEATURE                 Location/Qualifiers
misc_feature            1..38
                        note = Primer
source                  1..38
                        mol_type = other DNA
                        organism = synthetic construct
SEQUENCE: 209
ctagatctcg agaagctttt aagctgccac gcactggg                               38

SEQ ID NO: 210          moltype = DNA   length = 27
FEATURE                 Location/Qualifiers
misc_feature            1..27
                        note = Primer
source                  1..27
                        mol_type = other DNA
                        organism = synthetic construct
SEQUENCE: 210
gaattcgagc tcggtacctt gaagttc                                           27

SEQ ID NO: 211          moltype = DNA   length = 31
FEATURE                 Location/Qualifiers
misc_feature            1..31
                        note = Primer
source                  1..31
                        mol_type = other DNA
                        organism = synthetic construct
SEQUENCE: 211
ggtggatccc cagttgtgta tatagaggat t                                      31

SEQ ID NO: 212          moltype = DNA   length = 26
FEATURE                 Location/Qualifiers
misc_feature            1..26
                        note = Primer
source                  1..26
                        mol_type = other DNA
                        organism = synthetic construct
SEQUENCE: 212
tgcgcggcgc ggctgggtcg actcta                                            26

SEQ ID NO: 213          moltype = DNA   length = 27
FEATURE                 Location/Qualifiers
misc_feature            1..27
                        note = Primer
source                  1..27
                        mol_type = other DNA
                        organism = synthetic construct
SEQUENCE: 213
ttcacacagg aaacagctat gaccatg                                           27

SEQ ID NO: 214          moltype = DNA   length = 25
FEATURE                 Location/Qualifiers
misc_feature            1..25
                        note = Primer
source                  1..25
                        mol_type = other DNA
                        organism = synthetic construct
SEQUENCE: 214
ctatatacac aactggggat ccacc                                             25

SEQ ID NO: 215          moltype = DNA   length = 26
FEATURE                 Location/Qualifiers
misc_feature            1..26
                        note = Primer
source                  1..26
                        mol_type = other DNA
                        organism = synthetic construct
SEQUENCE: 215
tagagtcgac ccagccgcgc cggcca                                            26

SEQ ID NO: 216          moltype = DNA   length = 10767
FEATURE                 Location/Qualifiers
misc_feature            1..10767
                        note = Synthetic DNA construct of plasmid pDAu770.
source                  1..10767
                        mol_type = other DNA
                        organism = synthetic construct
```

SEQUENCE: 216

```
taggcgtatc acgaggccct tcgtctcgc gcgtttcggt gatgacggtg aaaacctctg    60
acacatgcag ctcccggaga cggtcacagc ttgtctgtaa gcggatgccg ggagcagaca   120
agcccgtcag ggcgcgtcag cgggtgttgg cgggtgtcgg ggctggctta actatgcggc   180
atcagagcag attgtactga gagtgcacca tatgcggtgt gaaataccgc acagatgcgt   240
aaggagaaaa taccgcatca ggcgccattc gccattcagg ctgcgcaact gttgggaagg   300
gcgatcggtg cgggcctctt cgctattacg ccagctggcg aaaggggat gtgctgcaag    360
gcgattaagt tgggtaacgc cagggttttc ccagtcacga cgttgtaaaa cgacggccag   420
tgaattggcc tccatggccg cggccgcgct ttgctaaaac tttggttgat ggaaggtatc   480
tggcgataaa ctccgacgac gtctagaagc aacaatctta tgcaaacgct cattggttct   540
tttcgaccgc aacatccatc atgaaactgg tattttgtct gtgtcagcag tctagaaccc   600
cttgccgggt attttagcat ttcattttc tataaaagg taccagcatg tatggatcgt     660
atcttccgta ccgtggttat taaatcccag cagaggccga taggcttaag aagtgaacat   720
ggcatggtta aggaagaagc cattactgag tatatatggc tagaataatc gctgggaaag   780
atttatgctt ccaagaggcg taggacggta taccatacag tacggtattt atgaacaatt   840
cgataatacc actccccaaa gcgggagata ggacacccgc ctcaggcacc aaccaccccc   900
ttttcaact gtcagtggtg cacgtttcca tcgagcataa gcttggtacc ctaaggatag    960
gccctaatct tatctacatg tgactgcatc gatgtgtttg gtcaaaatga ggcatggtc   1020
tcacccaca ggcggagaaa cgtgtggcta gtgcatgaca gtcccctcca tagattcaat   1080
ttaattttc gcggcaattg tcgtgcagtt tgtatctaca tttcattcca tatatcaaga   1140
gttagtagtt ggacatcctg attattttgt ctaattactg aaaactcgaa gtactaacct   1200
actaataagc cagtttcaac cactaagtgc tcatttatac aatatttgca gaaccccgcg   1260
ctaccccctcc atcgccaaca tgtcttccaa gtcgcaattg acctacacgg cacgcgctag   1320
caagcacccc aatgcgctcg taaagaagct cttcgaggtt gccgaggcca agaaaaccaa   1380
tgtcaccgtt tccgccgacg tgacaaccac caaagagctg ctggatttgg ctgaccgtat   1440
gcgcaccggg gttgaagttc ctattccgag ttcctattct tcaaatagta taggaacttc   1500
attagtttaa acgtacgatt ttgcattttg ctccattgtc gaggatggat ggaacgagcg   1560
gcgtgcgcca cgaaagtgag gctattgcct atcagctctt tgctacattc cggaaacaaa   1620
catccctttt tgtgaattat ctacgcaact tagatggcgt gaacgcatct tcaaagtctt   1680
tcggcaggtc cggcacgact tttgcatcca gagaagcgcc tacatgtgta ttcgaccacc   1740
tcctagcgcg cttggatatg aggaaatatt actgagagtc gaaaacaagc tccaccgcac   1800
cagctcttct tggagttta tattaaagaa tattcccagc tcgttgtatt attctttttc    1860
taccgtgcta atgtatcaag actttggta cctattaacg ttattattcg tgtgctattc    1920
ccaaacataa ccctgtatat gtttcgaacg ccgttatgac ccatgtctta catactcatt   1980
aagtcattcc cttggataat ctcgactcag atgcggcggt tgatgtagga ggagaggtaa   2040
tcgaggacct cctgggagat gatgccgttc caggcgggt agcggatgga gccctcggcg    2100
gagcccttga gctgctcgat atgctgccac tcctcgatgg ggttggtctc atccttgagg   2160
gcgatcatct ccttggagat gggatcgtag gcgtagtagc gggagactag tgcgaagtaa   2220
tgatcgggga tggcggtgat ctgatgggtg taggtgtgc gggcgacggc ggaggcgcgc   2280
ttatcggacc agttgccgac gacgttggtg agctcggtga ggcccttcat ggagaggaag   2340
gaggtcatga gatggcggcc gatatgggac ttggggccgt tcttgatggc gaagatggag   2400
tagggggcgt tcttcttgag ggccttgttg taggagcgga cgaggttatc cttgaggagc   2460
tggtactcct gcttgttgga ggaggagttg ccggtgcgct tgacgcgct gaggacgggc    2520
tcggagttgc ggaggaactc atcgaggtag acgagggat cgatgcgcc gcgggcggag     2580
aagaagtaga tatggcggga gacggaggtc ttggtctcgg tgacgaggca ctggatgatg   2640
acgccgaggt acttgttctg gacgagcttg aaggacttgg gatcgacgtt cttgatatcg   2700
gagaagcgac cgcagttgat gaaggtggcg aggaagagga actggtagag ggtcttggtc   2760
ttggtgaagc gggaggtgta ctcgaaggag ttgaggatct tctcggtgat ctcccagatg   2820
gactcgccct cggagaggag ggccttgagc atcttcttgg aatgggagtt gcccttatcg   2880
gcctcctcgg aggactcgaa ctggagctgg agggaggaga cgatatcggt gatatcggac   2940
tgatgcttct ggccgtagta ggggatgatg gtgaactccc aggcggggat gagcttcttg   3000
agggaggcct ccaggatggt ggccttctgg gtcttgtact tgaactggag ggacttgttg   3060
acgatatcga aggagaggga gttggagatg atggtgttgt aggacatgaa ggtggcgcgc   3120
ttgatgcggt tgccgttatg ggtgatcatc cagcagaggt aggtgagctc ggcggcgcag   3180
agggcgatct tctcgccgga ggggcgctcg aagcgctcga cgaactggcg gacgaggacc   3240
ttgggggggg tcttgcagag gatatcgaac tgggggcatgg tgctcagata ctacggctga   3300
tcgcgtagag gtactgagca aaacagatgt cagtaaggag aagagttgaa tgaatggaag   3360
aagagtagga aaggaggtat gggggaaaga tatacgtact gatgcggacg aagagagaaa   3420
gaaggaaaaa agttgtggga gggaaggag ggggaatcct tatatggagg ggcaagcgag    3480
aaggcgaatt agtgggcggg cttaagccct cgaccgccgc ccttatcatt ggacatggag   3540
gggtaatgcc cccaccacgc atgtgcggga ccgacgcaga atctgcacgg cggagtctct   3600
tccagactgt tgacttttgg gcgatgactc ttgttgctgc ggccttttgg gtacaccaac   3660
ctcgttgatc ttgtttcctt ggttctcttt cgctcggaga cccgaccatg accccaccat   3720
cagtcactat cctgcctcgt cgataaaaat tttttcttcc ctctgattgt tacatagtat   3780
gtttccacct ttccggtgga tttcggacag tcaaactggg catcaacgca gtggtgggct   3840
gcttcgtttg ctgcgtgttg tacttgtttg catttgaacc ccgcggtcgt tcgagtcctt   3900
aattggtccg ctcccggtca acacccaagc agctgtggcc cggccgagtg gcgcctgtct   3960
ggtccacagt taattaaagg agagagttga acctggacgc cgcgcaaaaa gcaaagacgc   4020
gcctcgtggg cggtggatca atgatcggat ttagtgcgag atggcatcac aggcggccaa   4080
tgaccaccgg gccaactggc cccgacattc cagcaatact gcctaattga ctccaccatg   4140
catctcggct attattgaac tgggtttgat ggatggggac cctcttggaa ttgtcaaaga   4200
ttttgaagcg aagacgatct attggacggt agagatatac tcttgattta gtcgttggga   4260
ggcccctggg gaaagcaatg atggggaatg ttgctgctcc actgtggacc tcggctatgg   4320
aatgcgtgc ttggatctaa gatgagctca tggctagaca gtgatatcag                4380
cagagcaagc agagaaggat ggaatgctaa ttttctagtg cttgtgcaa gggtaaatca    4440
gggactgtct gtctggtctt ctacacgaag gaaagaccat ggcttcacg gtgtctgtat    4500
ttccggatat cctcaattcc gtcggtcgat tacaatcaca tgacttggct tccatttcac   4560
tactattatg cacaccccact acatacatga tcatataacc aattgccctc atccccatcc   4620
tttaactata gcgaaatgga ttgattgtct accgccaggt gtcagtcacc ctctagatct   4680
```

```
cgagctcgct agagtcgacc tatggagtca ccacatttcc cagcaacttc cccacttcct 4740
ctgcaatcgc caacgtcctc tcttcactga gtctccgtcc gataacctgc actgcaaccg 4800
gtgcccatg  gtacgcctcc ggatcatact cttcctgcac gagggcatca agctcactaa 4860
ccgccttgaa actctcattc ttcttatcga tgttcttatc cgcaaaggta accggaacaa 4920
ccacgctcgt gaaatccagc aggttgatca cagaggcata cccatagtac cggaactggt 4980
catgccgtac cgcagcggta ggcgtaatcg gcgcgatgat ggcgtccagt tccttcccgg 5040
ccttttcttc agcctcccgc catttctcaa ggtactccat ctggtaattc cacttctgga 5100
gatgcgtgtc ccagagctcg ttcatgttaa cagctttgat gttcgggttc agtaggtctt 5160
tgatatttgg aatcgccggc tcgccggatg cactgatatc gcgcattacg tcggcgctgc 5220
cgtcagccgc gtagatatgg gagatgagat cgtggccgaa atcgtgcttg tatgcgtcc  5280
acggggtcac ggtgtgaccg gctttggcga gtgcggcgac ggtggtttcc acgccgcgca 5340
ggataggagg gtgtggaagg acattgccgt cgaagttgta gtagccgata ttgagcccgc 5400
cgttcttgat cttggaggca ataatgtccg actcggactg gcgccagggc atgggatga  5460
ccttggagtc gtatttccat ggctcctgac cgaggacgga tttggtgaag aggcggagtcc 5520
ctaacatact tcatcagtga ctgccggtct cgtatatagt ataaaaagca agaaaggagg 5580
acagtgagg  cctggtatag agcaggaaaa gaaggaagag gcgaaggact caccctcaac 5640
agagtgcgta atcggcccga caacgctgtg caccgtctcc tgaccctcca tgctgttcgc 5700
catctttgca tacggcagcc gcccatgact cggccttaga ccgtacagga agttgaacgc 5760
ggccggcact cgaatcgagc caccgatatc cgttcctaca ccgatgacgc caccacgaat 5820
cccaacgatc gcaccctcac caccagaact gccgccgcac gaccagttct tgttgcgtgg 5880
gttgacggtg cgcccgatga tgttgttgac tgtctcgcag accatcaggg tctgcgggac 5940
agaggtcttg acgtagaaga cggcaccggc tttgcggagc atggttgtca gaaccgagtc 6000
cccttcgtcg tacttgttta gccatgagat gtagcccatt gatgtttcgt agccctggtg 6060
gcatatgtta gctgacaaaa agggacatct aacgactttag gggcaacggt gtaccttgac 6120
tcgaagctgc tctttgagag agatgggag  gccatggagt ggaccaacgg gtctcttgtg 6180
ctttgcgtag tattcatcga gttcccttgc ctgcgcgagga gcgcgtcag ggaagaactc 6240
gtgggcgcag tttgtctgca cagaagccag cgtcagcttg atagtccat  aaggtggcgt 6300
tgttacatct ccctgagagg tagaggggac cctactaact gctgggcgat tgctgcccgt 6360
ttacagaatg ctagcgtaac ttccaccgag gtcaactctc cggccgccag cttggacaca 6420
agatctgcag cggaggcctc tgtgatcttc agttcggcct ctgaaaggat caccgatttc 6480
tttgggaaat caataacgct gtcttccgca ggcagcgtct ggactttcca ttcatcaggg 6540
atggtttttg cgaggcggc  gcgcttatca gcggccagtt cttcccagga ttgaggcatg 6600
tgcatgcaat gtgtgtttat gtggaagtaa gatacgacga gtttgattga gaaaagacag 6660
ggtgattgtc aagttcagta tggaagaaag agtagaagaa gatcagacga caggagaag  6720
cgatgacata aaaggtggaa gacggaagaa aaacgaacca aatcaatccc actctatggc 6780
gggggtttgga ctgcctgagg ccggcactgg tggggcttat cgataagttc tcgtcaccgg 6840
atgcaatgcg ctgtcaactg ctgacttggc cctgaacatc ctgtcctcta cagatccata 6900
ctatacaatg atcccagtta tagtgcggta aggtgcatat catatctcat tctcatgact 6960
cattcgactt ttttttagag aaagtacata cgtggaacat acactaaacg caacaggtcg 7020
cgacaacact ggtatacaaa acggtcccgg tgaatgacg  ttattagtgt ctatccccca 7080
ctcacacccg aaaagaataa tagaaactaa cagaaaaagc ggcccgagga taagaggaac 7140
attcaaacag aaggggaatc ataaaaaccg aaaaatgcaa ggaaaagaga actcaaatca 7200
ataattttca taatactgtc gagagtaata cggaccagcg tctctcaggg acatgcgtcg 7260
gcgcaaggca tcatccaatc tctcatctaa cacatccagc attcgtgttc gatagtctaa 7320
ctgcttctct cggcgctcaa gtcttgcttc ccgatcatcg agttaattaa gaagttccta 7380
tactttctag agaataggaa ctcggaatag gaacttcaag gtaccgagct ctatcctcaa 7440
taccctattt tccacgattc cattgtcata tccaattccg ttttcttttc ttgttttccc 7500
ctcatccaat cccgtccatc atttactcct tttctctgtg aatgcaagtg gcactaagaa 7560
atccaacccc cagacaaatt ttcctactca ggaacacaaa aacctcgttt ctgctcccttt 7620
ctcgtacttc attcctatcg tctcggaatt tcctcaacaa ccctttccga cttttgcgaca 7680
gcgtcgcgat tccagactta tgtgttctcg ttcctactgt cgttaccagt ctatttattc 7740
cgaaacctct gatcgctgaa tttcacacac aacacccccc cgttgatgct ggtggagaat 7800
ccgtagcgtc aagagttgaa ttcactccat gttgtaacga agtccacgaa ttgagacgat 7860
tgatgattac aaccccgcga tcgcctatcg acgattcgac gagatgccat tctcatcctc 7920
ctcatcctcc tccacccccg aggtgtctac caccccgctc gcagattact tctggatcgc 7980
aggtgtcgat ggcgcggaaa tcttagagac tttccaaaga ctcggcgacg aatacagggc 8040
aaacagtgcc accgctcctg gccccgctct tgccggacacg atcgaggaag atgcggacgc 8100
ggaggaggca cacgaccccc gtctggactc cctctctcga cccaattcca tggctggggg 8160
ccgcaattcc ttccagcggt tctcaatgcg ctcaggagac tccagtgagt ccagtgggaa 8220
tggtaccagc agcaaccgga gcagtctgac catcaaggt  aatcagtcgc ccagagggtc 8280
gtcgtttcta gaagatttcg actttgcaa  ggccctgttc aagtttgcaa acgagcggga 8340
gtcgttcctg tcggatctga gtctcagtgc cggagcaatc actcccacct cccgtcctag 8400
gtccaggtta cgtacacaga agattgtctc cgaggaaagt ccctcccagc catccagctt 8460
gcttcgatca ggcattggta gtgtgcgcg  tcatatggtt ctcagagaca tgaatagtat 8520
gaaacggcag ccgtcagttg ctcgtcgcgg ccgcagcttg gcgtaatcat ggtcatagct 8580
gtttcctgtg tgaaattgtt atccgctcac aattccacac aacatacgag ccggaagcat 8640
aaagtgtaaa gcctggggtg cctaatgagt gagctaactc acattaattg cgttgcgctc 8700
actgcccgct ttccagtcgg gaaacctgtc gtgccagctg cattaatgaa tcggccaacg 8760
cgcggggaga ggcggtttgc gtattgggcg ctcttccgct tcctcgctca ctgactcgct 8820
gcgctcggtc gttcggctgc ggcgagcggt atcagctcac tcaaaggcgg taatacggtt 8880
atccacagaa tcagggata  acgcaggaaa gaacatgtga gcaaaaggcc agcaaaaggc 8940
caggaaccgt aaaaaggccg cgttgctggc gttttttccat aggctccgcc ccctgacga  9000
gcatcacaaa aatcgacgct caagtcagag gtggcgaaac ccgacaggac tataaagata 9060
ccaggcgttt ccccctggaa gctccctcgt gcgctctcct gttccgaccc tgccgcttac 9120
cggatacctg tccgccttttt tcccttcggg aagcgtggcg ctttctcata gctcacgctg 9180
taggtatctc agttcggtgt aggtcgttcg ctccaagctg ggctgtgtgc acgaaccccc 9240
cgttcagccc gaccgctgcg ccttatccgg taactatcgt cttgagtcca acccggtaag 9300
acacgactta tcgccactgg cagcagccac tggtaacagg attagcagag cgaggtatgt 9360
aggcggtgct acagagttct tgaagtggtg gcctaactac ggctacacta agaagaacagt 9420
```

```
atttggtatc tgcgctctgc tgaagccagt taccttcgga aaaagagttg gtagctcttg   9480
atccggcaaa caaaccaccg ctggtagcgg tggttttttt gtttgcaagc agcagattac   9540
gcgcagaaaa aaaggatctc aagaagatcc tttgatcttt tctacggggt ctgacgctca   9600
gtggaacgaa aactcacgtt aagggatttt ggtcatgaga ttatcaaaaa ggatcttcac   9660
ctagatcctt ttaaattaaa aatgaagttt taaatcaatc taaagtatat atgagtaaac   9720
ttggtctgac agttaccaat gcttaatcag tgaggcacct atctcagcga tctgtctatt   9780
tcgttcatcc atagttgcct gactcccgt cgtgtagata actacgatac gggagggctt   9840
accatctggc cccagtgctg caatgatacc gcgagaccca cgctcaccgg ctccagattt   9900
atcagcaata aaccagccag ccggaagggc cgagcgcaga agtggtcctg caactttatc   9960
cgcctccatc cagtctatta attgttgccg ggaagctaga gtaagtagtt cgccagttaa  10020
tagtttcgc aacgttgttg ccattgctac aggcatcgtg gtgtcacgct cgtcgtttgg  10080
tatggcttca ttcagctccg gttcccaacg atcaaggcga gttacatgat cccccatgtt  10140
gtgcaaaaaa gcggttagct ccttcggtcc tccgatcgtt gtcagaagta agttggccgc  10200
agtgttatca ctcatggtta tggcagcact gcataattct cttactgtca tgccatccgt  10260
aagatgcttt tctgtgactg gtgagtactc aaccaagtca ttctgagaat agtgtatgcg  10320
gcgaccgagt tgctcttgcc cggcgtcaat acgggataat accgcgccac atagcagaac  10380
tttaaaagtg ctcatcattg gaaaacgttc tcggggcgaa aactctcaa ggatcttacc  10440
gctgttgaga tccagttcga tgtaacccac tcgtgcaccc aactgatctt cagcatcttt  10500
tactttcacc agcgtttctg ggtgagcaaa aacaggaagg caaaatgccg caaaaaaggg  10560
aataagggcg acacggaaat gttgaatact catactcttc ctttttcaat attattgaag  10620
catttatcag ggttattgtc tcatgagcgg atacatattt gaatgtattt agaaaaataa  10680
acaaataggg gttccgcgca catttccccg aaaagtgcca cctgacgtct aagaaaccat  10740
tattatcatg acattaacct ataaaaa                                       10767

SEQ ID NO: 217           moltype = DNA  length = 1052
FEATURE                  Location/Qualifiers
sig_peptide              1..51
mat_peptide              52..1049
source                   1..1052
                         mol_type = genomic DNA
                         organism = Flammulina velutipes
CDS                      1..157
CDS                      213..347
CDS                      401..451
CDS                      504..600
CDS                      659..666
CDS                      715..838
CDS                      895..981
CDS                      1037..1049
SEQUENCE: 217
atgcgcatct tactcttcat cgctgtgacc attgcactcg gcgtccatgc tcgtctcaat   60
ggcatcgacg tttccgggta tcagccgaac gtcaactggg ccactgtcaa ggctaatggc  120
gtctcattcg cgtatatcaa ggccaccgaa ggcactgtca agttcacttc ctatatcctt  180
ttggtccagt gctgatatca tcgacaaccc agcttatacg aacccgtcgt tctcatcgca  240
atacaccgga gctaccaaag ctggactcat tcgaggatcg taccattttg cgcacccaag  300
tagtagcacg ggcgctgcac aggccagata ctttgtcgcg catggcggta ggaattgatc  360
catctttgtgt ggcgtccccc attgacacaa tccttgatag ctggtggctg gggagacgga  420
atcactctgc ctggggcgct ggatatagaa tgtaatgatc agtcagatct attacgtttt  480
gagtcacatt gacaacttct tagacaatcc aagtggcgca acttgctacg gcctgagtac  540
ctcatcaatg gtcaattgga ttgccgactt ctctaacact taccattccc tcactggaag  600
gttaggcttc gtaaacacaa gccatgtact gccgtagtaa cgctaatctc catttcagat  660
accctggtac accaatccca caatcatttt gagtctgctc atctcccctg acagtaattt  720
acaccaccgc agactggtgg aggacatgta ctggtaacag tgcatccttt gccaacaaca  780
gtcctctctg gattgcgaga tatgccagta ccatcggtac actccctgct ggatggaggt  840
gcgaccccttc tacttattcg atgactctgt tctgaaccaa gtgttcattc taagctacgc  900
cacattctgg cagtacgctg actcgggtag taatcccgga gatcaggatt atttcaacgg  960
ggatgctgca ggtctcaaac ggtaaattga tatcttttta tatatcttca cctgcgagac  1020
taatccatgt ttataggctt gccaccagtt ga                                1052

SEQ ID NO: 218           moltype = AA  length = 224
FEATURE                  Location/Qualifiers
source                   1..224
                         mol_type = protein
                         organism = Flammulina velutipes
SEQUENCE: 218
MRILLFIAVT IALGVHARLN GIDVSGYQPN VNWATVKANG VSFAYIKATE GTTYTNPSFS   60
SQYTGATKAG LIRGSYHFAH PSSSTGAAQA RYFVAHGGGW SGDGITLPGA LDIEYNPSGA  120
TCYGLSTSSM VNWIADFSNT YHSLTGRYPV IYTTADWWRT CTGNSASFAN NSPLWIARYA  180
STIGTLPAGW SYATFWQYAD SGSNPGDQDY FNGDAAGLKR LATS                   224

SEQ ID NO: 219           moltype = DNA  length = 711
FEATURE                  Location/Qualifiers
misc_feature             1..711
                         note = Codon optimised sequence
sig_peptide              20..70
mat_peptide              71..691
source                   1..711
                         mol_type = other DNA
                         organism = synthetic construct
```

```
CDS                     20..691
SEQUENCE: 219
acacaactgg ggatccacca tgcgaatcct cttgttcatc gcagtcacaa tcgcgttggg    60
agtccatgcc aggctcaacg gcatcgatgt ctcgggatac cagccgaacg tcaactgggc   120
cacggtcaaa gcgaacggcg tgtccttcgc gtacatcaag gcaaccgagg gcaccacgta   180
tacaaacccc tcgttctcct cccagtacac cggagcaaca aaagccggat tgatcagggg   240
ctcctaccat ttcgcgcatc cttcgtcgtc cacaggcgca gcacaggcac gatacttcgt   300
ggcacatggc ggtggttggt ccggtgatgg tatcaccttg cctggtgcgc tcgatatcga   360
gtataaccct tcgggtgcga catgttacgg cctctcgacc tcgtccatgg tgaactggat   420
cgccgatttc tccaacactt atcactcgct cacaggcagg taccccgtca tttacaccac   480
tgccgattgg tggcgaacct gtaccggcaa ctccgcatcc ttcgcaaaca actgcctct   540
ctggattgcg cgttacgcgt cgactatcgg tacgctccct gccggatggt cgtacgcgac   600
cttctggcag tatgcggatt cgggctccaa ccctggcgat caggattact caacggtga   660
cgcagcgggc tcaagcgtc tcgcgacatc gtaataagct tctcgagatc t            711

SEQ ID NO: 220          moltype = AA   length = 224
FEATURE                 Location/Qualifiers
REGION                  1..224
                        note = Synthetic Construct
source                  1..224
                        mol_type = protein
                        organism = synthetic construct
SEQUENCE: 220
MRILLFIAVT IALGVHARLN GIDVSGYQPN VNWATVKANG VSFAYIKATE GTTYTNPSFS    60
SQYTGATKAG LIRGSYHFAH PSSSTGAAQA RYFVAHGGGW SGDGITLPGA LDIEYNPSGA   120
TCYGLSTSSM VNWIADFSNT YHSLTGRYPV IYTTADWWRT CTGNSASFAN NSPLWIARYA   180
STIGTLPAGW SYATFWQYAD SGSNPGDQDY FNGDAAGLKR LATS                    224

SEQ ID NO: 221          moltype = AA   length = 207
FEATURE                 Location/Qualifiers
source                  1..207
                        mol_type = protein
                        organism = Flammulina velutipes
SEQUENCE: 221
RLNGIDVSGY QPNVNWATVK ANGVSFAYIK ATEGTTYTNP SFSSQYTGAT KAGLIRGSYH    60
FAHPSSSTGA AQARYFVAHG GGWSGDGITL PGALDIEYNP SGATCYGLST SSMVNWIADF   120
SNTYHSLTGR YPVIYTTADW WRTCTGNSAS FANNSPLWIA RYASTIGTLP AGWSYATFWQ   180
YADSGSNPGD QDYFNGDAAG LKRLATS                                       207

SEQ ID NO: 222          moltype = DNA   length = 921
FEATURE                 Location/Qualifiers
sig_peptide             1..57
mat_peptide             58..918
source                  1..921
                        mol_type = genomic DNA
                        organism = Deconica coprophila
CDS                     1..390
CDS                     449..547
CDS                     600..683
CDS                     751..779
CDS                     843..918
SEQUENCE: 222
atgcttttcg caacctttct ttgtcttgcg agctacgcgt ttggatcggc ctatgcactc    60
gtgcatgcc tagactcttc ttccctcgtc tccaccgcca ctttctccaa ggcaaagtct   120
gaaggcttta ccaaggcagt catccgcgtta taccaggagc cttgcggaag tggtggacgc   180
gtcgaccca actttgttca gacataacaag aacgcaaggg ccgcaggaat taccaacatc   240
gacacctact ggtatccatg caatggatcc ggcaacagct gcaagtccta cgcaaagcaa   300
attgcgggta tcagcgccac gttcaacgcg cattccatga gatcggcag gatttggatc   360
gacatcgaga aagattctat ttgcaacaac gtaagtgggg ttgtcatact tttatctacc   420
cacctctaaa aactgcgtta ccactcagtg gaactacggc acttctggaa atagggacca   480
tgccaagaag ttgattaccg ccatcaagaa ctccggcttc aaatatggaa tctacagctc   540
tcctggggta agtgcatcca tgccctgaa cgcgaccgac acagtaactc cctatacagg   600
aatggagcac tatcttcggc tccgagagct tcgacctcga tagcggggcg ccactgtggt   660
ttgcgacatg gaacaacgtt caggtacgca ggttatgact cgtaactcta ggaggtgaa   720
tcactcatac gatatattat gcatacacag actctgacac tcggcacgca ctttggaggg   780
taagtctcta ggtttaaagg gttcgatata gatccataga ctaatccacg ttactctaat   840
aggtggacaa cgctcatgg acaccagtac acggataagt cagcctcggg tcaatttgac   900
ctcaacgtct tttcctcgta a                                             921

SEQ ID NO: 223          moltype = AA   length = 226
FEATURE                 Location/Qualifiers
source                  1..226
                        mol_type = protein
                        organism = Deconica coprophila
SEQUENCE: 223
MLFATFLCLA SYAFGSAYAL VHAVDSSSLV STATFSKAKS EGFTKAVIRG YQEACGSGGR    60
VDPNFVQTYK NARAAGITNI DTYWYPCNGS GNSCKSYAKQ IAGISATFNA HSMKIGRIWI   120
DIEKDSICNN WNYGTSGNRD HAKKLITAIK NSGFKYGIYS SPGEWSTIFG SESFDLDSGA   180
PLWFATWNNV QTLTLGTHFG GWTSAHGHQY TDKSASGQFD LNVFSS                  226
```

```
SEQ ID NO: 224          moltype = AA   length = 207
FEATURE                 Location/Qualifiers
source                  1..207
                        mol_type = protein
                        organism = Deconica coprophila
SEQUENCE: 224
LVHAVDSSSL VSTATFSKAK SEGFTKAVIR GYQEACGSGG RVDPNFVQTY KNARAAGITN    60
IDTYWYPCNG SGNSCKSYAK QIAGISATFN AHSMKIGRIW IDIEKDSICN NWNYGTSGNR   120
DHAKKLITAI KNSGFKYGIY SSPGEWSTIF GSESFDLDSG APLWFATWNN VQTLTLGTHF   180
GGWTSAHGHQ YTDKSASGQF DLNVFSS                                      207

SEQ ID NO: 225          moltype = DNA   length = 944
FEATURE                 Location/Qualifiers
sig_peptide             1..60
mat_peptide             61..941
source                  1..944
                        mol_type = genomic DNA
                        organism = Rhizomucor pusillus
CDS                     1..181
CDS                     242..484
CDS                     555..688
CDS                     757..825
CDS                     885..941
SEQUENCE: 225
atgaagtttg cactcctagt atctgctatc gcaggccttg cagcaaccgc cgtccaagcc    60
tacgaaactg gcgttgatgt ctctgccttg acttccacct ccgcctggag ctgtgcaaag   120
aaactcggtt acgatcacgc tattgtccgc tgctacattg aggcatacgg aggcaaccct   180
gcaagtatca tgcatcagag aagacgacta ctacgttcta gcgtgctaac aatgtactag   240
ggtggtaaaa ttgacagcaa ctgcttccag aactacaaga acgcaaagc aggtggattc   300
accagcgttg acatttacat gttccctgc actggccgct ccacatgcaa gtcgcccgct   360
gctcaggtca aggaggttgt tgactacgtt ggctccaaca agatgactgt tggacgtctc   420
tggctcgacg tcgaaatcga tccttctgct aacaactggc catccgccag tagcgctcgc   480
agcagtaaga aagaggacaa gaaaccaatt caggatgctc acaatgttgc taacattttt   540
tattacttgt taagccttga agtccttcaa gtctgctctt gactcgactg gctggaaata   600
cggtatctat tcttctgctt cccaatggtc gcagatcacc ggatcctcct cctgggagct   660
tgattcctcg ttgccacttt ggtacgctgt aagtagctct cacgttattc cgtatattgt   720
gggagaacgt ggctgatctg aatttattac cacaagcact acgacgcttc tctcagcttc   780
agcgactttt cgccatttgg tggctggact aagcctacca tcaaggtaaa tattcaggtc   840
atccggtgct tgacgcatat gtactcaatt aaattgccat ttagcaatat gctggctctg   900
taagcttctg ctccgctggc tgggacaaga actactatgg ctaa                   944

SEQ ID NO: 226          moltype = AA   length = 228
FEATURE                 Location/Qualifiers
source                  1..228
                        mol_type = protein
                        organism = Rhizomucor pusillus
SEQUENCE: 226
MKFALLVSAI AGLAATAVQA YETGVDVSAL TSTSAWSCAK KLGYDHAIVR CYIEAYGGNP    60
GGKIDSNCFQ NYKNAKAGGF TSVDIYMFPC TGRSTCKSPA AQVKEVVDYV GSNKMTVGRL   120
WLDVEIDPSA NNWPSASSAR STLKSFKSAL DSTGWKYGIY SSASQWSQIT GSSSWELDSS   180
LPLWYAHYDA SLSFSDFSPF GGWTKPTIKQ YAGSVSFCSA GWDKNYYG                228

SEQ ID NO: 227          moltype = AA   length = 208
FEATURE                 Location/Qualifiers
source                  1..208
                        mol_type = protein
                        organism = Rhizomucor pusillus
SEQUENCE: 227
YETGVDVSAL TSTSAWSCAK KLGYDHAIVR CYIEAYGGNP GGKIDSNCFQ NYKNAKAGGF    60
TSVDIYMFPC TGRSTCKSPA AQVKEVVDYV GSNKMTVGRL WLDVEIDPSA NNWPSASSAR   120
STLKSFKSAL DSTGWKYGIY SSASQWSQIT GSSSWELDSS LPLWYAHYDA SLSFSDFSPF   180
GGWTKPTIKQ YAGSVSFCSA GWDKNYYG                                     208

SEQ ID NO: 228          moltype = DNA   length = 909
FEATURE                 Location/Qualifiers
sig_peptide             1..60
mat_peptide             61..906
source                  1..909
                        mol_type = genomic DNA
                        organism = Stropharia semiglobata
CDS                     1..393
CDS                     447..545
CDS                     608..691
CDS                     744..772
CDS                     831..906
SEQUENCE: 228
atgttctctt tcgtcaaagc gctcatacta ctcccgaccc ttgtgacctc cgcatacgcc    60
cttgtatatg gcgtagactc gtccactcta gtctctactg caacgtacag taaagccaag   120
```

```
agcgagggct tcactaaggc tatcatccgc gggtatcagg aagcatgtgg cagtggtgga    180
cgcgtcgacc ccaacttcgt cgcgacctac aagaatgcac gggccgcggg tatcaccgat    240
atcgacatgt actggttccc atgcaacggg tccgtaact catgcaagtc gtacgctaag     300
cagctctccg agatcgcgaa tgtcttcagt gcgaatagca tgaaaattgg gacaatttgg    360
attgattttg agaaggattc tggttgcaac aacgtgagtt tcatggacat tatgtccttc    420
ataataaatt gacggatttt atcaagtgga actacggcac cacgggtaat ctcaaccatg    480
caaaggcact catctccgcg attaaagcga ctgggtttaa attcggtatc tacagctcac    540
ctggcgtaag gcttttacc tttcgtatcc gcttcatcaa gttaacttag tccgcgactc     600
gttttaggaa tggggtaccc tgtttgggtc caccggggta gtactcgata gctcggcccc    660
cctttggttc gctacgtgga acaatgtaaa ggtatgtgac cccgcctact acagaaataa    720
catctctcaa agtttaacca tagactctta ccttgggaac gcatttcggg gggtaagtgc    780
aatatatata catcgaaata tgggatattg aatactgacg ttgcttgaag gtggactaaa    840
gccgttggcc accagtatac agatgtgtcc gcctctggcc aattcgacct caatgtcttt    900
gcaaattaa                                                            909

SEQ ID NO: 229         moltype = AA  length = 227
FEATURE                Location/Qualifiers
source                 1..227
                       mol_type = protein
                       organism = Striopharia semiglobata
SEQUENCE: 229
MFSFVKALIL LPTLVTSAYA LVYGVDSSTL VSTATYSKAK SEGFTKAIIR GYQEACGSGG     60
RVDPNFVATY KNARAAGITD IDMYWFPCNG SGNSCKSYAK QLSEIANVFS ANSMKIGTIW    120
IDFEKDSGCN NWNYGTTGNL NHAKALISAI KATGFKFGIY SSPGEWGTLF GSTGVVLDSS    180
APLWFATWNN VKTLTLGTHF GGWTKAVGHQ YTDVSASGQF DLNVFAN                  227

SEQ ID NO: 230         moltype = AA  length = 207
FEATURE                Location/Qualifiers
source                 1..207
                       mol_type = protein
                       organism = Striopharia semiglobata
SEQUENCE: 230
LVYGVDSSTL VSTATYSKAK SEGFTKAIIR GYQEACGSGG RVDPNFVATY KNARAAGITD     60
IDMYWFPCNG SGNSCKSYAK QLSEIANVFS ANSMKIGTIW IDFEKDSGCN NWNYGTTGNL    120
NHAKALISAI KATGFKFGIY SSPGEWGTLF GSTGVVLDSS APLWFATWNN VKTLTLGTHF    180
GGWTKAVGHQ YTDVSASGQF DLNVFAN                                        207

SEQ ID NO: 231         moltype = DNA  length = 910
FEATURE                Location/Qualifiers
sig_peptide            1..60
mat_peptide            61..907
source                 1..910
                       mol_type = genomic DNA
                       organism = Striopharia semiglobata
CDS                    1..393
CDS                    447..545
CDS                    608..691
CDS                    744..772
CDS                    832..907
SEQUENCE: 231
atgttccctt tcgtcaaaac gctcatcctc ctcccggccc ttgtgacttc cgcgtatgcc     60
ctcgtatatg gcgtagactc gtctaccttg gtttctactg caacctacaa gaaagccaag    120
agcgagggct tcactaaggc tatcatccgc gggtatcagg aagcatgtgg cagtggtgga    180
cgcgtcgacc ccaacttcgt cgcgacctac aagaatgcac gggccgcggg tatcaccgat    240
atcgacatgt actggttccc atgcaacggg tccgtaact catgcaagtc gtacgctaag     300
cagctctccg agatcgcgaa tgtcttcagt gcgaatagca tgaaaattgg gacaatttgg    360
attgattttg agaaggattc tggttgcaac aacgtgagtt tcatggacat tatgtccttc    420
ataataaaat gacggatttt atcaagtgga actacggcac cacgggtaat ctcaaccatg    480
caaaggcact catctccgcg attaaagcga ctgggtttaa attcggtatc tacagctcac    540
ctggcgtaag gcttttacc tttcgtatcc gcttcatcaa gttaacttag tccgcgactc     600
gttttaggaa tggggtaccc tgtttgggtc caccggggta gtactcgata gctcggcccc    660
cctttggttc gctacgtgga acaatgtaaa ggtatgtgac cccgcctact acagaaataa    720
catctctcaa agtttaacca tagactctta ccttgggaac gcatttcggg gggtaagtgc    780
aatatatata catcgaaaga tgaataatt aaatactgat ctcgcttaaa ggtggactac     840
agccgcgggt caccagtaca cagacgtgtc ttcctctggc caattcgacc tcaatgtgtt    900
tgcaaattaa                                                           910

SEQ ID NO: 232         moltype = AA  length = 227
FEATURE                Location/Qualifiers
source                 1..227
                       mol_type = protein
                       organism = Striopharia semiglobata
SEQUENCE: 232
MFPFVKTLIL LPALVTSAYA LVYGVDSSTL VSTATYKKAK SEGFTKAIIR GYQEACGSGG     60
RVDPNFVATY KNARAAGITD IDMYWFPCNG SGNSCKSYAK QLSEIANVFS ANSMKIGTIW    120
IDFEKDSGCN NWNYGTTGNL NHAKALISAI KATGFKFGIY SSPGEWGTLF GSTGVVLDSS    180
APLWFATWNN VKTLTLGTHF GGWTTAAGHQ YTDVSSSGQF DLNVFAN                  227

SEQ ID NO: 233         moltype = AA  length = 207
```

```
FEATURE              Location/Qualifiers
source               1..207
                     mol_type = protein
                     organism = Stropharia semiglobata
SEQUENCE: 233
LVYGVDSSTL VSTATYKKAK SEGFTKAIIR GYQEACGSGG RVDPNFVATY KNARAAGITD    60
IDMYWFPCNG SGNSCKSYAK QLSEIANVFS ANSMKIGTIW IDFEKDSGCN NWNYGTTGNL   120
NHAKALISAI KATGFKFGIY SSPGEWGTLF GSTGVVLDSS APLWFATWNN VKTLTLGTHF   180
GGWTTAAGHQ YTDVSSSGQF DLNVFAN                                      207

SEQ ID NO: 234       moltype = DNA  length = 47
FEATURE              Location/Qualifiers
misc_feature         1..47
                     note = SEQ ID NO: 225 is the forward primer C8VSE-F.
source               1..47
                     mol_type = other DNA
                     organism = synthetic construct
SEQUENCE: 234
acacaactgg ggatccacca tgcttttcgc aacctttctt tgtcttg                  47

SEQ ID NO: 235       moltype = DNA  length = 45
FEATURE              Location/Qualifiers
misc_feature         1..45
                     note = SEQ ID NO: 226 is the reverse primer C8VSE-R.
source               1..45
                     mol_type = other DNA
                     organism = synthetic construct
SEQUENCE: 235
agatctcgag aagcttacga ggaaaagacg ttgaggtcaa attga                    45
```

POLYPEPTIDES HAVING LYSOZYME ACTIVITY, POLYNUCLEOTIDES ENCODING SAME AND USES AND COMPOSITIONS THEREOF

CROSS-REFERENCE TO RELATED APPLICATIONS

The present application is divisional of U.S. patent application Ser. No. 16/462,764, filed May 21, 2019, which is itself a 35 U.S.C. 371 national application of International Patent Application No. PCT/CN2017/117765, filed Dec. 21, 2017, which claims priority to International Patent Application Nos. PCT/CN2016/111317 and PCT/CN2017/075978, filed Dec. 21, 2016, and Mar. 8, 2017, respectively. The contents of the aforementioned applications are fully incorporated herein by reference.

REFERENCE TO A SEQUENCE LISTING

This application contains a Sequence Listing in computer readable form, which is incorporated herein by reference.

FIELD OF THE INVENTION

The present invention relates animal feed or animal feed additives comprising one or more polypeptides having lysozyme activity. The invention also relates to polypeptides having lysozyme activity, polynucleotides encoding the polypeptides nucleic acid constructs, vectors, and host cells comprising the polynucleotides as well as methods of producing and using the polypeptides.

BACKGROUND OF THE INVENTION

Lysozyme is an O-glycosyl hydrolase produced as a defensive mechanism against bacteria by many organisms. The enzyme causes the hydrolysis of bacterial cell walls by cleaving the glycosidic bonds of peptidoglycan; an important structural molecule in bacteria. After having their cell walls weakened by lysozyme action, bacterial cells lyse as a result of unbalanced osmotic pressure.

Lysozyme naturally occurs in many organisms such as viruses, plants, insects, birds, reptiles and mammals. In mammals, Lysozyme has been isolated from nasal secretions, saliva, tears, intestinal content, urine and milk. The enzyme cleaves the glycosidic bond between carbon number 1 of N-acetylmuramic acid and carbon number 4 of N-acetyl-D-glucosamine. In vivo, these two carbohydrates are polymerized to form the cell wall polysaccharide of many microorganisms.

Lysozyme has been classified into five different glycoside hydrolase (GH) families (CAZy, www.cazy.org): hen egg-white lysozyme (GH22), goose egg-white lysozyme (GH23), bacteriophage T4 lysozyme (GH24), Sphingomonas flagellar protein (GH73) and Chalaropsis lysozymes (GH25). Lysozymes from the families GH23 and GH24 are primarily known from bacteriophages and have recently been identified in fungi. The lysozyme family GH25 has been found to be structurally unrelated to the other lysozyme families.

Lysozyme extracted from hen egg white is the primary product available on the commercial market, but does not cleave N,6-O-diacetylmuramic acid in e.g. Staphylococcus aureus cell walls and is thus unable to lyse this important human pathogen among others (Masschalck B, Deckers D, Michiels C W (2002), "Lytic and nonlytic mechanism of inactivation of gram-positive bacteria by lysozyme under atmospheric and high hydrostatic pressure", J Food Prot. 65(12):1916-23).

Antimicrobial growth promoters (AGP's) have traditionally been used for growth promotion in animals, and probably work by preventing low level infections by pathogens such as Clostridium perfringens. However, AGP's are increasingly being banned worldwide and therefore new solutions to promote animal growth but which are not AGP's are of interest.

WO2013/076253 and WO2005/080559 disclose GH25 lysozymes for use in animal feed. However, said lysozymes are not highly active in degrading the cell wall from Micrococcus lysodeikticus (a typical lysozyme activity assay) and more active lysozymes would be desired.

The object of the present invention is to provide new and more active lysozymes which could be suitable for animal health.

SUMMARY OF THE INVENTION

The invention relates to polypeptides which have improved lysozyme activity against the peptidoglycans found in the cell walls of Micrococcus lysodeikticus. The lysozymes of the invention are all GH25 lysozymes and all have improved ability to lyse bacterial cell walls of Micrococcus lysodeikticus, thereby rendering them suitable for use in animal feed to improve the animal health. The lysozymes of the invention have improved activity compared to the lysozyme described in WO2013/076253 (it is described herein as SEQ ID NO 159). A large subset of the GH25 lysozymes have surprisingly been found to furthermore have lysozyme activity against Lactobacillus johnsonii. Lactobacillus johnsonii is an important bacterium of the intestinal flora of animals. Without being bound to a particular theory, it is believed that removal of dead Lactobacillus johnsonii cells from the intestinal flora, by means of enzymatic lyses of the partially degraded bacterial cell wall, to be an important contributor to intestinal health of an animal.

An aspect of the invention is directed to an isolated GH25 polypeptide having lysozyme activity selected from the group consisting of:
(a) a polypeptide having at least 80% sequence identity to the polypeptide of SEQ ID NO: 3;
(b) a polypeptide having at least 84% sequence identity to the polypeptide of SEQ ID NO: 6;
(c) a polypeptide having at least 80% sequence identity to the polypeptide of SEQ ID NO: 9;
(d) a polypeptide having at least 80% sequence identity to the polypeptide of SEQ ID NO: 12;
(e) a polypeptide having at least 80% sequence identity to the polypeptide of SEQ ID NO: 15;
(f) a polypeptide having at least 80% sequence identity to the polypeptide of SEQ ID NO: 18;
(g) a polypeptide having at least 80% sequence identity to the polypeptide of SEQ ID NO: 21;
(h) a polypeptide having at least 80% sequence identity to the polypeptide of SEQ ID NO: 24;
(i) a polypeptide having at least 80% sequence identity to the polypeptide of SEQ ID NO: 27;
(j) a polypeptide having at least 84% sequence identity to the polypeptide of SEQ ID NO: 30;
(k) a polypeptide having at least 80% sequence identity to the polypeptide of SEQ ID NO: 33;
(l) a polypeptide having at least 80% sequence identity to the polypeptide of SEQ ID NO: 36;

(m) a polypeptide having at least 84% sequence identity to the polypeptide of SEQ ID NO: 39;
(n) a polypeptide having at least 80% sequence identity to the polypeptide of SEQ ID NO: 42;
(o) a polypeptide having at least 80% sequence identity to the polypeptide of SEQ ID NO: 45;
(p) a polypeptide having at least 80% sequence identity to the polypeptide of SEQ ID NO: 48;
(q) a polypeptide having at least 80% sequence identity to the polypeptide of SEQ ID NO: 51;
(r) a polypeptide having at least 80% sequence identity to the polypeptide of SEQ ID NO: 54;
(s) a polypeptide having at least 80% sequence identity to the polypeptide of SEQ ID NO: 57;
(t) a polypeptide having at least 80% sequence identity to the polypeptide of SEQ ID NO: 60;
(u) a polypeptide having at least 80% sequence identity to the polypeptide of SEQ ID NO: 63;
(v) a polypeptide having at least 80% sequence identity to the polypeptide of SEQ ID NO: 66;
(w) a polypeptide having at least 80% sequence identity to the polypeptide of SEQ ID NO: 69;
(x) a polypeptide having at least 84% sequence identity to the polypeptide of SEQ ID NO: 72;
(y) a polypeptide having at least 80% sequence identity to the polypeptide of SEQ ID NO: 75;
(z) a polypeptide having at least 80% sequence identity to the polypeptide of SEQ ID NO: 80;
(aa) a polypeptide having at least 80% sequence identity to the polypeptide of SEQ ID NO: 83;
(ab) a polypeptide having at least 80% sequence identity to the polypeptide of SEQ ID NO: 86;
(ac) a polypeptide having at least 86% sequence identity to the polypeptide of SEQ ID NO: 89;
(ad) a polypeptide having at least 82% sequence identity to the polypeptide of SEQ ID NO: 92;
(ae) a polypeptide having at least 82% sequence identity to the polypeptide of SEQ ID NO: 95;
(af) a polypeptide having at least 80% sequence identity to the polypeptide of SEQ ID NO: 98;
(ag) a polypeptide having at least 80% sequence identity to the polypeptide of SEQ ID NO: 101;
(ah) a polypeptide having at least 80% sequence identity to the polypeptide of SEQ ID NO: 104;
(ai) a polypeptide having at least 80% sequence identity to the polypeptide of SEQ ID NO: 107;
(aj) a polypeptide having at least 82% sequence identity to the polypeptide of SEQ ID NO: 110;
(ak) a polypeptide having at least 81% sequence identity to the polypeptide of SEQ ID NO: 113;
(al) a polypeptide having at least 80% sequence identity to the polypeptide of SEQ ID NO: 116;
(am) a polypeptide having at least 80% sequence identity to the polypeptide of SEQ ID NO: 119;
(an) a polypeptide having at least 80% sequence identity to the polypeptide of SEQ ID NO: 122;
(ao) a polypeptide having at least 80% sequence identity to the polypeptide of SEQ ID NO: 125;
(ap) a polypeptide having at least 80% sequence identity to the polypeptide of SEQ ID NO: 128;
(aq) a polypeptide having at least 80% sequence identity to the polypeptide of SEQ ID NO: 131;
(ar) a polypeptide having at least 80% sequence identity to the polypeptide of SEQ ID NO: 134;
(as) a polypeptide having at least 80% sequence identity to the polypeptide of SEQ ID NO: 137;
(at) a polypeptide having at least 80% sequence identity to the polypeptide of SEQ ID NO: 140;
(au) a polypeptide having at least 80% sequence identity to the polypeptide of SEQ ID NO: 143;
(av) a polypeptide having at least 80% sequence identity to the polypeptide of SEQ ID NO: 146;
(aw) a polypeptide having at least 80% sequence identity to the polypeptide of SEQ ID NO: 149;
(ax) a polypeptide having at least 80% sequence identity to the polypeptide of SEQ ID NO: 152;
(ay) a polypeptide having at least 80% sequence identity to the polypeptide of SEQ ID NO: 155;
(az) a polypeptide having at least 80% sequence identity to the polypeptide of SEQ ID NO: 158;
(ba) a polypeptide having at least 80% sequence identity to the polypeptide of SEQ ID NO: 221;
(bb) a polypeptide having at least 80% sequence identity to the polypeptide of SEQ ID NO: 224;
(bc) a polypeptide having at least 80% sequence identity to the polypeptide of SEQ ID NO: 227;
(bd) a polypeptide having at least 80% sequence identity to the polypeptide of SEQ ID NO: 230;
(be) a polypeptide having at least 80% sequence identity to the polypeptide of SEQ ID NO: 233;
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27 or 28 positions;
(bg) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal His-tag and/or HQ-tag;
(bh) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal extension of up to 10 amino acids, e.g. 1, 2, 3, 4, 5, 6, 7, 8, 9 or 10 amino acids; and (bi) a fragment of the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) having lysozyme activity and having at least 90% of the length of the mature polypeptide.

A further aspect of the invention is directed to an isolated GH25 polypeptide having lysozyme activity selected from the group consisting of:

(a) a polypeptide having at least 90% sequence identity to the polypeptide of SEQ ID NO: 3;
(b) a polypeptide having at least 90% sequence identity to the polypeptide of SEQ ID NO: 6;
(e) a polypeptide having at least 90% sequence identity to the polypeptide of SEQ ID NO: 15;
(f) a polypeptide having at least 90% sequence identity to the polypeptide of SEQ ID NO: 18;
(g) a polypeptide having at least 90% sequence identity to the polypeptide of SEQ ID NO: 21;
(h) a polypeptide having at least 90% sequence identity to the polypeptide of SEQ ID NO: 24;
(k) a polypeptide having at least 90% sequence identity to the polypeptide of SEQ ID NO: 33;
(l) a polypeptide having at least 90% sequence identity to the polypeptide of SEQ ID NO: 36;
(m) a polypeptide having at least 90% sequence identity to the polypeptide of SEQ ID NO: 39;
(o) a polypeptide having at least 90% sequence identity to the polypeptide of SEQ ID NO: 45;
(p) a polypeptide having at least 90% sequence identity to the polypeptide of SEQ ID NO: 48;
(q) a polypeptide having at least 90% sequence identity to the polypeptide of SEQ ID NO: 51;
(r) a polypeptide having at least 90% sequence identity to the polypeptide of SEQ ID NO: 54;
(s) a polypeptide having at least 90% sequence identity to the polypeptide of SEQ ID NO: 57;
(t) a polypeptide having at least 90% sequence identity to the polypeptide of SEQ ID NO: 60;
(x) a polypeptide having at least 90% sequence identity to the polypeptide of SEQ ID NO: 72;
(y) a polypeptide having at least 90% sequence identity to the polypeptide of SEQ ID NO: 75;
(z) a polypeptide having at least 90% sequence identity to the polypeptide of SEQ ID NO: 80;
(ac) a polypeptide having at least 90% sequence identity to the polypeptide of SEQ ID NO: 89;
(ae) a polypeptide having at least 90% sequence identity to the polypeptide of SEQ ID NO: 95;
(af) a polypeptide having at least 90% sequence identity to the polypeptide of SEQ ID NO: 98;
(ag) a polypeptide having at least 90% sequence identity to the polypeptide of SEQ ID NO: 101;
(ak) a polypeptide having at least 90% sequence identity to the polypeptide of SEQ ID NO: 113;
(al) a polypeptide having at least 90% sequence identity to the polypeptide of SEQ ID NO: 116;
(am) a polypeptide having at least 90% sequence identity to the polypeptide of SEQ ID NO: 119;
(an) a polypeptide having at least 90% sequence identity to the polypeptide of SEQ ID NO: 122;
(aq) a polypeptide having at least 90% sequence identity to the polypeptide of SEQ ID NO: 131;
(as) a polypeptide having at least 90% sequence identity to the polypeptide of SEQ ID NO: 137;
(au) a polypeptide having at least 90% sequence identity to the polypeptide of SEQ ID NO: 143;
(av) a polypeptide having at least 90% sequence identity to the polypeptide of SEQ ID NO: 146;
(aw) a polypeptide having at least 90% sequence identity to the polypeptide of SEQ ID NO: 149;
(ax) a polypeptide having at least 90% sequence identity to the polypeptide of SEQ ID NO: 152;
(ay) a polypeptide having at least 90% sequence identity to the polypeptide of SEQ ID NO: 155;
(ba) a polypeptide having at least 90% sequence identity to the polypeptide of SEQ ID NO: 221;
(bd) a polypeptide having at least 90% sequence identity to the polypeptide of SEQ ID NO: 230;
(be) a polypeptide having at least 90% sequence identity to the polypeptide of SEQ ID NO: 233; and
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions.

As stated, the polypeptides of the invention have improved lysozyme activity. An interesting embodiment of the invention relates to the polypeptides of the invention having improved lysozyme activity a) compared to the lysozyme activity of hen eggwhite lysozyme (HEWL) or b) compared to the lysozyme activity of of SEQ ID NO: 159 as determined by any one of i) Method for the Determination of Lysozyme Activity Against *Micrococcus lysodeikticus* and ii) Method for the Determination of Lysozyme Activity Against *Lactobacillus johnsonii*.

A further aspect of the invention is directed to a method of hydrolysing peptidoglycan in bacterial cell walls comprising treating bacterial cells with one or more GH25 polypeptides having lysozyme activity, wherein the polypeptide is as defined above.

The invention is furthermore directed to a method of increasing the digestibility of peptidoglycans in animal feed comprising the use of a polypeptide as described herein and to an animal feed additive or animal feed comprising the polypeptide as defined herein. A related aspect of the invention is directed to a zootechnical additive for use in feed for poultry or swine, said additive comprising the polypeptide as defined herein.

An aspect of the invention is directed to a method of improving the intestinal health in an animal comprising reducing the amount of dead *Lactobacillus johnsonii* cells, or cell wall debris therefrom, in the digestive tract of said animal, comprising feeding the animal with a feed or feed additive comprising a polypeptide as defined by the invention.

An aspect of the invention is directed to a method of improving the intestinal health in an animal comprising reducing the amount of dead *Lactobacillus johnsonii* cells, or cell wall debris therefrom, in the digestive tract of said animal, comprising feeding the animal with a feed or feed additive comprising a polypeptide selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 159.

An aspect of the invention is directed to a method of promoting the elimination of dead *Lactobacillus johnsonii* cells, or cell wall debris therefrom, from the digestive tract of an animal comprising feeding said animal a polypeptide or source of a polypeptide selected from the group consisting of a polypeptide having at least 90% sequence identity to the polypeptide of SEQ ID NO: 15, a polypeptide having at least 90% sequence identity to the polypeptide of SEQ ID NO: 36, a polypeptide having at least 90% sequence identity to the polypeptide of SEQ ID NO: 75, a polypeptide having at least 90% sequence identity to the polypeptide of SEQ ID NO: 80, and a polypeptide having at least 90% sequence identity to the polypeptide of SEQ ID NO: 119 or a polypeptide or source of a polypeptide selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 159.

The invention also relates to a granule comprising one or more GH25 polypeptides as described above. The invention further relates to an isolated polypeptide having lysozyme activity as described in the claims.

The invention further relates to compositions comprising the polypeptide of the invention, such as animal feed additives or animal feed; use of the polypeptide of the invention in animal feed, in animal feed additives, in the preparation of a composition for use in animal feed, for improving one or more performance parameters in an animal; and isolated polynucleotides encoding the polypeptides of the invention, recombinant host cells and method of producing the polypeptide of the invention.

Overview of Sequence Listing

SEQ ID NO: 1 is the cDNA sequence of a GH25 lysozyme as isolated from *Sporormia fimetaria*.
SEQ ID NO: 2 is the amino acid sequence as deduced from SEQ ID NO: 1.
SEQ ID NO: 3 is the amino acid sequence of the mature GH25 lysozyme from *Sporormia fimetaria*.
SEQ ID NO: 4 is the cDNA sequence of a GH25 lysozyme as isolated from *Poronia punctata*.
SEQ ID NO: 5 is the amino acid sequence as deduced from SEQ ID NO: 4.
SEQ ID NO: 6 is the amino acid sequence of the mature GH25 lysozyme from *Poronia punctata*.
SEQ ID NO: 7 is the cDNA sequence of a GH25 lysozyme as isolated from *Poronia punctata*.
SEQ ID NO: 8 is the amino acid sequence as deduced from SEQ ID NO: 7.
SEQ ID NO: 9 is the amino acid sequence of the mature GH25 lysozyme from *Poronia punctata*.
SEQ ID NO: 10 is the cDNA sequence of a GH25 lysozyme as isolated from *Lecanicillium* sp. VVMM742.
SEQ ID NO: 11 is the amino acid sequence as deduced from SEQ ID NO: 10.
SEQ ID NO: 12 is the amino acid sequence of the mature GH25 lysozyme from *Lecanicillium* sp. VVMM742.
SEQ ID NO: 13 is the cDNA sequence of a GH25 lysozyme as isolated from *Lecanicillium* sp. VVMM742.
SEQ ID NO: 14 is the amino acid sequence as deduced from SEQ ID NO: 13.
SEQ ID NO: 15 is the amino acid sequence of the mature GH25 lysozyme from *Lecanicillium* sp. VVMM742.
SEQ ID NO: 16 is the cDNA sequence of a GH25 lysozyme as isolated from *Onygena equina*.
SEQ ID NO: 17 is the amino acid sequence as deduced from SEQ ID NO: 16.
SEQ ID NO: 18 is the amino acid sequence of the mature GH25 lysozyme from *Onygena equina*.
SEQ ID NO: 19 is the cDNA sequence of a GH25 lysozyme as isolated from *Purpureocillium lilacinum*.
SEQ ID NO: 20 is the amino acid sequence as deduced from SEQ ID NO: 19.
SEQ ID NO: 21 is the amino acid sequence of the mature GH25 lysozyme from *Purpureocillium lilacinum*.
SEQ ID NO: 22 is the cDNA sequence of a GH25 lysozyme as isolated from *Trichobolus zukalii*.
SEQ ID NO: 23 is the amino acid sequence as deduced from SEQ ID NO: 22.
SEQ ID NO: 24 is the amino acid sequence of the mature GH25 lysozyme from *Trichobolus zukalii*.
SEQ ID NO: 25 is the cDNA sequence of a GH25 lysozyme as isolated from *Penicillium citrinum*.
SEQ ID NO: 26 is the amino acid sequence as deduced from SEQ ID NO: 25.
SEQ ID NO: 27 is the amino acid sequence of the mature GH25 lysozyme from *Penicillium citrinum*.
SEQ ID NO: 28 is the cDNA sequence of a GH25 lysozyme as isolated from *Cladorrhinum bulbillosum*.
SEQ ID NO: 29 is the amino acid sequence as deduced from SEQ ID NO: 28.
SEQ ID NO: 30 is the amino acid sequence of the mature GH25 lysozyme from *Cladorrhinum bulbillosum*.
SEQ ID NO: 31 is the cDNA sequence of a GH25 lysozyme as isolated from *Umbelopsis westeae*.
SEQ ID NO: 32 is the amino acid sequence as deduced from SEQ ID NO: 31.
SEQ ID NO: 33 is the amino acid sequence of the mature GH25 lysozyme from *Umbelopsis westeae*.
SEQ ID NO: 34 is the cDNA sequence of a GH25 lysozyme as isolated from *Zygomycetes* sp. XZ2655.
SEQ ID NO: 35 is the amino acid sequence as deduced from SEQ ID NO: 34.
SEQ ID NO: 36 is the amino acid sequence of the mature GH25 lysozyme from *Zygomycetes* sp. XZ2655.
SEQ ID NO: 37 is the cDNA sequence of a GH25 lysozyme as isolated from *Chaetomium cupreum*.
SEQ ID NO: 38 is the amino acid sequence as deduced from SEQ ID NO: 37.
SEQ ID NO: 39 is the amino acid sequence of the mature GH25 lysozyme from *Chaetomium cupreum*.
SEQ ID NO: 40 is the cDNA sequence of a GH25 lysozyme as isolated from *Cordyceps cardinalis*.

SEQ ID NO: 41 is the amino acid sequence as deduced from SEQ ID NO: 40.
SEQ ID NO: 42 is the amino acid sequence of the mature GH25 lysozyme from *Cordyceps cardinalis*.
SEQ ID NO: 43 is the cDNA sequence of a GH25 lysozyme as isolated from *Penicillium* sp. 'qii'.
SEQ ID NO: 44 is the amino acid sequence as deduced from SEQ ID NO: 43.
SEQ ID NO: 45 is the amino acid sequence of the mature GH25 lysozyme from *Penicillium* sp. 'qii'.
SEQ ID NO: 46 is the cDNA sequence of a GH25 lysozyme as isolated from *Aspergillus* sp. nov. XZ2609.
SEQ ID NO: 47 is the amino acid sequence as deduced from SEQ ID NO: 46.
SEQ ID NO: 48 is the amino acid sequence of the mature GH25 lysozyme from *Aspergillus* sp. nov. XZ2609.
SEQ ID NO: 49 is the cDNA sequence of a GH25 lysozyme as isolated from *Paecilomyces* sp. XZ2658.
SEQ ID NO: 50 is the amino acid sequence as deduced from SEQ ID NO: 49.
SEQ ID NO: 51 is the amino acid sequence of the mature GH25 lysozyme from *Paecilomyces* sp. XZ2658.
SEQ ID NO: 52 is the cDNA sequence of a GH25 lysozyme as isolated from *Paecilomyces* sp. XZ2658.
SEQ ID NO: 53 is the amino acid sequence as deduced from SEQ ID NO: 52.
SEQ ID NO: 54 is the amino acid sequence of the mature GH25 lysozyme from *Paecilomyces* sp. XZ2658.
SEQ ID NO: 55 is the cDNA sequence of a GH25 lysozyme as isolated from *Rhizomucor pusillus*.
SEQ ID NO: 56 is the amino acid sequence as deduced from SEQ ID NO: 55.
SEQ ID NO: 57 is the amino acid sequence of the mature GH25 lysozyme from *Rhizomucor pusillus*.
SEQ ID NO: 58 is the cDNA sequence of a GH25 lysozyme as isolated from *Pycnidiophora* cf. *dispera*.
SEQ ID NO: 59 is the amino acid sequence as deduced from SEQ ID NO: 58.
SEQ ID NO: 60 is the amino acid sequence of the mature GH25 lysozyme from *Pycnidiophora* cf. *dispera*.
SEQ ID NO: 61 is the cDNA sequence of a GH25 lysozyme as isolated from *Thermomucor indicae-seudaticae*.
SEQ ID NO: 62 is the amino acid sequence as deduced from SEQ ID NO: 61.
SEQ ID NO: 63 is the amino acid sequence of the mature GH25 lysozyme from *Thermomucor indicae-seudaticae*.
SEQ ID NO: 64 is the cDNA sequence of a GH25 lysozyme as isolated from *Isaria farinosa*.
SEQ ID NO: 65 is the amino acid sequence as deduced from SEQ ID NO: 64.
SEQ ID NO: 66 is the amino acid sequence of the mature GH25 lysozyme from *Isaria farinosa*.
SEQ ID NO: 67 is the cDNA sequence of a GH25 lysozyme as isolated from *Lecanicillium* sp. WMM742.
SEQ ID NO: 68 is the amino acid sequence as deduced from SEQ ID NO: 67.
SEQ ID NO: 69 is the amino acid sequence of the mature GH25 lysozyme from *Lecanicillium* sp. WMM742.
SEQ ID NO: 70 is the cDNA sequence of a GH25 lysozyme as isolated from *Zopfiella* sp. t180-6.
SEQ ID NO: 71 is the amino acid sequence as deduced from SEQ ID NO: 70.
SEQ ID NO: 72 is the amino acid sequence of the mature GH25 lysozyme from *Zopfiella* sp. t180-6.
SEQ ID NO: 73 is the cDNA sequence of a GH25 lysozyme as isolated from *Malbranchea flava*.
SEQ ID NO: 74 is the amino acid sequence as deduced from SEQ ID NO: 73.
SEQ ID NO: 75 is the amino acid sequence of the mature GH25 lysozyme from *Malbranchea flava*.
SEQ ID NO: 76 is the cDNA sequence of a GH25 lysozyme as isolated from *Hypholoma polytrichi*.
SEQ ID NO: 77 is the amino acid sequence as deduced from SEQ ID NO: 76.
SEQ ID NO: 78 is the codon optimised DNA the GH25 lysozyme as isolated from *Hypholoma polytrichi*.
SEQ ID NO: 79 is the amino acid sequence as deduced from SEQ ID NO: 78.
SEQ ID NO: 80 is the amino acid sequence of the mature GH25 lysozyme from *Hypholoma polytrichi*.
SEQ ID NO: 81 is the cDNA sequence of a GH25 lysozyme as isolated from *Aspergillus deflectus*.
SEQ ID NO: 82 is the amino acid sequence as deduced from SEQ ID NO: 81.
SEQ ID NO: 83 is the amino acid sequence of the mature GH25 lysozyme from *Aspergillus deflectus*.
SEQ ID NO: 84 is the cDNA sequence of a GH25 lysozyme as isolated from *Ascobolus stictoideus*.
SEQ ID NO: 85 is the amino acid sequence as deduced from SEQ ID NO: 84.
SEQ ID NO: 86 is the amino acid sequence of the mature GH25 lysozyme from *Ascobolus stictoideus*.
SEQ ID NO: 87 is the cDNA sequence of a GH25 lysozyme as isolated from *Coniochaeta* sp.
SEQ ID NO: 88 is the amino acid sequence as deduced from SEQ ID NO: 87.
SEQ ID NO: 89 is the amino acid sequence of the mature GH25 lysozyme from *Coniochaeta* sp.
SEQ ID NO: 90 is the cDNA sequence of a GH25 lysozyme as isolated from *Daldinia fissa*.
SEQ ID NO: 91 is the amino acid sequence as deduced from SEQ ID NO: 90.
SEQ ID NO: 92 is the amino acid sequence of the mature GH25 lysozyme from *Daldinia fissa*.
SEQ ID NO: 93 is the cDNA sequence of a GH25 lysozyme as isolated from *Rosellinia* sp.
SEQ ID NO: 94 is the amino acid sequence as deduced from SEQ ID NO: 93.
SEQ ID NO: 95 is the amino acid sequence of the mature GH25 lysozyme from *Rosellinia* sp.
SEQ ID NO: 96 is the cDNA sequence of a GH25 lysozyme as isolated from *Ascobolus* sp. ZY179.
SEQ ID NO: 97 is the amino acid sequence as deduced from SEQ ID NO: 96.
SEQ ID NO: 98 is the amino acid sequence of the mature GH25 lysozyme from *Ascobolus* sp. ZY179.
SEQ ID NO: 99 is the cDNA sequence of a GH25 lysozyme as isolated from *Curreya* sp. XZ2623.
SEQ ID NO: 100 is the amino acid sequence as deduced from SEQ ID NO: 99.
SEQ ID NO: 101 is the amino acid sequence of the mature GH25 lysozyme from *Curreya* sp. XZ2623.
SEQ ID NO: 102 is the cDNA sequence of a GH25 lysozyme as isolated from *Coniothyrium* sp.
SEQ ID NO: 103 is the amino acid sequence as deduced from SEQ ID NO: 102.
SEQ ID NO: 104 is the amino acid sequence of the mature GH25 lysozyme from *Coniothyrium* sp.

SEQ ID NO: 105 is the cDNA sequence of a GH25 lysozyme as isolated from *Hypoxylon* sp.
SEQ ID NO: 106 is the amino acid sequence as deduced from SEQ ID NO: 105.
SEQ ID NO: 107 is the amino acid sequence of the mature GH25 lysozyme from *Hypoxylon* sp.
SEQ ID NO: 108 is the cDNA sequence of a GH25 lysozyme as isolated from *Xylariaceae* sp. 1653h.
SEQ ID NO: 109 is the amino acid sequence as deduced from SEQ ID NO: 108.
SEQ ID NO: 110 is the amino acid sequence of the mature GH25 lysozyme from *Xylariaceae* sp. 1653h.
SEQ ID NO: 111 is the cDNA sequence of a GH25 lysozyme as isolated from *Hypoxylon* sp.
SEQ ID NO: 112 is the amino acid sequence as deduced from SEQ ID NO: 111.
SEQ ID NO: 113 is the amino acid sequence of the mature GH25 lysozyme from *Hypoxylon* sp.
SEQ ID NO: 114 is the cDNA sequence of a GH25 lysozyme as isolated from *Yunnania penicillata*.
SEQ ID NO: 115 is the amino acid sequence as deduced from SEQ ID NO: 114.
SEQ ID NO: 116 is the amino acid sequence of the mature GH25 lysozyme from *Yunnania penicillata*.
SEQ ID NO: 117 is the cDNA sequence of a GH25 lysozyme as isolated from *Engyodontium album*.
SEQ ID NO: 118 is the amino acid sequence as deduced from SEQ ID NO: 117.
SEQ ID NO: 119 is the amino acid sequence of the mature GH25 lysozyme from *Engyodontium album*.
SEQ ID NO: 120 is the cDNA sequence of a GH25 lysozyme as isolated from *Metapochonia bulbillosa*.
SEQ ID NO: 121 is the amino acid sequence as deduced from SEQ ID NO: 120.
SEQ ID NO: 122 is the amino acid sequence of the mature GH25 lysozyme from *Metapochonia bulbillosa*.
SEQ ID NO: 123 is the cDNA sequence of a GH25 lysozyme as isolated from *Hamigera paravellanea*.
SEQ ID NO: 124 is the amino acid sequence as deduced from SEQ ID NO: 123.
SEQ ID NO: 125 is the amino acid sequence of the mature GH25 lysozyme from *Hamigera paravellanea*.
SEQ ID NO: 126 is the cDNA sequence of a GH25 lysozyme as isolated from *Metarhizium iadini*.
SEQ ID NO: 127 is the amino acid sequence as deduced from SEQ ID NO: 126.
SEQ ID NO: 128 is the amino acid sequence of the mature GH25 lysozyme from *Metarhizium iadini*.
SEQ ID NO: 129 is the cDNA sequence of a GH25 lysozyme as isolated from *Thermoascus aurantiacus*.
SEQ ID NO: 130 is the amino acid sequence as deduced from SEQ ID NO: 129.
SEQ ID NO: 131 is the amino acid sequence of the mature GH25 lysozyme from *Thermoascus aurantiacus*.
SEQ ID NO: 132 is the cDNA sequence of a GH25 lysozyme as isolated from *Clonostachys rossmaniae*.
SEQ ID NO: 133 is the amino acid sequence as deduced from SEQ ID NO: 132.
SEQ ID NO: 134 is the amino acid sequence of the mature GH25 lysozyme from *Clonostachys rossmaniae*.
SEQ ID NO: 135 is the cDNA sequence of a GH25 lysozyme as isolated from *Simplicillium obclavatum*.
SEQ ID NO: 136 is the amino acid sequence as deduced from SEQ ID NO: 135.
SEQ ID NO: 137 is the amino acid sequence of the mature GH25 lysozyme from *Simplicillium obclavatum*.
SEQ ID NO: 138 is the cDNA sequence of a GH25 lysozyme as isolated from *Aspergillus inflatus*.
SEQ ID NO: 139 is the amino acid sequence as deduced from SEQ ID NO: 138.
SEQ ID NO: 140 is the amino acid sequence of the mature GH25 lysozyme from *Aspergillus inflatus*.
SEQ ID NO: 141 is the cDNA sequence of a GH25 lysozyme as isolated from *Paracremonium inflatum*.
SEQ ID NO: 142 is the amino acid sequence as deduced from SEQ ID NO: 141.
SEQ ID NO: 143 is the amino acid sequence of the mature GH25 lysozyme from *Paracremonium inflatum*.
SEQ ID NO: 144 is the cDNA sequence of a GH25 lysozyme as isolated from *Westerdykella* sp.
SEQ ID NO: 145 is the amino acid sequence as deduced from SEQ ID NO: 144.
SEQ ID NO: 146 is the amino acid sequence of the mature GH25 lysozyme from *Westerdykella* sp.
SEQ ID NO: 147 is the cDNA sequence of a GH25 lysozyme as isolated from *Stropharia semiglobata*.
SEQ ID NO: 148 is the amino acid sequence as deduced from SEQ ID NO: 147.
SEQ ID NO: 149 is the amino acid sequence of the mature GH25 lysozyme from *Stropharia semiglobata*.
SEQ ID NO: 150 is the cDNA sequence of a GH25 lysozyme as isolated from *Stropharia semiglobata*.
SEQ ID NO: 151 is the amino acid sequence as deduced from SEQ ID NO: 150.
SEQ ID NO: 152 is the amino acid sequence of the mature GH25 lysozyme from *Stropharia semiglobata*.
SEQ ID NO: 153 is the cDNA sequence of a GH25 lysozyme as isolated from *Stropharia semiglobata*.
SEQ ID NO: 154 is the amino acid sequence as deduced from SEQ ID NO: 153.
SEQ ID NO: 155 is the amino acid sequence of the mature GH25 lysozyme from *Stropharia semiglobata*.
SEQ ID NO: 156 is the cDNA sequence of a GH25 lysozyme as isolated from *Gelasinospora cratophora*.
SEQ ID NO: 157 is the amino acid sequence as deduced from SEQ ID NO: 156.
SEQ ID NO: 158 is the amino acid sequence of the mature GH25 lysozyme from *Gelasinospora cratophora*.
SEQ ID NO: 159 is the mature amino acid sequence of a wild type GH25 lysozyme from *Acremonium alcalophilum* as described in WO 2013/076253.
SEQ ID NO: 160 is the conserved motif YKNA.
SEQ ID NO: 161 is the conserved motif FGGW[S/T].
SEQ ID NO: 162 is the forward primer C8VRJ-F.
SEQ ID NO: 163 is the reverse primer C8VRJ-R.
SEQ ID NO: 164 is the forward primer C8VRQ-F.
SEQ ID NO: 165 is the reverse primer C8VRQ-R.
SEQ ID NO: 166 is the forward primer C8VS9-F.
SEQ ID NO: 167 is the reverse primer C8VS9-R.
SEQ ID NO: 168 is the forward primer C8VSA-F.
SEQ ID NO: 169 is the reverse primer C8VSA-R.
SEQ ID NO: 170 is the forward primer C8VSC-F.
SEQ ID NO: 171 is the reverse primer C8VSC-R.
SEQ ID NO: 172 is the forward primer C8VRT-F.
SEQ ID NO: 173 is the reverse primer C8VRT-R.
SEQ ID NO: 174 is the forward primer C8VS8-F.
SEQ ID NO: 175 is the reverse primer C8VS8-R.
SEQ ID NO: 176 is the forward primer C122P5-F.
SEQ ID NO: 177 is the reverse primer C122P5-R.
SEQ ID NO: 178 is the forward primer C6ZGC-F.
SEQ ID NO: 179 is the reverse primer C6ZGC-R.
SEQ ID NO: 180 is the forward primer C6ZG7-FF.
SEQ ID NO: 181 is the reverse primer C6ZG7-R.

SEQ ID NO: 182 is the forward primer C122PC-F.
SEQ ID NO: 183 is the reverse primer C122PC-R.
SEQ ID NO: 184 is the forward primer C122PA-F.
SEQ ID NO: 185 is the reverse primer C122PA-R.
SEQ ID NO: 186 is the forward primer C122P9-F.
SEQ ID NO: 187 is the reverse primer C122P9-R.
SEQ ID NO: 188 is the forward primer WIN1054-F.
SEQ ID NO: 189 is the reverse primer WIN1054-R.
SEQ ID NO: 190 is the forward primer WIN1065-F.
SEQ ID NO: 191 is the reverse primer WIN1065-R.
SEQ ID NO: 192 is the forward primer WIN1057-F.
SEQ ID NO: 193 is the reverse primer WIN1057-R.
SEQ ID NO: 194 is the forward primer WIN1058-F.
SEQ ID NO: 195 is the reverse primer WIN1058-R.
SEQ ID NO: 196 is the forward primer KKSC0132-F.
SEQ ID NO: 197 is the reverse primer KKSC0132-R.
SEQ ID NO: 198 is the forward primer KKSC0133-F.
SEQ ID NO: 199 is the reverse primer KKSC0133-R.
SEQ ID NO: 200 is the forward primer KKSC0311-F.
SEQ ID NO: 201 is the reverse primer KKSC0311-R.
SEQ ID NO: 202 is the forward primer KKSC0314-F.
SEQ ID NO: 203 is the reverse primer KKSC0314-R.
SEQ ID NO: 204 is the forward primer KKSC0862-F.
SEQ ID NO: 205 is the reverse primer KKSC0862-R.
SEQ ID NO: 206 is the forward primer KKSC0819-F.
SEQ ID NO: 207 is the reverse primer KKSC0819-R.
SEQ ID NO: 208 is the forward primer KKSC0317-F.
SEQ ID NO: 209 is the reverse primer KKSC0317-F.
SEQ ID NO: 210 is forward primer F1.
SEQ ID NO: 211 is reverse primer F1.
SEQ ID NO: 212 is forward primer F3.
SEQ ID NO: 213 is reverse primer F3.
SEQ ID NO: 214 is primer bind forward.
SEQ ID NO: 215 is primer bind reverse.
SEQ ID NO: 216 is the synthetic DNA construct of plasmid pDAu770.
SEQ ID NO: 217 is the cDNA sequence of a GH25 lysozyme as isolated from *Flammulina velutipes*.
SEQ ID NO: 218 is the amino acid sequence as deduced from SEQ ID NO: 217.
SEQ ID NO: 219 is the codon optimised DNA the GH25 lysozyme as isolated from *Flammulina velutipes*.
SEQ ID NO: 220 is the amino acid sequence as deduced from SEQ ID NO: 219.
SEQ ID NO: 221 is the amino acid sequence of the mature GH25 lysozyme from *Flammulina velutipes*.
SEQ ID NO: 222 is the cDNA sequence of a GH25 lysozyme as isolated from *Deconica coprophila*.
SEQ ID NO: 223 is the amino acid sequence as deduced from SEQ ID NO: 222.
SEQ ID NO: 224 is the amino acid sequence of the mature GH25 lysozyme from *Deconica coprophila*.
SEQ ID NO: 225 is the cDNA sequence of a GH25 lysozyme as isolated from *Rhizomucor pusillus*.
SEQ ID NO: 226 is the amino acid sequence as deduced from SEQ ID NO: 225.
SEQ ID NO: 227 is the amino acid sequence of the mature GH25 lysozyme from *Rhizomucor pusillus*.
SEQ ID NO: 228 is the cDNA sequence of a GH25 lysozyme as isolated from *Stropharia semiglobata*.
SEQ ID NO: 229 is the amino acid sequence as deduced from SEQ ID NO: 228.
SEQ ID NO: 230 is the amino acid sequence of the mature GH25 lysozyme from *Stropharia semiglobata*.
SEQ ID NO: 231 is the cDNA sequence of a GH25 lysozyme as isolated from *Stropharia semiglobata*.
SEQ ID NO: 232 is the amino acid sequence as deduced from SEQ ID NO: 231.
SEQ ID NO: 233 is the amino acid sequence of the mature GH25 lysozyme from *Stropharia semiglobata*.
SEQ ID NO: 234 is the forward primer C8VSE-F.
SEQ ID NO: 235 is the reverse primer C8VSE-R.

The top panel represents the locus amy2 with the integration of the FLP landing pad composed of FRT-F and FRT-F3 the FLPase recognition site, as well as the amdS (acetamide) selection marker and the FLPase expression cassette. A split PyrG marker has been used and at the amy2 locus the 5' end of the pyrG marker is inserted.

The middle panel represents the transforming DNA, in particular the region that is integrated at the FLP landing pad by site specific recombination mediated by FLPase. The plasmid or PCR product must contain FRT-F and F3 sites as well as the remaining 3' part of the pyrG marker.

The bottom panel represents the resulting amy2 locus after site specific integration of the transforming DNA between the FRT sites. The amdS and FLP cassettes have been exchanged with the GOI expression cassette and the 3' part of the pyrG marker reconstituting a fully functional selection marker.

Figure 3:
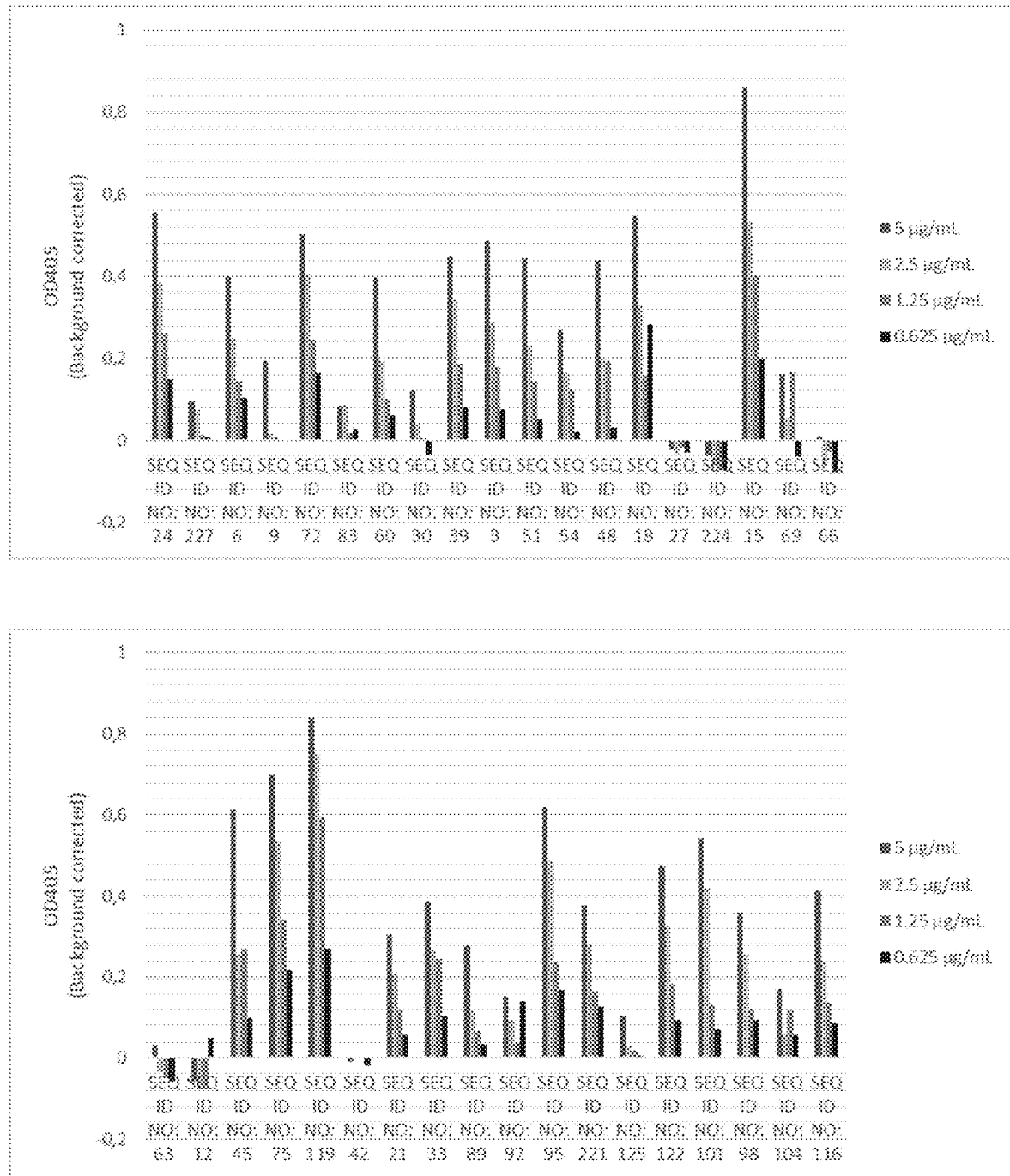
Figure 4:
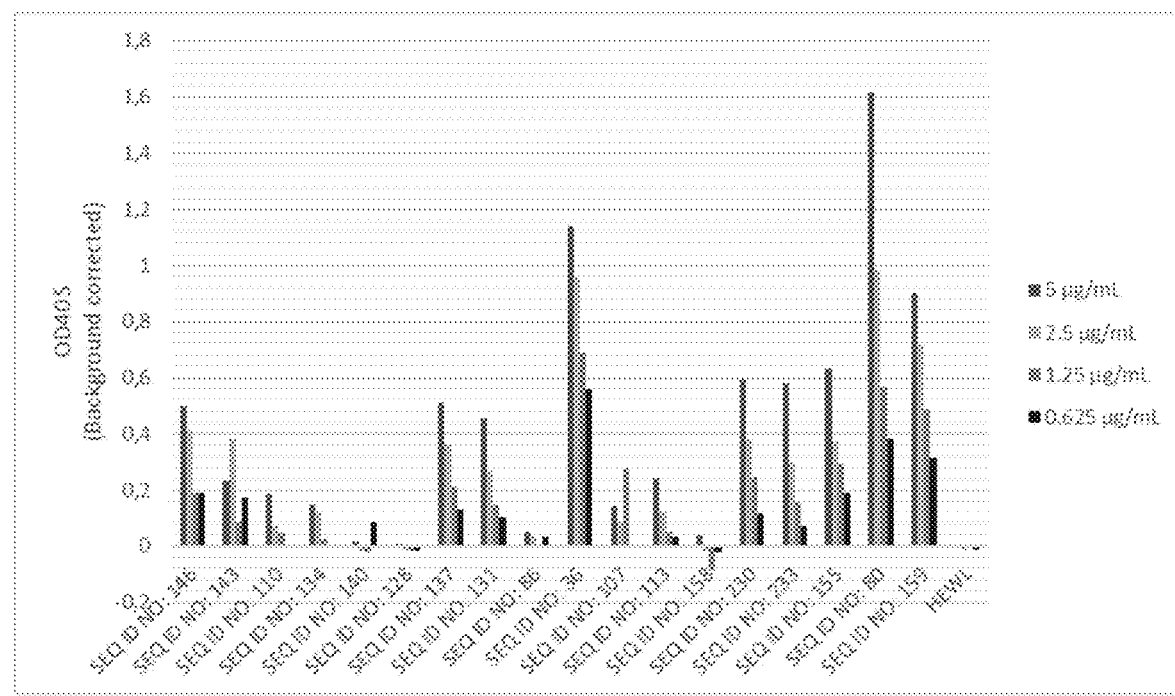

FIGS. 3 and 4 are a series of panels each illustrating the results of Example 56: Method for the Determination of Lysozyme Activity (OD405) Against *Lactobacillus johnsonii* at concentrations of the enzymes of 0.625 ppm, 1.25 ppm, 2.5 ppm and 5 ppm. Each OD measurement represents the difference after the original (background) reading was subtracted and represents the average of two OD measurements.

The Figures illustrate that a number of the enzymes that have improved lysozyme activity against the peptidoglycans found in the cell walls of *Micrococcus lysodeikticus* also have excellent lysozyme activity against the peptidoglycans found in the cell walls of *Lactobacillus johnsonii* even at very low doses.

Figure 5:
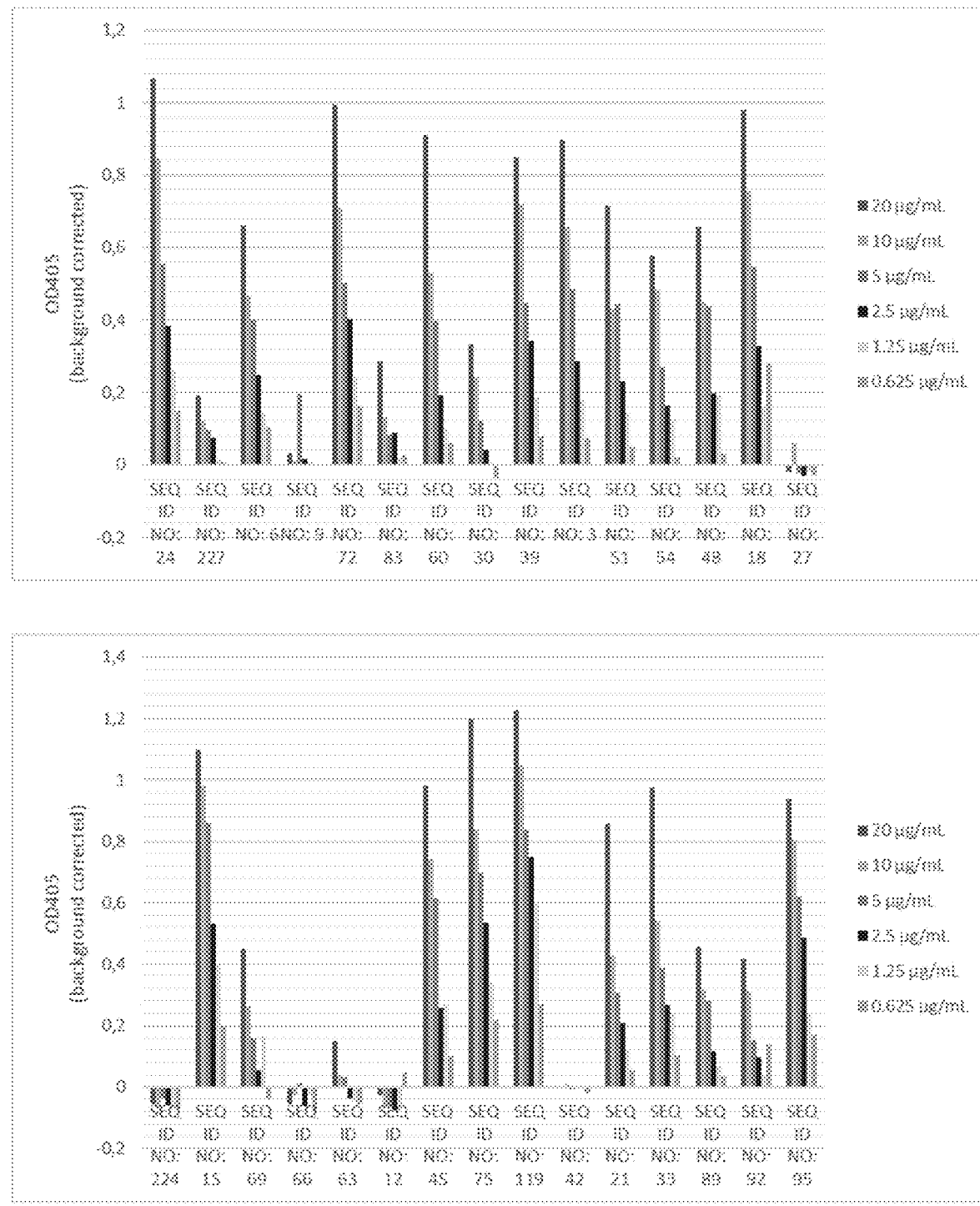
Figure 6:
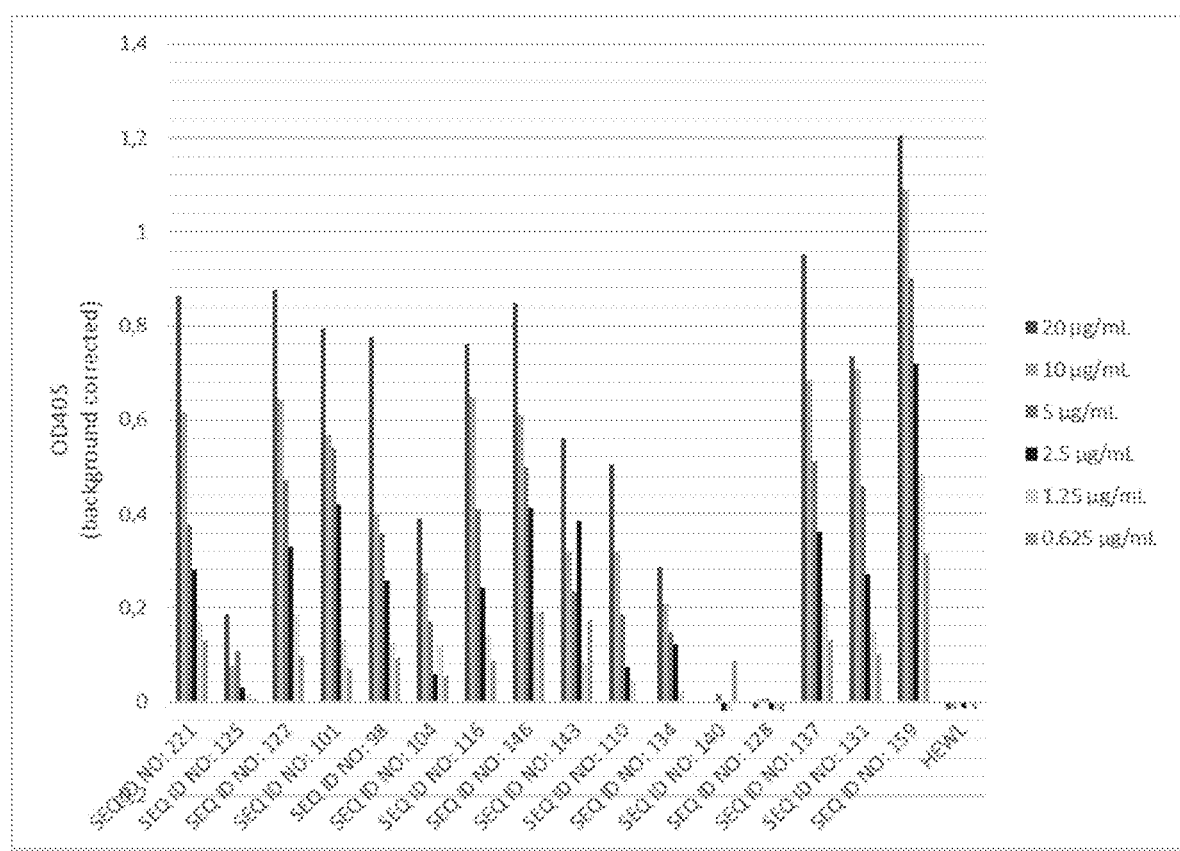

FIGS. 5 and 6 represents a series of panels each illustrating the results of Example 56: Method for the Determination of Lysozyme Activity (OD405) Against *Lactobacillus johnsonii* at concentrations of the enzymes of 0.625 ppm, 1.25 ppm, 2.5 ppm, 5 ppm, 10 and 20 ppm. Each OD measurement represents the difference after the original (background) reading was subtracted and represents the average of two OD measurements.

The Figures illustrate that a number of the enzymes that have improved lysozyme activity against the peptidoglycans found in the cell walls of *Micrococcus lysodeikticus* also have excellent lysozyme activity against the peptidoglycans found in the cell walls of *Lactobacillus johnsonii*, even at very low doses.

DETAILED DESCRIPTION OF THE INVENTION

Animal: The term "animal" refers to any animal except humans. Examples of animals are monogastric animals, including but not limited to pigs or swine (including, but not limited to, piglets, growing pigs, and sows); poultry such as turkeys, ducks, quail, guinea fowl, geese, pigeons (including squabs) and chicken (including but not limited to broiler chickens (referred to herein as broiles), chicks, layer hens (referred to herein as layers)); horses (including but not limited to hotbloods, coldbloods and warm bloods) crustaceans (including but not limited to shrimps and prawns) and fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish).

Animal feed: The term "animal feed" refers to any compound, preparation, or mixture suitable for, or intended for intake by an animal. Animal feed for a monogastric animal typically comprises concentrates as well as vitamins, minerals, enzymes, direct fed microbial, amino acids and/or other feed ingredients (such as in a premix) whereas animal feed for ruminants generally comprises forage (including roughage and silage) and may further comprise concentrates as well as vitamins, minerals, enzymes direct fed microbial, amino acid and/or other feed ingredients (such as in a premix).

Antimicrobial activity: The term "antimicrobial activity" is defined herein as an activity that kills or inhibits the growth of microorganisms, such as, algae, archea, bacteria, fungi and/or protozoans. The antimicrobial activity can, for example, be bactericidal meaning the killing of bacteria or bacteriostatic meaning the prevention of bacterial growth. The antimicrobial activity can include catalyzing the hydrolysis of 1,4-beta-linkages between N-acetylmuramic acid and N-acetyl-D-glucosamine residues in a peptidoglycan and between N-acetyl-D-glucosamine residues in chitodextrins. Antimicrobial activity can also include the lysozyme binding to the surface of the microorganism and inhibiting its growth. The antimicrobial effect can also include the use of the lysozymes of the present invention for activation of bacterial autolysins, as an immunostimulator, by inhibiting or reducing bacterial toxins and by an opsonin effect.

Body Weight Gain: The term "body weight gain" means an increase in live weight of an animal during a given period of time e.g. the increase in weight from day 1 to day 21.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Concentrates: The term "concentrates" means feed with high protein and energy concentrations, such as fish meal, molasses, oligosaccharides, sorghum, seeds and grains (either whole or prepared by crushing, milling, etc. from e.g. corn, oats, rye, barley, wheat), oilseed press cake (e.g. from cottonseed, safflower, sunflower, soybean (such as soybean meal), rapeseed/canola, peanut or groundnut), palm kernel cake, yeast derived material and distillers grains (such as wet distillers grains (WDS) and dried distillers grains with solubles (DDGS)).

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

European Production Efficacy Factor (EPEF): The "European Production Efficacy Factor" is a way of comparing the performance of animals. This single-figure facilitates comparison of performance within and among farms and can be used to assess environmental, climatic and managemental variables. The EPEF is calculated as [(liveability (%)×Liveweight (kg))/(Age at depletion (days)×FCR)]×100, wherein livability is the percentage of animals alive at slaughter, Liveweight is the average weight of the animals at slaughter, age of depletion is the age of the animals at slaughter and FCR is the feed conversion ratio at slaughter.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Feed Conversion Ratio (FCR): FCR is a measure of an animal's efficiency in converting feed mass into increases of the desired output. Animals raised for meat—such as swine, poultry and fish—the output is the mass gained by the animal. Specifically, FCR is calculated as feed intake divided by weight gain, all over a specified period. Improvement in FCR means reduction of the FCR value. A FCR improvement of 2% means that the FCR was reduced by 2%.

Feed efficiency: The term "feed efficiency" means the amount of weight gain per unit of feed when the animal is fed ad-libitum or a specified amount of food during a period of time. By "increased feed efficiency" it is meant that the use of a feed additive composition according the present invention in feed results in an increased weight gain per unit of feed intake compared with an animal fed without said feed additive composition being present.

Forage: The term "forage" as defined herein also includes roughage. Forage is fresh plant material such as hay and silage from forage plants, grass and other forage plants, seaweed, sprouted grains and legumes, or any combination thereof. Examples of forage plants are Alfalfa (lucerne), birdsfoot trefoil, brassica (e.g. kale, rapeseed (canola), rutabaga (swede), turnip), clover (e.g. alsike clover, red clover, subterranean clover, white clover), grass (e.g. Bermuda grass, brome, false oat grass, fescue, heath grass, meadow grasses, orchard grass, ryegrass, Timothy-grass), corn (maize), millet, barley, oats, rye, sorghum, soybeans and wheat and vegetables such as beets. Forage further includes crop residues from grain production (such as corn stover; straw from wheat, barley, oat, rye and other grains); residues from vegetables like beet tops; residues from oilseed production like stems and leaves form soy beans, rapeseed and other legumes; and fractions from the refining of grains for animal or human consumption or from fuel production or other industries.

Fragment: The term "fragment" means a polypeptide having one or more (e.g., several) amino acids absent from the amino and/or carboxyl terminus of a mature polypeptide or domain; wherein the fragment has lysozyme activity.

In one aspect, the fragment comprises at least 90% of the length of the mature polypeptide, such as at least 186 amino acids of SEQ ID NO: 2, at least 186 amino acids of SEQ ID NO: 3, at least 180 amino acids of SEQ ID NO: 5, at least 180 amino acids of SEQ ID NO: 6, at least 180 amino acids of SEQ ID NO: 8, at least 180 amino acids of SEQ ID NO: 9, at least 182 amino acids of SEQ ID NO: 11, at least 182 amino acids of SEQ ID NO: 12, at least 187 amino acids of SEQ ID NO: 14, at least 187 amino acids of SEQ ID NO: 15, at least 186 amino acids of SEQ ID NO: 17, at least 186 amino acids of SEQ ID NO: 18, at least 187 amino acids of SEQ ID NO: 20, at least 187 amino acids of SEQ ID NO: 21, at least 186 amino acids of SEQ ID NO: 23, at least 186 amino acids of SEQ ID NO: 24, at least 186 amino acids of SEQ ID NO: 26, at least 186 amino acids of SEQ ID NO: 27, at least 186 amino acids of SEQ ID NO: 29, at least 186 amino acids of SEQ ID NO: 30, at least 187 amino acids of SEQ ID NO: 32, at least 187 amino acids of SEQ ID NO: 33, at least 187 amino acids of SEQ ID NO: 35, at least 187 amino acids of SEQ ID NO: 36, at least 185 amino acids of SEQ ID NO: 38, at least 185 amino acids of SEQ ID NO: 39, at least 186 amino acids of SEQ ID NO: 41, at least 186 amino acids of SEQ ID NO: 42, at least 194 amino acids of SEQ ID NO: 44, at least 194 amino acids of SEQ ID NO: 45, at least 196 amino acids of SEQ ID NO: 47, at least 196 amino acids of SEQ ID NO: 48, at least 183 amino acids of SEQ ID NO: 50, at least 183 amino acids of SEQ ID NO: 51, at least 182 amino acids of SEQ ID NO: 53, at least 182 amino acids of SEQ ID NO: 54, at least 188 amino acids of SEQ ID NO: 56, at least 188 amino acids of SEQ ID NO: 57, at least 187 amino acids of SEQ ID NO: 59, at least 187 amino acids of SEQ ID NO: 60, at least 189 amino acids of SEQ ID NO: 62, at least 189 amino acids of SEQ ID NO: 63, at least 186 amino acids of SEQ ID NO: 65, at least 186 amino acids of SEQ ID NO: 66, at least 186 amino acids of SEQ ID NO: 68, at least 186 amino acids of SEQ ID NO: 69, at least 187 amino acids of SEQ ID NO: 71, at least 187 amino acids of SEQ ID NO: 72, at least 195 amino acids of SEQ ID NO: 74, at least 195 amino acids of SEQ ID NO: 75, at least 187 amino acids of SEQ ID NO: 77, at least 187 amino acids of SEQ ID NO: 79, at least 187 amino acids of SEQ ID NO: 80, at least 180 amino acids of SEQ ID NO: 82, at least 180 amino acids of SEQ ID NO: 83, at least 181 amino acids of SEQ ID NO: 85, at least 181 amino acids of SEQ ID NO: 86, at least 186 amino acids of SEQ ID NO: 88, at least 186 amino acids of SEQ ID NO: 89, at least 181 amino acids of SEQ ID NO: 91, at least 181 amino acids of SEQ ID NO: 92, at least 180 amino acids of SEQ ID NO: 94, at least 180 amino acids of SEQ ID NO: 95, at least 181 amino acids of SEQ ID NO: 97, at least 181 amino acids of SEQ ID NO: 98, at least 185 amino acids of SEQ ID NO: 100, at least 185 amino acids of SEQ ID NO: 101, at least 181 amino acids of SEQ ID NO: 103, at least 181 amino acids of SEQ ID NO: 104, at least 181 amino acids of SEQ ID NO: 106, at least 181 amino acids of SEQ ID NO: 107, at least 181 amino acids of SEQ ID NO: 109, at least 181 amino acids of SEQ ID NO: 110, at least 181 amino acids of SEQ ID NO: 112, at least 181 amino acids of SEQ ID NO: 113, at least 185 amino acids of SEQ ID NO: 115, at least 185 amino acids of SEQ ID NO: 116, at least 186 amino acids of SEQ ID NO: 118, at least 186 amino acids of SEQ ID NO: 119, at least 187 amino acids of SEQ ID NO: 121, at least 187 amino acids of SEQ ID NO: 122, at least 193 amino acids of SEQ ID NO: 124, at least 193 amino acids of SEQ ID NO: 125, at least 195 amino acids of SEQ ID NO: 127, at least 195 amino acids of SEQ ID NO: 128, at least 192 amino acids of SEQ ID NO: 130, at least 192 amino acids of SEQ ID NO: 131, at least 187 amino acids of SEQ ID NO: 133, at least 187 amino acids of SEQ ID NO: 134, at least 182 amino acids of SEQ ID NO: 136, at least 182 amino acids of SEQ ID NO: 137, at least 194 amino acids of SEQ ID NO: 139, at least 194 amino acids of SEQ ID NO: 140, at least 186 amino acids of SEQ ID NO: 142, at least 186 amino acids of SEQ ID NO: 143, at least 187 amino acids of SEQ ID NO: 145, at least 187 amino acids of SEQ ID NO: 146, at least 186 amino acids of SEQ ID NO: 148, at least 186 amino acids of SEQ ID NO: 149, at least 186 amino acids of SEQ ID NO: 151, at least 186 amino acids of SEQ ID NO: 152, at least 186 amino acids of SEQ ID NO: 154, at least 186 amino acids of SEQ ID NO: 155, at least 187 amino acids of SEQ ID NO: 157, at least 187 amino acids of SEQ ID NO: 158, at least 186 amino acids of SEQ ID NO: 218, at least 186 amino acids of SEQ ID NO: 220, at least 186 amino acids of SEQ ID NO: 221, at least 186 amino acids of SEQ ID NO: 223, at least 186 amino acids of SEQ ID NO: 224, at least 187 amino acids of SEQ ID NO: 226, at least 187 amino acids of SEQ ID NO: 227, at least 186 amino acids of SEQ ID NO: 229, at least 186 amino acids of SEQ ID NO: 230, at least 186 amino acids of SEQ ID NO: 232, or at least 186 amino acids of SEQ ID NO: 233.

In one aspect, the fragment comprises at least 92% of the length of the mature polypeptide, such as at least 190 amino acids of SEQ ID NO: 2, at least 190 amino acids of SEQ ID NO: 3, at least 184 amino acids of SEQ ID NO: 5, at least 184 amino acids of SEQ ID NO: 6, at least 184 amino acids of SEQ ID NO: 8, at least 184 amino acids of SEQ ID NO:

9, at least 186 amino acids of SEQ ID NO: 11, at least 186 amino acids of SEQ ID NO: 12, at least 191 amino acids of SEQ ID NO: 14, at least 191 amino acids of SEQ ID NO: 15, at least 190 amino acids of SEQ ID NO: 17, at least 190 amino acids of SEQ ID NO: 18, at least 191 amino acids of SEQ ID NO: 20, at least 191 amino acids of SEQ ID NO: 21, at least 190 amino acids of SEQ ID NO: 23, at least 190 amino acids of SEQ ID NO: 24, at least 190 amino acids of SEQ ID NO: 26, at least 190 amino acids of SEQ ID NO: 27, at least 190 amino acids of SEQ ID NO: 29, at least 190 amino acids of SEQ ID NO: 30, at least 191 amino acids of SEQ ID NO: 32, at least 191 amino acids of SEQ ID NO: 33, at least 191 amino acids of SEQ ID NO: 35, at least 191 amino acids of SEQ ID NO: 36, at least 189 amino acids of SEQ ID NO: 38, at least 189 amino acids of SEQ ID NO: 39, at least 190 amino acids of SEQ ID NO: 41, at least 190 amino acids of SEQ ID NO: 42, at least 198 amino acids of SEQ ID NO: 44, at least 198 amino acids of SEQ ID NO: 45, at least 200 amino acids of SEQ ID NO: 47, at least 200 amino acids of SEQ ID NO: 48, at least 187 amino acids of SEQ ID NO: 50, at least 187 amino acids of SEQ ID NO: 51, at least 186 amino acids of SEQ ID NO: 53, at least 186 amino acids of SEQ ID NO: 54, at least 192 amino acids of SEQ ID NO: 56, at least 192 amino acids of SEQ ID NO: 57, at least 191 amino acids of SEQ ID NO: 59, at least 191 amino acids of SEQ ID NO: 60, at least 193 amino acids of SEQ ID NO: 62, at least 193 amino acids of SEQ ID NO: 63, at least 190 amino acids of SEQ ID NO: 65, at least 190 amino acids of SEQ ID NO: 66, at least 190 amino acids of SEQ ID NO: 68, at least 190 amino acids of SEQ ID NO: 69, at least 191 amino acids of SEQ ID NO: 71, at least 191 amino acids of SEQ ID NO: 72, at least 199 amino acids of SEQ ID NO: 74, at least 199 amino acids of SEQ ID NO: 75, at least 191 amino acids of SEQ ID NO: 77, at least 191 amino acids of SEQ ID NO: 79, at least 191 amino acids of SEQ ID NO: 80, at least 184 amino acids of SEQ ID NO: 82, at least 184 amino acids of SEQ ID NO: 83, at least 185 amino acids of SEQ ID NO: 85, at least 185 amino acids of SEQ ID NO: 86, at least 190 amino acids of SEQ ID NO: 88, at least 190 amino acids of SEQ ID NO: 89, at least 185 amino acids of SEQ ID NO: 91, at least 185 amino acids of SEQ ID NO: 92, at least 184 amino acids of SEQ ID NO: 94, at least 184 amino acids of SEQ ID NO: 95, at least 185 amino acids of SEQ ID NO: 97, at least 185 amino acids of SEQ ID NO: 98, at least 189 amino acids of SEQ ID NO: 100, at least 189 amino acids of SEQ ID NO: 101, at least 185 amino acids of SEQ ID NO: 103, at least 185 amino acids of SEQ ID NO: 104, at least 185 amino acids of SEQ ID NO: 106, at least 185 amino acids of SEQ ID NO: 107, at least 185 amino acids of SEQ ID NO: 109, at least 185 amino acids of SEQ ID NO: 110, at least 185 amino acids of SEQ ID NO: 112, at least 185 amino acids of SEQ ID NO: 113, at least 189 amino acids of SEQ ID NO: 115, at least 189 amino acids of SEQ ID NO: 116, at least 190 amino acids of SEQ ID NO: 118, at least 190 amino acids of SEQ ID NO: 119, at least 191 amino acids of SEQ ID NO: 121, at least 191 amino acids of SEQ ID NO: 122, at least 197 amino acids of SEQ ID NO: 124, at least 197 amino acids of SEQ ID NO: 125, at least 199 amino acids of SEQ ID NO: 127, at least 199 amino acids of SEQ ID NO: 128, at least 196 amino acids of SEQ ID NO: 130, at least 196 amino acids of SEQ ID NO: 131, at least 191 amino acids of SEQ ID NO: 133, at least 191 amino acids of SEQ ID NO: 134, at least 186 amino acids of SEQ ID NO: 136, at least 186 amino acids of SEQ ID NO: 137, at least 198 amino acids of SEQ ID NO: 139, at least 198 amino acids of SEQ ID NO: 140, at least 190 amino acids of SEQ ID NO: 142, at least 190 amino acids of SEQ ID NO: 143, at least 191 amino acids of SEQ ID NO: 145, at least 191 amino acids of SEQ ID NO: 146, at least 190 amino acids of SEQ ID NO: 148, at least 190 amino acids of SEQ ID NO: 149, at least 190 amino acids of SEQ ID NO: 151, at least 190 amino acids of SEQ ID NO: 152, at least 190 amino acids of SEQ ID NO: 154, at least 190 amino acids of SEQ ID NO: 155, at least 191 amino acids of SEQ ID NO: 157, at least 191 amino acids of SEQ ID NO: 158, at least 190 amino acids of SEQ ID NO: 218, at least 190 amino acids of SEQ ID NO: 220, at least 190 amino acids of SEQ ID NO: 221, at least 190 amino acids of SEQ ID NO: 223, at least 190 amino acids of SEQ ID NO: 224, at least 191 amino acids of SEQ ID NO: 226, at least 191 amino acids of SEQ ID NO: 227, at least 190 amino acids of SEQ ID NO: 229, at least 190 amino acids of SEQ ID NO: 230, at least 190 amino acids of SEQ ID NO: 232, or at least 190 amino acids of SEQ ID NO: 233.

In one aspect, the fragment comprises at least 94% of the length of the mature polypeptide, such as at least 194 amino acids of SEQ ID NO: 2, at least 194 amino acids of SEQ ID NO: 3, at least 188 amino acids of SEQ ID NO: 5, at least 188 amino acids of SEQ ID NO: 6, at least 188 amino acids of SEQ ID NO: 8, at least 188 amino acids of SEQ ID NO: 9, at least 190 amino acids of SEQ ID NO: 11, at least 190 amino acids of SEQ ID NO: 12, at least 195 amino acids of SEQ ID NO: 14, at least 195 amino acids of SEQ ID NO: 15, at least 194 amino acids of SEQ ID NO: 17, at least 194 amino acids of SEQ ID NO: 18, at least 195 amino acids of SEQ ID NO: 20, at least 195 amino acids of SEQ ID NO: 21, at least 194 amino acids of SEQ ID NO: 23, at least 194 amino acids of SEQ ID NO: 24, at least 194 amino acids of SEQ ID NO: 26, at least 194 amino acids of SEQ ID NO: 27, at least 194 amino acids of SEQ ID NO: 29, at least 194 amino acids of SEQ ID NO: 30, at least 195 amino acids of SEQ ID NO: 32, at least 195 amino acids of SEQ ID NO: 33, at least 195 amino acids of SEQ ID NO: 35, at least 195 amino acids of SEQ ID NO: 36, at least 193 amino acids of SEQ ID NO: 38, at least 193 amino acids of SEQ ID NO: 39, at least 194 amino acids of SEQ ID NO: 41, at least 194 amino acids of SEQ ID NO: 42, at least 203 amino acids of SEQ ID NO: 44, at least 203 amino acids of SEQ ID NO: 45, at least 204 amino acids of SEQ ID NO: 47, at least 204 amino acids of SEQ ID NO: 48, at least 191 amino acids of SEQ ID NO: 50, at least 191 amino acids of SEQ ID NO: 51, at least 190 amino acids of SEQ ID NO: 53, at least 190 amino acids of SEQ ID NO: 54, at least 196 amino acids of SEQ ID NO: 56, at least 196 amino acids of SEQ ID NO: 57, at least 195 amino acids of SEQ ID NO: 59, at least 195 amino acids of SEQ ID NO: 60, at least 197 amino acids of SEQ ID NO: 62, at least 197 amino acids of SEQ ID NO: 63, at least 194 amino acids of SEQ ID NO: 65, at least 194 amino acids of SEQ ID NO: 66, at least 194 amino acids of SEQ ID NO: 68, at least 194 amino acids of SEQ ID NO: 69, at least 195 amino acids of SEQ ID NO: 71, at least 195 amino acids of SEQ ID NO: 72, at least 203 amino acids of SEQ ID NO: 74, at least 203 amino acids of SEQ ID NO: 75, at least 195 amino acids of SEQ ID NO: 77, at least 195 amino acids of SEQ ID NO: 79, at least 195 amino acids of SEQ ID NO: 80, at least 188 amino acids of SEQ ID NO: 82, at least 188 amino acids of SEQ ID NO: 83, at least 189 amino acids of SEQ ID NO: 85, at least 189 amino acids of SEQ ID NO: 86, at least 194 amino acids of SEQ ID NO: 88, at least 194 amino acids of SEQ ID NO: 89, at least 189 amino acids of SEQ ID NO: 91, at least 189 amino acids of SEQ ID NO: 92, at least 188 amino acids of SEQ ID NO: 94, at least 188 amino acids of SEQ ID NO: 95, at least 189 amino acids of SEQ ID NO: 97, at least 189 amino acids of SEQ ID NO: 98, at least 193 amino acids of SEQ ID NO: 100, at least 193 amino acids of SEQ ID NO: 101, at least 189 amino acids of SEQ ID NO: 103, at least 189 amino acids of SEQ ID NO: 104, at least 189 amino acids of SEQ ID NO: 106, at least 189 amino acids of SEQ ID NO: 107, at least 189 amino acids of SEQ ID NO: 109, at least 189 amino acids of SEQ ID NO: 110, at least 189 amino acids of SEQ ID NO: 112, at least 189 amino acids of SEQ ID NO: 113, at least 193 amino acids of SEQ ID NO: 115, at least 193 amino acids of SEQ ID NO: 116, at least 194 amino acids of SEQ ID NO: 118, at least 194 amino acids of SEQ ID NO: 119, at least 195 amino acids of SEQ ID NO: 121, at least 195 amino acids of SEQ ID NO: 122, at least 202 amino acids of SEQ ID NO: 124, at least 202 amino acids of SEQ ID NO: 125, at least 203 amino acids of SEQ ID NO: 127, at least 203 amino acids of SEQ ID NO: 128, at least 201 amino acids of SEQ ID NO: 130, at least 201 amino acids of SEQ ID NO: 131, at least 195 amino acids of SEQ ID NO: 133, at least 195 amino acids of SEQ ID NO: 134, at least 190 amino acids of SEQ ID NO: 136, at least 190 amino acids of SEQ ID NO: 137, at least 203 amino acids of SEQ ID NO: 139, at least 203 amino acids of SEQ ID NO: 140, at least 194 amino acids of SEQ ID NO: 142, at least 194 amino acids of SEQ ID NO: 143, at least 195 amino acids of SEQ ID NO: 145, at least 195 amino acids of SEQ ID NO: 146, at least 194 amino acids of SEQ ID NO: 148, at least 194 amino acids of SEQ ID NO: 149, at least 194 amino acids of SEQ ID NO: 151, at least 194 amino acids of SEQ ID NO: 152, at least 194 amino acids of SEQ ID NO: 154, at least 194 amino acids of SEQ ID NO: 155, at least 195 amino acids of SEQ ID NO: 157, at least 195 amino acids of SEQ ID NO: 158, at least 194 amino acids of SEQ ID NO: 218, at least 194 amino acids of SEQ ID NO: 220, at least 194 amino acids of SEQ ID NO: 221, at least 194 amino acids of SEQ ID NO: 223, at least 194 amino acids of SEQ ID NO: 224, at least 195 amino acids of SEQ ID NO: 226, at least 195 amino acids of SEQ ID NO: 227, at least 194 amino acids of SEQ ID NO: 229, at least 194 amino acids of SEQ ID NO: 230, at least 194 amino acids of SEQ ID NO: 232, or at least 194 amino acids of SEQ ID NO: 233.

In one aspect, the fragment comprises at least 96% of the length of the mature polypeptide, such as at least 198 amino acids of SEQ ID NO: 2, at least 198 amino acids of SEQ ID NO: 3, at least 192 amino acids of SEQ ID NO: 5, at least 192 amino acids of SEQ ID NO: 6, at least 192 amino acids of SEQ ID NO: 8, at least 192 amino acids of SEQ ID NO: 9, at least 194 amino acids of SEQ ID NO: 11, at least 194 amino acids of SEQ ID NO: 12, at least 199 amino acids of SEQ ID NO: 14, at least 199 amino acids of SEQ ID NO: 15, at least 198 amino acids of SEQ ID NO: 17, at least 198 amino acids of SEQ ID NO: 18, at least 199 amino acids of SEQ ID NO: 20, at least 199 amino acids of SEQ ID NO: 21, at least 198 amino acids of SEQ ID NO: 23, at least 198 amino acids of SEQ ID NO: 24, at least 198 amino acids of SEQ ID NO: 26, at least 198 amino acids of SEQ ID NO: 27, at least 198 amino acids of SEQ ID NO: 29, at least 198 amino acids of SEQ ID NO: 30, at least 199 amino acids of SEQ ID NO: 32, at least 199 amino acids of SEQ ID NO: 33, at least 199 amino acids of SEQ ID NO: 35, at least 199 amino acids of SEQ ID NO: 36, at least 197 amino acids of SEQ ID NO: 38, at least 197 amino acids of SEQ ID NO: 39, at least 198 amino acids of SEQ ID NO: 41, at least 198 amino acids of SEQ ID NO: 42, at least 207 amino acids of SEQ ID NO: 44, at least 207 amino acids of SEQ ID NO: 45, at least 209 amino acids of SEQ ID NO: 47, at least 209 amino acids of SEQ ID NO: 48, at least 195 amino acids of SEQ ID NO: 50, at least 195 amino acids of SEQ ID NO: 51, at least 194 amino acids of SEQ ID NO: 53, at least 194 amino acids of SEQ ID NO: 54, at least 200 amino acids of SEQ ID NO: 56, at least 200 amino acids of SEQ ID NO: 57, at least 199 amino acids of SEQ ID NO: 59, at least 199 amino acids of SEQ ID NO: 60, at least 201 amino acids of SEQ ID NO: 62, at least 201 amino acids of SEQ ID NO: 63, at least 198 amino acids of SEQ ID NO: 65, at least 198 amino acids of SEQ ID NO: 66, at least 198 amino acids of SEQ ID NO: 68, at least 198 amino acids of SEQ ID NO: 69, at least 199 amino acids of SEQ ID NO: 71, at least 199 amino acids of SEQ ID NO: 72, at least 208 amino acids of SEQ ID NO: 74, at least 208 amino acids of SEQ ID NO: 75, at least 199 amino acids of SEQ ID NO: 77, at least 199 amino acids of SEQ ID NO: 79, at least 199 amino acids of SEQ ID NO: 80, at least 192 amino acids of SEQ ID NO: 82, at least 192 amino acids of SEQ ID NO: 83, at least 193 amino acids of SEQ ID NO: 85, at least 193 amino acids of SEQ ID NO: 86, at least 198 amino acids of SEQ ID NO: 88, at least 198 amino acids of SEQ ID NO: 89, at least 193 amino acids of SEQ ID NO: 91, at least 193 amino acids of SEQ ID NO: 92, at least 192 amino acids of SEQ ID NO: 94, at least 192 amino acids of SEQ ID NO: 95, at least 193 amino acids of SEQ ID NO: 97, at least 193 amino acids of SEQ ID NO: 98, at least 197 amino acids of SEQ ID NO: 100, at least 197 amino acids of SEQ ID NO: 101, at least 193 amino acids of SEQ ID NO: 103, at least 193 amino acids of SEQ ID NO: 104, at least 193 amino acids of SEQ ID NO: 106, at least 193 amino acids of SEQ ID NO: 107, at least 193 amino acids of SEQ ID NO: 109, at least 193 amino acids of SEQ ID NO: 110, at least 193 amino acids of SEQ ID NO: 112, at least 193 amino acids of SEQ ID NO: 113, at least 197 amino acids of SEQ ID NO: 115, at least 197 amino acids of SEQ ID NO: 116, at least 198 amino acids of SEQ ID NO: 118, at least 198 amino acids of SEQ ID NO: 119, at least 199 amino acids of SEQ ID NO: 121, at least 199 amino acids of SEQ ID NO: 122, at least 206 amino acids of SEQ ID NO: 124, at least 206 amino acids of SEQ ID NO: 125, at least 208 amino acids of SEQ ID NO: 127, at least 208 amino acids of SEQ ID NO: 128, at least 205 amino acids of SEQ ID NO: 130, at least 205 amino acids of SEQ ID NO: 131, at least 199 amino acids of SEQ ID NO: 133, at least 199 amino acids of SEQ ID NO: 134, at least 194 amino acids of SEQ ID NO: 136, at least 194 amino acids of SEQ ID NO: 137, at least 207 amino acids of SEQ ID NO: 139, at least 207 amino acids of SEQ ID NO: 140, at least 198 amino acids of SEQ ID NO: 142, at least 198 amino acids of SEQ ID NO: 143, at least 199 amino acids of SEQ ID NO: 145, at least 199 amino acids of SEQ ID NO: 146, at least 198 amino acids of SEQ ID NO: 148, at least 198 amino acids of SEQ ID NO: 149, at least 198 amino acids of SEQ ID NO: 151, at least 198 amino acids of SEQ ID NO: 152, at least 198 amino acids of SEQ ID NO: 154, at least 198 amino acids of SEQ ID NO: 155, at least 199 amino acids of SEQ ID NO: 157, at least 199 amino acids of SEQ ID NO: 158, at least 198 amino acids of SEQ ID NO: 218, at least 198 amino acids of SEQ ID NO: 220, at least 198 amino acids of SEQ ID NO: 221, at least 198 amino acids of SEQ ID NO: 223, at least 198 amino acids of SEQ ID NO: 224, at least 199 amino acids of SEQ ID NO: 226, at least 199 amino acids of SEQ ID NO: 227, at least 198 amino acids of SEQ ID NO: 229, at least 198 amino acids of SEQ ID NO: 230, at least 198 amino acids of SEQ ID NO: 232, or at least 198 amino acids of SEQ ID NO: 233.

In one aspect, the fragment comprises at least 98% of the length of the mature polypeptide, such as at least 202 amino acids of SEQ ID NO: 2, at least 202 amino acids of SEQ ID NO: 3, at least 196 amino acids of SEQ ID NO: 5, at least 196 amino acids of SEQ ID NO: 6, at least 196 amino acids of SEQ ID NO: 8, at least 196 amino acids of SEQ ID NO: 9, at least 198 amino acids of SEQ ID NO: 11, at least 198 amino acids of SEQ ID NO: 12, at least 203 amino acids of SEQ ID NO: 14, at least 203 amino acids of SEQ ID NO: 15, at least 202 amino acids of SEQ ID NO: 17, at least 202 amino acids of SEQ ID NO: 18, at least 203 amino acids of SEQ ID NO: 20, at least 203 amino acids of SEQ ID NO: 21, at least 202 amino acids of SEQ ID NO: 23, at least 202 amino acids of SEQ ID NO: 24, at least 202 amino acids of SEQ ID NO: 26, at least 202 amino acids of SEQ ID NO: 27, at least 202 amino acids of SEQ ID NO: 29, at least 202 amino acids of SEQ ID NO: 30, at least 203 amino acids of SEQ ID NO: 32, at least 203 amino acids of SEQ ID NO: 33, at least 203 amino acids of SEQ ID NO: 35, at least 203 amino acids of SEQ ID NO: 36, at least 201 amino acids of SEQ ID NO: 38, at least 201 amino acids of SEQ ID NO: 39, at least 202 amino acids of SEQ ID NO: 41, at least 202 amino acids of SEQ ID NO: 42, at least 211 amino acids of SEQ ID NO: 44, at least 211 amino acids of SEQ ID NO: 45, at least 213 amino acids of SEQ ID NO: 47, at least 213 amino acids of SEQ ID NO: 48, at least 199 amino acids of SEQ ID NO: 50, at least 199 amino acids of SEQ ID NO: 51, at least 198 amino acids of SEQ ID NO: 53, at least 198 amino acids of SEQ ID NO: 54, at least 204 amino acids of SEQ ID NO: 56, at least 204 amino acids of SEQ ID NO: 57, at least 203 amino acids of SEQ ID NO: 59, at least 203 amino acids of SEQ ID NO: 60, at least 205 amino acids of SEQ ID NO: 62, at least 205 amino acids of SEQ ID NO: 63, at least 202 amino acids of SEQ ID NO: 65, at least 202 amino acids of SEQ ID NO: 66, at least 202 amino acids of SEQ ID NO: 68, at least 202 amino acids of SEQ ID NO: 69, at least 203 amino acids of SEQ ID NO: 71, at least 203 amino acids of SEQ ID NO: 72, at least 212 amino acids of SEQ ID NO: 74, at least 212 amino acids of SEQ ID NO: 75, at least 203 amino acids of SEQ ID NO: 77, at least 203 amino acids of SEQ ID NO: 79, at least 203 amino acids of SEQ ID NO: 80, at least 196 amino acids of SEQ ID NO: 82, at least 196 amino acids of SEQ ID NO: 83, at least 197 amino acids of SEQ ID NO: 85, at least 197 amino acids of SEQ ID NO: 86, at least 202 amino acids of SEQ ID NO: 88, at least 202 amino acids of SEQ ID NO: 89, at least 197 amino acids of SEQ ID NO: 91, at least 197 amino acids of SEQ ID NO: 92, at least 196 amino acids of SEQ ID NO: 94, at least 196 amino acids of SEQ ID NO: 95, at least 197 amino acids of SEQ ID NO: 97, at least 197 amino acids of SEQ ID NO: 98, at least 201 amino acids of SEQ ID NO: 100, at least 201 amino acids of SEQ ID NO: 101, at least 197 amino acids of SEQ ID NO: 103, at least 197 amino acids of SEQ ID NO: 104, at least 197 amino acids of SEQ ID NO: 106, at least 197 amino acids of SEQ ID NO: 107, at least 197 amino acids of SEQ ID NO: 109, at least 197 amino acids of SEQ ID NO: 110, at least 197 amino acids of SEQ ID NO: 112, at least 197 amino acids of SEQ ID NO: 113, at least 201 amino acids of SEQ ID NO: 115, at least 201 amino acids of SEQ ID NO: 116, at least 202 amino acids of SEQ ID NO: 118, at least 202 amino acids of SEQ ID NO: 119, at least 203 amino acids of SEQ ID NO: 121, at least 203 amino acids of SEQ ID NO: 122, at least 210 amino acids of SEQ ID NO: 124, at least 210 amino acids of SEQ ID NO: 125, at least 212 amino acids of SEQ ID NO: 127, at least 212 amino acids of SEQ ID NO: 128, at least 209 amino acids of SEQ ID NO: 130, at least 209 amino acids of SEQ ID NO: 131, at least 203 amino acids of SEQ ID NO: 133, at least 203 amino acids of SEQ ID NO: 134, at least 198 amino acids of SEQ ID NO: 136, at least 198 amino acids of SEQ ID NO: 137, at least 211 amino acids of SEQ ID NO: 139, at least 211 amino acids of SEQ ID NO: 140, at least 202 amino acids of SEQ ID NO: 142, at least 202 amino acids of SEQ ID NO: 143, at least 203 amino acids of SEQ ID NO: 145, at least 203 amino acids of SEQ ID NO: 146, at least 202 amino acids of SEQ ID NO: 148, at least 202 amino acids of SEQ ID NO: 149, at least 202 amino acids of SEQ ID NO: 151, at least 202 amino acids of SEQ ID NO: 152, at least 202 amino acids of SEQ ID NO: 154, at least 202 amino acids of SEQ ID NO: 155, at least 203 amino acids of SEQ ID NO: 157, at least 203 amino acids of SEQ ID NO: 158, at least 202 amino acids of SEQ ID NO: 218, at least 202 amino acids of SEQ ID NO: 220, at least 202 amino acids of SEQ ID NO: 221, at least 202 amino acids of SEQ ID NO: 223, at least 202 amino acids of SEQ ID NO: 224, at least 203 amino acids of SEQ ID NO: 226, at least 203 amino acids of SEQ ID NO: 227, at least 202 amino acids of SEQ ID NO: 229, at least 202 amino acids of SEQ ID NO: 230, at least 202 amino acids of SEQ ID NO: 232, or at least 202 amino acids of SEQ ID NO: 233.

In one aspect, the fragment comprises at least 99% of the length of the mature polypeptide, such as at least 204 amino acids of SEQ ID NO: 2, at least 204 amino acids of SEQ ID NO: 3, at least 198 amino acids of SEQ ID NO: 5, at least 198 amino acids of SEQ ID NO: 6, at least 198 amino acids of SEQ ID NO: 8, at least 198 amino acids of SEQ ID NO: 9, at least 200 amino acids of SEQ ID NO: 11, at least 200 amino acids of SEQ ID NO: 12, at least 205 amino acids of SEQ ID NO: 14, at least 205 amino acids of SEQ ID NO: 15, at least 204 amino acids of SEQ ID NO: 17, at least 204 amino acids of SEQ ID NO: 18, at least 205 amino acids of SEQ ID NO: 20, at least 205 amino acids of SEQ ID NO: 21, at least 204 amino acids of SEQ ID NO: 23, at least 204 amino acids of SEQ ID NO: 24, at least 204 amino acids of SEQ ID NO: 26, at least 204 amino acids of SEQ ID NO: 27, at least 204 amino acids of SEQ ID NO: 29, at least 204 amino acids of SEQ ID NO: 30, at least 205 amino acids of SEQ ID NO: 32, at least 205 amino acids of SEQ ID NO: 33, at least 205 amino acids of SEQ ID NO: 35, at least 205 amino acids of SEQ ID NO: 36, at least 203 amino acids of SEQ ID NO: 38, at least 203 amino acids of SEQ ID NO: 39, at least 204 amino acids of SEQ ID NO: 41, at least 204 amino acids of SEQ ID NO: 42, at least 213 amino acids of SEQ ID NO: 44, at least 213 amino acids of SEQ ID NO: 45, at least 215 amino acids of SEQ ID NO: 47, at least 215 amino acids of SEQ ID NO: 48, at least 201 amino acids of SEQ ID NO: 50, at least 201 amino acids of SEQ ID NO: 51, at least 200 amino acids of SEQ ID NO: 53, at least 200 amino acids of SEQ ID NO: 54, at least 206 amino acids of SEQ ID NO: 56, at least 206 amino acids of SEQ ID NO: 57, at least 205 amino acids of SEQ ID NO: 59, at least 205 amino acids of SEQ ID NO: 60, at least 207 amino acids of SEQ ID NO: 62, at least 207 amino acids of SEQ ID NO: 63, at least 204 amino acids of SEQ ID NO: 65, at least 204 amino acids of SEQ ID NO: 66, at least 204 amino acids of SEQ ID NO: 68, at least 204 amino acids of SEQ ID NO: 69, at least 205 amino acids of SEQ ID NO: 71, at least 205 amino acids of SEQ ID NO: 72, at least 214 amino acids of SEQ ID NO: 74, at least 214 amino acids of SEQ ID NO: 75, at least 205 amino acids of SEQ ID NO: 77, at least 205 amino acids of SEQ ID NO: 79, at least 205 amino acids of SEQ ID NO: 80, at least 198 amino acids of SEQ ID NO: 82, at least 198 amino acids of SEQ ID NO: 83, at least 199 amino acids of SEQ ID NO: 85, at least 199 amino acids of SEQ ID NO: 86, at least 204 amino acids of SEQ ID NO: 88, at least 199 amino acids of SEQ ID NO: 91, at least 199 amino acids of SEQ ID NO: 92, at least 198 amino acids of SEQ ID NO:

94, at least 198 amino acids of SEQ ID NO: 95, at least 199 amino acids of SEQ ID NO: 97, at least 199 amino acids of SEQ ID NO: 98, at least 203 amino acids of SEQ ID NO: 100, at least 203 amino acids of SEQ ID NO: 101, at least 199 amino acids of SEQ ID NO: 103, at least 199 amino acids of SEQ ID NO: 104, at least 199 amino acids of SEQ ID NO: 106, at least 199 amino acids of SEQ ID NO: 107, at least 199 amino acids of SEQ ID NO: 109, at least 199 amino acids of SEQ ID NO: 110, at least 199 amino acids of SEQ ID NO: 112, at least 199 amino acids of SEQ ID NO: 113, at least 203 amino acids of SEQ ID NO: 115, at least 203 amino acids of SEQ ID NO: 116, at least 204 amino acids of SEQ ID NO: 118, at least 204 amino acids of SEQ ID NO: 119, at least 205 amino acids of SEQ ID NO: 121, at least 205 amino acids of SEQ ID NO: 122, at least 212 amino acids of SEQ ID NO: 124, at least 212 amino acids of SEQ ID NO: 125, at least 214 amino acids of SEQ ID NO: 127, at least 214 amino acids of SEQ ID NO: 128, at least 211 amino acids of SEQ ID NO: 130, at least 211 amino acids of SEQ ID NO: 131, at least 205 amino acids of SEQ ID NO: 133, at least 205 amino acids of SEQ ID NO: 134, at least 200 amino acids of SEQ ID NO: 136, at least 200 amino acids of SEQ ID NO: 137, at least 213 amino acids of SEQ ID NO: 139, at least 213 amino acids of SEQ ID NO: 140, at least 204 amino acids of SEQ ID NO: 142, at least 204 amino acids of SEQ ID NO: 143, at least 205 amino acids of SEQ ID NO: 145, at least 205 amino acids of SEQ ID NO: 146, at least 204 amino acids of SEQ ID NO: 148, at least 204 amino acids of SEQ ID NO: 149, at least 204 amino acids of SEQ ID NO: 151, at least 204 amino acids of SEQ ID NO: 152, at least 204 amino acids of SEQ ID NO: 154, at least 204 amino acids of SEQ ID NO: 155, at least 205 amino acids of SEQ ID NO: 157, at least 205 amino acids of SEQ ID NO: 158, at least 204 amino acids of SEQ ID NO: 218, at least 204 amino acids of SEQ ID NO: 220, at least 204 amino acids of SEQ ID NO: 221, at least 204 amino acids of SEQ ID NO: 223, at least 204 amino acids of SEQ ID NO: 224, at least 205 amino acids of SEQ ID NO: 226, at least 205 amino acids of SEQ ID NO: 227, at least 204 amino acids of SEQ ID NO: 229, at least 204 amino acids of SEQ ID NO: 230, at least 204 amino acids of SEQ ID NO: 232, or at least 204 amino acids of SEQ ID NO: 233.

Fusion polypeptide: The term "fusion polypeptide" is a polypeptide in which one polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779). A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Hybrid polypeptide: The term "hybrid polypeptide" means a polypeptide comprising domains from two or more polypeptides, e.g., a binding domain from one polypeptide and a catalytic domain from another polypeptide. The domains may be fused at the N-terminus or the C-terminus.

Isolated: The term "isolated" means a substance in a form that does not occur in nature or in an environment in which the substance does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Lysozyme activity: The term "lysozyme activity" means the hydrolysis of the 1,4-beta-linkages between N-acetylmuramic acid and N-acetyl-D-glucosamine residues in a peptidoglycan or between N-acetyl-D-glucosamine residues in chitodextrins, resulting in bacteriolysis. Lysozyme belongs to the enzyme class EC 3.2.1.17. Lysozyme activity is typically measured by the lytic action of the lysozyme on *Micrococcus luteus* ATCC 4698. In appropriate experimental conditions these changes are proportional to the amount of lysozyme in the medium (c.f. INS 1105 of the Combined Compendium of Food Additive Specifications of the Food and Agriculture Organisation of the UN (www.fao.org)). For the purpose of the present invention, lysozyme activity is determined according to the reducing-ends assay described in example 1 ("Determination of Lysozyme Activity"). The polypeptide has lysozyme activity if it shows activity against *Micrococcus luteus* ATCC 4698, and specifically the lysozymes of the invention exhibit improved activity compared to the prior art lysozyme of SEQ ID NO: 159 wherein lysozyme activity is determined as described in example 1.

In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159. In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as follows: lysozyme (50 μL of 0.7 μg/mL lysozyme in phosphate buffer (5 mM citrate, 5 mM $K_2HPO_4$, 0.01% TritonX-100, pH 5.0)) is mixed with *Micrococcus lysodeikticus* solution (450 μL of 1% lyophilized *Micrococcus lysodeikticus* ATCC No. 4698 in milli-Q water) and incubated at 40° C. with shaking (500 rpm) for 45 min; the sample is centrifuged (4000 g, 5 min); supernatant (100 μL) is mixed with HCl (50 μL 3.2M) and incubated at 95° C. for 80 min; NaOH (50 μL, 3.5 M) is added and 150 μL of the sample is added to 4-hydroxybenzhydrazide in K-Na tartrate/NaOH buffer (75 μL of 50 g/L K-Na tartrate+20 g/L NaOH); the mixture is incubated at 95° C. for 10 min; and the optical density is measured at 405 nm.

Mature polypeptide: The term "mature polypeptide" means a polypeptide in its final form following translation and any post-translational modifications, such as N-terminal processing, C-terminal truncation, glycosylation, phosphorylation, etc.

In one aspect, the mature polypeptide is amino acids 1 to 207 of SEQ ID NO: 2 and amino acids −17 to −1 of SEQ ID NO: 2 are a signal peptide. In another aspect, the mature polypeptide is amino acids 1 to 207 of SEQ ID NO: 3.

In one aspect, the mature polypeptide is amino acids 1 to 201 of SEQ ID NO: 5 and amino acids −17 to −1 of SEQ ID NO: 5 are a signal peptide. In another aspect, the mature polypeptide is amino acids 1 to 201 of SEQ ID NO: 6.

In one aspect, the mature polypeptide is amino acids 1 to 201 of SEQ ID NO: 8 and amino acids −16 to −1 of SEQ ID NO: 8 are a signal peptide. In another aspect, the mature polypeptide is amino acids 1 to 201 of SEQ ID NO: 9.

In one aspect, the mature polypeptide is amino acids 1 to 203 of SEQ ID NO: 11 and amino acids −21 to −1 of SEQ ID NO: 11 are a signal peptide. In another aspect, the mature polypeptide is amino acids 1 to 203 of SEQ ID NO: 12.

In one aspect, the mature polypeptide is amino acids 1 to 208 of SEQ ID NO: 14 and amino acids −20 to −1 of SEQ ID NO: 14 are a signal peptide. In another aspect, the mature polypeptide is amino acids 1 to 208 of SEQ ID NO: 15.

In one aspect, the mature polypeptide is amino acids 1 to 207 of SEQ ID NO: 17 and amino acids −18 to −1 of SEQ ID NO: 17 are a signal peptide. In another aspect, the mature polypeptide is amino acids 1 to 207 of SEQ ID NO: 18.

In one aspect, the mature polypeptide is amino acids 1 to 208 of SEQ ID NO: 20 and amino acids −19 to −1 of SEQ ID NO: 20 are a signal peptide. In another aspect, the mature polypeptide is amino acids 1 to 208 of SEQ ID NO: 21.

In one aspect, the mature polypeptide is amino acids 1 to 207 of SEQ ID NO: 23 and amino acids −18 to −1 of SEQ ID NO: 23 are a signal peptide. In another aspect, the mature polypeptide is amino acids 1 to 207 of SEQ ID NO: 24.

In one aspect, the mature polypeptide is amino acids 1 to 207 of SEQ ID NO: 26 and amino acids −16 to −1 of SEQ ID NO: 26 are a signal peptide. In another aspect, the mature polypeptide is amino acids 1 to 207 of SEQ ID NO: 27.

In one aspect, the mature polypeptide is amino acids 1 to 207 of SEQ ID NO: 29 and amino acids −22 to −1 of SEQ ID NO: 29 are a signal peptide. In another aspect, the mature polypeptide is amino acids 1 to 207 of SEQ ID NO: 30.

In one aspect, the mature polypeptide is amino acids 1 to 208 of SEQ ID NO: 32 and amino acids −20 to −1 of SEQ ID NO: 32 are a signal peptide. In another aspect, the mature polypeptide is amino acids 1 to 208 of SEQ ID NO: 33.

In one aspect, the mature polypeptide is amino acids 1 to 208 of SEQ ID NO: 35 and amino acids −19 to −1 of SEQ ID NO: 35 are a signal peptide. In another aspect, the mature polypeptide is amino acids 1 to 208 of SEQ ID NO: 36.

In one aspect, the mature polypeptide is amino acids 1 to 206 of SEQ ID NO: 38 and amino acids −17 to −1 of SEQ ID NO: 38 are a signal peptide. In another aspect, the mature polypeptide is amino acids 1 to 206 of SEQ ID NO: 39.

In one aspect, the mature polypeptide is amino acids 1 to 207 of SEQ ID NO: 41 and amino acids −17 to −1 of SEQ ID NO: 41 are a signal peptide. In another aspect, the mature polypeptide is amino acids 1 to 207 of SEQ ID NO: 42.

In one aspect, the mature polypeptide is amino acids 1 to 216 of SEQ ID NO: 44 and amino acids −17 to −1 of SEQ ID NO: 44 are a signal peptide. In another aspect, the mature polypeptide is amino acids 1 to 216 of SEQ ID NO: 45.

In one aspect, the mature polypeptide is amino acids 1 to 218 of SEQ ID NO: 47 and amino acids −18 to −1 of SEQ ID NO: 47 are a signal peptide. In another aspect, the mature polypeptide is amino acids 1 to 218 of SEQ ID NO: 48.

In one aspect, the mature polypeptide is amino acids 1 to 204 of SEQ ID NO: 50 and amino acids −19 to −1 of SEQ ID NO: 50 are a signal peptide. In another aspect, the mature polypeptide is amino acids 1 to 204 of SEQ ID NO: 51.

In one aspect, the mature polypeptide is amino acids 1 to 203 of SEQ ID NO: 53 and amino acids −19 to −1 of SEQ ID NO: 53 are a signal peptide. In another aspect, the mature polypeptide is amino acids 1 to 203 of SEQ ID NO: 54.

In one aspect, the mature polypeptide is amino acids 1 to 209 of SEQ ID NO: 56 and amino acids −20 to −1 of SEQ ID NO: 56 are a signal peptide. In another aspect, the mature polypeptide is amino acids 1 to 209 of SEQ ID NO: 57.

In one aspect, the mature polypeptide is amino acids 1 to 208 of SEQ ID NO: 59 and amino acids −17 to −1 of SEQ ID NO: 59 are a signal peptide. In another aspect, the mature polypeptide is amino acids 1 to 208 of SEQ ID NO: 60.

In one aspect, the mature polypeptide is amino acids 1 to 210 of SEQ ID NO: 62 and amino acids −22 to −1 of SEQ ID NO: 62 are a signal peptide. In another aspect, the mature polypeptide is amino acids 1 to 210 of SEQ ID NO: 63.

In one aspect, the mature polypeptide is amino acids 1 to 207 of SEQ ID NO: 65 and amino acids −17 to −1 of SEQ ID NO: 65 are a signal peptide. In another aspect, the mature polypeptide is amino acids 1 to 207 of SEQ ID NO: 66.

In one aspect, the mature polypeptide is amino acids 1 to 207 of SEQ ID NO: 68 and amino acids −19 to −1 of SEQ ID NO: 68 are a signal peptide. In another aspect, the mature polypeptide is amino acids 1 to 207 of SEQ ID NO: 69.

In one aspect, the mature polypeptide is amino acids 1 to 208 of SEQ ID NO: 71 and amino acids −17 to −1 of SEQ ID NO: 71 are a signal peptide. In another aspect, the mature polypeptide is amino acids 1 to 208 of SEQ ID NO: 72.

In one aspect, the mature polypeptide is amino acids 1 to 217 of SEQ ID NO: 74 and amino acids −18 to −1 of SEQ ID NO: 74 are a signal peptide. In another aspect, the mature polypeptide is amino acids 1 to 217 of SEQ ID NO: 75.

In one aspect, the mature polypeptide is amino acids 1 to 208 of SEQ ID NO: 77 and amino acids −20 to −1 of SEQ ID NO: 77 are a signal peptide. In another aspect, the mature polypeptide is amino acids 1 to 208 of SEQ ID NO: 80.

In one aspect, the mature polypeptide is amino acids 1 to 201 of SEQ ID NO: 82 and amino acids −15 to −1 of SEQ ID NO: 82 are a signal peptide. In another aspect, the mature polypeptide is amino acids 1 to 201 of SEQ ID NO: 83.

In one aspect, the mature polypeptide is amino acids 1 to 202 of SEQ ID NO: 85 and amino acids −16 to −1 of SEQ ID NO: 85 are a signal peptide. In another aspect, the mature polypeptide is amino acids 1 to 202 of SEQ ID NO: 86.

In one aspect, the mature polypeptide is amino acids 1 to 207 of SEQ ID NO: 88 and amino acids −17 to −1 of SEQ ID NO: 88 are a signal peptide. In another aspect, the mature polypeptide is amino acids 1 to 207 of SEQ ID NO: 89.

In one aspect, the mature polypeptide is amino acids 1 to 202 of SEQ ID NO: 91 and amino acids −20 to −1 of SEQ ID NO: 91 are a signal peptide. In another aspect, the mature polypeptide is amino acids 1 to 202 of SEQ ID NO: 92.

In one aspect, the mature polypeptide is amino acids 1 to 201 of SEQ ID NO: 94 and amino acids −17 to −1 of SEQ ID NO: 94 are a signal peptide. In another aspect, the mature polypeptide is amino acids 1 to 201 of SEQ ID NO: 95.

In one aspect, the mature polypeptide is amino acids 1 to 202 of SEQ ID NO: 97 and amino acids −16 to −1 of SEQ ID NO: 97 are a signal peptide. In another aspect, the mature polypeptide is amino acids 1 to 202 of SEQ ID NO: 98.

In one aspect, the mature polypeptide is amino acids 1 to 206 of SEQ ID NO: 100 and amino acids −18 to −1 of SEQ ID NO: 100 are a signal peptide. In another aspect, the mature polypeptide is amino acids 1 to 206 of SEQ ID NO: 101.

In one aspect, the mature polypeptide is amino acids 1 to 202 of SEQ ID NO: 103 and amino acids −16 to −1 of SEQ ID NO: 103 are a signal peptide. In another aspect, the mature polypeptide is amino acids 1 to 202 of SEQ ID NO: 104.

In one aspect, the mature polypeptide is amino acids 1 to 202 of SEQ ID NO: 106 and amino acids −17 to −1 of SEQ ID NO: 106 are a signal peptide. In another aspect, the mature polypeptide is amino acids 1 to 202 of SEQ ID NO: 107.

In one aspect, the mature polypeptide is amino acids 1 to 202 of SEQ ID NO: 109 and amino acids −17 to −1 of SEQ ID NO: 109 are a signal peptide. In another aspect, the mature polypeptide is amino acids 1 to 202 of SEQ ID NO: 110.

In one aspect, the mature polypeptide is amino acids 1 to 202 of SEQ ID NO: 112 and amino acids −17 to −1 of SEQ ID NO: 112 are a signal peptide. In another aspect, the mature polypeptide is amino acids 1 to 202 of SEQ ID NO: 113.

In one aspect, the mature polypeptide is amino acids 1 to 206 of SEQ ID NO: 115 and amino acids −18 to −1 of SEQ ID NO: 115 are a signal peptide. In another aspect, the mature polypeptide is amino acids 1 to 206 of SEQ ID NO: 116.

In one aspect, the mature polypeptide is amino acids 1 to 207 of SEQ ID NO: 118 and amino acids −20 to −1 of SEQ ID NO: 118 are a signal peptide. In another aspect, the mature polypeptide is amino acids 1 to 207 of SEQ ID NO: 119.

In one aspect, the mature polypeptide is amino acids 1 to 208 of SEQ ID NO: 121 and amino acids −19 to −1 of SEQ ID NO: 121 are a signal peptide. In another aspect, the mature polypeptide is amino acids 1 to 208 of SEQ ID NO: 122.

In one aspect, the mature polypeptide is amino acids 1 to 215 of SEQ ID NO: 124 and amino acids −18 to −1 of SEQ ID NO: 124 are a signal peptide. In another aspect, the mature polypeptide is amino acids 1 to 215 of SEQ ID NO: 125.

In one aspect, the mature polypeptide is amino acids 1 to 217 of SEQ ID NO: 127 and amino acids −20 to −1 of SEQ ID NO: 127 are a signal peptide. In another aspect, the mature polypeptide is amino acids 1 to 217 of SEQ ID NO: 128.

In one aspect, the mature polypeptide is amino acids 1 to 214 of SEQ ID NO: 130 and amino acids −16 to −1 of SEQ ID NO: 130 are a signal peptide. In another aspect, the mature polypeptide is amino acids 1 to 214 of SEQ ID NO: 131.

In one aspect, the mature polypeptide is amino acids 1 to 208 of SEQ ID NO: 133 and amino acids −18 to −1 of SEQ ID NO: 133 are a signal peptide. In another aspect, the mature polypeptide is amino acids 1 to 208 of SEQ ID NO: 134.

In one aspect, the mature polypeptide is amino acids 1 to 203 of SEQ ID NO: 136 and amino acids −19 to −1 of SEQ ID NO: 136 are a signal peptide. In another aspect, the mature polypeptide is amino acids 1 to 203 of SEQ ID NO: 137.

In one aspect, the mature polypeptide is amino acids 1 to 216 of SEQ ID NO: 139 and amino acids −17 to −1 of SEQ ID NO: 139 are a signal peptide. In another aspect, the mature polypeptide is amino acids 1 to 216 of SEQ ID NO: 140.

In one aspect, the mature polypeptide is amino acids 1 to 207 of SEQ ID NO: 142 and amino acids −21 to −1 of SEQ ID NO: 142 are a signal peptide. In another aspect, the mature polypeptide is amino acids 1 to 207 of SEQ ID NO: 143.

In one aspect, the mature polypeptide is amino acids 1 to 208 of SEQ ID NO: 145 and amino acids −17 to −1 of SEQ ID NO: 145 are a signal peptide. In another aspect, the mature polypeptide is amino acids 1 to 208 of SEQ ID NO: 146.

In one aspect, the mature polypeptide is amino acids 1 to 207 of SEQ ID NO: 148 and amino acids −20 to −1 of SEQ ID NO: 148 are a signal peptide. In another aspect, the mature polypeptide is amino acids 1 to 207 of SEQ ID NO: 149.

In one aspect, the mature polypeptide is amino acids 1 to 207 of SEQ ID NO: 151 and amino acids −20 to −1 of SEQ ID NO: 151 are a signal peptide. In another aspect, the mature polypeptide is amino acids 1 to 207 of SEQ ID NO: 152.

In one aspect, the mature polypeptide is amino acids 1 to 207 of SEQ ID NO: 154 and amino acids −19 to −1 of SEQ ID NO: 154 are a signal peptide. In another aspect, the mature polypeptide is amino acids 1 to 207 of SEQ ID NO: 155.

In one aspect, the mature polypeptide is amino acids 1 to 208 of SEQ ID NO: 157 and amino acids −18 to −1 of SEQ ID NO: 157 are a signal peptide. In another aspect, the mature polypeptide is amino acids 1 to 208 of SEQ ID NO: 158.

In one aspect, the mature polypeptide is amino acids 1 to 207 of SEQ ID NO: 218 and amino acids −17 to −1 of SEQ ID NO: 218 are a signal peptide. In another aspect, the mature polypeptide is amino acids 1 to 207 of SEQ ID NO: 221.

In one aspect, the mature polypeptide is amino acids 1 to 207 of SEQ ID NO: 223 and amino acids −19 to −1 of SEQ ID NO: 223 are a signal peptide. In another aspect, the mature polypeptide is amino acids 1 to 207 of SEQ ID NO: 224.

In one aspect, the mature polypeptide is amino acids 1 to 208 of SEQ ID NO: 226 and amino acids −20 to −1 of SEQ ID NO: 226 are a signal peptide. In another aspect, the mature polypeptide is amino acids 1 to 208 of SEQ ID NO: 227.

In one aspect, the mature polypeptide is amino acids 1 to 207 of SEQ ID NO: 229 and amino acids −20 to −1 of SEQ ID NO: 229 are a signal peptide. In another aspect, the mature polypeptide is amino acids 1 to 207 of SEQ ID NO: 230.

In one aspect, the mature polypeptide is amino acids 1 to 207 of SEQ ID NO: 232 and amino acids −20 to −1 of SEQ ID NO: 232 are a signal peptide. In another aspect, the mature polypeptide is amino acids 1 to 207 of SEQ ID NO: 233.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having lysozyme activity.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Obtained or obtainable from: The term "obtained or obtainable from" means that the polypeptide may be found in an organism from a specific taxonomic rank. In one embodiment, the polypeptide is obtained or obtainable from the kingdom Fungi, wherein the term kingdom is the taxonomic rank. In a preferred embodiment, the polypeptide is obtained or obtainable from the phylum Ascomycota, wherein the term phylum is the taxonomic rank. In another preferred embodiment, the polypeptide is obtained or obtainable from the subphylum Pezizomycotina, wherein the term subphylum is the taxonomic rank.

If the taxonomic rank of a polypeptide is not known, it can easily be determined by a person skilled in the art by performing a BLASTP search of the polypeptide (using e.g. the National Center for Biotechnology Information (NCI B) website http://www.ncbi.nlm.nih.gov/) and comparing it to the closest homologues. An unknown polypeptide which is a fragment of a known polypeptide is considered to be of the same taxonomic species. An unknown natural polypeptide or artificial variant which comprises a substitution, deletion and/or insertion in up to 10 positions is considered to be from the same taxonomic species as the known polypeptide.

Operably linked: The term "operably linked" means a configuration in which a control sequence is placed at an appropriate position relative to the coding sequence of a polynucleotide such that the control sequence directs expression of the coding sequence.

Roughage: The term "roughage" means dry plant material with high levels of fiber, such as fiber, bran, husks from seeds and grains and crop residues (such as stover, copra, straw, chaff, sugar beet waste).

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labelled "longest identity" (obtained using the −nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labelled "longest identity" (obtained using the −nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having lysozyme activity.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

Variant: The term "variant" means a polypeptide having lysozyme activity comprising an alteration, i.e., a substitution, insertion, and/or deletion, of one or more (several) amino acid residues at one or more (e.g., several) positions. A substitution means replacement of the amino acid occupying a position with a different amino acid; a deletion means removal of the amino acid occupying a position; and an insertion means adding 1, 2, or 3 amino acids adjacent to and immediately following the amino acid occupying the position.

In one aspect, a lysozyme variant according to the invention may comprise from 1 to 5; from 1 to 10; from 1 to 15; from 1 to 20; from 1 to 25; from 1 to 30; from 1 to 35; from 1 to 40; from 1 to 45; or from 1-50, i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 alterations and have at least 150%, e.g., at least 175%, at least 200%, at least 225%, at least 250%, at least 275%, at least 300%, at least 350%, or at least 400% of the lysozyme activity of SEQ ID NO: 159.

In one aspect, the variant of the present invention has at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In one aspect, the variant of the present invention has at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as follows: lysozyme (50 µL of 0.7 µg/mL lysozyme in phosphate buffer (5 mM citrate, 5 mM $K_2HPO_4$, 0.01% TritonX-100, pH 5.0)) is mixed with *Micrococcus lysodeikticus* solution (450 µL of 1% lyophilized *Micrococcus lysodeikticus* ATCC No. 4698 in milli-Q water) and incubated at 40° C. with shaking (500 rpm) for 45 min; the sample is centrifuged (4000 g, 5 min); supernatant (100 µL) is mixed with HCl (50 µL 3.2M) and incubated at 95° C. for 80 min; NaOH (50 µL, 3.5 M) is added and 150 µL of the sample is added to 4-hydroxybenzhydrazide in K-Na tartrate/NaOH buffer (75 µL of 50 g/L K-Na tartrate+20 g/L NaOH); the mixture is incubated at 95° C. for 10 min; and the optical density is measured at 405 nm.

Nomenclature

For purposes of the present invention, the nomenclature [E/Q] means that the amino acid at this position may be a glutamic acid (Glu, E) or a glutamine (Gln, Q). Likewise the nomenclature [V/G/A/I] means that the amino acid at this position may be a valine (Val, V), glycine (Gly, G), alanine (Ala, A) or isoleucine (Ile, I), and so forth for other combinations as described herein. Unless otherwise limited further, the amino acid X is defined such that it may be any of the 20 natural amino acids.

Methods of Hydrolysing Peptidoglycan in Bacterial Cell Walls

In the first aspect, the invention relates to a method of hydrolysing peptidoglycan in bacterial cell walls comprising treating bacterial cells with one or more GH25 polypeptides having lysozyme activity, wherein the polypeptide is selected from the group consisting of:

(a) a polypeptide having at least 80%, such as at least 85%, at least 90% or at least 95% sequence identity to the polypeptide of SEQ ID NO: 3;
(b) a polypeptide having at least 84%, such as at least 85%, at least 90% or at least 95% sequence identity to the polypeptide of SEQ ID NO: 6;
(c) a polypeptide having at least 80%, such as at least 85%, at least 90% or at least 95% sequence identity to the polypeptide of SEQ ID NO: 9;
(d) a polypeptide having at least 80%, such as at least 85%, at least 90% or at least 95% sequence identity to the polypeptide of SEQ ID NO: 12;
(e) a polypeptide having at least 80%, such as at least 85%, at least 90% or at least 95% sequence identity to the polypeptide of SEQ ID NO: 15;
(f) a polypeptide having at least 80%, such as at least 85%, at least 90% or at least 95% sequence identity to the polypeptide of SEQ ID NO: 18;
(g) a polypeptide having at least 80%, such as at least 85%, at least 90% or at least 95% sequence identity to the polypeptide of SEQ ID NO: 21;
(h) a polypeptide having at least 80%, such as at least 85%, at least 90% or at least 95% sequence identity to the polypeptide of SEQ ID NO: 24;
(i) a polypeptide having at least 80%, such as at least 85%, at least 90% or at least 95% sequence identity to the polypeptide of SEQ ID NO: 27;
(j) a polypeptide having at least 84%, such as at least 85%, at least 90% or at least 95% sequence identity to the polypeptide of SEQ ID NO: 30;
(k) a polypeptide having at least 80%, such as at least 85%, at least 90% or at least 95% sequence identity to the polypeptide of SEQ ID NO: 33;
(l) a polypeptide having at least 80%, such as at least 85%, at least 90% or at least 95% sequence identity to the polypeptide of SEQ ID NO: 36;
(m) a polypeptide having at least 84%, such as at least 85%, at least 90% or at least 95% sequence identity to the polypeptide of SEQ ID NO: 39;
(n) a polypeptide having at least 80%, such as at least 85%, at least 90% or at least 95% sequence identity to the polypeptide of SEQ ID NO: 42;
(o) a polypeptide having at least 80%, such as at least 85%, at least 90% or at least 95% sequence identity to the polypeptide of SEQ ID NO: 45;
(p) a polypeptide having at least 80%, such as at least 85%, at least 90% or at least 95% sequence identity to the polypeptide of SEQ ID NO: 48;
(q) a polypeptide having at least 80%, such as at least 85%, at least 90% or at least 95% sequence identity to the polypeptide of SEQ ID NO: 51;
(r) a polypeptide having at least 80%, such as at least 85%, at least 90% or at least 95% sequence identity to the polypeptide of SEQ ID NO: 54;
(s) a polypeptide having at least 80%, such as at least 85%, at least 90% or at least 95% sequence identity to the polypeptide of SEQ ID NO: 57;
(t) a polypeptide having at least 80%, such as at least 85%, at least 90% or at least 95% sequence identity to the polypeptide of SEQ ID NO: 60;
(u) a polypeptide having at least 80%, such as at least 85%, at least 90% or at least 95% sequence identity to the polypeptide of SEQ ID NO: 63;
(v) a polypeptide having at least 80%, such as at least 85%, at least 90% or at least 95% sequence identity to the polypeptide of SEQ ID NO: 66;
(w) a polypeptide having at least 80%, such as at least 85%, at least 90% or at least 95% sequence identity to the polypeptide of SEQ ID NO: 69;
(x) a polypeptide having at least 84%, such as at least 85%, at least 90% or at least 95% sequence identity to the polypeptide of SEQ ID NO: 72;
(y) a polypeptide having at least 80%, such as at least 85%, at least 90% or at least 95% sequence identity to the polypeptide of SEQ ID NO: 75;
(z) a polypeptide having at least 80%, such as at least 85%, at least 90% or at least 95% sequence identity to the polypeptide of SEQ ID NO: 80;
(aa) a polypeptide having at least 80%, such as at least 85%, at least 90% or at least 95% sequence identity to the polypeptide of SEQ ID NO: 83;
(ab) a polypeptide having at least 80%, such as at least 85%, at least 90% or at least 95% sequence identity to the polypeptide of SEQ ID NO: 86;
(ac) a polypeptide having at least 86%, such as at least 90% or at least 95% sequence identity to the polypeptide of SEQ ID NO: 89;

(ad) a polypeptide having at least 82%, such as at least 85%, at least 90% or at least 95% sequence identity to the polypeptide of SEQ ID NO: 92;
(ae) a polypeptide having at least 82%, such as at least 85%, at least 90% or at least 95% sequence identity to the polypeptide of SEQ ID NO: 95;
(af) a polypeptide having at least 80%, such as at least 85%, at least 90% or at least 95% sequence identity to the polypeptide of SEQ ID NO: 98;
(ag) a polypeptide having at least 80%, such as at least 85%, at least 90% or at least 95% sequence identity to the polypeptide of SEQ ID NO: 101;
(ah) a polypeptide having at least 80%, such as at least 85%, at least 90% or at least 95% sequence identity to the polypeptide of SEQ ID NO: 104;
(ai) a polypeptide having at least 80%, such as at least 85%, at least 90% or at least 95% sequence identity to the polypeptide of SEQ ID NO: 107;
(aj) a polypeptide having at least 82%, such as at least 85%, at least 90% or at least 95% sequence identity to the polypeptide of SEQ ID NO: 110;
(ak) a polypeptide having at least 81%, such as at least 85%, at least 90% or at least 95% sequence identity to the polypeptide of SEQ ID NO: 113;
(al) a polypeptide having at least 80%, such as at least 85%, at least 90% or at least 95% sequence identity to the polypeptide of SEQ ID NO: 116;
(am) a polypeptide having at least 80%, such as at least 85%, at least 90% or at least 95% sequence identity to the polypeptide of SEQ ID NO: 119;
(an) a polypeptide having at least 80%, such as at least 85%, at least 90% or at least 95% sequence identity to the polypeptide of SEQ ID NO: 122;
(ao) a polypeptide having at least 80%, such as at least 85%, at least 90% or at least 95% sequence identity to the polypeptide of SEQ ID NO: 125;
(ap) a polypeptide having at least 80%, such as at least 85%, at least 90% or at least 95% sequence identity to the polypeptide of SEQ ID NO: 128;
(aq) a polypeptide having at least 80%, such as at least 85%, at least 90% or at least 95% sequence identity to the polypeptide of SEQ ID NO: 131;
(ar) a polypeptide having at least 80%, such as at least 85%, at least 90% or at least 95% sequence identity to the polypeptide of SEQ ID NO: 134;
(as) a polypeptide having at least 80%, such as at least 85%, at least 90% or at least 95% sequence identity to the polypeptide of SEQ ID NO: 137;
(at) a polypeptide having at least 80%, such as at least 85%, at least 90% or at least 95% sequence identity to the polypeptide of SEQ ID NO: 140;
(au) a polypeptide having at least 80%, such as at least 85%, at least 90% or at least 95% sequence identity to the polypeptide of SEQ ID NO: 143;
(av) a polypeptide having at least 80%, such as at least 85%, at least 90% or at least 95% sequence identity to the polypeptide of SEQ ID NO: 146;
(aw) a polypeptide having at least 80%, such as at least 85%, at least 90% or at least 95% sequence identity to the polypeptide of SEQ ID NO: 149;
(ax) a polypeptide having at least 80%, such as at least 85%, at least 90% or at least 95% sequence identity to the polypeptide of SEQ ID NO: 152;
(ay) a polypeptide having at least 80%, such as at least 85%, at least 90% or at least 95% sequence identity to the polypeptide of SEQ ID NO: 155;
(az) a polypeptide having at least 80%, such as at least 85%, at least 90% or at least 95% sequence identity to the polypeptide of SEQ ID NO: 158;
(ba) a polypeptide having at least 80%, such as at least 85%, at least 90% or at least 95% sequence identity to the polypeptide of SEQ ID NO: 221;
(bb) a polypeptide having at least 80%, such as at least 85%, at least 90% or at least 95% sequence identity to the polypeptide of SEQ ID NO: 224;
(bc) a polypeptide having at least 80%, such as at least 85%, at least 90% or at least 95% sequence identity to the polypeptide of SEQ ID NO: 227;
(bd) a polypeptide having at least 80%, such as at least 85%, at least 90% or at least 95% sequence identity to the polypeptide of SEQ ID NO: 230;
(be) a polypeptide having at least 80%, such as at least 85%, at least 90% or at least 95% sequence identity to the polypeptide of SEQ ID NO: 233;
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27 or 28 positions;
(bg) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal His-tag and/or HQ-tag;
(bh) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal extension of up to 10 amino acids, e.g. 1, 2, 3, 4, 5, 6, 7, 8, 9 or 10 amino acids; and
(bi) a fragment of the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) having lysozyme activity and having at least 90% of the length of the mature polypeptide.

In an embodiment, the one or more GH25 polypeptides comprises the motif YKNA (SEQ ID NO: 160) and/or the motif FGGW[S/T] (SEQ ID NO: 161), and preferably is selected from the group selected from SEQ ID NO: 12, SEQ ID NO: 27, SEQ ID NO: 42, SEQ ID NO: 57, SEQ ID NO: 63, SEQ ID NO: 66, SEQ ID NO: 80, SEQ ID NO: 149, SEQ ID NO:152, SEQ ID NO: 155, SEQ ID NO: 224, SEQ ID NO: 227, SEQ ID NO: 230 and SEQ ID NO: 233.

In an embodiment, the polypeptide comprises or consists of amino acids 1 to 207 of SEQ ID NO: 3, amino acids 1 to 201 of SEQ ID NO: 6, amino acids 1 to 201 of SEQ ID NO: 9, amino acids 1 to 203 of SEQ ID NO: 12, amino acids 1 to 208 of SEQ ID NO: 15, amino acids 1 to 207 of SEQ ID NO: 18, amino acids 1 to 208 of SEQ ID NO: 21, amino acids 1 to 207 of SEQ ID NO: 24, amino acids 1 to 207 of SEQ ID NO: 27, amino acids 1 to 207 of SEQ ID NO: 30, amino acids 1 to 208 of SEQ ID NO: 33, amino acids 1 to 208 of SEQ ID NO: 36, amino acids 1 to 206 of SEQ ID NO: 39, amino acids 1 to 207 of SEQ ID NO: 42, amino acids 1 to 216 of SEQ ID NO: 45, amino acids 1 to 218 of SEQ ID NO: 48, amino acids 1 to 204 of SEQ ID NO: 51, amino acids 1 to 203 of SEQ ID NO: 54, amino acids 1 to 209 of SEQ ID NO: 57, amino acids 1 to 208 of SEQ ID NO: 60, amino acids 1 to 210 of SEQ ID NO: 63, amino acids 1 to 207 of SEQ ID NO: 66, amino acids 1 to 207 of SEQ ID NO: 69, amino acids 1 to 208 of SEQ ID NO: 72, amino acids 1 to 217 of SEQ ID NO: 75, amino acids 1 to 208 of SEQ ID NO: 80, amino acids 1 to 201 of SEQ ID NO: 83, amino acids 1 to 202 of SEQ ID NO: 86, amino acids 1 to 207 of SEQ ID NO: 89, amino acids 1 to 202 of SEQ ID NO: 92, amino acids 1 to 201 of SEQ ID NO: 95, amino acids 1 to 202 of SEQ ID NO: 98, amino acids 1 to 206 of SEQ ID NO: 101, amino acids 1 to 202 of SEQ ID NO: 104, amino acids 1 to 202 of SEQ ID NO: 107, amino acids 1 to 202 of SEQ ID NO: 110, amino acids 1 to 202 of SEQ ID NO: 113, amino acids 1 to 206 of SEQ ID NO: 116, amino acids 1 to 207 of SEQ ID NO: 119, amino acids 1 to 208 of SEQ ID NO: 122, amino acids 1 to 215 of SEQ ID NO: 125, amino acids 1 to 217 of SEQ ID NO: 128, amino acids 1 to 214 of SEQ ID NO: 131, amino acids 1 to 208 of SEQ ID NO: 134, amino acids 1 to 203 of SEQ ID NO: 137, amino acids 1 to 216 of SEQ ID NO: 140, amino acids 1 to 207 of SEQ ID NO: 143, amino acids 1 to 208 of SEQ ID NO: 146, amino acids 1 to 207 of SEQ ID NO: 149, amino acids 1 to 207 of SEQ ID NO: 152, amino acids 1 to 207 of SEQ ID NO: 155, amino acids 1 to 208 of SEQ ID NO: 158, amino acids 1 to 207 of SEQ ID NO: 221, amino acids 1 to 207 of SEQ ID NO: 224, amino acids 1 to 208 of SEQ ID NO: 227, amino acids 1 to 207 of SEQ ID NO: 230 or amino acids 1 to 207 of SEQ ID NO: 233.

In a preferred embodiment, the polypeptide has at least 150%, such as at least 175%, at least 200%, at least 225%, at least 250%, at least 275%, at least 300%, at least 350%, or at least 400% of the lysozyme activity of SEQ ID NO: 159. In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as follows: lysozyme (50 µL of 0.7 µg/mL lysozyme in phosphate buffer (5 mM citrate, 5 mM $K_2HPO_4$, 0.01% TritonX-100, pH 5.0)) is mixed with *Micrococcus lysodeikticus* solution (450 µL of 1% lyophilized *Micrococcus lysodeikticus* ATCC No. 4698 in milli-Q water) and incubated at 40° C. with shaking (500 rpm) for 45 min; the sample is centrifuged (4000 g, 5 min); supernatant (100 µL) is mixed with HCl (50 µL 3.2M) and incubated at 95° C. for 80 min; NaOH (50 µL, 3.5 M) is added and 150 µL of the sample is added to 4-hydroxybenzhydrazide in K-Na tartrate/NaOH buffer (75 µL of 50 g/L K-Na tartrate+20 g/L NaOH); the mixture is incubated at 95° C. for 10 min; and the optical density is measured at 405 nm.

Granules Comprising Polypeptides Having Lysozyme Activity

In a second aspect, the invention relates to a granule comprising one or more GH25 polypeptides having lysozyme activity, wherein the polypeptide is selected from the group consisting of:

(a) a polypeptide having at least 80%, such as at least 85%, at least 90% or at least 95% sequence identity to the polypeptide of SEQ ID NO: 3;

(b) a polypeptide having at least 84%, such as at least 85%, at least 90% or at least 95% sequence identity to the polypeptide of SEQ ID NO: 6;

(c) a polypeptide having at least 80%, such as at least 85%, at least 90% or at least 95% sequence identity to the polypeptide of SEQ ID NO: 9;

(d) a polypeptide having at least 80%, such as at least 85%, at least 90% or at least 95% sequence identity to the polypeptide of SEQ ID NO: 12;

(e) a polypeptide having at least 80%, such as at least 85%, at least 90% or at least 95% sequence identity to the polypeptide of SEQ ID NO: 15;

(f) a polypeptide having at least 80%, such as at least 85%, at least 90% or at least 95% sequence identity to the polypeptide of SEQ ID NO: 18;

(g) a polypeptide having at least 80%, such as at least 85%, at least 90% or at least 95% sequence identity to the polypeptide of SEQ ID NO: 21;

(h) a polypeptide having at least 80%, such as at least 85%, at least 90% or at least 95% sequence identity to the polypeptide of SEQ ID NO: 24;

(i) a polypeptide having at least 80%, such as at least 85%, at least 90% or at least 95% sequence identity to the polypeptide of SEQ ID NO: 27;

(j) a polypeptide having at least 84%, such as at least 85%, at least 90% or at least 95% sequence identity to the polypeptide of SEQ ID NO: 30;

(k) a polypeptide having at least 80%, such as at least 85%, at least 90% or at least 95% sequence identity to the polypeptide of SEQ ID NO: 33;

(l) a polypeptide having at least 80%, such as at least 85%, at least 90% or at least 95% sequence identity to the polypeptide of SEQ ID NO: 36;

(m) a polypeptide having at least 84%, such as at least 85%, at least 90% or at least 95% sequence identity to the polypeptide of SEQ ID NO: 39;

(n) a polypeptide having at least 80%, such as at least 85%, at least 90% or at least 95% sequence identity to the polypeptide of SEQ ID NO: 42;

(o) a polypeptide having at least 80%, such as at least 85%, at least 90% or at least 95% sequence identity to the polypeptide of SEQ ID NO: 45;

(p) a polypeptide having at least 80%, such as at least 85%, at least 90% or at least 95% sequence identity to the polypeptide of SEQ ID NO: 48;
(q) a polypeptide having at least 80%, such as at least 85%, at least 90% or at least 95% sequence identity to the polypeptide of SEQ ID NO: 51;
(r) a polypeptide having at least 80%, such as at least 85%, at least 90% or at least 95% sequence identity to the polypeptide of SEQ ID NO: 54;
(s) a polypeptide having at least 80%, such as at least 85%, at least 90% or at least 95% sequence identity to the polypeptide of SEQ ID NO: 57;
(t) a polypeptide having at least 80%, such as at least 85%, at least 90% or at least 95% sequence identity to the polypeptide of SEQ ID NO: 60;
(u) a polypeptide having at least 80%, such as at least 85%, at least 90% or at least 95% sequence identity to the polypeptide of SEQ ID NO: 63;
(v) a polypeptide having at least 80%, such as at least 85%, at least 90% or at least 95% sequence identity to the polypeptide of SEQ ID NO: 66;
(w) a polypeptide having at least 80%, such as at least 85%, at least 90% or at least 95% sequence identity to the polypeptide of SEQ ID NO: 69;
(x) a polypeptide having at least 84%, such as at least 85%, at least 90% or at least 95% sequence identity to the polypeptide of SEQ ID NO: 72;
(y) a polypeptide having at least 80%, such as at least 85%, at least 90% or at least 95% sequence identity to the polypeptide of SEQ ID NO: 75;
(z) a polypeptide having at least 80%, such as at least 85%, at least 90% or at least 95% sequence identity to the polypeptide of SEQ ID NO: 80;
(aa) a polypeptide having at least 80%, such as at least 85%, at least 90% or at least 95% sequence identity to the polypeptide of SEQ ID NO: 83;
(ab) a polypeptide having at least 80%, such as at least 85%, at least 90% or at least 95% sequence identity to the polypeptide of SEQ ID NO: 86;
(ac) a polypeptide having at least 86%, such as at least 90% or at least 95% sequence identity to the polypeptide of SEQ ID NO: 89;
(ad) a polypeptide having at least 82%, such as at least 85%, at least 90% or at least 95% sequence identity to the polypeptide of SEQ ID NO: 92;
(ae) a polypeptide having at least 82%, such as at least 85%, at least 90% or at least 95% sequence identity to the polypeptide of SEQ ID NO: 95;
(af) a polypeptide having at least 80%, such as at least 85%, at least 90% or at least 95% sequence identity to the polypeptide of SEQ ID NO: 98;
(ag) a polypeptide having at least 80%, such as at least 85%, at least 90% or at least 95% sequence identity to the polypeptide of SEQ ID NO: 101;
(ah) a polypeptide having at least 80%, such as at least 85%, at least 90% or at least 95% sequence identity to the polypeptide of SEQ ID NO: 104;
(ai) a polypeptide having at least 80%, such as at least 85%, at least 90% or at least 95% sequence identity to the polypeptide of SEQ ID NO: 107;
(aj) a polypeptide having at least 82%, such as at least 85%, at least 90% or at least 95% sequence identity to the polypeptide of SEQ ID NO: 110;
(ak) a polypeptide having at least 81%, such as at least 85%, at least 90% or at least 95% sequence identity to the polypeptide of SEQ ID NO: 113;
(al) a polypeptide having at least 80%, such as at least 85%, at least 90% or at least 95% sequence identity to the polypeptide of SEQ ID NO: 116;
(am) a polypeptide having at least 80%, such as at least 85%, at least 90% or at least 95% sequence identity to the polypeptide of SEQ ID NO: 119;
(an) a polypeptide having at least 80%, such as at least 85%, at least 90% or at least 95% sequence identity to the polypeptide of SEQ ID NO: 122;
(ao) a polypeptide having at least 80%, such as at least 85%, at least 90% or at least 95% sequence identity to the polypeptide of SEQ ID NO: 125;
(ap) a polypeptide having at least 80%, such as at least 85%, at least 90% or at least 95% sequence identity to the polypeptide of SEQ ID NO: 128;
(aq) a polypeptide having at least 80%, such as at least 85%, at least 90% or at least 95% sequence identity to the polypeptide of SEQ ID NO: 131;
(ar) a polypeptide having at least 80%, such as at least 85%, at least 90% or at least 95% sequence identity to the polypeptide of SEQ ID NO: 134;
(as) a polypeptide having at least 80%, such as at least 85%, at least 90% or at least 95% sequence identity to the polypeptide of SEQ ID NO: 137;
(at) a polypeptide having at least 80%, such as at least 85%, at least 90% or at least 95% sequence identity to the polypeptide of SEQ ID NO: 140;
(au) a polypeptide having at least 80%, such as at least 85%, at least 90% or at least 95% sequence identity to the polypeptide of SEQ ID NO: 143;
(av) a polypeptide having at least 80%, such as at least 85%, at least 90% or at least 95% sequence identity to the polypeptide of SEQ ID NO: 146;
(aw) a polypeptide having at least 80%, such as at least 85%, at least 90% or at least 95% sequence identity to the polypeptide of SEQ ID NO: 149;
(ax) a polypeptide having at least 80%, such as at least 85%, at least 90% or at least 95% sequence identity to the polypeptide of SEQ ID NO: 152;
(ay) a polypeptide having at least 80%, such as at least 85%, at least 90% or at least 95% sequence identity to the polypeptide of SEQ ID NO: 155;
(az) a polypeptide having at least 80%, such as at least 85%, at least 90% or at least 95% sequence identity to the polypeptide of SEQ ID NO: 158;
(ba) a polypeptide having at least 80%, such as at least 85%, at least 90% or at least 95% sequence identity to the polypeptide of SEQ ID NO: 221;
(bb) a polypeptide having at least 80%, such as at least 85%, at least 90% or at least 95% sequence identity to the polypeptide of SEQ ID NO: 224;
(bc) a polypeptide having at least 80%, such as at least 85%, at least 90% or at least 95% sequence identity to the polypeptide of SEQ ID NO: 227;
(bd) a polypeptide having at least 80%, such as at least 85%, at least 90% or at least 95% sequence identity to the polypeptide of SEQ ID NO: 230;
(be) a polypeptide having at least 80%, such as at least 85%, at least 90% or at least 95% sequence identity to the polypeptide of SEQ ID NO: 233;
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27 or 28 positions;

(bg) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal His-tag and/or HQ-tag;

(bh) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal extension of up to 10 amino acids, e.g. 1, 2, 3, 4, 5, 6, 7, 8, 9 or 10 amino acids; and (bi) a fragment of the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) having lysozyme activity and having at least 90% of the length of the mature polypeptide.

In an embodiment, the one or more GH25 polypeptides comprises the motif YKNA (SEQ ID NO: 160) and/or the motif FGGW[S/T] (SEQ ID NO: 161), and preferably is selected from the group selected from SEQ ID NO: 12, SEQ ID NO: 27, SEQ ID NO: 42, SEQ ID NO: 57, SEQ ID NO: 63, SEQ ID NO: 66, SEQ ID NO: 80, SEQ ID NO: 149, SEQ ID NO:152, SEQ ID NO: 155, SEQ ID NO: 224, SEQ ID NO: 227, SEQ ID NO: 230 and SEQ ID NO: 233.

In an embodiment, the polypeptide comprises or consists of amino acids 1 to 207 of SEQ ID NO: 3, amino acids 1 to 201 of SEQ ID NO: 6, amino acids 1 to 201 of SEQ ID NO: 9, amino acids 1 to 203 of SEQ ID NO: 12, amino acids 1 to 208 of SEQ ID NO: 15, amino acids 1 to 207 of SEQ ID NO: 18, amino acids 1 to 208 of SEQ ID NO: 21, amino acids 1 to 207 of SEQ ID NO: 24, amino acids 1 to 207 of SEQ ID NO: 27, amino acids 1 to 207 of SEQ ID NO: 30, amino acids 1 to 208 of SEQ ID NO: 33, amino acids 1 to 208 of SEQ ID NO: 36, amino acids 1 to 206 of SEQ ID NO: 39, amino acids 1 to 207 of SEQ ID NO: 42, amino acids 1 to 216 of SEQ ID NO: 45, amino acids 1 to 218 of SEQ ID NO: 48, amino acids 1 to 204 of SEQ ID NO: 51, amino acids 1 to 203 of SEQ ID NO: 54, amino acids 1 to 209 of SEQ ID NO: 57, amino acids 1 to 208 of SEQ ID NO: 60, amino acids 1 to 210 of SEQ ID NO: 63, amino acids 1 to 207 of SEQ ID NO: 66, amino acids 1 to 207 of SEQ ID NO: 69, amino acids 1 to 208 of SEQ ID NO: 72, amino acids 1 to 217 of SEQ ID NO: 75, amino acids 1 to 208 of SEQ ID NO: 80, amino acids 1 to 201 of SEQ ID NO: 83, amino acids 1 to 202 of SEQ ID NO: 86, amino acids 1 to 207 of SEQ ID NO: 89, amino acids 1 to 202 of SEQ ID NO: 92, amino acids 1 to 201 of SEQ ID NO: 95, amino acids 1 to 202 of SEQ ID NO: 98, amino acids 1 to 206 of SEQ ID NO: 101, amino acids 1 to 202 of SEQ ID NO: 104, amino acids 1 to 202 of SEQ ID NO: 107, amino acids 1 to 202 of SEQ ID NO: 110, amino acids 1 to 202 of SEQ ID NO: 113, amino acids 1 to 206 of SEQ ID NO: 116, amino acids 1 to 207 of SEQ ID NO: 119, amino acids 1 to 208 of SEQ ID NO: 122, amino acids 1 to 215 of SEQ ID NO: 125, amino acids 1 to 217 of SEQ ID NO: 128, amino acids 1 to 214 of SEQ ID NO: 131, amino acids 1 to 208 of SEQ ID NO: 134, amino acids 1 to 203 of SEQ ID NO: 137, amino acids 1 to 216 of SEQ ID NO: 140, amino acids 1 to 207 of SEQ ID NO: 143, amino acids 1 to 208 of SEQ ID NO: 146, amino acids 1 to 207 of SEQ ID NO: 149, amino acids 1 to 207 of SEQ ID NO: 152, amino acids 1 to 207 of SEQ ID NO: 155, amino acids 1 to 208 of SEQ ID NO: 158, amino acids 1 to 207 of SEQ ID NO: 221, amino acids 1 to 207 of SEQ ID NO: 224, amino acids 1 to 208 of SEQ ID NO: 227, amino acids 1 to 207 of SEQ ID NO: 230 or amino acids 1 to 207 of SEQ ID NO: 233.

In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159. In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as follows: lysozyme (50 μL of 0.7 μg/mL lysozyme in phosphate buffer (5 mM citrate, 5 mM $K_2HPO_4$, 0.01% TritonX-100, pH 5.0)) is mixed with *Micrococcus lysodeikticus* solution (450 μL of 1% lyophilized *Micrococcus lysodeikticus* ATCC No. 4698 in milli-Q water) and incubated at 40° C. with shaking (500 rpm) for 45 min; the sample is centrifuged (4000 g, 5 min); supernatant (100 μL) is mixed with HCl (50 μL 3.2M) and incubated at 95° C. for 80 min; NaOH (50 μL, 3.5 M) is added and 150 μL of the sample is added to 4-hydroxybenzhydrazide in K-Na tartrate/NaOH buffer (75 μL of 50 g/L K-Na tartrate+20 g/L NaOH); the mixture is incubated at 95° C. for 10 min; and the optical density is measured at 405 nm.

In one embodiment of the second aspect, the granule comprises one or more formulating agents (such as those described herein), preferably a formulating agent selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose, preferably selected from the list consisting of 1,2-propylene glycol, 1,3-propylene glycol, sodium sulfate, dextrin, cellulose, sodium thiosulfate, kaolin and calcium carbonate.

In a further embodiment to any part of the second aspect, the granule comprises a core particle and one or more coatings. In a preferred embodiment, the coating comprises salt and/or wax and/or flour.

In one embodiment, the granule comprises one or more additional enzymes. The one or more additional enzymes is preferably selected from the group consisting of phytase, xylanase, galactanase, alpha-galactosidase, beta-galactosidase, protease, phospholipase A1, phospholipase A2, lysophospholipase, phospholipase C, phospholipase D, amylase, lysozyme, arabinofuranosidase, beta-xylosidase, acetyl xylan esterase, feruloyl esterase, cellulase, cellobiohydrolases, beta-glucosidase, pullulanase, and beta-glucanase or any combination thereof.

In one embodiment, the granule comprises one or more probiotics. The one or more probiotics is preferably selected from the group consisting of *Bacillus subtilis*, *Bacillus licheniformis*, *Bacillus amyloliquefaciens*, *Bacillus cereus*, *Bacillus pumilus*, *Bacillus polymyxa*, *Bacillus megaterium*, *Bacillus coagulans*, *Bacillus circulans*, *Bifidobacterium bifidum*, *Bifidobacterium animalis*, *Bifidobacterium* sp., *Carnobacterium* sp., *Clostridium butyricum*, *Clostridium* sp., *Enterococcus faecium*, *Enterococcus* sp., *Lactobacillus* sp., *Lactobacillus acidophilus*, *Lactobacillus farciminus*, *Lactobacillus rhamnosus*, *Lactobacillus reuteri*, *Lactobacillus salivarius*, *Lactococcus lactis*, *Lactococcus* sp., *Leuconostoc* sp., *Megasphaera elsdenii*, *Megasphaera* sp., *Pediococcus acidilactici*, *Pediococcus* sp., *Propionibacterium thoenii*, *Propionibacterium* sp. and *Streptococcus* sp. or any combination thereof.

Polypeptides Having Lysozyme Activity

In a third aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 2.

In a continuation of the third aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 3. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 3.

In one embodiment, the invention relates to polypeptides having lysozyme activity and having a sequence identity to SEQ ID NO: 3 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 3 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 3 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 3 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 2. In one embodiment, the polypeptide preferably comprises or consists of the amino acid sequence of SEQ ID NO: 3; comprises the amino acid sequence of SEQ ID NO: 3 and a N-terminal and/or C-terminal His-tag and/or HQ-tag; comprises the amino acid sequence of SEQ ID NO: 3 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 3. In one embodiment, the polypeptide comprises or consists of amino acids 1 to 207 of SEQ ID NO: 3. In an embodiment, the polypeptide has been isolated.

In a continuation of the third aspect, the invention relates to a polypeptide having lysozyme activity encoded by a polynucleotide having a sequence identity to the mature polypeptide coding sequence of SEQ ID NO: 1 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the third aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the third aspect, the invention relates to variants of SEQ ID NO: 3 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 3 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 3 is not more than 10, e.g., 1, 2, 3, 4, 5, 6, 7, 8, 9 or 10. In one embodiment, the number of substitutions and/or deletions and/or insertions in SEQ ID NO: 3 is not more than 10, e.g., 1, 2, 3, 4, 5, 6, 7, 8, 9 or 10. In a further embodiment, the number of substitutions, preferably conservative substitutions, in SEQ ID NO: 3 is not more than 10, e.g., 1, 2, 3, 4, 5, 6, 7, 8, 9 or 10.

In an embodiment of the third aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly. Other examples of conservative substitutions are G to A; A to G, S; V to I, L, A, T, S; I to V, L, M; L to I, M, V; M to L, I, V; P to A, S, N; F to Y, W, H; Y to F, W, H; W to Y, F, H; R to K, E, D; K to R, E, D; H to Q, N, S; D to N, E, K, R, Q; E to Q, D, K, R, N; S to T, A; T to S, V, A; C to S, T, A; N to D, Q, H, S; Q to E, N, H, K, R.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for lysozyme activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labelling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide or a fusion polypeptide.

In a fourth aspect the invention relates to polypeptides having lysozyme activity having at least 89%, e.g., at least 90%, at least 91%, at least 92%, at least 93%, at least 94%, at least 95%, at least 96%, at least 97%, at least 98%, at least 99%, or 100% sequence identity to the mature polypeptide of SEQ ID NO: 5. In one embodiment, the polypeptides differ by up to 22 amino acids, e.g., 1, 2, 3, 4, 5, 6, 7, 8, 9, 10, 11, 12, 13, 14, 15, 16, 17, 18, 19, 20, 21 or 22 amino acids from the mature polypeptide of SEQ ID NO: 5.

In a continuation of the fourth aspect, the invention relates to polypeptides having lysozyme activity having at least 89%, e.g., at least 90%, at least 91%, at least 92%, at least 93%, at least 94%, at least 95%, at least 96%, at least 97%, at least 98%, at least 99%, or 100% sequence identity to SEQ ID NO: 6. In one embodiment, the polypeptides differ by up to 22 amino acids, e.g., 1, 2, 3, 4, 5, 6, 7, 8, 9, 10, 11, 12, 13, 14, 15, 16, 17, 18, 19, 20, 21 or 22 amino acids from the mature polypeptide of SEQ ID NO: 6.

In one embodiment, the invention relates to polypeptides having lysozyme activity and having a sequence identity to SEQ ID NO: 6 of at least 89% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 6 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 6 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 5. In one embodiment, the polypeptide preferably comprises or consists of the amino acid sequence of SEQ ID NO: 6; comprises the amino acid sequence of SEQ ID NO: 6 and a N-terminal and/or C-terminal His-tag and/or HQ-tag; comprises the amino acid sequence of SEQ ID NO: 6 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 6. In one embodiment, the polypeptide comprises or consists of amino acids 1 to 201 of SEQ ID NO: 6. In an embodiment, the polypeptide has been isolated.

In a continuation of the fourth aspect, the invention relates to a polypeptide having lysozyme activity encoded by a polynucleotide having a sequence identity to the mature polypeptide coding sequence of SEQ ID NO: 4 of at least 89%, e.g., at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fourth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fourth aspect, the invention relates to variants of SEQ ID NO: 6 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 6 is not more than 22, e.g., 1, 2, 3, 4, 5, 6, 7, 8, 9, 10, 11, 12, 13, 14, 15, 16, 17, 18, 19, 20, 21 or 22. In an embodiment, the number of positions comprising one or more amino acid substitutions, and/or one or more amino acid deletions, and/or one or more amino acid insertions or any combination thereof in SEQ ID NO: 6 is not more than 10, e.g., 1, 2, 3, 4, 5, 6, 7, 8, 9 or 10. In one embodiment, the number of substitutions and/or deletions and/or insertions in SEQ ID NO: 6 is not more than 10, e.g., 1, 2, 3, 4, 5, 6, 7, 8, 9 or 10. In a further embodiment, the number of substitutions, preferably conservative substitutions, in SEQ ID NO: 6 is not more than 10, e.g., 1, 2, 3, 4, 5, 6, 7, 8, 9 or 10. Examples of amino acid changes and conservative substitutions are described in the third aspect of the invention.

In an embodiment of the fourth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a fifth aspect the invention relates to polypeptides having lysozyme activity having at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 8. In one embodiment, the polypeptides differ by up to 38 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 acids from the mature polypeptide of SEQ ID NO: 8.

In a continuation of the fifth aspect, the invention relates to polypeptides having lysozyme activity having at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 9. In one embodiment, the polypeptides differ by up to 38 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 amino acids from the mature polypeptide of SEQ ID NO: 9.

In one embodiment, the invention relates to polypeptides having lysozyme activity and having a sequence identity to SEQ ID NO: 9 of at least 81% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 9 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 9 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 9 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 8. In one embodiment, the polypeptide preferably comprises or consists of the amino acid sequence of SEQ ID NO: 9; comprises the amino acid sequence of SEQ ID NO: 9 and a N-terminal and/or C-terminal His-tag and/or HQ-tag; comprises the amino acid sequence of SEQ ID NO: 9 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 9. In one embodiment, the polypeptide comprises or consists of amino acids 1 to 201 of SEQ ID NO: 9. In an embodiment, the polypeptide has been isolated.

In a continuation of the fifth aspect, the invention relates to a polypeptide having lysozyme activity encoded by a polynucleotide having a sequence identity to the mature polypeptide coding sequence of SEQ ID NO: 7 of at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fifth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fifth aspect, the invention relates to variants of SEQ ID NO: 9 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 9 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 9 is not more than 10, e.g., 1, 2, 3, 4, 5, 6, 7, 8, 9 or 10. In one embodiment, the number of substitutions and/or deletions and/or insertions in SEQ ID NO: 9 is not more than 10, e.g., 1, 2, 3, 4, 5, 6, 7, 8, 9 or 10. In a further embodiment, the number of substitutions, preferably conservative substitutions, in SEQ ID NO: 9 is not more than 10, e.g., 1, 2, 3, 4, 5, 6, 7, 8, 9 or 10. Examples of amino acid changes and conservative substitutions are described in the third aspect of the invention.

In an embodiment of the fifth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a sixth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 11. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 11.

In a continuation of the sixth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 12. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 12.

In one embodiment, the invention relates to polypeptides having lysozyme activity and having a sequence identity to SEQ ID NO: 12 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 12 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 12 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 12 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 11. In one embodiment, the polypeptide preferably comprises or consists of the amino acid sequence of SEQ ID NO: 12; comprises the amino acid sequence of SEQ ID NO: 12 and a N-terminal and/or C-terminal His-tag and/or HQ-tag; comprises the amino acid sequence of SEQ ID NO: 12 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 12. In one embodiment, the polypeptide comprises or consists of amino acids 1 to 203 of SEQ ID NO: 12. In an embodiment, the polypeptide has been isolated.

In a continuation of the sixth aspect, the invention relates to a polypeptide having lysozyme activity encoded by a polynucleotide having a sequence identity to the mature polypeptide coding sequence of SEQ ID NO: 10 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the sixth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the sixth aspect, the invention relates to variants of SEQ ID NO: 12 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 12 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 12 is not more than 10, e.g., 1, 2, 3, 4, 5, 6, 7, 8, 9 or 10. In one embodiment, the number of substitutions and/or deletions and/or insertions in SEQ ID NO: 12 is not more than 10, e.g., 1, 2, 3, 4, 5, 6, 7, 8, 9 or 10. In a further embodiment, the number of substitutions, preferably conservative substitutions, in SEQ ID NO: 12 is not more than 10, e.g., 1, 2, 3, 4, 5, 6, 7, 8, 9 or 10. Examples of amino acid changes and conservative substitutions are described in the third aspect of the invention.

In an embodiment of the sixth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the sixth aspect comprises the motif YKNA (SEQ ID NO: 160) and/or the motif FGGW[S/T] (SEQ ID NO: 161).

In a seventh aspect the invention relates to polypeptides having lysozyme activity having at least 97%, e.g., at least 97.5%, at least 98%, at least 98.5%, at least 99%, at least 99.5%, or 100% sequence identity to the mature polypeptide of SEQ ID NO: 14. In one embodiment, the polypeptides differ by up to 6 amino acids, e.g., 1, 2, 3, 4, 5 or 6 amino acids from the mature polypeptide of SEQ ID NO: 14.

In a continuation of the seventh aspect, the invention relates to polypeptides having lysozyme activity having at least 97%, e.g., at least 97.5%, at least 98%, at least 98.5%, at least 99%, at least 99.5%, or 100% sequence identity to SEQ ID NO: 15. In one embodiment, the polypeptides differ by up to 6 amino acids, e.g., 1, 2, 3, 4, 5 or 6 amino acids from the mature polypeptide of SEQ ID NO: 15.

In one embodiment, the invention relates to polypeptides having lysozyme activity and having a sequence identity to SEQ ID NO: 15 of at least 97% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 15 of at least 98% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 15 of at least 99% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 14. In one embodiment, the polypeptide preferably comprises or consists of the amino acid sequence of SEQ ID NO: 15; comprises the amino acid sequence of SEQ ID NO: 15 and a N-terminal and/or C-terminal His-tag and/or HQ-tag; comprises the amino acid sequence of SEQ ID NO: 15 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 15. In one embodiment, the polypeptide comprises or consists of amino acids 1 to 208 of SEQ ID NO: 15. In an embodiment, the polypeptide has been isolated.

In a continuation of the seventh aspect, the invention relates to a polypeptide having lysozyme activity encoded by a polynucleotide having a sequence identity to the mature polypeptide coding sequence of SEQ ID NO: 13 of at least 97%, e.g., at least 97.5%, at least 98%, at least 98.5%, at least 99%, at least 99.5%, or 100%. In a further embodiment, the polypeptide has been isolated.

In an embodiment of the seventh aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the seventh aspect, the invention relates to variants of SEQ ID NO: 15 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 15 is not more than 6, e.g., 1, 2, 3, 4, 5 or 6. In an embodiment, the number of positions comprising one or more amino acid substitutions, and/or one or more amino acid deletions, and/or one or more amino acid insertions or any combination thereof in SEQ ID NO: 15 is not more than 6, e.g., 1, 2, 3, 4, 5 or 6. In one embodiment, the number of substitutions and/or deletions and/or insertions in SEQ ID NO: 15 is not more than 6, e.g., 1, 2, 3, 4, 5 or 6. In a further embodiment, the number of substitutions, preferably conservative substitutions, in SEQ ID NO: 15 is not more than 6, e.g., 1, 2, 3, 4, 5 or 6. Examples of amino acid changes and conservative substitutions are described in the third aspect of the invention.

In an embodiment of the seventh aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an eighth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 17. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 17.

In a continuation of the eighth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 18. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 18.

In one embodiment, the invention relates to polypeptides having lysozyme activity and having a sequence identity to SEQ ID NO: 18 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 18 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 18 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID having a sequence identity to SEQ ID NO: 18 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 17. In one embodiment, the polypeptide preferably comprises or consists of the amino acid sequence of SEQ ID NO: 18; comprises the amino acid sequence of SEQ ID NO: 18 and a N-terminal and/or C-terminal His-tag and/or HQ-tag; comprises the amino acid sequence of SEQ ID NO: 18 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 18. In one embodiment, the polypeptide comprises or consists of amino acids 1 to 207 of SEQ ID NO: 18. In an embodiment, the polypeptide has been isolated.

In a continuation of the eighth aspect, the invention relates to a polypeptide having lysozyme activity encoded by a polynucleotide having a sequence identity to the mature polypeptide coding sequence of SEQ ID NO: 16 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the eighth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the eighth aspect, the invention relates to variants of SEQ ID NO: 18 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 18 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 18 is not more than 10, e.g., 1, 2, 3, 4, 5, 6, 7, 8, 9 or 10. In one embodiment, the number of substitutions and/or deletions and/or insertions in SEQ ID NO: 18 is not more than 10, e.g., 1, 2, 3, 4, 5, 6, 7, 8, 9 or 10. In a further embodiment, the number of substitutions, preferably conservative substitutions, in SEQ ID NO: 18 is not more than 10, e.g., 1, 2, 3, 4, 5, 6, 7, 8, 9 or 10. Examples of amino acid changes and conservative substitutions are described in the third aspect of the invention.

In an embodiment of the eighth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a ninth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 23. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 23.

In a continuation of the ninth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 24. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 24.

In one embodiment, the invention relates to polypeptides having lysozyme activity and having a sequence identity to SEQ ID NO: 24 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 24 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 24 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 24 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 23. In one embodiment, the polypeptide preferably comprises or consists of the amino acid sequence of SEQ ID NO: 24; comprises the amino acid sequence of SEQ ID NO: 24 and a N-terminal and/or C-terminal His-tag and/or HQ-tag; comprises the amino acid sequence of SEQ ID NO: 24 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 24. In one embodiment, the polypeptide comprises or consists of amino acids 1 to 207 of SEQ ID NO: 24. In an embodiment, the polypeptide has been isolated.

In a continuation of the ninth aspect, the invention relates to a polypeptide having lysozyme activity encoded by a polynucleotide having a sequence identity to the mature polypeptide coding sequence of SEQ ID NO: 22 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the ninth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the ninth aspect, the invention relates to variants of SEQ ID NO: 24 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 24 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 24 is not more than 10, e.g., 1, 2, 3, 4, 5, 6, 7, 8, 9 or 10. In one embodiment, the number of substitutions and/or deletions and/or insertions in SEQ ID NO: 24 is not more than 10, e.g., 1, 2, 3, 4, 5, 6, 7, 8, 9 or 10. In a further embodiment, the number of substitutions, preferably conservative substitutions, in SEQ ID NO: 24 is not more than 10, e.g., 1, 2, 3, 4, 5, 6, 7, 8, 9 or 10. Examples of amino acid changes and conservative substitutions are described in the third aspect of the invention.

In an embodiment of the ninth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a tenth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 26. In one embodiment, the polypeptides differ by up to 40 amino acids, e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 26.

In a continuation of the tenth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 27.

In one embodiment, the invention relates to polypeptides having lysozyme activity and having a sequence identity to SEQ ID NO: 27 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 27 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 27 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 27 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 26. In one embodiment, the polypeptide preferably comprises or consists of the amino acid sequence of SEQ ID NO: 27; comprises the amino acid sequence of SEQ ID NO: 27 and a N-terminal and/or C-terminal His-tag and/or HQ-tag; comprises the amino acid sequence of SEQ ID NO: 27 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 27. In one embodiment, the polypeptide comprises or consists of amino acids 1 to 207 of SEQ ID NO: 27. In an embodiment, the polypeptide has been isolated.

In a continuation of the tenth aspect, the invention relates to a polypeptide having lysozyme activity encoded by a polynucleotide having a sequence identity to the mature polypeptide coding sequence of SEQ ID NO: 25 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the tenth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the tenth aspect, the invention relates to variants of SEQ ID NO: 27 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 27 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 27 is not more than 10, e.g., 1, 2, 3, 4, 5, 6, 7, 8, 9 or 10. In one embodiment, the number of substitutions and/or deletions and/or insertions in SEQ ID NO: 27 is not more than 10, e.g., 1, 2, 3, 4, 5, 6, 7, 8, 9 or 10. In a further embodiment, the number of substitutions, preferably conservative substitutions, in SEQ ID NO: 27 is not more than 10, e.g., 1, 2, 3, 4, 5, 6, 7, 8, 9 or 10. Examples of amino acid changes and conservative substitutions are described in the third aspect of the invention.

In an embodiment of the tenth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the tenth aspect comprises the motif YKNA (SEQ ID NO: 160) and/or the motif FGGW[S/T] (SEQ ID NO: 161).

In an eleventh aspect the invention relates to polypeptides having lysozyme activity having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 29. In one embodiment, the polypeptides differ by up to 35 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids from the mature polypeptide of SEQ ID NO: 29.

In a continuation of the eleventh aspect, the invention relates to polypeptides having lysozyme activity having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 30. In one embodiment, the polypeptides differ by up to 35 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids from the mature polypeptide of SEQ ID NO: 30.

In one embodiment, the invention relates to polypeptides having lysozyme activity and having a sequence identity to SEQ ID NO: 30 of at least 83% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 30 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 30 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 30 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 29. In one embodiment, the polypeptide preferably comprises or consists of the amino acid sequence of SEQ ID NO: 30; comprises the amino acid sequence of SEQ ID NO: 30 and a N-terminal and/or C-terminal His-tag and/or HQ-tag; comprises the amino acid sequence of SEQ ID NO: 30 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 30. In one embodiment, the polypeptide comprises or consists of amino acids 1 to 207 of SEQ ID NO: 30. In an embodiment, the polypeptide has been isolated.

In a continuation of the eleventh aspect, the invention relates to a polypeptide having lysozyme activity encoded by a polynucleotide having a sequence identity to the mature polypeptide coding sequence of SEQ ID NO: 28 of at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the eleventh aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the eleventh aspect, the invention relates to variants of SEQ ID NO: 30 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 30 is not more than 33, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33. In an embodiment, the number of positions comprising one or more amino acid substitutions, and/or one or more amino acid deletions, and/or one or more amino acid insertions or any combination thereof in SEQ ID NO: 30 is not more than 10, e.g., 1, 2, 3, 4, 5, 6, 7, 8, 9 or 10. In one embodiment, the number of substitutions and/or deletions and/or insertions in SEQ ID NO: 30 is not more than 10, e.g., 1, 2, 3, 4, 5, 6, 7, 8, 9 or 10. In a further embodiment, the number of substitutions, preferably conservative substitutions, in SEQ ID NO: 30 is not more than 10, e.g., 1, 2, 3, 4, 5, 6, 7, 8, 9 or 10. Examples of amino acid changes and conservative substitutions are described in the third aspect of the invention.

In an embodiment of the eleventh aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a twelfth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 32. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 32.

In a continuation of the twelfth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 33. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 33.

In one embodiment, the invention relates to polypeptides having lysozyme activity and having a sequence identity to SEQ ID NO: 33 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 33 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 33 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 33 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 32. In one embodiment, the polypeptide preferably comprises or consists of the amino acid sequence of SEQ ID NO: 33; comprises the amino acid sequence of SEQ ID NO: 33 and a N-terminal and/or C-terminal His-tag and/or HQ-tag; comprises the amino acid sequence of SEQ ID NO: 33 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 33. In one embodiment, the polypeptide comprises or consists of amino acids 1 to 208 of SEQ ID NO: 33. In an embodiment, the polypeptide has been isolated.

In a continuation of the twelfth aspect, the invention relates to a polypeptide having lysozyme activity encoded by a polynucleotide having a sequence identity to the mature polypeptide coding sequence of SEQ ID NO: 31 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twelfth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the twelfth aspect, the invention relates to variants of SEQ ID NO: 33 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 33 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 33 is not more than 10, e.g., 1, 2, 3, 4, 5, 6, 7, 8, 9 or 10. In one embodiment, the number of substitutions and/or deletions and/or insertions in SEQ ID NO: 33 is not more than 10, e.g., 1, 2, 3, 4, 5, 6, 7, 8, 9 or 10. In a further embodiment, the number of substitutions, preferably conservative substitutions, in SEQ ID NO: 33 is not more than 10, e.g., 1, 2, 3, 4, 5, 6, 7, 8, 9 or 10. Examples of amino acid changes and conservative substitutions are described in the third aspect of the invention.

In an embodiment of the twelfth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a thirteenth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 35. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 35.

In a continuation of the thirteenth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 36. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 36.

In one embodiment, the invention relates to polypeptides having lysozyme activity and having a sequence identity to SEQ ID NO: 36 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 36 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 36 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 36 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 35. In one embodiment, the polypeptide preferably comprises or consists of the amino acid sequence of SEQ ID NO: 36; comprises the amino acid sequence of SEQ ID NO: 36 and a N-terminal and/or C-terminal His-tag and/or HQ-tag; comprises the amino acid sequence of SEQ ID NO: 36 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 36. In one embodiment, the polypeptide comprises or consists of amino acids 1 to 208 of SEQ ID NO: 36. In an embodiment, the polypeptide has been isolated.

In a continuation of the thirteenth aspect, the invention relates to a polypeptide having lysozyme activity encoded by a polynucleotide having a sequence identity to the mature polypeptide coding sequence of SEQ ID NO: 34 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the thirteenth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the thirteenth aspect, the invention relates to variants of SEQ ID NO: 36 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 36 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 36 is not more than 10, e.g., 1, 2, 3, 4, 5, 6, 7, 8, 9 or 10. In one embodiment, the number of substitutions and/or deletions and/or insertions in SEQ ID NO: 36 is not more than 10, e.g., 1, 2, 3, 4, 5, 6, 7, 8, 9 or 10. In a further embodiment, the number of substitutions, preferably conservative substitutions, in SEQ ID NO: 36 is not more than 10, e.g., 1, 2, 3, 4, 5, 6, 7, 8, 9 or 10. Examples of amino acid changes and conservative substitutions are described in the third aspect of the invention.

In an embodiment of the thirteenth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a fourteenth aspect the invention relates to polypeptides having lysozyme activity having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 38. In one embodiment, the polypeptides differ by up to 35 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids from the mature polypeptide of SEQ ID NO: 38.

In a continuation of the fourteenth aspect, the invention relates to polypeptides having lysozyme activity having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 39. In one embodiment, the polypeptides differ by up to 35 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids from the mature polypeptide of SEQ ID NO: 39.

In one embodiment, the invention relates to polypeptides having lysozyme activity and having a sequence identity to SEQ ID NO: 39 of at least 83% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 39 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 39 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 39 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 38. In one embodiment, the polypeptide preferably comprises or consists of the amino acid sequence of SEQ ID NO: 39; comprises the amino acid sequence of SEQ ID NO: 39 and a N-terminal and/or C-terminal His-tag and/or HQ-tag; comprises the amino acid sequence of SEQ ID NO: 39 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 39. In one embodiment, the polypeptide comprises or consists of amino acids 1 to 206 of SEQ ID NO: 39. In an embodiment, the polypeptide has been isolated.

In a continuation of the fourteenth aspect, the invention relates to a polypeptide having lysozyme activity encoded by a polynucleotide having a sequence identity to the mature polypeptide coding sequence of SEQ ID NO: 37 of at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fourteenth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fourteenth aspect, the invention relates to variants of SEQ ID NO: 39 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 39 is not more than 33, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33. In an embodiment, the number of positions comprising one or more amino acid substitutions, and/or one or more amino acid deletions, and/or one or more amino acid insertions or any combination thereof in SEQ ID NO: 39 is not more than 10, e.g., 1, 2, 3, 4, 5, 6, 7, 8, 9 or 10. In one embodiment, the number of substitutions and/or deletions and/or insertions in SEQ ID NO: 39 is not more than 10, e.g., 1, 2, 3, 4, 5, 6, 7, 8, 9 or 10. In a further embodiment, the number of substitutions, preferably conservative substitutions, in SEQ ID NO: 39 is not more than 10, e.g., 1, 2, 3, 4, 5, 6, 7, 8, 9 or 10. Examples of amino acid changes and conservative substitutions are described in the third aspect of the invention.

In an embodiment of the fourteenth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a fifteenth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 41. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 41.

In a continuation of the fifteenth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 42. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 42.

In one embodiment, the invention relates to polypeptides having lysozyme activity and having a sequence identity to SEQ ID NO: 42 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 42 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 42 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 42 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 41. In one embodiment, the polypeptide preferably comprises or consists of the amino acid sequence of SEQ ID NO: 42; comprises the amino acid sequence of SEQ ID NO: 42 and a N-terminal and/or C-terminal His-tag and/or HQ-tag; comprises the amino acid sequence of SEQ ID NO: 42 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 42. In one embodiment, the polypeptide comprises or consists of amino acids 1 to 207 of SEQ ID NO: 42. In an embodiment, the polypeptide has been isolated.

In a continuation of the fifteenth aspect, the invention relates to a polypeptide having lysozyme activity encoded by a polynucleotide having a sequence identity to the mature polypeptide coding sequence of SEQ ID NO: 40 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fifteenth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fifteenth aspect, the invention relates to variants of SEQ ID NO: 42 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 42 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 42 is not more than 10, e.g., 1, 2, 3, 4, 5, 6, 7, 8, 9 or 10. In one embodiment, the number of substitutions and/or deletions and/or insertions in SEQ ID NO: 42 is not more than 10, e.g., 1, 2, 3, 4, 5, 6, 7, 8, 9 or 10. In a further embodiment, the number of substitutions, preferably conservative substitutions, in SEQ ID NO: 42 is not more than 10, e.g., 1, 2, 3, 4, 5, 6, 7, 8, 9 or 10. Examples of amino acid changes and conservative substitutions are described in the third aspect of the invention.

In an embodiment of the fifteenth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the fifteenth aspect comprises the motif YKNA (SEQ ID NO: 160) and/or the motif FGGW[S/T] (SEQ ID NO: 161).

In a sixteenth aspect the invention relates to polypeptides having lysozyme activity having at least 86%, e.g., at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 44. In one embodiment, the polypeptides differ by up to 30 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids from the mature polypeptide of SEQ ID NO: 44.

In a continuation of the sixteenth aspect, the invention relates to polypeptides having lysozyme activity having at least 86%, e.g., at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 45. In one embodiment, the polypeptides differ by up to 30 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids from the mature polypeptide of SEQ ID NO: 45.

In one embodiment, the invention relates to polypeptides having lysozyme activity and having a sequence identity to SEQ ID NO: 45 of at least 86% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 45 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 45 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 44. In one embodiment, the polypeptide preferably comprises or consists of the amino acid sequence of SEQ ID NO: 45; comprises the amino acid sequence of SEQ ID NO: 45 and a N-terminal and/or C-terminal His-tag and/or HQ-tag; comprises the amino acid sequence of SEQ ID NO: 45 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 45. In one embodiment, the polypeptide comprises or consists of amino acids 1 to 216 of SEQ ID NO: 45. In an embodiment, the polypeptide has been isolated.

In a continuation of the sixteenth aspect, the invention relates to a polypeptide having lysozyme activity encoded by a polynucleotide having a sequence identity to the mature polypeptide coding sequence of SEQ ID NO: 43 of at least 86%, e.g., at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the sixteenth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the sixteenth aspect, the invention relates to variants of SEQ ID NO: 45 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 45 is not more than 30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30. In an embodiment, the number of positions comprising one or more amino acid substitutions, and/or one or more amino acid deletions, and/or one or more amino acid insertions or any combination thereof in SEQ ID NO: 45 is not more than 10, e.g., 1, 2, 3, 4, 5, 6, 7, 8, 9 or 10. In one embodiment, the number of substitutions and/or deletions and/or insertions in SEQ ID NO: 45 is not more than 10, e.g., 1, 2, 3, 4, 5, 6, 7, 8, 9 or 10. In a further embodiment, the number of substitutions, preferably conservative substitutions, in SEQ ID NO: 45 is not more than 10, e.g., 1, 2, 3, 4, 5, 6, 7, 8, 9 or 10. Examples of amino acid changes and conservative substitutions are described in the third aspect of the invention.

In an embodiment of the sixteenth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a seventeenth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 47. In one embodiment, the polypeptides differ by up to 40 amino acids, e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 47.

In a continuation of the seventeenth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 48. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 48.

In one embodiment, the invention relates to polypeptides having lysozyme activity and having a sequence identity to SEQ ID NO: 48 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 48 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 48 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 48 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 47. In one embodiment, the polypeptide preferably comprises or consists of the amino acid sequence of SEQ ID NO: 48; comprises the amino acid sequence of SEQ ID NO: 48 and a N-terminal and/or C-terminal His-tag and/or HQ-tag; comprises the amino acid sequence of SEQ ID NO: 48 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 48. In one embodiment, the polypeptide comprises or consists of amino acids 1 to 218 of SEQ ID NO: 48. In an embodiment, the polypeptide has been isolated.

In a continuation of the seventeenth aspect, the invention relates to a polypeptide having lysozyme activity encoded by a polynucleotide having a sequence identity to the mature polypeptide coding sequence of SEQ ID NO: 46 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the seventeenth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the seventeenth aspect, the invention relates to variants of SEQ ID NO: 48 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 48 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 48 is not more than 10, e.g., 1, 2, 3, 4, 5, 6, 7, 8, 9 or 10. In one embodiment, the number of substitutions and/or deletions and/or insertions in SEQ ID NO: 48 is not more than 10, e.g., 1, 2, 3, 4, 5, 6, 7, 8, 9 or 10. In a further embodiment, the number of substitutions, preferably conservative substitutions, in SEQ ID NO: 48 is not more than 10, e.g., 1, 2, 3, 4, 5, 6, 7, 8, 9 or 10. Examples of amino acid changes and conservative substitutions are described in the third aspect of the invention.

In an embodiment of the seventeenth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an eighteenth aspect, the invention relates to polypeptides having lysozyme activity having at least 92%, e.g., at least 93%, at least 94%, at least 95%, at least 96%, at least 97%, at least 98%, at least 99%, or 100% sequence identity to the mature polypeptide of SEQ ID NO: 50. In one embodiment, the polypeptides differ by up to 16 amino acids, e.g., 1, 2, 3, 4, 5, 6, 7, 8, 9, 10, 11, 12, 13, 14, 15 or 16 amino acids from the mature polypeptide of SEQ ID NO: 50.

In a continuation of the eighteenth aspect, the invention relates to polypeptides having lysozyme activity having at least 92%, e.g., at least 93%, at least 94%, at least 95%, at least 96%, at least 97%, at least 98%, at least 99%, or 100% sequence identity to SEQ ID NO: 51. In one embodiment, the polypeptides differ by up to 16 amino acids, e.g., 1, 2, 3, 4, 5, 6, 7, 8, 9, 10, 11, 12, 13, 14, 15 or 16 amino acids from the mature polypeptide of SEQ ID NO: 51.

In one embodiment, the invention relates to polypeptides having lysozyme activity and having a sequence identity to SEQ ID NO: 51 of at least 92% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 51 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 50. In one embodiment, the polypeptide preferably comprises or consists of the amino acid sequence of SEQ ID NO: 51; comprises the amino acid sequence of SEQ ID NO: 51 and a N-terminal and/or C-terminal His-tag and/or HQ-tag; comprises the amino acid sequence of SEQ ID NO: 51 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 51. In one embodiment, the polypeptide comprises or consists of amino acids 1 to 204 of SEQ ID NO: 51. In an embodiment, the polypeptide has been isolated.

In a continuation of the eighteenth aspect, the invention relates to a polypeptide having lysozyme activity encoded by a polynucleotide having a sequence identity to the mature polypeptide coding sequence of SEQ ID NO: 49 of at least 92%, e.g., at least 93%, at least 94%, at least 95%, at least 96%, at least 97%, at least 98%, at least 99%, or 100%. In a further embodiment, the polypeptide has been isolated.

In an embodiment of the eighteenth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the eighteenth aspect, the invention relates to variants of SEQ ID NO: 51 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 51 is not more than 16, e.g., 1, 2, 3, 4, 5, 6, 7, 8, 9, 10, 11, 12, 13, 14, 15 or 16. In an embodiment, the number of positions comprising one or more amino acid substitutions, and/or one or more amino acid deletions, and/or one or more amino acid insertions or any combination thereof in SEQ ID NO: 51 is not more than 10, e.g., 1, 2, 3, 4, 5, 6, 7, 8, 9 or 10. In one embodiment, the number of substitutions and/or deletions and/or insertions in SEQ ID NO: 51 is not more than 10, e.g., 1, 2, 3, 4, 5, 6, 7, 8, 9 or 10. In a further embodiment, the number of substitutions, preferably conservative substitutions, in SEQ ID NO: 51 is not more than 10, e.g., 1, 2, 3, 4, 5, 6, 7, 8, 9 or 10. Examples of amino acid changes and conservative substitutions are described in the third aspect of the invention.

In an embodiment of the eighteenth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a nineteenth aspect the invention relates to polypeptides having lysozyme activity having at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 53. In one embodiment, the polypeptides differ by up to 38 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 amino acids from the mature polypeptide of SEQ ID NO: 53.

In a continuation of the nineteenth aspect, the invention relates to polypeptides having lysozyme activity having at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 54. In one embodiment, the polypeptides differ by up to 38 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 amino acids from the mature polypeptide of SEQ ID NO: 54.

In one embodiment, the invention relates to polypeptides having lysozyme activity and having a sequence identity to SEQ ID NO: 54 of at least 81% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 54 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 54 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 54 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 53. In one embodiment, the polypeptide preferably comprises or consists of the amino acid sequence of SEQ ID NO: 54; comprises the amino acid sequence of SEQ ID NO: 54 and a N-terminal and/or C-terminal His-tag and/or HQ-tag; comprises the amino acid sequence of SEQ ID NO: 54 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 54. In one embodiment, the polypeptide comprises or consists of amino acids 1 to 203 of SEQ ID NO: 54. In an embodiment, the polypeptide has been isolated.

In a continuation of the nineteenth aspect, the invention relates to a polypeptide having lysozyme activity encoded by a polynucleotide having a sequence identity to the mature polypeptide coding sequence of SEQ ID NO: 52 of at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the nineteenth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the nineteenth aspect, the invention relates to variants of SEQ ID NO: 54 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 54 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 54 is not more than 10, e.g., 1, 2, 3, 4, 5, 6, 7, 8, 9 or 10. In one embodiment, the number of substitutions and/or deletions and/or insertions in SEQ ID NO: 54 is not more than 10, e.g., 1, 2, 3, 4, 5, 6, 7, 8, 9 or 10. In a further embodiment, the number of substitutions, preferably conservative substitutions, in SEQ ID NO: 54 is not more than 10, e.g., 1, 2, 3, 4, 5, 6, 7, 8, 9 or 10. Examples of amino acid changes and conservative substitutions are described in the third aspect of the invention.

In an embodiment of the nineteenth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a twentieth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 56. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 56.

In a continuation of the twentieth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 57. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 57.

In one embodiment, the invention relates to polypeptides having lysozyme activity and having a sequence identity to SEQ ID NO: 57 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 57 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 57 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 57 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 56. In one embodiment, the polypeptide preferably comprises or consists of the amino acid sequence of SEQ ID NO: 57; comprises the amino acid sequence of SEQ ID NO: 57 and a N-terminal and/or C-terminal His-tag and/or HQ-tag; comprises the amino acid sequence of SEQ ID NO: 57 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 57. In one embodiment, the polypeptide comprises or consists of amino acids 1 to 209 of SEQ ID NO: 57. In an embodiment, the polypeptide has been isolated.

In a continuation of the twentieth aspect, the invention relates to a polypeptide having lysozyme activity encoded by a polynucleotide having a sequence identity to the mature polypeptide coding sequence of SEQ ID NO: 55 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twentieth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the twentieth aspect, the invention relates to variants of SEQ ID NO: 57 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 57 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 57 is not more than 10, e.g., 1, 2, 3, 4, 5, 6, 7, 8, 9 or 10. In one embodiment, the number of substitutions and/or deletions and/or insertions in SEQ ID NO: 57 is not more than 10, e.g., 1, 2, 3, 4, 5, 6, 7, 8, 9 or 10. In a further embodiment, the number of substitutions, preferably conservative substitutions, in SEQ ID NO: 57 is not more than 10, e.g., 1, 2, 3, 4, 5, 6, 7, 8, 9 or 10. Examples of amino acid changes and conservative substitutions are described in the third aspect of the invention.

In an embodiment of the twentieth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the twentieth aspect comprises the motif YKNA (SEQ ID NO: 160) and/or the motif FGGW[S/T] (SEQ ID NO: 161).

In a twenty-first aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 59. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 59.

In a continuation of the twenty-first aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 60. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 60.

In one embodiment, the invention relates to polypeptides having lysozyme activity and having a sequence identity to SEQ ID NO: 60 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 60 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 60 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 60 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 59. In one embodiment, the polypeptide preferably comprises or consists of the amino acid sequence of SEQ ID NO: 60; comprises the amino acid sequence of SEQ ID NO: 60 and a N-terminal and/or C-terminal His-tag and/or HQ-tag; comprises the amino acid sequence of SEQ ID NO: 60 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 60. In one embodiment, the polypeptide comprises or consists of amino acids 1 to 208 of SEQ ID NO: 60. In an embodiment, the polypeptide has been isolated.

In a continuation of the twenty-first aspect, the invention relates to a polypeptide having lysozyme activity encoded by a polynucleotide having a sequence identity to the mature polypeptide coding sequence of SEQ ID NO: 58 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twenty-first aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the twenty-first aspect, the invention relates to variants of SEQ ID NO: 60 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 60 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 60 is not more than 10, e.g., 1, 2, 3, 4, 5, 6, 7, 8, 9 or 10. In one embodiment, the number of substitutions and/or deletions and/or insertions in SEQ ID NO: 60 is not more than 10, e.g., 1, 2, 3, 4, 5, 6, 7, 8, 9 or 10. In a further embodiment, the number of substitutions, preferably conservative substitutions, in SEQ ID NO: 60 is not more than 10, e.g., 1, 2, 3, 4, 5, 6, 7, 8, 9 or 10. Examples of amino acid changes and conservative substitutions are described in the third aspect of the invention.

In an embodiment of the twenty-first aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a twenty-second aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 62. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 62.

In a continuation of the twenty-second aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 63. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 63.

In one embodiment, the invention relates to polypeptides having lysozyme activity and having a sequence identity to SEQ ID NO: 63 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 63 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 63 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 63 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 62. In one embodiment, the polypeptide preferably comprises or consists of the amino acid sequence of SEQ ID NO: 63; comprises the amino acid sequence of SEQ ID NO: 63 and a N-terminal and/or C-terminal His-tag and/or HQ-tag; comprises the amino acid sequence of SEQ ID NO: 63 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 63. In one embodiment, the polypeptide comprises or consists of amino acids 1 to 210 of SEQ ID NO: 63. In an embodiment, the polypeptide has been isolated.

In a continuation of the twenty-second aspect, the invention relates to a polypeptide having lysozyme activity encoded by a polynucleotide having a sequence identity to the mature polypeptide coding sequence of SEQ ID NO: 61 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twenty-second aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the twenty-second aspect, the invention relates to variants of SEQ ID NO: 63 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 63 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 63 is not more than 10, e.g., 1, 2, 3, 4, 5, 6, 7, 8, 9 or 10. In one embodiment, the number of substitutions and/or deletions and/or insertions in SEQ ID NO: 63 is not more than 10, e.g., 1, 2, 3, 4, 5, 6, 7, 8, 9 or 10. In a further embodiment, the number of substitutions, preferably conservative substitutions, in SEQ ID NO: 63 is not more than 10, e.g., 1, 2, 3, 4, 5, 6, 7, 8, 9 or 10. Examples of amino acid changes and conservative substitutions are described in the third aspect of the invention.

In an embodiment of the twenty-second aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the twenty-second aspect comprises the motif YKNA (SEQ ID NO: 160) and/or the motif FGGW[S/T] (SEQ ID NO: 161).

In a twenty-third aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 65. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 65.

In a continuation of the twenty-third aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 66. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 66.

In one embodiment, the invention relates to polypeptides having lysozyme activity and having a sequence identity to SEQ ID NO: 66 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 66 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 66 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 66 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 65. In one embodiment, the polypeptide preferably comprises or consists of the amino acid sequence of SEQ ID NO: 66; comprises the amino acid sequence of SEQ ID NO: 66 and a N-terminal and/or C-terminal His-tag and/or HQ-tag; comprises the amino acid sequence of SEQ ID NO: 66 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 66. In one embodiment, the polypeptide comprises or consists of amino acids 1 to 207 of SEQ ID NO: 66. In an embodiment, the polypeptide has been isolated.

In a continuation of the twenty-third aspect, the invention relates to a polypeptide having lysozyme activity encoded by a polynucleotide having a sequence identity to the mature polypeptide coding sequence of SEQ ID NO: 64 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twenty-third aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the twenty-third aspect, the invention relates to variants of SEQ ID NO: 66 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 66 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 66 is not more than 10, e.g., 1, 2, 3, 4, 5, 6, 7, 8, 9 or 10. In one embodiment, the number of substitutions and/or deletions and/or insertions in SEQ ID NO: 66 is not more than 10, e.g., 1, 2, 3, 4, 5, 6, 7, 8, 9 or 10. In a further embodiment, the number of substitutions, preferably conservative substitutions, in SEQ ID NO: 66 is not more than 10, e.g., 1, 2, 3, 4, 5, 6, 7, 8, 9 or 10. Examples of amino acid changes and conservative substitutions are described in the third aspect of the invention.

In an embodiment of the twenty-third aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the twenty-third aspect comprises the motif YKNA (SEQ ID NO: 160) and/or the motif FGGW[S/T] (SEQ ID NO: 161).

In a twenty-fourth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 68. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 68.

In a continuation of the twenty-fourth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 69. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 69.

In one embodiment, the invention relates to polypeptides having lysozyme activity and having a sequence identity to SEQ ID NO: 69 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 69 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 69 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID having a sequence identity to SEQ ID NO: 69 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 68. In one embodiment, the polypeptide preferably comprises or consists of the amino acid sequence of SEQ ID NO: 69; comprises the amino acid sequence of SEQ ID NO: 69 and a N-terminal and/or C-terminal His-tag and/or HQ-tag; comprises the amino acid sequence of SEQ ID NO: 69 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 69. In one embodiment, the polypeptide comprises or consists of amino acids 1 to 207 of SEQ ID NO: 69. In an embodiment, the polypeptide has been isolated.

In a continuation of the twenty-fourth aspect, the invention relates to a polypeptide having lysozyme activity encoded by a polynucleotide having a sequence identity to the mature polypeptide coding sequence of SEQ ID NO: 67 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twenty-fourth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the twenty-fourth aspect, the invention relates to variants of SEQ ID NO: 69 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 69 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 69 is not more than 10, e.g., 1, 2, 3, 4, 5, 6, 7, 8, 9 or 10. In one embodiment, the number of substitutions and/or deletions and/or insertions in SEQ ID NO: 69 is not more than 10, e.g., 1, 2, 3, 4, 5, 6, 7, 8, 9 or 10. In a further embodiment, the number of substitutions, preferably conservative substitutions, in SEQ ID NO: 69 is not more than 10, e.g., 1, 2, 3, 4, 5, 6, 7, 8, 9 or 10. Examples of amino acid changes and conservative substitutions are described in the third aspect of the invention.

In an embodiment of the twenty-fourth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a twenty-fifth aspect the invention relates to polypeptides having lysozyme activity having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 71. In one embodiment, the polypeptides differ by up to 33 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 amino acids from the mature polypeptide of SEQ ID NO: 71.

In a continuation of the twenty-fifth aspect, the invention relates to polypeptides having lysozyme activity having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 72. In one embodiment, the polypeptides differ by up to 33 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 amino acids from the mature polypeptide of SEQ ID NO: 72.

In one embodiment, the invention relates to polypeptides having lysozyme activity and having a sequence identity to SEQ ID NO: 72 of at least 84% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 72 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 72 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 72 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 71. In one embodiment, the polypeptide preferably comprises or consists of the amino acid sequence of SEQ ID NO: 72; comprises the amino acid sequence of SEQ ID NO: 72 and a N-terminal and/or C-terminal His-tag and/or HQ-tag; comprises the amino acid sequence of SEQ ID NO: 72 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 72. In one embodiment, the polypeptide comprises or consists of amino acids 1 to 208 of SEQ ID NO: 72. In an embodiment, the polypeptide has been isolated.

In a continuation of the twenty-fifth aspect, the invention relates to a polypeptide having lysozyme activity encoded by a polynucleotide having a sequence identity to the mature polypeptide coding sequence of SEQ ID NO: 70 of at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twenty-fifth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the twenty-fifth aspect, the invention relates to variants of SEQ ID NO: 72 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 72 is not more than 33, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33. In an embodiment, the number of positions comprising one or more amino acid substitutions, and/or one or more amino acid deletions, and/or one or more amino acid insertions or any combination thereof in SEQ ID NO: 72 is not more than 10, e.g., 1, 2, 3, 4, 5, 6, 7, 8, 9 or 10. In one embodiment, the number of substitutions and/or deletions and/or insertions in SEQ ID NO: 72 is not more than 10, e.g., 1, 2, 3, 4, 5, 6, 7, 8, 9 or 10. In a further embodiment, the number of substitutions, preferably conservative substitutions, in SEQ ID NO: 72 is not more than 10, e.g., 1, 2, 3, 4, 5, 6, 7, 8, 9 or 10. Examples of amino acid changes and conservative substitutions are described in the third aspect of the invention.

In an embodiment of the twenty-fifth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a twenty-sixth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 74. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 74.

In a continuation of the twenty-sixth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 75. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 75.

In one embodiment, the invention relates to polypeptides having lysozyme activity and having a sequence identity to SEQ ID NO: 75 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 75 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 75 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 75 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 74. In one embodiment, the polypeptide preferably comprises or consists of the amino acid sequence of SEQ ID NO: 75; comprises the amino acid sequence of SEQ ID NO: 75 and a N-terminal and/or C-terminal His-tag and/or HQ-tag; comprises the amino acid sequence of SEQ ID NO: 75 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 75. In one embodiment, the polypeptide comprises or consists of amino acids 1 to 217 of SEQ ID NO: 75. In an embodiment, the polypeptide has been isolated.

In a continuation of the twenty-sixth aspect, the invention relates to a polypeptide having lysozyme activity encoded by a polynucleotide having a sequence identity to the mature polypeptide coding sequence of SEQ ID NO: 73 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twenty-sixth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the twenty-sixth aspect, the invention relates to variants of SEQ ID NO: 75 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 75 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 75 is not more than 10, e.g., 1, 2, 3, 4, 5, 6, 7, 8, 9 or 10. In one embodiment, the number of substitutions and/or deletions and/or insertions in SEQ ID NO: 75 is not more than 10, e.g., 1, 2, 3, 4, 5, 6, 7, 8, 9 or 10. In a further embodiment, the number of substitutions, preferably conservative substitutions, in SEQ ID NO: 75 is not more than 10, e.g., 1, 2, 3, 4, 5, 6, 7, 8, 9 or 10. Examples of amino acid changes and conservative substitutions are described in the third aspect of the invention.

In an embodiment of the twenty-sixth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a twenty-seventh aspect the invention relates to polypeptides having lysozyme activity having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 77. In one embodiment, the polypeptides differ by up to 33 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 amino acids from the mature polypeptide of SEQ ID NO: 77.

In a continuation of the twenty-seventh aspect, the invention relates to polypeptides having lysozyme activity having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 79. In one embodiment, the polypeptides differ by up to 33 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 amino acids from the mature polypeptide of SEQ ID NO: 79.

In a continuation of the twenty-seventh aspect, the invention relates to polypeptides having lysozyme activity having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 80. In one embodiment, the polypeptides differ by up to 33 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 amino acids from SEQ ID NO: 80.

In one embodiment, the invention relates to polypeptides having lysozyme activity and having a sequence identity to SEQ ID NO: 80 of at least 84% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 80 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 80 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 80 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 77. In one embodiment, the polypeptide comprises or consists of the mature polypeptide of SEQ ID NO: 79. In one embodiment, the polypeptide preferably comprises or consists of the amino acid sequence of SEQ ID NO: 80; comprises the amino acid sequence of SEQ ID NO: 80 and a N-terminal and/or C-terminal His-tag and/or HQ-tag; comprises the amino acid sequence of SEQ ID NO: 80 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 80. In one embodiment, the polypeptide comprises or consists of amino acids 1 to 208 of SEQ ID NO: 80. In an embodiment, the polypeptide has been isolated.

In a continuation of the twenty-seventh aspect, the invention relates to a polypeptide having lysozyme activity encoded by a polynucleotide having a sequence identity to the mature polypeptide coding sequence of SEQ ID NO: 76 of at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twenty-seventh aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the twenty-seventh aspect, the invention relates to variants of SEQ ID NO: 80 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 80 is not more than 33, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33. In an embodiment, the number of positions comprising one or more amino acid substitutions, and/or one or more amino acid deletions, and/or one or more amino acid insertions or any combination thereof in SEQ ID NO: 80 is not more than 10, e.g., 1, 2, 3, 4, 5, 6, 7, 8, 9 or 10. In one embodiment, the number of substitutions and/or deletions and/or insertions in SEQ ID NO: 80 is not more than 10, e.g., 1, 2, 3, 4, 5, 6, 7, 8, 9 or 10. In a further embodiment, the number of substitutions, preferably conservative substitutions, in SEQ ID NO: 80 is not more than 10, e.g., 1, 2, 3, 4, 5, 6, 7, 8, 9 or 10. Examples of amino acid changes and conservative substitutions are described in the third aspect of the invention.

In an embodiment of the twenty-seventh aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the twenty-seventh aspect comprises the motif YKNA (SEQ ID NO: 160) and/or the motif FGGW[S/T] (SEQ ID NO: 161).

In a twenty-eighth aspect the invention relates to polypeptides having lysozyme activity having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 82. In one embodiment, the polypeptides differ by up to 36 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 amino acids from the mature polypeptide of SEQ ID NO: 82.

In a continuation of the twenty-eighth aspect, the invention relates to polypeptides having lysozyme activity having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 83. In one embodiment, the polypeptides differ by up to 36 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 amino acids from the mature polypeptide of SEQ ID NO: 83.

In one embodiment, the invention relates to polypeptides having lysozyme activity and having a sequence identity to SEQ ID NO: 83 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 83 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 83 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 83 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 82. In one embodiment, the polypeptide preferably comprises or consists of the amino acid sequence of SEQ ID NO: 83; comprises the amino acid sequence of SEQ ID NO: 83 and a N-terminal and/or C-terminal His-tag and/or HQ-tag; comprises the amino acid sequence of SEQ ID NO: 83 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 83. In one embodiment, the polypeptide comprises or consists of amino acids 1 to 201 of SEQ ID NO: 83. In an embodiment, the polypeptide has been isolated.

In a continuation of the twenty-eighth aspect, the invention relates to a polypeptide having lysozyme activity encoded by a polynucleotide having a sequence identity to the mature polypeptide coding sequence of SEQ ID NO: 81 of at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twenty-eighth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the twenty-eighth aspect, the invention relates to variants of SEQ ID NO: 83 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 83 is not more than 36 e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36. In an embodiment, the number of positions comprising one or more amino acid substitutions, and/or one or more amino acid deletions, and/or one or more amino acid insertions or any combination thereof in SEQ ID NO: 83 is not more than 10, e.g., 1, 2, 3, 4, 5, 6, 7, 8, 9 or 10. In one embodiment, the number of substitutions and/or deletions and/or insertions in SEQ ID NO: 83 is not more than 10, e.g., 1, 2, 3, 4, 5, 6, 7, 8, 9 or 10. In a further embodiment, the number of substitutions, preferably conservative substitutions, in SEQ ID NO: 83 is not more than 10, e.g., 1, 2, 3, 4, 5, 6, 7, 8, 9 or 10. Examples of amino acid changes and conservative substitutions are described in the third aspect of the invention.

In an embodiment of the twenty-eighth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a twenty-ninth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 85. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 85.

In a continuation of the twenty-ninth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 86. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 86.

In one embodiment, the invention relates to polypeptides having lysozyme activity and having a sequence identity to SEQ ID NO: 86 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 86 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 86 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 86 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 85. In one embodiment, the polypeptide preferably comprises or consists of the amino acid sequence of SEQ ID NO: 86; comprises the amino acid sequence of SEQ ID NO: 86 and a N-terminal and/or C-terminal His-tag and/or HQ-tag; comprises the amino acid sequence of SEQ ID NO: 86 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 86. In one embodiment, the polypeptide comprises or consists of amino acids 1 to 202 of SEQ ID NO: 86. In an embodiment, the polypeptide has been isolated.

In a continuation of the twenty-ninth aspect, the invention relates to a polypeptide having lysozyme activity encoded by a polynucleotide having a sequence identity to the mature polypeptide coding sequence of SEQ ID NO: 84 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twenty-ninth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the twenty-ninth aspect, the invention relates to variants of SEQ ID NO: 86 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 86 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 86 is not more than 10, e.g., 1, 2, 3, 4, 5, 6, 7, 8, 9 or 10. In one embodiment, the number of substitutions and/or deletions and/or insertions in SEQ ID NO: 86 is not more than 10, e.g., 1, 2, 3, 4, 5, 6, 7, 8, 9 or 10. In a further embodiment, the number of substitutions, preferably conservative substitutions, in SEQ ID NO: 86 is not more than 10, e.g., 1, 2, 3, 4, 5, 6, 7, 8, 9 or 10. Examples of amino acid changes and conservative substitutions are described in the third aspect of the invention.

In an embodiment of the twenty-ninth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a thirtieth aspect the invention relates to polypeptides having lysozyme activity having at least 86%, e.g., at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 88. In one embodiment, the polypeptides differ by up to 28 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27 or 28 amino acids from the mature polypeptide of SEQ ID NO: 88.

In a continuation of the thirtieth aspect, the invention relates to polypeptides having lysozyme activity having at least 86%, e.g., at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 89. In one embodiment, the polypeptides differ by up to 28 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27 or 28 amino acids from the mature polypeptide of SEQ ID NO: 89.

In one embodiment, the invention relates to polypeptides having lysozyme activity and having a sequence identity to SEQ ID NO: 89 of at least 86% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 89 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 89 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 88. In one embodiment, the polypeptide preferably comprises or consists of the amino acid sequence of SEQ ID NO: 89; comprises the amino acid sequence of SEQ ID NO: 89 and a N-terminal and/or C-terminal His-tag and/or HQ-tag; comprises the amino acid sequence of SEQ ID NO: 89 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 89. In one embodiment, the polypeptide comprises or consists of amino acids 1 to 207 of SEQ ID NO: 89. In an embodiment, the polypeptide has been isolated.

In a continuation of the thirtieth aspect, the invention relates to a polypeptide having lysozyme activity encoded by a polynucleotide having a sequence identity to the mature polypeptide coding sequence of SEQ ID NO: 87 of at least 86%, e.g., at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the thirtieth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the thirtieth aspect, the invention relates to variants of SEQ ID NO: 89 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 89 is not more than 28, e.g., 1, 2, 3, 4, 5, 6, 7, 8, 9, 10, 11, 12, 13, 14, 15, 16, 17, 18, 19, 20, 21, 22, 23, 24, 25, 26, 27 or 28. In an embodiment, the number of positions comprising one or more amino acid substitutions, and/or one or more amino acid deletions, and/or one or more amino acid insertions or any combination thereof in SEQ ID NO: 89 is not more than 10, e.g., 1, 2, 3, 4, 5, 6, 7, 8, 9 or 10. In one embodiment, the number of substitutions and/or deletions and/or insertions in SEQ ID NO: 89 is not more than 10, e.g., 1, 2, 3, 4, 5, 6, 7, 8, 9 or 10. In a further embodiment, the number of substitutions, preferably conservative substitutions, in SEQ ID NO: 89 is not more than 10, e.g., 1, 2, 3, 4, 5, 6, 7, 8, 9 or 10. Examples of amino acid changes and conservative substitutions are described in the third aspect of the invention.

In an embodiment of the thirtieth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a thirty-first aspect the invention relates to polypeptides having lysozyme activity having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 91. In one embodiment, the polypeptides differ by up to 36 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 amino acids from the mature polypeptide of SEQ ID NO: 91.

In a continuation of the thirty-first aspect, the invention relates to polypeptides having lysozyme activity having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 92. In one embodiment, the polypeptides differ by up to 36 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 amino acids from the mature polypeptide of SEQ ID NO: 92.

In one embodiment, the invention relates to polypeptides having lysozyme activity and having a sequence identity to SEQ ID NO: 92 of at least 82% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 92 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 92 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 92 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 91. In one embodiment, the polypeptide preferably comprises or consists of the amino acid sequence of SEQ ID NO: 92; comprises the amino acid sequence of SEQ ID NO: 92 and a N-terminal and/or C-terminal His-tag and/or HQ-tag; comprises the amino acid sequence of SEQ ID NO: 92 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 92. In one embodiment, the polypeptide comprises or consists of amino acids 1 to 202 of SEQ ID NO: 92. In an embodiment, the polypeptide has been isolated.

In a continuation of the thirty-first aspect, the invention relates to a polypeptide having lysozyme activity encoded by a polynucleotide having a sequence identity to the mature polypeptide coding sequence of SEQ ID NO: 90 of at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the thirty-first aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the thirty-first aspect, the invention relates to variants of SEQ ID NO: 92 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 92 is not more than 36, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36. In an embodiment, the number of positions comprising one or more amino acid substitutions, and/or one or more amino acid deletions, and/or one or more amino acid insertions or any combination thereof in SEQ ID NO: 92 is not more than 10, e.g., 1, 2, 3, 4, 5, 6, 7, 8, 9 or 10. In one embodiment, the number of substitutions and/or deletions and/or insertions in SEQ ID NO: 92 is not more than 10, e.g., 1, 2, 3, 4, 5, 6, 7, 8, 9 or 10. In a further embodiment, the number of substitutions, preferably conservative substitutions, in SEQ ID NO: 92 is not more than 10, e.g., 1, 2, 3, 4, 5, 6, 7, 8, 9 or 10. Examples of amino acid changes and conservative substitutions are described in the third aspect of the invention.

In an embodiment of the thirty-first aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a thirty-second aspect the invention relates to polypeptides having lysozyme activity having at least 94%, e.g., at least 95%, at least 96%, at least 97%, at least 98%, at least 99%, or 100% sequence identity to the mature polypeptide of SEQ ID NO: 94. In one embodiment, the polypeptides differ by up to 12 amino acids, e.g., 1, 2, 3, 4, 5, 6, 7, 8, 9, 10, 11 or 12 amino acids from the mature polypeptide of SEQ ID NO: 94.

In a continuation of the thirty-second aspect, the invention relates to polypeptides having lysozyme activity having at least 94%, e.g., at least 95%, at least 96%, at least 97%, at least 98%, at least 99%, or 100% sequence identity to SEQ ID NO: 95. In one embodiment, the polypeptides differ by up to 12 amino acids, e.g., 1, 2, 3, 4, 5, 6, 7, 8, 9, 10, 11 or 12 amino acids from the mature polypeptide of SEQ ID NO: 95.

In one embodiment, the invention relates to polypeptides having lysozyme activity and having a sequence identity to SEQ ID NO: 95 of at least 94% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 95 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 94. In one embodiment, the polypeptide preferably comprises or consists of the amino acid sequence of SEQ ID NO: 95; comprises the amino acid sequence of SEQ ID NO: 95 and a N-terminal and/or C-terminal His-tag and/or HQ-tag; comprises the amino acid sequence of SEQ ID NO: 95 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 95. In one embodiment, the polypeptide comprises or consists of amino acids 1 to 201 of SEQ ID NO: 95. In an embodiment, the polypeptide has been isolated.

In a continuation of the thirty-second aspect, the invention relates to a polypeptide having lysozyme activity encoded by a polynucleotide having a sequence identity to the mature polypeptide coding sequence of SEQ ID NO: 93 of at least 94%, e.g., at least 95%, at least 96%, at least 97%, at least 98%, at least 99%, or 100%. In a further embodiment, the polypeptide has been isolated.

In an embodiment of the thirty-second aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the thirty-second aspect, the invention relates to variants of SEQ ID NO: 95 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 95 is not more than 12, e.g., 1, 2, 3, 4, 5, 6, 7, 8, 9, 10, 11 or 12. In an embodiment, the number of positions comprising one or more amino acid substitutions, and/or one or more amino acid deletions, and/or one or more amino acid insertions or any combination thereof in SEQ ID NO: 95 is not more than 10, e.g., 1, 2, 3, 4, 5, 6, 7, 8, 9 or 10. In one embodiment, the number of substitutions and/or deletions and/or insertions in SEQ ID NO: 95 is not more than 10, e.g., 1, 2, 3, 4, 5, 6, 7, 8, 9 or 10. In a further embodiment, the number of substitutions, preferably conservative substitutions, in SEQ ID NO: 95 is not more than 10, e.g., 1, 2, 3, 4, 5, 6, 7, 8, 9 or 10. Examples of amino acid changes and conservative substitutions are described in the third aspect of the invention.

In an embodiment of the thirty-second aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a thirty-third aspect the invention relates to polypeptides having lysozyme activity having at least 94%, e.g., at least 95%, at least 96%, at least 97%, at least 98%, at least 99%, or 100% sequence identity to the mature polypeptide of SEQ ID NO: 97. In one embodiment, the polypeptides differ by up to 12 amino acids, e.g., 1, 2, 3, 4, 5, 6, 7, 8, 9, 10, 11 or 12 amino acids from the mature polypeptide of SEQ ID NO: 97.

In a continuation of the thirty-third aspect, the invention relates to polypeptides having lysozyme activity having at least 94%, e.g., at least 95%, at least 96%, at least 97%, at least 98%, at least 99%, or 100% sequence identity to SEQ ID NO: 98. In one embodiment, the polypeptides differ by up to 12 amino acids, e.g., 1, 2, 3, 4, 5, 6, 7, 8, 9, 10, 11 or 12 amino acids from the mature polypeptide of SEQ ID NO: 98.

In one embodiment, the invention relates to polypeptides having lysozyme activity and having a sequence identity to SEQ ID NO: 98 of at least 94% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 98 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 97. In one embodiment, the polypeptide preferably comprises or consists of the amino acid sequence of SEQ ID NO: 98; comprises the amino acid sequence of SEQ ID NO: 98 and a N-terminal and/or C-terminal His-tag and/or HQ-tag; comprises the amino acid sequence of SEQ ID NO: 98 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 98. In one embodiment, the polypeptide comprises or consists of amino acids 1 to 202 of SEQ ID NO: 98. In an embodiment, the polypeptide has been isolated.

In a continuation of the thirty-third aspect, the invention relates to a polypeptide having lysozyme activity encoded by a polynucleotide having a sequence identity to the mature polypeptide coding sequence of SEQ ID NO: 96 of at least 94%, e.g., at least 95%, at least 96%, at least 97%, at least 98%, at least 99%, or 100%. In a further embodiment, the polypeptide has been isolated.

In an embodiment of the thirty-third aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the thirty-third aspect, the invention relates to variants of SEQ ID NO: 98 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 98 is not more than 12, e.g., 1, 2, 3, 4, 5, 6, 7, 8, 9, 10, 11 or 12. In an embodiment, the number of positions comprising one or more amino acid substitutions, and/or one or more amino acid deletions, and/or one or more amino acid insertions or any combination thereof in SEQ ID NO: 98 is not more than 10, e.g., 1, 2, 3, 4, 5, 6, 7, 8, 9 or 10. In one embodiment, the number of substitutions and/or deletions and/or insertions in SEQ ID NO: 98 is not more than 10, e.g., 1, 2, 3, 4, 5, 6, 7, 8, 9 or 10. In a further embodiment, the number of substitutions, preferably conservative substitutions, in SEQ ID NO: 98 is not more than 10, e.g., 1, 2, 3, 4, 5, 6, 7, 8, 9 or 10. Examples of amino acid changes and conservative substitutions are described in the third aspect of the invention.

In an embodiment of the thirty-third aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a thirty-fourth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 100. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 100.

In a continuation of the thirty-fourth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 101. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 101.

In one embodiment, the invention relates to polypeptides having lysozyme activity and having a sequence identity to SEQ ID NO: 101 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 101 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 101 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 101 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 100. In one embodiment, the polypeptide preferably comprises or consists of the amino acid sequence of SEQ ID NO: 101; comprises the amino acid sequence of SEQ ID NO: 101 and a N-terminal and/or C-terminal His-tag and/or HQ-tag; comprises the amino acid sequence of SEQ ID NO: 101 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 101. In one embodiment, the polypeptide comprises or consists of amino acids 1 to 206 of SEQ ID NO: 101. In an embodiment, the polypeptide has been isolated.

In a continuation of the thirty-fourth aspect, the invention relates to a polypeptide having lysozyme activity encoded by a polynucleotide having a sequence identity to the mature polypeptide coding sequence of SEQ ID NO: 99 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the thirty-fourth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the thirty-fourth aspect, the invention relates to variants of SEQ ID NO: 101 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 101 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 101 is not more than 10, e.g., 1, 2, 3, 4, 5, 6, 7, 8, 9 or 10. In one embodiment, the number of substitutions and/or deletions and/or insertions in SEQ ID NO: 101 is not more than 10, e.g., 1, 2, 3, 4, 5, 6, 7, 8, 9 or 10. In a further embodiment, the number of substitutions, preferably conservative substitutions, in SEQ ID NO: 101 is not more than 10, e.g., 1, 2, 3, 4, 5, 6, 7, 8, 9 or 10. Examples of amino acid changes and conservative substitutions are described in the third aspect of the invention.

In an embodiment of the thirty-fourth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a thirty-fifth aspect the invention relates to polypeptides having lysozyme activity having at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 103. In one embodiment, the polypeptides differ by up to 38 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 amino acids from the mature polypeptide of SEQ ID NO: 103.

In a continuation of the thirty-fifth aspect, the invention relates to polypeptides having lysozyme activity having at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 104. In one embodiment, the polypeptides differ by up to 38 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 amino acids from the mature polypeptide of SEQ ID NO: 104.

In one embodiment, the invention relates to polypeptides having lysozyme activity and having a sequence identity to SEQ ID NO: 104 of at least 81% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 104 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 104 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 104 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 103. In one embodiment, the polypeptide preferably comprises or consists of the amino acid sequence of SEQ ID NO: 104; comprises the amino acid sequence of SEQ ID NO: 104 and a N-terminal and/or C-terminal His-tag and/or HQ-tag; comprises the amino acid sequence of SEQ ID NO: 104 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 104. In one embodiment, the polypeptide comprises or consists of amino acids 1 to 202 of SEQ ID NO: 104. In an embodiment, the polypeptide has been isolated.

In a continuation of the thirty-fifth aspect, the invention relates to a polypeptide having lysozyme activity encoded by a polynucleotide having a sequence identity to the mature polypeptide coding sequence of SEQ ID NO: 102 of at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the thirty-fifth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the thirty-fifth aspect, the invention relates to variants of SEQ ID NO: 104 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 104 is not more than 38, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38. In an embodiment, the number of positions comprising one or more amino acid substitutions, and/or one or more amino acid deletions, and/or one or more amino acid insertions or any combination thereof in SEQ ID NO: 104 is not more than 10, e.g., 1, 2, 3, 4, 5, 6, 7, 8, 9 or 10. In one embodiment, the number of substitutions and/or deletions and/or insertions in SEQ ID NO: 104 is not more than 10, e.g., 1, 2, 3, 4, 5, 6, 7, 8, 9 or 10. In a further embodiment, the number of substitutions, preferably conservative substitutions, in SEQ ID NO: 104 is not more than 10, e.g., 1, 2, 3, 4, 5, 6, 7, 8, 9 or 10. Examples of amino acid changes and conservative substitutions are described in the third aspect of the invention.

In an embodiment of the thirty-fifth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a thirty-sixth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 106. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 106.

In a continuation of the thirty-sixth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 107. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 107.

In one embodiment, the invention relates to polypeptides having lysozyme activity and having a sequence identity to SEQ ID NO: 107 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 107 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 107 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 107 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 106. In one embodiment, the polypeptide preferably comprises or consists of the amino acid sequence of SEQ ID NO: 107; comprises the amino acid sequence of SEQ ID NO: 107 and a N-terminal and/or C-terminal His-tag and/or HQ-tag; comprises the amino acid sequence of SEQ ID NO: 107 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 107. In one embodiment, the polypeptide comprises or consists of amino acids 1 to 202 of SEQ ID NO: 107. In an embodiment, the polypeptide has been isolated.

In a continuation of the thirty-sixth aspect, the invention relates to a polypeptide having lysozyme activity encoded by a polynucleotide having a sequence identity to the mature polypeptide coding sequence of SEQ ID NO: 105 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the thirty-sixth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the thirty-sixth aspect, the invention relates to variants of SEQ ID NO: 107 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 107 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 107 is not more than 10, e.g., 1, 2, 3, 4, 5, 6, 7, 8, 9 or 10. In one embodiment, the number of substitutions and/or deletions and/or insertions in SEQ ID NO: 107 is not more than 10, e.g., 1, 2, 3, 4, 5, 6, 7, 8, 9 or 10. In a further embodiment, the number of substitutions, preferably conservative substitutions, in SEQ ID NO: 107 is not more than 10, e.g., 1, 2, 3, 4, 5, 6, 7, 8, 9 or 10. Examples of amino acid changes and conservative substitutions are described in the third aspect of the invention.

In an embodiment of the thirty-sixth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a thirty-seventh aspect the invention relates to polypeptides having lysozyme activity having at least 88%, e.g., at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 109. In one embodiment, the polypeptides differ by up to 24 amino acids, e.g., 1, 2, 3, 4, 5, 6, 7, 8, 9, 10, 11, 12, 13, 14, 15, 16, 17, 18, 19, 20, 21, 22, 23 or 24 amino acids from the mature polypeptide of SEQ ID NO: 109.

In a continuation of the thirty-seventh aspect, the invention relates to polypeptides having lysozyme activity having at least 88%, e.g., at least 89%, at least 90%, at least 91%, at least 92%, at least 93%, at least 94%, at least 95%, at least 96%, at least 97%, at least 98%, at least 99%, or 100% sequence identity to SEQ ID NO: 110. In one embodiment, the polypeptides differ by up to 24 amino acids, e.g., 1, 2, 3, 4, 5, 6, 7, 8, 9, 10, 11, 12, 13, 14, 15, 16, 17, 18, 19, 20, 21, 22, 23 or 24 amino acids from the mature polypeptide of SEQ ID NO: 110.

In one embodiment, the invention relates to polypeptides having lysozyme activity and having a sequence identity to SEQ ID NO: 110 of at least 88% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 110 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 110 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 109. In one embodiment, the polypeptide preferably comprises or consists of the amino acid sequence of SEQ ID NO: 110; comprises the amino acid sequence of SEQ ID NO: 110 and a N-terminal and/or C-terminal His-tag and/or HQ-tag; comprises the amino acid sequence of SEQ ID NO: 110 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 110. In one embodiment, the polypeptide comprises or consists of amino acids 1 to 202 of SEQ ID NO: 110. In an embodiment, the polypeptide has been isolated.

In a continuation of the thirty-seventh aspect, the invention relates to a polypeptide having lysozyme activity encoded by a polynucleotide having a sequence identity to the mature polypeptide coding sequence of SEQ ID NO: 108 of at least 88%, e.g., at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the thirty-seventh aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the thirty-seventh aspect, the invention relates to variants of SEQ ID NO: 110 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 110 is not more than 24, e.g., 1, 2, 3, 4, 5, 6, 7, 8, 9, 10, 11, 12, 13, 14, 15, 16, 17, 18, 19, 20, 21, 22, 23 or 24. In an embodiment, the number of positions comprising one or more amino acid substitutions, and/or one or more amino acid deletions, and/or one or more amino acid insertions or any combination thereof in SEQ ID NO: 110 is not more than 10, e.g., 1, 2, 3, 4, 5, 6, 7, 8, 9 or 10. In one embodiment, the number of substitutions and/or deletions and/or insertions in SEQ ID NO: 110 is not more than 10, e.g., 1, 2, 3, 4, 5, 6, 7, 8, 9 or 10. In a further embodiment, the number of substitutions, preferably conservative substitutions, in SEQ ID NO: 110 is not more than 10, e.g., 1, 2, 3, 4, 5, 6, 7, 8, 9 or 10. Examples of amino acid changes and conservative substitutions are described in the third aspect of the invention.

In an embodiment of the thirty-seventh aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a thirty-eighth aspect the invention relates to polypeptides having lysozyme activity having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 112. In one embodiment, the polypeptides differ by up to 30 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids from the mature polypeptide of SEQ ID NO: 112.

In a continuation of the thirty-eighth aspect, the invention relates to polypeptides having lysozyme activity having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 113. In one embodiment, the polypeptides differ by up to 30 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids from the mature polypeptide of SEQ ID NO: 113.

In one embodiment, the invention relates to polypeptides having lysozyme activity and having a sequence identity to SEQ ID NO: 113 of at least 85% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 113 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 113 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 112. In one embodiment, the polypeptide preferably comprises or consists of the amino acid sequence of SEQ ID NO: 113; comprises the amino acid sequence of SEQ ID NO: 113 and a N-terminal and/or C-terminal His-tag and/or HQ-tag; comprises the amino acid sequence of SEQ ID NO: 113 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 113. In one embodiment, the polypeptide comprises or consists of amino acids 1 to 202 of SEQ ID NO: 113. In an embodiment, the polypeptide has been isolated.

In a continuation of the thirty-eighth aspect, the invention relates to a polypeptide having lysozyme activity encoded by a polynucleotide having a sequence identity to the mature polypeptide coding sequence of SEQ ID NO: 111 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the thirty-eighth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the thirty-eighth aspect, the invention relates to variants of SEQ ID NO: 113 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 113 is not more than 30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30. In an embodiment, the number of positions comprising one or more amino acid substitutions, and/or one or more amino acid deletions, and/or one or more amino acid insertions or any combination thereof in SEQ ID NO: 113 is not more than 10, e.g., 1, 2, 3, 4, 5, 6, 7, 8, 9 or 10. In one embodiment, the number of substitutions and/or deletions and/or insertions in SEQ ID NO: 113 is not more than 10, e.g., 1, 2, 3, 4, 5, 6, 7, 8, 9 or 10. In a further embodiment, the number of substitutions, preferably conservative substitutions, in SEQ ID NO: 113 is not more than 10, e.g., 1, 2, 3, 4, 5, 6, 7, 8, 9 or 10. Examples of amino acid changes and conservative substitutions are described in the third aspect of the invention.

In an embodiment of the thirty-eighth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a thirty-ninth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 115. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 115.

In a continuation of the thirty-ninth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 116. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 116.

In one embodiment, the invention relates to polypeptides having lysozyme activity and having a sequence identity to SEQ ID NO: 116 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 116 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 116 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 116 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 115. In one embodiment, the polypeptide preferably comprises or consists of the amino acid sequence of SEQ ID NO: 116; comprises the amino acid sequence of SEQ ID NO: 116 and a N-terminal and/or C-terminal His-tag and/or HQ-tag; comprises the amino acid sequence of SEQ ID NO: 116 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 116. In one embodiment, the polypeptide comprises or consists of amino acids 1 to 206 of SEQ ID NO: 116. In an embodiment, the polypeptide has been isolated.

In a continuation of the thirty-ninth aspect, the invention relates to a polypeptide having lysozyme activity encoded by a polynucleotide having a sequence identity to the mature polypeptide coding sequence of SEQ ID NO: 114 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the thirty-ninth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the thirty-ninth aspect, the invention relates to variants of SEQ ID NO: 116 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 116 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 116 is not more than 10, e.g., 1, 2, 3, 4, 5, 6, 7, 8, 9 or 10. In one embodiment, the number of substitutions and/or deletions and/or insertions in SEQ ID NO: 116 is not more than 10, e.g., 1, 2, 3, 4, 5, 6, 7, 8, 9 or 10. In a further embodiment, the number of substitutions, preferably conservative substitutions, in SEQ ID NO: 116 is not more than 10, e.g., 1, 2, 3, 4, 5, 6, 7, 8, 9 or 10. Examples of amino acid changes and conservative substitutions are described in the third aspect of the invention.

In an embodiment of the thirty-ninth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a fortieth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 118. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 118.

In a continuation of the fortieth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 119. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 119.

In one embodiment, the invention relates to polypeptides having lysozyme activity and having a sequence identity to SEQ ID NO: 119 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 119 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 119 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 119 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 118. In one embodiment, the polypeptide preferably comprises or consists of the amino acid sequence of SEQ ID NO: 119; comprises the amino acid sequence of SEQ ID NO: 119 and a N-terminal and/or C-terminal His-tag and/or HQ-tag; comprises the amino acid sequence of SEQ ID NO: 119 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 119. In one embodiment, the polypeptide comprises or consists of amino acids 1 to 207 of SEQ ID NO: 119. In an embodiment, the polypeptide has been isolated.

In a continuation of the fortieth aspect, the invention relates to a polypeptide having lysozyme activity encoded by a polynucleotide having a sequence identity to the mature polypeptide coding sequence of SEQ ID NO: 117 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fortieth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fortieth aspect, the invention relates to variants of SEQ ID NO: 119 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 119 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 119 is not more than 10, e.g., 1, 2, 3, 4, 5, 6, 7, 8, 9 or 10. In one embodiment, the number of substitutions and/or deletions and/or insertions in SEQ ID NO: 119 is not more than 10, e.g., 1, 2, 3, 4, 5, 6, 7, 8, 9 or 10. In a further embodiment, the number of substitutions, preferably conservative substitutions, in SEQ ID NO: 119 is not more than 10, e.g., 1, 2, 3, 4, 5, 6, 7, 8, 9 or 10. Examples of amino acid changes and conservative substitutions are described in the third aspect of the invention.

In an embodiment of the fortieth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a forty-first aspect the invention relates to polypeptides having lysozyme activity having at least 96.5%, e.g., at least 97%, at least 97.5%, at least 98%, at least 98.5%, at least 99%, at least 99.5%, or 100% sequence identity to the mature polypeptide of SEQ ID NO: 121. In one embodiment, the polypeptides differ by up to 7 amino acids, e.g., 1, 2, 3, 4, 5, 6 or 7 amino acids from the mature polypeptide of SEQ ID NO: 121.

In a continuation of the forty-first aspect, the invention relates to polypeptides having lysozyme activity having at least 96.5%, e.g., at least 97%, at least 97.5%, at least 98%, at least 98.5%, at least 99%, at least 99.5%, or 100% sequence identity to SEQ ID NO: 122. In one embodiment, the polypeptides differ by up to 7 amino acids, e.g., 1, 2, 3, 4, 5, 6 or 7 amino acids from the mature polypeptide of SEQ ID NO: 122.

In one embodiment, the invention relates to polypeptides having lysozyme activity and having a sequence identity to SEQ ID NO: 122 of at least 96.5% and wherein the polypeptide has at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 121. In one embodiment, the polypeptide preferably comprises or consists of the amino acid sequence of SEQ ID NO: 122; comprises the amino acid sequence of SEQ ID NO: 122 and a N-terminal and/or C-terminal His-tag and/or HQ-tag; comprises the amino acid sequence of SEQ ID NO: 122 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 122. In one embodiment, the polypeptide comprises or consists of amino acids 1 to 208 of SEQ ID NO: 122. In an embodiment, the polypeptide has been isolated.

In a continuation of the forty-first aspect, the invention relates to a polypeptide having lysozyme activity encoded by a polynucleotide having a sequence identity to the mature polypeptide coding sequence of SEQ ID NO: 120 of at least 96.5%, e.g., at least 97%, at least 97.5%, at least 98%, at least 98.5%, at least 99%, at least 99.5%, or 100%. In a further embodiment, the polypeptide has been isolated.

In an embodiment of the forty-first aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the forty-first aspect, the invention relates to variants of SEQ ID NO: 122 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 122 is not more than 7, e.g., 1, 2, 3, 4, 5, 6 or 7. In one embodiment, the number of substitutions and/or deletions and/or insertions in SEQ ID NO: 122 is not more than 7, e.g., 1, 2, 3, 4, 5, 6 or 7. In a further embodiment, the number of substitutions, preferably conservative substitutions, in SEQ ID NO: 122 is not more than 7, e.g., 1, 2, 3, 4, 5, 6 or 7. Examples of amino acid changes and conservative substitutions are described in the third aspect of the invention.

In an embodiment of the forty-first aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a forty-second aspect the invention relates to polypeptides having lysozyme activity having at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 124. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 124.

In a continuation of the forty-second aspect, the invention relates to polypeptides having lysozyme activity having at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 125. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 125.

In one embodiment, the invention relates to polypeptides having lysozyme activity and having a sequence identity to SEQ ID NO: 125 of at least 81% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 125 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 125 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 125 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 124. In one embodiment, the polypeptide preferably comprises or consists of the amino acid sequence of SEQ ID NO: 125; comprises the amino acid sequence of SEQ ID NO: 125 and a N-terminal and/or C-terminal His-tag and/or HQ-tag; comprises the amino acid sequence of SEQ ID NO: 125 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 125. In one embodiment, the polypeptide comprises or consists of amino acids 1 to 215 of SEQ ID NO: 125. In an embodiment, the polypeptide has been isolated.

In a continuation of the forty-second aspect, the invention relates to a polypeptide having lysozyme activity encoded by a polynucleotide having a sequence identity to the mature polypeptide coding sequence of SEQ ID NO: 123 of at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the forty-second aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the forty-second aspect, the invention relates to variants of SEQ ID NO: 125 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 125 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 125 is not more than 10, e.g., 1, 2, 3, 4, 5, 6, 7, 8, 9 or 10. In one embodiment, the number of substitutions and/or deletions and/or insertions in SEQ ID NO: 125 is not more than 10, e.g., 1, 2, 3, 4, 5, 6, 7, 8, 9 or 10. In a further embodiment, the number of substitutions, preferably conservative substitutions, in SEQ ID NO: 125 is not more than 10, e.g., 1, 2, 3, 4, 5, 6, 7, 8, 9 or 10. Examples of amino acid changes and conservative substitutions are described in the third aspect of the invention.

In an embodiment of the forty-second aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a forty-third aspect the invention relates to polypeptides having lysozyme activity having at least 89%, e.g., at least 90%, at least 91%, at least 92%, at least 93%, at least 94%, at least 95%, at least 96%, at least 97%, at least 98%, at least 99%, or 100% sequence identity to the mature polypeptide of SEQ ID NO: 127. In one embodiment, the polypeptides differ by up to 23 amino acids, e.g., 1, 2, 3, 4, 5, 6, 7, 8, 9, 10, 11, 12, 13, 14, 15, 16, 17, 18, 19, 20, 21, 22 or 23 amino acids from the mature polypeptide of SEQ ID NO: 127.

In a continuation of the forty-third aspect, the invention relates to polypeptides having lysozyme activity having at least 89%, e.g., at least 90%, at least 91%, at least 92%, at least 93%, at least 94%, at least 95%, at least 96%, at least 97%, at least 98%, at least 99%, or 100% sequence identity to SEQ ID NO: 128. In one embodiment, the polypeptides differ by up to 23 amino acids, e.g., 1, 2, 3, 4, 5, 6, 7, 8, 9, 10, 11, 12, 13, 14, 15, 16, 17, 18, 19, 20, 21, 22 or 23 amino acids from the mature polypeptide of SEQ ID NO: 128.

In one embodiment, the invention relates to polypeptides having lysozyme activity and having a sequence identity to SEQ ID NO: 128 of at least 89% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 128 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 128 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 127. In one embodiment, the polypeptide preferably comprises or consists of the amino acid sequence of SEQ ID NO: 128; comprises the amino acid sequence of SEQ ID NO: 128 and a N-terminal and/or C-terminal His-tag and/or HQ-tag; comprises the amino acid sequence of SEQ ID NO: 128 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 128. In one embodiment, the polypeptide comprises or consists of amino acids 1 to 217 of SEQ ID NO: 128. In an embodiment, the polypeptide has been isolated.

In a continuation of the forty-third aspect, the invention relates to a polypeptide having lysozyme activity encoded by a polynucleotide having a sequence identity to the mature polypeptide coding sequence of SEQ ID NO: 126 of at least 89%, e.g., at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the forty-third aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the forty-third aspect, the invention relates to variants of SEQ ID NO: 128 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 128 is not more than 23, e.g., 1, 2, 3, 4, 5, 6, 7, 8, 9, 10, 11, 12, 13, 14, 15, 16, 17, 18, 19, 20, 21, 22 or 23. In an embodiment, the number of positions comprising one or more amino acid substitutions, and/or one or more amino acid deletions, and/or one or more amino acid insertions or any combination thereof in SEQ ID NO: 128 is not more than 10, e.g., 1, 2, 3, 4, 5, 6, 7, 8, 9 or 10. In one embodiment, the number of substitutions and/or deletions and/or insertions in SEQ ID NO: 128 is not more than 10, e.g., 1, 2, 3, 4, 5, 6, 7, 8, 9 or 10. In a further embodiment, the number of substitutions, preferably conservative substitutions, in SEQ ID NO: 128 is not more than 10, e.g., 1, 2, 3, 4, 5, 6, 7, 8, 9 or 10. Examples of amino acid changes and conservative substitutions are described in the third aspect of the invention.

In an embodiment of the forty-third aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a forty-fourth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 130. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 130.

In a continuation of the forty-fourth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 131. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 131.

In one embodiment, the invention relates to polypeptides having lysozyme activity and having a sequence identity to SEQ ID NO: 131 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 131 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 131 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 131 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 130. In one embodiment, the polypeptide preferably comprises or consists of the amino acid sequence of SEQ ID NO: 131; comprises the amino acid sequence of SEQ ID NO: 131 and a N-terminal and/or C-terminal His-tag and/or HQ-tag; comprises the amino acid sequence of SEQ ID NO: 131 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 131. In one embodiment, the polypeptide comprises or consists of amino acids 1 to 214 of SEQ ID NO: 131. In an embodiment, the polypeptide has been isolated.

In a continuation of the forty-fourth aspect, the invention relates to a polypeptide having lysozyme activity encoded by a polynucleotide having a sequence identity to the mature polypeptide coding sequence of SEQ ID NO: 129 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the forty-fourth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the forty-fourth aspect, the invention relates to variants of SEQ ID NO: 131 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 131 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 131 is not more than 10, e.g., 1, 2, 3, 4, 5, 6, 7, 8, 9 or 10. In one embodiment, the number of substitutions and/or deletions and/or insertions in SEQ ID NO: 131 is not more than 10, e.g., 1, 2, 3, 4, 5, 6, 7, 8, 9 or 10. In a further embodiment, the number of substitutions, preferably conservative substitutions, in SEQ ID NO: 131 is not more than 10, e.g., 1, 2, 3, 4, 5, 6, 7, 8, 9 or 10. Examples of amino acid changes and conservative substitutions are described in the third aspect of the invention.

In an embodiment of the forty-fourth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a forty-fifth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 133. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 133.

In a continuation of the forty-fifth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 134. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 134.

In one embodiment, the invention relates to polypeptides having lysozyme activity and having a sequence identity to SEQ ID NO: 134 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 134 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 134 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 134 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 133. In one embodiment, the polypeptide preferably comprises or consists of the amino acid sequence of SEQ ID NO: 134; comprises the amino acid sequence of SEQ ID NO: 134 and a N-terminal and/or C-terminal His-tag and/or HQ-tag; comprises the amino acid sequence of SEQ ID NO: 134 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 134. In one embodiment, the polypeptide comprises or consists of amino acids 1 to 208 of SEQ ID NO: 134. In an embodiment, the polypeptide has been isolated.

In a continuation of the forty-fifth aspect, the invention relates to a polypeptide having lysozyme activity encoded by a polynucleotide having a sequence identity to the mature polypeptide coding sequence of SEQ ID NO: 132 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the forty-fifth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the forty-fifth aspect, the invention relates to variants of SEQ ID NO: 134 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 134 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 134 is not more than 10, e.g., 1, 2, 3, 4, 5, 6, 7, 8, 9 or 10. In one embodiment, the number of substitutions and/or deletions and/or insertions in SEQ ID NO: 134 is not more than 10, e.g., 1, 2, 3, 4, 5, 6, 7, 8, 9 or 10. In a further embodiment, the number of substitutions, preferably conservative substitutions, in SEQ ID NO: 134 is not more than 10, e.g., 1, 2, 3, 4, 5, 6, 7, 8, 9 or 10. Examples of amino acid changes and conservative substitutions are described in the third aspect of the invention.

In an embodiment of the forty-fifth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a forty-sixth aspect the invention relates to polypeptides having lysozyme activity having at least 90%, e.g., at least 91%, at least 92%, at least 93%, at least 94%, at least 95%, at least 96%, at least 97%, at least 98%, at least 99%, or 100% sequence identity to the mature polypeptide of SEQ ID NO: 136. In one embodiment, the polypeptides differ by up to 20 amino acids, e.g., 1, 2, 3, 4, 5, 6, 7, 8, 9, 10, 11, 12, 13, 14, 15, 16, 17, 18, 19 or 20 amino acids from the mature polypeptide of SEQ ID NO: 136.

In a continuation of the forty-sixth aspect, the invention relates to polypeptides having lysozyme activity having at least 90%, e.g., at least 91%, at least 92%, at least 93%, at least 94%, at least 95%, at least 96%, at least 97%, at least 98%, at least 99%, or 100% sequence identity to SEQ ID NO: 137. In one embodiment, the polypeptides differ by up to 20 amino acids, e.g., 1, 2, 3, 4, 5, 6, 7, 8, 9, 10, 11, 12, 13, 14, 15, 16, 17, 18, 19 or 20 amino acids from the mature polypeptide of SEQ ID NO: 137.

In one embodiment, the invention relates to polypeptides having lysozyme activity and having a sequence identity to SEQ ID NO: 137 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 137 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 136. In one embodiment, the polypeptide preferably comprises or consists of the amino acid sequence of SEQ ID NO: 137; comprises the amino acid sequence of SEQ ID NO: 137 and a N-terminal and/or C-terminal His-tag and/or HQ-tag; comprises the amino acid sequence of SEQ ID NO: 137 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 137. In one embodiment, the polypeptide comprises or consists of amino acids 1 to 203 of SEQ ID NO: 137. In an embodiment, the polypeptide has been isolated.

In a continuation of the forty-sixth aspect, the invention relates to a polypeptide having lysozyme activity encoded by a polynucleotide having a sequence identity to the mature polypeptide coding sequence of SEQ ID NO: 135 of at least 90%, e.g., at least 91%, at least 92%, at least 93%, at least 94%, at least 95%, at least 96%, at least 97%, at least 98%, at least 99%, or 100%. In a further embodiment, the polypeptide has been isolated.

In an embodiment of the forty-sixth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the forty-sixth aspect, the invention relates to variants of SEQ ID NO: 137 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 137 is not more than 20, e.g., 1, 2, 3, 4, 5, 6, 7, 8, 9, 10, 11, 12, 13, 14, 15, 16, 17, 18, 19 or 20. In an embodiment, the number of positions comprising one or more amino acid substitutions, and/or one or more amino acid deletions, and/or one or more amino acid insertions or any combination thereof in SEQ ID NO: 137 is not more than 10, e.g., 1, 2, 3, 4, 5, 6, 7, 8, 9 or 10. In one embodiment, the number of substitutions and/or deletions and/or insertions in SEQ ID NO: 137 is not more than 10, e.g., 1, 2, 3, 4, 5, 6, 7, 8, 9 or 10. In a further embodiment, the number of substitutions, preferably conservative substitutions, in SEQ ID NO: 137 is not more than 10, e.g., 1, 2, 3, 4, 5, 6, 7, 8, 9 or 10. Examples of amino acid changes and conservative substitutions are described in the third aspect of the invention.

In an embodiment of the forty-sixth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a forty-seventh aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 139. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 139.

In a continuation of the forty-seventh aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 140. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 140.

In one embodiment, the invention relates to polypeptides having lysozyme activity and having a sequence identity to SEQ ID NO: 140 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 140 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 140 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 140 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 139. In one embodiment, the polypeptide preferably comprises or consists of the amino acid sequence of SEQ ID NO: 140; comprises the amino acid sequence of SEQ ID NO: 140 and a N-terminal and/or C-terminal His-tag and/or HQ-tag; comprises the amino acid sequence of SEQ ID NO: 140 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 140. In one embodiment, the polypeptide comprises or consists of amino acids 1 to 216 of SEQ ID NO: 140. In an embodiment, the polypeptide has been isolated.

In a continuation of the forty-seventh aspect, the invention relates to a polypeptide having lysozyme activity encoded by a polynucleotide having a sequence identity to the mature polypeptide coding sequence of SEQ ID NO: 138 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the forty-seventh aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the forty-seventh aspect, the invention relates to variants of SEQ ID NO: 140 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 140 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 140 is not more than 10, e.g., 1, 2, 3, 4, 5, 6, 7, 8, 9 or 10. In one embodiment, the number of substitutions and/or deletions and/or insertions in SEQ ID NO: 140 is not more than 10, e.g., 1, 2, 3, 4, 5, 6, 7, 8, 9 or 10. In a further embodiment, the number of substitutions, preferably conservative substitutions, in SEQ ID NO: 140 is not more than 10, e.g., 1, 2, 3, 4, 5, 6, 7, 8, 9 or 10. Examples of amino acid changes and conservative substitutions are described in the third aspect of the invention.

In an embodiment of the forty-seventh aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a forty-eighth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 142. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 142.

In a continuation of the forty-eighth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 143. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 143.

In one embodiment, the invention relates to polypeptides having lysozyme activity and having a sequence identity to SEQ ID NO: 143 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 143 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 143 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 143 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 142. In one embodiment, the polypeptide preferably comprises or consists of the amino acid sequence of SEQ ID NO: 143; comprises the amino acid sequence of SEQ ID NO: 143 and a N-terminal and/or C-terminal His-tag and/or HQ-tag; comprises the amino acid sequence of SEQ ID NO: 143 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 143. In one embodiment, the polypeptide comprises or consists of amino acids 1 to 207 of SEQ ID NO: 143. In an embodiment, the polypeptide has been isolated.

In a continuation of the forty-eighth aspect, the invention relates to a polypeptide having lysozyme activity encoded by a polynucleotide having a sequence identity to the mature polypeptide coding sequence of SEQ ID NO: 141 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the forty-eighth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the forty-eighth aspect, the invention relates to variants of SEQ ID NO: 143 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 143 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 143 is not more than 10, e.g., 1, 2, 3, 4, 5, 6, 7, 8, 9 or 10. In one embodiment, the number of substitutions and/or deletions and/or insertions in SEQ ID NO: 143 is not more than 10, e.g., 1, 2, 3, 4, 5, 6, 7, 8, 9 or 10. In a further embodiment, the number of substitutions, preferably conservative substitutions, in SEQ ID NO: 143 is not more than 10, e.g., 1, 2, 3, 4, 5, 6, 7, 8, 9 or 10. Examples of amino acid changes and conservative substitutions are described in the third aspect of the invention.

In an embodiment of the forty-eighth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a forty-ninth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 145. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 145.

In a continuation of the forty-ninth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 146. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 146.

In one embodiment, the invention relates to polypeptides having lysozyme activity and having a sequence identity to SEQ ID NO: 146 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 146 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 146 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 146 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 145. In one embodiment, the polypeptide preferably comprises or consists of the amino acid sequence of SEQ ID NO: 146; comprises the amino acid sequence of SEQ ID NO: 146 and a N-terminal and/or C-terminal His-tag and/or HQ-tag; comprises the amino acid sequence of SEQ ID NO: 146 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 146. In one embodiment, the polypeptide comprises or consists of amino acids 1 to 208 of SEQ ID NO: 146. In an embodiment, the polypeptide has been isolated.

In a continuation of the forty-ninth aspect, the invention relates to a polypeptide having lysozyme activity encoded by a polynucleotide having a sequence identity to the mature polypeptide coding sequence of SEQ ID NO: 144 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the forty-ninth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the forty-ninth aspect, the invention relates to variants of SEQ ID NO: 146 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 146 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 146 is not more than 10, e.g., 1, 2, 3, 4, 5, 6, 7, 8, 9 or 10. In one embodiment, the number of substitutions and/or deletions and/or insertions in SEQ ID NO: 146 is not more than 10, e.g., 1, 2, 3, 4, 5, 6, 7, 8, 9 or 10. In a further embodiment, the number of substitutions, preferably conservative substitutions, in SEQ ID NO: 146 is not more than 10, e.g., 1, 2, 3, 4, 5, 6, 7, 8, 9 or 10. Examples of amino acid changes and conservative substitutions are described in the third aspect of the invention.

In an embodiment of the forty-ninth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a fiftieth aspect the invention relates to polypeptides having lysozyme activity having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 148. In one embodiment, the polypeptides differ by up to 31 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 amino acids from the mature polypeptide of SEQ ID NO: 148.

In a continuation of the fiftieth aspect, the invention relates to polypeptides having lysozyme activity having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 149.

In one embodiment, the polypeptides differ by up to 31 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 amino acids from the mature polypeptide of SEQ ID NO: 149.

In one embodiment, the invention relates to polypeptides having lysozyme activity and having a sequence identity to SEQ ID NO: 149 of at least 85% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 149 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 149 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 148. In one embodiment, the polypeptide preferably comprises or consists of the amino acid sequence of SEQ ID NO: 149; comprises the amino acid sequence of SEQ ID NO: 149 and a N-terminal and/or C-terminal His-tag and/or HQ-tag; comprises the amino acid sequence of SEQ ID NO: 149 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 149. In one embodiment, the polypeptide comprises or consists of amino acids 1 to 207 of SEQ ID NO: 149. In an embodiment, the polypeptide has been isolated.

In a continuation of the fiftieth aspect, the invention relates to a polypeptide having lysozyme activity encoded by a polynucleotide having a sequence identity to the mature polypeptide coding sequence of SEQ ID NO: 147 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fiftieth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fiftieth aspect, the invention relates to variants of SEQ ID NO: 149 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 149 is not more than 31, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31. In an embodiment, the number of positions comprising one or more amino acid substitutions, and/or one or more amino acid deletions, and/or one or more amino acid insertions or any combination thereof in SEQ ID NO: 149 is not more than 10, e.g., 1, 2, 3, 4, 5, 6, 7, 8, 9 or 10. In one embodiment, the number of substitutions and/or deletions and/or insertions in SEQ ID NO: 149 is not more than 10, e.g., 1, 2, 3, 4, 5, 6, 7, 8, 9 or 10. In a further embodiment, the number of substitutions, preferably conservative substitutions, in SEQ ID NO: 149 is not more than 10, e.g., 1, 2, 3, 4, 5, 6, 7, 8, 9 or 10. Examples of amino acid changes and conservative substitutions are described in the third aspect of the invention.

In an embodiment of the fiftieth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the fiftieth aspect comprises the motif YKNA (SEQ ID NO: 160) and/or the motif FGGW[S/T] (SEQ ID NO: 161).

In a fifty-first aspect the invention relates to polypeptides having lysozyme activity having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 151. In one embodiment, the polypeptides differ by up to 31 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 amino acids from the mature polypeptide of SEQ ID NO: 151.

In a continuation of the fifty-first aspect, the invention relates to polypeptides having lysozyme activity having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 152. In one embodiment, the polypeptides differ by up to 31 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 amino acids from the mature polypeptide of SEQ ID NO: 152.

In one embodiment, the invention relates to polypeptides having lysozyme activity and having a sequence identity to SEQ ID NO: 152 of at least 85% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 152 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 152 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 151. In one embodiment, the polypeptide preferably comprises or consists of the amino acid sequence of SEQ ID NO: 152; comprises the amino acid sequence of SEQ ID NO: 152 and a N-terminal and/or C-terminal His-tag and/or HQ-tag; comprises the amino acid sequence of SEQ ID NO: 152 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 152. In one embodiment, the polypeptide comprises or consists of amino acids 1 to 207 of SEQ ID NO: 152. In an embodiment, the polypeptide has been isolated.

In a continuation of the fifty-first aspect, the invention relates to a polypeptide having lysozyme activity encoded by a polynucleotide having a sequence identity to the mature polypeptide coding sequence of SEQ ID NO: 150 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fifty-first aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fifty-first aspect, the invention relates to variants of SEQ ID NO: 152 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 152 is not more than 31, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31. In an embodiment, the number of positions comprising one or more amino acid substitutions, and/or one or more amino acid deletions, and/or one or more amino acid insertions or any combination thereof in SEQ ID NO: 152 is not more than 10, e.g., 1, 2, 3, 4, 5, 6, 7, 8, 9 or 10. In one embodiment, the number of substitutions and/or deletions and/or insertions in SEQ ID NO: 152 is not more than 10, e.g., 1, 2, 3, 4, 5, 6, 7, 8, 9 or 10. In a further embodiment, the number of substitutions, preferably conservative substitutions, in SEQ ID NO: 152 is not more than 10, e.g., 1, 2, 3, 4, 5, 6, 7, 8, 9 or 10. Examples of amino acid changes and conservative substitutions are described in the third aspect of the invention.

In an embodiment of the fifty-first aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the fifty-first aspect comprises the motif YKNA (SEQ ID NO: 160) and/or the motif FGGW[S/T] (SEQ ID NO: 161).

In a fifty-second aspect the invention relates to polypeptides having lysozyme activity having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 154. In one embodiment, the polypeptides differ by up to 33 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 amino acids from the mature polypeptide of SEQ ID NO: 154.

In a continuation of the fifty-second aspect, the invention relates to polypeptides having lysozyme activity having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 155. In one embodiment, the polypeptides differ by up to 33 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 amino acids from the mature polypeptide of SEQ ID NO: 155.

In one embodiment, the invention relates to polypeptides having lysozyme activity and having a sequence identity to SEQ ID NO: 155 of at least 84% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 155 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 155 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID having a sequence identity to SEQ ID NO: 155 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 154. In one embodiment, the polypeptide preferably comprises or consists of the amino acid sequence of SEQ ID NO: 155; comprises the amino acid sequence of SEQ ID NO: 155 and a N-terminal and/or C-terminal His-tag and/or HQ-tag; comprises the amino acid sequence of SEQ ID NO: 155 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 155. In one embodiment, the polypeptide comprises or consists of amino acids 1 to 207 of SEQ ID NO: 155. In an embodiment, the polypeptide has been isolated.

In a continuation of the fifty-second aspect, the invention relates to a polypeptide having lysozyme activity encoded by a polynucleotide having a sequence identity to the mature polypeptide coding sequence of SEQ ID NO: 153 of at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fifty-second aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fifty-second aspect, the invention relates to variants of SEQ ID NO: 155 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 155 is not more than 33, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33. In an embodiment, the number of positions comprising one or more amino acid substitutions, and/or one or more amino acid deletions, and/or one or more amino acid insertions or any combination thereof in SEQ ID NO: 155 is not more than 10, e.g., 1, 2, 3, 4, 5, 6, 7, 8, 9 or 10. In one embodiment, the number of substitutions and/or deletions and/or insertions in SEQ ID NO: 155 is not more than 10, e.g., 1, 2, 3, 4, 5, 6, 7, 8, 9 or 10. In a further embodiment, the number of substitutions, preferably conservative substitutions, in SEQ ID NO: 155 is not more than 10, e.g., 1, 2, 3, 4, 5, 6, 7, 8, 9 or 10. Examples of amino acid changes and conservative substitutions are described in the third aspect of the invention.

In an embodiment of the fifty-second aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the fifty-second aspect comprises the motif YKNA (SEQ ID NO: 160) and/or the motif FGGW[S/T] (SEQ ID NO: 161).

In a fifty-third aspect the invention relates to polypeptides having lysozyme activity having at least 95%, e.g., at least 96%, at least 97%, at least 98%, at least 99%, or 100% sequence identity to the mature polypeptide of SEQ ID NO: 157. In one embodiment, the polypeptides differ by up to 10 amino acids, e.g., 1, 2, 3, 4, 5, 6, 7, 8, 9 or 10 amino acids from the mature polypeptide of SEQ ID NO: 157.

In a continuation of the fifty-third aspect, the invention relates to polypeptides having lysozyme activity having at least 95%, e.g., at least 96%, at least 97%, at least 98%, at least 99%, or 100% sequence identity to SEQ ID NO: 158. In one embodiment, the polypeptides differ by up to 10 amino acids, e.g., 1, 2, 3, 4, 5, 6, 7, 8, 9 or 10 amino acids from the mature polypeptide of SEQ ID NO: 158.

In one embodiment, the invention relates to polypeptides having lysozyme activity and having a sequence identity to SEQ ID NO: 158 of at least 95% and wherein the polypeptide has at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 157. In one embodiment, the polypeptide preferably comprises or consists of the amino acid sequence of SEQ ID NO: 158; comprises the amino acid sequence of SEQ ID NO: 158 and a N-terminal and/or C-terminal His-tag and/or HQ-tag; comprises the amino acid sequence of SEQ ID NO: 158 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 158. In one embodiment, the polypeptide comprises or consists of amino acids 1 to 208 of SEQ ID NO: 158. In an embodiment, the polypeptide has been isolated.

In a continuation of the fifty-third aspect, the invention relates to a polypeptide having lysozyme activity encoded by a polynucleotide having a sequence identity to the mature polypeptide coding sequence of SEQ ID NO: 156 of at least 95%, e.g., at least 96%, at least 97%, at least 98%, at least 99%, or 100%. In a further embodiment, the polypeptide has been isolated.

In an embodiment of the fifty-third aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fifty-third aspect, the invention relates to variants of SEQ ID NO: 158 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 158 is not more than 10, e.g., 1, 2, 3, 4, 5, 6, 7, 8, 9 or 10. In one embodiment, the number of substitutions and/or deletions and/or insertions in SEQ ID NO: 158 is not more than 10, e.g., 1, 2, 3, 4, 5, 6, 7, 8, 9 or 10. In a further embodiment, the number of substitutions, preferably conservative substitutions, in SEQ ID NO: 158 is not more than 10, e.g., 1, 2, 3, 4, 5, 6, 7, 8, 9 or 10. Examples of amino acid changes and conservative substitutions are described in the third aspect of the invention.

In an embodiment of the fifty-third aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a fifty-fourth aspect the invention relates to polypeptides having lysozyme activity having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 218. In one embodiment, the polypeptides differ by up to 35 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids from the mature polypeptide of SEQ ID NO: 218.

In a continuation of the fifty-fourth aspect, the invention relates to polypeptides having lysozyme activity having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 220. In one embodiment, the polypeptides differ by up to 35 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids from the mature polypeptide of SEQ ID NO: 220.

In a continuation of the fifty-fourth aspect, the invention relates to polypeptides having lysozyme activity having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 221. In one embodiment, the polypeptides differ by up to 35 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids from SEQ ID NO: 221.

In one embodiment, the invention relates to polypeptides having lysozyme activity and having a sequence identity to SEQ ID NO: 221 of at least 83% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 221 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 221 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 221 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 218. In one embodiment, the polypeptide comprises or consists of the mature polypeptide of SEQ ID NO: 220. In one embodiment, the polypeptide preferably comprises or consists of the amino acid sequence of SEQ ID NO: 221; comprises the amino acid sequence of SEQ ID NO: 221 and a N-terminal and/or C-terminal His-tag and/or HQ-tag; comprises the amino acid sequence of SEQ ID NO: 221 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 221. In one embodiment, the polypeptide comprises or consists of amino acids 1 to 207 of SEQ ID NO: 221. In an embodiment, the polypeptide has been isolated.

In a continuation of the fifty-fourth aspect, the invention relates to a polypeptide having lysozyme activity encoded by a polynucleotide having a sequence identity to the mature polypeptide coding sequence of SEQ ID NO: 217 of at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fifty-fourth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fifty-fourth aspect, the invention relates to variants of SEQ ID NO: 221 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 221 is not more than 35, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35. In an embodiment, the number of positions comprising one or more amino acid substitutions, and/or one or more amino acid deletions, and/or one or more amino acid insertions or any combination thereof in SEQ ID NO: 221 is not more than 10, e.g., 1, 2, 3, 4, 5, 6, 7, 8, 9 or 10. In one embodiment, the number of substitutions and/or deletions and/or insertions in SEQ ID NO: 221 is not more than 10, e.g., 1, 2, 3, 4, 5, 6, 7, 8, 9 or 10. In a further embodiment, the number of substitutions, preferably conservative substitutions, in SEQ ID NO: 221 is not more than 10, e.g., 1, 2, 3, 4, 5, 6, 7, 8, 9 or 10. Examples of amino acid changes and conservative substitutions are described in the third aspect of the invention.

In an embodiment of the fifty-fourth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a forty-sixth aspect the invention relates to polypeptides having lysozyme activity having at least 90%, e.g., at least 91%, at least 92%, at least 93%, at least 94%, at least 95%, at least 96%, at least 97%, at least 98%, at least 99%, or 100% sequence identity to the mature polypeptide of SEQ ID NO: 136. In one embodiment, the polypeptides differ by up to 20 amino acids, e.g., 1, 2, 3, 4, 5, 6, 7, 8, 9, 10, 11, 12, 13, 14, 15, 16, 17, 18, 19 or 20 amino acids from the mature polypeptide of SEQ ID NO: 136.

In a continuation of the forty-sixth aspect, the invention relates to polypeptides having lysozyme activity having at least 90%, e.g., at least 91%, at least 92%, at least 93%, at least 94%, at least 95%, at least 96%, at least 97%, at least 98%, at least 99%, or 100% sequence identity to SEQ ID NO: 137. In one embodiment, the polypeptides differ by up to 20 amino acids, e.g., 1, 2, 3, 4, 5, 6, 7, 8, 9, 10, 11, 12, 13, 14, 15, 16, 17, 18, 19 or 20 amino acids from the mature polypeptide of SEQ ID NO: 137.

In one embodiment, the invention relates to polypeptides having lysozyme activity and having a sequence identity to SEQ ID NO: 137 of at least 90% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 137 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 136. In one embodiment, the polypeptide preferably comprises or consists of the amino acid sequence of SEQ ID NO: 137; comprises the amino acid sequence of SEQ ID NO: 137 and a N-terminal and/or C-terminal His-tag and/or HQ-tag; comprises the amino acid sequence of SEQ ID NO: 137 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 137. In one embodiment, the polypeptide comprises or consists of amino acids 1 to 203 of SEQ ID NO: 137. In an embodiment, the polypeptide has been isolated.

In a continuation of the forty-sixth aspect, the invention relates to a polypeptide having lysozyme activity encoded by a polynucleotide having a sequence identity to the mature polypeptide coding sequence of SEQ ID NO: 135 of at least 90%, e.g., at least 91%, at least 92%, at least 93%, at least 94%, at least 95%, at least 96%, at least 97%, at least 98%, at least 99%, or 100%. In a further embodiment, the polypeptide has been isolated.

In an embodiment of the forty-sixth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the forty-sixth aspect, the invention relates to variants of SEQ ID NO: 137 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 137 is not more than 20, e.g., 1, 2, 3, 4, 5, 6, 7, 8, 9, 10, 11, 12, 13, 14, 15, 16, 17, 18, 19 or 20. In an embodiment, the number of positions comprising one or more amino acid substitutions, and/or one or more amino acid deletions, and/or one or more amino acid insertions or any combination thereof in SEQ ID NO: 137 is not more than 10, e.g., 1, 2, 3, 4, 5, 6, 7, 8, 9 or 10. In one embodiment, the number of substitutions and/or deletions and/or insertions in SEQ ID NO: 137 is not more than 10, e.g., 1, 2, 3, 4, 5, 6, 7, 8, 9 or 10. In a further embodiment, the number of substitutions, preferably conservative substitutions, in SEQ ID NO: 137 is not more than 10, e.g., 1, 2, 3, 4, 5, 6, 7, 8, 9 or 10. Examples of amino acid changes and conservative substitutions are described in the third aspect of the invention.

In an embodiment of the forty-sixth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a fifty-fifth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 223. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 223.

In a continuation of the fifty-fifth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 224. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 224.

In one embodiment, the invention relates to polypeptides having lysozyme activity and having a sequence identity to SEQ ID NO: 224 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 224 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 224 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID having a sequence identity to SEQ ID NO: 224 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 223. In one embodiment, the polypeptide preferably comprises or consists of the amino acid sequence of SEQ ID NO: 224; comprises the amino acid sequence of SEQ ID NO: 224 and a N-terminal and/or C-terminal His-tag and/or HQ-tag; comprises the amino acid sequence of SEQ ID NO: 224 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 224. In one embodiment, the polypeptide comprises or consists of amino acids 1 to 207 of SEQ ID NO: 224. In an embodiment, the polypeptide has been isolated.

In a continuation of the fifty-fifth aspect, the invention relates to a polypeptide having lysozyme activity encoded by a polynucleotide having a sequence identity to the mature polypeptide coding sequence of SEQ ID NO: 222 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fifty-fifth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fifty-fifth aspect, the invention relates to variants of SEQ ID NO: 224 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 224 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 224 is not more than 10, e.g., 1, 2, 3, 4, 5, 6, 7, 8, 9 or 10. In one embodiment, the number of substitutions and/or deletions and/or insertions in SEQ ID NO: 224 is not more than 10, e.g., 1, 2, 3, 4, 5, 6, 7, 8, 9 or 10. In a further embodiment, the number of substitutions, preferably conservative substitutions, in SEQ ID NO: 224 is not more than 10, e.g., 1, 2, 3, 4, 5, 6, 7, 8, 9 or 10. Examples of amino acid changes and conservative substitutions are described in the third aspect of the invention.

In an embodiment of the fifty-fifth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the fifty-fifth aspect comprises the motif YKNA (SEQ ID NO: 160) and/or the motif FGGW[S/T] (SEQ ID NO: 161).

In a fifty-sixth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 226. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 226.

In a continuation of the fifty-sixth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 227. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 227.

In one embodiment, the invention relates to polypeptides having lysozyme activity and having a sequence identity to SEQ ID NO: 227 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 227 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 227 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID having a sequence identity to SEQ ID NO: 227 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 226. In one embodiment, the polypeptide preferably comprises or consists of the amino acid sequence of SEQ ID NO: 227; comprises the amino acid sequence of SEQ ID NO: 227 and a N-terminal and/or C-terminal His-tag and/or HQ-tag; comprises the amino acid sequence of SEQ ID NO: 227 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 227. In one embodiment, the polypeptide comprises or consists of amino acids 1 to 208 of SEQ ID NO: 227. In an embodiment, the polypeptide has been isolated.

In a continuation of the fifty-sixth aspect, the invention relates to a polypeptide having lysozyme activity encoded by a polynucleotide having a sequence identity to the mature polypeptide coding sequence of SEQ ID NO: 225 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fifty-sixth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fifty-sixth aspect, the invention relates to variants of SEQ ID NO: 227 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 227 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 227 is not more than 10, e.g., 1, 2, 3, 4, 5, 6, 7, 8, 9 or 10. In one embodiment, the number of substitutions and/or deletions and/or insertions in SEQ ID NO: 227 is not more than 10, e.g., 1, 2, 3, 4, 5, 6, 7, 8, 9 or 10. In a further embodiment, the number of substitutions, preferably conservative substitutions, in SEQ ID NO: 227 is not more than 10, e.g., 1, 2, 3, 4, 5, 6, 7, 8, 9 or 10. Examples of amino acid changes and conservative substitutions are described in the third aspect of the invention.

In an embodiment of the fifty-sixth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the fifty-sixth aspect comprises the motif YKNA (SEQ ID NO: 160) and/or the motif FGGW[S/T] (SEQ ID NO: 161).

In a fifty-seventh aspect the invention relates to polypeptides having lysozyme activity having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 229. In one embodiment, the polypeptides differ by up to 31 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 amino acids from the mature polypeptide of SEQ ID NO: 229.

In a continuation of the fifty-seventh aspect, the invention relates to polypeptides having lysozyme activity having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 230. In one embodiment, the polypeptides differ by up to 31 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 amino acids from the mature polypeptide of SEQ ID NO: 230.

In one embodiment, the invention relates to polypeptides having lysozyme activity and having a sequence identity to SEQ ID NO: 230 of at least 85% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 230 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 230 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 229. In one embodiment, the polypeptide preferably comprises or consists of the amino acid sequence of SEQ ID NO: 230; comprises the amino acid sequence of SEQ ID NO: 230 and a N-terminal and/or C-terminal His-tag and/or HQ-tag; comprises the amino acid sequence of SEQ ID NO: 230 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 230. In one embodiment, the polypeptide comprises or consists of amino acids 1 to 207 of SEQ ID NO: 230. In an embodiment, the polypeptide has been isolated.

In a continuation of the fifty-seventh aspect, the invention relates to a polypeptide having lysozyme activity encoded by a polynucleotide having a sequence identity to the mature polypeptide coding sequence of SEQ ID NO: 228 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fifty-seventh aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fifty-seventh aspect, the invention relates to variants of SEQ ID NO: 230 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 230 is not more than 31, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31. In an embodiment, the number of positions comprising one or more amino acid substitutions, and/or one or more amino acid deletions, and/or one or more amino acid insertions or any combination thereof in SEQ ID NO: 230 is not more than 10, e.g., 1, 2, 3, 4, 5, 6, 7, 8, 9 or 10. In one embodiment, the number of substitutions and/or deletions and/or insertions in SEQ ID NO: 230 is not more than 10, e.g., 1, 2, 3, 4, 5, 6, 7, 8, 9 or 10. In a further embodiment, the number of substitutions, preferably conservative substitutions, in SEQ ID NO: 230 is not more than 10, e.g., 1, 2, 3, 4, 5, 6, 7, 8, 9 or 10. Examples of amino acid changes and conservative substitutions are described in the third aspect of the invention.

In an embodiment of the fifty-seventh aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the fifty-seventh aspect comprises the motif YKNA (SEQ ID NO: 160) and/or the motif FGGW[S/T] (SEQ ID NO: 161).

In a fifty-eighth aspect the invention relates to polypeptides having lysozyme activity having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 232. In one embodiment, the polypeptides differ by up to 31 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 amino acids from the mature polypeptide of SEQ ID NO: 232.

In a continuation of the fifty-eighth aspect, the invention relates to polypeptides having lysozyme activity having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 233. In one embodiment, the polypeptides differ by up to 31 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 amino acids from the mature polypeptide of SEQ ID NO: 233.

In one embodiment, the invention relates to polypeptides having lysozyme activity and having a sequence identity to SEQ ID NO: 233 of at least 85% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 233 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 233 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 232. In one embodiment, the polypeptide preferably comprises or consists of the amino acid sequence of SEQ ID NO: 233; comprises the amino acid sequence of SEQ ID NO: 233 and a N-terminal and/or C-terminal His-tag and/or HQ-tag; comprises the amino acid sequence of SEQ ID NO: 233 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 233. In one embodiment, the polypeptide comprises or consists of amino acids 1 to 207 of SEQ ID NO: 233. In an embodiment, the polypeptide has been isolated.

In a continuation of the fifty-eighth aspect, the invention relates to a polypeptide having lysozyme activity encoded by a polynucleotide having a sequence identity to the mature polypeptide coding sequence of SEQ ID NO: 231 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fifty-eighth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fifty-eighth aspect, the invention relates to variants of SEQ ID NO: 233 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 233 is not more than 31, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31. In an embodiment, the number of positions comprising one or more amino acid substitutions, and/or one or more amino acid deletions, and/or one or more amino acid insertions or any combination thereof in SEQ ID NO: 233 is not more than 10, e.g., 1, 2, 3, 4, 5, 6, 7, 8, 9 or 10. In one embodiment, the number of substitutions and/or deletions and/or insertions in SEQ ID NO: 233 is not more than 10, e.g., 1, 2, 3, 4, 5, 6, 7, 8, 9 or 10. In a further embodiment, the number of substitutions, preferably conservative substitutions, in SEQ ID NO: 233 is not more than 10, e.g., 1, 2, 3, 4, 5, 6, 7, 8, 9 or 10. Examples of amino acid changes and conservative substitutions are described in the third aspect of the invention.

In an embodiment of the fifty-eighth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the fifty-eighth aspect comprises the motif YKNA (SEQ ID NO: 160) and/or the motif FGGW[S/T] (SEQ ID NO: 161).

Taxonoimic and Structural Families

In one embodiment, the GH25 polypeptide comprises the motif YKNA (SEQ ID NO: 160) and/or the motif FGGW [S/T] (SEQ ID NO: 161), and preferably is selected from the group selected from SEQ ID NO: 12, SEQ ID NO: 27, SEQ ID NO: 42, SEQ ID NO: 57, SEQ ID NO: 63, SEQ ID NO: 66, SEQ ID NO: 80, SEQ ID NO: 149, SEQ ID NO:152, SEQ ID NO: 155, SEQ ID NO: 224, SEQ ID NO: 227, SEQ ID NO: 230 and SEQ ID NO: 233.

In one embodiment, the GH25 polypeptide is obtained or is obtainable from the taxonomic order Agaricales and is preferably is selected from the group selected from SEQ ID NO: 80, SEQ ID NO: 149, SEQ ID NO:152, SEQ ID NO: 155, SEQ ID NO: 221, SEQ ID NO: 224, SEQ ID NO: 230 and SEQ ID NO: 233.

In one embodiment, the GH25 polypeptide is obtained or is obtainable from the taxonomic order Agaricales, preferably the taxonomic family Strophariaceae. In one embodiment, the GH25 polypeptide is obtained or is obtainable from the taxonomic family Strophariaceae and is selected from the group selected from SEQ ID NO: 80, SEQ ID NO: 155, SEQ ID NO: 224, SEQ ID NO: 230 and SEQ ID NO: 233.

In one embodiment, the GH25 polypeptide is obtained or is obtainable from the taxonomic class Dothideomycetes, preferably the taxonomic order Pleosporales. In one embodiment, the GH25 polypeptide is obtained or is obtainable from the taxonomic class Dothideomycetes, preferably the taxonomic order Pleosporales and is selected from the group selected from SEQ ID NO: 3, SEQ ID NO: 60, SEQ ID NO: 95, SEQ ID NO:101, SEQ ID NO:104 and SEQ ID NO: 146.

In one embodiment, the GH25 polypeptide is obtained or is obtainable from the taxonomic class Eurotiomycetes but not from the taxonomic genus *Aspergillus fumigatus*. In one embodiment, the GH25 polypeptide is obtained or is obtainable from the taxonomic class Eurotiomycetes but not from the taxonomic genus *Aspergillus fumigatus* and is selected from the group selected from SEQ ID NO: 18, SEQ ID NO: 27, SEQ ID NO: 45, SEQ ID NO: 48, SEQ ID NO: 75, SEQ ID NO: 82, SEQ ID NO: 125, SEQ ID NO: 131 and SEQ ID NO: 140.

In one embodiment, the GH25 polypeptide is obtained or is obtainable from the taxonomic order Eurotiales but not from the taxonomic genus *Aspergillus fumigatus*. In one embodiment, the GH25 polypeptide is obtained or is obtainable from the taxonomic order Eurotiales but not from the taxonomic genus *Aspergillus fumigatus* and is selected from the group selected from SEQ ID NO: 27, SEQ ID NO: 45, SEQ ID NO: 48, SEQ ID NO: 82, SEQ ID NO: 125, SEQ ID NO: 131 and SEQ ID NO: 140.

In one embodiment, the GH25 polypeptide is obtained or is obtainable from the taxonomic family Aspergillaceae but not from the taxonomic genus *Aspergillus fumigatus*. In one embodiment, the GH25 polypeptide is obtained or is obtainable from the taxonomic family Aspergillaceae but not from the taxonomic genus *Aspergillus fumigatus* and is selected from the group selected from SEQ ID NO: 27, SEQ ID NO: 45, SEQ ID NO: 48, SEQ ID NO: 82, SEQ ID NO: 125 and SEQ ID NO: 140.

In one embodiment, the GH25 polypeptide is obtained or is obtainable from the taxonomic class Pezizomycetes, preferably the taxonomic order Pezizales, more preferably the taxonomic family Ascobolaceae. In one embodiment, the GH25 polypeptide is obtained or is obtainable from the taxonomic class Pezizomycetes, preferably the taxonomic order Pezizales, more preferably the taxonomic family Ascobolaceae and is selected from the group selected from SEQ ID NO: 86 and SEQ ID NO: 98.

In one embodiment, the GH25 polypeptide is obtained or is obtainable from the taxonomic order Coniochaetales. In one embodiment, the GH25 polypeptide is obtained or is obtainable from the taxonomic order Coniochaetales and is selected from the group selected from SEQ ID NO: 89.

In one embodiment, the GH25 polypeptide is obtained or is obtainable from the taxonomic order Hypocreales but not from the taxonomic genus *Trichoderma reesei*. In one embodiment, the GH25 polypeptide is obtained or is obtainable from the taxonomic order Hypocreales but not from the taxonomic genus *Trichoderma reesei* and is selected from the group selected from SEQ ID NO: 12, SEQ ID NO: 15, SEQ ID NO: 21, SEQ ID NO: 42, SEQ ID NO: 51, SEQ ID NO: 54, SEQ ID NO: 66, SEQ ID NO: 69, SEQ ID NO: 122, SEQ ID NO: 128, SEQ ID NO: 134, SEQ ID NO: 137 and SEQ ID NO: 143.

In one embodiment, the GH25 polypeptide is obtained or is obtainable from the taxonomic family Clavicipitaceae. In one embodiment, the GH25 polypeptide is obtained or is obtainable from the taxonomic family Clavicipitaceae and is selected from the group selected from SEQ ID NO: 51, SEQ ID NO: 54, SEQ ID NO: 122 and SEQ ID NO: 128.

In one embodiment, the GH25 polypeptide is obtained or is obtainable from the taxonomic family Cordycipitaceae. In one embodiment, the GH25 polypeptide is obtained or is obtainable from the taxonomic family Cordycipitaceae and is selected from the group selected from SEQ ID NO: 12, SEQ ID NO: 15, SEQ ID NO: 42, SEQ ID NO: 66, SEQ ID NO: 69 and SEQ ID NO: 137.

In one embodiment, the GH25 polypeptide is obtained or is obtainable from the taxonomic order Microascales. In one embodiment, the GH25 polypeptide is obtained or is obtainable from the taxonomic order Microascales and is selected from the group selected from SEQ ID NO: 16.

In one embodiment, the GH25 polypeptide is obtained or is obtainable from the taxonomic order Sordariales. In one embodiment, the GH25 polypeptide is obtained or is obtainable from the taxonomic order Sordariales and is selected from the group selected from SEQ ID NO: 30, SEQ ID NO: 39, SEQ ID NO: 7, and SEQ ID NO: 158.

In one embodiment, the GH25 polypeptide is obtained or is obtainable from the taxonomic order Sordariales. In one embodiment, the GH25 polypeptide is obtained or is obtainable from the taxonomic order Sordariales and is selected from the group selected from SEQ ID NO: 30, SEQ ID NO: 39, SEQ ID NO: 7, and SEQ ID NO: 158.

In one embodiment, the GH25 polypeptide is obtained or is obtainable from the taxonomic order Xylariales. In one embodiment, the GH25 polypeptide is obtained or is obtainable from the taxonomic order Xylariales and is selected from the group selected from SEQ ID NO: 6, SEQ ID NO: 9, SEQ ID NO: 92, SEQ ID NO: 107, SEQ ID NO: 110 and SEQ ID NO: 113.

Sources of Polypeptides Having Lysozyme Activity

A polypeptide having lysozyme activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. In one aspect, the polypeptide is a polypeptide having lysozyme activity from a fungus of the class Eurotiomycetes, such as from the order Eurotiales, or from the family Aspergillaceae, or from the genus *Aspergillus* or from the species *Aspergillus* sp. nov. XZ2609.

In another aspect, the polypeptide may be a fungal polypeptide. In one aspect, the polypeptide is a polypeptide having lysozyme activity from a fungus of the class Sordariomycetes, such as from the order Sordariales, or from the family Chaetomiaceae, or from the genus *Chaetomium* or from the species *Chaetomium cupreum*.

In another aspect, the polypeptide may be a fungal polypeptide. In one aspect, the polypeptide is a polypeptide having lysozyme activity from a fungus of the class Sordariomycetes, such as from the order Sordariales, or from the family Lasiosphaeriaceae, or from the genus *Cladorrhinum* or from the species *Cladorrhinum bulbillosum*.

In another aspect, the polypeptide may be a fungal polypeptide. In one aspect, the polypeptide is a polypeptide having lysozyme activity from a fungus of the class Sordariomycetes, such as from the order Hypocreales, or from the family Cordycipitaceae, or from the genus *Cordyceps* or from the species *Cordyceps cardinalis*.

In another aspect, the polypeptide may be a fungal polypeptide. In one aspect, the polypeptide is a polypeptide having lysozyme activity from a fungus of the class Agaricomycetes, such as from the order Agaricales, or from the family Strophariaceae, or from the genus *Hypholoma* or from the species *Hypholoma polytrichi*.

In another aspect, the polypeptide may be a fungal polypeptide. In one aspect, the polypeptide is a polypeptide having lysozyme activity from a fungus of the class Sordariomycetes, such as from the order Hypocreales, or from the family Cordycipitaceae, or from the genus *Isaria* or from the species *Isaria farinosa*.

In another aspect, the polypeptide may be a fungal polypeptide. In one aspect, the polypeptide is a polypeptide having lysozyme activity from a fungus of the class Sordariomycetes, such as from the order Hypocreales, or from the family Cordycipitaceae, or from the genus *Lecanicillium* or from the species *Lecanicillium* sp. WMM742.

In another aspect, the polypeptide may be a fungal polypeptide. In one aspect, the polypeptide is a polypeptide having lysozyme activity from a fungus of the class Eurotiomycetes, such as from the order Onygenales, or from the genus *Malbranchea* or from the species *Malbranchea flava*.

In another aspect, the polypeptide may be a fungal polypeptide. In one aspect, the polypeptide is a polypeptide having lysozyme activity from a fungus of the class Eurotiomycetes, such as from the order Onygenales, or from the family Onygenaceae, or from the genus *Onygena* or from the species *Onygena equina*.

In another aspect, the polypeptide may be a fungal polypeptide. In one aspect, the polypeptide is a polypeptide having lysozyme activity from a fungus of the class Sordariomycetes, such as from the order Hypocreales, or from the family Clavicipitaceae, or from the genus *Paecilomyces* or from the species *Paecilomyces* sp. XZ2658.

In another aspect, the polypeptide may be a fungal polypeptide. In one aspect, the polypeptide is a polypeptide having lysozyme activity from a fungus of the class Eurotiomycetes, such as from the order Eurotiales, or from the family Aspergillaceae, or from the genus *Penicillium* or from the species *Penicillium citrinum*.

In another aspect, the polypeptide may be a fungal polypeptide. In one aspect, the polypeptide is a polypeptide having lysozyme activity from a fungus of the class Eurotiomycetes, such as from the order Eurotiales, or from the family Aspergillaceae, or from the genus *Penicillium* or from the species *Penicillium citrinum* or *Penicillium* sp. 'qii'.

In another aspect, the polypeptide may be a fungal polypeptide. In one aspect, the polypeptide is a polypeptide having lysozyme activity from a fungus of the class Sordariomycetes, such as from the order Xylariales, or from the family *Xylariaceae*, or from the genus *Poronia* or from the species *Poronia punctata*.

In another aspect, the polypeptide may be a fungal polypeptide. In one aspect, the polypeptide is a polypeptide having lysozyme activity from a fungus of the class Dothideomycetes, such as from the order Pleosporales, or from the family Sporormiaceae, or from the genus *Pycnidiophora* or from the species *Pycnidiophora* cf. *dispera*.

In another aspect, the polypeptide may be a fungal polypeptide. In one aspect, the polypeptide is a polypeptide having lysozyme activity from a fungus of the order Mucorales, such as from the family Lichtheimiaceae, or from the genus *Rhizomucor* or from the species *Rhizomucor pusillus*.

In another aspect, the polypeptide may be a fungal polypeptide. In one aspect, the polypeptide is a polypeptide having lysozyme activity from a fungus of the class Dothideomycetes, such as from the order Pleosporales, or from the family Sporormiaceae, or from the genus *Sporormia* or from the species *Sporormia fimetaria*.

In another aspect, the polypeptide may be a fungal polypeptide. In one aspect, the polypeptide is a polypeptide having lysozyme activity from a fungus of the order Mucorales, such as from the family Lichtheimiaceae, or from the genus *Thermomucor* or from the species *Thermomucor indicae-seudaticae*.

In another aspect, the polypeptide may be a fungal polypeptide. In one aspect, the polypeptide is a polypeptide having lysozyme activity from a fungus of the genus Trichobolus or from the species *Trichobolus zukalii*.

In another aspect, the polypeptide may be a fungal polypeptide. In one aspect, the polypeptide is a polypeptide having lysozyme activity from a fungus of the order Mucorales, such as from the family Umbelopsidaceae, or from the genus *Umbelopsis* or from the species *Umbelopsis westeae*.

In another aspect, the polypeptide may be a fungal polypeptide. In one aspect, the polypeptide is a polypeptide having lysozyme activity from a fungus of the class Sordariomycetes, such as from the order Sordariales, or from the family Chaetomiaceae, or from the genus *Zopfiella* or from the species *Zopfiella* sp. t180-6.

In another aspect, the polypeptide may be a fungal polypeptide. In one aspect, the polypeptide is a polypeptide having lysozyme activity from a fungus of the genus *Zygomycetes* or from the species *Zygomycetes* sp. XZ2655.

In another aspect, the polypeptide may be a fungal polypeptide. In one aspect, the polypeptide is a polypeptide having lysozyme activity from a fungus of the class Sordariomycetes, such as from the order Sordariales, or from the family Sordariaceae, or from the genus *Gelasinospora*, or from the species *Gelasinospora cratophora*.

In another aspect, the polypeptide may be a fungal polypeptide. In one aspect, the polypeptide is a polypeptide having lysozyme activity from a fungus of the class Agaricomycetes, such as from the order Agaricales, or from the family Strophariaceae, or from the genus *Stropharia*, or from the species *Stropharia semiglobata*.

In another aspect, the polypeptide may be a fungal polypeptide. In one aspect, the polypeptide is a polypeptide having lysozyme activity from a fungus of the class Sordariomycetes, such as from the order Hypocreales, or from the family Bionectriaceae, or from the genus *Clonostachys*, or from the species *Clonostachys rossmaniae*.

In another aspect, the polypeptide may be a fungal polypeptide. In one aspect, the polypeptide is a polypeptide having lysozyme activity from a fungus of the class Sordariomycetes, such as from the order Hypocreales, or from the family Nectriaceae, or from the genus *Paracremonium*, or from the species *Paracremonium inflatum*.

In another aspect, the polypeptide may be a fungal polypeptide. In one aspect, the polypeptide is a polypeptide having lysozyme activity from a fungus of the class Dothideomycetes, such as from the order Pleosporales, or from the family Cucurbitariaceae, or from the genus *Curreya*, or from the species *Curreya* sp. XZ2623.

In another aspect, the polypeptide may be a fungal polypeptide. In one aspect, the polypeptide is a polypeptide having lysozyme activity from a fungus of the class Sordariomycetes, such as from the order Hypocreales, or from the family Clavicipitaceae, or from the genus *Metapochonia*, or from the species *Metapochonia bulbillosa*.

In another aspect, the polypeptide may be a fungal polypeptide. In one aspect, the polypeptide is a polypeptide having lysozyme activity from a fungus of the class Eurotiomycetes, such as from the order Eurotiales, or from the family Aspergillaceae, or from the genus *Aspergillus*, or from the species *Aspergillus inflatus*.

In another aspect, the polypeptide may be a fungal polypeptide. In one aspect, the polypeptide is a polypeptide having lysozyme activity from a fungus of the class Pezizomycetes, such as from the order Pezizales, or from the family Ascobolaceae, or from the genus *Ascobolus*, or from the species *Ascobolus* sp. ZY179.

In another aspect, the polypeptide may be a fungal polypeptide. In one aspect, the polypeptide is a polypeptide having lysozyme activity from a fungus of the class Sordariomycetes, such as from the order Xylariales, or from the family *Xylariaceae*, or from the genus *Daldinia*, or from the species *Daldinia fissa*.

In another aspect, the polypeptide may be a fungal polypeptide. In one aspect, the polypeptide is a polypeptide having lysozyme activity from a fungus of the class Sordariomycetes, such as from the order Coniochaetales, or from the family Coniochaetaceae, or from the genus *Coniochaeta*, or from the species *Coniochaeta* sp.

In another aspect, the polypeptide may be a fungal polypeptide. In one aspect, the polypeptide is a polypeptide having lysozyme activity from a fungus of the class Eurotiomycetes, such as from the order Eurotiales, or from the family Aspergillaceae, or from the genus *Aspergillus*, or from the species *Aspergillus deflectus*.

In another aspect, the polypeptide may be a fungal polypeptide. In one aspect, the polypeptide is a polypeptide having lysozyme activity from a fungus of the class Dothideomycetes, such as from the order Pleosporales, or from the family Delitschiaceae, or from the genus *Delitschia*, or from the species *Delitschia* sp.

In another aspect, the polypeptide may be a fungal polypeptide. In one aspect, the polypeptide is a polypeptide having lysozyme activity from a fungus of the class Sordariomycetes, such as from the order Hypocreales, or from the family Clavicipitaceae, or from the genus Metarhizium, or from the species *Metarhizium iadini*.

In another aspect, the polypeptide may be a fungal polypeptide. In one aspect, the polypeptide is a polypeptide having lysozyme activity from a fungus of the class Sordariomycetes, such as from the order Xylariales, or from the family *Xylariaceae*, or from the genus *Hypoxylon*, or from the species *Hypoxylon* sp.

In another aspect, the polypeptide may be a fungal polypeptide. In one aspect, the polypeptide is a polypeptide having lysozyme activity from a fungus of the class Sordariomycetes, such as from the order Xylariales, or from the family *Xylariaceae*, or from the genus *Hypoxylon*, or from the species *Hypoxylon* sp.

In another aspect, the polypeptide may be a fungal polypeptide. In one aspect, the polypeptide is a polypeptide having lysozyme activity from a fungus of the class Sordariomycetes, such as from the order Hypocreales, or from the family Cordycipitaceae, or from the genus *Simplicillium*, or from the species *Simplicillium obclavatum*.

In another aspect, the polypeptide may be a fungal polypeptide. In one aspect, the polypeptide is a polypeptide having lysozyme activity from a fungus of the class Sordariomycetes, such as from the order Microascales, or from the family Microascaceae, or from the genus *Yunnania*, or from the species *Yunnania penicillate*.

In another aspect, the polypeptide may be a fungal polypeptide. In one aspect, the polypeptide is a polypeptide having lysozyme activity from a fungus of the class Dothideomycetes, such as from the order Pleosporales, or from the family Sporormiaceae, or from the genus *Westerdykella*, or from the species *Westerdykella* sp.

In another aspect, the polypeptide may be a fungal polypeptide. In one aspect, the polypeptide is a polypeptide having lysozyme activity from a fungus of the class Eurotiomycetes, such as from the order Eurotiales, or from the family Thermoascaceae, or from the genus *Thermoascus*, or from the species *Thermoascus aurantiacus*.

In another aspect, the polypeptide may be a fungal polypeptide. In one aspect, the polypeptide is a polypeptide having lysozyme activity from a fungus of the class Dothideomycetes, such as from the order Pleosporales, or from the family Coniothyriaceae, or from the genus *Coniothyrium*, or from the species *Coniothyrium* sp.

In another aspect, the polypeptide may be a fungal polypeptide. In one aspect, the polypeptide is a polypeptide having lysozyme activity from a fungus of the class Pezizomycetes, such as from the order Pezizales, or from the family Ascobolaceae, or from the genus *Ascobolus*, or from the species *Ascobolus stictoideus*.

In another aspect, the polypeptide may be a fungal polypeptide. In one aspect, the polypeptide is a polypeptide having lysozyme activity from a fungus of the class Eurotiomycetes, such as from the order Eurotiales, or from the family Aspergillaceae, or from the genus *Hamigera*, or from the species *Hamigera paravellanea*.

In another aspect, the polypeptide may be a fungal polypeptide. In one aspect, the polypeptide is a polypeptide having lysozyme activity from a fungus of the phylum Ascomycota, such as from the genus *Engyodontium*, or from the species *Engyodontium album*.

In another aspect, the polypeptide may be a fungal polypeptide. In one aspect, the polypeptide is a polypeptide having lysozyme activity from a fungus of the class Sordariomycetes, such as from the order Xylariales, or from the genus *Xylariaceae*, or from the species *Xylariaceae* sp. 1653h.

In another aspect, the polypeptide may be a fungal polypeptide. In one aspect, the polypeptide is a polypeptide having lysozyme activity from a fungus of the class Agaricomycetes, such as from the order Agaricales, or from the family Strophariaceae, or from the genus *Deconica* or from the species *Deconica coprophile*.

In another aspect, the polypeptide may be a fungal polypeptide. In one aspect, the polypeptide is a polypeptide having lysozyme activity from a fungus of the class Agaricomycetes, such as from the order Agaricales, or from the family Physalacriaceae, or from the genus *Flammulina* or from the species *Flammulina velutipes*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to polynucleotides encoding a polypeptide of the present invention, as described herein. In an embodiment, the polynucleotide encoding the polypeptide of the present invention has been isolated.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Applications*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Trichophaea* or a strain of *Trichoderma*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), Bacillus licheniformis alpha-amylase gene (amyL), Bacillus licheniformis penicillinase gene (penP), Bacillus stearothermophilus maltogenic amylase gene (amyM), Bacillus subtilis levansucrase gene (sacB), Bacillus subtilis xylA and xylB genes, Bacillus thuringiensis cryIIIA gene (Agaisse and Lereclus, 1994, Molecular Microbiology 13: 97-107), E. coli lac operon, E. coli trc promoter (Egon et al., 1988, Gene 69: 301-315), Streptomyces coelicolor agarase gene (dagA), and prokaryotic beta-lactamase gene (Villa-Kamaroff et al., 1978, Proc. Natl. Acad. Sci. USA 75: 3727-3731), as well as the tac promoter (DeBoer et al., 1983, Proc. Natl. Acad. Sci. USA 80: 21-25). Further promoters are described in "Useful proteins from recombinant bacteria" in Gilbert et al., 1980, Scientific American 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for Aspergillus nidulans acetamidase, Aspergillus niger neutral alpha-amylase, Aspergillus niger acid stable alpha-amylase, Aspergillus niger or Aspergillus awamori glucoamylase (glaA), Aspergillus oryzae TAKA amylase, Aspergillus oryzae alkaline protease, Aspergillus oryzae triose phosphate isomerase, Fusarium oxysporum trypsin-like protease (WO 96/00787), Fusarium venenatum amyloglucosidase (WO 00/56900), Fusarium venenatum Dania (WO 00/56900), Fusarium venenatum Quinn (WO 00/56900), Rhizomucor miehei lipase, Rhizomucor miehei aspartic proteinase, Trichoderma reesei beta-glucosidase, Trichoderma reesei cellobiohydrolase I, Trichoderma reesei cellobiohydrolase II, Trichoderma reesei endoglucanase I, Trichoderma reesei endoglucanase II, Trichoderma reesei endoglucanase III, Trichoderma reesei endoglucanase V, Trichoderma reesei xylanase I, Trichoderma reesei xylanase II, Trichoderma reesei xylanase III, Trichoderma reesei beta-xylosidase, and Trichoderma reesei translation elongation factor, as well as the NA2-tpi promoter (a modified promoter from an Aspergillus neutral alpha-amylase gene in which the untranslated leader has been replaced by an untranslated leader from an Aspergillus triose phosphate isomerase gene; non-limiting examples include modified promoters from an Aspergillus niger neutral alpha-amylase gene in which the untranslated leader has been replaced by an untranslated leader from an Aspergillus nidulans or Aspergillus oryzae triose phosphate isomerase gene); and mutant, truncated, and hybrid promoters thereof. Other promoters are described in U.S. Pat. No. 6,011,147.

In a yeast host, useful promoters are obtained from the genes for Saccharomyces cerevisiae enolase (ENO-1), Saccharomyces cerevisiae galactokinase (GAL1), Saccharomyces cerevisiae alcohol dehydrogenase/glyceraldehyde-3-phosphate dehydrogenase (ADH1, ADH2/GAP), Saccharomyces cerevisiae triose phosphate isomerase (TPI), Saccharomyces cerevisiae metallothionein (CUP1), and Saccharomyces cerevisiae 3-phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for Bacillus clausii alkaline protease (aprH), Bacillus licheniformis alpha-amylase (amyL), and Escherichia coli ribosomal RNA (rrnB).

Preferred terminators for filamentous fungal host cells are obtained from the genes for Aspergillus nidulans acetamidase, Aspergillus nidulans anthranilate synthase, Aspergillus niger glucoamylase, Aspergillus niger alpha-glucosidase, Aspergillus oryzae TAKA amylase, Fusarium oxysporum trypsin-like protease, Trichoderma reesei beta-glucosidase, Trichoderma reesei cellobiohydrolase I, Trichoderma reesei cellobiohydrolase II, Trichoderma reesei endoglucanase I, Trichoderma reesei endoglucanase II, Trichoderma reesei endoglucanase III, Trichoderma reesei endoglucanase V, Trichoderma reesei xylanase I, Trichoderma reesei xylanase II, Trichoderma reesei xylanase III, Trichoderma reesei beta-xylosidase, and Trichoderma reesei translation elongation factor.

Preferred terminators for yeast host cells are obtained from the genes for Saccharomyces cerevisiae enolase, Saccharomyces cerevisiae cytochrome C (CYC1), and Saccharomyces cerevisiae glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a Bacillus thuringiensis cryIIIA gene (WO 94/25612) and a Bacillus subtilis SP82 gene (Hue et al., 1995, Journal of Bacteriology 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for Aspergillus oryzae TAKA amylase and Aspergillus nidulans triose phosphate isomerase.

Suitable leaders for yeast host cells are obtained from the genes for Saccharomyces cerevisiae enolase (ENO-1), Saccharomyces cerevisiae 3-phosphoglycerate kinase, Saccharomyces cerevisiae alpha-factor, and Saccharomyces cerevisiae alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for Aspergillus nidulans anthranilate synthase, Aspergillus niger glucoamylase, Aspergillus niger alpha-glucosidase Aspergillus oryzae TAKA amylase, and Fusarium oxysporum trypsin-like protease.

Useful polyadenylation sequences for yeast host cells are described by Guo and Sherman, 1995, Mol. Cellular Biol. 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for Bacillus NCIB 11837 maltogenic amylase, Bacillus licheniformis subtilisin, Bacillus licheniformis beta-lactamase, Bacillus stearothermophilus alpha-amylase, Bacillus stearothermophilus neutral proteases (nprT, nprS, nprM), and Bacillus subtilis prsA. Further signal peptides are described by Simonen and Palva, 1993, Microbiological Reviews 57: 109-137.

Effective signal peptide coding sequences for filamentous fungal host cells are the signal peptide coding sequences obtained from the genes for Aspergillus niger neutral amylase, Aspergillus niger glucoamylase, Aspergillus oryzae TAKA amylase, Humicola insolens cellulase, Humicola insolens endoglucanase V, Humicola lanuginosa lipase, and Rhizomucor miehei aspartic proteinase.

Useful signal peptides for yeast host cells are obtained from the genes for Saccharomyces cerevisiae alpha-factor and Saccharomyces cerevisiae invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for Bacillus subtilis alkaline protease (aprE), Bacillus subtilis neutral protease (nprT), Myceliophthora thermophila laccase (WO 95/33836), Rhizomucor miehei aspartic proteinase, and Saccharomyces cerevisiae alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the Aspergillus niger glucoamylase promoter, Aspergillus oryzae TAKA alpha-amylase promoter, and Aspergillus oryzae glucoamylase promoter, Trichoderma reesei cellobiohydrolase I promoter, and Trichoderma reesei cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are Bacillus licheniformis or Bacillus subtilis dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an Aspergillus cell are Aspergillus nidulans or Aspergillus oryzae amdS and pyrG genes and a Streptomyces hygroscopicus bar gene. Preferred for use in a Trichoderma cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

In some embodiments, the polypeptide is heterologous to the recombinant host cell.

In some embodiments, at least one of the one or more control sequences is heterologous to the polynucleotide encoding the polypeptide.

In some embodiments, the recombinant host cell comprises at least two copies, e.g., three, four, or five, of the polynucleotide of the present invention.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram-negative bacteria include, but are not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides.

Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

For example, the filamentous fungal host cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is an *Aspergillus* sp. nov. XZ2609 cell. In one aspect, the cell is a *Chaetomium cupreum* cell. In one aspect, the cell is a *Cladorrhinum bulbillosum* cell. In one aspect, the cell is a *Cordyceps cardinalis* cell. In one aspect, the cell is a *Hypholoma polytrichi* cell. In one aspect, the cell is a Isaria *farinosa* cell. In one aspect, the cell is a *Lecanicillium* sp. WMM742 cell. In one aspect, the cell is a *Malbranchea flava* cell. In one aspect, the cell is a *Onygena equina* cell. In one aspect, the cell is a *Paecilomyces* sp. XZ2658 cell. In one aspect, the cell is a *Penicillium citrinum* cell. In one aspect, the cell is a *Penicillium* sp. 'qii' cell. In one aspect, the cell is a *Poronia punctata* cell. In one aspect, the cell is a *Pycnidiophora* cf. *dispera* cell. In one aspect, the cell is a *Rhizomucor pusillus* cell. In one aspect, the cell is a *Sporormia fimetaria* cell. In one aspect, the cell is a *Thermomucor indicae-seudaticae* cell. In one aspect, the cell is a *Trichobolus zukalii* cell. In one aspect, the cell is a *Umbelopsis westeae* cell. In one aspect, the cell is a *Zopfiella* sp. t180-6 cell. In one aspect, the cell is a *Zygomycetes* sp. XZ2655 cell.

In one aspect, the cell is a *Gelasinospora cratophora* cell. In one aspect, the cell is a *Stropharia semiglobata* cell. In one aspect, the cell is a *Clonostachys rossmaniae* cell. In one aspect, the cell is a *Paracremonium inflatum* cell. In one aspect, the cell is a *Curreya* sp. XZ2623 cell. In one aspect, the cell is a *Metapochonia bulbillosa* cell. In one aspect, the cell is a *Aspergillus inflatus* cell. In one aspect, the cell is a *Ascobolus* sp. ZY179 cell. In one aspect, the cell is a *Daldinia fissa* cell. In one aspect, the cell is a *Coniochaeta* sp. cell. In one aspect, the cell is a *Aspergillus deflectus* cell. In one aspect, the cell is a *Delitschia* sp. cell. In one aspect, the cell is a *Metarhizium iadini* cell. In one aspect, the cell is a *Hypoxylon* sp. cell. In one aspect, the cell is a *Hypoxylon* sp. cell. In one aspect, the cell is a *Simplicillium obclavatum* cell. In one aspect, the cell is a *Yunnania penicillata* cell. In one aspect, the cell is a *Westerdykella* sp. cell. In one aspect, the cell is a *Thermoascus aurantiacus* cell. In one aspect, the cell is a *Coniothyrium* sp. cell. In one aspect, the cell is a *Ascobolus stictoideus* cell. In one aspect, the cell is a *Hamigera paravellanea* cell. In one aspect, the cell is a *Engyodontium album* cell. In one aspect, the cell is a *Xylariaceae* sp. 1653h cell. In one aspect, the cell is a *Deconica coprophila* cell. In one aspect, the cell is a *Flammulina velutipes* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the fermentation medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca*, *Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems.

Plant cells and specific plant cell compartments, such as chloroplasts, apoplasts, mitochondria, vacuoles, peroxisomes and cytoplasm are also considered to be a plant part.

Also included within the scope of the present invention are the progeny of such plants, plant parts, and plant cells.

The transgenic plant or plant cell expressing the polypeptide or domain may be constructed in accordance with methods known in the art.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In some embodiments, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In some embodiments, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In some embodiments, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a polypeptide of the present invention. Preferably, the compositions are enriched in the polypeptide of the invention. The term "enriched" indicates that the lysozyme activity of the composition has been increased, e.g., with an enrichment factor of at least 1.1, such as at least 1.2, at least 1.3, at least 1.4, at least 1.5, at least 2.0, at least 3.0, at least 4.0, at least 5.0, at least 10.

In a preferred embodiment, the composition comprises one or more lysozymes selected from the list consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233.

In an embodiment, the composition comprises the polypeptide of the invention and one or more formulating agents, as described below.

The compositions may further comprise multiple enzymatic activities, such as one or more (e.g., several) enzymes selected from the group consisting of phytase, xylanase, galactanase, alpha-galactosidase, beta-galactosidase, protease, phospholipase A1, phospholipase A2, lysophospholipase, phospholipase C, phospholipase D, amylase, lysozyme, arabinofuranosidase, beta-xylosidase, acetyl xylan esterase, feruloyl esterase, cellulase, cellobiohydrolases, beta-glucosidase, pullulanase, and beta-glucanase or any combination thereof.

The compositions may further comprise one or more probiotics. In an embodiment, the probiotic is selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococcus acidilactici, Pediococcus* sp., *Propionibacterium thoenii, Propionibacterium* sp. and *Streptococcus* sp. or any combination thereof.

In an embodiment, the composition comprises one or more formulating agents as disclosed herein, preferably one or more of the compounds selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose.

In an embodiment, the composition comprises one or more components selected from the list consisting of vitamins, minerals and amino acids.

Formulation

The enzyme of the invention may be formulated as a liquid or a solid. For a liquid formulation, the formulating agent may comprise a polyol (such as e.g. glycerol, ethylene glycol or propylene glycol), a salt (such as e.g. sodium chloride, sodium benzoate, potassium sorbate) or a sugar or sugar derivative (such as e.g. dextrin, glucose, sucrose, and sorbitol). Thus in one embodiment, the composition is a liquid composition comprising the polypeptide of the invention and one or more formulating agents selected from the list consisting of glycerol, ethylene glycol, 1,2-propylene glycol, 1,3-propylene glycol, sodium chloride, sodium benzoate, potassium sorbate, dextrin, glucose, sucrose, and sorbitol. The liquid formulation may be sprayed onto the feed after it has been pelleted or may be added to drinking water given to the animals.

For a solid formulation, the formulation may be for example as a granule, spray dried powder or agglomerate (e.g. as disclosed in WO 00/70034). The formulating agent may comprise a salt (organic or inorganic zinc, sodium, potassium or calcium salts such as e.g. such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol).

In one embodiment, the composition is a solid composition, such as a spray dried composition, comprising the lysozyme of the invention and one or more formulating agents selected from the list consisting of sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose. In a preferred embodiment, the formulating agent is selected from one or more of the following compounds: sodium sulfate, dextrin, cellulose, sodium thiosulfate, magnesium sulfate and calcium carbonate.

The present invention also relates to enzyme granules/particles comprising the lysozyme of the invention optionally combined with one or more additional enzymes. The granule is composed of a core, and optionally one or more coatings (outer layers) surrounding the core.

Typically the granule/particle size, measured as equivalent spherical diameter (volume based average particle size), of the granule is 20-2000 µm, particularly 50-1500 µm, 100-1500 µm or 250-1200 µm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier. Preparation methods include known feed and granule formulation technologies, e.g.:

a) spray dried products, wherein a liquid enzyme-containing solution is atomized in a spray drying tower to form small droplets which during their way down the drying tower dry to form an enzyme-containing particulate material;

b) layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found. This type of product is described in, e.g., WO 97/23606;

c) absorbed core particles, wherein rather than coating the enzyme as a layer around the core, the enzyme is absorbed onto and/or into the surface of the core. Such a process is described in WO 97/39116.

d) extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme;

e) prilled products, wherein an enzyme-containing powder is suspended in molten wax and the suspension is sprayed, e.g., through a rotating disk atomiser, into a cooling chamber where the droplets quickly solidify (Michael S. Showell (editor); Powdered detergents; Surfactant Science Series; 1998; vol. 71; page 140-142; Marcel Dekker). The product obtained is one wherein the enzyme is uniformly distributed throughout an inert material instead of being concentrated on its surface. Also U.S. Pat. Nos. 4,016,040 and 4,713,245 are documents relating to this technique;

f) mixer granulation products, wherein a liquid is added to a dry powder composition of, e.g., conventional granulating components, the enzyme being introduced either via the liquid or the powder or both. The liquid and the powder are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 and related documents EP 170360, EP 304332, EP 304331, WO 90/09440 and WO 90/09428. In a particular product of this process wherein various high-shear mixers can be used as granulators, granulates consisting of enzyme as enzyme, fillers and binders etc. are mixed with cellulose fibres to reinforce the particles to give the so-called T-granulate. Reinforced particles, being more robust, release less enzymatic dust.

g) size reduction, wherein the cores are produced by milling or crushing of larger particles, pellets, tablets, briquettes etc. containing the enzyme. The wanted core particle fraction is obtained by sieving the milled or crushed product. Over and undersized particles can be recycled. Size reduction is described in (Martin Rhodes (editor); Principles of Powder Technology; 1990; Chapter 10; John Wiley & Sons);

h) fluid bed granulation, which involves suspending particulates in an air stream and spraying a liquid onto the fluidized particles via nozzles. Particles hit by spray droplets get wetted and become tacky. The tacky particles collide with other particles and adhere to them and form a granule;

i) the cores may be subjected to drying, such as in a fluid bed drier. Other known methods for drying granules in the feed or detergent industry can be used by the skilled person. The drying preferably takes place at a product temperature of from 25 to 90° C. For some enzymes it is important the cores comprising the enzyme contain a low amount of water before coating. If water sensitive enzymes are coated before excessive water is removed, it will be trapped within the core and it may affect the activity of the enzyme negatively. After drying, the cores preferably contain 0.1-10% w/w water.

The core may include additional materials such as fillers, fibre materials (cellulose or synthetic fibres), stabilizing agents, solubilizing agents, suspension agents, viscosity regulating agents, light spheres, plasticizers, salts, lubricants and fragrances.

The core may include a binder, such as synthetic polymer, wax, fat, or carbohydrate.

The core may include a salt of a multivalent cation, a reducing agent, an antioxidant, a peroxide decomposing catalyst and/or an acidic buffer component, typically as a homogenous blend.

In one embodiment, the core comprises a material selected from the group consisting of salts (such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol), sugar or sugar derivative (such as e.g. sucrose, dextrin, glucose, lactose, sorbitol), small organic molecules, starch, flour, cellulose and minerals and clay minerals (also known as hydrous aluminium phyllosilicates). In one embodiment, the core comprises a clay mineral such as kaolinite or kaolin.

The core may include an inert particle with the enzyme absorbed into it, or applied onto the surface, e.g., by fluid bed coating.

The core may have a diameter of 20-2000 µm, particularly 50-1500 µm, 100-1500 µm or 250-1200 µm.

The core may be surrounded by at least one coating, e.g., to improve the storage stability, to reduce dust formation during handling, or for coloring the granule. The optional coating(s) may include a salt and/or wax and/or flour coating, or other suitable coating materials.

The coating may be applied in an amount of at least 0.1% by weight of the core, e.g., at least 0.5%, 1% or 5%. The amount may be at most 100%, 70%, 50%, 40% or 30%.

The coating is preferably at least 0.1 µm thick, particularly at least 0.5 µm, at least 1 µm or at least 5 µm. In some embodiments the thickness of the coating is below 100 µm, such as below 60 µm, or below 40 µm.

The coating should encapsulate the core unit by forming a substantially continuous layer. A substantially continuous layer is to be understood as a coating having few or no holes, so that the core unit is encapsulated or enclosed with few or no uncoated areas. The layer or coating should in particular be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight of a salt, e.g., at least 65%, at least 70%, at least 75%, at least 80%, at least 85%, at least 90%, at least 95% or at least 99% by weight.

The salt may be added from a salt solution where the salt is completely dissolved or from a salt suspension wherein the fine particles are less than 50 µm, such as less than 10 µm or less than 5 µm.

The salt coating may comprise a single salt or a mixture of two or more salts. The salt may be water soluble, in particular having a solubility at least 0.1 g in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, sorbate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO1997/05245, WO1998/54980, WO1998/55599, WO2000/70034, WO2006/034710, WO2008/017661, WO2008/017659, WO2000/020569, WO2001/004279, WO1997/05245, WO2000/01793, WO2003/059086, WO2003/059087, WO2007/031483, WO2007/031485, WO2007/044968, WO2013/192043, WO2014/014647 and WO2015/197719 or polymer coating such as described in WO 2001/00042.

Specific examples of suitable salts are NaCl (CH20° C.=76%), Na2CO3 (CH20° C.=92%), NaNO3 (CH20° C.=73%), Na2HPO4 (CH20° C.=95%), Na3PO4 (CH25° C.=92%), NH4Cl (CH20° C.=79.5%), (NH4)$_2$HPO4 (CH20° C.=93.0%), NH4H2PO4 (CH20° C.=93.1%), (NH4)2SO4 (CH20° C.=81.1%), KCl (CH20° C.=85%), K2HPO4 (CH20° C.=92%), KH2PO4 (CH20° C.=96.5%), KNO3 (CH20° C.=93.5%), Na2SO4 (CH20° C.=93%), K2SO4 (CH20° C.=98%), KHSO4 (CH20° C.=86%), MgSO4 (CH20° C.=90%), ZnSO4 (CH20° C.=90%) and sodium citrate (CH25° C.=86%). Other examples include NaH2PO4, (NH4)H2PO4, CuSO4, Mg(NO3)2, magnesium acetate, calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, sodium acetate, sodium benzoate, sodium citrate, sodium sulfate, zinc acetate, zinc benzoate, zinc carbonate, zinc chloride, zinc citrate and zinc sorbate.

The salt may be in anhydrous form, or it may be a hydrated salt, i.e. a crystalline salt hydrate with bound water(s) of crystallization, such as described in WO 99/32595. Specific examples include anhydrous sodium sulfate (Na2SO4), anhydrous magnesium sulfate (MgSO4), magnesium sulfate heptahydrate (MgSO4·7H2O), zinc sulfate heptahydrate (ZnSO4·7H2O), sodium phosphate dibasic heptahydrate (Na2HPO4·7H2O), magnesium nitrate hexahydrate (Mg(NO3)2(6H2O)), sodium citrate dihydrate and magnesium acetate tetrahydrate.

Preferably the salt is applied as a solution of the salt, e.g., using a fluid bed.

A wax coating may comprise at least 60% by weight of a wax, e.g., at least 65%, at least 70%, at least 75%, at least 80%, at least 85%, at least 90%, at least 95% or at least 99% by weight.

Specific examples of waxes are polyethylene glycols; polypropylenes; Carnauba wax; Candelilla wax; bees wax; hydrogenated plant oil or animal tallow such as polyethylene glycol (PEG), methyl hydroxy-propyl cellulose (MHPC), polyvinyl alcohol (PVA), hydrogenated ox tallow, hydrogenated palm oil, hydrogenated cotton seeds and/or hydrogenated soy bean oil; fatty acid alcohols; mono-glycerides and/or di-glycerides, such as glyceryl stearate, wherein stearate is a mixture of stearic and palmitic acid; microcrystalline wax; paraffin's; and fatty acids, such as hydrogenated linear long chained fatty acids and derivatives thereof. A preferred wax is palm oil or hydrogenated palm oil.

The granule may comprise a core comprising the lysozyme of the invention, one or more salt coatings and one or more wax coatings. Examples of enzyme granules with multiple coatings are shown in WO1993/07263, WO1997/23606 and WO2016/149636.

Non-dusting granulates may be produced, e.g., as disclosed in U.S. Pat. Nos. 4,106,991 and 4,661,452 and may optionally be coated by methods known in the art. The coating materials can be waxy coating materials and film-forming coating materials. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

The granulate may further comprise one or more additional enzymes. Each enzyme will then be present in more granules securing a more uniform distribution of the enzymes, and also reduces the physical segregation of different enzymes due to different particle sizes. Methods for producing multi-enzyme co-granulates is disclosed in the ip.com disclosure IPCOM000200739D.

Another example of formulation of enzymes by the use of co-granulates is disclosed in WO 2013/188331.

The present invention also relates to protected enzymes prepared according to the method disclosed in EP 238,216.

Thus, in a further aspect, the present invention provides a granule, which comprises:
  (a) a core comprising a lysozyme according to the invention, and
  (b) a coating consisting of one or more layer(s) surrounding the core.

In one embodiment, the coating comprises a salt coating as described herein. In one embodiment, the coating comprises a wax coating as described herein. In one embodiment, the coating comprises a salt coating followed by a wax coating as described herein.

Animal Feed Additives

The present invention also relates to animal feed additives comprising one or more lysozymes of the invention. Thus in one embodiment, the invention relates to an animal feed additive comprising one or more GH25 polypeptides having lysozyme activity, wherein the polypeptide is selected from the group consisting of:
  (a) a polypeptide having at least 80%, such as at least 85%, at least 90% or at least 95% sequence identity to the polypeptide of SEQ ID NO: 3;
  (b) a polypeptide having at least 84%, such as at least 85%, at least 90% or at least 95% sequence identity to the polypeptide of SEQ ID NO: 6;
  (c) a polypeptide having at least 80%, such as at least 85%, at least 90% or at least 95% sequence identity to the polypeptide of SEQ ID NO: 9;
  (d) a polypeptide having at least 80%, such as at least 85%, at least 90% or at least 95% sequence identity to the polypeptide of SEQ ID NO: 12;
  (e) a polypeptide having at least 80%, such as at least 85%, at least 90% or at least 95% sequence identity to the polypeptide of SEQ ID NO: 15;
  (f) a polypeptide having at least 80%, such as at least 85%, at least 90% or at least 95% sequence identity to the polypeptide of SEQ ID NO: 18;
  (g) a polypeptide having at least 80%, such as at least 85%, at least 90% or at least 95% sequence identity to the polypeptide of SEQ ID NO: 21;
  (h) a polypeptide having at least 80%, such as at least 85%, at least 90% or at least 95% sequence identity to the polypeptide of SEQ ID NO: 24;
  (i) a polypeptide having at least 80%, such as at least 85%, at least 90% or at least 95% sequence identity to the polypeptide of SEQ ID NO: 27;
  (j) a polypeptide having at least 84%, such as at least 85%, at least 90% or at least 95% sequence identity to the polypeptide of SEQ ID NO: 30;
  (k) a polypeptide having at least 80%, such as at least 85%, at least 90% or at least 95% sequence identity to the polypeptide of SEQ ID NO: 33;
  (l) a polypeptide having at least 80%, such as at least 85%, at least 90% or at least 95% sequence identity to the polypeptide of SEQ ID NO: 36;
  (m) a polypeptide having at least 84%, such as at least 85%, at least 90% or at least 95% sequence identity to the polypeptide of SEQ ID NO: 39;
  (n) a polypeptide having at least 80%, such as at least 85%, at least 90% or at least 95% sequence identity to the polypeptide of SEQ ID NO: 42;
  (o) a polypeptide having at least 80%, such as at least 85%, at least 90% or at least 95% sequence identity to the polypeptide of SEQ ID NO: 45;
  (p) a polypeptide having at least 80%, such as at least 85%, at least 90% or at least 95% sequence identity to the polypeptide of SEQ ID NO: 48;
  (q) a polypeptide having at least 80%, such as at least 85%, at least 90% or at least 95% sequence identity to the polypeptide of SEQ ID NO: 51;
  (r) a polypeptide having at least 80%, such as at least 85%, at least 90% or at least 95% sequence identity to the polypeptide of SEQ ID NO: 54;
  (s) a polypeptide having at least 80%, such as at least 85%, at least 90% or at least 95% sequence identity to the polypeptide of SEQ ID NO: 57;
  (t) a polypeptide having at least 80%, such as at least 85%, at least 90% or at least 95% sequence identity to the polypeptide of SEQ ID NO: 60;
  (u) a polypeptide having at least 80%, such as at least 85%, at least 90% or at least 95% sequence identity to the polypeptide of SEQ ID NO: 63;
  (v) a polypeptide having at least 80%, such as at least 85%, at least 90% or at least 95% sequence identity to the polypeptide of SEQ ID NO: 66;
  (w) a polypeptide having at least 80%, such as at least 85%, at least 90% or at least 95% sequence identity to the polypeptide of SEQ ID NO: 69;
  (x) a polypeptide having at least 84%, such as at least 85%, at least 90% or at least 95% sequence identity to the polypeptide of SEQ ID NO: 72;
  (y) a polypeptide having at least 80%, such as at least 85%, at least 90% or at least 95% sequence identity to the polypeptide of SEQ ID NO: 75;
  (z) a polypeptide having at least 80%, such as at least 85%, at least 90% or at least 95% sequence identity to the polypeptide of SEQ ID NO: 80;

(aa) a polypeptide having at least 80%, such as at least 85%, at least 90% or at least 95% sequence identity to the polypeptide of SEQ ID NO: 83;
(ab) a polypeptide having at least 80%, such as at least 85%, at least 90% or at least 95% sequence identity to the polypeptide of SEQ ID NO: 86;
(ac) a polypeptide having at least 86%, such as at least 90% or at least 95% sequence identity to the polypeptide of SEQ ID NO: 89;
(ad) a polypeptide having at least 82%, such as at least 85%, at least 90% or at least 95% sequence identity to the polypeptide of SEQ ID NO: 92;
(ae) a polypeptide having at least 82%, such as at least 85%, at least 90% or at least 95% sequence identity to the polypeptide of SEQ ID NO: 95;
(af) a polypeptide having at least 80%, such as at least 85%, at least 90% or at least 95% sequence identity to the polypeptide of SEQ ID NO: 98;
(ag) a polypeptide having at least 80%, such as at least 85%, at least 90% or at least 95% sequence identity to the polypeptide of SEQ ID NO: 101;
(ah) a polypeptide having at least 80%, such as at least 85%, at least 90% or at least 95% sequence identity to the polypeptide of SEQ ID NO: 104;
(ai) a polypeptide having at least 80%, such as at least 85%, at least 90% or at least 95% sequence identity to the polypeptide of SEQ ID NO: 107;
(aj) a polypeptide having at least 82%, such as at least 85%, at least 90% or at least 95% sequence identity to the polypeptide of SEQ ID NO: 110;
(ak) a polypeptide having at least 81%, such as at least 85%, at least 90% or at least 95% sequence identity to the polypeptide of SEQ ID NO: 113;
(al) a polypeptide having at least 80%, such as at least 85%, at least 90% or at least 95% sequence identity to the polypeptide of SEQ ID NO: 116;
(am) a polypeptide having at least 80%, such as at least 85%, at least 90% or at least 95% sequence identity to the polypeptide of SEQ ID NO: 119;
(an) a polypeptide having at least 80%, such as at least 85%, at least 90% or at least 95% sequence identity to the polypeptide of SEQ ID NO: 122;
(ao) a polypeptide having at least 80%, such as at least 85%, at least 90% or at least 95% sequence identity to the polypeptide of SEQ ID NO: 125;
(ap) a polypeptide having at least 80%, such as at least 85%, at least 90% or at least 95% sequence identity to the polypeptide of SEQ ID NO: 128;
(aq) a polypeptide having at least 80%, such as at least 85%, at least 90% or at least 95% sequence identity to the polypeptide of SEQ ID NO: 131;
(ar) a polypeptide having at least 80%, such as at least 85%, at least 90% or at least 95% sequence identity to the polypeptide of SEQ ID NO: 134;
(as) a polypeptide having at least 80%, such as at least 85%, at least 90% or at least 95% sequence identity to the polypeptide of SEQ ID NO: 137;
(at) a polypeptide having at least 80%, such as at least 85%, at least 90% or at least 95% sequence identity to the polypeptide of SEQ ID NO: 140;
(au) a polypeptide having at least 80%, such as at least 85%, at least 90% or at least 95% sequence identity to the polypeptide of SEQ ID NO: 143;
(av) a polypeptide having at least 80%, such as at least 85%, at least 90% or at least 95% sequence identity to the polypeptide of SEQ ID NO: 146;
(aw) a polypeptide having at least 80%, such as at least 85%, at least 90% or at least 95% sequence identity to the polypeptide of SEQ ID NO: 149;
(ax) a polypeptide having at least 80%, such as at least 85%, at least 90% or at least 95% sequence identity to the polypeptide of SEQ ID NO: 152;
(ay) a polypeptide having at least 80%, such as at least 85%, at least 90% or at least 95% sequence identity to the polypeptide of SEQ ID NO: 155;
(az) a polypeptide having at least 80%, such as at least 85%, at least 90% or at least 95% sequence identity to the polypeptide of SEQ ID NO: 158;
(ba) a polypeptide having at least 80%, such as at least 85%, at least 90% or at least 95% sequence identity to the polypeptide of SEQ ID NO: 221;
(bb) a polypeptide having at least 80%, such as at least 85%, at least 90% or at least 95% sequence identity to the polypeptide of SEQ ID NO: 224;
(bc) a polypeptide having at least 80%, such as at least 85%, at least 90% or at least 95% sequence identity to the polypeptide of SEQ ID NO: 227;
(bd) a polypeptide having at least 80%, such as at least 85%, at least 90% or at least 95% sequence identity to the polypeptide of SEQ ID NO: 230;
(be) a polypeptide having at least 80%, such as at least 85%, at least 90% or at least 95% sequence identity to the polypeptide of SEQ ID NO: 233;
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27 or 28 positions;
(bg) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal His-tag and/or HQ-tag;
(bh) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal extension of up to 10 amino acids, e.g. 1, 2, 3, 4, 5, 6, 7, 8, 9 or 10 amino acids; and (bi) a fragment of the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) having lysozyme activity and having at least 90% of the length of the mature polypeptide.

In an embodiment, the one or more GH25 polypeptides comprises the motif YKNA (SEQ ID NO: 160) and/or the motif FGGW[S/1] (SEQ ID NO: 161), and preferably is selected from the group selected from SEQ ID NO: 12, SEQ ID NO: 27, SEQ ID NO: 42, SEQ ID NO: 57, SEQ ID NO: 63, SEQ ID NO: 66, SEQ ID NO: 80, SEQ ID NO: 149, SEQ ID NO:152, SEQ ID NO: 155, SEQ ID NO: 224, SEQ ID NO: 227, SEQ ID NO: 230 and SEQ ID NO: 233.

In an embodiment, the polypeptide comprises or consists of amino acids 1 to 207 of SEQ ID NO: 3, amino acids 1 to 201 of SEQ ID NO: 6, amino acids 1 to 201 of SEQ ID NO: 9, amino acids 1 to 203 of SEQ ID NO: 12, amino acids 1 to 208 of SEQ ID NO: 15, amino acids 1 to 207 of SEQ ID NO: 18, amino acids 1 to 208 of SEQ ID NO: 21, amino acids 1 to 207 of SEQ ID NO: 24, amino acids 1 to 207 of SEQ ID NO: 27, amino acids 1 to 207 of SEQ ID NO: 30, amino acids 1 to 208 of SEQ ID NO: 33, amino acids 1 to 208 of SEQ ID NO: 36, amino acids 1 to 206 of SEQ ID NO: 39, amino acids 1 to 207 of SEQ ID NO: 42, amino acids 1 to 216 of SEQ ID NO: 45, amino acids 1 to 218 of SEQ ID NO: 48, amino acids 1 to 204 of SEQ ID NO: 51, amino acids 1 to 203 of SEQ ID NO: 54, amino acids 1 to 209 of SEQ ID NO: 57, amino acids 1 to 208 of SEQ ID NO: 60, amino acids 1 to 210 of SEQ ID NO: 63, amino acids 1 to 207 of SEQ ID NO: 66, amino acids 1 to 207 of SEQ ID NO: 69, amino acids 1 to 208 of SEQ ID NO: 72, amino acids 1 to 217 of SEQ ID NO: 75, amino acids 1 to 208 of SEQ ID NO: 80, amino acids 1 to 201 of SEQ ID NO: 83, amino acids 1 to 202 of SEQ ID NO: 86, amino acids 1 to 207 of SEQ ID NO: 89, amino acids 1 to 202 of SEQ ID NO: 92, amino acids 1 to 201 of SEQ ID NO: 95, amino acids 1 to 202 of SEQ ID NO: 98, amino acids 1 to 206 of SEQ ID NO: 101, amino acids 1 to 202 of SEQ ID NO: 104, amino acids 1 to 202 of SEQ ID NO: 107, amino acids 1 to 202 of SEQ ID NO: 110, amino acids 1 to 202 of SEQ ID NO: 113, amino acids 1 to 206 of SEQ ID NO: 116, amino acids 1 to 207 of SEQ ID NO: 119, amino acids 1 to 208 of SEQ ID NO: 122, amino acids 1 to 215 of SEQ ID NO: 125, amino acids 1 to 217 of SEQ ID NO: 128, amino acids 1 to 214 of SEQ ID NO: 131, amino acids 1 to 208 of SEQ ID NO: 134, amino acids 1 to 203 of SEQ ID NO: 137, amino acids 1 to 216 of SEQ ID NO: 140, amino acids 1 to 207 of SEQ ID NO: 143, amino acids 1 to 208 of SEQ ID NO: 146, amino acids 1 to 207 of SEQ ID NO: 149, amino acids 1 to 207 of SEQ ID NO: 152, amino acids 1 to 207 of SEQ ID NO: 155, amino acids 1 to 208 of SEQ ID NO: 158, amino acids 1 to 207 of SEQ ID NO: 221, amino acids 1 to 207 of SEQ ID NO: 224, amino acids 1 to 208 of SEQ ID NO: 227, amino acids 1 to 207 of SEQ ID NO: 230 or amino acids 1 to 207 of SEQ ID NO: 233.

In a preferred embodiment, the polypeptide has at least 150%, such as at least 175%, at least 200%, at least 225%, at least 250%, at least 275%, at least 300%, at least 350%, or at least 400% of the lysozyme activity of SEQ ID NO: 159. In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as follows: lysozyme (50 µL of 0.7 µg/mL lysozyme in phosphate buffer (5 mM citrate, 5 mM $K_2HPO_4$, 0.01% TritonX-100, pH 5.0)) is mixed with *Micrococcus lysodeikticus* solution (450 µL of 1% lyophilized *Micrococcus lysodeikticus* ATCC No. 4698 in milli-Q water) and incubated at 40° C. with shaking (500 rpm) for 45 min; the sample is centrifuged (4000 g, 5 min); supernatant (100 µL) is mixed with HCl (50 µL 3.2M) and incubated at 95° C. for 80 min; NaOH (50 µL, 3.5 M) is added and 150 µL of the sample is added to 4-hydroxybenzhydrazide in K-Na tartrate/NaOH buffer (75 µL of 50 g/L K-Na tartrate+20 g/L NaOH); the mixture is incubated at 95° C. for 10 min; and the optical density is measured at 405 nm.

In an embodiment, the animal feed additive comprises one or more formulating agents, preferably as described herein above.

In an embodiment, the animal feed additive comprises one or more additional enzymes, preferably as described herein below.

In an embodiment, the animal feed additive comprises one or more probiotics, preferably as described herein below.

In an embodiment, the animal feed additive comprises one or more vitamins, preferably as described herein below.

In an embodiment, the animal feed additive comprises one or more minerals, preferably as described herein below.

In an embodiment, the animal feed additive comprises one or more amino acids, preferably as described herein below.

In an embodiment, the animal feed additive comprises one or more prebiotics, preferably as described herein below.

In an embodiment, the animal feed additive comprises one or more organic acids, preferably as described herein below.

In an embodiment, the animal feed additive comprises one or more phytogenics, preferably as described herein below.

Animal Feed

The present invention also relates to animal feed compositions comprising one or more lysozymes of the invention. In one embodiment, the invention relates to an animal feed comprising the granule as described herein and plant based material. In one embodiment, the invention relates to an animal feed comprising the animal feed additive as described herein and plant based material.

Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

An animal feed composition according to the invention has a crude protein content of 50-800 g/kg, and furthermore comprises at least one lysozyme as claimed herein.

Furthermore, or in the alternative (to the crude protein content indicated above), the animal feed composition of the invention has a content of metabolisable energy of 10-30

MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington DC).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen bv, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Distillers Grains with Solubles (DDGS), typically in amounts of 0-30%.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

The animal feed may comprise vegetable proteins. In particular embodiments, the protein content of the vegetable proteins is at least 10, 20, 30, 40, 50, 60, 70, 80, or 90% (w/w). Vegetable proteins may be derived from vegetable protein sources, such as legumes and cereals, for example, materials from plants of the families Fabaceae (Leguminosae), Cruciferaceae, Chenopodiaceae, and Poaceae, such as soy bean meal, lupin meal, rapeseed meal, and combinations thereof.

In a particular embodiment, the vegetable protein source is material from one or more plants of the family Fabaceae, e.g., soybean, lupine, pea, or bean. In another particular embodiment, the vegetable protein source is material from one or more plants of the family Chenopodiaceae, e.g. beet, sugar beet, spinach or quinoa. Other examples of vegetable protein sources are rapeseed, and cabbage. In another particular embodiment, soybean is a preferred vegetable protein source. Other examples of vegetable protein sources are cereals such as barley, wheat, rye, oat, maize (corn), rice, and sorghum.

Animal diets can e.g. be manufactured as mash feed (non-pelleted) or pelleted feed. Typically, the milled feedstuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed the (liquid or solid) lysozyme/enzyme preparation may also be added before or during the feed ingredient step. Typically a liquid lysozyme/enzyme preparation comprises the lysozyme of the invention optionally with a polyol, such as glycerol, ethylene glycol or propylene glycol, and is added after the pelleting step, such as by spraying the liquid formulation onto the pellets. The enzyme may also be incorporated in a feed additive or premix.

Alternatively, the lysozyme can be prepared by freezing a mixture of liquid enzyme solution with a bulking agent such as ground soybean meal, and then lyophilizing the mixture.

The final enzyme concentration in the diet is within the range of 0.01-200 mg enzyme protein per kg diet, preferably between 0.05-100 mg/kg diet, more preferably 0.1-50 mg, even more preferably 0.2-20 mg enzyme protein per kg animal diet.

It is at present contemplated that the enzyme is administered in one or more of the following amounts (dosage ranges): 0.01-200; 0.05-100; 0.1-50; 0.2-20; 0.1-1; 0.2-2; 0.5-5; or 1-10;—all these ranges being in mg lysozyme protein per kg feed (ppm).

For determining mg lysozyme protein per kg feed, the lysozyme is purified from the feed composition, and the specific activity of the purified lysozyme is determined using a relevant assay (see under lysozyme activity). The lysozyme activity of the feed composition as such is also determined using the same assay, and on the basis of these two determinations, the dosage in mg lysozyme protein per kg feed is calculated.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The same principles apply for determining mg lysozyme protein in feed additives. Of course, if a sample is available of the lysozyme used for preparing the feed additive or the feed, the specific activity is determined from this sample (no need to purify the lysozyme from the feed composition or the additive).

Thus in a further aspect, the present invention also relates to an animal feed comprising one or more lysozymes of the invention and plant based material. In another aspect, the present invention also relates to an animal feed comprising the animal feed additive of the invention (as described herein above) and plant based material.

Thus in one embodiment, the invention relates to an animal feed additive comprising plant based material and one or more GH25 polypeptides having lysozyme activity, wherein the polypeptide is selected from the group consisting of:
  (a) a polypeptide having at least 80%, such as at least 85%, at least 90% or at least 95% sequence identity to the polypeptide of SEQ ID NO: 3;
  (b) a polypeptide having at least 84%, such as at least 85%, at least 90% or at least 95% sequence identity to the polypeptide of SEQ ID NO: 6;

(c) a polypeptide having at least 80%, such as at least 85%, at least 90% or at least 95% sequence identity to the polypeptide of SEQ ID NO: 9;
(d) a polypeptide having at least 80%, such as at least 85%, at least 90% or at least 95% sequence identity to the polypeptide of SEQ ID NO: 12;
(e) a polypeptide having at least 80%, such as at least 85%, at least 90% or at least 95% sequence identity to the polypeptide of SEQ ID NO: 15;
(f) a polypeptide having at least 80%, such as at least 85%, at least 90% or at least 95% sequence identity to the polypeptide of SEQ ID NO: 18;
(g) a polypeptide having at least 80%, such as at least 85%, at least 90% or at least 95% sequence identity to the polypeptide of SEQ ID NO: 21;
(h) a polypeptide having at least 80%, such as at least 85%, at least 90% or at least 95% sequence identity to the polypeptide of SEQ ID NO: 24;
(i) a polypeptide having at least 80%, such as at least 85%, at least 90% or at least 95% sequence identity to the polypeptide of SEQ ID NO: 27;
(j) a polypeptide having at least 84%, such as at least 85%, at least 90% or at least 95% sequence identity to the polypeptide of SEQ ID NO: 30;
(k) a polypeptide having at least 80%, such as at least 85%, at least 90% or at least 95% sequence identity to the polypeptide of SEQ ID NO: 33;
(l) a polypeptide having at least 80%, such as at least 85%, at least 90% or at least 95% sequence identity to the polypeptide of SEQ ID NO: 36;
(m) a polypeptide having at least 84%, such as at least 85%, at least 90% or at least 95% sequence identity to the polypeptide of SEQ ID NO: 39;
(n) a polypeptide having at least 80%, such as at least 85%, at least 90% or at least 95% sequence identity to the polypeptide of SEQ ID NO: 42;
(o) a polypeptide having at least 80%, such as at least 85%, at least 90% or at least 95% sequence identity to the polypeptide of SEQ ID NO: 45;
(p) a polypeptide having at least 80%, such as at least 85%, at least 90% or at least 95% sequence identity to the polypeptide of SEQ ID NO: 48;
(q) a polypeptide having at least 80%, such as at least 85%, at least 90% or at least 95% sequence identity to the polypeptide of SEQ ID NO: 51;
(r) a polypeptide having at least 80%, such as at least 85%, at least 90% or at least 95% sequence identity to the polypeptide of SEQ ID NO: 54;
(s) a polypeptide having at least 80%, such as at least 85%, at least 90% or at least 95% sequence identity to the polypeptide of SEQ ID NO: 57;
(t) a polypeptide having at least 80%, such as at least 85%, at least 90% or at least 95% sequence identity to the polypeptide of SEQ ID NO: 60;
(u) a polypeptide having at least 80%, such as at least 85%, at least 90% or at least 95% sequence identity to the polypeptide of SEQ ID NO: 63;
(v) a polypeptide having at least 80%, such as at least 85%, at least 90% or at least 95% sequence identity to the polypeptide of SEQ ID NO: 66;
(w) a polypeptide having at least 80%, such as at least 85%, at least 90% or at least 95% sequence identity to the polypeptide of SEQ ID NO: 69;
(x) a polypeptide having at least 84%, such as at least 85%, at least 90% or at least 95% sequence identity to the polypeptide of SEQ ID NO: 72;
(y) a polypeptide having at least 80%, such as at least 85%, at least 90% or at least 95% sequence identity to the polypeptide of SEQ ID NO: 75;
(z) a polypeptide having at least 80%, such as at least 85%, at least 90% or at least 95% sequence identity to the polypeptide of SEQ ID NO: 80;
(aa) a polypeptide having at least 80%, such as at least 85%, at least 90% or at least 95% sequence identity to the polypeptide of SEQ ID NO: 83;
(ab) a polypeptide having at least 80%, such as at least 85%, at least 90% or at least 95% sequence identity to the polypeptide of SEQ ID NO: 86;
(ac) a polypeptide having at least 86%, such as at least 90% or at least 95% sequence identity to the polypeptide of SEQ ID NO: 89;
(ad) a polypeptide having at least 82%, such as at least 85%, at least 90% or at least 95% sequence identity to the polypeptide of SEQ ID NO: 92;
(ae) a polypeptide having at least 82%, such as at least 85%, at least 90% or at least 95% sequence identity to the polypeptide of SEQ ID NO: 95;
(af) a polypeptide having at least 80%, such as at least 85%, at least 90% or at least 95% sequence identity to the polypeptide of SEQ ID NO: 98;
(ag) a polypeptide having at least 80%, such as at least 85%, at least 90% or at least 95% sequence identity to the polypeptide of SEQ ID NO: 101;
(ah) a polypeptide having at least 80%, such as at least 85%, at least 90% or at least 95% sequence identity to the polypeptide of SEQ ID NO: 104;
(ai) a polypeptide having at least 80%, such as at least 85%, at least 90% or at least 95% sequence identity to the polypeptide of SEQ ID NO: 107;
(aj) a polypeptide having at least 82%, such as at least 85%, at least 90% or at least 95% sequence identity to the polypeptide of SEQ ID NO: 110;
(ak) a polypeptide having at least 81%, such as at least 85%, at least 90% or at least 95% sequence identity to the polypeptide of SEQ ID NO: 113;
(al) a polypeptide having at least 80%, such as at least 85%, at least 90% or at least 95% sequence identity to the polypeptide of SEQ ID NO: 116;
(am) a polypeptide having at least 80%, such as at least 85%, at least 90% or at least 95% sequence identity to the polypeptide of SEQ ID NO: 119;
(an) a polypeptide having at least 80%, such as at least 85%, at least 90% or at least 95% sequence identity to the polypeptide of SEQ ID NO: 122;
(ao) a polypeptide having at least 80%, such as at least 85%, at least 90% or at least 95% sequence identity to the polypeptide of SEQ ID NO: 125;
(ap) a polypeptide having at least 80%, such as at least 85%, at least 90% or at least 95% sequence identity to the polypeptide of SEQ ID NO: 128;
(aq) a polypeptide having at least 80%, such as at least 85%, at least 90% or at least 95% sequence identity to the polypeptide of SEQ ID NO: 131;
(ar) a polypeptide having at least 80%, such as at least 85%, at least 90% or at least 95% sequence identity to the polypeptide of SEQ ID NO: 134;
(as) a polypeptide having at least 80%, such as at least 85%, at least 90% or at least 95% sequence identity to the polypeptide of SEQ ID NO: 137;
(at) a polypeptide having at least 80%, such as at least 85%, at least 90% or at least 95% sequence identity to the polypeptide of SEQ ID NO: 140;

(au) a polypeptide having at least 80%, such as at least 85%, at least 90% or at least 95% sequence identity to the polypeptide of SEQ ID NO: 143;
(av) a polypeptide having at least 80%, such as at least 85%, at least 90% or at least 95% sequence identity to the polypeptide of SEQ ID NO: 146;
(aw) a polypeptide having at least 80%, such as at least 85%, at least 90% or at least 95% sequence identity to the polypeptide of SEQ ID NO: 149;
(ax) a polypeptide having at least 80%, such as at least 85%, at least 90% or at least 95% sequence identity to the polypeptide of SEQ ID NO: 152;
(ay) a polypeptide having at least 80%, such as at least 85%, at least 90% or at least 95% sequence identity to the polypeptide of SEQ ID NO: 155;
(az) a polypeptide having at least 80%, such as at least 85%, at least 90% or at least 95% sequence identity to the polypeptide of SEQ ID NO: 158;
(ba) a polypeptide having at least 80%, such as at least 85%, at least 90% or at least 95% sequence identity to the polypeptide of SEQ ID NO: 221;
(bb) a polypeptide having at least 80%, such as at least 85%, at least 90% or at least 95% sequence identity to the polypeptide of SEQ ID NO: 224;
(bc) a polypeptide having at least 80%, such as at least 85%, at least 90% or at least 95% sequence identity to the polypeptide of SEQ ID NO: 227;
(bd) a polypeptide having at least 80%, such as at least 85%, at least 90% or at least 95% sequence identity to the polypeptide of SEQ ID NO: 230;
(be) a polypeptide having at least 80%, such as at least 85%, at least 90% or at least 95% sequence identity to the polypeptide of SEQ ID NO: 233;
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27 or 28 positions;
(bg) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal His-tag and/or HQ-tag;
(bh) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal extension of up to 10 amino acids, e.g. 1, 2, 3, 4, 5, 6, 7, 8, 9 or 10 amino acids; and
(bi) a fragment of the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) having lysozyme activity and having at least 90% of the length of the mature polypeptide.

In an embodiment, the one or more GH25 polypeptides comprises the motif YKNA (SEQ ID NO: 160) and/or the motif FGGW[S/1] (SEQ ID NO: 161), and preferably is selected from the group selected from SEQ ID NO: 12, SEQ ID NO: 27, SEQ ID NO: 42, SEQ ID NO: 57, SEQ ID NO: 63, SEQ ID NO: 66, SEQ ID NO: 80, SEQ ID NO: 149, SEQ ID NO:152, SEQ ID NO: 155, SEQ ID NO: 224, SEQ ID NO: 227, SEQ ID NO: 230 and SEQ ID NO: 233.

In an embodiment, the polypeptide comprises or consists of amino acids 1 to 207 of SEQ ID NO: 3, amino acids 1 to 201 of SEQ ID NO: 6, amino acids 1 to 201 of SEQ ID NO: 9, amino acids 1 to 203 of SEQ ID NO: 12, amino acids 1 to 208 of SEQ ID NO: 15, amino acids 1 to 207 of SEQ ID NO: 18, amino acids 1 to 208 of SEQ ID NO: 21, amino acids 1 to 207 of SEQ ID NO: 24, amino acids 1 to 207 of SEQ ID NO: 27, amino acids 1 to 207 of SEQ ID NO: 30, amino acids 1 to 208 of SEQ ID NO: 33, amino acids 1 to 208 of SEQ ID NO: 36, amino acids 1 to 206 of SEQ ID NO: 39, amino acids 1 to 207 of SEQ ID NO: 42, amino acids 1 to 216 of SEQ ID NO: 45, amino acids 1 to 218 of SEQ ID NO: 48, amino acids 1 to 204 of SEQ ID NO: 51, amino acids 1 to 203 of SEQ ID NO: 54, amino acids 1 to 209 of SEQ ID NO: 57, amino acids 1 to 208 of SEQ ID NO: 60, amino acids 1 to 210 of SEQ ID NO: 63, amino acids 1 to 207 of SEQ ID NO: 66, amino acids 1 to 207 of SEQ ID NO: 69, amino acids 1 to 208 of SEQ ID NO: 72, amino acids 1 to 217 of SEQ ID NO: 75, amino acids 1 to 208 of SEQ ID NO: 80, amino acids 1 to 201 of SEQ ID NO: 83, amino acids 1 to 202 of SEQ ID NO: 86, amino acids 1 to 207 of SEQ ID NO: 89, amino acids 1 to 202 of SEQ ID NO: 92, amino acids 1 to 201 of SEQ ID NO: 95, amino acids 1 to 202 of SEQ ID NO: 98, amino acids 1 to 206 of SEQ ID NO: 101, amino acids 1 to 202 of SEQ ID NO: 104, amino acids 1 to 202 of SEQ ID NO: 107, amino acids 1 to 202 of SEQ ID NO: 110, amino acids 1 to 202 of SEQ ID NO: 113, amino acids 1 to 206 of SEQ ID NO: 116, amino acids 1 to 207 of SEQ ID NO: 119, amino acids 1 to 208 of SEQ ID NO: 122, amino acids 1 to 215 of SEQ ID NO: 125, amino acids 1 to 217 of SEQ ID NO: 128, amino acids 1 to 214 of SEQ ID NO: 131, amino acids 1 to 208 of SEQ ID NO: 134, amino acids 1 to 203 of SEQ ID NO: 137, amino acids 1 to 216 of SEQ ID NO: 140, amino acids 1 to 207 of SEQ ID NO: 143, amino acids 1 to 208 of SEQ ID NO: 146, amino acids 1 to 207 of SEQ ID NO: 149, amino acids 1 to 207 of SEQ ID NO: 152, amino acids 1 to 207 of SEQ ID NO: 155, amino acids 1 to 208 of SEQ ID NO: 158, amino acids 1 to 207 of SEQ ID NO: 221, amino acids 1 to 207 of SEQ ID NO: 224, amino acids 1 to 208 of SEQ ID NO: 227, amino acids 1 to 207 of SEQ ID NO: 230 or amino acids 1 to 207 of SEQ ID NO: 233.

In a preferred embodiment, the polypeptide has at least 150%, such as at least 175%, at least 200%, at least 225%, at least 250%, at least 275%, at least 300%, at least 350%, or at least 400% of the lysozyme activity of SEQ ID NO: 159. In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as follows: lysozyme (50 µL of 0.7 µg/mL lysozyme in phosphate buffer (5 mM citrate, 5 mM $K_2HPO_4$, 0.01% TritonX-100, pH 5.0)) is mixed with *Micrococcus lysodeikticus* solution (450 µL of 1% lyophilized *Micrococcus lysodeikticus* ATCC No. 4698 in milli-Q water) and incubated at 40° C. with shaking (500 rpm) for 45 min; the sample is centrifuged (4000 g, 5 min); supernatant (100 µL) is mixed with HCl (50 µL 3.2M) and incubated at 95° C. for 80 min; NaOH (50 µL, 3.5 M) is added and 50 µL of the sample is added to 4-hydroxybenzhydrazide in K-Na tartrate/NaOH buffer (75 µL of 50 g/L K-Na tartrate+20 g/L NaOH); the mixture is incubated at 95° C. for 10 min; and the optical density is measured at 405 nm.

In an embodiment, the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.

In a further embodiment, the animal feed has been pelleted.

Additional Enzymes

In another embodiment, the compositions described herein optionally include one or more enzymes. Enzymes can be classified on the basis of the handbook Enzyme Nomenclature from NC-IUBMB, 1992, see also the ENZYME site at the internet: http://www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch A. The ENZYME database, 2000, Nucleic Acids Res 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, xylanase, galactanase, mannanase, dextranase, lysozyme and galactosidase is described in Henrissat et al, "The carbohydrate-active enzymes database (CAZy) in 2013", *Nucl. Acids Res*. (1 Jan. 2014) 42 (D1): D490-D495; see also www.cazy.org.

Thus the composition of the invention may also comprise at least one other enzyme selected from the group comprising of phytase (EC 3.1.3.8 or 3.1.3.26); xylanase (EC 3.2.1.8); galactanase (EC 3.2.1.89); alpha-galactosidase (EC 3.2.1.22); protease (EC 3.4); phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); arabinofuranosidase (EC 3.2.1.55); beta-xylosidase (EC 3.2.1.37); acetyl xylan esterase (EC 3.1.1.72); feruloyl esterase (EC 3.1.1.73); cellulase (EC 3.2.1.4); cellobiohydrolases (EC 3.2.1.91); beta-glucosidase (EC 3.2.1.21); pullulanase (EC 3.2.1.41), alpha-mannosidase (EC 3.2.1.24), mannanase (EC 3.2.1.25) and beta-glucanase (EC 3.2.1.4 or EC 3.2.1.6), or any mixture thereof.

In a particular embodiment, the composition of the invention comprises a phytase (EC 3.1.3.8 or 3.1.3.26). Examples of commercially available phytases include Bio-Feed™ Phytase (Novozymes), Ronozyme® P, Ronozyme® NP and Ronozyme® HiPhos (DSM Nutritional Products), Natuphos™ (BASF), Natuphos™ E (BASF), Finase® and Quantum® Blue (AB Enzymes), OptiPhos® (Huvepharma), AveMix® Phytase (Aveve Biochem), Phyzyme® XP (Verenium/DuPont) and Axtra® PHY (DuPont). Other preferred phytases include those described in e.g. WO 98/28408, WO 00/43503, and WO 03/066847.

In a particular embodiment, the composition of the invention comprises a xylanase (EC 3.2.1.8). Examples of commercially available xylanases include Ronozyme® \A/X (DSM Nutritional Products), Econase® XT and Barley (AB Vista), Xylathin® (Verenium), Hostazym® X (Huvepharma), Axtra® XB (Xylanase/beta-glucanase, DuPont) and Axtra® XAP (Xylanase/amylase/protease, DuPont), AveMix® XG 10 (xylanase/glucanase) and AveMix® 02 CS (xylanase/glucanase/pectinase, Aveve Biochem), and Naturgrain (BASF).

In a particular embodiment, the composition of the invention comprises a protease (EC 3.4). Examples of commercially available proteases include Ronozyme® ProAct (DSM Nutritional Products).

In a particular embodiment, the composition of the invention comprises an alpha-amylase (EC 3.2.1.1). Examples of commercially available alpha-amylases include Ronozyme® A and RONOZYME® RumiStar™ (DSM Nutritional Products).

In one embodiment, the composition of the invention comprises a multicomponent enzyme product, such as FRA® Octazyme (Framelco), Ronozyme® G2, Ronozyme® VP and Ronozyme® MultiGrain (DSM Nutritional Products), Rovabio® Excel or Rovabio® Advance (Adisseo).

Eubiotics

Eubiotics are compounds which are designed to give a healthy balance of the micro-flora in the gastrointestinal tract. Eubiotics cover a number of different feed additives, such as probiotics, prebiotics, phytogenics (essential oils) and organic acids which are described in more detail below.

Probiotics

In an embodiment, the animal feed composition further comprises one or more additional probiotic. In a particular embodiment, the animal feed composition further comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof.

In a preferred embodiment, animal feed composition further comprises a bacterium from one or more of the following strains: *Bacillus subtilis, Bacillus licheniformis,*

*Bacillus amyloliquefaciens, Bacillus cereus, Bacillus pumilus, Bacillus polymyxa, Bacillus megaterium, Bacillus coagulans, Bacillus circulans, Enterococcus faecium, Enterococcus* spp and *Pediococcus* spp, *Lactobacillus* spp, *Bifidobacterium* spp, *Lactobacillus acidophilus, Pediococsus acidilactici, Lactococcus lactis, Bifidobacterium bifidum, Propionibacterium thoenii, Lactobacillus farciminus, Lactobacillus rhamnosus, Clostridium butyricum, Bifidobacterium animalis* ssp. *animalis, Lactobacillus reuteri, Lactobacillus salivarius* ssp. *salivarius, Megasphaera elsdenii, Propionibacteria* sp.

In a more preferred embodiment, composition, animal feed additive or animal feed further comprises a bacterium from one or more of the following strains of *Bacillus subtilis*: 3A-P4 (PTA-6506), 15A-P4 (PTA-6507), 22C-P1 (PTA-6508), 2084 (NRRL B-500130), LSSA01 (NRRL-B-50104), BS27 (NRRL B-501 05), BS 18 (NRRL B-50633), BS 278 (NRRL B-50634), DSM 29870, DSM 29871, DSM 32315, NRRL B-50136, NRRL B-50605, NRRL B-50606, NRRL B-50622 and PTA-7547.

In a more preferred embodiment, composition, animal feed additive or animal feed further comprises a bacterium from one or more of the following strains of *Bacillus pumilus*: NRRL B-50016, ATCC 700385, NRRL B-50885 or NRRL B-50886.

In a more preferred embodiment, composition, animal feed additive or animal feed further comprises a bacterium from one or more of the following strains of *Bacillus lichenformis*: NRRL B 50015, NRRL B-50621 or NRRL B-50623.

In a more preferred embodiment, composition, animal feed additive or animal feed further comprises a bacterium from one or more of the following strains of *Bacillus amyloliquefaciens*: DSM 29869, DSM 29869, NRRL B 50607, PTA-7543, PTA-7549, NRRL B-50349, NRRL B-50606, NRRL B-50013, NRRL B-50151, NRRL B-50141, NRRL B-50147 or NRRL B-50888.

The bacterial count of each of the bacterial strains in the animal feed composition is between $1\times10^4$ and $1\times10^{14}$ CFU/kg of dry matter, preferably between $1\times10^6$ and $1\times10^{12}$ CFU/kg of dry matter, and more preferably between $1\times10^7$ and $1\times10^{11}$ CFU/kg of dry matter. In a more preferred embodiment the bacterial count of each of the bacterial strains in the animal feed composition is between $1\times10^8$ and $1\times10^{10}$ CFU/kg of dry matter.

The bacterial count of each of the bacterial strains in the animal feed composition is between $1\times10^5$ and $1\times10^{15}$ CFU/animal/day, preferably between $1\times10^7$ and $1\times10^{13}$ CFU/animal/day, and more preferably between $1\times10^8$ and $1\times10^{12}$ CFU/animal/day. In a more preferred embodiment the bacterial count of each of the bacterial strains in the animal feed composition is between $1\times10^9$ and $1\times10^{11}$ CFU/animal/day.

In another embodiment, the one or more bacterial strains are present in the form of a stable spore.

Examples of commercial products are Cylactin® (DSM Nutritional Products), Alterion (Adisseo), Enviva PRO (DuPont Animal Nutrition), Syncra® (mix enzyme+probiotic, DuPont Animal Nutrition), Ecobiol® and Fecinor® (Norel/Evonik) and GutCare® PY1 (Evonik).

Prebiotics

Prebiotics are substances that induce the growth or activity of microorganisms (e.g., bacteria and fungi) that contribute to the well-being of their host. Prebiotics are typically non-digestible fiber compounds that pass undigested through the upper part of the gastrointestinal tract and stimulate the growth or activity of advantageous bacteria that colonize the large bowel by acting as substrate for them. Normally, prebiotics increase the number or activity of bifidobacteria and lactic acid bacteria in the GI tract.

Yeast derivatives (inactivated whole yeasts or yeast cell walls) can also be considered as prebiotics. They often comprise mannan-oligosaccharids, yeast beta-glucans or protein contents and are normally derived from the cell wall of the yeast, *Saccharomyces cerevisiae*.

Examples of yeast products are Yang® and Agrimos (Lallemand Animal Nutrition).

Phytogenics

Phytogenics are a group of natural growth promoters or non-antibiotic growth promoters used as feed additives, derived from herbs, spices or other plants. Phytogenics can be single substances prepared from essential oils/extracts, essential oils/extracts, single plants and mixture of plants (herbal products) or mixture of essential oils/extracts/plants (specialized products).

Examples of phytogenics are rosemary, sage, oregano, thyme, clove, and lemongrass. Examples of essential oils are thymol, eugenol, meta-cresol, vaniline, salicylate, resorcine, guajacol, gingerol, lavender oil, ionones, irone, eucalyptol, menthol, peppermint oil, alpha-pinene; limonene, anethol, linalool, methyl dihydrojasmonate, carvacrol, propionic acid/propionate, acetic acid/acetate, butyric acid/butyrate, rosemary oil, clove oil, geraniol, terpineol, citronellol, amyl and/or benzyl salicylate, cinnamaldehyde, plant polyphenol (tannin), turmeric and curcuma extract.

Examples of commercial products are Crina® (DSM Nutritional Products); Cinergy™ Biacid™, ProHacid™ Classic and ProHacid™ Advance™ (all Promivi/Cargill) and Envivo EO (DuPont Animal Nutrition).

Organic Acids

Organic acids (C1-C7) are widely distributed in nature as normal constituents of plants or animal tissues. They are also formed through microbial fermentation of carbohydrates mainly in the large intestine. They are often used in swine and poultry production as a replacement of antibiotic growth promoters since they have a preventive effect on the intestinal problems like necrotic enteritis in chickens and *Escherichia coli* infection in young pigs. Organic acids can be sold as mono component or mixtures of typically 2 or 3 different organic acids. Examples of organic acids are propionic acid, formic acid, citric acid, lactic acid, sorbic acid, malic acid, acetic acid, fumaric acid, benzoic acid, butyric acid and tartaric acid or their salt (typically sodium or potassium salt such as potassium diformate or sodium butyrate). Examples of commercial products are VevoVitall® (DSM Nutritional Products), Amasil®, Luprisil®, Lupro-Grain®, Lupro-Cid®, Lupro-Mix® (BASF), n-Butyric Acid AF (OXEA) and Adimix Precision (Nutriad).

Premix

The incorporation of the composition of feed additives as exemplified herein above to animal feeds, for example poultry feeds, is in practice carried out using a concentrate or a premix. A premix designates a preferably uniform mixture of one or more microingredients with diluent and/or carrier. Premixes are used to facilitate uniform dispersion of micro-ingredients in a larger mix. A premix according to the invention can be added to feed ingredients or to the drinking water as solids (for example as water soluble powder) or liquids.

Amino Acids

The composition of the invention may further comprise one or more amino acids. Examples of amino acids which are used in animal feed are lysine, alanine, beta-alanine, threonine, methionine and tryptophan.

Vitamins and Minerals

In another embodiment, the animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals.

Usually fat- and water-soluble vitamins, as well as trace minerals form part of a so-called premix intended for addition to the feed, whereas macro minerals are usually separately added to the feed.

Non-limiting examples of fat-soluble vitamins include vitamin A, vitamin D3, vitamin E, and vitamin K, e.g., vitamin K3.

Non-limiting examples of water-soluble vitamins include vitamin C, vitamin B12, biotin and choline, vitamin B1, vitamin B2, vitamin B6, niacin, folic acid and panthothenate, e.g., Ca-D-panthothenate.

Non-limiting examples of trace minerals include boron, cobalt, chloride, chromium, copper, fluoride, iodine, iron, manganese, molybdenum, iodine, selenium and zinc.

Non-limiting examples of macro minerals include calcium, magnesium, phosphorus, potassium and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below Table 1 (for piglet diets, and broiler diets, respectively).

dants, anti-microbial peptides, anti-fungal polypeptides and mycotoxin management compounds.

Examples of colouring agents are carotenoids such as beta-carotene, astaxanthin, and lutein.

Examples of aroma compounds/flavourings are creosol, anethol, deca-, undeca- and/or dodeca-lactones, ionones, irone, gingerol, piperidine, propylidene phatalide, butylidene phatalide, capsaicin and tannin.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

Antioxidants can be used to limit the number of reactive oxygen species which can be generated such that the level of reactive oxygen species is in balance with antioxidants.

Mycotoxins, such as deoxynivalenol, aflatoxin, zearalenone and fumonisin can be found in animal feed and can result in negative animal performance or illness. Compounds which can manage the levels of mycotoxin, such as via deactivation of the mycotoxin or via binding of the mycotoxin, can be added to the feed to ameliorate these negative effects. Examples of mycotoxin management compounds are Vitafix®, Vitafix Ultra (Nuscience), Mycofix®, Mycofix® Secure, FUMzyme®, Biomin® BBSH, Biomin® MTV (Biomin), Mold-Nile, Toxy-Nil® and Unike® Plus (Nutriad).

TABLE 1

Typical vitamin recommendations

| Vitamin | Piglet diet | Broiler diet |
|---|---|---|
| Vitamin A | 10,000-15,000 IU/kg feed | 8-12,500 IU/kg feed |
| Vitamin D3 | 1800-2000 IU/kg feed | 3000-5000 IU/kg feed |
| Vitamin E | 60-100 mg/kg feed | 150-240 mg/kg feed |
| Vitamin K3 | 2-4 mg/kg feed | 2-4 mg/kg feed |
| Vitamin B1 | 2-4 mg/kg feed | 2-3 mg/kg feed |
| Vitamin B2 | 6-10 mg/kg feed | 7-9 mg/kg feed |
| Vitamin B6 | 4-8 mg/kg feed | 3-6 mg/kg feed |
| Vitamin B12 | 0.03-0.05 mg/kg feed | 0.015-0.04 mg/kg feed |
| Niacin (Vitamin B3) | 30-50 mg/kg feed | 50-80 mg/kg feed |
| Pantothenic acid | 20-40 mg/kg feed | 10-18 mg/kg feed |
| Folic acid | 1-2 mg/kg feed | 1-2 mg/kg feed |
| Biotin | 0.15-0.4 mg/kg feed | 0.15-0.3 mg/kg feed |
| Choline chloride | 200-400 mg/kg feed | 300-600 mg/kg feed |

Other Feed Ingredients

The composition of the invention may further comprise colouring agents, stabilisers, growth improving additives and aroma compounds/flavourings, polyunsaturated fatty acids (PUFAs); reactive oxygen generating species, antioxi- Uses
Use in Animal Feed A lysozyme of the invention may also be used in animal feed, wherein the term "animal" refers to all animals except humans. Examples of animals are mono-gastric animals, e.g. pigs or swine (including, but not limited to, piglets, growing pigs, and sows); poultry (including but not limited to poultry, turkey, duck, quail, guinea fowl, goose, pigeon, squab, chicken, broiler, layer, pullet and chick); fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish); and crustaceans (including but not limited to shrimps and prawns).

In the use according to the invention the lysozymes can be fed to the animal before, after, or simultaneously with the diet. The latter is preferred.

In a particular embodiment, the lysozyme, in the form in which it is added to the feed, or when being included in a feed additive, is well-defined. Well-defined means that the lysozyme preparation is at least 50% pure as determined by Size-exclusion chromatography (see Example 12 of WO 01/58275). In other particular embodiments the lysozyme preparation is at least 60, 70, 80, 85, 88, 90, 92, 94, or at least 95% pure as determined by this method.

A well-defined lysozyme preparation is advantageous. For instance, it is much easier to dose correctly to the feed a lysozyme that is essentially free from interfering or contaminating other lysozymes. The term dose correctly refers in particular to the objective of obtaining consistent and constant results, and the capability of optimizing dosage based upon the desired effect.

For the use in animal feed, however, the lysozyme need not be pure; it may e.g. include other enzymes, in which case it could be termed a lysozyme preparation.

The lysozyme preparation can be (a) added directly to the feed, or (b) it can be used in the production of one or more intermediate compositions such as feed additives or premixes that is subsequently added to the feed (or used in a treatment process). The degree of purity described above refers to the purity of the original lysozyme preparation, whether used according to (a) or (b) above.

The lysozyme of the present invention could also be used in the treatment of necrotic enteritis and/or *Clostridium perfringens*.

Methods of Improving Animal Performance

In an embodiment, the present invention also relates to a method of improving the performance of an animal comprising administering to the animal the animal feed or the animal feed additive of the invention.

In a preferred embodiment, the method of improving the performance of an animal comprises administering to the animal the animal feed or the animal feed additive comprising the lysozyme selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233.

In an embodiment, the present invention also relates to the use of the animal feed or an animal feed additive of the invention for improving the performance of an animal. In another embodiment, the invention relates to the use of one or more lysozymes of the invention for improving the performance of an animal.

In one embodiment, 'improving the performance of an animal' means that there is an increase in body weight gain. In another embodiment, 'improving the performance of an animal' means that there is an improved feed conversion ratio. In a further embodiment, 'improving the performance of an animal' means that there is an increased feed efficiency. In a further embodiment, 'improving the performance of an animal' means that there is an increase in body weight gain and/or an improved feed conversion ratio and/or an increased feed efficiency.

In an embodiment, the the animal feed comprises plant based material selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.

Methods of Preparing an Animal Feed

In an embodiment, the present invention provides a method for preparing an animal feed comprising adding one or more lysozymes of the present invention to one or more animal feed ingredients. Animal feed ingredients include, but are not limited to concentrates (as defined herein), forage (as defined herein), enzymes, probiotic, vitamins, minerals and amino acids.

In a preferred embodiment, the method of preparing an animal feed comprises mixing plant based material with the lysozyme selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233.

In an embodiment, the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, *quinoa*, or pea, in a processed form thereof (such as soybean meal, rapeseed meal) or any combination thereof.

EMBODIMENTS

Herein follows a list of embodiments of the invention.
1. A method of hydrolysing peptidoglycan in bacterial cell walls comprising treating bacterial cells with one or more GH25 polypeptides having lysozyme activity, wherein the polypeptide is selected from the group consisting of:
(a) a polypeptide having at least 80% sequence identity to the polypeptide of SEQ ID NO: 3;
(b) a polypeptide having at least 84% sequence identity to the polypeptide of SEQ ID NO: 6;
(c) a polypeptide having at least 80% sequence identity to the polypeptide of SEQ ID NO: 9;
(d) a polypeptide having at least 80% sequence identity to the polypeptide of SEQ ID NO: 12;
(e) a polypeptide having at least 80% sequence identity to the polypeptide of SEQ ID NO: 15;
(f) a polypeptide having at least 80% sequence identity to the polypeptide of SEQ ID NO: 18;
(g) a polypeptide having at least 80% sequence identity to the polypeptide of SEQ ID NO: 21;
(h) a polypeptide having at least 80% sequence identity to the polypeptide of SEQ ID NO: 24;
(i) a polypeptide having at least 80% sequence identity to the polypeptide of SEQ ID NO: 27;
(j) a polypeptide having at least 84% sequence identity to the polypeptide of SEQ ID NO: 30;
(k) a polypeptide having at least 80% sequence identity to the polypeptide of SEQ ID NO: 33;
(l) a polypeptide having at least 80% sequence identity to the polypeptide of SEQ ID NO: 36;
(m) a polypeptide having at least 84% sequence identity to the polypeptide of SEQ ID NO: 39;
(n) a polypeptide having at least 80% sequence identity to the polypeptide of SEQ ID NO: 42;
(o) a polypeptide having at least 80% sequence identity to the polypeptide of SEQ ID NO: 45;
(p) a polypeptide having at least 80% sequence identity to the polypeptide of SEQ ID NO: 48;
(q) a polypeptide having at least 80% sequence identity to the polypeptide of SEQ ID NO: 51;
(r) a polypeptide having at least 80% sequence identity to the polypeptide of SEQ ID NO: 54;
(s) a polypeptide having at least 80% sequence identity to the polypeptide of SEQ ID NO: 57;
(t) a polypeptide having at least 80% sequence identity to the polypeptide of SEQ ID NO: 60;
(u) a polypeptide having at least 80% sequence identity to the polypeptide of SEQ ID NO: 63;
(v) a polypeptide having at least 80% sequence identity to the polypeptide of SEQ ID NO: 66;
(w) a polypeptide having at least 80% sequence identity to the polypeptide of SEQ ID NO: 69;
(x) a polypeptide having at least 84% sequence identity to the polypeptide of SEQ ID NO: 72;
(y) a polypeptide having at least 80% sequence identity to the polypeptide of SEQ ID NO: 75;
(z) a polypeptide having at least 80% sequence identity to the polypeptide of SEQ ID NO: 80;
(aa) a polypeptide having at least 80% sequence identity to the polypeptide of SEQ ID NO: 83;
(ab) a polypeptide having at least 80% sequence identity to the polypeptide of SEQ ID NO: 86;
(ac) a polypeptide having at least 86% sequence identity to the polypeptide of SEQ ID NO: 89;
(ad) a polypeptide having at least 82% sequence identity to the polypeptide of SEQ ID NO: 92;
(ae) a polypeptide having at least 82% sequence identity to the polypeptide of SEQ ID NO: 95;
(af) a polypeptide having at least 80% sequence identity to the polypeptide of SEQ ID NO: 98;
(ag) a polypeptide having at least 80% sequence identity to the polypeptide of SEQ ID NO: 101;
(ah) a polypeptide having at least 80% sequence identity to the polypeptide of SEQ ID NO: 104;
(ai) a polypeptide having at least 80% sequence identity to the polypeptide of SEQ ID NO: 107;
(aj) a polypeptide having at least 82% sequence identity to the polypeptide of SEQ ID NO: 110;
(ak) a polypeptide having at least 81% sequence identity to the polypeptide of SEQ ID NO: 113;
(al) a polypeptide having at least 80% sequence identity to the polypeptide of SEQ ID NO: 116;
(am) a polypeptide having at least 80% sequence identity to the polypeptide of SEQ ID NO: 119;
(an) a polypeptide having at least 80% sequence identity to the polypeptide of SEQ ID NO: 122;
(ao) a polypeptide having at least 80% sequence identity to the polypeptide of SEQ ID NO: 125;
(ap) a polypeptide having at least 80% sequence identity to the polypeptide of SEQ ID NO: 128;
(aq) a polypeptide having at least 80% sequence identity to the polypeptide of SEQ ID NO: 131;
(ar) a polypeptide having at least 80% sequence identity to the polypeptide of SEQ ID NO: 134;
(as) a polypeptide having at least 80% sequence identity to the polypeptide of SEQ ID NO: 137;
(at) a polypeptide having at least 80% sequence identity to the polypeptide of SEQ ID NO: 140;
(au) a polypeptide having at least 80% sequence identity to the polypeptide of SEQ ID NO: 143;
(av) a polypeptide having at least 80% sequence identity to the polypeptide of SEQ ID NO: 146;
(aw) a polypeptide having at least 80% sequence identity to the polypeptide of SEQ ID NO: 149;
(ax) a polypeptide having at least 80% sequence identity to the polypeptide of SEQ ID NO: 152;
(ay) a polypeptide having at least 80% sequence identity to the polypeptide of SEQ ID NO: 155;
(az) a polypeptide having at least 80% sequence identity to the polypeptide of SEQ ID NO: 158;
(ba) a polypeptide having at least 80% sequence identity to the polypeptide of SEQ ID NO: 221;
(bb) a polypeptide having at least 80% sequence identity to the polypeptide of SEQ ID NO: 224;
(bc) a polypeptide having at least 80% sequence identity to the polypeptide of SEQ ID NO: 227;
(bd) a polypeptide having at least 80% sequence identity to the polypeptide of SEQ ID NO: 230;
(be) a polypeptide having at least 80% sequence identity to the polypeptide of SEQ ID NO: 233;
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27 or 28 positions;

(bg) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal His-tag and/or HQ-tag;

(bh) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal extension of up to 10 amino acids, e.g. 1, 2, 3, 4, 5, 6, 7, 8, 9 or 10 amino acids; and (bi) a fragment of the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) having lysozyme activity and having at least 90% of the length of the mature polypeptide.

2. The method of item 1, wherein the polypeptide is selected from the group consisting of: (a) a polypeptide having at least 85% sequence identity to the polypeptide of SEQ ID NO: 3;

(b) a polypeptide having at least 85% sequence identity to the polypeptide of SEQ ID NO: 6;

(c) a polypeptide having at least 85% sequence identity to the polypeptide of SEQ ID NO: 9;

(d) a polypeptide having at least 85% sequence identity to the polypeptide of SEQ ID NO: 12;

(e) a polypeptide having at least 85% sequence identity to the polypeptide of SEQ ID NO: 15;

(f) a polypeptide having at least 85% sequence identity to the polypeptide of SEQ ID NO: 18;

(g) a polypeptide having at least 85% sequence identity to the polypeptide of SEQ ID NO: 21;

(h) a polypeptide having at least 85% sequence identity to the polypeptide of SEQ ID NO: 24;

(i) a polypeptide having at least 85% sequence identity to the polypeptide of SEQ ID NO: 27;

(j) a polypeptide having at least 85% sequence identity to the polypeptide of SEQ ID NO: 30;

(k) a polypeptide having at least 85% sequence identity to the polypeptide of SEQ ID NO: 33;

(l) a polypeptide having at least 85% sequence identity to the polypeptide of SEQ ID NO: 36;

(m) a polypeptide having at least 85% sequence identity to the polypeptide of SEQ ID NO: 39;

(n) a polypeptide having at least 85% sequence identity to the polypeptide of SEQ ID NO: 42;

(o) a polypeptide having at least 85% sequence identity to the polypeptide of SEQ ID NO: 45;

(p) a polypeptide having at least 85% sequence identity to the polypeptide of SEQ ID NO: 48;

(q) a polypeptide having at least 85% sequence identity to the polypeptide of SEQ ID NO: 51;

(r) a polypeptide having at least 85% sequence identity to the polypeptide of SEQ ID NO: 54;

(s) a polypeptide having at least 85% sequence identity to the polypeptide of SEQ ID NO: 57;

(t) a polypeptide having at least 85% sequence identity to the polypeptide of SEQ ID NO: 60;

(u) a polypeptide having at least 85% sequence identity to the polypeptide of SEQ ID NO: 63;

(v) a polypeptide having at least 85% sequence identity to the polypeptide of SEQ ID NO: 66;

(w) a polypeptide having at least 85% sequence identity to the polypeptide of SEQ ID NO: 69;

(x) a polypeptide having at least 85% sequence identity to the polypeptide of SEQ ID NO: 72;

(y) a polypeptide having at least 85% sequence identity to the polypeptide of SEQ ID NO: 75;

(z) a polypeptide having at least 85% sequence identity to the polypeptide of SEQ ID NO: 80;

(aa) a polypeptide having at least 85% sequence identity to the polypeptide of SEQ ID NO: 83;

(ab) a polypeptide having at least 85% sequence identity to the polypeptide of SEQ ID NO: 86;

(ac) a polypeptide having at least 86% sequence identity to the polypeptide of SEQ ID NO: 89;

(ad) a polypeptide having at least 85% sequence identity to the polypeptide of SEQ ID NO: 92;

(ae) a polypeptide having at least 85% sequence identity to the polypeptide of SEQ ID NO: 95;

(af) a polypeptide having at least 85% sequence identity to the polypeptide of SEQ ID NO: 98;

(ag) a polypeptide having at least 85% sequence identity to the polypeptide of SEQ ID NO: 101;

(ah) a polypeptide having at least 85% sequence identity to the polypeptide of SEQ ID NO: 104;

(ai) a polypeptide having at least 85% sequence identity to the polypeptide of SEQ ID NO: 107;

(aj) a polypeptide having at least 85% sequence identity to the polypeptide of SEQ ID NO: 110;

(ak) a polypeptide having at least 85% sequence identity to the polypeptide of SEQ ID NO: 113;

(al) a polypeptide having at least 85% sequence identity to the polypeptide of SEQ ID NO: 116;

(am) a polypeptide having at least 85% sequence identity to the polypeptide of SEQ ID NO: 119;

(an) a polypeptide having at least 85% sequence identity to the polypeptide of SEQ ID NO: 122;

(ao) a polypeptide having at least 85% sequence identity to the polypeptide of SEQ ID NO: 125;

(ap) a polypeptide having at least 85% sequence identity to the polypeptide of SEQ ID NO: 128;

(aq) a polypeptide having at least 85% sequence identity to the polypeptide of SEQ ID NO: 131;

(ar) a polypeptide having at least 85% sequence identity to the polypeptide of SEQ ID NO: 134;

(as) a polypeptide having at least 85% sequence identity to the polypeptide of SEQ ID NO: 137;
(at) a polypeptide having at least 85% sequence identity to the polypeptide of SEQ ID NO: 140;
(au) a polypeptide having at least 85% sequence identity to the polypeptide of SEQ ID NO: 143;
(av) a polypeptide having at least 85% sequence identity to the polypeptide of SEQ ID NO: 146;
(aw) a polypeptide having at least 85% sequence identity to the polypeptide of SEQ ID NO: 149;
(ax) a polypeptide having at least 85% sequence identity to the polypeptide of SEQ ID NO: 152;
(ay) a polypeptide having at least 85% sequence identity to the polypeptide of SEQ ID NO: 155;
(az) a polypeptide having at least 85% sequence identity to the polypeptide of SEQ ID NO: 158;
(ba) a polypeptide having at least 85% sequence identity to the polypeptide of SEQ ID NO: 221;
(bb) a polypeptide having at least 85% sequence identity to the polypeptide of SEQ ID NO: 224;
(bc) a polypeptide having at least 85% sequence identity to the polypeptide of SEQ ID NO: 227;
(bd) a polypeptide having at least 85% sequence identity to the polypeptide of SEQ ID NO: 230; and
(be) a polypeptide having at least 85% sequence identity to the polypeptide of SEQ ID NO: 233.

3. The method of item 1, wherein the polypeptide is selected from the group consisting of:
(a) a polypeptide having at least 90% sequence identity to the polypeptide of SEQ ID NO: 3;
(b) a polypeptide having at least 90% sequence identity to the polypeptide of SEQ ID NO: 6;
(c) a polypeptide having at least 90% sequence identity to the polypeptide of SEQ ID NO: 9;
(d) a polypeptide having at least 90% sequence identity to the polypeptide of SEQ ID NO: 12;
(e) a polypeptide having at least 90% sequence identity to the polypeptide of SEQ ID NO: 15;
(f) a polypeptide having at least 90% sequence identity to the polypeptide of SEQ ID NO: 18;
(g) a polypeptide having at least 90% sequence identity to the polypeptide of SEQ ID NO: 21;
(h) a polypeptide having at least 90% sequence identity to the polypeptide of SEQ ID NO: 24;
(i) a polypeptide having at least 90% sequence identity to the polypeptide of SEQ ID NO: 27;
(j) a polypeptide having at least 90% sequence identity to the polypeptide of SEQ ID NO: 30;
(k) a polypeptide having at least 90% sequence identity to the polypeptide of SEQ ID NO: 33;
(l) a polypeptide having at least 90% sequence identity to the polypeptide of SEQ ID NO: 36;
(m) a polypeptide having at least 90% sequence identity to the polypeptide of SEQ ID NO: 39;
(n) a polypeptide having at least 90% sequence identity to the polypeptide of SEQ ID NO: 42;
(o) a polypeptide having at least 90% sequence identity to the polypeptide of SEQ ID NO: 45;
(p) a polypeptide having at least 90% sequence identity to the polypeptide of SEQ ID NO: 48;
(q) a polypeptide having at least 90% sequence identity to the polypeptide of SEQ ID NO: 51;
(r) a polypeptide having at least 90% sequence identity to the polypeptide of SEQ ID NO: 54;
(s) a polypeptide having at least 90% sequence identity to the polypeptide of SEQ ID NO: 57;
(t) a polypeptide having at least 90% sequence identity to the polypeptide of SEQ ID NO: 60;
(u) a polypeptide having at least 90% sequence identity to the polypeptide of SEQ ID NO: 63;
(v) a polypeptide having at least 90% sequence identity to the polypeptide of SEQ ID NO: 66;
(w) a polypeptide having at least 90% sequence identity to the polypeptide of SEQ ID NO: 69;
(x) a polypeptide having at least 90% sequence identity to the polypeptide of SEQ ID NO: 72;
(y) a polypeptide having at least 90% sequence identity to the polypeptide of SEQ ID NO: 75;
(z) a polypeptide having at least 90% sequence identity to the polypeptide of SEQ ID NO: 80;
(aa) a polypeptide having at least 90% sequence identity to the polypeptide of SEQ ID NO: 83;
(ab) a polypeptide having at least 90% sequence identity to the polypeptide of SEQ ID NO: 86;
(ac) a polypeptide having at least 90% sequence identity to the polypeptide of SEQ ID NO: 89;
(ad) a polypeptide having at least 90% sequence identity to the polypeptide of SEQ ID NO: 92;
(ae) a polypeptide having at least 90% sequence identity to the polypeptide of SEQ ID NO: 95;
(af) a polypeptide having at least 90% sequence identity to the polypeptide of SEQ ID NO: 98;
(ag) a polypeptide having at least 90% sequence identity to the polypeptide of SEQ ID NO: 101;
(ah) a polypeptide having at least 90% sequence identity to the polypeptide of SEQ ID NO: 104;
(ai) a polypeptide having at least 90% sequence identity to the polypeptide of SEQ ID NO: 107;
(aj) a polypeptide having at least 90% sequence identity to the polypeptide of SEQ ID NO: 110;
(ak) a polypeptide having at least 90% sequence identity to the polypeptide of SEQ ID NO: 113;
(al) a polypeptide having at least 90% sequence identity to the polypeptide of SEQ ID NO: 116;
(am) a polypeptide having at least 90% sequence identity to the polypeptide of SEQ ID NO: 119;
(an) a polypeptide having at least 90% sequence identity to the polypeptide of SEQ ID NO: 122;
(ao) a polypeptide having at least 90% sequence identity to the polypeptide of SEQ ID NO: 125;
(ap) a polypeptide having at least 90% sequence identity to the polypeptide of SEQ ID NO: 128;
(aq) a polypeptide having at least 90% sequence identity to the polypeptide of SEQ ID NO: 131;
(ar) a polypeptide having at least 90% sequence identity to the polypeptide of SEQ ID NO: 134;
(as) a polypeptide having at least 90% sequence identity to the polypeptide of SEQ ID NO: 137;
(at) a polypeptide having at least 90% sequence identity to the polypeptide of SEQ ID NO: 140;
(au) a polypeptide having at least 90% sequence identity to the polypeptide of SEQ ID NO: 143;
(av) a polypeptide having at least 90% sequence identity to the polypeptide of SEQ ID NO: 146;
(aw) a polypeptide having at least 90% sequence identity to the polypeptide of SEQ ID NO: 149;
(ax) a polypeptide having at least 90% sequence identity to the polypeptide of SEQ ID NO: 152;
(ay) a polypeptide having at least 90% sequence identity to the polypeptide of SEQ ID NO: 155;
(az) a polypeptide having at least 90% sequence identity to the polypeptide of SEQ ID NO: 158;

(ba) a polypeptide having at least 90% sequence identity to the polypeptide of SEQ ID NO: 221;
(bb) a polypeptide having at least 90% sequence identity to the polypeptide of SEQ ID NO: 224;
(bc) a polypeptide having at least 90% sequence identity to the polypeptide of SEQ ID NO: 227;
(bd) a polypeptide having at least 90% sequence identity to the polypeptide of SEQ ID NO: 230;
(be) a polypeptide having at least 90% sequence identity to the polypeptide of SEQ ID NO: 233; and
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions.

4. The method of item 1, wherein the polypeptide is selected from the group consisting of:
(a) a polypeptide having at least 95% sequence identity to the polypeptide of SEQ ID NO: 3;
(b) a polypeptide having at least 95% sequence identity to the polypeptide of SEQ ID NO: 6;
(c) a polypeptide having at least 95% sequence identity to the polypeptide of SEQ ID NO: 9;
(d) a polypeptide having at least 95% sequence identity to the polypeptide of SEQ ID NO: 12;
(e) a polypeptide having at least 95% sequence identity to the polypeptide of SEQ ID NO: 15;
(f) a polypeptide having at least 95% sequence identity to the polypeptide of SEQ ID NO: 18;
(g) a polypeptide having at least 95% sequence identity to the polypeptide of SEQ ID NO: 21;
(h) a polypeptide having at least 95% sequence identity to the polypeptide of SEQ ID NO: 24;
(i) a polypeptide having at least 95% sequence identity to the polypeptide of SEQ ID NO: 27;
(j) a polypeptide having at least 95% sequence identity to the polypeptide of SEQ ID NO: 30;
(k) a polypeptide having at least 95% sequence identity to the polypeptide of SEQ ID NO: 33;
(l) a polypeptide having at least 95% sequence identity to the polypeptide of SEQ ID NO: 36;
(m) a polypeptide having at least 95% sequence identity to the polypeptide of SEQ ID NO: 39;
(n) a polypeptide having at least 95% sequence identity to the polypeptide of SEQ ID NO: 42;
(o) a polypeptide having at least 95% sequence identity to the polypeptide of SEQ ID NO: 45;
(p) a polypeptide having at least 95% sequence identity to the polypeptide of SEQ ID NO: 48;
(q) a polypeptide having at least 95% sequence identity to the polypeptide of SEQ ID NO: 51;
(r) a polypeptide having at least 95% sequence identity to the polypeptide of SEQ ID NO: 54;
(s) a polypeptide having at least 95% sequence identity to the polypeptide of SEQ ID NO: 57;
(t) a polypeptide having at least 95% sequence identity to the polypeptide of SEQ ID NO: 60;
(u) a polypeptide having at least 95% sequence identity to the polypeptide of SEQ ID NO: 63;
(v) a polypeptide having at least 95% sequence identity to the polypeptide of SEQ ID NO: 66;
(w) a polypeptide having at least 95% sequence identity to the polypeptide of SEQ ID NO: 69;
(x) a polypeptide having at least 95% sequence identity to the polypeptide of SEQ ID NO: 72;
(y) a polypeptide having at least 95% sequence identity to the polypeptide of SEQ ID NO: 75;
(z) a polypeptide having at least 95% sequence identity to the polypeptide of SEQ ID NO: 80;
(aa) a polypeptide having at least 95% sequence identity to the polypeptide of SEQ ID NO: 83;
(ab) a polypeptide having at least 95% sequence identity to the polypeptide of SEQ ID NO: 86;
(ac) a polypeptide having at least 95% sequence identity to the polypeptide of SEQ ID NO: 89;
(ad) a polypeptide having at least 95% sequence identity to the polypeptide of SEQ ID NO: 92;
(ae) a polypeptide having at least 95% sequence identity to the polypeptide of SEQ ID NO: 95;
(af) a polypeptide having at least 95% sequence identity to the polypeptide of SEQ ID NO: 98;
(ag) a polypeptide having at least 95% sequence identity to the polypeptide of SEQ ID NO: 101;
(ah) a polypeptide having at least 95% sequence identity to the polypeptide of SEQ ID NO: 104;
(ai) a polypeptide having at least 95% sequence identity to the polypeptide of SEQ ID NO: 107;
(aj) a polypeptide having at least 95% sequence identity to the polypeptide of SEQ ID NO: 110;
(ak) a polypeptide having at least 95% sequence identity to the polypeptide of SEQ ID NO: 113;
(al) a polypeptide having at least 95% sequence identity to the polypeptide of SEQ ID NO: 116;
(am) a polypeptide having at least 95% sequence identity to the polypeptide of SEQ ID NO: 119;
(an) a polypeptide having at least 95% sequence identity to the polypeptide of SEQ ID NO: 122;
(ao) a polypeptide having at least 95% sequence identity to the polypeptide of SEQ ID NO: 125;
(ap) a polypeptide having at least 95% sequence identity to the polypeptide of SEQ ID NO: 128;
(aq) a polypeptide having at least 95% sequence identity to the polypeptide of SEQ ID NO: 131;
(ar) a polypeptide having at least 95% sequence identity to the polypeptide of SEQ ID NO: 134;
(as) a polypeptide having at least 95% sequence identity to the polypeptide of SEQ ID NO: 137;
(at) a polypeptide having at least 95% sequence identity to the polypeptide of SEQ ID NO: 140;
(au) a polypeptide having at least 95% sequence identity to the polypeptide of SEQ ID NO: 143;

(av) a polypeptide having at least 95% sequence identity to the polypeptide of SEQ ID NO: 146;
(aw) a polypeptide having at least 95% sequence identity to the polypeptide of SEQ ID NO: 149;
(ax) a polypeptide having at least 95% sequence identity to the polypeptide of SEQ ID NO: 152;
(ay) a polypeptide having at least 95% sequence identity to the polypeptide of SEQ ID NO: 155;
(az) a polypeptide having at least 95% sequence identity to the polypeptide of SEQ ID NO: 158;
(ba) a polypeptide having at least 95% sequence identity to the polypeptide of SEQ ID NO: 221;
(bb) a polypeptide having at least 95% sequence identity to the polypeptide of SEQ ID NO: 224;
(bc) a polypeptide having at least 95% sequence identity to the polypeptide of SEQ ID NO: 227;
(bd) a polypeptide having at least 95% sequence identity to the polypeptide of SEQ ID NO: 230;
(be) a polypeptide having at least 95% sequence identity to the polypeptide of SEQ ID NO: 233; and
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9 or 10 positions.

5. The method of item 1, wherein the polypeptide comprises or consists of amino acids 1 to 207 of SEQ ID NO: 3, amino acids 1 to 201 of SEQ ID NO: 6, amino acids 1 to 201 of SEQ ID NO: 9, amino acids 1 to 203 of SEQ ID NO: 12, amino acids 1 to 208 of SEQ ID NO: 15, amino acids 1 to 207 of SEQ ID NO: 18, amino acids 1 to 208 of SEQ ID NO: 21, amino acids 1 to 207 of SEQ ID NO: 24, amino acids 1 to 207 of SEQ ID NO: 27, amino acids 1 to 207 of SEQ ID NO: 30, amino acids 1 to 208 of SEQ ID NO: 33, amino acids 1 to 208 of SEQ ID NO: 36, amino acids 1 to 206 of SEQ ID NO: 39, amino acids 1 to 207 of SEQ ID NO: 42, amino acids 1 to 216 of SEQ ID NO: 45, amino acids 1 to 218 of SEQ ID NO: 48, amino acids 1 to 204 of SEQ ID NO: 51, amino acids 1 to 203 of SEQ ID NO: 54, amino acids 1 to 209 of SEQ ID NO: 57, amino acids 1 to 208 of SEQ ID NO: 60, amino acids 1 to 210 of SEQ ID NO: 63, amino acids 1 to 207 of SEQ ID NO: 66, amino acids 1 to 207 of SEQ ID NO: 69, amino acids 1 to 208 of SEQ ID NO: 72, amino acids 1 to 217 of SEQ ID NO: 75, amino acids 1 to 208 of SEQ ID NO: 80, amino acids 1 to 201 of SEQ ID NO: 83, amino acids 1 to 202 of SEQ ID NO: 86, amino acids 1 to 207 of SEQ ID NO: 89, amino acids 1 to 202 of SEQ ID NO: 92, amino acids 1 to 201 of SEQ ID NO: 95, amino acids 1 to 202 of SEQ ID NO: 98, amino acids 1 to 206 of SEQ ID NO: 101, amino acids 1 to 202 of SEQ ID NO: 104, amino acids 1 to 202 of SEQ ID NO: 107, amino acids 1 to 202 of SEQ ID NO: 110, amino acids 1 to 202 of SEQ ID NO: 113, amino acids 1 to 206 of SEQ ID NO: 116, amino acids 1 to 207 of SEQ ID NO: 119, amino acids 1 to 208 of SEQ ID NO: 122, amino acids 1 to 215 of SEQ ID NO: 125, amino acids 1 to 217 of SEQ ID NO: 128, amino acids 1 to 214 of SEQ ID NO: 131, amino acids 1 to 208 of SEQ ID NO: 134, amino acids 1 to 203 of SEQ ID NO: 137, amino acids 1 to 216 of SEQ ID NO: 140, amino acids 1 to 207 of SEQ ID NO: 143, amino acids 1 to 208 of SEQ ID NO: 146, amino acids 1 to 207 of SEQ ID NO: 149, amino acids 1 to 207 of SEQ ID NO: 152, amino acids 1 to 207 of SEQ ID NO: 155, amino acids 1 to 208 of SEQ ID NO: 158, amino acids 1 to 207 of SEQ ID NO: 221, amino acids 1 to 207 of SEQ ID NO: 224, amino acids 1 to 208 of SEQ ID NO: 227, amino acids 1 to 207 of SEQ ID NO: 230 or amino acids 1 to 207 of SEQ ID NO: 233.

6. The method of any of items 1 to 5, wherein the polypeptide has at least 150%, at least 175%, at least 200%, at least 225%, at least 250%, at least 275%, at least 300%, at least 350%, or at least 400% of the lysozyme activity of SEQ ID NO: 159.

7 The method of item 6, wherein the polypeptide has at least 150%, at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

8. The method of item 6, wherein the polypeptide has at least 150%, at least 175%, at least 200%, at least 225%, at least 250%, at least 275%, at least 300%, at least 350%, or at least 400% of the lysozyme activity of SEQ ID NO: 159 wherein lysozyme activity is determined as follows: lysozyme (50 μL of 0.7 μg/mL lysozyme in phosphate buffer (5 mM citrate, 5 mM $K_2HPO_4$, 0.01% TritonX-100, pH 5.0)) is mixed with *Micrococcus lysodeikticus* solution (450 μL of 1% lyophilized *Micrococcus lysodeikticus* ATCC No. 4698 in milli-Q water) and incubated at 40° C. with shaking (500 rpm) for 45 min; the sample is centrifuged (4000 g, 5 min); supernatant (100 μL) is mixed with HCl (50 μL 3.2M) and incubated at 95° C. for 80 min; NaOH (50 μL, 3.5 M) is added and 150 μL of the sample is added to 4-hydroxybenzhydrazide in K-Na tartrate/NaOH buffer (75 μL of 50 g/L K-Na tartrate+20 g/L NaOH); the mixture is incubated at 95° C. for 10 min; and the optical density is measured at 405 nm.

9. A granule comprising one or more GH25 polypeptides having lysozyme activity, wherein the polypeptide is selected from the group consisting of:
(a) a polypeptide having at least 80% sequence identity to the polypeptide of SEQ ID NO: 3;
(b) a polypeptide having at least 84% sequence identity to the polypeptide of SEQ ID NO: 6;
(c) a polypeptide having at least 80% sequence identity to the polypeptide of SEQ ID NO: 9;
(d) a polypeptide having at least 80% sequence identity to the polypeptide of SEQ ID NO: 12;
(e) a polypeptide having at least 80% sequence identity to the polypeptide of SEQ ID NO: 15;

(f) a polypeptide having at least 80% sequence identity to the polypeptide of SEQ ID NO: 18;
(g) a polypeptide having at least 80% sequence identity to the polypeptide of SEQ ID NO: 21;
(h) a polypeptide having at least 80% sequence identity to the polypeptide of SEQ ID NO: 24;
(i) a polypeptide having at least 80% sequence identity to the polypeptide of SEQ ID NO: 27;
(j) a polypeptide having at least 84% sequence identity to the polypeptide of SEQ ID NO: 30;
(k) a polypeptide having at least 80% sequence identity to the polypeptide of SEQ ID NO: 33;
(l) a polypeptide having at least 80% sequence identity to the polypeptide of SEQ ID NO: 36;
(m) a polypeptide having at least 84% sequence identity to the polypeptide of SEQ ID NO: 39;
(n) a polypeptide having at least 80% sequence identity to the polypeptide of SEQ ID NO: 42;
(o) a polypeptide having at least 80% sequence identity to the polypeptide of SEQ ID NO: 45;
(p) a polypeptide having at least 80% sequence identity to the polypeptide of SEQ ID NO: 48;
(q) a polypeptide having at least 80% sequence identity to the polypeptide of SEQ ID NO: 51;
(r) a polypeptide having at least 80% sequence identity to the polypeptide of SEQ ID NO: 54;
(s) a polypeptide having at least 80% sequence identity to the polypeptide of SEQ ID NO: 57;
(t) a polypeptide having at least 80% sequence identity to the polypeptide of SEQ ID NO: 60;
(u) a polypeptide having at least 80% sequence identity to the polypeptide of SEQ ID NO: 63;
(v) a polypeptide having at least 80% sequence identity to the polypeptide of SEQ ID NO: 66;
(w) a polypeptide having at least 80% sequence identity to the polypeptide of SEQ ID NO: 69;
(x) a polypeptide having at least 84% sequence identity to the polypeptide of SEQ ID NO: 72;
(y) a polypeptide having at least 80% sequence identity to the polypeptide of SEQ ID NO: 75;
(z) a polypeptide having at least 80% sequence identity to the polypeptide of SEQ ID NO: 80;
(aa) a polypeptide having at least 80% sequence identity to the polypeptide of SEQ ID NO: 83;
(ab) a polypeptide having at least 80% sequence identity to the polypeptide of SEQ ID NO: 86;
(ac) a polypeptide having at least 86% sequence identity to the polypeptide of SEQ ID NO: 89;
(ad) a polypeptide having at least 82% sequence identity to the polypeptide of SEQ ID NO: 92;
(ae) a polypeptide having at least 82% sequence identity to the polypeptide of SEQ ID NO: 95;
(af) a polypeptide having at least 80% sequence identity to the polypeptide of SEQ ID NO: 98;
(ag) a polypeptide having at least 80% sequence identity to the polypeptide of SEQ ID NO: 101;
(ah) a polypeptide having at least 80% sequence identity to the polypeptide of SEQ ID NO: 104;
(ai) a polypeptide having at least 80% sequence identity to the polypeptide of SEQ ID NO: 107;
(aj) a polypeptide having at least 82% sequence identity to the polypeptide of SEQ ID NO: 110;
(ak) a polypeptide having at least 81% sequence identity to the polypeptide of SEQ ID NO: 113;
(al) a polypeptide having at least 80% sequence identity to the polypeptide of SEQ ID NO: 116;
(am) a polypeptide having at least 80% sequence identity to the polypeptide of SEQ ID NO: 119;
(an) a polypeptide having at least 80% sequence identity to the polypeptide of SEQ ID NO: 122;
(ao) a polypeptide having at least 80% sequence identity to the polypeptide of SEQ ID NO: 125;
(ap) a polypeptide having at least 80% sequence identity to the polypeptide of SEQ ID NO: 128;
(aq) a polypeptide having at least 80% sequence identity to the polypeptide of SEQ ID NO: 131;
(ar) a polypeptide having at least 80% sequence identity to the polypeptide of SEQ ID NO: 134;
(as) a polypeptide having at least 80% sequence identity to the polypeptide of SEQ ID NO: 137;
(at) a polypeptide having at least 80% sequence identity to the polypeptide of SEQ ID NO: 140;
(au) a polypeptide having at least 80% sequence identity to the polypeptide of SEQ ID NO: 143;
(av) a polypeptide having at least 80% sequence identity to the polypeptide of SEQ ID NO: 146;
(aw) a polypeptide having at least 80% sequence identity to the polypeptide of SEQ ID NO: 149;
(ax) a polypeptide having at least 80% sequence identity to the polypeptide of SEQ ID NO: 152;
(ay) a polypeptide having at least 80% sequence identity to the polypeptide of SEQ ID NO: 155;
(az) a polypeptide having at least 80% sequence identity to the polypeptide of SEQ ID NO: 158;
(ba) a polypeptide having at least 80% sequence identity to the polypeptide of SEQ ID NO: 221;
(bb) a polypeptide having at least 80% sequence identity to the polypeptide of SEQ ID NO: 224;
(bc) a polypeptide having at least 80% sequence identity to the polypeptide of SEQ ID NO: 227;
(bd) a polypeptide having at least 80% sequence identity to the polypeptide of SEQ ID NO: 230;
(be) a polypeptide having at least 80% sequence identity to the polypeptide of SEQ ID NO: 233;
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27 or 28 positions;
(bg) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal His-tag and/or HQ-tag;

(bh) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal extension of up to 10 amino acids, e.g. 1, 2, 3, 4, 5, 6, 7, 8, 9 or 10 amino acids; and (bi) a fragment of the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) having lysozyme activity and having at least 90% of the length of the mature polypeptide.

10. The granule of item 9, wherein the polypeptide is selected from the group consisting of:
(a) a polypeptide having at least 85% sequence identity to the polypeptide of SEQ ID NO: 3;
(b) a polypeptide having at least 85% sequence identity to the polypeptide of SEQ ID NO: 6;
(c) a polypeptide having at least 85% sequence identity to the polypeptide of SEQ ID NO: 9;
(d) a polypeptide having at least 85% sequence identity to the polypeptide of SEQ ID NO: 12;
(e) a polypeptide having at least 85% sequence identity to the polypeptide of SEQ ID NO: 15;
(f) a polypeptide having at least 85% sequence identity to the polypeptide of SEQ ID NO: 18;
(g) a polypeptide having at least 85% sequence identity to the polypeptide of SEQ ID NO: 21;
(h) a polypeptide having at least 85% sequence identity to the polypeptide of SEQ ID NO: 24;
(i) a polypeptide having at least 85% sequence identity to the polypeptide of SEQ ID NO: 27;
(j) a polypeptide having at least 85% sequence identity to the polypeptide of SEQ ID NO: 30;
(k) a polypeptide having at least 85% sequence identity to the polypeptide of SEQ ID NO: 33;
(l) a polypeptide having at least 85% sequence identity to the polypeptide of SEQ ID NO: 36;
(m) a polypeptide having at least 85% sequence identity to the polypeptide of SEQ ID NO: 39;
(n) a polypeptide having at least 85% sequence identity to the polypeptide of SEQ ID NO: 42;
(o) a polypeptide having at least 85% sequence identity to the polypeptide of SEQ ID NO: 45;
(p) a polypeptide having at least 85% sequence identity to the polypeptide of SEQ ID NO: 48;
(q) a polypeptide having at least 85% sequence identity to the polypeptide of SEQ ID NO: 51;
(r) a polypeptide having at least 85% sequence identity to the polypeptide of SEQ ID NO: 54;
(s) a polypeptide having at least 85% sequence identity to the polypeptide of SEQ ID NO: 57;
(t) a polypeptide having at least 85% sequence identity to the polypeptide of SEQ ID NO: 60;
(u) a polypeptide having at least 85% sequence identity to the polypeptide of SEQ ID NO: 63;
(v) a polypeptide having at least 85% sequence identity to the polypeptide of SEQ ID NO: 66;
(w) a polypeptide having at least 85% sequence identity to the polypeptide of SEQ ID NO: 69;
(x) a polypeptide having at least 85% sequence identity to the polypeptide of SEQ ID NO: 72;
(y) a polypeptide having at least 85% sequence identity to the polypeptide of SEQ ID NO: 75;
(z) a polypeptide having at least 85% sequence identity to the polypeptide of SEQ ID NO: 80;
(aa) a polypeptide having at least 85% sequence identity to the polypeptide of SEQ ID NO: 83;
(ab) a polypeptide having at least 85% sequence identity to the polypeptide of SEQ ID NO: 86;
(ac) a polypeptide having at least 86% sequence identity to the polypeptide of SEQ ID NO: 89;
(ad) a polypeptide having at least 85% sequence identity to the polypeptide of SEQ ID NO: 92;
(ae) a polypeptide having at least 85% sequence identity to the polypeptide of SEQ ID NO: 95;
(af) a polypeptide having at least 85% sequence identity to the polypeptide of SEQ ID NO: 98;
(ag) a polypeptide having at least 85% sequence identity to the polypeptide of SEQ ID NO: 101;
(ah) a polypeptide having at least 85% sequence identity to the polypeptide of SEQ ID NO: 104;
(ai) a polypeptide having at least 85% sequence identity to the polypeptide of SEQ ID NO: 107;
(aj) a polypeptide having at least 85% sequence identity to the polypeptide of SEQ ID NO: 110;
(ak) a polypeptide having at least 85% sequence identity to the polypeptide of SEQ ID NO: 113;
(al) a polypeptide having at least 85% sequence identity to the polypeptide of SEQ ID NO: 116;
(am) a polypeptide having at least 85% sequence identity to the polypeptide of SEQ ID NO: 119;
(an) a polypeptide having at least 85% sequence identity to the polypeptide of SEQ ID NO: 122;
(ao) a polypeptide having at least 85% sequence identity to the polypeptide of SEQ ID NO: 125;
(ap) a polypeptide having at least 85% sequence identity to the polypeptide of SEQ ID NO: 128;
(aq) a polypeptide having at least 85% sequence identity to the polypeptide of SEQ ID NO: 131;
(ar) a polypeptide having at least 85% sequence identity to the polypeptide of SEQ ID NO: 134;
(as) a polypeptide having at least 85% sequence identity to the polypeptide of SEQ ID NO: 137;
(at) a polypeptide having at least 85% sequence identity to the polypeptide of SEQ ID NO: 140;
(au) a polypeptide having at least 85% sequence identity to the polypeptide of SEQ ID NO: 143;
(av) a polypeptide having at least 85% sequence identity to the polypeptide of SEQ ID NO: 146;
(aw) a polypeptide having at least 85% sequence identity to the polypeptide of SEQ ID NO: 149;
(ax) a polypeptide having at least 85% sequence identity to the polypeptide of SEQ ID NO: 152;
(ay) a polypeptide having at least 85% sequence identity to the polypeptide of SEQ ID NO: 155;
(az) a polypeptide having at least 85% sequence identity to the polypeptide of SEQ ID NO: 158;
(ba) a polypeptide having at least 85% sequence identity to the polypeptide of SEQ ID NO: 221;
(bb) a polypeptide having at least 85% sequence identity to the polypeptide of SEQ ID NO: 224;

(bc) a polypeptide having at least 85% sequence identity to the polypeptide of SEQ ID NO: 227;
(bd) a polypeptide having at least 85% sequence identity to the polypeptide of SEQ ID NO: 230; and
(be) a polypeptide having at least 85% sequence identity to the polypeptide of SEQ ID NO: 233.

11. The granule of item 9, wherein the polypeptide is selected from the group consisting of:
(a) a polypeptide having at least 90% sequence identity to the polypeptide of SEQ ID NO: 3;
(b) a polypeptide having at least 90% sequence identity to the polypeptide of SEQ ID NO: 6;
(c) a polypeptide having at least 90% sequence identity to the polypeptide of SEQ ID NO: 9;
(d) a polypeptide having at least 90% sequence identity to the polypeptide of SEQ ID NO: 12;
(e) a polypeptide having at least 90% sequence identity to the polypeptide of SEQ ID NO: 15;
(f) a polypeptide having at least 90% sequence identity to the polypeptide of SEQ ID NO: 18;
(g) a polypeptide having at least 90% sequence identity to the polypeptide of SEQ ID NO: 21;
(h) a polypeptide having at least 90% sequence identity to the polypeptide of SEQ ID NO: 24;
(i) a polypeptide having at least 90% sequence identity to the polypeptide of SEQ ID NO: 27;
(j) a polypeptide having at least 90% sequence identity to the polypeptide of SEQ ID NO: 30;
(k) a polypeptide having at least 90% sequence identity to the polypeptide of SEQ ID NO: 33;
(l) a polypeptide having at least 90% sequence identity to the polypeptide of SEQ ID NO: 36;
(m) a polypeptide having at least 90% sequence identity to the polypeptide of SEQ ID NO: 39;
(n) a polypeptide having at least 90% sequence identity to the polypeptide of SEQ ID NO: 42;
(o) a polypeptide having at least 90% sequence identity to the polypeptide of SEQ ID NO: 45;
(p) a polypeptide having at least 90% sequence identity to the polypeptide of SEQ ID NO: 48;
(q) a polypeptide having at least 90% sequence identity to the polypeptide of SEQ ID NO: 51;
(r) a polypeptide having at least 90% sequence identity to the polypeptide of SEQ ID NO: 54;
(s) a polypeptide having at least 90% sequence identity to the polypeptide of SEQ ID NO: 57;
(t) a polypeptide having at least 90% sequence identity to the polypeptide of SEQ ID NO: 60;
(u) a polypeptide having at least 90% sequence identity to the polypeptide of SEQ ID NO: 63;
(v) a polypeptide having at least 90% sequence identity to the polypeptide of SEQ ID NO: 66;
(w) a polypeptide having at least 90% sequence identity to the polypeptide of SEQ ID NO: 69;
(x) a polypeptide having at least 90% sequence identity to the polypeptide of SEQ ID NO: 72;
(y) a polypeptide having at least 90% sequence identity to the polypeptide of SEQ ID NO: 75;
(z) a polypeptide having at least 90% sequence identity to the polypeptide of SEQ ID NO: 80;
(aa) a polypeptide having at least 90% sequence identity to the polypeptide of SEQ ID NO: 83;
(ab) a polypeptide having at least 90% sequence identity to the polypeptide of SEQ ID NO: 86;
(ac) a polypeptide having at least 90% sequence identity to the polypeptide of SEQ ID NO: 89;
(ad) a polypeptide having at least 90% sequence identity to the polypeptide of SEQ ID NO: 92;
(ae) a polypeptide having at least 90% sequence identity to the polypeptide of SEQ ID NO: 95;
(af) a polypeptide having at least 90% sequence identity to the polypeptide of SEQ ID NO: 98;
(ag) a polypeptide having at least 90% sequence identity to the polypeptide of SEQ ID NO: 101;
(ah) a polypeptide having at least 90% sequence identity to the polypeptide of SEQ ID NO: 104;
(ai) a polypeptide having at least 90% sequence identity to the polypeptide of SEQ ID NO: 107;
(aj) a polypeptide having at least 90% sequence identity to the polypeptide of SEQ ID NO: 110;
(ak) a polypeptide having at least 90% sequence identity to the polypeptide of SEQ ID NO: 113;
(al) a polypeptide having at least 90% sequence identity to the polypeptide of SEQ ID NO: 116;
(am) a polypeptide having at least 90% sequence identity to the polypeptide of SEQ ID NO: 119;
(an) a polypeptide having at least 90% sequence identity to the polypeptide of SEQ ID NO: 122;
(ao) a polypeptide having at least 90% sequence identity to the polypeptide of SEQ ID NO: 125;
(ap) a polypeptide having at least 90% sequence identity to the polypeptide of SEQ ID NO: 128;
(aq) a polypeptide having at least 90% sequence identity to the polypeptide of SEQ ID NO: 131;
(ar) a polypeptide having at least 90% sequence identity to the polypeptide of SEQ ID NO: 134;
(as) a polypeptide having at least 90% sequence identity to the polypeptide of SEQ ID NO: 137;
(at) a polypeptide having at least 90% sequence identity to the polypeptide of SEQ ID NO: 140;
(au) a polypeptide having at least 90% sequence identity to the polypeptide of SEQ ID NO: 143;
(av) a polypeptide having at least 90% sequence identity to the polypeptide of SEQ ID NO: 146;
(aw) a polypeptide having at least 90% sequence identity to the polypeptide of SEQ ID NO: 149;
(ax) a polypeptide having at least 90% sequence identity to the polypeptide of SEQ ID NO: 152;
(ay) a polypeptide having at least 90% sequence identity to the polypeptide of SEQ ID NO: 155;
(az) a polypeptide having at least 90% sequence identity to the polypeptide of SEQ ID NO: 158;
(ba) a polypeptide having at least 90% sequence identity to the polypeptide of SEQ ID NO: 221;
(bb) a polypeptide having at least 90% sequence identity to the polypeptide of SEQ ID NO: 224;
(bc) a polypeptide having at least 90% sequence identity to the polypeptide of SEQ ID NO: 227;
(bd) a polypeptide having at least 90% sequence identity to the polypeptide of SEQ ID NO: 230;
(be) a polypeptide having at least 90% sequence identity to the polypeptide of SEQ ID NO: 233; and
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions.

12. The granule of item 9, wherein the polypeptide is selected from the group consisting of:
(a) a polypeptide having at least 95% sequence identity to the polypeptide of SEQ ID NO: 3;
(b) a polypeptide having at least 95% sequence identity to the polypeptide of SEQ ID NO: 6;
(c) a polypeptide having at least 95% sequence identity to the polypeptide of SEQ ID NO: 9;
(d) a polypeptide having at least 95% sequence identity to the polypeptide of SEQ ID NO: 12;
(e) a polypeptide having at least 95% sequence identity to the polypeptide of SEQ ID NO: 15;
(f) a polypeptide having at least 95% sequence identity to the polypeptide of SEQ ID NO: 18;
(g) a polypeptide having at least 95% sequence identity to the polypeptide of SEQ ID NO: 21;
(h) a polypeptide having at least 95% sequence identity to the polypeptide of SEQ ID NO: 24;
(i) a polypeptide having at least 95% sequence identity to the polypeptide of SEQ ID NO: 27;
(j) a polypeptide having at least 95% sequence identity to the polypeptide of SEQ ID NO: 30;
(k) a polypeptide having at least 95% sequence identity to the polypeptide of SEQ ID NO: 33;
(l) a polypeptide having at least 95% sequence identity to the polypeptide of SEQ ID NO: 36;
(m) a polypeptide having at least 95% sequence identity to the polypeptide of SEQ ID NO: 39;
(n) a polypeptide having at least 95% sequence identity to the polypeptide of SEQ ID NO: 42;
(o) a polypeptide having at least 95% sequence identity to the polypeptide of SEQ ID NO: 45;
(p) a polypeptide having at least 95% sequence identity to the polypeptide of SEQ ID NO: 48;
(q) a polypeptide having at least 95% sequence identity to the polypeptide of SEQ ID NO: 51;
(r) a polypeptide having at least 95% sequence identity to the polypeptide of SEQ ID NO: 54;
(s) a polypeptide having at least 95% sequence identity to the polypeptide of SEQ ID NO: 57;
(t) a polypeptide having at least 95% sequence identity to the polypeptide of SEQ ID NO: 60;
(u) a polypeptide having at least 95% sequence identity to the polypeptide of SEQ ID NO: 63;
(v) a polypeptide having at least 95% sequence identity to the polypeptide of SEQ ID NO: 66;
(w) a polypeptide having at least 95% sequence identity to the polypeptide of SEQ ID NO: 69;
(x) a polypeptide having at least 95% sequence identity to the polypeptide of SEQ ID NO: 72;
(y) a polypeptide having at least 95% sequence identity to the polypeptide of SEQ ID NO: 75;
(z) a polypeptide having at least 95% sequence identity to the polypeptide of SEQ ID NO: 80;
(aa) a polypeptide having at least 95% sequence identity to the polypeptide of SEQ ID NO: 83;
(ab) a polypeptide having at least 95% sequence identity to the polypeptide of SEQ ID NO: 86;
(ac) a polypeptide having at least 95% sequence identity to the polypeptide of SEQ ID NO: 89;
(ad) a polypeptide having at least 95% sequence identity to the polypeptide of SEQ ID NO: 92;
(ae) a polypeptide having at least 95% sequence identity to the polypeptide of SEQ ID NO: 95;
(af) a polypeptide having at least 95% sequence identity to the polypeptide of SEQ ID NO: 98;
(ag) a polypeptide having at least 95% sequence identity to the polypeptide of SEQ ID NO: 101;
(ah) a polypeptide having at least 95% sequence identity to the polypeptide of SEQ ID NO: 104;
(ai) a polypeptide having at least 95% sequence identity to the polypeptide of SEQ ID NO: 107;
(aj) a polypeptide having at least 95% sequence identity to the polypeptide of SEQ ID NO: 110;
(ak) a polypeptide having at least 95% sequence identity to the polypeptide of SEQ ID NO: 113;
(al) a polypeptide having at least 95% sequence identity to the polypeptide of SEQ ID NO: 116;
(am) a polypeptide having at least 95% sequence identity to the polypeptide of SEQ ID NO: 119;
(an) a polypeptide having at least 95% sequence identity to the polypeptide of SEQ ID NO: 122;
(ao) a polypeptide having at least 95% sequence identity to the polypeptide of SEQ ID NO: 125;
(ap) a polypeptide having at least 95% sequence identity to the polypeptide of SEQ ID NO: 128;
(aq) a polypeptide having at least 95% sequence identity to the polypeptide of SEQ ID NO: 131;
(ar) a polypeptide having at least 95% sequence identity to the polypeptide of SEQ ID NO: 134;
(as) a polypeptide having at least 95% sequence identity to the polypeptide of SEQ ID NO: 137;
(at) a polypeptide having at least 95% sequence identity to the polypeptide of SEQ ID NO: 140;
(au) a polypeptide having at least 95% sequence identity to the polypeptide of SEQ ID NO: 143;
(av) a polypeptide having at least 95% sequence identity to the polypeptide of SEQ ID NO: 146;
(aw) a polypeptide having at least 95% sequence identity to the polypeptide of SEQ ID NO: 149;
(ax) a polypeptide having at least 95% sequence identity to the polypeptide of SEQ ID NO: 152;
(ay) a polypeptide having at least 95% sequence identity to the polypeptide of SEQ ID NO: 155;
(az) a polypeptide having at least 95% sequence identity to the polypeptide of SEQ ID NO: 158;
(ba) a polypeptide having at least 95% sequence identity to the polypeptide of SEQ ID NO: 221;
(bb) a polypeptide having at least 95% sequence identity to the polypeptide of SEQ ID NO: 224;
(bc) a polypeptide having at least 95% sequence identity to the polypeptide of SEQ ID NO: 227;
(bd) a polypeptide having at least 95% sequence identity to the polypeptide of SEQ ID NO: 230;
(be) a polypeptide having at least 95% sequence identity to the polypeptide of SEQ ID NO: 233; and (bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9 or 10 positions.

13. The granule of item 9, wherein the polypeptide comprises or consists of amino acids 1 to 207 of SEQ ID NO: 3, amino acids 1 to 201 of SEQ ID NO: 6, amino acids 1 to 201 of SEQ ID NO: 9, amino acids 1 to 203 of SEQ ID NO: 12, amino acids 1 to 208 of SEQ ID NO: 15, amino acids 1 to 207 of SEQ ID NO: 18, amino acids 1 to 208 of SEQ ID NO: 21, amino acids 1 to 207 of SEQ ID NO: 24, amino acids 1 to 207 of SEQ ID NO: 27, amino acids 1 to 207 of SEQ ID NO: 30, amino acids 1 to 208 of SEQ ID NO: 33, amino acids 1 to 208 of SEQ ID NO: 36, amino acids 1 to 206 of SEQ ID NO: 39, amino acids 1 to 207 of SEQ ID NO: 42, amino acids 1 to 216 of SEQ ID NO: 45, amino acids 1 to 218 of SEQ ID NO: 48, amino acids 1 to 204 of SEQ ID NO: 51, amino acids 1 to 203 of SEQ ID NO: 54, amino acids 1 to 209 of SEQ ID NO: 57, amino acids 1 to 208 of SEQ ID NO: 60, amino acids 1 to 210 of SEQ ID NO: 63, amino acids 1 to 207 of SEQ ID NO: 66, amino acids 1 to 207 of SEQ ID NO: 69, amino acids 1 to 208 of SEQ ID NO: 72, amino acids 1 to 217 of SEQ ID NO: 75, amino acids 1 to 208 of SEQ ID NO: 80, amino acids 1 to 201 of SEQ ID NO: 83, amino acids 1 to 202 of SEQ ID NO: 86, amino acids 1 to 207 of SEQ ID NO: 89, amino acids 1 to 202 of SEQ ID NO: 92, amino acids 1 to 201 of SEQ ID NO: 95, amino acids 1 to 202 of SEQ ID NO: 98, amino acids 1 to 206 of SEQ ID NO: 101, amino acids 1 to 202 of SEQ ID NO: 104, amino acids 1 to 202 of SEQ ID NO: 107, amino acids 1 to 202 of SEQ ID NO: 110, amino acids 1 to 202 of SEQ ID NO: 113, amino acids 1 to 206 of SEQ ID NO: 116, amino acids 1 to 207 of SEQ ID NO: 119, amino acids 1 to 208 of SEQ ID NO: 122, amino acids 1 to 215 of SEQ ID NO: 125, amino acids 1 to 217 of SEQ ID NO: 128, amino acids 1 to 214 of SEQ ID NO: 131, amino acids 1 to 208 of SEQ ID NO: 134, amino acids 1 to 203 of SEQ ID NO: 137, amino acids 1 to 216 of SEQ ID NO: 140, amino acids 1 to 207 of SEQ ID NO: 143, amino acids 1 to 208 of SEQ ID NO: 146, amino acids 1 to 207 of SEQ ID NO: 149, amino acids 1 to 207 of SEQ ID NO: 152, amino acids 1 to 207 of SEQ ID NO: 155, amino acids 1 to 208 of SEQ ID NO: 158, amino acids 1 to 207 of SEQ ID NO: 221, amino acids 1 to 207 of SEQ ID NO: 224, amino acids 1 to 208 of SEQ ID NO: 227, amino acids 1 to 207 of SEQ ID NO: 230 or amino acids 1 to 207 of SEQ ID NO: 233.

14. The granule of any of items 9 to 13, wherein the polypeptide has at least 150%, at least 175%, at least 200%, at least 225%, at least 250%, at least 275%, at least 300%, at least 350%, or at least 400% of the lysozyme activity of SEQ ID NO: 159.

15. The granule of item 14, wherein the polypeptide has at least 150%, at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

16. The granule of item 14, wherein the polypeptide has at least 150%, at least 175%, at least 200%, at least 225%, at least 250%, at least 275%, at least 300%, at least 350%, or at least 400% of the lysozyme activity of SEQ ID NO: 159 wherein lysozyme activity is determined as follows: lysozyme (50 µL of 0.7 µg/mL lysozyme in phosphate buffer (5 mM citrate, 5 mM $K_2HPO_4$, 0.01% TritonX-100, pH 5.0)) is mixed with *Micrococcus lysodeikticus* solution (450 µL of 1% lyophilized *Micrococcus lysodeikticus* ATCC No. 4698 in milli-Q water) and incubated at 40° C. with shaking (500 rpm) for 45 min; the sample is centrifuged (4000 g, 5 min); supernatant (100 µL) is mixed with HCl (50 µL 3.2M) and incubated at 95° C. for 80 min; NaOH (50 µL, 3.5 M) is added and 150 µL of the sample is added to 4-hydroxybenzhydrazide in K-Na tartrate/NaOH buffer (75 µL of 50 g/L K-Na tartrate+20 g/L NaOH); the mixture is incubated at 95° C. for 10 min; and the optical density is measured at 405 nm.

17. The granule of any of items 9 to 16, wherein the granule comprises one or more formulating agents.

18. The granule of item 17, wherein the formulating agent is selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose, preferably selected from the list consisting of 1,2-propylene glycol, 1,3-propylene glycol, sodium sulfate, dextrin, cellulose, sodium thiosulfate, kaolin and calcium carbonate.

19. The granule of any of items 9 to 18, wherein the granule comprises a core particle and one or more coatings.

20. The granule of item 19, wherein the coating comprises salt and/or wax and/or flour.

21. The granule of any of items 9 to 20 further comprising one or more additional enzymes.

22. The granule of item 21, wherein the one or more additional enzymes is selected from the group consisting of phytase, xylanase, galactanase, alpha-galactosidase, beta-galactosidase, protease, phospholipase A1, phospholipase A2, lysophospholipase, phospholipase C, phospholipase D, amylase, lysozyme, arabinofuranosidase, beta-xylosidase, acetyl xylan esterase, feruloyl esterase, cellulase, cellobiohydrolases, beta-glucosidase, pullulanase, and beta-glucanase or any combination thereof.

23. The granule of any of items 9 to 22 further comprising one or more probiotics.

24. The granule of item 23, wherein the one or more probiotics is selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococsus acidilactici, Pediococcus* sp., *Propionibacterium thoenii, Propionibacterium* sp. and *Streptococcus* sp. or any combination thereof.

25. An isolated polypeptide having lysozyme activity, selected from the group consisting of:
 (a) a polypeptide having at least 80% sequence identity to the polypeptide of SEQ
 (b) a polypeptide having at least 89% sequence identity to the polypeptide of SEQ ID NO: 6;
 (c) a polypeptide having at least 81% sequence identity to the polypeptide of SEQ ID NO: 9;
 (d) a polypeptide having at least 80% sequence identity to the polypeptide of SEQ ID NO: 12;
 (e) a polypeptide having at least 97% sequence identity to the polypeptide of SEQ ID NO: 15;
 (f) a polypeptide having at least 80% sequence identity to the polypeptide of SEQ ID NO: 18;
 (g) a polypeptide having at least 80% sequence identity to the polypeptide of SEQ ID NO: 24;
 (h) a polypeptide having at least 80% sequence identity to the polypeptide of SEQ ID NO: 27;
 (i) a polypeptide having at least 83% sequence identity to the polypeptide of SEQ ID NO: 30;
 (j) a polypeptide having at least 80% sequence identity to the polypeptide of SEQ ID NO: 33;
 (k) a polypeptide having at least 80% sequence identity to the polypeptide of SEQ ID NO: 36;
 (l) a polypeptide having at least 83% sequence identity to the polypeptide of SEQ ID NO: 39;
 (m) a polypeptide having at least 80% sequence identity to the polypeptide of SEQ ID NO: 42;
 (n) a polypeptide having at least 86% sequence identity to the polypeptide of SEQ ID NO: 45;
 (o) a polypeptide having at least 80% sequence identity to the polypeptide of SEQ ID NO: 48;
 (p) a polypeptide having at least 92% sequence identity to the polypeptide of SEQ ID NO: 51;
 (q) a polypeptide having at least 81% sequence identity to the polypeptide of SEQ ID NO: 54;
 (r) a polypeptide having at least 80% sequence identity to the polypeptide of SEQ ID NO: 57;
 (s) a polypeptide having at least 80% sequence identity to the polypeptide of SEQ ID NO: 60;
 (t) a polypeptide having at least 80% sequence identity to the polypeptide of SEQ ID NO: 63;
 (u) a polypeptide having at least 80% sequence identity to the polypeptide of SEQ ID NO: 66;
 (v) a polypeptide having at least 80% sequence identity to the polypeptide of SEQ ID NO: 69;
 (w) a polypeptide having at least 84% sequence identity to the polypeptide of SEQ ID NO: 72;
 (x) a polypeptide having at least 80% sequence identity to the polypeptide of SEQ ID NO: 75;
 (y) a polypeptide having at least 84% sequence identity to the polypeptide of SEQ ID NO: 80;
 (z) a polypeptide having at least 82% sequence identity to the polypeptide of SEQ ID NO: 83;
 (aa) a polypeptide having at least 80% sequence identity to the polypeptide of SEQ ID NO: 86;
 (ab) a polypeptide having at least 86% sequence identity to the polypeptide of SEQ ID NO: 89;
 (ac) a polypeptide having at least 82% sequence identity to the polypeptide of SEQ ID NO: 92;
 (ad) a polypeptide having at least 94% sequence identity to the polypeptide of SEQ ID NO: 95;
 (ae) a polypeptide having at least 94% sequence identity to the polypeptide of SEQ ID NO: 98;
 (af) a polypeptide having at least 80% sequence identity to the polypeptide of SEQ ID NO: 101;
 (ag) a polypeptide having at least 81% sequence identity to the polypeptide of SEQ ID NO: 104;
 (ah) a polypeptide having at least 80% sequence identity to the polypeptide of SEQ ID NO: 107;
 (ai) a polypeptide having at least 88% sequence identity to the polypeptide of SEQ ID NO: 110;
 (aj) a polypeptide having at least 85% sequence identity to the polypeptide of SEQ ID NO: 113;
 (ak) a polypeptide having at least 80% sequence identity to the polypeptide of SEQ ID NO: 116;
 (al) a polypeptide having at least 80% sequence identity to the polypeptide of SEQ ID NO: 119;
 (am) a polypeptide having at least 96.5% sequence identity to the polypeptide of SEQ ID NO: 122;
 (an) a polypeptide having at least 81% sequence identity to the polypeptide of SEQ ID NO: 125;
 (ao) a polypeptide having at least 89% sequence identity to the polypeptide of SEQ ID NO: 128;
 (ap) a polypeptide having at least 80% sequence identity to the polypeptide of SEQ ID NO: 131;
 (aq) a polypeptide having at least 80% sequence identity to the polypeptide of SEQ ID NO: 134;
 (ar) a polypeptide having at least 90% sequence identity to the polypeptide of SEQ ID NO: 137;
 (as) a polypeptide having at least 80% sequence identity to the polypeptide of SEQ ID NO: 140;
 (at) a polypeptide having at least 80% sequence identity to the polypeptide of SEQ ID NO: 143;
 (au) a polypeptide having at least 80% sequence identity to the polypeptide of SEQ ID NO: 146;
 (av) a polypeptide having at least 85% sequence identity to the polypeptide of SEQ ID NO: 149;
 (aw) a polypeptide having at least 85% sequence identity to the polypeptide of SEQ ID NO: 152;
 (ax) a polypeptide having at least 84% sequence identity to the polypeptide of SEQ ID NO: 155;
 (ay) a polypeptide having at least 95% sequence identity to the polypeptide of SEQ ID NO: 158;
 (az) a polypeptide having at least 80% sequence identity to the polypeptide of SEQ ID NO: 221;
 (ba) a polypeptide having at least 80% sequence identity to the polypeptide of SEQ ID NO: 224;
 (bb) a polypeptide having at least 80% sequence identity to the polypeptide of SEQ ID NO: 227;
 (bc) a polypeptide having at least 85% sequence identity to the polypeptide of SEQ ID NO: 230;
 (bd) a polypeptide having at least 85% sequence identity to the polypeptide of SEQ ID NO: 233;
 (be) a variant of the polypeptide selected from the group consisting of SEQ ID NO: 3, SEQ ID NO: 12, SEQ ID NO: 18, SEQ ID NO: 24 SEQ ID NO: 27, SEQ ID NO: 33, SEQ ID NO: 36, SEQ ID NO: 42, SEQ ID NO: 48, SEQ ID NO: 57, SEQ ID NO: 60, SEQ ID NO: 63, SEQ ID NO: 66, SEQ ID NO: 69, SEQ ID NO: 75, SEQ ID NO: 86, SEQ ID NO:101, SEQ ID NO: 107, SEQ ID NO: 116, SEQ ID NO: 119, SEQ ID NO: 125, SEQ ID NO: 131, SEQ ID NO: 134, SEQ ID NO: 140, SEQ ID NO: 143, SEQ ID NO: 146, SEQ ID NO: 221, SEQ ID NO: 224 and SEQ ID NO: 227, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 positions;

(bf) a variant of the polypeptide selected from the group consisting of SEQ ID NO: 9, SEQ ID NO: 54 and SEQ ID NO: 104, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 positions;

(bg) a variant of the polypeptide selected from the group consisting of SEQ ID NO: 83 and SEQ ID NO: 92, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 positions;

(bh) a variant of the polypeptide selected from the group consisting of SEQ ID NO: 30 and SEQ ID NO: 39, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 positions;

(bi) a variant of the polypeptide selected from the group consisting of SEQ ID NO: 72, SEQ ID NO: 80 and SEQ ID NO: 155, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 positions;

(bj) a variant of the polypeptide selected from the group consisting of SEQ ID NO: 149, SEQ ID NO: 152, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 positions;

(bk) a variant of the polypeptide selected from the group consisting of SEQ ID NO: 45 and SEQ ID NO: 113, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 positions;

(bl) a variant of SEQ ID NO: 89, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27 or 28 positions;

(bm) a variant of SEQ ID NO: 110, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23 or 24 positions;

(bn) a variant of SEQ ID NO: 128, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22 or 23 positions;

(bo) a variant of SEQ ID NO: 6, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21 or 22 positions;

(bp) a variant of SEQ ID NO: 137, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;

(bq) a variant of SEQ ID NO: 51, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15 or 16 positions;

(br) a variant of the polypeptide selected from the group consisting of SEQ ID NO: 95 and SEQ ID NO: 98, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11 or 12 positions;

(bs) a variant of SEQ ID NO: 158, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9 or 10 positions;

(bt) a variant of SEQ ID NO: 122, wherein the variant has lysozyme activity and comprises one or more amino acid substitutions, and/or one or more amino acid deletions, and/or one or more amino acid insertions or any combination thereof in 1, 2, 3, 4, 5, 6 or 7 positions;

(bu) a variant of SEQ ID NO: 15, wherein the variant has lysozyme activity and comprises one or more amino acid substitutions, and/or one or more amino acid deletions, and/or one or more amino acid insertions or any combination thereof in 1, 2, 3, 4, 5 or 6 positions;

(bv) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be), (bf), (bg), (bh), (bi), (bj), (bk), (bl), (bm), (bn), (bo), (bp), (bq), (br), (bs), (bt) or (bu) and a N-terminal and/or C-terminal His-tag and/or HQ-tag;

(bw) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be), (bf), (bg), (bh), (bi), (bj), (bk), (bl), (bm), (bn), (bo), (bp), (bq), (br), (bs), (bt) or (bu) and a N-terminal and/or C-terminal extension of up to 10 amino acids, e.g. 1, 2, 3, 4, 5, 6, 7, 8, 9 or 10 amino acids; and (bx) a fragment of the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be), (bf), (bg), (bh), (bi), (bj), (bk), (bl), (bm), (bn), (bo), (bp), (bq), (br), (bs), (bt) or (bu) having lysozyme activity and having at least 90% of the length of the mature polypeptide.

26. The polypeptide of item 25, wherein the polypeptide comprises or consists of amino acids 1 to 207 of SEQ ID NO: 3, amino acids 1 to 201 of SEQ ID NO: 6, amino acids 1 to 201 of SEQ ID NO: 9, amino acids 1 to 203 of SEQ ID NO: 12, amino acids 1 to 208 of SEQ ID NO: 15, amino acids 1 to 207 of SEQ ID NO: 18, amino acids 1 to 208 of SEQ ID NO: 21, amino acids 1 to 207 of SEQ ID NO: 27, amino acids 1 to 207 of SEQ ID NO: 30, amino acids 1 to 208 of SEQ ID NO: 33, amino acids 1 to 208 of SEQ ID NO: 36, amino acids 1 to 206 of SEQ ID NO: 39, amino acids 1 to 207 of SEQ ID NO: 42, amino acids 1 to 216 of SEQ ID NO: 45, amino acids 1 to 218 of SEQ ID NO: 48, amino acids 1 to 204 of SEQ ID NO: 51, amino acids 1 to 203 of SEQ ID NO: 54, amino acids 1 to 209 of SEQ ID NO: 57, amino acids 1 to 208 of SEQ ID NO: 60, amino acids 1 to 210 of SEQ ID NO: 63, amino acids 1 to 207 of SEQ ID NO: 66, amino acids 1 to 207 of SEQ ID NO: 69, amino acids 1 to 208 of SEQ ID NO: 72, amino acids 1 to 217 of SEQ ID NO: 75, amino acids 1 to 208 of SEQ ID NO: 80, amino acids 1 to 201 of SEQ ID NO: 83, amino acids 1 to 202 of SEQ ID NO: 86, amino acids 1 to 207 of SEQ ID NO: 89, amino acids 1 to 202 of SEQ ID NO: 92, amino acids 1 to 201 of SEQ ID NO: 95, amino acids 1 to 202 of SEQ ID NO: 98, amino acids 1 to 206 of SEQ ID NO: 101, amino acids 1 to 202 of SEQ ID NO: 104, amino acids 1 to 202 of SEQ ID NO: 107, amino acids 1 to 202 of SEQ ID NO: 110, amino acids 1 to 202 of SEQ ID NO: 113, amino acids 1 to 206 of SEQ ID NO: 116, amino acids 1 to 207 of SEQ ID NO: 119, amino acids 1 to 208 of SEQ ID NO: 122, amino acids 1 to 215 of SEQ ID NO: 125, amino acids 1 to 217 of SEQ ID NO: 128, amino acids 1 to 214 of SEQ ID NO: 131, amino acids 1 to 208 of SEQ ID NO: 134, amino acids 1 to 203 of SEQ ID NO: 137, amino acids 1 to 216 of SEQ ID NO: 140, amino acids 1 to 207 of SEQ ID NO: 143, amino acids 1 to 208 of SEQ ID NO: 146, amino acids 1 to 207 of SEQ ID NO: 149, amino acids 1 to 207 of SEQ ID NO: 152, amino acids 1 to 207 of SEQ ID NO: 155, amino acids 1 to 208 of SEQ ID NO: 158, amino acids 1 to 207 of SEQ ID NO: 221, amino acids 1 to 207 of SEQ ID NO: 224, amino acids 1 to 208 of SEQ ID NO: 227, amino acids 1 to 207 of SEQ ID NO: 230 or amino acids 1 to 207 of SEQ ID NO: 233.

27. The polypeptide of any of items 25 to 26, wherein the polypeptide has at least 150%, at least 175%, at least 200%, at least 225%, at least 250%, at least 275%, at least 300%, at least 350%, or at least 400% of the lysozyme activity of SEQ ID NO: 159.

28. The polypeptide of any of items 25 to 27, wherein the polypeptide has at least 150%, at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

29. The polypeptide of item 28, wherein the polypeptide has at least 150%, at least 175%, at least 200%, at least 225%, at least 250%, at least 275%, at least 300%, at least 350%, or at least 400% of the lysozyme activity of SEQ ID NO: 159 wherein lysozyme activity is determined as follows: lysozyme (50 µL of 0.7 µg/mL lysozyme in phosphate buffer (5 mM citrate, 5 mM $K_2HPO_4$, 0.01% TritonX-100, pH 5.0)) is mixed with *Micrococcus lysodeikticus* solution (450 µL of 1% lyophilized *Micrococcus lysodeikticus* ATCC No. 4698 in milli-Q water) and incubated at 40° C. with shaking (500 rpm) for 45 min; the sample is centrifuged (4000 g, 5 min); supernatant (100 µL) is mixed with HCl (50 µL 3.2M) and incubated at 95° C. for 80 min; NaOH (50 µL, 3.5 M) is added and 150 µL of the sample is added to 4-hydroxybenzhydrazide in K-Na tartrate/NaOH buffer (75 µL of 50 g/L K-Na tartrate+20 g/L NaOH); the mixture is incubated at 95° C. for 10 min; and the optical density is measured at 405 nm.

30. A composition comprising the polypeptide of any of items 25 to 29.

31. The composition of item 30 further comprising one or more formulating agents.

32. The composition of item 31 wherein the formulating agent comprises one or more of the following compounds: glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose.

33. An animal feed additive comprising the lysozyme as disclosed in any of items 1 to 8, the granule of any of items 9 to 24, the polypeptide of any of items 25 to 29 or the composition of any of items 30 to 32.

34. The animal feed additive of item 33 further comprising one or more components selected from the list consisting of:
one or more vitamins;
one or more minerals;
one or more amino acids;
one or more prebiotics;
one or more organic acids; and
one or more other feed ingredients.

35. The animal feed additive of any of items 33 to 34 further comprising one or more additional enzymes.
36. The animal feed additive of item 35, wherein the one or more additional enzymes is selected from the group consisting of phytase, lysozyme, galactanase, alpha-galactosidase, beta-galactosidase, protease, phospholipase A1, phospholipase A2, lysophospholipase, phospholipase C, phospholipase D, amylase, lysozyme, arabinofuranosidase, beta-xylosidase, acetyl xylan esterase, feruloyl esterase, cellulase, cellobiohydrolases, beta-glucosidase, pullulanase, and beta-glucanase or any combination thereof.
37. The animal feed additive of any of items 33 to 36 further comprising one or more probiotics.
38. The animal feed additive of item 37, wherein the one or more probiotics is selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococcus acidilactici, Pediococcus* sp., *Propionibacterium thoenii, Propionibacterium* sp. and *Streptococcus* sp. or any combination thereof.
39. The animal feed additive of any of items 33 to 38 further comprising one or more phytogenics.
40. The animal feed additive of item 39, wherein the phytogenic is selected from the group consisting of rosemary, sage, oregano, thyme, clove, lemongrass, essential oils, thymol, eugenol, meta-cresol, vaniline, salicylate, resorcine, guajacol, gingerol, lavender oil, ionones, irone, eucalyptol, menthol, peppermint oil, alpha-pinene; limonene, anethol, linalool, methyl dihydrojasmonate, carvacrol, propionic acid/propionate, acetic acid/acetate, butyric acid/butyrate, rosemary oil, clove oil, geraniol, terpineol, citronellol, amyl and/or benzyl salicylate, cinnamaldehyde, plant polyphenol (tannin), turmeric and *curcuma* extract or any combination thereof.
41. An animal feed comprising the lysozyme as disclosed in any of items 1 to 8, the granule of any of items 9 to 24, the polypeptide of any of items 25 to 29, the composition of any of items 30 to 32 or the animal feed additive of any of items 33 to 40 and plant based material.
42. The animal feed of item 41, wherein the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.
43. A pelleted animal feed comprising the lysozyme as disclosed in any of items 1 to 8, the granule of any of items 9 to 24, the polypeptide of any of items 25 to 29, the composition of any of items 30 to 32 or the animal feed additive of any of items 33 to 40 and plant based material.
44. The pelleted animal feed of item 43, wherein the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.
45. A method of improving one or more performance parameters of an animal comprising administering to one or more animals the lysozyme as disclosed in any of items 1 to 8, the granule of any of items 9 to 24, the polypeptide of any of items 25 to 29, the composition of any of items 30 to 32, the animal feed additive of any of items 33 to 40, the animal feed of any of items 41 to 42 or the pelleted animal feed of any of items 43 to 44.
46. The method of item 45, wherein improving the performance of an animal means improved body weight gain, improved European Production Efficiency Factor (EPEF) and/or improved FCR.
47. A method of preparing an animal feed comprising mixing the lysozyme as disclosed in any of items 1 to 8, the granule of any of items 9 to 24, the polypeptide of any of items 25 to 29, the composition of any of items 30 to 32 or the animal feed additive of any of items 33 to 40 with plant based material.
48. The method of item 47, wherein the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.
49. A method for improving the nutritional value of an animal feed, comprising adding to the feed the lysozyme as disclosed in any of items 1 to 8, the granule of any of items 9 to 24, the polypeptide of any of items 25 to 29, the composition of any of items 30 to 32 or the animal feed additive of any of items 33 to 40.
50. The method of item 49, wherein the feed is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.
51. A polynucleotide encoding the polypeptide of any of items 25 to 29.
52. A nucleic acid construct or expression vector comprising the polynucleotide of item 51 operably linked to one or more control sequences that direct the production of the polypeptide in an expression host.

53. A recombinant host cell comprising the polynucleotide of item 51 operably linked to one or more control sequences that direct the production of the polypeptide.

54. A method of producing the polypeptide of any of items 25 to 29, comprising:
   (a) cultivating a cell, which in its wild-type form produces the polypeptide, under conditions conductive for production of the polypeptide; and
   (b) recovering the polypeptide.

55. A method of producing the polypeptide of any of items 25 to 29, comprising:
   (a) cultivating a host cell of item 53 under conditions conducive for production of the polypeptide; and
   (b) recovering the polypeptide.

56. A transgenic plant, plant part or plant cell transformed with a polynucleotide encoding the polypeptide of any of items 25 to 29.

57. A whole broth formulation or cell culture composition comprising a polypeptide of any of items 25 to 29.

58. Use of the lysozyme as disclosed in any of any of items 1 to 8, the granule of any of items 9 to 24, the polypeptide of any of items 25 to 29, the composition of any of items 30 to 32 or the animal feed additive of any of items 33 to 40:
   in animal feed;
   in animal feed additives;
   in the preparation of a composition for use in animal feed;
   for improving the nutritional value of an animal feed; and/or
   for improving one or more performance parameters in an animal.

59. An isolated GH25 polypeptide having lysozyme activity selected from the group consisting of:
   (a) a polypeptide having at least 80% sequence identity to the polypeptide of SEQ ID NO: 3;
   (b) a polypeptide having at least 84% sequence identity to the polypeptide of SEQ ID NO: 6;
   (c) a polypeptide having at least 80% sequence identity to the polypeptide of SEQ ID NO: 9;
   (d) a polypeptide having at least 80% sequence identity to the polypeptide of SEQ ID NO: 12;
   (e) a polypeptide having at least 80% sequence identity to the polypeptide of SEQ ID NO: 15;
   (f) a polypeptide having at least 80% sequence identity to the polypeptide of SEQ ID NO: 18;
   (g) a polypeptide having at least 80% sequence identity to the polypeptide of SEQ ID NO: 21;
   (h) a polypeptide having at least 80% sequence identity to the polypeptide of SEQ ID NO: 24;
   (i) a polypeptide having at least 80% sequence identity to the polypeptide of SEQ ID NO: 27;
   (j) a polypeptide having at least 84% sequence identity to the polypeptide of SEQ ID NO: 30;
   (k) a polypeptide having at least 80% sequence identity to the polypeptide of SEQ ID NO: 33;
   (l) a polypeptide having at least 80% sequence identity to the polypeptide of SEQ ID NO: 36;
   (m) a polypeptide having at least 84% sequence identity to the polypeptide of SEQ ID NO: 39;
   (n) a polypeptide having at least 80% sequence identity to the polypeptide of SEQ ID NO: 42;
   (o) a polypeptide having at least 80% sequence identity to the polypeptide of SEQ ID NO: 45;
   (p) a polypeptide having at least 80% sequence identity to the polypeptide of SEQ ID NO: 48;
   (q) a polypeptide having at least 80% sequence identity to the polypeptide of SEQ ID NO: 51;
   (r) a polypeptide having at least 80% sequence identity to the polypeptide of SEQ ID NO: 54;
   (s) a polypeptide having at least 80% sequence identity to the polypeptide of SEQ ID NO: 57;
   (t) a polypeptide having at least 80% sequence identity to the polypeptide of SEQ ID NO: 60;
   (u) a polypeptide having at least 80% sequence identity to the polypeptide of SEQ ID NO: 63;
   (v) a polypeptide having at least 80% sequence identity to the polypeptide of SEQ ID NO: 66;
   (w) a polypeptide having at least 80% sequence identity to the polypeptide of SEQ ID NO: 69;
   (x) a polypeptide having at least 84% sequence identity to the polypeptide of SEQ ID NO: 72;
   (y) a polypeptide having at least 80% sequence identity to the polypeptide of SEQ ID NO: 75;
   (z) a polypeptide having at least 80% sequence identity to the polypeptide of SEQ ID NO: 80;
   (aa) a polypeptide having at least 80% sequence identity to the polypeptide of SEQ ID NO: 83;
   (ab) a polypeptide having at least 80% sequence identity to the polypeptide of SEQ ID NO: 86;
   (ac) a polypeptide having at least 86% sequence identity to the polypeptide of SEQ ID NO: 89;
   (ad) a polypeptide having at least 82% sequence identity to the polypeptide of SEQ ID NO: 92;
   (ae) a polypeptide having at least 82% sequence identity to the polypeptide of SEQ ID NO: 95;
   (af) a polypeptide having at least 80% sequence identity to the polypeptide of SEQ ID NO: 98;
   (ag) a polypeptide having at least 80% sequence identity to the polypeptide of SEQ ID NO: 101;
   (ah) a polypeptide having at least 80% sequence identity to the polypeptide of SEQ ID NO: 104;
   (ai) a polypeptide having at least 80% sequence identity to the polypeptide of SEQ ID NO: 107;
   (aj) a polypeptide having at least 82% sequence identity to the polypeptide of SEQ ID NO: 110;
   (ak) a polypeptide having at least 81% sequence identity to the polypeptide of SEQ ID NO: 113;
   (al) a polypeptide having at least 80% sequence identity to the polypeptide of SEQ ID NO: 116;
   (am) a polypeptide having at least 80% sequence identity to the polypeptide of SEQ ID NO: 119;
   (an) a polypeptide having at least 80% sequence identity to the polypeptide of SEQ ID NO: 122;
   (ao) a polypeptide having at least 80% sequence identity to the polypeptide of SEQ ID NO: 125;
   (ap) a polypeptide having at least 80% sequence identity to the polypeptide of SEQ ID NO: 128;
   (aq) a polypeptide having at least 80% sequence identity to the polypeptide of SEQ ID NO: 131;
   (ar) a polypeptide having at least 80% sequence identity to the polypeptide of SEQ ID NO: 134;
   (as) a polypeptide having at least 80% sequence identity to the polypeptide of SEQ ID NO: 137;
   (at) a polypeptide having at least 80% sequence identity to the polypeptide of SEQ ID NO: 140;
   (au) a polypeptide having at least 80% sequence identity to the polypeptide of SEQ ID NO: 143;
   (av) a polypeptide having at least 80% sequence identity to the polypeptide of SEQ ID NO: 146;
   (aw) a polypeptide having at least 80% sequence identity to the polypeptide of SEQ ID NO: 149;

(ax) a polypeptide having at least 80% sequence identity to the polypeptide of SEQ ID NO: 152;
(ay) a polypeptide having at least 80% sequence identity to the polypeptide of SEQ ID NO: 155;
(az) a polypeptide having at least 80% sequence identity to the polypeptide of SEQ ID NO: 158;
(ba) a polypeptide having at least 80% sequence identity to the polypeptide of SEQ ID NO: 221;
(bb) a polypeptide having at least 80% sequence identity to the polypeptide of SEQ ID NO: 224;
(bc) a polypeptide having at least 80% sequence identity to the polypeptide of SEQ ID NO: 227;
(bd) a polypeptide having at least 80% sequence identity to the polypeptide of SEQ ID NO: 230;
(be) a polypeptide having at least 80% sequence identity to the polypeptide of SEQ ID NO: 233;
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27 or 28 positions;
(bg) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal His-tag and/or HQ-tag;
(bh) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal extension of up to 10 amino acids, e.g. 1, 2, 3, 4, 5, 6, 7, 8, 9 or 10 amino acids; and
(bi) a fragment of the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) having lysozyme activity and having at least 90% of the length of the mature polypeptide.

60. The polypeptide according to embodiment 59, wherein the polypeptide is selected from the group consisting of:
(a) a polypeptide having at least 90% sequence identity to the polypeptide of SEQ ID NO: 3;
(b) a polypeptide having at least 90% sequence identity to the polypeptide of SEQ ID NO: 6;
(c) a polypeptide having at least 90% sequence identity to the polypeptide of SEQ ID NO: 9;
(d) a polypeptide having at least 90% sequence identity to the polypeptide of SEQ ID NO: 12;
(e) a polypeptide having at least 90% sequence identity to the polypeptide of SEQ ID NO: 15;
(f) a polypeptide having at least 90% sequence identity to the polypeptide of SEQ ID NO: 18;
(g) a polypeptide having at least 90% sequence identity to the polypeptide of SEQ ID NO: 21;
(h) a polypeptide having at least 90% sequence identity to the polypeptide of SEQ ID NO: 24;
(i) a polypeptide having at least 90% sequence identity to the polypeptide of SEQ ID NO: 27;
(j) a polypeptide having at least 90% sequence identity to the polypeptide of SEQ ID NO: 30;
(k) a polypeptide having at least 90% sequence identity to the polypeptide of SEQ ID NO: 33;
(l) a polypeptide having at least 90% sequence identity to the polypeptide of SEQ ID NO: 36;
(m) a polypeptide having at least 90% sequence identity to the polypeptide of SEQ ID NO: 39;
(n) a polypeptide having at least 90% sequence identity to the polypeptide of SEQ ID NO: 42;
(o) a polypeptide having at least 90% sequence identity to the polypeptide of SEQ ID NO: 45;
(p) a polypeptide having at least 90% sequence identity to the polypeptide of SEQ ID NO: 48;
(q) a polypeptide having at least 90% sequence identity to the polypeptide of SEQ ID NO: 51;
(r) a polypeptide having at least 90% sequence identity to the polypeptide of SEQ ID NO: 54;
(s) a polypeptide having at least 90% sequence identity to the polypeptide of SEQ ID NO: 57;
(t) a polypeptide having at least 90% sequence identity to the polypeptide of SEQ ID NO: 60;
(u) a polypeptide having at least 90% sequence identity to the polypeptide of SEQ ID NO: 63;
(v) a polypeptide having at least 90% sequence identity to the polypeptide of SEQ ID NO: 66;
(w) a polypeptide having at least 90% sequence identity to the polypeptide of SEQ ID NO: 69;
(x) a polypeptide having at least 90% sequence identity to the polypeptide of SEQ ID NO: 72;
(y) a polypeptide having at least 90% sequence identity to the polypeptide of SEQ ID NO: 75;
(z) a polypeptide having at least 90% sequence identity to the polypeptide of SEQ ID NO: 80;
(aa) a polypeptide having at least 90% sequence identity to the polypeptide of SEQ ID NO: 83;
(ab) a polypeptide having at least 90% sequence identity to the polypeptide of SEQ ID NO: 86;
(ac) a polypeptide having at least 90% sequence identity to the polypeptide of SEQ ID NO: 89;
(ad) a polypeptide having at least 90% sequence identity to the polypeptide of SEQ ID NO: 92;
(ae) a polypeptide having at least 90% sequence identity to the polypeptide of SEQ ID NO: 95;

(af) a polypeptide having at least 90% sequence identity to the polypeptide of SEQ ID NO: 98;
(ag) a polypeptide having at least 90% sequence identity to the polypeptide of SEQ ID NO: 101;
(ah) a polypeptide having at least 90% sequence identity to the polypeptide of SEQ ID NO: 104;
(ai) a polypeptide having at least 90% sequence identity to the polypeptide of SEQ ID NO: 107;
(aj) a polypeptide having at least 90% sequence identity to the polypeptide of SEQ ID NO: 110;
(ak) a polypeptide having at least 90% sequence identity to the polypeptide of SEQ ID NO: 113;
(al) a polypeptide having at least 90% sequence identity to the polypeptide of SEQ ID NO: 116;
(am) a polypeptide having at least 90% sequence identity to the polypeptide of SEQ ID NO: 119;
(an) a polypeptide having at least 90% sequence identity to the polypeptide of SEQ ID NO: 122;
(ao) a polypeptide having at least 90% sequence identity to the polypeptide of SEQ ID NO: 125;
(ap) a polypeptide having at least 90% sequence identity to the polypeptide of SEQ ID NO: 128;
(aq) a polypeptide having at least 90% sequence identity to the polypeptide of SEQ ID NO: 131;
(ar) a polypeptide having at least 90% sequence identity to the polypeptide of SEQ ID NO: 134;
(as) a polypeptide having at least 90% sequence identity to the polypeptide of SEQ ID NO: 137;
(at) a polypeptide having at least 90% sequence identity to the polypeptide of SEQ ID NO: 140;
(au) a polypeptide having at least 90% sequence identity to the polypeptide of SEQ ID NO: 143;
(av) a polypeptide having at least 90% sequence identity to the polypeptide of SEQ ID NO: 146;
(aw) a polypeptide having at least 90% sequence identity to the polypeptide of SEQ ID NO: 149;
(ax) a polypeptide having at least 90% sequence identity to the polypeptide of SEQ ID NO: 152;
(ay) a polypeptide having at least 90% sequence identity to the polypeptide of SEQ ID NO: 155;
(az) a polypeptide having at least 90% sequence identity to the polypeptide of SEQ ID NO: 158;
(ba) a polypeptide having at least 90% sequence identity to the polypeptide of SEQ ID NO: 221;
(bb) a polypeptide having at least 90% sequence identity to the polypeptide of SEQ ID NO: 224;
(bc) a polypeptide having at least 90% sequence identity to the polypeptide of SEQ ID NO: 227;
(bd) a polypeptide having at least 90% sequence identity to the polypeptide of SEQ ID NO: 230;
(be) a polypeptide having at least 90% sequence identity to the polypeptide of SEQ ID NO: 233; and
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions.

61. An isolated GH25 polypeptide having lysozyme activity selected from the group consisting of:
(a) a polypeptide having at least 90% sequence identity to the polypeptide of SEQ
(b) a polypeptide having at least 90% sequence identity to the polypeptide of SEQ ID NO: 6;
(e) a polypeptide having at least 90% sequence identity to the polypeptide of SEQ ID NO: 15;
(f) a polypeptide having at least 90% sequence identity to the polypeptide of SEQ ID NO: 18;
(g) a polypeptide having at least 90% sequence identity to the polypeptide of SEQ ID NO: 21;
(h) a polypeptide having at least 90% sequence identity to the polypeptide of SEQ ID NO: 24;
(k) a polypeptide having at least 90% sequence identity to the polypeptide of SEQ ID NO: 33;
(l) a polypeptide having at least 90% sequence identity to the polypeptide of SEQ ID NO: 36;
(m) a polypeptide having at least 90% sequence identity to the polypeptide of SEQ ID NO: 39;
(o) a polypeptide having at least 90% sequence identity to the polypeptide of SEQ ID NO: 45;
(p) a polypeptide having at least 90% sequence identity to the polypeptide of SEQ ID NO: 48;
(q) a polypeptide having at least 90% sequence identity to the polypeptide of SEQ ID NO: 51;
(r) a polypeptide having at least 90% sequence identity to the polypeptide of SEQ ID NO: 54;
(s) a polypeptide having at least 90% sequence identity to the polypeptide of SEQ ID NO: 57;
(t) a polypeptide having at least 90% sequence identity to the polypeptide of SEQ ID NO: 60;
(x) a polypeptide having at least 90% sequence identity to the polypeptide of SEQ ID NO: 72;
(y) a polypeptide having at least 90% sequence identity to the polypeptide of SEQ ID NO: 75;
(z) a polypeptide having at least 90% sequence identity to the polypeptide of SEQ ID NO: 80;
(ac) a polypeptide having at least 90% sequence identity to the polypeptide of SEQ ID NO: 89;
(ae) a polypeptide having at least 90% sequence identity to the polypeptide of SEQ ID NO: 95;
(af) a polypeptide having at least 90% sequence identity to the polypeptide of SEQ ID NO: 98;
(ag) a polypeptide having at least 90% sequence identity to the polypeptide of SEQ ID NO: 101;
(ak) a polypeptide having at least 90% sequence identity to the polypeptide of SEQ ID NO: 113;
(al) a polypeptide having at least 90% sequence identity to the polypeptide of SEQ ID NO: 116;
(am) a polypeptide having at least 90% sequence identity to the polypeptide of SEQ ID NO: 119;
(an) a polypeptide having at least 90% sequence identity to the polypeptide of SEQ ID NO: 122;

(aq) a polypeptide having at least 90% sequence identity to the polypeptide of SEQ ID NO: 131;
(as) a polypeptide having at least 90% sequence identity to the polypeptide of SEQ ID NO: 137;
(au) a polypeptide having at least 90% sequence identity to the polypeptide of SEQ ID NO: 143;
(av) a polypeptide having at least 90% sequence identity to the polypeptide of SEQ ID NO: 146;
(aw) a polypeptide having at least 90% sequence identity to the polypeptide of SEQ ID NO: 149;
(ax) a polypeptide having at least 90% sequence identity to the polypeptide of SEQ ID NO: 152;
(ay) a polypeptide having at least 90% sequence identity to the polypeptide of SEQ ID NO: 155;
(ba) a polypeptide having at least 90% sequence identity to the polypeptide of SEQ ID NO: 221;
(bd) a polypeptide having at least 90% sequence identity to the polypeptide of SEQ ID NO: 230;
(be) a polypeptide having at least 90% sequence identity to the polypeptide of SEQ ID NO: 233; and
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions.

62. The polypeptide according to embodiments 59 to 61 having improved lysozyme activity a) compared to the lysozyme activity of hen eggwhite lysozyme (HEWL) or b) compared to the lysozyme activity of of SEQ ID NO: 39 as determined by the Method for the Determination of Lysozyme Activity Against *Micrococcus lysodeikticus*.

63. The polypeptide according to embodiment 59 to 61 having improved lysozyme activity a) compared to the lysozyme activity of hen eggwhite lysozyme (HEWL) and/or b) compared to the lysozyme activity of of SEQ ID NO: 39 as determined by any one of i) Method for the Determination of Lysozyme Activity Against *Micrococcus lysodeikticus* and ii) Method for the Determination of Lysozyme Activity Against *Lactobacillus johnsonii*.

64. The peptide according any of embodiment 59 to 63, wherein the polypeptide comprises or consists of amino acids 1 to 207 of SEQ ID NO: 3, amino acids 1 to 201 of SEQ ID NO: 6, amino acids 1 to 208 of SEQ ID NO: 15, amino acids 1 to 207 of SEQ ID NO: 18, amino acids 1 to 208 of SEQ ID NO: 21, amino acids 1 to 207 of SEQ ID NO: 24, amino acids 1 to 208 of SEQ ID NO: 33, amino acids 1 to 208 of SEQ ID NO: 36, amino acids 1 to 206 of SEQ ID NO: 39, amino acids 1 to 216 of SEQ ID NO: 45, amino acids 1 to 218 of SEQ ID NO: 48, amino acids 1 to 204 of SEQ ID NO: 51, amino acids 1 to 203 of SEQ ID NO: 54, amino acids 1 to 208 of SEQ ID NO: 60, amino acids 1 to 208 of SEQ ID NO: 72, amino acids 1 to 217 of SEQ ID NO: 75, amino acids 1 to 208 of SEQ ID NO: 80, amino acids 1 to 207 of SEQ ID NO: 89, amino acids 1 to 201 of SEQ ID NO: 95, amino acids 1 to 202 of SEQ ID NO: 98, amino acids 1 to 206 of SEQ ID NO: 101, amino acids 1 to 202 of SEQ ID NO: 113, amino acids 1 to 206 of SEQ ID NO: 116, amino acids 1 to 207 of SEQ ID NO: 119, amino acids 1 to 208 of SEQ ID NO: 122, amino acids 1 to 215 of SEQ ID NO: 125, amino acids 1 to 217 of SEQ ID NO: 128, amino acids 1 to 214 of SEQ ID NO: 131, amino acids 1 to 203 of SEQ ID NO: 137, amino acids 1 to 207 of SEQ ID NO: 143, amino acids 1 to 208 of SEQ ID NO: 146, amino acids 1 to 207 of SEQ ID NO: 155, amino acids 1 to 207 of SEQ ID NO: 221, amino acids 1 to 207 of SEQ ID NO: 230 or amino acids 1 to 207 of SEQ ID NO: 233.

65. The polypeptide according to embodiment 59 to 63, wherein the polypeptide is selected from the group consisting of a polypeptide having at least 90% sequence identity to the polypeptide of SEQ ID NO: 15, a polypeptide having at least 90% sequence identity to the polypeptide of SEQ ID NO: 36, a polypeptide having at least 90% sequence identity to the polypeptide of SEQ ID NO: 75, a polypeptide having at least 90% sequence identity to the polypeptide of SEQ ID NO: 80, and a polypeptide having at least 90% sequence identity to the polypeptide of SEQ ID NO: 119.

66. A method of hydrolysing peptidoglycan in bacterial cell walls comprising treating bacterial cells with one or more GH25 polypeptides having lysozyme activity, wherein the polypeptide is as defined in any one of embodiment 59 to 63.

67. A method of increasing the digestibility of peptidoglycans in animal feed comprising the use of a peptide as defined in any of embodiment 59 to 63.

68. An animal feed additive comprising the polypeptide as defined in any of embodiment 59 to 63.

68. An animal feed additive according to embodiment 67 further comprising one or more components selected from the list consisting of:
one or more vitamins;
one or more minerals;
one or more amino acids;
one or more prebiotics;
one or more organic acids;
one or more other feed ingredients;
one or more additional enzymes;
one or more probiotics; and
one or more phytogenics 69. An animal feed comprising the polypeptide as defined in any of embodiment 59 to 63.

70. An animal feed according to embodiment 69 further comprising plant based material.

71. A composition comprising the polypeptide of any of embodiment 59 to 63.

72. A polynucleotide encoding the polypeptide of any of embodiment 59 to 63.

73. A recombinant host cell comprising the polynucleotide of embodiment 72 operably linked to one or more control sequences that direct the production of the polypeptide.
74. A method of producing the polypeptide of any of embodiment 59 to 63 comprising:
    (a) cultivating a host cell of claim 16 under conditions conducive for production of the polypeptide; and
    (b) recovering the polypeptide.
75. Use of the polypeptide as disclosed in any of embodiment 59 to 63:
    in animal feed;
    in animal feed additives;
    in the preparation of a composition for use in animal feed; and/or
    for improving the intestinal health in an animal.
76. A zootechnical additive for use in feed for poultry or swine, said additive comprising the polypeptide as defined in any of embodiment 59 to 63.
77. A method of improving the intestinal health in an animal comprising reducing the amount of dead *Lactobacillus johnsonii* cells in the digestive tract of said animal, comprising feeding the animal with a feed or feed additive comprising a polypeptide as defined in any of embodiments 59 to 63.
78. A method of improving the intestinal health in an animal comprising reducing the amount of dead *Lactobacillus johnsonii* cells, or cell wall debris therefrom, in the digestive tract of said animal, comprising feeding the animal with a feed or feed additive comprising a polypeptide selected from the group consisting of a polypeptide having at least 90% sequence identity to the polypeptide of SEQ ID NO: 15, a polypeptide having at least 90% sequence identity to the polypeptide of SEQ ID NO: 36, a polypeptide having at least 90% sequence identity to the polypeptide of SEQ ID NO: 75, a polypeptide having at least 90% sequence identity to the polypeptide of SEQ ID NO: 80, and a polypeptide having at least 90% sequence identity to the polypeptide of SEQ ID NO: 119, preferably selected from the group consisting of a polypeptide having at least 90% sequence identity to the polypeptide of SEQ ID NO: 15, a polypeptide having at least 90% sequence identity to the polypeptide of SEQ ID NO: 36, a polypeptide having at least 90% sequence identity to the polypeptide of SEQ ID NO: 80, and a polypeptide having at least 90% sequence identity to the polypeptide of SEQ ID NO: 119, more preferably a polypeptide having at least 90% sequence identity to the polypeptide of SEQ ID NO: 36 and a polypeptide having at least 90% sequence identity to the polypeptide of SEQ ID NO: 80.
79. A method of improving the intestinal health in an animal comprising reducing the amount of dead *Lactobacillus johnsonii* cells, or cell wall debris therefrom, in the digestive tract of said animal, comprising feeding the animal with a feed or feed additive comprising a polypeptide selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 159.
80. A method of promoting the elimination of dead *Lactobacillus johnsonii* cells, or cell wall debris therefrom, from the digestive tract of an animal comprising feeding said animal a source of a polypeptide as defined in any of embodiment 61 to 63.
81. A method of promoting the elimination of dead *Lactobacillus johnsonii* cells, or cell wall debris therefrom, from the digestive tract of an animal comprising feeding said animal a source of a polypeptide selected from the group consisting of a polypeptide having at least 90% sequence identity to the polypeptide of SEQ ID NO: 15, a polypeptide having at least 90% sequence identity to the polypeptide of SEQ ID NO: 36, a polypeptide having at least 90% sequence identity to the polypeptide of SEQ ID NO: 75, a polypeptide having at least 90% sequence identity to the polypeptide of SEQ ID NO: 80, and a polypeptide having at least 90% sequence identity to the polypeptide of SEQ ID NO: 119, preferably selected from the group consisting of a polypeptide having at least 90% sequence identity to the polypeptide of SEQ ID NO: 15, a polypeptide having at least 90% sequence identity to the polypeptide of SEQ ID NO: 36, a polypeptide having at least 90% sequence identity to the polypeptide of SEQ ID NO: 80, and a polypeptide having at least 90% sequence identity to the polypeptide of SEQ ID NO: 119, more preferably a polypeptide having at least 90% sequence identity to the polypeptide of SEQ ID NO: 36 and a polypeptide having at least 90% sequence identity to the polypeptide of SEQ ID NO: 80.
82. A method of promoting the elimination of dead *Lactobacillus johnsonii* cells, or cell wall debris therefrom, from the digestive tract of an animal comprising feeding said animal a source of a polypeptide selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 159.
83. The method according to any one of embodiments 77 to 82 wherein the polypeptide has a lysozyme activity against *Lactobacillus johnsonii* at 5 ppm that increases optical density (OD) measurement at 405 nm of at least 0.20 as determined by Method for the Determination of Lysozyme Activity Against *Lactobacillus johnsonii*.

The present invention is further described by the following examples that should not be construed as limiting the scope of the invention.

EXAMPLES

Strains

*Escherichia coli* Top-10 strain was purchased from Invitrogen (Life Technologies, Carlsbad, CA, USA) and was used to propagate the expression vectors encoding for lysozyme polypeptides.

*Aspergillus oryzae* strain MT3568 was used for heterologous expression of the lysozyme polypeptide encoding sequences. *A. oryzae* MT3568 is an amdS (acetamidase) disrupted gene derivative of *Aspergillus oryzae* JaL355 (WO 2002/40694) in which pyrG auxotrophy was restored by disrupting the *A. oryzae* acetamidase (amdS) gene with the pyrG gene.

*Aspergillus niger* MBin118 is disclosed in WO 2004/090155.

The fungal strain NN047801 was isolated from litter samples collected from China, in 2003 by the dilution plate method with PDA medium, 25 C. It was then purified by transferring a single conidium onto a PDA agar plate. The strain NN047801 was identified as *Sporormia fimetaria*, based on both morphological characteristics and ITS rDNA sequence.

Strain *Poronia punctata* NN009607 was isolated from Sweden. The strain was inoculated onto a PDA plate and incubated for 7 days at 26° C. in the darkness. Mycelia and spores from the plate were inoculated into 500 ml shake flasks containing 100 mls of YPG medium. The flasks were incubated for 5 days at 26° C. with shaking at 100 rpm.

The fungal strain NN054002 was isolated from soil samples collected from Tibet, China, in 2011 by the dilution plate method with PDA medium, 10 C. It was then purified by transferring a single conidium onto a PDA agar plate. The strain NN054002 was identified as *Lecanicillium* sp., based on both morphological characteristics and ITS rDNA sequence.

Strain *Onygena equina* NN056731 was isolated on Gotland, Sweden. The strain was inoculated onto a PDA plate and incubated for 18 days at 20° C. in the darkness. Mycelia and spores from the plate were inoculated into 500 ml shake flasks containing 100 mls of YPG medium. The flasks were incubated for 18 days at 20° C. with shaking at 100 rpm.

Strain *Purpureocillium lilacinum* NN070261 was isolated from a soil sample from the United States, and inoculated onto a PDA plate and incubated for 8 days at 26° C. in the darkness. Mycelia and spores from the plate were inoculated into 500 ml shake flasks containing 100 mls of YPG medium. The flasks were incubated for 3 days at 26° C. with shaking at 100 rpm.

Strain *Trichobolus zukalii* CBS720.69 was purchased CBS-KNAW Fungal Biodiversity Centre, and inoculated onto a PDA plate and incubated for 7 days at 26° C. in the darkness. Mycelia and spores from the plate were inoculated into 500 ml shake flasks containing 100 mls of YPG medium. The flasks were incubated for 3 days at 26° C. with shaking at 100 rpm.

Strain *Penicillium citrinum* NN070248 was isolated from *Antarctica*. The strain was inoculated onto a PDA plate and incubated for 7 days at 26° C. in the darkness. Mycelia and spores from the plate were inoculated into 500 ml shake flasks containing 100 mls of YPG medium. The flasks were incubated for 6 days at 26° C. with shaking at 100 rpm.

The fungal strain NN057876 was from Professor Cai Lei in Institute of Microbiology, CAS. The strain was collected from a compost sample from China, in 2014 by the dilution plate method with PDA medium, 37 C. It was then purified by transferring a single conidium onto a PDA agar plate. The strain NN047801 was identified as *Cladorrhinum bulbillosum*, based on both morphological characteristics and ITS rDNA sequence.

Strain *Umbelopsis westeae* CBS871.85 was purchased CBS-KNAW Fungal Biodiversity Centre, and inoculated onto a PDA plate and incubated for 7 days at 26° C. in the darkness. Mycelia and spores from the plate were inoculated into 500 ml shake flasks containing 100 mls of YPG medium. The flasks were incubated for 3 days at 26° C. with shaking at 100 rpm.

The fungal strain NN058098 was isolated from soil samples collected from Guizhou Province, China, in 2014 by the dilution plate method with PDA medium pH3, 25C. It was then purified by transferring a single conidium onto a PDA agar plate. The strain NN058098 was identified as *Zygomycetes* sp., based on both morphological characteristics and ITS rDNA sequence.

The fungal strain NN058297 was isolated from litter samples collected from Guizhou Province, China, in 2014 by the dilution plate method with PDA medium, 25C. It was then purified by transferring a single conidium onto a PDA agar plate. The strain NN058297 was identified as *Chaetomium cupreum*, based on both morphological characteristics and ITS rDNA sequence.

*Cordyceps cardinalis* CBS113411 was purchased from CBS-KNAW Fungal Biodiversity Centre, Uppsalalaan 8, 3584 CT, Utrecht, The Netherlands and inoculated onto a PDA plate and incubated for 8 days at 26° C. in the darkness. Several mycelia-PDA plugs were inoculated into 500 ml shake flasks containing 100 mls of YPG medium. The flasks were incubated for 5 days at 26° C. with shaking at 100 rpm.

The fungal strain NN044232 was isolated from soil samples collected from China, in 1998 by the dilution plate method with PDA medium, pH7, 25C. It was then purified by transferring a single conidium onto a PDA agar plate. The strain NN044232 was identified as *Penicillium* sp. 'qii', based on both morphological characteristics and ITS rDNA sequence.

The fungal strain NN058292 was isolated from soil samples collected from Guizhou Province, China, in 2014 by the dilution plate method with PDA medium pH3. It was then purified by transferring a single conidium onto a PDA agar plate. The strain NN058292 was identified as *Aspergillus* sp. nov. XZ2609, based on both morphological characteristics and ITS rDNA sequence.

The fungal strain NN058101 was isolated from soil samples collected from Guizhou Province, China, in 2014 by the dilution plate method with PDA medium pH3, 25C. It was then purified by transferring a single conidium onto a PDA agar plate. The strain NN058101 was identified as *Paecilomyces* sp. XZ2658, based on both morphological characteristics and ITS rDNA sequence.

The fungal strain NN046782 was isolated from soil samples collected from China, in 1998 by the dilution plate method with YG medium, pH7, 45C. It was then purified by transferring a single conidium onto another YG plate. The strain NN046782 was identified as *Rhizomucor pusillus* T185-2, based on both morphological characteristics and ITS rDNA sequence.

The fungal strain NN051201 was isolated from litter samples collected from China, in 2008 by the dilution plate method with PDA medium, 25C. It was then purified by transferring a single conidium onto a PDA agar plate. The strain NN051201 was identified as *Pycnidiophora* cf. *dispera*, based on both morphological characteristics and ITS rDNA sequence.

The fungal strain NN000400 was from CBS with access number as CBS104.75. The strain NN000400 was identified as *Thermomucor indicae-seudaticae*, based on both morphological characteristics and ITS rDNA sequence.

The fungal strain NN054449 was isolated from dead insect samples collected from Tibet, China, in 2012 by the dilution plate method with Horikoshi medium, pH10, 15C. It was then purified by transferring a single conidium onto a PDA agar plate. The strain NN054449 was identified as *Isaria farinosa*, based on both morphological characteristics and ITS rDNA sequence.

The fungal strain NN046871 was isolated from soil samples collected from China, in 2000 by the dilution plate method with YG medium, 37C. It was then purified by transferring a single conidium onto a PDA agar plate. The strain NN046871 was identified as *Zopfiella* sp., based on both morphological characteristics and ITS rDNA sequence.

Strain *Malbranchea flava* CBS132.77 was purchased CBS-KNAW Fungal Biodiversity Centre, and inoculated onto a PDA plate and incubated for 14 days at 26° C. in the darkness. Mycelia and spores from the plate were inoculated into 500 ml shake flasks containing 100 mls of YPG medium. The flasks were incubated for 20 days at 26° C. with shaking at 100 rpm.

Strain *Hypholoma polytrichi* NN057040 was isolated from the Utsjoki region at the northernmost tip of Finland (69° 45' N, 27° 01' E). The strain was inoculated onto a PDA plate and incubated for 10 days at 26° C. in the darkness. Mycelia and spores from the plate were inoculated into 500 ml shake flasks containing 100 mls of YPG medium. The flasks were incubated for 15 days at 26° C. with shaking at 100 rpm.

Strain *Aspergillus deflectus* NN051662 was isolated from Jilin province in China. Please consult NZ China for propagation and DNA isolation conditions otherwise, the following would work: The strain was inoculated onto a PDA plate and incubated for 7 days at 26° C. in the darkness. Mycelia and spores from the plate were inoculated into 500 ml shake flasks containing 100 mls of YPG medium. The flasks were incubated for 5 days at 26° C. with shaking at 100 rpm.

Strain *Ascobolus stictoideus* NN007614 (original code A4-1.1) an isolate from Denmark was purchased from the Institut for Sporeplanter, University of Copenhagen. The strain was inoculated onto a PDA plate and incubated for 7 days at 26° C. in the darkness. Mycelia and spores from the plate were inoculated into 500 ml shake flasks containing 100 mls of YPG medium. The flasks were incubated for 5 days at 26° C. with shaking at 100 rpm.

The fungal strain NN053834 was isolated from soil samples collected from China with a collaboration with the Institute of Microbiology, CAS, in 2011, by the dilution plate method with PDA medium, pH7, 10C. It was then purified by transferring a single conidium onto a PDA agar plate. The strain NN053834 was identified as *Coniochaeta* sp., based on both morphological characteristics and ITS rDNA sequence.

The fungal strain NN054033 was isolated from soil samples collected from China with a collaboration with the Institute of Microbiology, CAS, in 2011, by the dilution plate method with PDA medium, pH7, 10C. It was then purified by transferring a single conidium onto a PDA agar plate. The strain NN054033 was identified as *Daldinia fissa*, based on both morphological characteristics and ITS rDNA sequence.

The fungal strain NN051542 was isolated from rotten corn stover samples collected from China, in 2007 by the dilution plate method with PDA medium, pH7, 25C. It was then purified by transferring a single conidium onto a PDA agar plate. The strain NN051542 was identified as *Rosellinia* sp., based on both morphological characteristics and ITS rDNA sequence.

The fungal strain NN057909 was obtained through a collaboration with Professor Cai Lei in Institute of Microbiology, CAS, in 2014. The strain was collected from China. It was identified as *Ascobolus* sp., based on both morphological characteristics and ITS rDNA sequence.

The fungal strain NN058306 was isolated from soil samples collected from Guizhou Province, China, in 2014 by the dilution plate method with PDA medium pH3. It was then purified by transferring a single conidium onto a PDA agar plate. The strain NN058306 was identified as *Curreya* sp., based on both morphological characteristics and ITS rDNA sequence.

The fungal strain NN043614 was isolated from soil samples collected from, China, in 1998 by the dilution plate method with PDA medium, pH7, 25C. It was then purified by transferring a single conidium onto a PDA agar plate. The strain NN043614 was identified as *Coniothyrium* sp., based on both morphological characteristics and ITS rDNA sequence.

The fungal strain NN047189 was isolated from soil samples collected from, China, in 1998 by the dilution plate method with PDA medium, pH7, 25C. It was then purified by transferring a single conidium onto a PDA agar plate. The strain NN047189 was identified as *Hypoxylon* sp., based on both morphological characteristics and ITS rDNA sequence.

The fungal strain NN043914 was isolated from soil samples collected from, China, in 1998 by the dilution plate method with PDA medium, pH7, 25C. It was then purified by transferring a single conidium onto a PDA agar plate. The strain NN043914 was identified as *Xylariaceae* sp., based on both morphological characteristics and ITS rDNA sequence.

The fungal strain NN046688 was isolated from soil samples collected from China, in 1998 by the dilution plate method with YG medium, pH7, 45C. It was then purified by transferring a single conidium onto another YG plate. The strain NN046688 was identified as *Hypoxylon* sp., based on both morphological characteristics and ITS rDNA sequence.

The fungal strain NN046158 was isolated from soil samples collected from China, in 1998 by the dilution plate method with PDA medium, pH10, 25C. It was then purified by transferring a single conidium onto a PDA agar plate. The strain NN046158 was identified as *Yunnania penicillata*, based on both morphological characteristics and ITS rDNA sequence.

Strain *Engyodontium album* NN042720 was isolated in Denmark. The strain was inoculated onto a PDA plate and incubated for 5 days at 26° C. in the darkness. Mycelia and spores from the plate were inoculated into 500 ml shake flasks containing 100 mls of YPG medium. The flasks were incubated for 5 days at 26° C. with shaking at 100 rpm.

Strain *Metapochonia bulbillosa* XZ2653 NN058096 was isolated from a soil sample from Guizhou China. The strain was inoculated onto a PDA plate and incubated for 5 days at 26° C. in the darkness. Mycelia and spores from the plate were inoculated into 500 ml shake flasks containing 100 mls of YPG medium. The flasks were incubated for 5 days at 26° C. with shaking at 100 rpm.

Strain *Hamigera paravellanea* A3661 NN102174 was isolated in Japan. The strain was inoculated onto a PDA plate and incubated for 5 days at 26° C. in the darkness. Mycelia and spores from the plate were inoculated into 500 ml shake flasks containing 100 mls of YPG medium. The flasks were incubated for 5 days at 26° C. with shaking at 100 rpm.

The fungal strain NN047633 was isolated from dead insect samples collected from China, in 2002 by the dilution plate method with PDA medium, pH7, 25C. It was then purified by transferring a single conidium onto a PDA agar plate. The strain NN047633 was identified as *Metarhizium iadini*, based on both morphological characteristics and ITS rDNA sequence.

The fungal strain NN044936 was isolated from soil samples collected from China, in 1998 by the dilution plate method with YG medium, pH7, 45C. It was then purified by transferring a single conidium onto another YG agar plate. The strain NN044936 was identified as *Thermoascus aurantiacus*, based on both morphological characteristics and ITS rDNA sequence.

The fungal strain NN071248 was isolated from soil samples collected from Shandong Province, China, in 2015 by the dilution plate method with Horikoshi medium, pH10, 25C. It was then purified by transferring a single conidium onto another Horikoshi plate. The strain NN071248 was identified as *Clonostachys rossmaniae*, based on both morphological characteristics and ITS rDNA sequence.

The fungal strain NN046572 was isolated from soil samples collected from China, in 1998 by the dilution plate method with PDA medium, pH7, 25C. It was then purified by transferring a single conidium onto a PDA agar plate. The strain NN046572 was identified as *Simplicillium obclavatum*, based on both morphological characteristics and ITS rDNA sequence.

The fungal strain NN058092 was isolated from soil samples collected from Guizhou Province, China, in 2014 by the dilution plate method with PDA medium pH3, 25C. It was then purified by transferring a single conidium onto a PDA agar plate. The strain NN058092 was identified as *Aspergillus inflatus*, based on both morphological characteristics and ITS rDNA sequence.

The fungal strain NN071247 was isolated from soil samples collected from Shandong Province, China, in 2015 by the dilution plate method with Horikoshi medium, pH10, 25C. It was then purified by transferring a single conidium onto another Horikoshi agar plate. The strain NN071247 was identified as *Paracremonium inflatum*, based on both morphological characteristics and ITS rDNA sequence.

The fungal strain NN046156 was isolated from soil samples collected from China, in 1998 by the dilution plate method with Horikoshi medium, pH10, 25C. It was then purified by transferring a single conidium onto another Horikoshi agar plate. The strain NN046156 was identified as *Westerdykella* sp., based on both morphological characteristics and ITS rDNA sequence.

Strain *Stropharia semiglobata* NN070885 was isolated in Kongstrup Bakker in Denmark. The strain was inoculated onto a PDA plate and incubated for 32 days at 26° C. in the darkness. Mycelia and spores from the plate were inoculated into 500 ml shake flasks containing 100 mls of YPG medium. The flasks were incubated for 14 days at 26° C. with shaking at 100 rpm.

Strain *Gelasinospora cratophora* NN070952 was isolated from a soil sample in Denmark. The strain was inoculated onto a PDA plate and incubated for 2 days at 26° C. in the darkness. Mycelia and spores from the plate were inoculated into 500 ml shake flasks containing 100 mls of YPG medium. The flasks were incubated for 4 days at 26° C. with shaking at 100 rpm.

Strain *Deconica coprophila* MS02928 was isolated from the Denmark. The strain was inoculated onto a half strength PDA plate and incubated for 10 days at 20° C. in the darkness. Mycelia and spores from the plate were inoculated into 500 ml shake flasks containing 100 mls of YPG medium. The flasks were incubated for 15 days at 26° C. with shaking at 100 rpm.

Media and Solutions

DAP4C-1 medium was composed of 0.5 g yeast extract, 10 g maltose, 20 g dextrose, 11 g magnesium sulphate heptahydrate, 1 g dipotassium phosphate, 2 g citric acid monohydrate, 5.2 g potassium phosphate tribasic monohydrate, 1 mL Dowfax 63N10 (antifoaming agent), 2.5 g calcium carbonate, supplemented with 1 mL KU6 metal solution, and deionised water to 1000 mL.

KU6 metal solution was composed of 6.8 g $ZnCl_2$, 2.5 g $CuSO_4·5H_2O$, 0.13 g $NiCl_2$, 13.9 g $FeSO_4·7H_2O$, 8.45 g $MnSO_4·H_2O$, 3 g $C_6H_8O_7·H_2O$, and deionised water to 1000 mL.

YP 2% glucose medium was composed of 10 g yeast extract, 20 g Bacto-peptone, 20 g glucose, and deionised water to 1000 mL.

LB plates were composed of 10 g of Bacto-tryptone, 5 g of yeast extract, 10 g of sodium chloride, 15 g of Bacto-agar, and deionised water to 1000 mL.

LB medium was composed of 10 g of Bacto-tryptone, 5 g of yeast extract, and 10 g of sodium chloride, and deionised water to 1000 mL.

COVE-Sucrose-T plates were composed of 342 g of sucrose, 20 g of agar powder, 20 mL of COVE salt solution, and deionised water to 1000 mL. The medium was sterilized by autoclaving at 15 psi for 15 minutes (Bacteriological Analytical Manual, 8th Edition, Revision A, 1998). The medium was cooled to 60° C. and 10 mM acetamide, Triton X-100 (50 μL/500 mL) were added.

COVE-N-Agar tubes were composed of 218 g Sorbitol, 10 g Dextrose, 2.02 g $KNO_3$, 25 g agar, 50 mL Cove salt solution, and deionised water up to 1000 mL.

COVE salt solution was composed of 26 g of $MgSO_4·7H_2O$, 26 g of KCL, 26 g of $KH_2PO_4$, 50 mL of COVE trace metal solution, and deionised water to 1000 mL.

COVE trace metal solution was composed of 0.04 g of $Na_2B_4O_7·10H_2O$, 0.4 g of $CuSO_4·5H_2O$, 1.2 g of $FeSO_4·7H_2O$, 0.7 g of $MnSO_4·H_2O$, 0.8 g of $Na_2Mo_4·2H_2O$, 10 g of $ZnSO_4·7H_2O$, and deionised water to 1000 mL.

YPM medium contained 1% of Yeast extract, 2% of Peptone and 2% of Maltose.

Hen eggwhite lysozyme (HEWL) was obtained from Sigma-Aldrich #62972

Example 1: Method for the Determination of Lysozyme Activity Against *Micrococcus lysodeikticus* (Reducing End Method)

The lysozyme was diluted in phosphate buffer (5 mM citrate, 5 mM $K_2HPO_4$, 0.01% TritonX-100, pH 5.0) to 50 μg/mL in polypropylene tubes. The diluted lysozyme was further diluted in a 96-well polypropylene microtiter plate to a concentration of 0.7 μg/mL in phosphate buffer (5 mM citrate, 5 mM $K_2HPO_4$, 0.01% TritonX-100, pH 5.0). In a polypropylene deepwell plate 50 μL of the lysozyme dilution was mixed with 450 μL 1% *Micrococcus lysodeikticus* solution (lyophilized *Micrococcus lysodeikticus* ATCC No. 4698 (Sigma M3770) in milli-Q water) and incubated at 40° C. with shaking (500 rpm) for 45 min. After incubation the deepwell plate was centrifuged (4000 g, 5 min) to pellet insoluble material and 100 μL of the supernatant was mixed with 50 μL 3.2M HCl in a 96-well PCR plate and incubated at 95° C. for 80 min. 50 μL of 3.5 M NaOH was added to each well of the PCR plate, and 150 μL of each sample was transferred to a new PCR plate containing 75 μL/well 4-hydroxybenzhydrazide solution in K-Na tartrate/NaOH buffer (50 g/L K-Na tartrate+20 g/L NaOH). The plate was incubated at 95° C. for 10 min before 100 μL/sample was transferred to a clear flat-bottomed microtiter plate for optical density (OD) measurement at 405 nm. OD measurements were performed on three times diluted samples (50 μL sample diluted in 100 μL in Milli-Q water). The OD measurement values represent the difference after the original (background) reading was subtracted. The average OD measurement for hen eggwhite lysozyme by the present method is 0.55 at 0.9 ppm and the average OD measurement for SEQ ID NO 159 is 0.34 at 0.9 ppm (data not shown).

Example 2: Genomic DNA Extraction from Strains
of *Sporormia fimetaria* (SEQ ID NO: 1), *Poronia
punctata* (SEQ ID NO: 4 and 7), *Lecanicillium* sp.
(SEQ ID NO: 10, 13 and 67), *Onygena equina*
(SEQ ID NO: 16), *Purpureocillium lilacinum* (SEQ
ID NO: 19), *Trichobolus zukalii* (SEQ ID NO: 22),
*Penicillium citrinum* (SEQ ID NO: 25), *Cladorrhinum bulbillosum* (SEQ ID NO: 28), *Umbelopsis
westeae* (SEQ ID NO: 31), *Zygomycetes* sp. (SEQ
ID NO: 34), *Chaetomium cupreum* (SEQ ID NO:
37), *Cordyceps cardinalis* (SEQ ID NO: 40), *Penicillium* sp. 'Qii' (SEQ ID NO: 43), *Aspergillus* sp.
Nov. XZ2609 (SEQ ID NO: 46), *Paecilomyces* sp.
XZ2658 (SEQ ID NO: 49 and 52), *Pycnidiophora*
cf. *Dispera* (SEQ ID NO: 58), *Isaria Farinosa*
(SEQ ID NO: 64), *Zopfiella* sp. (SEQ ID NO: 70),
*Malbranchea flava* (SEQ ID NO: 73), *Hypholoma
polytrichi* (SEQ ID NO: 76), *Aspergillus deflectus*
(SEQ ID NO: 81), *Ascobolus stictoideus* (SEQ ID
NO: 84), *Coniochaeta* sp. (SEQ ID NO: 87), *Ascobolus* sp. ZY179 (SEQ ID NO: 96), *Curreya* sp.
XZ2623 (SEQ ID NO: 99), *Coniothyrium* sp. (SEQ
ID NO: 102), *Hypoxylon* sp. (105 and 111), *Xylariaceae* sp. 1653h (SEQ ID NO: 108), *Engyodontium
album* (SEQ ID NO: 117), *Metapochonia Bulbillosa* XZ2653 (SEQ ID NO: 120), *Hamigera paravellanea* A3661 (SEQ ID NO: 123), *Metarhizium
iadini* (SEQ ID NO: 126), *Clonostachys rossmaniae* (SEQ ID NO: 132), *Aspergillus inflatus* (SEQ
ID NO: 138), *Paracremonium inflatum* (SEQ ID
NO: 141), *Westerdykella* sp. (SEQ ID NO: 144),
*Stropharia semiglobata* (SEQ ID NO: 228, 231 and
153), and *Gelasinospora cratophora* (SEQ ID NO:
156)

*Sporormia fimetaria* strain NN047801 was inoculated onto a PDA plate and incubated for 7 days at 28° C. in the darkness. Several mycelia-PDA plugs were inoculated into 500 ml shake flasks containing 100 ml of YPG medium. The flasks were incubated for 3 days at 28° C. with shaking at 160 rpm.

Strain *Poronia punctata* NN009607 was inoculated onto a PDA plate and incubated for 7 days at 26° C. in the darkness. Mycelia and spores from the plate were inoculated into 500 ml shake flasks containing 100 mls of YPG medium. The flasks were incubated for 5 days at 26° C. with shaking at 100 rpm.

*Lecanicillium* sp. strain NN054002 was inoculated onto a PDA plate and incubated for 7 days at 15° C. in the darkness. Several mycelia-PDA plugs were inoculated into 500 ml shake flasks containing 100 ml of YPG medium. The flasks were incubated for 5 days at 20° C. with shaking at 160 rpm.

Strain *Onygena equina* NN056731 was inoculated onto a PDA plate and incubated for 18 days at 20° C. in the darkness. Mycelia and spores from the plate were inoculated into 500 ml shake flasks containing 100 mls of YPG medium. The flasks were incubated for 18 days at 20° C. with shaking at 100 rpm.

Strain *Purpureocillium lilacinum* NN070261 was isolated from a soil sample from the United States, and inoculated onto a PDA plate and incubated for 8 days at 26° C. in the darkness. Mycelia and spores from the plate were inoculated into 500 ml shake flasks containing 100 mls of YPG medium. The flasks were incubated for 3 days at 26° C. with shaking at 100 rpm.

Strain *Trichobolus zukalii* CBS720.69 was purchased CBS-KNAW Fungal Biodiversity Centre, and inoculated onto a PDA plate and incubated for 7 days at 26° C. in the darkness. Mycelia and spores from the plate were inoculated into 500 ml shake flasks containing 100 mls of YPG medium. The flasks were incubated for 3 days at 26° C. with shaking at 100 rpm.

Strain *Penicillium citrinum* NN070248 was inoculated onto a PDA plate and incubated for 7 days at 26° C. in the darkness. Mycelia and spores from the plate were inoculated into 500 ml shake flasks containing 100 mls of YPG medium. The flasks were incubated for 6 days at 26° C. with shaking at 100 rpm.

*Cladorrhinum bulbillosum* strain NN057876 was inoculated onto a PDA plate and incubated for 7 days at 37° C. in the darkness. Several mycelia-PDA plugs were inoculated into 500 ml shake flasks containing 100 ml of YPG medium. The flasks were incubated for 3 days at 37° C. with shaking at 160 rpm.

Strain *Umbelopsis westeae* NN070463 was inoculated onto a PDA plate and incubated for 7 days at 26° C. in the darkness. Mycelia and spores from the plate were inoculated into 500 ml shake flasks containing 100 mls of YPG medium. The flasks were incubated for 3 days at 26° C. with shaking at 100 rpm.

*Zygomycetes* sp. Strain NN058098, *Chaetomium cupreum* strain NN058297 and *Pycnidiophora* cf. *dispera* strain NN051201 were inoculated onto a PDA plate and incubated for 7 days at 25° C. in the darkness. Several mycelia-PDA plugs were inoculated into 500 ml shake flasks containing 100 ml of YPG medium. The flasks were incubated for 3 days at 25° C. with shaking at 160 rpm.

*Cordyceps cardinalis* NN070475 was inoculated onto a PDA plate and incubated for 8 days at 26° C. in the darkness. Several mycelia-PDA plugs were inoculated into 500 ml shake flasks containing 100 mls of YPG medium. The flasks were incubated for 5 days at 26° C. with shaking at 100 rpm.

Strain *Penicillium* sp. 'qii' NN044232 was inoculated onto a PDA plate and incubated for 5 days at 25° C. in the darkness. Mycelia and spores from the plate were inoculated into 500 ml shake flasks containing 100 ml of YPG medium. The flasks were incubated for 4 days at 25° C. with shaking at 100 rpm.

Strain *Aspergillus* sp. nov. XZ2609 NN058292 was inoculated onto a PDA plate and incubated for 5 days at 25° C. in the darkness. Mycelia and spores from the plate were inoculated into 500 ml shake flasks containing 100 ml of YPG medium. The flasks were incubated for 7 days at 25° C. with shaking at 100 rpm.

Strain *Paecilomyces* sp. XZ2658 NN058101 was inoculated onto a PDA plate and incubated for 5 days at 25° C. in the darkness. Mycelia and spores from the plate were inoculated into 500 ml shake flasks containing 100 mls of YPG medium. The flasks were incubated for 5 days at 25° C. with shaking at 100 rpm.

*Isaria farinosa* strain NN054449 was inoculated onto a PDA plate and incubated for 7 days at 15° C. in the darkness. Several mycelia-PDA plugs were inoculated into 500 ml shake flasks containing 100 ml of YPG medium. The flasks were incubated for 4 days at 25° C. with shaking at 160 rpm.

*Zopfiella* sp. strain NN046871 was inoculated onto a PDA plate and incubated for 7 days at 37° C. in the darkness. Several mycelia-PDA plugs were inoculated into 500 ml shake flasks containing 100 ml of YPG medium. The flasks were incubated for 2 days at 37° C. with shaking at 160 rpm.

Strain *Malbranchea flava* NN070411 was inoculated onto a PDA plate and incubated for 14 days at 26° C. in the darkness. Mycelia and spores from the plate were inoculated into 500 ml shake flasks containing 100 mls of YPG medium. The flasks were incubated for 20 days at 26° C. with shaking at 100 rpm.

Strain *Hypholoma polytrichi* NN057040 was inoculated onto a PDA plate and incubated for 10 days at 26° C. in the darkness. Mycelia and spores from the plate were inoculated into 500 ml shake flasks containing 100 mls of YPG medium. The flasks were incubated for 15 days at 26° C. with shaking at 100 rpm.

Strain *Aspergillus deflectus* NN051662 was was inoculated onto a PDA plate and incubated for 7 days at 26° C. in the darkness. Mycelia and spores from the plate were inoculated into 500 ml shake flasks containing 100 mls of YPG medium. The flasks were incubated for 5 days at 26° C. with shaking at 100 rpm.

Strain *Ascobolus stictoideus* NN007614 was inoculated onto a PDA plate and incubated for 7 days at 26° C. in the darkness. Mycelia and spores from the plate were inoculated into 500 ml shake flasks containing 100 mls of YPG medium. The flasks were incubated for 5 days at 26° C. with shaking at 100 rpm.

Strain *Coniochaeta* sp. NN053834 were inoculated onto a PDA plate and incubated for 7 days at 20° C. in the darkness. Several mycelia-PDA plugs were inoculated into 500 ml shake flasks containing 100 ml of YPG medium. The flasks were incubated for 4 days at 20° C. with shaking at 160 rpm.

Strain *Ascobolus* sp. ZY179 NN057909 were inoculated onto a PDA plate and incubated for 7 days at 37° C. in the darkness. Several mycelia-PDA plugs were inoculated into 500 ml shake flasks containing 100 ml of YPG medium. The flasks were incubated for 5 days at 37° C. with shaking at 160 rpm.

Strain *Curreya* sp. XZ2623 NN058306 were inoculated onto a PDA plate and incubated for 7 days at 25° C. in the darkness. Several mycelia-PDA plugs were inoculated into 500 ml shake flasks containing 100 ml of YPG medium. The flasks were incubated for 7 days at 25° C. with shaking at 160 rpm.

Strain *Coniothyrium* sp. NN043614 were inoculated onto a PDA plate and incubated for 7 days at 25° C. in the darkness. Several mycelia-PDA plugs were inoculated into 500 ml shake flasks containing 100 ml of YPG medium. The flasks were incubated for 7 days at 25° C. with shaking at 160 rpm.

Strain *Hypoxylon* sp. NN047189 were inoculated onto a PDA plate and incubated for 7 days at 25° C. in the darkness. Several mycelia-PDA plugs were inoculated into 500 ml shake flasks containing 100 ml of YPG medium. The flasks were incubated for 7 days at 25° C. with shaking at 160 rpm.

Strain *Xylariaceae* sp. 1653h NN043914 were inoculated onto a PDA plate and incubated for 7 days at 37° C. in the darkness. Several mycelia-PDA plugs were inoculated into 500 ml shake flasks containing 100 ml of YPG medium. The flasks were incubated for 5 days at 37° C. with shaking at 160 rpm.

Strain *Hypoxylon* sp. NN046688 were inoculated onto a PDA plate and incubated for 7 days at 37° C. in the darkness. Several mycelia-PDA plugs were inoculated into 500 ml shake flasks containing 100 ml of YPG medium. The flasks were incubated for 4 days at 37° C. with shaking at 160 rpm.

Strain *Engyodontium album* NN042720 was inoculated onto a PDA plate and incubated for 5 days at 26° C. in the darkness. Mycelia and spores from the plate were inoculated into 500 ml shake flasks containing 100 mls of YPG medium. The flasks were incubated for 5 days at 26° C. with shaking at 100 rpm.

Strain *Metapochonia bulbillosa* XZ2653 NN058096 was inoculated onto a PDA plate and incubated for 5 days at 26° C. in the darkness. Mycelia and spores from the plate were inoculated into 500 ml shake flasks containing 100 mls of YPG medium. The flasks were incubated for 5 days at 26° C. with shaking at 100 rpm.

Strain *Hamigera paravellanea* A3661 NN102174 was inoculated onto a PDA plate and incubated for 5 days at 26° C. in the darkness. Mycelia and spores from the plate were inoculated into 500 ml shake flasks containing 100 mls of YPG medium. The flasks were incubated for 5 days at 26° C. with shaking at 100 rpm.

Strain *Metarhizium iadini* NN047633 were inoculated onto a PDA plate and incubated for 7 days at 25° C. in the darkness. Several mycelia-PDA plugs were inoculated into 500 ml shake flasks containing 100 ml of YPG medium. The flasks were incubated for 5 days at 25° C. with shaking at 160 rpm.

Strain *Clonostachys rossmaniae* NN071248 were inoculated onto a PDA plate and incubated for 7 days at 25° C. in the darkness. Several mycelia-PDA plugs were inoculated into 500 ml shake flasks containing 100 ml of YPG medium. The flasks were incubated for 4 days at 25° C. with shaking at 160 rpm.

Strain *Aspergillus inflatus* NN058092 were inoculated onto a PDA plate and incubated for 7 days at 25° C. in the darkness. Several mycelia-PDA plugs were inoculated into 500 ml shake flasks containing 100 ml of YPG medium. The flasks were incubated for 5 days at 25° C. with shaking at 160 rpm.

Strain *Paracremonium inflatum* NN071247 were inoculated onto a PDA plate and incubated for 7 days at 25° C. in the darkness. Several mycelia-PDA plugs were inoculated into 500 ml shake flasks containing 100 ml of YPG medium. The flasks were incubated for 4 days at 25° C. with shaking at 160 rpm.

Strain *Westerdykella* sp. NN046156 were inoculated onto a PDA plate and incubated for 7 days at 25° C. in the darkness. Several mycelia-PDA plugs were inoculated into 500 ml shake flasks containing 100 ml of YPG medium. The flasks were incubated for 7 days at 25° C. with shaking at 160 rpm.

Strain *Stropharia semiglobata* NN070885 was inoculated onto a PDA plate and incubated for 32 days at 26° C. in the darkness. Mycelia and spores from the plate were inoculated into 500 ml shake flasks containing 100 mls of YPG medium. The flasks were incubated for 14 days at 26° C. with shaking at 100 rpm.

Strain *Gelasinospora cratophora* NN070952 was inoculated onto a PDA plate and incubated for 2 days at 26° C. in the darkness. Mycelia and spores from the plate were inoculated into 500 ml shake flasks containing 100 mls of YPG medium. The flasks were incubated for 4 days at 26° C. with shaking at 100 rpm.

Strain *Deconica coprophila* MS02928 was inoculated onto a half strength PDA plate and incubated for 10 days at 20° C. in the darkness. Mycelia and spores from the plate were inoculated into 500 ml shake flasks containing 100 mls of YPG medium. The flasks were incubated for 15 days at 26° C. with shaking at 100 rpm.

In all cases, the mycelia were collected by filtration through MIRACLOTH® (Calbiochem, La Jolla, CA, USA) and frozen under liquid nitrogen. Frozen mycelia were ground, by a mortar and a pestle, to a fine powder, and genomic DNA was isolated using DNeasy Plant Maxi Kit (24) (QIAGEN GmbH, Hilden, Germany) following the manufacturer's instructions.

Example 3: Genomic DNA Extraction from *Rhizomucor pusillus* T185-2 (SEQ ID NO: 225) and *Thermomucor indicae-Seudaticae* (SEQ ID NO: 61)

*Rhizomucor pusillus* T185-2 NN046782 was inoculated onto a PDA plate and incubated for 3 days at 45° C. in the darkness. Mycelia and spores from the plate were inoculated into 500 ml shake flasks containing 100 mls of FG4 medium. The flasks were incubated for 3 days at 45° C. with shaking at 100 rpm.

*Thermomucor indicae-seudaticae* strain NN000400 was inoculated onto a PDA plate and incubated for 7 days at 45° C. in the darkness. Several mycelia-PDA plugs were inoculated into 500 ml shake flasks containing 100 ml of YPG medium. The flasks were incubated for 3 days at 45° C. with shaking at 160 rpm.

In all cases, the mycelia were collected by filtration through MIRACLOTH® (Calbiochem, La Jolla, CA, USA) and frozen under liquid nitrogen. Frozen mycelia were ground, by a mortar and a pestle, to a fine powder, and genomic DNA was isolated using a method developed by Scott O. Rogers & Arnold J. Bendich (Plant Molecular Biology 5: 69-76, 1985).

Example 4: Genomic DNA Extraction from *Daldinia fissa* (SEQ ID NO: 90)

Strain *Daldinia fissa* NN054033 were inoculated onto a PDA plate and incubated for 15 days at 15° C. in the darkness.

The mycelia were collected by scraping from agar plate with the sterilized scalpel and frozen under liquid nitrogen. Frozen mycelia were ground, by a mortar and a pestle, to a fine powder, and genomic DNA was isolated using FastDNA spin kit for soil (MP Biomedicals, Santa Ana, California, USA) following the manufacturer's instruction.

Example 5: Genomic DNA Extraction from *Rosellinia* sp-51542 (SEQ ID NO: 93), *Yunnania penicillata* (SEQ ID NO: 114) and *Simplicillium obclavatum* (SEQ ID NO: 135)

Strain *Rosellinia* sp-51542 NN051542 were inoculated onto a PDA plate and incubated for 7 days at 37° C. in the darkness. Several mycelia-PDA plugs were inoculated into 500 ml shake flasks containing 100 ml of YPG medium. The flasks were incubated for 4 days at 37° C. with shaking at 160 rpm.

Strain *Yunnania penicillata* NN046158 were inoculated onto a PDA plate and incubated for 7 days at 25° C. in the darkness. Several mycelia-PDA plugs were inoculated into 500 ml shake flasks containing 100 ml of YPG medium. The flasks were incubated for 4 days at 25° C. with shaking at 160 rpm.

Strain *Simplicillium obclavatum* NN046572 were inoculated onto a PDA plate and incubated for 7 days at 25° C. in the darkness. Several mycelia-PDA plugs were inoculated into 500 ml shake flasks containing 100 ml of YPG medium. The flasks were incubated for 4 days at 25° C. with shaking at 160 rpm.

In all cases, the mycelia were collected by filtration through MIRACLOTH® (Calbiochem, La Jolla, CA, USA) and frozen under liquid nitrogen. Frozen mycelia were ground, by a mortar and a pestle, to a fine powder, and genomic DNA was isolated using MP Faster DNA spin Kit (MP Biomedicals, Santa Ana, California, USA) following the manufacturer's instruction.

Example 6: Genomic DNA Extraction from *Thermoascus aurantiacus* (SEQ ID NO: 129)

Strain *Thermoascus aurantiacus* NN044936 were inoculated onto a PDA plate and incubated for 7 days at 45° C. in the darkness. Several mycelia-PDA plugs were inoculated into 500 ml shake flasks containing 100 ml of YPG medium. The flasks were incubated for 3 days at 45° C. with shaking at 160 rpm.

The mycelia were collected by filtration through MIRACLOTH® (Calbiochem, La Jolla, CA, USA) and frozen under liquid nitrogen. Frozen mycelia were ground, by a mortar and a pestle, to a fine powder, and genomic DNA was isolated using Large-Scale Column Fungal DNAout (Win Honor Bioscience Limited, Beijing, China) following the manufacturer's instruction.

Example 7: Genome Sequencing, Assembly and Annotation of *Sporormia fimetaria* (SEQ ID NO: 1), *Thermomucor indicae-Seudaticae* (SEQ ID NO: 61), *Thermoascus aurantiacus* (SEQ ID NO: 129)

The extracted genomic DNA samples of *Thermoascus aurantiacus*, *Sporormia fimetaria* and *Thermomucor indicae-seudaticae* were delivered to Beijing Genome Institute (BGI, Shenzhen, China) for genome sequencing using an ILLUMINA® GA2 System (Illumina, Inc., San Diego, CA, USA). The raw reads were assembled at BGI using program SOAPdenovo (Li et al., 2010, *Genome Research*, 20: 265-72). The assembled sequences were analyzed using standard bioinformatics methods for gene identification and functional prediction. GeneMark-ES fungal version (Ter-Hovhannisyan V et al., 2008, *Genome Research*, 18(12): 1979-1990) was used for gene prediction. Blastall version 2.2.10 (Altschul et al., 1990, *Journal of Molecular Biology*, 215(3): 403-410, ftp://ftp.ncbi.nlm.nih.gov/blast/executables/release/2.2.10/) and HMMER version 2.1.1 (National Center for Biotechnology Information (NCBI), Bethesda, MD, USA) were used to predict function based on structural homology. The GH25 family lysozymes were identified directly by analysis of the Blast results. The Agene program (Munch and Krogh, 2006, *BMC Bioinformatics*, 7:263) and SignalP program (Nielsen et al., 1997, *Protein Engineering*, 10: 1-6) were used to identify start codons. SignalP program was further used to predict signal peptides. Pepstats (Rice et al., 2000, *Trends Genet*, 16(6): 276-277) was used to predict isoelectric points and molecular weights.

Example 8: Genome Sequencing, Assembly and Annotation of *Cladorrhinum Bulbillosum* (SEQ ID NO: 28), *Zygomycetes* sp. (SEQ ID NO: 34), *Chaetomium cupreum* (SEQ ID NO: 37), *Ascobolus* sp. ZY179 (SEQ ID NO: 96), *Curreya* sp. XZ2623 (SEQ ID NO: 99), *Hypoxylon* sp. (105 and 111), *Xylariaceae* sp. 1653h (SEQ ID NO: 108), *Metarhizium iadini* (SEQ ID NO: 126), *Clonostachys rossmaniae* (SEQ ID NO: 132), *Simplicillium obclavatum* (SEQ ID NO: 135), *Paracremonium inflatum* (SEQ ID NO: 141) and *Westerdykella* sp. (SEQ ID NO: 144)

The extracted genomic DNA samples of *Cladorrhinum bulbillosum*, *Zygomycetes* sp. *Ascobolus* sp. ZY179, *Curreya* sp. XZ2623, *Coniothyrium* sp., *Hypoxylon* sp., *Xylari*- aceae sp. 1653h, *Metarhizium iadini, Clonostachys* rossmaniae, *Simplicillium obclavatum, Paracremonium inflatum, Westerdykella* sp. and *Chaetomium cupreum* were delivered to Novozymes Davis (USA) for genome sequencing using an ILLUMINA® MiSeq System. The raw reads were assembled at Novozymes Denmark using program Spades (Anton Bankevich et al., 2012, *Journal of Computational Biology*, 19(5): 455-477). The assembled sequences were analyzed using standard bioinformatics methods for gene identification and function prediction. GeneMark-ES fungal version (Ter-Hovhannisyan V et al., 2008, *Genome Research* 18(12): 1979-1990) was used for gene prediction. Blastall version 2.2.10 (Altschul et al., 1990, *Journal of Molecular Biology*, 215(3): 403-410, ftp://ftp.ncbi.nlm.nih.gov/blast/executables/release/2.2.10/) and HMMER version 2.1.1 (National Center for Biotechnology Information (NCBI), Bethesda, MD, USA) were used to predict function based on structural homology. The GH25 family lysozymes were identified directly by analysis of the Blast results. The Agene program (Munch and Krogh, 2006, *BMC Bioinformatics*, 7:263) and SignalP program (Nielsen et al., 1997, *Protein Engineering*, 10: 1-6) were used to identify start codons. SignalP program was further used to predict signal peptides. Pepstats (Rice et al., 2000, *Trends Genet*, 16(6): 276-277) was used to predict isoelectric points and molecular weights.

Example 9: Genome Sequencing, Assembly and Annotation of *Lecanicillium* sp. (SEQ ID NO: 10, 13 and 67), *Pycnidiophora* cf. *Dispera* (SEQ ID NO: 58), *Isaria farinosa* (SEQ ID NO: 64), *Zopfiella* sp. (SEQ ID NO: 70), *Coniochaeta* sp. (SEQ ID NO: 87), *Daldinia fissa* (SEQ ID NO: 90), *Rosellinia* sp-51542 (SEQ ID NO: 93), *Coniothyrium* sp. (SEQ ID NO: 102) and *Yunnania penicillata* (SEQ ID NO: 114)

The extracted genomic DNA samples of *Coniochaeta* sp., *Daldinia fissa, Rosellinia* sp., *Yunnania penicillata, Lecanicillium* sp., *lsaria farinosa, Pycnidiophora* cf. *dispera* and *Zopfiella* sp. were delivered to Fasteris (Switzerland) for genome sequencing using an ILLUMINA® HiSeq 2000 System (Illumina, Inc., San Diego, CA, USA). The raw reads were assembled at Novozymes Denmark using program Idba (Peng, Yu et al., 2010, *Research in Computational Molecular Biology*, 6044:426-440. Springer Berlin Heidelberg.). The assembled sequences were analyzed using standard bioinformatics methods for gene identification and function prediction. GeneMark-ES fungal version (Ter-Hovhannisyan V et al., 2008, *Genome Research* 18(12): 1979-1990) was used for gene prediction. Blastall version 2.2.10 (Altschul et al., 1990, *Journal of Molecular Biology*, 215(3): 403-410, ftp://ftp.ncbi.nlm.nih.gov/blast/executables/release/2.2.10/) and HMMER version 2.1.1 (National Center for Biotechnology Information (NCBI), Bethesda, MD, USA) were used to predict function based on structural homology. The GH25 family lysozymes were identified directly by analysis of the Blast results. The Agene program (Munch and Krogh, 2006, *BMC Bioinformatics*, 7:263) and SignalP program (Nielsen et al., 1997, *Protein Engineering*, 10: 1-6) were used to identify start codons. SignalP program was further used to predict signal peptides. Pepstats (Rice et al., 2000, *Trends Genet*, 16(6): 276-277) was used to predict isoelectric points and molecular weights.

Example 10: Genome Sequencing, Assembly and Annotation of *Aspergillus inflatus* (SEQ ID NO: 138)

The extracted genomic DNA samples of *Aspergillus inflatus* were delivered to Exiqon A/S (Denmark) for genome sequencing using an ILLUMINA® MiSeq System (Illumina, Inc., San Diego, CA, USA). The raw reads were assembled at Novozymes Denmark using program Spades (Anton Bankevich et al., 2012, *Journal of Computational Biology*, 19(5): 455-477). The assembled sequences were analyzed using standard bioinformatics methods for gene identification and function prediction. GeneMark-ES fungal version (Ter-Hovhannisyan V et al., 2008, *Genome Research* 18(12): 1979-1990) was used for gene prediction. Blastall version 2.2.10 (Altschul et al., 1990, *Journal of Molecular Biology*, 215(3): 403-410, ftp://ftp.ncbi.nlm.nih.gov/blast/executables/release/2.2.10/) and HMMER version 2.1.1 (National Center for Biotechnology Information (NCBI), Bethesda, MD, USA) were used to predict function based on structural homology. The GH25 family lysozymes were identified directly by analysis of the Blast results. The Agene program (Munch and Krogh, 2006, *BMC Bioinformatics*, 7:263) and SignalP program (Nielsen et al., 1997, *Protein Engineering*, 10: 1-6) were used to identify start codons. SignalP program was further used to predict signal peptides. Pepstats (Rice et al., 2000, *Trends Genet*, 16(6): 276-277) was used to predict isoelectric points and molecular weights.

Example 11: Genome Sequencing, Assembly and Annotation of *Poronia punctata* (SEQ ID NO: 4 and 7), *Onygena equina* (SEQ ID NO: 16), *Purpureocillium lilacinum* (SEQ ID NO: 19), *Trichobolus Zukaffi* (SEQ ID NO: 22), *Penicillium citrinum* (SEQ ID NO: 25), *Umbelopsis westeae* (SEQ ID NO: 31), *Cordyceps cardinalis* (SEQ ID NO: 40), *Penicillium* Sp. 'Qii' (SEQ ID NO: 43), *Aspergillus* sp. Nov. XZ2609 (SEQ ID NO: 46), *Paecilomyces* sp. XZ2658 (SEQ ID NO: 49 and 52), *Rhizomucor pusillus* T185-2 (SEQ ID NO: 225), *Malbranchea flava* (SEQ ID NO: 73), *Hypholoma polytrichi* (SEQ ID NO: 76), *Aspergillus deflectus* (SEQ ID NO: 81), *Ascobolus stictoideus* (SEQ ID NO: 84), *Engyodontium Album* (SEQ ID NO: 117), *Metapochonia bulbillosa* XZ2653 (SEQ ID NO: 120), *Hamigera paravellanea* A3661 (SEQ ID NO: 123), *Stropharia semiglobata* (SEQ ID NO: 228, 231 and 153) and *Gelasinospora cratophora* (SEQ ID NO: 156)

The extracted genomic DNA samples of *Cordyceps cardinalis, Malbranchea flava, Poronia punctata, Gelasinospora cratophora, Penicillium* sp. 'qii', *Paecilomyces* sp. XZ2658 *Aspergillus* sp. nov. XZ2609, *Metapochonia bulbillosa* XZ2653, *Stropharia semiglobata, Hamigera paravellanea, Rhizomucor pusillus* T185-2, *Umbelopsis westeae, Hypholoma polytrichi, Trichobolus zukalii, Purpureocillium lilacinum, Penicillium citrinum, Ascobolus stictoideus, Engyodontium album, Onygena equina* and *Aspergillus deflectus* were genome sequenced using an ILLUMINA® HiSeq 2000 System (Illumina, Inc., San Diego, CA, USA).

The raw reads of *Cordyceps cardinalis, Malbranchea flava, Poronia punctata, Gelasinospora cratophora, Penicillium* sp. 'qii', *Paecilomyces* sp. XZ2658 *Aspergillus* sp. nov. XZ2609, *Metapochonia bulbillosa* XZ2653, *Stropharia semiglobata* and *Umbelopsis westeae* were assembled using program Spades (Anton Bankevich et al., 2012, Journal of Computational Biology, 19(5): 455-477). *Hypholoma polytrichi, Trichobolus zukalii, Purpureocillium lilacinum, Penicillium citrinum, Ascobolus stictoideus, Engyodontium album, Onygena* equine, *Hamigera paravellanea, Rhizomucor pusillus* T185-2 and *Aspergillus deflectus* were assembled using program Idba (Peng Yu et al., 2010, Research in Computational Molecular Biology. 6044:426-440. Springer Berlin Heidelberg.) The assembled sequences were analyzed using standard bioinformatics methods for gene identification and function prediction. GeneMark-ES fungal version (Ter-Hovhannisyan V et al., 2008, Genome Research 18(12): 1979-1990) was used for gene prediction. Blastall version 2.2.10 (Altschul et al., 1990, Journal of Molecular Biology. 215(3): 403-410, ftp://ftp.ncbi.nlm.nih.gov/blast/executables/release/2.2.10/) and HMMER version 2.1.1 (National Center for Biotechnology Information (NCBI), Bethesda, MD, USA) were used to predict function based on structural homology. The GH25 family lysozyme polypeptides were identified directly by analysis of the Blast results. The Agene program (Munch and Krogh, 2006, BMC Bioinformatics 7: 263) and SignalP program (Nielsen et al., 1997, Protein Engineering 10: 1-6) were used to identify start codons. SignalP program was further used to predict signal peptides. Pepstats (Rice et al., 2000, Trends in Genetics. 16(6): 276-277) was used to predict isoelectric points and molecular weights.

Example 12: Cloning and Expression of GH25 Lysozymes (SEQ ID NO: 1, 10, 13, 28, 34, 37, 58, 61, 64, 67 and 70)

Eleven fungal GH25 lysozyme wild type sequences were cloned from *Sporormia fimetaria* (SEQ ID NO: 1), *Lecanicillium* sp. WMM742 (SEQ ID NO: 10, 13, 67), *Cladorrhinum bulbillosum* (SEQ ID NO: 28), *Zygomycetes* sp. (SEQ ID NO: 34), *Chaetomium cupreum* (SEQ ID NO: 37), *Pycnidiophora* cf. *dispera* (SEQ ID NO: 58), *Thermomucor indicae-seudaticae* (SEQ ID NO:61), *lsaria farinosa* (SEQ ID NO: 64) and *Zopfiella* sp. (SEQ ID NO: 70).

The fungal GH25 lysozymes were cloned into an *Aspergillus oryzae* expression vector pCaHj505 as described in WO2013029496. The transcription of the GH25 lysozyme coding sequence with the native secretion signal was under the control of an *Aspergillus oryzae* alpha-amylase gene promoter.

The final expression plasmids were individually transformed into an *Aspergillus oryzae* expression host. The GH25 lysozyme genes were integrated by homologous recombination into the *Aspergillus oryzae* host genome upon transformation. Four transformants of each transformation were selected from the selective media agar plate and inoculated to 3 ml of YPM medium in 24-well plate and incubated at 30° C., 150 rpm. After 3 days incubation, 20 µl of supernatant from each transformant were analyzed on NuPAGE Novex 4-12% Bis-Tris Gel w/MES according to the manufacturer's instructions. The resulting gel was stained with Instant Blue. SDS-PAGE profiles of the cultures showed that all 11 genes were expressed with 1 or 2 protein bands each detected at 20 KD, 25 KD, 25 KD, 20 KD, 20 KD, 20 KD, 20 KD, 18 & 22 KD, 25 KD, 25 KD and 20 KD respectively. The recombinant *Aspergillus oryzae* strain with the strongest protein band were selected for shaking flask culturing and were inoculated on slant made of slant medium and incubated at 37 C for 6-7 days. When strains were well grown to fully sporulated, they were inoculated to 2 L shaking flasks each containing 400 ml of YPM and 4-8 flasks for each strain. Flasks were shaking at 80 rpm, 30C. Cultures were harvested on day 3 and filtered using a 0.45 µm DURAPORE Membrane and were purified as described in Examples 20 to 30 respectively.

Example 13: Cloning and Expression of GH25 Lysozymes (SEQ ID NO: 87, 90, 93, 96, 99, 102, 105, 108, 111, 114, 126, 129, 132, 135, 138, 141 and 144)

Seventeen fungal GH25 lysozyme wild type sequences were cloned from *Coniochaeta* sp. (SEQ ID NO: 87), *Daldinia fissa* (SEQ ID NO: 90), *Rosellinia* sp. (SEQ ID NO: 93), *Ascobolus* sp. (SEQ ID NO: 96), *Curreya* sp. (SEQ ID NO: 99), *Coniothyrium* sp. (SEQ ID NO: 102), *Hypoxylon* sp. (SEQ ID NO:105), *Xylariaceae* sp. (SEQ ID NO: 108), *Hypoxylon* sp. (SEQ ID NO: 111), *Yunnania penicillata* (SEQ ID NO: 114), *Metarhizium iadini* (SEQ ID NO: 126), *Thermoascus aurantiacus* (SEQ ID NO: 129), *Clonostachys rossmaniae* (SEQ ID NO: 132), *Simplicillium obclavatum* (SEQ ID NO: 135), *Aspergillus inflatus* (SEQ ID NO: 138), *Paracremonium inflatum* (SEQ ID NO: 141), and *Westerdykella* sp. (SEQ ID NO: 144). The fungal GH25 lysozymes were cloned into an *Aspergillus oryzae* expression vector pCaHj505 as described in WO2013029496. The transcription of the GH25 lysozyme coding sequence with the native secretion signal was under the control of an *Aspergillus oryzae* alpha-amylase gene promoter.

The final expression plasmids were individually transformed into an *Aspergillus oryzae* expression host. The GH25 lysozyme genes were integrated by homologous recombination into the *Aspergillus oryzae* host genome upon transformation. Four transformants of each transformation were selected from the selective media agar plate and inoculated to 3 ml of YPM or Dap4C medium in 24-well plate and incubated at 30° C., 150 rpm. After 3 days incubation, 20 µl of supernatant from each transformant were analyzed on NuPAGE Novex 4-12% Bis-Tris Gel w/MES according to the manufacturer's instructions. The resulting gel was stained with Instant Blue. SDS-PAGE profiles of the cultures showed that all 17 genes were expressed with 1 or 2 protein bands each detected at 20 KD, 20 KD, 20 KD, 20 KD, 20 KD, 20 KD, 20 KD, 20 KD, 20 KD, 20 KD, 25 & 28 KD, 25 KD, 26 KD, 24 KD, 26 KD, 26 KD and 20 KD respectively. The recombinant *Aspergillus oryzae* strain with the strongest protein band were selected for shaking flask culturing and were inoculated on slant made of slant medium and incubated at 37 C for 6-7 days. When strains were well grown to fully sporulated, they were inoculated to 2 L shaking flasks each containing 400 ml of Dap4C and 2-6 flasks for each strain. Flasks were shaking at 80 rpm, 30C. Cultures were harvested on day 3 and filtered using a 0.45 µm DURAPORE Membrane and were purified as described in Examples 31 to 47 respectively.

Example 13: Construction of the Improved Split-Marker *Aspergillus oryzae* Host (DAU)

Figure 1:
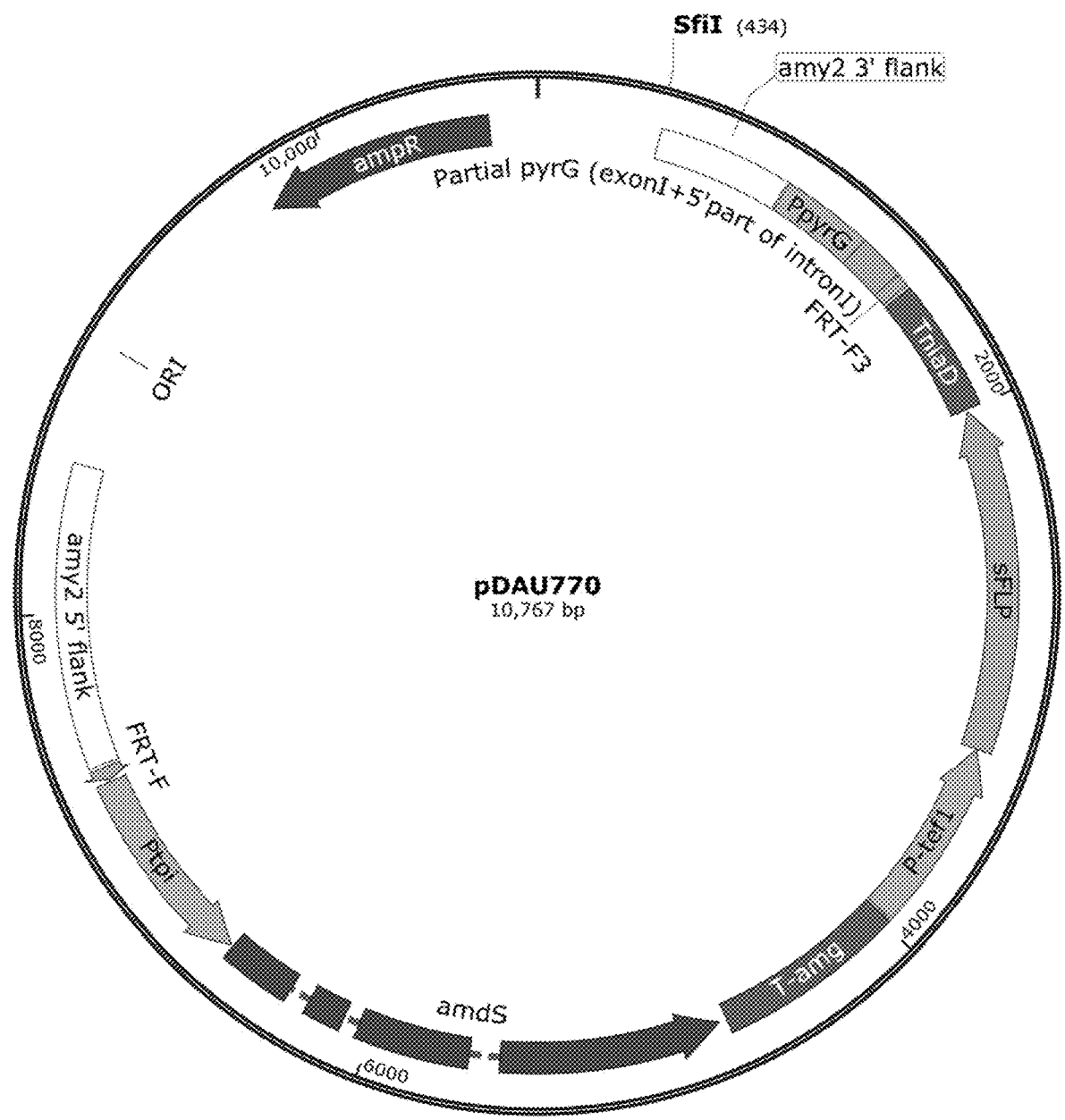
FIG. 1 represents the map of the different DNA features included on the plasmid pDAu770. The amy2 locus flanking regions (3' and 5') are indicated by white boxes. Promoter regions are indicated by green boxes for the promoter region of the pyrG, tef1 and tpi gene. The purple boxes indicate the selection cassette (ampR for ampicillin resistance and amdS for acetamide selection). The terminator regions are indicated by blue boxes for the terminator region of the niaD and amg genes. The coding region of the FLPase (sFLP) and the first exon of the pyrG gene are indicated in orange. The 5' region of the pyrG intron is indicated in grey. The origin of replication of the plasmid is indicated by ORI.
Figure 2:
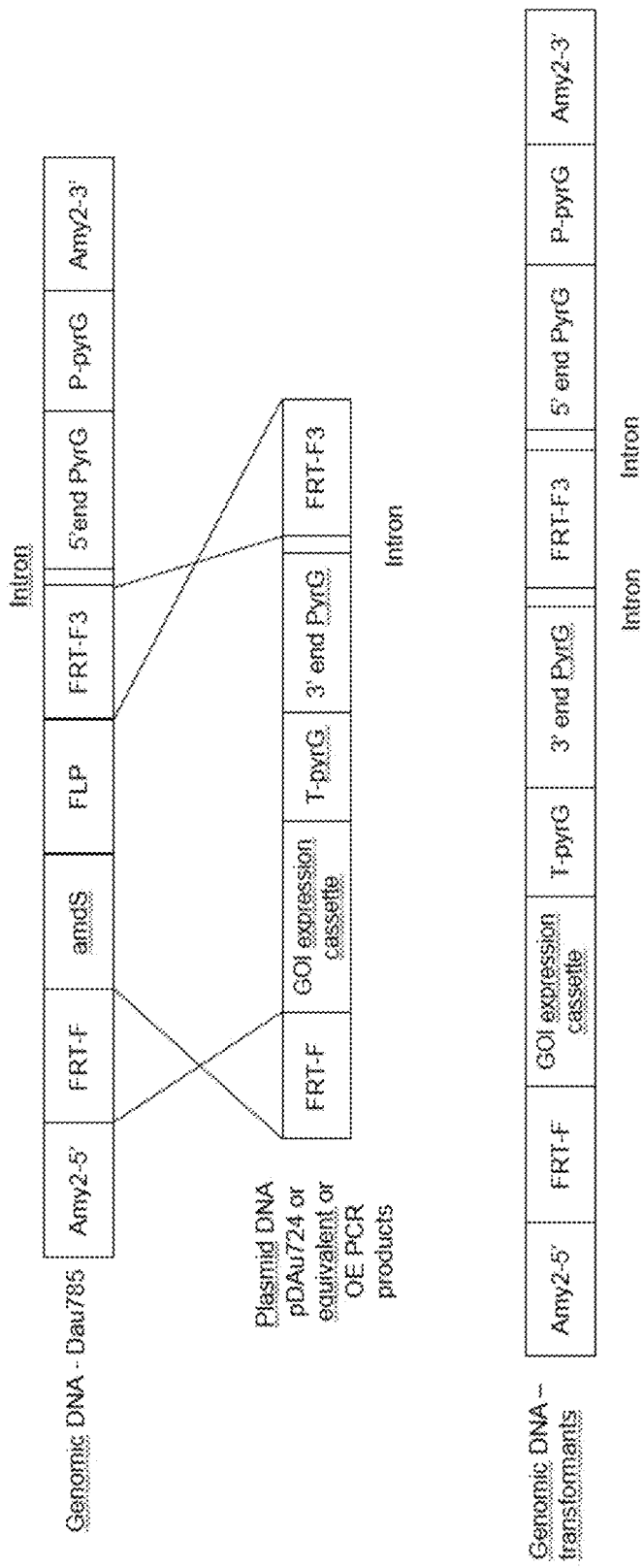
FIG. 2 is the schematic representation of transformation of the host strain DAu785 by the transforming DNA (either plasmid pDAu724 or derivatives or OverlapExtension PCR products.

An improved *Aspergillus oryzae* host/vector system comparable to the one described in example 5 disclosed in WO 2016026938A1 was constructed. The improvement was made to reduce the size of the transforming DNA by moving the FLPase expression cassette located on PART-11 of the plasmid pDAu724 (see page 34 in WO 2016026938A1, FIG. 7 and SEQ ID NO: 30) to the integration locus amy2 in the genome of the host strain. The cloning of the FLPase expression cassette into pDAu703 (WO 2016026938A1 page 32 and FIG. 6 and SEQ ID NO: 29) was done by amplification of the FLPase expression cassette from pDAu724 and cloning in between FRT-F3 and the amdS selection marker of pDAu703 to give the plasmid pDAu770 (FIG. 1, SEQ ID NO: 216). The same protocol as described in WO 2016026938A1 page 33 was used to transform the linearized plasmid pDAu770 into protoplasts of *A. oryzae* strain Jal1338 (disclosed in WO2012/160097). Transformants were selected on AmdS selection plates to obtain strain DAu785. The resulting recombinant host strain DAu785 has a modified amy2 locus comparable to the one in DAU716 (WO2016/026938) with the addition of the FLPase expression cassette (FIG. 2, top panel). The host strain DAu785 is now constitutively expressing the FLPase site specific recombinase allowing the integration at the FRT sites of the transforming DNA in this case the PCR fragments obtained by Overlap Extension PCR reaction (FIG. 2, middle and bottom panels) and described in Example 17 below.

Example 14: PCR Amplification and InFusion Cloning of Lysozyme Encoding Sequences SEQ ID NO: 16, 19, 25, 31, 40, 73 and 117

Based on the lysozyme gene sequences identified by genome mining in *Onygena equina, Purpureocillium lilacinum, Malbranchea flava, Engyodontium album, Penicillium citrinum, Umbelopsis westeae,* and *Cordyceps cardinalis,* InFusion cloning primers were designed and ordered (Sigma Aldrich, Darmstadt, Germany) (see list in table 2 below).

TABLE 2

InFusion cloning primers

| Primer* | Primer SEQ ID NO: | Primer to lysozyme SEQ ID NO: | Sequence |
|---|---|---|---|
| C8VRJ-F | 162 | 16 | ACACAACTGGGGATCCACCATGTTGAAAA CAATTATCTATACCACCCTTGCC |
| C8VRJ-R | 163 | 16 | AGATCTCGAGAAGCTTAGCCCTTTGCAAA TCGTTGCAATCC |
| C8VRQ-F | 164 | 19 | ACACAACTGGGGATCCACCATGAAGTTCG CATCCGTCGCC |
| C8VRQ-R | 165 | 19 | AGATCTCGAGAAGCTTAACCGGCGTTGGC AATCTTCTT |
| C8VS9-F | 166 | 25 | ACACAACTGGGGATCCACCATGCGCCCCT CCGTCATATTGC |
| C8VS9-R | 167 | 25 | AGATCTCGAGAAGCTTAAGCAGAAAACAC GTTCAAATCAAACTTCTTACT |
| C8VSA-F | 168 | 31 | ACACAACTGGGGATCCACCATGAAGCTCA CCTTTGCCTCTCTAACT |
| C8VSA-R | 169 | 31 | AGATCTCGAGAAGCTTAGGCTCCTTTGGC CATCCTAGACA |
| C8VSC-F | 170 | 40 | ACACAACTGGGGATCCACCATGCGCGCCT TTATTCCAGTCTT |
| C8VSC-R | 171 | 40 | AGATCTCGAGAAGCTTAGGCAGAGAAAAC GTTGAGATCAAATTTCTTG |
| C8VRT-F | 172 | 73 | ACACAACTGGGGATCCACCATGAAGCTGT CTCTCCTCCTTATTGTTGC |
| C8VRT-R | 173 | 73 | AGATCTCGAGAAGCTTAACCTAGGGCCAT TCTCTTCAACCC |
| C8VS8-F | 174 | 117 | ACACAACTGGGGATCCACCATGAAGTCTT TTGGTGTTATTGCTACCGG |
| C8VS8-R | 175 | 117 | AGATCTCGAGAAGCTTAGCCTCTGGCGAT TCTCTGAAGC |

*-F—forward primer; -R—reverse primer

PCR amplifications of SEQ ID NO: 16, 19, 25, 31, 40, 73 and 117 encoding for lysozyme polypeptides were carried out using Phusion High-Fidelity DNA polymerase (New England Biolabs, BioNordika Denmark A/S, Herlev, Denmark) in a 50 μL volume reaction. The PCR reaction mixes were consisting of 10 μL Phusion reaction buffer HF (5×); 1 μL of PCR nucleotide Mix (10 mM); 2 μL forward cloning primers (2.5 mM); 2 μL reverse cloning primers (2.5 mM); 1 μL Phusion High-Fidelity DNA Polymerase #M0530L (2000 U/mL); and PCR grade water up to 50 μL. PCR reactions were incubated on a thermocycler T100 (Biorad, Hercules, California, USA) using the following program: initial denaturation of 2 min at 98° C. followed by 30 cycles of 10 sec at 98° C., 2 min at 72° C. and ending up by a final elongation of 10 min at 72° C. PCR amplicons were purified using AMPure XP beads system kit (Agencourt, Beverly, Massachusetts, USA) adapted on a Biomek FXp Liquid handler (Beckman Coulter, Brea, California, USA).

InFusion cloning was made using InFusion HD Plus EcoDry Cloning system kit (Takara, Kusatsu, Japan) in expression vector pDAu109 (WO 2005042735) previously digested with BamHI and HindIII restriction enzymes and following manufacturer's instructions.

A 2.5 μL volume of the five time diluted ligation mixtures was used to transform *E. coli* TOP10 (see strain chapter) chemically competent cells (Life Technologies, Carlsbad, CA, USA). Three colonies were selected from LB agar plates containing 100 μg of ampicillin per ml and cultivated overnight in 3 mL of LB medium supplemented with 100 μg of ampicillin per ml. Plasmids DNA were purified using a Qiagen Spin Miniprep kit (Cat. 27106) (QIAGEN GmbH, Hilden, Germany) according to the manufacturer's instructions.

Lysozyme sequences cloned by InFusion were scrutinized for errors by Sanger DNA sequencing.

Forward and reverse oligonucleotide primers shown below were designed to PCR amplify the GH25 open reading frame from the genomic DNA samples. An IN-FUSION™ Cloning Kit (Clontech, Mountain View, CA, USA) was used to clone the fragment directly into the expression vector pDau109 (WO 2005/042735).

Example 15: PCR Amplification and InFusion Cloning of Lysozyme Encoding Sequences SEQ ID NO: 43, 46, 49 and 52

BamHI-XhoI based cloning from *Penicillium* sp. 'qii' (SEQ ID NO: 43), *Paecilomyces* sp. XZ2658 (SEQ ID NO: 46 and 49) and *Aspergillus* sp. nov. XZ2609 (SEQ ID NO: 52).

The forward and reverse PCR primers shown in table 3 were used to generate an EcoRI-XhoI flanked cloning cassette from the genomic DNA prepared above for the following samples:

TABLE 3

PCR primers

| Primer* | Primer SEQ ID NO: | Primer to lysozyme SEQ ID NO: | Sequence |
|---|---|---|---|
| WIN1054-F | 188 | 43 | 5'-ACACAACTGGGGATCCACCATGAAG ACTACGGGTGTC |
| WIN1054-R | 189 | 43 | 5'-CCCTCTAGATCTCGAGTTAAGAACC CTTGGCAAAG |
| WIN1065-F | 190 | 46 | 5'-ACACAACTGGGGATCCACCATGAAG TTCACTACCATTGC |
| WIN1065-R | 191 | 46 | 5'-CCCTCTAGATCTCGAGCTACCCCTC GACAATCTT |
| WIN1057-F | 192 | 49 | 5'-ACACAACTGGGGATCCACCATGAAG TCTGTTGCTGTCT |
| WIN1057-R | 193 | 49 | 5'-CCCTCTAGATCTCGAGCTAAGAAGC ATTCGCAATGC |
| WIN1058-F | 194 | 52 | 5'-ACACAACTGGGGATCCACCATGAAG CTCACGAGTGTG |
| WIN1058-R | 195 | 52 | 5'-CCCTCTAGATCTCGAGTTACGAACC TCTAGCAAGC |

*-F—forward primer; -R—reverse primer

Bold letters represent coding sequence. The underlined sequence is homologous to the insertion sites of pDau109.

The PCR reaction (25 μl) was composed of 12.5 μl of 2×IPROOF™ HF Master Mix, 0.5 μl of appropriate forward primer (100 μM), 0.5 μl of the appropriate reverse primer (100 μM), 0.5 μl of genomic (100 ng/μl), and 11 μl of deionized water. The PCR reaction was incubated in a DYAD® Dual-Block Thermal Cycler (MJ Research Inc., Waltham, MA, USA) programmed for 1 cycle at 98° C. for 30 seconds; 30 cycles each at 98° C. for 10 seconds, 55° C. for 10 seconds, and 72° C. for 60 seconds; and 1 cycle at 72° C. for 10 minutes. Samples were cooled to 10° C. before removal and further processing.

Five μl of the PCR reaction were analyzed by 1% agarose gel electrophoresis using TAE buffer where an DNA band of the appropriate size was observed. In the case of WIN1054 for example, an approximately 700 base pair band was observed. The remaining PCR reactions were purified using an ILLUSTRA™ GFX™ PCR DNA and Gel Band Purification Kit according to the manufacturer's instructions.

The fragments were then cloned into BamHI and XhoI digested pDau109 using an IN-FUSION™ Cloning Kit resulting in plasmids containing the inserts. Cloning of the GH25 lysozyme PCR inserts into Bam HI-XhoI digested pDau109 resulted in the transcription of the cloned genes under the control of a NA2-tpi double promoter. NA2-tpi is a modified promoter from the gene encoding the *Aspergillus niger* neutral alpha-amylase in which the untranslated leader has been replaced by an untranslated leader from the gene encoding the *Aspergillus nidulans* triose phosphate isomerase. Isolated plasmids were sequenced with vector primers in order to determine a representative plasmid expression clone that was free of PCR errors.

Example 16: PCR Amplification and InFusion Cloning of Lysozyme Encoding Sequences SEQ ID NO: 4, 7, 22, 225, 76, 81 and 84

BamHI-HindIII based cloning of *Hypholoma polytrichi* (SEQ ID NO: 76), *Aspergillus deflectus* (SEQ ID NO: 81), *Trichobolus zukalii* (SEQ ID NO: 22), *Rhizomucor pusillus* (SEQ ID NO: 225), *Poronia punctata* (SEQ ID NO: 4 and 7) and *Ascobolus stictoideus* (SEQ ID NO: 84).

The forward and reverse PCR primers shown in table 4 were used to generate an BamHI-HindIII flanked cloning cassette from the genomic DNA prepared above for the following samples.

TABLE 4

| | | | |
|---|---|---|---|
| PCR primers | | | |
| Primer* | Primer SEQ ID NO: | Primer to lysozyme SEQ ID NO: | Sequence |
| KKSC0132-F | 196 | 4 | 5'-ACACAACTGGGGATCCACCATGAA GTCTTACATCGCCCCC |
| KKSC0132-R | 197 | 4 | 5'-GTGCGGCCGCAAGCTTAATCAGAG GCTTCCTCCCATAGG |
| KKSC0133-F | 198 | 7 | 5'-ACACAACTGGGGATCCACCATGAA GTATCTCGTTCCCCTTTTG |
| KKSC0133-R | 199 | 7 | 5'-AGATCTCGAGAAGCTTATTAGCCC TTAGCCAGTCTCTT |
| KKSC0311-F | 200 | 22 | 5'-ACACAACTGGGGATCCACCATGAA GCTCACCACTTTTATCACG |
| KKSC0311-R | 201 | 22 | 5'-CTAGATCTCGAGAAGCTTTTAAGT CCCCTTGGCAAGCG |
| KKSC0314-F | 202 | 225 | 5'-ACACAACTGGGGATCCACCATGAA GTTTGCACTCCTAGTATCTG |
| KKSC0314-R | 203 | 225 | 5'-CTAGATCTCGAGAAGCTTTTAGCC ATAGTAGTTCTTGTCCCA |
| KKSC0862-F | 204 | 76 | 5'-ACACAACTGGGGATCCACCATGGC AAAGCTCCTCAAG |
| KKSC0862-R | 205 | 76 | 5'-AGATCTCGAGAAGCTTATTAGTGG GCGAAGACGTT |
| KKSC0819-F | 206 | 81 | 5-ACACAACTGGGGATCCACCATGAAG CTTCTTTCCGCCCT |
| KKSC0819-R | 207 | 81 | 5'-AGATCTCGAGAAGCTTATCACTGA GAGGCAAACTTGAC |
| KKSC0317-F | 208 | 84 | 5'-ACACAACTGGGGATCCACCATGGC TTCCAGACTGACCCT |
| KKSC0317-F | 209 | 84 | 5'-CTAGATCTCGAGAAGCTTTTAAGC TGCCACGCACTGGG |

*-F—forward primer; -R—reverse primer

Bold letters represent coding sequence. The underlined sequence is homologous to the insertion sites of pDau109.

The PCR reaction (25 µl) was composed of 12.5 µl of 2×IPROOF™ HF Master Mix, 0.5 µl of appropriate forward primer (100 µM), 0.5 µl of the appropriate reverse primer (100 µM), 0.5 µl of genomic (100 ng/µl), and 11 µl of deionized water. The PCR reaction was incubated in a DYAD® Dual-Block Thermal Cycler (MJ Research Inc., Waltham, MA, USA) programmed for 1 cycle at 98° C. for 30 seconds; 30 cycles each at 98° C. for 10 seconds, 55° C. for 10 seconds, and 72° C. for 60 seconds; and 1 cycle at 72° C. for 10 minutes. Samples were cooled to 10° C. before removal and further processing.

Five µl of the PCR reaction were analyzed by 1% agarose gel electrophoresis using TAE buffer where an DNA band of the appropriate size was observed. In the case of KKSC0317 for example, an approximately 860 base pair band was observed. The remaining PCR reactions were purified using an ILLUSTRA™ GFX™ PCR DNA and Gel Band Purification Kit according to the manufacturer's instructions.

The fragments were then cloned into BamHI and HindIII digested pDau109 using an IN-FUSION™ HD Plus EcoDry Cloning system kit (Takara, Kusatsu, Japan). Cloning of the GH25 lysozyme PCR inserts into BamHI-HindIII digested pDau109 resulted in the transcription of the cloned genes under the control of a NA2-tpi double promoter. NA2-tpi is a modified promoter from the gene encoding the *Aspergillus niger* neutral alpha-amylase in which the untranslated leader has been replaced by an untranslated leader from the gene encoding the *Aspergillus nidulans* triose phosphate isomerase. Isolated plasmids were sequenced with vector primers in order to determine a representative plasmid expression clone that was free of PCR errors.

Example 17: Overlap Extension PCR Cloning (SEQ ID NO: 120, 123, 228, 231, 153 and 156)

pDAu724 plasmid was used as DNA template to amplify two PCR products (F1 and F3) in reactions composed of 10 µL of KAPA polymerase buffer 5×, 1 µL 10 mM KAPA PCR Nucleotide Mix, 1 µL of 10 µM of the appropriate forward primers (SEQ ID NO: 210 for F1 and SEQ ID NO: 212 for F3), 1 µL of 10 µM of the appropriate reverse primers (SEQ ID NO: 211 for F1 and SEQ ID NO: 213 for F3), 1 to 10 ng of pDAu724 plasmid, 1 µL of KAPA Biosystems polymerase KK2502 (1 unit) and PCR-grade water up to 50 µL.

PCR amplification reactions were carried out on a DYAD® Dual-Block Thermal Cycler (MJ Research Inc., Waltham, MA, USA) programmed for 2 min. at 98° C. and followed by 35 cycles of 10 sec. at 98° C. and 2 min. at 72° C. and one final cycle of 10 min. at 72° C.

Five µl of the PCR reaction were analyzed by 1% agarose gel electrophoresis using TAE buffer where DNA bands of the appropriate size were observed. The remaining PCR reactions were purified using an ILLUSTRA™ GFX™ PCR DNA and Gel Band Purification Kit according to the manufacturer's instructions.

```
Forward primer F1:
SEQ ID NO: 210: GAATTCGAGCTCGGTACCTTGAAGTTC

Reverse primer F1:
SEQ ID NO: 211: GGTGGATCCCCAGTTGTGTATATAGAGGATT

Forward primer F3:
SEQ ID NO: 212: TGCGCGGCGCGGCTGGGTCGACTCTA

Reverse primer F3:
SEQ ID NO: 213: TTCACACAGGAAACAGCTATGACCATG
```

Overlap Extension PCR reaction for cloning lysozyme genes amplified from *Gelasinospora cratophora*, *Metapochonia bulbillosa*, *Hamigera paravellanea*, and *Stropharia semiglobata* (3 sequences) gDNAs were composed of 10 µL KAPA polymerase buffer (5×), 1 µL 10 mM KAPA PCR Nucleotide Mix, 50 ng of PCR fragment F1 and equimolar amounts of PCR fragment F3 and lysozyme genes encoding for SEQ ID NO: 120, 123, 228, 231, 153 and 156, 1 µl KAPA Biosystems polymerase KK2502 (1 unit) and PCR-grade water up to 48 µL. Reaction were incubated on a DYAD® Dual-Block Thermal Cycler (MJ Research Inc., Waltham, MA, USA) using a program composed of 2 min. at 98° C.; followed by 5 cycles each composed of 10 sec. at 98° C., 30 sec. at 68° C., and 5 min. at 72° C. and completed by a final extension of 8 min. at 72° C.

During the OE PCR reactions, annealing between fragment F1 and lysozyme genes encoding for SEQ ID NO: 120, 123, 228, 231, 153 and 156 respectively were ensured by overlap SEQ ID NO: 214 included in the forward cloning primers (C6ZGC-F; C6ZG7-F; C122PC-F; C122PA-F; C122P9-F and C122P5-F respectively, table 4a) and annealing between fragment F3 and the lysozyme genes encoding for SEQ ID NO: 120, 123, 228, 231, 153 and 156 respectively were ensured by the overlapping SEQ ID NO: 215 included in the reverse cloning primers (C6ZGC-R; C6ZG7-R; C122PC-R; C122PA-R; C122P9-R and C122P5-R respectively, table 4a).

TABLE 4a

Cloning primers

| Primer* | Primer SEQ ID NO: | Primer to lysozyme SEQ ID NO: | Sequence |
| --- | --- | --- | --- |
| C122P5-F | 176 | 156 | CTATATACACAACTGGGGATCCACCATGA AGTCCTTCGTCCTCACGGC |
| C122P5-R | 177 | 156 | TAGAGTCGACCCAGCCGCGCCGGCCATTA AGATCCCTTAGCAAGAGCCTTAAGGC |
| C6ZGC-F | 178 | 120 | CTATATACACAACTGGGGATCCACCATGA AGTCTGTTACTTTCATCGCCAGTCT |
| C6ZGC-R | 179 | 120 | TAGAGTCGACCCAGCCGCGCCGGCCATTA CGAAGCGTTAGCAATACGCTTAAGC |

TABLE 4a-continued

Cloning primers

| Primer* | Primer SEQ ID NO: | Primer to lysozyme SEQ ID NO: | Sequence |
|---|---|---|---|
| C6ZG7-F | 180 | 123 | CTATATACACAACTGGGGATCCACCATGA AGGCTTCTTCCATCCTCTCCC |
| C6ZG7-R | 181 | 123 | TAGAGTCGACCCAGCCGCGCCGGCCATCA TCCACTCGCCAACTTCTTCAAC |
| C122PC-F | 182 | 228 | CTATATACACAACTGGGGATCCACCATGT TCTCTTTCGTCAAAGCGCTCA |
| C122PC-R | 183 | 228 | TAGAGTCGACCCAGCCGCGCCGGCCATTA ATTTGCAAAGACATTGAGGTCGAATTGGC |
| C122PA-F | 184 | 231 | CTATATACACAACTGGGGATCCACCATGT TCCCTTTCGTCAAAACGCTCA |
| C122PA-R | 185 | 231 | TAGAGTCGACCCAGCCGCGCCGGCCATTA ATTTGCAAACACATTGAGGTCGAATTGG |
| C122P9-F | 186 | 153 | CTATATACACAACTGGGGATCCACCATGG TCAAAATCTTGAGCCTTCTAGCC |
| C122P9-R | 187 | 153 | TAGAGTCGACCCAGCCGCGCCGGCCACTA TGCGAATACGCTCAGGTCGAATTG |

One μL of 10 μM primer SEQ1 and 1 μL of 10 μM primer SEQ4 were added to the OE PCR reactions and the reactions were incubated a second time on a DYAD® Dual-Block Thermal Cycler (MJ Research Inc., Waltham, MA, USA) using a program composed of 2 min at 98° C.; followed by 25 cycles each composed of 10 sec. at 98° C., and 4 min. at 72° C. and completed by a final extension of 10 min. at 72° C.

Five μl of the PCR reactions were analyzed by 1% agarose gel electrophoresis using TAE buffer where an DNA bands of the appropriate size were observed. The remaining PCR reactions were up-concentrated to 20 μL by heating the tubes at 60° C. 10 μL of those reactions were used for *Aspergillus oryzae* DAu785 protoplasts transformation.

Primer bind forward SEQ ID NO: 214:
CTATATACACAACTGGGGATCCACC

Primer bind reverse SEQ ID NO: 215:
TAGAGTCGACCCAGCCGCGCCGGCCA

Example 18: Preparation and Expression of *Aspergillus* Protoplasts (SEQ ID NO: 16, 19, 25, 31, 40, 73, 117, 120, 123, 228, 231, 153 and 156)

Protoplasts of *Aspergillus oryzae* MT3568 were prepared according to WO 95/002043. One hundred μl of protoplasts were mixed with 1-3 μg of the *Aspergillus* expression vectors or OE PCRs (for SEQ ID NO: 16, 19, 25, 31, 40, 73, 117, 120, 123, 228, 231, 153 and 156) and 250 μL of 60% PEG 4000 (Applichem, Darmstadt, Germany) (polyethylene glycol, molecular weight 4,000), 10 mM $CaCl_2$, and 10 mM Tris-HCl pH 7.5 and gently mixed. The mixtures were incubated at 37° C. for 30 minutes and the protoplasts were spread onto COVE plates for selection. After incubation for 4-7 days at 37° C. spores of four transformants were inoculated into 0.2 mL of YP+2% glucose or DAP4C-1 medium in 96 well microtiter plates. After 4 days cultivation at 30° C., the culture broths were analysed by SDS-PAGE to identify transformants producing the highest amounts of lysozyme enzymes.

Spores of the best transformants for each transformation were spread onto COVE plates containing 0.01% TRITON® X-100 in order to isolate single colonies. The spreading was repeated twice in total on COVE plates containing 10 mM sodium nitrate. Spores were then inoculated into 500 mL shake flasks containing 100 mL of YP+2% glucose and incubated for 4 days at 30° C. with shaking at 100 rpm.

Previously selected strains were inoculated in 250 mL shake flasks with baffle containing 100 to 150 mL of DAP4C-1 supplemented lactic acid and with diammonium phosphate or YP2% glucose medium and fermented during 4 days at a temperature of 30° C. under 150 rpm agitation. Culture broths were harvested by filtration using a 0.2 μm filter device.

The culture broths can be purified as described in Example 48.

Example 19: Expression of GH25 Lysozymes in *Aspergillus oryzae* (SEQ ID NO: 4, 7, 22, 43, 46, 49, 52, 225, 76, 81 and 84)

Protoplasts of *Aspergillus oryzae* MT3568 were prepared according to WO 95/002043. One hundred μl of protoplasts were mixed with 1-3 μg of one of the following *Aspergillus* expression vectors: SEQ ID NO: 4, 7, 22, 43, 46, 49, 52, 225, 76, 81 and 84.

Six ul containing about 3.0 μg total DNA was used for the transformation. The DNA was gently added to 100 μl of *A. oryzae* MT3568 protoplasts and 250 μl of 60% PEG 4000 (Sigma-Aldrich cat. No. 95904). The 60% (W/V) PEG 4000 was prepared in the following manner: PEG 4000 powder was dissolved in double distilled $H_2O$ and then heated for 10-20 seconds in a microwave oven at 800 watt until dissolved. The dissolved solution was cooled down to room temperature and then then adjusted with CaCl2) solution and Tris-HCl solution (pH 7.5) for a final concentration of 10 mM of each. After adding the 60% PEG 4000 solution, the tube was gently mixed and incubated at 37° C. for 30 minutes. The mix was added to 6 ml of top agar with 10 mM acetamide and plated onto COVE-sorbitol plates with 10 mM acetamide.

The plates were incubated at 37° C. for 3 or more days and then moved to 26° C. for two days. Spores from 4 to 8 individual colonies were picked by first dipping a white 10 µl inoculation pin (Nunc A/S, Denmark) in a 0.1% TWEEN® 80 solution, contacting the sporulating colony on the selection plate, and restreaking with the pin onto fresh COVE sorbitol plates containing 10 mM acetamide. After 5 days at 26° C., spores from the restreaked colonies were used to inoculate a 96 well deep dish plate (NUNC, cat. no. 260251, Thermoscientific, USA). The wells of the deep dish plate contained 500 uls of either YP+2% glucose or DAP4C media. The inoculated plate was sealed with gas permeable tape (89009-656, VWR.com). Plates were incubated stationary at 30 C for 5 days. Expression was verified by analysis of 20 uls of harvested culture fluid on SDS-PAGE using a NUPAGE® 10% Bis-Tris gel (Invitrogen, Carlsbad, CA, USA) and Coomassie blue staining. One transformant for each transformation experiment was selected for further work.

Spores of of each designated transformant were inoculated into both YP+2% glucose medium and DAP-4C-1 medium (100 mls in 500 ml Erlenmeyer shake flask with baffles). The cultures were incubated at 26° C. and 150 rpm, 3 days and if necessary 4 days. An SDS gel was run as above to test protein amount.

After incubation for 4-7 days at 37° C. spores of four transformants were inoculated into 0.2 mL of YP+2% glucose or DAP4C-1 medium in 96 well microtiter plates. After 4 days cultivation at 30° C., the culture broths were analysed by SDS-PAGE to identify transformants producing the highest amounts of lysozyme enzymes.

The culture broths were purified as described in Example 48.

Example 20: Purification of SEQ ID NO: 3

The culture supernatant of O23CD8 was firstly precipitated with ammonium sulfate (80% saturation), then the precipitation was added water to adjust conductance to about 170 mS/cm. The solution was filtered with 0.45 um filter and then loaded into Phenyl Sepharose 6 Fast Flow column (GE Healthcare) equilibrated with 20 mM NaAc at pH5.0 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity. The fractions with lysozyme activity were analyzed by SDS-PAGE, and then concentrated, changed buffer by 20 mM PBS at pH6.0 for further evaluation. The protein concentration was determined by Qubit® Protein Assay Kit (Invitrogen, cat Q33212).

Example 21: Purification of SEQ ID NO: 12

The culture supernatant of O23T24 was firstly precipitated with ammonium sulfate (80% saturation), then dialyzed with 20 mM NaAc at pH5.5. The solution was filtered with 0.45 um filter and then loaded into SP Fast Flow column (GE Healthcare) equilibrated with 20 mM NaAc at pH5.5. A gradient increase of NaCl concentration was applied as elution buffer from zero to 1M, and then elution fractions and flow-through fraction were collected to detect lysozyme activity. The fractions with lysozyme activity were analyzed by SDS-PAGE, and then pooled and concentrated for further evaluation. The protein concentration was determined by Qubit® Protein Assay Kit (Invitrogen, cat Q33212).

Example 22: Purification of SEQ ID NO: 15

The culture supernatant of O23T22 was firstly precipitated with ammonium sulfate (80% saturation), then dialyzed with 20 mM NaAc at pH4.5. The solution was filtered with 0.45 um filter and then loaded into SP Fast Flow column (GE Healthcare) equilibrated with 20 mM NaAc at pH4.5. A gradient increase of NaCl concentration was applied as elution buffer from zero to 1M, and then elution fractions and flow-through fraction were collected to detect lysozyme activity. The fractions with lysozyme activity were analyzed by SDS-PAGE, and then pooled together.

Since the purified sample has more than two bands, the conductivity of sample was adjusted to 140 mS/cm, and then loaded into a Phenyl HP column (GE Healthcare), which was equilibrated by 20 mM PBS at pH6.0 with 1.2M $(NH_4)_2SO_4$ added. A gradient decrease of $(NH_4)_2SO_4$ concentration was applied as elution buffer from 1.2M to zero, and then elution fractions and flow-through fraction were collected to detect lysozyme activity. The fractions with lysozyme activity were analyzed by SDS-PAGE, and then pooled and concentrated. The buffer of sample was changed by 20 mM PBS at pH6.0 for further evaluation. The protein concentration was determined by Qubit® Protein Assay Kit (Invitrogen, cat Q33212).

Example 23: Purification of SEQ ID NO: 30

The culture supernatant of O233Q7 was firstly precipitated with ammonium sulfate (80% saturation), then dialyzed with 20 mM NaAc at pH4.5. The solution was filtered with 0.45 um filter and then loaded into SP Fast Flow column (GE Healthcare) equilibrated with 20 mM NaAc at pH4.5. A gradient increase of NaCl concentration was applied as elution buffer from zero to 1M, and then elution fractions and flow-through fraction were collected to detect lysozyme activity. The fractions with lysozyme activity were analyzed by SDS-PAGE, and then pooled and concentrated for further evaluation. The protein concentration was determined by Qubit® Protein Assay Kit (Invitrogen, cat Q33212).

Example 24: Purification of SEQ ID NO: 36

The culture supernatant of O23CD9 was firstly precipitated with ammonium sulfate (80% saturation), then the precipitation was added water to adjust conductance to about 170 mS/cm. The solution was filtered with 0.45 um filter and then loaded into Phenyl Sepharose 6 Fast Flow column (GE Healthcare) equilibrated with 20 mM PBS at pH7.5 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity. The fractions with lysozyme activity were analyzed by SDS-PAGE, and then concentrated, changed buffer by 20 mM PBS at pH6.0 for further evaluation. The protein concentration was determined by Qubit® Protein Assay Kit (Invitrogen, cat Q33212).

Example 25: Purification of SEQ ID NO: 39

The culture supernatant of O233Q9 was firstly precipitated with ammonium sulfate (80% saturation), then the precipitation was added water to adjust conductance to about 190 mS/cm. The solution was filtered with 0.45 um filter and then loaded into Phenyl Sepharose 6 Fast Flow column (GE Healthcare) equilibrated with 20 mM PBS at pH6.5 with 1.8M $(NH_4)_2SO_4$ added. A gradient decrease of $(NH_4)_2SO_4$ concentration was applied as elution buffer from 1.8M to zero, and then elution fractions and flow-through fraction were collected to detect lysozyme activity. The fractions with lysozyme activity were analyzed by SDS-PAGE, pooled together, and then concentrated. The buffer of final sample was changed by 20 mM PBS at pH6.0 for further evaluation. The protein concentration was determined by Qubit® Protein Assay Kit (Invitrogen, cat Q33212).

Example 26: Purification of SEQ ID NO: 60

The culture supernatant of O234A2 was firstly precipitated with ammonium sulfate (80% saturation), then dialyzed with 20 mM NaAc at pH4.5. The solution was filtered with 0.45 um filter and then loaded into Capto SP column (GE Healthcare) equilibrated with 20 mM NaAc at pH4.5. A gradient increase of NaCl concentration was applied as elution buffer from zero to 1M, and then elution fractions and flow-through fraction were collected to detect lysozyme activity. The fractions with lysozyme activity were analyzed by SDS-PAGE, pooled together, and then concentrated for further evaluation. The protein concentration was determined by Qubit® Protein Assay Kit (Invitrogen, cat Q33212).

Example 27: Purification of SEQ ID NO: 63

The culture supernatant of 0241RS was firstly precipitated with ammonium sulfate (80% saturation), then the precipitation was added water to adjust conductance to about 160 mS/cm. The solution was filtered with 0.45 um filter and then loaded into Phenyl Sepharose 6 Fast Flow column (GE Healthcare) equilibrated with 20 mM NaAc at pH4.5 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity.

Since most lysozyme activity was kept in flow-through fraction, the conductivity of sample was adjusted to 180 mS/cm and loaded again into Phenyl Sepharose 6 Fast Flow column (GE Healthcare) equilibrated with 20 mM NaAc at pH4.5 with 1.8M $(NH_4)_2SO_4$ added. A gradient decrease of $(NH_4)_2SO_4$ concentration was applied as elution buffer from 1.8M to zero, and then elution fractions and flow-through fraction were collected to detect lysozyme activity. The fractions with lysozyme activity were analyzed by SDS-PAGE, but two major protein bands were found.

The fractions with lysozyme activity were pooled together and dialyzed with 20 mM NaAc at pH4.5. The sample was loaded into Capto SP column (GE Healthcare) equilibrated with 20 mM NaAc at pH4.5. A concentration gradient of NaCl was applied as elution buffer from zero to 1M, and then elution fractions and flow-through fraction were collected to detect lysozyme activity. The fractions with lysozyme activity were analyzed by SDS-PAGE and two bands also were found. The fractions were pooled together and loaded into SP High Performance column (GE Healthcare) for further purification, but the two bands still could not be separated. Finally, the fractions were pooled together, and then concentrated. The protein concentration was determined by Qubit® Protein Assay Kit (Invitrogen, cat Q33212).

Example 28: Purification of SEQ ID NO: 66

The culture supernatant of O23T25 was firstly precipitated with ammonium sulfate (80% saturation), then dialyzed with 20 mM NaAc at pH4.5. The solution was filtered with 0.45 um filter and then loaded into Capto SP column (GE Healthcare) equilibrated with 20 mM NaAc at pH4.5. A gradient increase of NaCl concentration was applied as elution buffer from zero to 1M, and then elution fractions and flow-through fraction were collected to detect lysozyme activity. The fractions with lysozyme activity were analyzed by SDS-PAGE, pooled together, and then concentrated for further evaluation. The protein concentration was determined by Qubit® Protein Assay Kit (Invitrogen, cat Q33212).

Example 29: Purification of SEQ ID NO: 69

The culture supernatant of O23T23 was firstly precipitated with ammonium sulfate (80% saturation), then the precipitation was added water to adjust conductance to about 160 mS/cm. The solution was filtered with 0.45 um filter and then loaded into Phenyl Sepharose 6 Fast Flow column (GE Healthcare) equilibrated with 20 mM NaAc at pH4.5 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity. The fractions with lysozyme activity were analyzed by SDS-PAGE, pooled together, and then concentrated. The buffer of final sample was changed by 20 mM NaAc at pH4.5 for further evaluation. The protein concentration was determined by Qubit® Protein Assay Kit (Invitrogen, cat Q33212).

Example 30: Purification of SEQ ID NO: 72

The culture supernatant of O14PP6 was firstly precipitated with ammonium sulfate (80% saturation), then dialyzed with 20 mM NaAc at pH4.5. The solution was filtered with 0.45 um filter and then loaded into SP Fast Flow column (GE Healthcare) equilibrated with 20 mM NaAc at pH4.5. A gradient increase of NaCl concentration was applied as elution buffer from zero to 1M, and then elution fractions and flow-through fraction were collected to detect lysozyme activity. The fractions with lysozyme activity were analyzed by SDS-PAGE, pooled together, and then concentrated for further evaluation. The protein concentration was determined by Qubit® Protein Assay Kit (Invitrogen, cat Q33212).

Example 31: Purification of SEQ ID NO: 89

The culture supernatant of O24KKU was firstly precipitated with ammonium sulfate (80% saturation), then the precipitation was added water to adjust conductance to about 170 mS/cm. The solution was filtered with 0.45 um filter and then loaded into Phenyl Sepharose High Performance column (GE Healthcare) equilibrated with 20 mM NaAc at pH5.0 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity. The fractions with lysozyme activity were analyzed by SDS-PAGE, pooled together, and then concentrated. The buffer of final sample was changed by 20 mM NaAc at pH5.0 for further evaluation. The protein concentration was determined by Qubit® Protein Assay Kit (Invitrogen, cat Q33212).

Example 32: Purification of SEQ ID NO: 92

The culture supernatant of O24KKV was firstly precipitated with ammonium sulfate (80% saturation), then the precipitation was added water to adjust conductance to about 170 mS/cm. The solution was filtered with 0.45 um filter and then loaded into Phenyl Sepharose High Performance column (GE Healthcare) equilibrated with 20 mM NaAc at pH4.5 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity. The fractions with lysozyme activity were analyzed by SDS-PAGE, pooled together, and then concentrated. The buffer of final sample was changed by 20 mM NaAc at pH4.5 for further evaluation. The protein concentration was determined by Qubit® Protein Assay Kit (Invitrogen, cat Q33212).

Example 33: Purification of SEQ ID NO: 95

The culture supernatant of O24KKX was firstly precipitated with ammonium sulfate (80% saturation), then the precipitation was added water to adjust conductance to about 140 mS/cm. The solution was filtered with 0.45 um filter and then loaded into Phenyl Sepharose High Performance column (GE Healthcare) equilibrated with 20 mM NaAc at pH4.5 with 1.2M $(NH_4)_2SO_4$ added. A gradient decrease of $(NH_4)_2SO_4$ concentration was applied as elution buffer from 1.2M to zero, and then elution fractions and flow-through fraction were collected to detect lysozyme activity. The fractions with lysozyme activity were analyzed by SDS-PAGE, pooled together, and then concentrated. The buffer of final sample was changed by 20 mM NaAc at pH4.5 for further evaluation. The protein concentration was determined by Qubit® Protein Assay Kit (Invitrogen, cat Q33212).

Example 34: Purification of SEQ ID NO: 98

The culture supernatant of O33DRM was firstly precipitated with ammonium sulfate (80% saturation), then the precipitation was added water to adjust conductance to about 170 mS/cm. The solution was filtered with 0.45 um filter and then loaded into Phenyl Sepharose 6 Fast Flow column (GE Healthcare) equilibrated with 20 mM Bis-Tris at pH6.5 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity. The fractions with lysozyme activity were analyzed by SDS-PAGE.

The fractions with lysozyme activity were pooled together and dialyzed with 20 mM Bis-Tris at pH6.5. The sample was loaded into Capto SP column (GE Healthcare) equilibrated with 20 mM Bis-Tris at pH6.5. A concentration gradient of NaCl was applied as elution buffer from zero to 1M, and then elution fractions and flow-through fraction were collected to detect lysozyme activity. The fractions with lysozyme activity were analyzed by SDS-PAGE. Finally, the fractions were pooled together, and then concentrated. The protein concentration was determined by Qubit® Protein Assay Kit (Invitrogen, cat Q33212).

Example 35: Purification of SEQ ID NO: 101

The culture supernatant of O33DRQ was firstly precipitated with ammonium sulfate (80% saturation), then the precipitation was added water to adjust conductance to about 170 mS/cm. The solution was filtered with 0.45 um filter and then loaded into Phenyl Sepharose 6 Fast Flow column (GE Healthcare) equilibrated with 20 mM PBS at pH7.0 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity. The fractions with lysozyme activity were analyzed by SDS-PAGE, pooled together, and then concentrated. The buffer of final sample was changed by 20 mM NaAc at pH5.0 for further evaluation. The protein concentration was determined by Qubit® Protein Assay Kit (Invitrogen, cat Q33212).

Example 36: Purification of SEQ ID NO: 104

The culture supernatant of O33DRN was firstly precipitated with ammonium sulfate (80% saturation), then the precipitation was added water to adjust conductance to about 140 mS/cm. The solution was filtered with 0.45 um filter and then loaded into Phenyl Sepharose High Performance column (GE Healthcare) equilibrated with 20 mM NaAc at pH5.5 with 1.2M $(NH_4)_2SO_4$ added. A gradient decrease of $(NH_4)_2SO_4$ concentration was applied as elution buffer from 1.2M to zero, and then elution fractions and flow-through fraction were collected to detect lysozyme activity. The fractions with lysozyme activity were analyzed by SDS-PAGE, pooled together, and then concentrated. The buffer of final sample was changed by 20 mM NaAc at pH5.0 for further evaluation. The protein concentration was determined by Qubit® Protein Assay Kit (Invitrogen, cat Q33212).

Example 37: Purification of SEQ ID NO: 107

The culture supernatant of O33DRS was firstly precipitated with ammonium sulfate (80% saturation), then the precipitation was added water to adjust conductance to about 170 mS/cm. The solution was filtered with 0.45 um filter and then loaded into Phenyl Sepharose High Performance column (GE Healthcare) equilibrated with 20 mM PBS at pH7.0 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity. The fractions with lysozyme activity were analyzed by SDS-PAGE, pooled together, and then concentrated. The buffer of final sample was changed by 20 mM NaAc at pH5.0 for further evaluation. The protein concentration was determined by Qubit® Protein Assay Kit (Invitrogen, cat Q33212).

Example 38: Purification of SEQ ID NO: 110

The culture supernatant of O33DRT was firstly precipitated with ammonium sulfate (80% saturation), then the precipitation was added water to adjust conductance to about 150 mS/cm. The solution was filtered with 0.45 um filter and then loaded into Phenyl Sepharose High Performance column (GE Healthcare) equilibrated with 20 mM NaAc at pH5.0 with 3M NaCl added. A gradient decrease of $(NH_4)_2SO_4$ concentration was applied as elution buffer from 1.2M to zero, and then elution fractions and flow-through fraction were collected to detect lysozyme activity. The fractions with lysozyme activity were analyzed by SDS-PAGE, pooled together, and then concentrated. The protein concentration was determined by Qubit® Protein Assay Kit (Invitrogen, cat Q33212).

Example 39: Purification of SEQ ID NO: 113

The culture supernatant of O33DRU was firstly precipitated with ammonium sulfate (80% saturation), then the precipitation was added water to adjust conductance to about 185 mS/cm. The solution was filtered with 0.45 um filter and then loaded into Phenyl Sepharose 6 Fast Flow column (GE Healthcare) equilibrated with 20 mM NaAc at pH5.0 with 1.8M $(NH_4)_2SO_4$ added. A gradient decrease of $(NH_4)_2SO_4$ concentration was applied as elution buffer from 1.8M to zero, and then elution fractions and flow-through fraction were collected to detect lysozyme activity. The fractions with lysozyme activity were analyzed by SDS-PAGE, pooled together, and then concentrated. The buffer of final sample was changed by 20 mM NaAc at pH5.0 for further evaluation. The protein concentration was determined by Qubit® Protein Assay Kit (Invitrogen, cat Q33212).

Example 40: Purification of SEQ ID NO: 116

The culture supernatant of O33V2R was firstly precipitated with ammonium sulfate (80% saturation), then the precipitation was added water to adjust conductance to about 170 mS/cm. The solution was filtered with 0.45 um filter and then loaded into Phenyl Sepharose 6 Fast Flow column (GE Healthcare) equilibrated with 20 mM NaAc at pH5.0 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity. The fractions with lysozyme activity were analyzed by SDS-PAGE, pooled together, and then concentrated. The buffer of final sample was changed by 20 mM NaAc at pH5.0 for further evaluation. The protein concentration was determined by Qubit® Protein Assay Kit (Invitrogen, cat Q33212).

Example 41: Purification of SEQ ID NO: 128

The culture supernatant of O34A3R was firstly precipitated with ammonium sulfate (80% saturation), then dialyzed with 20 mM NaAc at pH5.5. The solution was filtered with 0.45 um filter and then loaded into Capto SP column (GE Healthcare) equilibrated with 20 mM NaAc at pH5.5. A gradient increase of NaCl concentration was applied as elution buffer from zero to 1M, and then elution fractions and flow-through fraction were collected to detect lysozyme activity. The fractions with lysozyme activity were analyzed by SDS-PAGE, pooled together, and then concentrated for further evaluation. The protein concentration was determined by Qubit® Protein Assay Kit (Invitrogen, cat Q33212).

Example 42: Purification of SEQ ID NO: 131

The culture supernatant of O34A3S was firstly precipitated with ammonium sulfate (80% saturation), then dialyzed with 20 mM NaAc at pH5.0. The solution was filtered with 0.45 um filter and then loaded into Capto SP column (GE Healthcare) equilibrated with 20 mM NaAc at pH5.0. A gradient increase of NaCl concentration was applied as elution buffer from zero to 1M, and then elution fractions and flow-through fraction were collected to detect lysozyme activity. The fractions with lysozyme activity were analyzed by SDS-PAGE, pooled together, and then concentrated for further evaluation. The protein concentration was determined by Qubit® Protein Assay Kit (Invitrogen, cat Q33212).

Example 43: Purification of SEQ ID NO: 134

The culture supernatant of O34A3T was firstly precipitated with ammonium sulfate (80% saturation), then dialyzed with 20 mM NaAc at pH5.5. The solution was filtered with 0.45 um filter and then loaded into Capto SP column (GE Healthcare) equilibrated with 20 mM NaAc at pH5.5. A gradient increase of NaCl concentration was applied as elution buffer from zero to 1M, and then elution fractions and flow-through fraction were collected to detect lysozyme activity. The fractions with lysozyme activity were analyzed by SDS-PAGE, pooled together, and then concentrated for further evaluation. The protein concentration was determined by Qubit® Protein Assay Kit (Invitrogen, cat Q33212).

Example 44: Purification of SEQ ID NO: 137

The culture supernatant of O34A3V was firstly precipitated with ammonium sulfate (80% saturation), then dialyzed with 20 mM NaAc at pH5.0. The solution was filtered with 0.45 um filter and then loaded into Capto SP column (GE Healthcare) equilibrated with 20 mM NaAc at pH5.0. A gradient increase of NaCl concentration was applied as elution buffer from zero to 1M, and then elution fractions and flow-through fraction were collected to detect lysozyme activity. The fractions with lysozyme activity were analyzed by SDS-PAGE, but two bands were found.

The fractions with lysozyme activity were pooled together and adjusted pH to 4.5, then loaded into SP High Performance column (GE Healthcare) equilibrated with 20 mM NaAc at pH4.5. A gradient increase of NaCl concentration was applied as elution buffer from zero to 1M, and then elution fractions and flow-through fraction were collected to detect lysozyme activity. The fractions with lysozyme activity were analyzed by SDS-PAGE. Two bands with lysozyme activity were collected separately, then concentrated for further evaluation with two different purification IDs. The protein concentration was determined by Qubit® Protein Assay Kit (Invitrogen, cat Q33212).

Example 45: Purification of SEQ ID NO: 140

The culture supernatant of O34A3W was firstly precipitated with ammonium sulfate (80% saturation), then dialyzed with 20 mM NaAc at pH4.5. The solution was filtered with 0.45 um filter and then loaded into SP Fast Flow column (GE Healthcare) equilibrated with 20 mM NaAc at pH4.5. A gradient increase of NaCl concentration was applied as elution buffer from zero to 1M, and then elution fractions and flow-through fraction were collected to detect lysozyme activity. The fractions with lysozyme activity were analyzed by SDS-PAGE, pooled together, and then concentrated for further evaluation. The protein concentration was determined by Qubit® Protein Assay Kit (Invitrogen, cat Q33212).

Example 46: Purification of SEQ ID NO: 143

The culture supernatant of O34A3X was firstly precipitated with ammonium sulfate (80% saturation), then the precipitation was added water to adjust conductance to about 200 mS/cm. The solution was filtered with 0.45 um filter and then loaded into Phenyl Sepharose High Performance column (GE Healthcare) equilibrated with 20 mM PBS at pH6.0 with 2.0M $(NH_4)_2SO_4$ added. A gradient decrease of $(NH_4)_2SO_4$ concentration was applied as elution buffer from 2.0M to zero, and then elution fractions and flow-through fraction were collected to detect lysozyme activity and analyzed by SDS-PAGE. The fractions with lysozyme activity were pooled together and then dialyzed with 20 mM NaAc at pH5.0. The sample was loaded into Capto SP column (GE Healthcare) equilibrated with 20 mM NaAc at pH5.0. A gradient increase of NaCl concentration was applied as elution buffer from zero to 1M, and then elution fractions and flow-through fraction were collected to detect lysozyme activity. The fractions with lysozyme activity were analyzed by SDS-PAGE, pooled together, and then concentrated. The protein concentration was determined by Qubit® Protein Assay Kit (Invitrogen, cat Q33212).

Example 47: Purification of SEQ ID NO: 146

The culture supernatant of O33X6Z was firstly precipitated with ammonium sulfate (80% saturation), then dialyzed with 20 mM NaAc at pH4.5. The solution was filtered with 0.45 um filter and then loaded into Capto SP column (GE Healthcare) equilibrated with 20 mM NaAc at pH4.5. A gradient increase of NaCl concentration was applied as elution buffer from zero to 1M, and then elution fractions and flow-through fraction were collected to detect lysozyme activity. The fractions with lysozyme activity were analyzed by SDS-PAGE, pooled together, and then concentrated for further evaluation. The protein concentration was determined by Qubit® Protein Assay Kit (Invitrogen, cat Q33212).

Example 48: Purification of GH25 Lysozymes

General Purification Procedure

The fermentation supernatant with the lysozyme was filtered through a Fast PES Bottle top filter with a 0.22 μm cut-off. pH was adjusted to 4.5 with 10% acetic acid. After the pH-adjustment the solution became a little cloudy and this was removed by filtration through a Fast PES Bottle top filter with a 0.22 μm cut-off.

After pretreatment about 650 ml of the lysozyme containing solution was purified by chromatography on SP Sepharose, approximately 50 ml in a XK26 column, using as buffer A 50 mM Na-acetate pH 4.5, and as buffer B 50 mM Na-acetate+1 M NaCl pH 4.5. The fractions from the column were pooled based on the chromatogram (absorption at 280 and 254 nm) and SDS-PAGE analysis. The pooled fractions were buffer-changed into 50 mM Na-acetate, pH 5.5 and concentrated using Amicon spin filters with a 10 kDa cut-off.

Purification of SEQ ID NO: 45, 48, 51 and 54

The fermentation broth biomass was separated by centrifugation. The sample filtration was then carried out by tangential flow filtration using hollow fiber 0.2 μcartridges mounted on a QuixStand® system and then loaded into a Hydrophobic column (TOYOPEARL® Phenyl-650M) equilibrated with 50 mM HEPES pH 8+1.5M Ammonium Sulphate at pH8.0. Step gradient decrease of ammonium sulphate concentration was applied as elution buffer from 1.5M to zero. The pooled elution peak fractions, wash and flow-through were collected and analysed on SDS gel. The peak with lysozyme band on gel was then buffer exchanged by 50 mM HEPES pH 8 and the protein concentration was determined by spectrophotometer (Agilent 8453 UV-visible Spectroscopy System).

Purification of SEQ ID NO: 6, 18, 21, 24, 27, 33, 42, 227, 75, 86, 119, 122, 230, 233 and 155

The fermentation supernatant with the lysozyme was filtered through a Fast PES Bottle top filter with a 0.22 μm cut-off.

Pretreatment of the filtered broth may be necessary if the expression level is low and/or conductivity is high (in general >10S/m). Pretreatment can be performed using ultrafiltration on a 3-5 kDa cutoff membrane, buffer exchange on a G25 gel filtration column or dialysis. SEQ ID NO: 33, 42, 75 and 122 were pretreated using a G25 gel filtration column using 50 mM acetate pH4.5 whilst SEQ ID NO: 18, 21 and 27 were pretreated in a dialysis membrane (6-8 KDa) overnight in 50 mM acetate 4.5.

pH was adjusted to 4.5. If the solution became cloudy after the pH-adjustment, this was removed by filtration through a Fast PES Bottle top filter with a 0.22 μm cut-off. The lysozyme containing solution was purified by chromatography on SP Sepharose, approximately 50 ml in a XK26 column, using as buffer A 50 mM Na-acetate pH 4.5, and as buffer B 50 mM Na-acetate+1 M NaCl pH 4.5 and a 0-100% gradient over ca. 10 CV. The fractions from the column were pooled based on the chromatogram (absorption at 280 and 254 nm) and SDS-PAGE analysis.

The molecular weight was estimated from SDS-PAGE and the purity was >90%.

Purification of SEQ ID NO: 9

The fermentation supernatant with the lysozyme was filtered through a Fast PES Bottle top filter with a 0.22 μm cut-off.

The pH adjusted to 7.5 and the sample was filtered through a Fast PES Bottle top filter with a 0.22 μm cut-off. The lysozyme containing solution was purified by chromatography on Q-Sepharose, approximately 70 ml in a XK26 column, using as buffer A 50 mM Tris pH 7.5 and as buffer B 50 mM Tris+1 M NaCl pH 7.5 and a 0-100% gradient over ca. 5CV. The fractions from the column were pooled based on the chromatogram (absorption at 280 and 254 nm) and SDS-PAGE analysis.

The molecular weight was estimated from SDS-PAGE and the purity was >90%.

Purification of SEQ ID NO: 78

The fermentation supernatant with the lysozyme was filtered through a Fast PES Bottle top filter with a 0.22 μm cut-off.

The sample was concentrated on a vivacelle (cut off 5000 kd). The sample was diluted 3× with Milli-Q water and pH adjusted to 7.5. The lysozyme containing solution was purified by chromatography on Q-Sepharose, approximately 30 ml in a XK26 column, using as buffer A 50 mM Hepes pH 7.5 and as buffer B 50 mM Hepes+1 M NaCl pH 7.5 and a 0-50% gradient over ca. 10 CV. The fractions from the column were pooled based on the chromatogram (absorption at 280 and 254 nm) and SDS-PAGE analysis.

The molecular weight was estimated from SDS-PAGE and the purity was >90%.

Purification of SEQ ID NO: 83

The fermentation supernatant with the lysozyme was filtered through a Fast PES Bottle top filter with a 0.22 μm cut-off.

The sample was ultrafiltreted and diafiltrated on Sartorius UF-system 10 kDa. If the solution became cloudy after the pH-adjustment, this was removed by filtration through a Fast PES Bottle top filter with a 0.22 μm cut-off. The lysozyme containing solution was purified by chromatography on Q-Sepharose, approximately 50 ml in a XK26 column, using as buffer A 50 mM Hepes pH 7.0 and as buffer B 50 mM Hepes+1 M NaCl pH 7.0 and a 0-100% gradient over ca. 10 CV. The fractions from the column were pooled based on the chromatogram (absorption at 280 and 254 nm) and SDS-PAGE analysis.

The molecular weight was estimated from SDS-PAGE and the purity was >90%.

Purification of SEQ ID NO: 125

The fermentation supernatant with the lysozyme was filtered through a Fast PES Bottle top filter with a 0.22 μm cut-off.

The sample was pretreated using a G25 gel filtration column using 50 mM Na-acetate pH and the eluant was purified by chromatography on Q-Sepharose, approximately 50 ml in a XK26 column, using as buffer A 50 mM Tris pH 8.0 and as buffer B 50 mM Tris+2 M NaCl pH 8.0 and a 0-100% gradient over ca. 10 CV. The fractions from the column were pooled based on the chromatogram (absorption at 280 and 254 nm) and SDS-PAGE analysis.

The molecular weight was estimated from SDS-PAGE and the purity was >90%.

Purification of SEQ ID NO: 158

The fermentation supernatant with the lysozyme was filtered through a Fast PES Bottle top filter with a 0.22 μm cut-off.

The sample was diluted 50% with milli-Q water and the pH was adjusted to pH 4.5. The sample was purified by chromatography on Capto S, approximately 50 ml in a XK26 column, using as buffer A 50 mM acetate pH 9.0 and as buffer B 50 mM acetate+2 M NaCl pH 9.0. The fractions from the column were pooled based on the chromatogram (absorption at 280 and 254 nm) and SDS-PAGE analysis.

The molecular weight was estimated from SDS-PAGE and the purity was >90%.

Example 49: Determination of Lysozyme Activity

Method for the Determination of Lysozyme Activity Against *Micrococcus lysodeikticus*

The lysozymes of the application were tested according to Example 1 in the same plate as a prior art lysozyme (a GH25 lysozyme from *Acremonium alcalophilum* as described in WO 2013/076253, herein denoted SEQ ID NO: 159). The ratio of OD measurements of the lysozyme of the invention to the lysozyme of SEQ ID NO: 159 was calculated and is shown in tables 5 to 32 below.

TABLE 5

OD Meaurement of SEQ ID NO: 24 and 227

| Lysozyme | OD Measurement | Ratio |
| --- | --- | --- |
| SEQ ID NO: 159 | 0.41 | — |
| SEQ ID NO: 227 | 1.34 | 3.3 |
| SEQ ID NO: 24 | 1.99 | 4.9 |

TABLE 6

OD Measurement of SEQ ID NO: 6 and 9

| Lysozyme | OD Measurement | Ratio |
| --- | --- | --- |
| SEQ ID NO: 159 | 0.37 | — |
| SEQ ID NO: 9 | 0.85 | 2.3 |
| SEQ ID NO: 6 | 1.78 | 4.8 |

TABLE 7

OD Measurement of SEQ ID NO: 72 and 83

| Lysozyme | OD Measurement | Ratio |
| --- | --- | --- |
| SEQ ID NO: 159 | 0.49 | — |
| SEQ ID NO: 83 | 0.99 | 2.0 |
| SEQ ID NO: 72 | 2.22 | 4.5 |

TABLE 8

OD Measurement of SEQ ID NO: 86

| Lysozyme | OD Measurement | Ratio |
| --- | --- | --- |
| SEQ ID NO: 159 | 0.65 | — |
| SEQ ID NO: 86 | 1.34 | 2.1 |

TABLE 9

OD Measurement of SEQ ID NO: 30 and 60

| Lysozyme | OD Measurement | Ratio |
| --- | --- | --- |
| SEQ ID NO: 159 | 0.61 | — |
| SEQ ID NO: 60 | 2.32 | 3.5 |
| SEQ ID NO: 30 | 2.14 | 3.2 |

TABLE 10

OD Measurement of SEQ ID NO: 3, 36 and 39

| Lysozyme | OD Measurement | Ratio |
| --- | --- | --- |
| SEQ ID NO: 159 | 0.52 | — |
| SEQ ID NO: 36 | 2.52 | 4.8 |
| SEQ ID NO: 3 | 2.60 | 5.0 |
| SEQ ID NO: 39 | 1.71 | 3.3 |

TABLE 11

OD Measurement of SEQ ID NO: 27 and 80

| Lysozyme | OD Measurement | Ratio |
| --- | --- | --- |
| SEQ ID NO: 159 | 0.62 | — |
| SEQ ID NO: 80 | 1.86 | 3.0 |
| SEQ ID NO: 27 | 1.20 | 2.0 |

TABLE 12

OD Measurement of SEQ ID NO: 18 and 21

| Lysozyme | OD Measurement | Ratio |
|---|---|---|
| SEQ ID NO: 159 | 0.69 | — |
| SEQ ID NO: 18 | 1.76 | 2.6 |
| SEQ ID NO: 21 | 2.62 | 3.8 |

TABLE 13

OD Measurement of SEQ ID NO: 63, 66 and 69

| Lysozyme | OD Measurement | Ratio |
|---|---|---|
| SEQ ID NO: 159 | 0.63 | — |
| SEQ ID NO: 63 | 1.38 | 2.2 |
| SEQ ID NO: 66 | 1.72 | 2.7 |
| SEQ ID NO: 69 | 2.03 | 3.2 |

TABLE 14

OD Measurement of SEQ ID NO: 12 and 15

| Lysozyme | OD Measurement | Ratio |
|---|---|---|
| SEQ ID NO: 159 | 0.71 | — |
| SEQ ID NO: 15 | 1.79 | 2.5 |
| SEQ ID NO: 12 | 1.47 | 2.1 |

TABLE 15

OD Measurement of SEQ ID NO: 45, 51 and 54

| Lysozyme | OD Measurement | Ratio |
|---|---|---|
| SEQ ID NO: 159 | 0.50 | — |
| SEQ ID NO: 51 | 2.06 | 4.2 |
| SEQ ID NO: 54 | 1.98 | 4.0 |
| SEQ ID NO: 45 | 2.07 | 4.2 |

TABLE 16

OD Measurement of SEQ ID NO: 48

| Lysozyme | OD Measurement | Ratio |
|---|---|---|
| SEQ ID NO: 159 | 0.44 | — |
| SEQ ID NO: 48 | 0.93 | 2.1 |

TABLE 17

OD Measurement of SEQ ID NO: 33 and 75

| Lysozyme | OD Measurement | Ratio |
|---|---|---|
| SEQ ID NO: 159 | 0.56 | — |
| SEQ ID NO: 75 | 1.56 | 2.8 |
| SEQ ID NO: 33 | 2.33 | 4.2 |

TABLE 18

OD Measurement of SEQ ID NO: 21 and 42

| Lysozyme | OD Measurement | Ratio |
|---|---|---|
| SEQ ID NO: 159 | 0.72 | — |
| SEQ ID NO: 21 | 3.13 | 4.4 |
| SEQ ID NO: 42 | 1.94 | 2.7 |

TABLE 19

OD Measurement of SEQ ID NO: 24 and 125

| Lysozyme | OD Measurement | Ratio |
|---|---|---|
| SEQ ID NO: 159 | 0.44 | — |
| SEQ ID NO: 24 | 1.97 | 4.5 |
| SEQ ID NO: 125 | 1.74 | 2.9 |

TABLE 20

OD Measurement of SEQ ID NO: 98

| Lysozyme | OD Measurement | Ratio |
|---|---|---|
| SEQ ID NO: 159 | 0.55 | — |
| SEQ ID NO: 98 | 1.79 | 3.3 |

TABLE 21

OD Measurement of SEQ ID NO: 104 and 122

| Lysozyme | OD Measurement | Ratio |
|---|---|---|
| SEQ ID NO: 159 | 0.44 | — |
| SEQ ID NO: 122 | 2.09 | 4.8 |
| SEQ ID NO: 104 | 1.23 | 2.8 |

TABLE 22

OD Measurement of SEQ ID NO: 89

| Lysozyme | OD Measurement | Ratio |
|---|---|---|
| SEQ ID NO: 159 | 0.63 | — |
| SEQ ID NO: 89 | 2.11 | 3.4 |

TABLE 23

OD Measurement of SEQ ID NO: 92, 95, 128, 134 and 143

| Lysozyme | OD Measurement | Ratio |
|---|---|---|
| SEQ ID NO: 159 | 0.49 | — |
| SEQ ID NO: 92 | 1.30 | 2.6 |
| SEQ ID NO: 95 | 1.59 | 3.2 |
| SEQ ID NO: 128 | 2.38 | 4.8 |
| SEQ ID NO: 134 | 1.24 | 2.5 |
| SEQ ID NO: 143 | 2.59 | 5.2 |

TABLE 24

OD Measurement of SEQ ID NO: 146

| Lysozyme | OD Measurement | Ratio |
|---|---|---|
| SEQ ID NO: 159 | 0.38 | — |
| SEQ ID NO: 146 | 1.94 | 5.1 |

TABLE 25

OD Measurement of SEQ ID NO: 110 and 116

| Lysozyme | OD Measurement | Ratio |
|---|---|---|
| SEQ ID NO: 159 | 0.46 | — |
| SEQ ID NO: 110 | 1.53 | 3.3 |
| SEQ ID NO: 116 | 1.28 | 2.8 |

TABLE 26

OD Measurement of SEQ ID NO: 131

| Lysozyme | OD Measurement | Ratio |
|---|---|---|
| SEQ ID NO: 159 | 0.30 | — |
| SEQ ID NO: 131 | 2.35 | 7.8 |

TABLE 27

OD Measurement of SEQ ID NO: 110, 128 and 137

| Lysozyme | OD Measurement | Ratio |
|---|---|---|
| SEQ ID NO: 159 | 0.34 | — |
| SEQ ID NO: 137 | 1.87 | 5.5 |
| SEQ ID NO: 137 | 1.48 | 4.4 |
| SEQ ID NO: 128 | 2.09 | 6.2 |
| SEQ ID NO: 110 | 1.50 | 4.5 |

TABLE 28

OD Measurement of SEQ ID NO: 131

| Lysozyme | OD Measurement | Ratio |
|---|---|---|
| SEQ ID NO: 159 | 0.40 | — |
| SEQ ID NO: 131 | 2.42 | 6.0 |

TABLE 29

OD Measurement of SEQ ID NO: 140

| Lysozyme | OD Measurement | Ratio |
|---|---|---|
| SEQ ID NO: 159 | 0.61 | — |
| SEQ ID NO: 140 | 2.03 | 3.3 |

TABLE 30

OD Measurement of SEQ ID NO: 158

| Lysozyme | OD Measurement | Ratio |
|---|---|---|
| SEQ ID NO: 159 | 0.56 | — |
| SEQ ID NO: 158 | 1.65 | 3.0 |

TABLE 31

OD Measurement of SEQ ID NO: 230, 233 and 155

| Lysozyme | OD Measurement | Ratio |
|---|---|---|
| SEQ ID NO: 159 | 0.48 | — |
| SEQ ID NO: 230 | 1.34 | 2.8 |
| SEQ ID NO: 233 | 1.52 | 3.2 |
| SEQ ID NO: 155 | 1.01 | 2.1 |

TABLE 32

OD Measurement of SEQ ID NO: 101, 107, 113 and 119

| Lysozyme | OD Measurement | Ratio |
|---|---|---|
| SEQ ID NO: 159 | 0.53 | — |
| SEQ ID NO: 113 | 1.77 | 3.4 |
| SEQ ID NO: 101 | 1.91 | 3.6 |
| SEQ ID NO: 107 | 1.50 | 2.9 |
| SEQ ID NO: 119 | 2.40 | 4.6 |

The results show that the lysozymes of the invention have increased activity compared to this prior art lysozyme.

Example 50: Animal Feed and Animal Feed Additives Comprising a Lysozyme of the Invention Animal Feed Additive A formulation of a lysozyme of the invention (e.g. SEQ ID NO: 3, 6, 9, 12, 15, 18, 21, 24, 27, 30, 33, 36, 39, 42, 45, 48, 51, 54, 57, 60, 63, 66, 69, 72, 75, 80, 83, 86, 89, 92, 95, 98, 101, 104, 107, 110, 113, 116, 119, 122, 125, 128, 131, 134, 137, 140, 143, 146, 149, 152, 155, 158, 221, 224, 227, 230 or 233) containing 0.01 g to 10 g enzyme protein is added to the following premix (per kilo of premix):

| 5000000 IE | Vitamin A |
|---|---|
| 1000000 IE | Vitamin D3 |
| 13333 mg | Vitamin E |
| 1000 mg | Vitamin K3 |
| 750 mg | Vitamin B1 |
| 2500 mg | Vitamin B2 |
| 1500 mg | Vitamin B6 |
| 7666 mcg | Vitamin B12 |
| 12333 mg | Niacin |
| 33333 mcg | Biotin |
| 300 mg | Folic Acid |
| 3000 mg | Ca-D-Panthothenate |
| 1666 mg | Cu |
| 16666 mg | Fe |
| 16666 mg | Zn |
| 23333 mg | Mn |
| 133 mg | Co |
| 66 mg | I |
| 66 mg | Se |
| 5.8% | Calcium |
| 25% | Sodium |

Animal Feed

This is an example of an animal feed (broiler feed) comprising the animal feed additive as described above:

62.55% Maize 33.8% Soybean meal (50% crude protein)

1.0% Soybean oil 0.2% DL-Methionine 0.22% DCP (dicalcium phosphate)

0.76% CaCO₃ (calcium carbonate)
0.32% Sand
0.15% NaCl (sodium chloride)
1% of the above Premix The ingredients are mixed, and the feed is pelleted at the desired temperature, e.g. 60, 65, 75, 80, 85, 90 or even 95° C.

Example 51: Cloning and Expression of *Flammulina velutipes* (SEQ ID NO: 221)

A GH25 lysozyme was identified from the downloaded genomic DNA assembly from the following project: Park Y J et al., "Whole genome and global gene expression analyses of the model mushroom *Flammulina velutipes* reveal a high capacity for lignocellulose degradation.", PLoS One, 2014 April 8; 9(4):e93560.

A codon optimized, intronless version of the *Flammulina velutipes* GH25 lysozyme (SEQ ID NO: 217) was ordered from GeneArt, Invitrogen having SEQ ID NO: 219.

SEQ ID NO: 219—the underlined portions are restriction enzymes used for cloning into pDau109.

```
                                                SEQ ID NO: 219
ACACAACTGGGGATCCACCATGCGAATCCTCTTGTTCATCGCAGTCACAATCGCGT

TGGGAGTCCATGCCAGGCTCAACGGCATCGATGTCTCGGGATACCAGCCGAACGTC

AACTGGGCCACGGTCAAAGCGAACGGCGTGTCCTTCGCGTACATCAAGGCAACCGA

GGGCACCACGTATACAAACCCCTCGTTCTCCTCCCAGTACACCGGAGCAACAAAAG

CCGGATTGATCAGGGGCTCCTACCATTTCGCGCATCCTTCGTCGTCCACAGGCGCA

GCACAGGCACGATACTTCGTGGCACATGGCGGTGGTTGGTCCGGTGATGGTATCAC

CTTGCCTGGTGCGCTCGATATCGAGTATAACCCTTCGGGTGCGACATGTTACGGCC

TCTCGACCTCGTCCATGGTGAACTGGATCGCCGATTTCTCCAACACTTATCACTCG

CTCACAGGCAGGTACCCCGTCATTTACACCACTGCCGATTGGTGGCGAACCTGTAC

CGGCAACTCCGCATCCTTCGCAAACAACTCGCCTCTCTGGATTGCGCGTTACGCGT

CGACTATCGGTACGCTCCCTGCCGGATGGTCGTACGCGACCTTCTGGCAGTATGCG

GATTCGGGCTCCAACCCTGGCGATCAGGATTACTTCAACGGTGACGCAGCGGGTCT

CAAGCGTCTCGCGACATCGTAATAAGCTTCTCGAGATCT
```

The synthetic gene was cloned directly into pDau109 as described in the Example 16 as a ligation into the BamHI-HindIII site of the vector. The GH25 lysozyme having SEQ ID NO: 221 was expressed as described in Example 19 and purified as described in Example 52.

Example 52: Purification of the GH25 Lysozyme from *Flammulina velutipes* (SEQ ID NO: 221

The fermentation supernatant with the lysozyme was filtered through a Fast PES Bottle top filter with a 0.22 μm cut-off.

The sample was pretreated using a G25 gel filtration column using 50 mM acetate pH4.5 and the eluant was purified by chromatography on SP Sepharose, approximately 50 ml in a XK26 column, using as buffer A 50 mM Na-acetate pH 4.5, and as buffer B 50 mM Na-acetate+2 M NaCl pH 4.5 and a 0-100% gradient over ca. 10 CV. The fractions from the column were pooled based on the chromatogram (absorption at 280 and 254 nm) and SDS-PAGE analysis.

Example 53: PCR Amplification and InFusion Cloning of Lysozyme Encoding Sequences SEQ ID NO: 222

The InFusion cloning primers given in table 33 were used to generate an BamHI-HindIII flanked cloning cassette from the genomic DNA as described in Example 16.

TABLE 33

InFusion cloning primers

| Primer* | Primer SEQ ID NO: | Primer to lysozyme SEQ ID NO: | Sequence |
|---|---|---|---|
| C8VSE-F | 225 | 222 | 5'-ACACAACTGGGGATCCACCATGCTTTT CGCAACCTTTCTTTGTCTTG |
| C8VSE-R | 226 | 222 | 5'-AGATCTCGAGAAGCTTACGAGGAAAAG ACGTTGAGGTCAAATTGA |

*-F—forward primer; -R—reverse primer

Bold letters represent coding sequence. The underlined sequence is homologous to the insertion sites of pDau109.

The GH25 lysozymes were expressed in *Aspergillus oryzae* as described in Example 19 and purified as described in Example 54.

Example 54: Purification of the GH25 Lysozyme from *Deconica coprophila* (SEQ ID NO: 222)

The fermentation supernatant with the lysozyme was filtered through a Fast PES Bottle top filter with a 0.22 μm cut-off.

The sample was pretreated using a G25 gel filtration column using 50 mM acetate pH4.5 and the eluant was purified by chromatography on SP Sepharose, approximately 50 ml in a XK26 column, using as buffer A 50 mM Na-acetate pH 4.5, and as buffer B 50 mM Na-acetate+2 M NaCl pH 4.5 and a 0-100% gradient over ca. 10 CV. The fractions from the column were pooled based on the chromatogram (absorption at 280 and 254 nm) and SDS-PAGE analysis.

The molecular weight was estimated from SDS-PAGE and the purity was >90%.

Example 55: Determination of Lysozyme Activity

The lysozymes of the application were tested according to Example 1 in the same plate as a prior art lysozyme (a GH25 lysozyme from *Acremonium alcalophilum* as described in WO 2013/076253, herein denoted SEQ ID NO: 159). The ratio of OD measurement of the lysozyme of the invention to the lysozyme of SEQ ID NO: 159 was calculated and is shown in Table 34 below.

TABLE 34

OD Measurement of SEQ ID NO: 221 and 224

| Lysozyme | OD Measurement | Ratio |
|---|---|---|
| SEQ ID NO: 159 | 0.51 | — |
| SEQ ID NO: 221 | 1.74 | 3.4 |
| SEQ ID NO: 224 | 1.80 | 3.5 |

The results show that the lysozymes of the invention have increased activity compared to this prior art lysozyme.

Example 56 Method for the Determination of Lysozyme Activity Against *Lactobacillus johnsonii*

Pgn Extraction:
Cultivation of *Lactobacillus johnsonii*:
Materials
  MRS broth, product number BD 288130, pH 6.3-6.7.
  MRS agar plates, BD 288130; Agar Oxoid LP0011; pH 6.3-6.7.
  0.9% NaCl, Merck 106404, Cas no. 7647145
  jars, supplier Merck 116387, Anaerocult anaerobic jar 2.5 L
  Anaerogen 2.5 L, ThermoScientific, catalogue no. AN0025A *Lactobacillus johnsonii*, DSM 10533
Procedure
  *L. johnsonii* was streaked from freeze stock to MRS agar plate and incubated under anaerobic conditions for 2 days, anaerobic jar with Anaerogen 2.5 L, 30° C. Some colonies were inoculated into 500 mLMRS broth in a 500 mL blue cap bottle and placed in an anaerobic jar with Anaerogen 2.5 L for 72 hours at 30° C.
  The culture was spun down (6000 rpm, 10 minutes) and the supernatant was poured off before another round of centrifugation was performed. The pellet was washed in 100 mL 0.9% NaCl and the suspension was mixed well and centrifuged at 6000 rpm for 10 minutes. The supernatant was poured off and the washing procedure in 0.9% NaCl was repeated to a total of three washes. Approximately 40 mL 0.9% NaCl was added to the pellet and the solution was transferred to a 50 mL falcon tube. The solution was centrifuged at 6000 rpm for 10 minutes and the supernatant was poured off. The pellet was stored at −18° C. until the extraction of the peptidoglycan was conducted.
Extraction Procedure:
Materials
  Protease from *Streptomyces griseus*, Sigma-Aldrich P5147, CAS 9036-06-0
  PBS pH 7.3:
  NaCl: 8 g, Sigma-Aldrich 31434, CAS 7647-14-5
  KCl: 0.2 g, Sigma-Aldrich P9333, CAS 7447-40-7
  $KH_2PO_4$: 0.24 g, Sigma-Aldrich P5655, CAS 7778-77-0

Na$_2$HPO$_4$. 2 H$_2$O: 1.44 g, Sigma-Aldrich 30412, CAS 10028-24-7
Add Milli-Q water to 1000 mL
1% Triton-X 100 solution:
1 mL Triton X100, Sigma-Aldrich X100, CAS 9002-93-1
Add Milli Q water to 100 mL
500 mM sodium carbonate buffer, pH 9.3:
500 mM sodium carbonate is made from 21 g Na$_2$CO$_3$ (Sigma-Aldrich S7795, CAS 497-19-8) in
500 mL MQ water
500 mM sodium bicarbonate is made from 72 g NaHCO$_3$ (Sigma-Aldrich S6014, CAS 144-55-8)
in 500 mL MW water
The pH 9.3 buffer is made from 320 mL NaHCO$_3$ and 80 mL Na$_2$CO$_3$ and adjusting pH with HCl
Phenol solution with 10 mM Tris HCl, pH 8.0, 1 mM EDTA, Sigma-Aldrich P4557, CAS 108-95-2
Acetone, Sigma-Aldrich 32201-M, CAS 67-64-1
Ethanol, 96%, CCS Healthcare 1680643, CAS 64-17-5

Procedure

*L. johnsonii* cell material was freeze dried. The freeze dried material (525 mg) was suspended in PBS (40 mL) in a 50 mL Falcon tube. The suspension was shaken for 2 h@700 rpm in a thermoshaker at room temperature. *Streptomyces griseus* protease (55 mg) was then added and the suspension was incubated 6 h@37 C in the thermoshaker. It was then centrifuged 20 min@1900 g at room temperature, and the supernatant was decanted. The pellet was re-suspended in 1% Triton X-100 (40 mL) and shaken overnight@37 C. After another centrifugation and decantation, the pellet was re-suspended in PBS (40 mL) and protease (55 mg) added again. The suspension was again incubated 6h@37 C, centrifuged and decanted. The pellet was re-suspended in PBS (40 mL) and shaken overnight@37 C. This washing procedure was repeated once more with PBS (40 mL, 30 min agitation), then with 50% ethanol/water (40 mL, 30 min agitation). The pellet was then split into two Falcon tubes. To each tube was added phenol solution (15 mL) pre-heated to 40 C. The suspensions were shaken 10 min@40 C, and then added 96% ethanol (25 mL to each tube), centrifuged and decanted. The pellets were further washed with acetone (40 mL in each tube) and 96% ethanol (40 mL in each tube), before being freeze dried. Combining the pellets from the two tubes yielded 80 mg purified peptidoglycan as a white powder.

Reducing End Assay

The lysozyme was diluted in phosphate dilution buffer (5 mM citrate, 5 mM K$_2$HPO$_4$, 0.01% TritonX-100, pH 5.0) to 200 or 50 µg/mL in polypropylene tubes, dependent on the strength of available stock solutions. The diluted lysozyme was further diluted in a 96-well polypropylene microtiter plate by preparing a two-fold dilution series down to a concentration of 6.3 µg/mL in phosphate dilution buffer (5 mM citrate, 5 mM K$_2$HPO$_4$, 0.01% TritonX-100, pH 5.0). A 50 mg/ml stock solution of *L. johnsonii* substrate in MillQ was prepared and diluted in phosphate buffer (50 mM citrate, 50 mM K$_2$HPO$_4$, pH 5.0) to 250 µg/ml. In a polypropylene deepwell plate 50 µL of the lysozyme dilution was mixed with 450 µL *L. johnsonii* solution and incubated at 40° C. with shaking (500 rpm) for 45 min. After incubation, the deepwell plate was centrifuged (3200 rpm, 7 min) to pellet insoluble material and 100 µL of the supernatant was mixed with 50 µL 3.2M HCl in a 96-well PCR plate and incubated at 95° C. for 80 min. 50 µL of 3.5 M NaOH was added to each well of the PCR plate, and 150 µL of each sample was transferred to a new PCR plate containing 75 µL/well 4-hydroxybenzhydrazide (PAHBAH) solution in K-Na tartrate/NaOH buffer (50 g/L K-Na tartrate+20 g/L NaOH). The plate was incubated at 95° C. for 10 min before 100 µL/sample was transferred to a clear flat-bottomed microtiter plate for optical density (OD) measurement at 405 nm. OD measurements were performed on three times diluted samples (50 µL sample diluted in 100 µL in Milli-Q water). The OD measurement values represent the difference after the original (background) reading was subtracted and represent the average of two OD measurement values. Results are shown in Table 35 and in FIGS. 3 and 4.

TABLE 35

Average OD405 measurements (background corrected) in Reducing End Assay

| | Concentration of lysozyme in µg/mL | | | | | |
|---|---|---|---|---|---|---|
| Lysozyme | 20 | 10 | 5 | 2.5 | 1.25 | 0.63 |
| SEQ ID NO: 24 | 1.07 | 0.85 | 0.56 | 0.39 | 0.26 | 0.15 |
| SEQ ID NO: 227 | 0.19 | 0.12 | 0.10 | 0.07 | 0.01 | 0.01 |
| SEQ ID NO: 6 | 0.66 | 0.47 | 0.40 | 0.25 | 0.14 | 0.10 |
| SEQ ID NO: 9 | 0.03 | 0.01 | 0.19 | 0.02 | 0.01 | 0.00 |
| SEQ ID NO: 72 | 1.00 | 0.71 | 0.50 | 0.40 | 0.24 | 0.16 |
| SEQ ID NO: 83 | 0.29 | 0.13 | 0.08 | 0.09 | 0.02 | 0.03 |
| SEQ ID NO: 60 | 0.91 | 0.53 | 0.40 | 0.19 | 0.10 | 0.06 |
| SEQ ID NO: 30 | 0.33 | 0.24 | 0.12 | 0.04 | 0.00 | −0.04 |
| SEQ ID NO: 39 | 0.85 | 0.72 | 0.45 | 0.34 | 0.19 | 0.08 |
| SEQ ID NO: 3 | 0.90 | 0.66 | 0.49 | 0.29 | 0.18 | 0.07 |
| SEQ ID NO: 51 | 0.71 | 0.43 | 0.45 | 0.23 | 0.14 | 0.05 |
| SEQ ID NO: 54 | 0.58 | 0.48 | 0.27 | 0.16 | 0.12 | 0.02 |
| SEQ ID NO: 48 | 0.66 | 0.45 | 0.44 | 0.20 | 0.19 | 0.03 |
| SEQ ID NO: 18 | 0.98 | 0.75 | 0.55 | 0.33 | 0.16 | 0.28 |
| SEQ ID NO: 27 | −0.02 | 0.06 | −0.02 | −0.03 | −0.02 | −0.03 |
| SEQ ID NO: 224 | −0.06 | −0.07 | −0.04 | −0.06 | −0.07 | −0.07 |
| SEQ ID NO: 15 | 1.10 | 0.98 | 0.86 | 0.53 | 0.40 | 0.20 |
| SEQ ID NO: 69 | 0.45 | 0.27 | 0.16 | 0.05 | 0.17 | −0.04 |
| SEQ ID NO: 66 | −0.06 | −0.03 | 0.01 | −0.06 | −0.03 | −0.08 |
| SEQ ID NO: 63 | 0.15 | 0.04 | 0.03 | −0.04 | −0.05 | −0.06 |
| SEQ ID NO: 12 | −0.03 | −0.07 | −0.06 | −0.07 | −0.08 | 0.05 |
| SEQ ID NO: 45 | 0.98 | 0.74 | 0.61 | 0.26 | 0.27 | 0.10 |
| SEQ ID NO: 75 | 1.20 | 0.84 | 0.70 | 0.53 | 0.34 | 0.22 |
| SEQ ID NO: 119 | 1.23 | 1.05 | 0.84 | 0.75 | 0.59 | 0.27 |
| SEQ ID NO: 42 | 0.00 | 0.01 | −0.01 | 0.00 | 0.00 | −0.02 |
| SEQ ID NO: 21 | 0.86 | 0.43 | 0.31 | 0.21 | 0.12 | 0.06 |
| SEQ ID NO: 33 | 0.97 | 0.54 | 0.39 | 0.27 | 0.24 | 0.10 |
| SEQ ID NO: 89 | 0.46 | 0.31 | 0.28 | 0.12 | 0.07 | 0.03 |
| SEQ ID NO: 92 | 0.42 | 0.31 | 0.15 | 0.10 | 0.04 | 0.14 |
| SEQ ID NO: 95 | 0.94 | 0.81 | 0.62 | 0.49 | 0.24 | 0.17 |
| SEQ ID NO: 221 | 0.86 | 0.62 | 0.38 | 0.28 | 0.17 | 0.13 |
| SEQ ID NO: 125 | 0.19 | 0.08 | 0.11 | 0.03 | 0.02 | 0.01 |
| SEQ ID NO: 122 | 0.88 | 0.64 | 0.47 | 0.33 | 0.18 | 0.10 |
| SEQ ID NO: 101 | 0.79 | 0.57 | 0.54 | 0.42 | 0.13 | 0.07 |
| SEQ ID NO: 98 | 0.78 | 0.40 | 0.36 | 0.26 | 0.12 | 0.09 |
| SEQ ID NO: 104 | 0.39 | 0.27 | 0.17 | 0.06 | 0.12 | 0.06 |
| SEQ ID NO: 116 | 0.76 | 0.65 | 0.41 | 0.24 | 0.14 | 0.09 |
| SEQ ID NO: 146 | 0.85 | 0.61 | 0.50 | 0.41 | 0.19 | 0.19 |
| SEQ ID NO: 143 | 0.56 | 0.32 | 0.24 | 0.38 | 0.08 | 0.17 |
| SEQ ID NO: 110 | 0.51 | 0.32 | 0.19 | 0.07 | 0.05 | 0.00 |
| SEQ ID NO: 134 | 0.28 | 0.21 | 0.15 | 0.12 | 0.02 | 0.00 |
| SEQ ID NO: 140 | 0.00 | 0.00 | 0.02 | −0.02 | −0.02 | 0.09 |
| SEQ ID NO: 128 | −0.01 | 0.01 | 0.01 | −0.02 | −0.02 | −0.02 |
| SEQ ID NO: 137 | 0.95 | 0.68 | 0.51 | 0.36 | 0.21 | 0.13 |
| SEQ ID NO: 131 | 0.74 | 0.71 | 0.46 | 0.27 | 0.15 | 0.10 |
| SEQ ID NO: 86 | ND | ND | 0.05 | 0.03 | −0.01 | 0.03 |
| SEQ ID NO: 36 | ND | ND | 1.14 | 0.96 | 0.69 | 0.56 |
| SEQ ID NO: 107 | ND | ND | 0.14 | 0.08 | 0.28 | 0.00 |
| SEQ ID NO: 113 | ND | ND | 0.25 | 0.13 | 0.05 | 0.03 |
| SEQ ID NO: 158 | ND | ND | 0.04 | −0.02 | −0.09 | −0.02 |
| SEQ ID NO: 230 | ND | ND | 0.59 | 0.38 | 0.25 | 0.12 |
| SEQ ID NO: 233 | ND | ND | 0.58 | 0.30 | 0.16 | 0.07 |
| SEQ ID NO: 155 | ND | ND | 0.63 | 0.37 | 0.29 | 0.19 |
| SEQ ID NO: 80 | ND | ND | 1.62 | 0.98 | 0.57 | 0.39 |
| SEQ ID NO: 159 | 1.21 | 1.09 | 0.90 | 0.72 | 0.49 | 0.32 |
| HEWL | −0.02 | −0.02 | 0.00 | −0.01 | 0.00 | −0.02 |

ND: not determined due to low concentration of enzyme stock solution

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A composition comprising one or more formulating agents and a GH25 polypeptide having lysozyme activity, wherein the polypeptide has at least 80% sequence identity to SEQ ID NO: 9.

2. The composition of claim 1, wherein the polypeptide has at least 85% sequence identity to SEQ ID NO: 9.

3. The composition of claim 1, wherein the polypeptide has at least 90% sequence identity to SEQ ID NO: 9.

4. The composition of claim 1, wherein the polypeptide has at least 95% sequence identity to SEQ ID NO: 9.

5. The composition of claim 1, wherein the polypeptide has at least 97% sequence identity to SEQ ID NO: 9.

6. The composition of claim 1, wherein the polypeptide comprises the amino acid sequence of SEQ ID NO: 9.

7. The composition of claim 1, wherein the polypeptide is a fragment of SEQ ID NO: 9 and wherein the fragment comprises at least 180 amino acids.

8. The composition of claim 1, wherein said one or more formulating agents comprise glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and/or cellulose.

9. The composition of claim 1, wherein said one or more formulating agents comprise 1,2-propylene glycol, 1,3-propylene glycol, sodium sulfate, dextrin, cellulose, sodium thiosulfate, kaolin and/or calcium carbonate.

10. The composition of claim 1, wherein said one or more formulating agents comprise calcium carbonate.

11. The composition of claim 1, wherein said composition further comprises one or more probiotics.

12. The composition of claim 1, wherein said composition further comprises one or more additional enzymes.

13. The composition of claim 1, wherein said composition is formulated as a granule.

14. The composition of claim 13, wherein said granule comprises a core particle and one or more coatings.

15. A method comprising introducing the composition of claim 1 into an animal feed.

16. The method of claim 15, wherein said animal feed comprises one or more plant materials.

17. A method comprising feeding the composition of claim 1 to an animal.

18. The method of claim 17, wherein said animal is monogastric.

19. The method of claim 17, wherein said animal is a poultry.

20. The method of claim 17, wherein said animal is a swine.

* * * * *